United States Patent
Ueno et al.

(10) Patent No.: US 9,533,985 B2
(45) Date of Patent: Jan. 3, 2017

(54) SULFONAMIDE DERIVATIVE AND MEDICINAL USE THEREOF

(71) Applicant: EA Pharma Co., Ltd., Tokyo (JP)

(72) Inventors: Hirokazu Ueno, Kawasaki (JP); Takashi Yamamoto, Kawasaki (JP); Ryuta Takashita, Kawasaki (JP); Ryohei Yokoyama, Kawasaki (JP); Toshihiko Sugiura, Kawasaki (JP); Shunsuke Kageyama, Kawasaki (JP); Ayatoshi Ando, Kawasaki (JP); Hiroyuki Eda, Kawasaki (JP); Agung Eviryanti, Kawasaki (JP); Tomoko Miyazawa, Kawasaki (JP); Aya Kirihara, Kawasaki (JP); Itsuya Tanabe, Kawasaki (JP); Tarou Nakamura, Kawasaki (JP); Misato Noguchi, Kawasaki (JP); Manami Shuto, Kawasaki (JP); Masayuki Sugiki, Kawasaki (JP); Mizuki Dohi, Kawasaki (JP)

(73) Assignee: EA Pharma Co., Ltd., Tokyo (JP)

( * ) Notice: Subject to any disclaimer, the term of this patent is extended or adjusted under 35 U.S.C. 154(b) by 0 days.

(21) Appl. No.: 14/397,078

(22) PCT Filed: Apr. 24, 2013

(86) PCT No.: PCT/JP2013/062121
§ 371 (c)(1),
(2) Date: Oct. 24, 2014

(87) PCT Pub. No.: WO2013/161904
PCT Pub. Date: Oct. 31, 2013

(65) Prior Publication Data
US 2015/0051395 A1    Feb. 19, 2015

(30) Foreign Application Priority Data

Apr. 24, 2012  (JP) ................. 2012-098562
Mar. 15, 2013  (JP) ................. 2013-054270

(51) Int. Cl.
| | |
|---|---|
| *C07D 471/04* | (2006.01) |
| *C07D 403/12* | (2006.01) |
| *C07D 401/14* | (2006.01) |
| *C07D 405/12* | (2006.01) |
| *C07D 239/54* | (2006.01) |
| *C07D 473/04* | (2006.01) |
| *C07D 401/12* | (2006.01) |
| *C07D 239/36* | (2006.01) |
| *A61P 29/00* | (2006.01) |

(52) U.S. Cl.
CPC .......... *C07D 471/04* (2013.01); *C07D 239/36* (2013.01); *C07D 239/54* (2013.01); *C07D 401/12* (2013.01); *C07D 401/14* (2013.01); *C07D 403/12* (2013.01); *C07D 405/12* (2013.01); *C07D 473/04* (2013.01)

(58) Field of Classification Search
CPC ... C07D 239/36; C07D 239/54; C07D 401/12; C07D 401/14; C07D 403/12; C07D 405/12; C07D 471/04; C07D 473/04
See application file for complete search history.

(56) References Cited

U.S. PATENT DOCUMENTS

| | | |
|---|---|---|
| 2003/0220268 A1 | 11/2003 | Makino et al. |
| 2005/0101779 A1 | 5/2005 | Sagi et al. |
| 2005/0222141 A1 | 10/2005 | Sagi et al. |
| 2005/0276803 A1 | 12/2005 | Chan et al. |
| 2006/0223836 A1 | 10/2006 | Makino et al. |
| 2009/0318688 A1 | 12/2009 | Kataoka et al. |
| 2011/0065918 A1 | 3/2011 | Makino et al. |

(Continued)

FOREIGN PATENT DOCUMENTS

| | | |
|---|---|---|
| CN | 1469867 A | 1/2004 |
| CN | 1917881 A | 2/2007 |

(Continued)

OTHER PUBLICATIONS

Chen et al. (Clinical Cancer Research, 2012, 18, pp. 5520-5525).*

(Continued)

*Primary Examiner* — Susanna Moore
(74) *Attorney, Agent, or Firm* — Oblon, McClelland, Maier & Neustadt, L.L.P.

(57) ABSTRACT

Sulfonamide compounds of a specific chemical structure in which a sulfonamide group having, as a substituent, a phenyl group or a heterocyclic group having a hetero atom(s) as a constituent element(s) is present at its terminal, and pharmaceutically acceptable salts thereof. These compounds are novel compounds having excellent α4 integrin-inhibitory action. The compounds have formulae represented by:

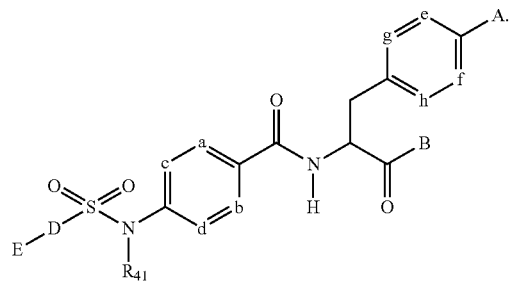

15 Claims, No Drawings

(56) References Cited

U.S. PATENT DOCUMENTS

2011/0313154 A1   12/2011  Kataoka et al.
2012/0253041 A1   10/2012  Makino et al.

FOREIGN PATENT DOCUMENTS

| CN | 101005854 A | 7/2007 |
|---|---|---|
| CN | 101589028 A | 11/2009 |
| EP | 1 477 482 A1 | 11/2004 |
| JP | 2007 532681 | 11/2007 |
| WO | 02 16329 | 2/2002 |
| WO | 03 070709 | 8/2003 |
| WO | 03 089410 | 10/2003 |
| WO | 2005 061466 | 7/2005 |
| WO | WO 2008/064823 A1 | 6/2008 |

OTHER PUBLICATIONS

Combined Chinese Office Action and Search Report issued Jul. 22, 2015 in Chinese Application 201380033106.5 with English translation of category of cited documents.
International Search Report Issued Jun. 4, 2013 in PCT/JP13/062121 Filed Apr. 24, 2013.
Extended European Search Report issued Aug. 17, 2015 in Patent Application No. 13781307.7.

* cited by examiner

SULFONAMIDE DERIVATIVE AND MEDICINAL USE THEREOF

TECHNICAL FIELD

The present invention relates to a sulfonamide derivative, a pharmaceutically acceptable salt thereof, and a pharmaceutical composition comprising any of these compounds as an active ingredient. Especially, the present invention relates to a compound useful as a drug for treating or preventing an inflammatory disease in which an α4 integrin-dependent adhesion process is associated with a pathological condition.

BACKGROUND ART

Orally administrable compounds have been already known which have α4 integrin-inhibitory action and which are useful as drugs for treating or preventing an inflammatory disease in which an α4 integrin-dependent adhesion process is associated with a pathological condition. For example, Patent Literature 1 discloses a phenylalanine derivative represented by general formula (1) and a pharmaceutically acceptable salt thereof, and representative compounds thereof have the following chemical structures.

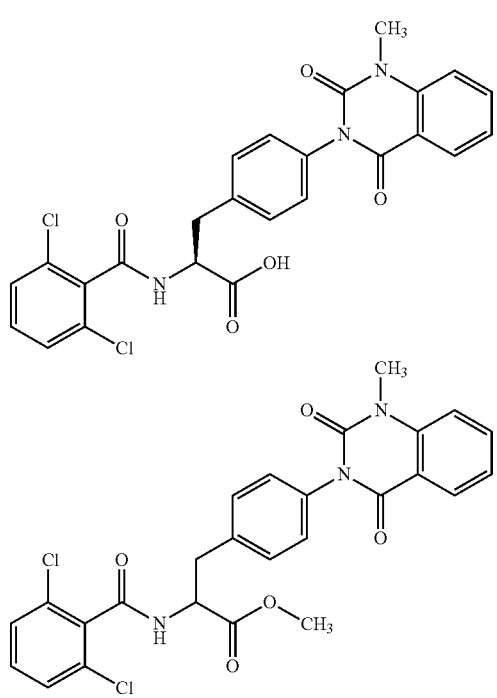

In addition, Patent Literature 1 shows results of VCAM inhibition activities (VCAM-1/α4β1 Binding Assay) and (VCAM-1/α4β7 Binding Assay).

Moreover, Patent Literature 2 discloses a phenylalanine derivative being represented by the following general formula (1) and having an R12(R13)N—X1-group at its terminal or a pharmaceutically acceptable salt thereof.

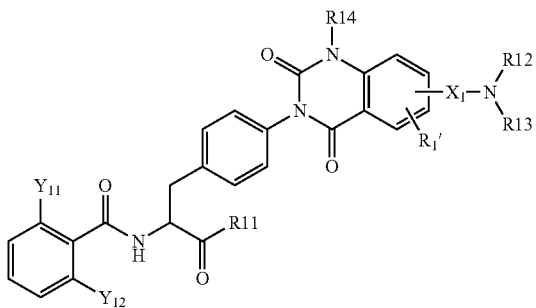

This compound was shown to have higher VCAM-1/α4β1 integrin inhibition activity in the presence of serum than the compound of Example 1 of Patent Literature 1. In addition, Patent Literature 3 also discloses a compound having α4 integrin-inhibitory action.

CITATION LIST

Patent Literatures

Patent Literature 1: WO02/16329A1
Patent Literature 2: WO05/061466A1
Patent Literature 3: WO03/070709A1

SUMMARY OF INVENTION

An object of the present invention is to provide a novel compound having a chemical structural formula which is not known yet and having excellent α4 integrin-inhibitory action.

In particular, an object of the present invention is to provide a novel compound having highly selective α4 integrin-inhibitory action with a low effect on α4β1 and a high effect on α4β7.

Another object of the present invention is to provide an orally administrable compound having excellent α4 integrin-inhibitory action.

Another object of the present invention is to provide a pharmaceutical composition comprising the above-described novel compound and a pharmaceutically acceptable carrier.

Another object of the present invention is to provide a drug comprising the above-described novel compound.

Another object of the present invention is to provide an agent for treating or preventing an inflammatory disease in which an α4β7 integrin-dependent adhesion process is associated with a pathological condition.

Another object of the present invention is to provide an α4 integrin inhibitor.

The present invention has been made on the basis of findings that sulfonamide derivatives having a specific chemical structure in which a sulfonamide group having, as a substituent, a phenyl group or a heterocyclic group containing a hetero atom(s) as constituent elements is present at its terminal and pharmaceutically acceptable salts thereof have excellent α4 integrin inhibition activity, and that the above-described objects can be achieved by using these compounds.

Specifically, the present invention includes the following modes [1] to [17].

[1] A sulfonamide derivative represented by the following general formula (1) or a pharmaceutically acceptable salt thereof:

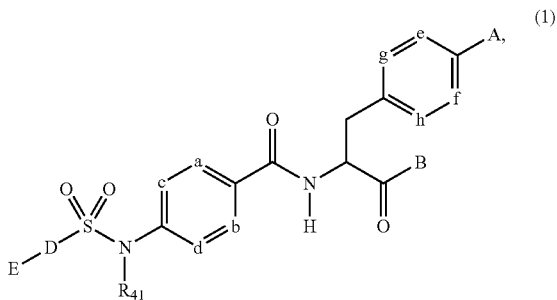

wherein
A represents a group represented by the following general formula (2-1), (2-2), or (2-3),

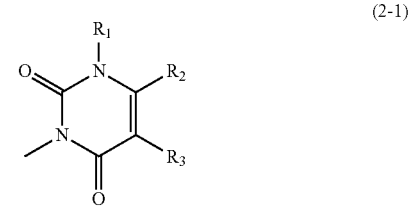

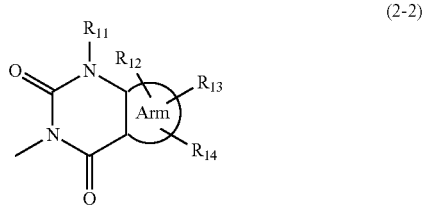

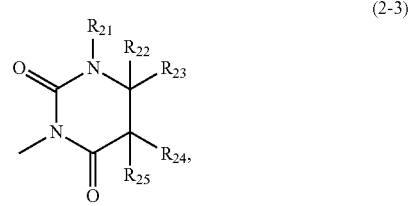

wherein
Arm is a cyclic alkyl group or aromatic ring containing 0, 1, 2, 3, or 4 hetero atoms selected from oxygen atoms, sulfur atoms, and nitrogen atoms, R1, R11, and R21 each independently represent any one of a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a lower alkylamino group, a (lower alkylamino) lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, R12, R13, and R14 each independently represent any one of a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a lower alkylamino group, a (lower alkylamino) lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, R2, R3, R22, R23, R24, and R25 each independently represent anyone of a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a lower alkylamino group, a (lower alkylamino) lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, B represents any one of a lower alkoxy group optionally substituted with an aryl group(s), a hydroxyl group(s), a lower alkyl group(s), a lower alkylamino group(s), and/or a heterocyclic group(s), a hydroxyl group, and a hydroxyamino group, R41 represents a hydrogen atom or a lower alkyl group, a, b, c, and d each independently represent C—R31, C—R32, C—R33, and C—R34, respectively, but one or two of a, b, c, and d may each represent a nitrogen atom, R31, R32, R33, and R34 each independently represent any one of a hydrogen atom, a halogen atom, a lower alkyl group, a lower alkoxy group, and a nitro group, provided that any one of R31, R32, R33, and R34 is a halogen atom or a lower alkyl group, e, f, g, and h each independently represent C—R35, C—R36, C—R37, and C—R38, respectively, but one or two of e, f, g, and h may each represent a nitrogen atom, R35, R36, R37, and R38 are each independently any one of a hydrogen atom, a halogen atom, a lower alkyl group, a lower alkoxy group, and a nitro group, D represents a phenyl group or heterocyclic group optionally having a substituent(s) selected from the group consisting of halogen atoms, hydroxyl groups, lower alkyl groups, lower alkenyl groups, lower alkynyl groups, lower alkoxy groups, lower alkylthio groups, lower hydroxyalkyl groups, lower hydroxyalkenyl groups, lower hydroxyalkoxy groups, lower halogenoalkyl groups, lower halogenoalkoxy groups, lower halogenoalkylthio groups, lower halogenoalkenyl groups, nitro groups, cyano groups, amino groups, carboxyl groups, lower alkyloxycarbonyl groups, carbamoyl groups, lower alkanoyl groups, aroyl groups, lower alkylsulfonyl groups, sulfamoyl groups, and ammonium groups, and E represents a 5- or 6-membered heterocyclic group optionally having a substituent(s) selected from the group consisting of halogen atoms, hydroxyl groups, lower alkyl groups, lower alkenyl groups, lower alkynyl groups, lower alkoxy groups, lower alkylthio groups, lower hydroxyalkyl groups, lower hydroxyalkenyl groups, lower hydroxyalkoxy groups, lower halogenoalkyl groups, lower halogenoalkoxy groups, lower halogenoalkylthio groups, lower halogenoalkenyl groups, nitro groups, cyano groups, amino groups, 4- to 6-membered cyclic amino groups, carboxyl groups, lower alkyloxycarbonyl groups, carbamoyl groups, lower alkanoyl groups, aroyl groups, lower alkylsulfonyl groups, sulfamoyl groups, and ammonium groups; an aminocarbonyl group optionally having a substituent(s) selected from the group consisting of hydroxyl groups, lower alkyl groups, lower alkenyl groups, lower alkynyl groups, lower alkoxy groups, lower hydroxyalkyl groups, lower hydroxyalkenyl groups, lower hydroxyalkoxy groups, lower halogenoalkyl groups, lower halogenoalkoxy groups, lower halogenoalkenyl groups, amino groups, lower alkylamino groups, aryl groups, heterocyclic groups, heterocycle-substituted lower alkyl groups, lower alkylsulfonyl groups, and sulfamoyl groups; a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a carboxyl group, a dihydroxyboryl group, a lower alkylcarbonyl group, a lower alkyloxycarbonyl group, a carbamoyl group, a lower alkanoyl group, an aroyl group, a lower alkylsulfonyl group, a sulfamoyl group, an ammonium group, or a lower alkylaminoalkylene group, provided that the lower alkylcarbonyl group and the lower alkyloxycarbonyl group may each be bonded to the phenyl group represented by D to form a condensed ring.

[2] The sulfonamide derivative according to [1] or a pharmaceutically acceptable salt thereof, wherein E represents a 5- or 6-membered heterocyclic group optionally having a substituent(s) selected from the group consisting of halogen atoms, hydroxyl groups, lower alkyl groups, lower alkenyl groups, lower alkynyl groups, lower alkoxy groups, lower alkylthio groups, lower hydroxyalkyl groups, lower hydroxyalkenyl groups, lower hydroxyalkoxy groups, lower halogenoalkyl groups, lower halogenoalkoxy groups, lower halogenoalkylthio groups, lower halogenoalkenyl groups, nitro groups, cyano groups, amino groups, carboxyl groups, lower alkyloxycarbonyl groups, carbamoyl groups, lower alkanoyl groups, aroyl groups, lower alkylsulfonyl groups, sulfamoyl groups, and ammonium groups; an aminocarbonyl group optionally having a substituent(s) selected from the group consisting of hydroxyl groups, lower alkyl groups, lower alkenyl groups, lower alkynyl groups, lower alkoxy groups, lower hydroxyalkyl groups, lower hydroxyalkenyl groups, lower hydroxyalkoxy groups, lower halogenoalkyl groups, lower halogenoalkoxy groups, lower halogenoalkenyl groups, amino groups, lower alkylamino groups, aryl groups, heterocyclic groups, lower alkylsulfonyl groups, and sulfamoyl groups; a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a carboxyl group, a dihydroxyboryl group, a lower alkyloxycarbonyl group, a carbamoyl group, a lower alkanoyl group, an aroyl group, a lower alkylsulfonyl group, a sulfamoyl group, an ammonium group, or a lower alkylaminoalkylene group.

[3] The sulfonamide derivative according to [1] or a pharmaceutically acceptable salt thereof, wherein D is a phenyl group optionally having a substituent(s) selected from the group consisting of lower alkyl groups, halogen atoms, hydroxyl groups, and lower alkoxy groups.

[4] The sulfonamide derivative according to [1] or a pharmaceutically acceptable salt thereof, wherein D is a 6-membered aromatic heterocyclic group containing a nitrogen atom(s) as a ring-constituent atom(s) and optionally having a substituent(s) selected from the group consisting of lower alkyl groups, halogen atoms, and lower alkoxy groups.

[5] The sulfonamide derivative according to [4] or a pharmaceutically acceptable salt thereof, wherein the heterocyclic group represented by D is a pyridyl group or pyrrole group optionally having a substituent(s) selected from the group consisting of lower alkyl groups, halogen atoms, and lower alkoxy groups.

[6] The sulfonamide derivative according to any one of [1] to [5] or a pharmaceutically acceptable salt thereof, wherein E is a 5- or 6-membered aromatic heterocyclic group containing 1, 2, 3, or 4 hetero atoms selected from oxygen atoms, sulfur atoms, and nitrogen atoms and optionally having a substituent(s) selected from the group consisting of lower alkyl groups, lower alkoxy groups, and halogen atoms.

[7] The sulfonamide derivative according to [6] or a pharmaceutically acceptable salt thereof, wherein the aromatic heterocyclic group is selected from the group consisting of a pyridyl group, a pyridazyl group, a pyrimidyl group, a pyrazinyl group, a pyrrolyl group, a furanyl group, a thiophenyl group, a thiazolyl group, an oxazolyl group, a triazolyl group, and a tetrazole group.

[8] The sulfonamide derivative according to any one of [1] to [4] or a pharmaceutically acceptable salt thereof, wherein E is an aminocarbonyl group or lower alkylaminoalkylene group optionally substituted with a lower alkyl group(s), a heterocyclic group(s), and/or a heterocycle-substituted lower alkyl group(s).

[9] The sulfonamide derivative according to any one of [1] to [6] and [8] or a pharmaceutically acceptable salt thereof, wherein each lower alkyl group is a linear, branched, or cyclic alkyl group.

[10] The sulfonamide derivative according to any one of [1] to [9] or a pharmaceutically acceptable salt thereof, wherein R1, R11, and R21 are lower alkyl groups.

[11] The sulfonamide derivative according to any one of [1] to [10] or a pharmaceutically acceptable salt thereof, wherein Arm is selected from the group consisting of a phenyl group, a pyridyl group, and an imidazolyl group.

[12] The sulfonamide derivative according to any one of [1] to [11] or a pharmaceutically acceptable salt thereof, wherein one of R31, R32, R33, and R34 is a halogen atom, and the rest are hydrogen atoms, or two of R31, R32, R33, and R34 are halogen atoms, and the rest are hydrogen atoms.

[13] The sulfonamide derivative according to [1] or a pharmaceutically acceptable salt thereof, wherein A is a group represented by general formula (2-1) or (2-2), in which Arm is a pyridyl group or an imidazolyl group, and R1 and R11 are lower alkyl groups, two of R31, R32, R33, and R34 are halogen atoms, and the rest are hydrogen atoms, g is a carbon or nitrogen atom, e is a carbon or nitrogen atom, D is a phenyl group optionally having a halogen atom(s), a lower alkyl group(s), and/or a lower alkoxy group(s), a furyl group, or a pyridyl group optionally having a halogen atom(s), a lower alkyl group(s), and/or a lower alkoxy group(s), and E is a pyridyl group, pyrimidyl group, triazolyl group, or pyrrolyl group optionally having a lower alkyl group(s) and/or a 4- to 6-membered cyclic amino group(s), or an aminocarbonyl group optionally substituted with a lower alky or heterocycle-substituted lower alkyl group(s).

[14] A pharmaceutical composition comprising the sulfonamide derivative according to any one of [1] to [13] or a pharmaceutically acceptable salt thereof.

[15] An agent for treating or preventing an inflammatory disease in which an α4β7 integrin-dependent adhesion process is associated with a pathological condition, the agent comprising, as an active ingredient, the sulfonamide derivative according to any one of [1] to [13] or a pharmaceutically acceptable salt thereof.

[16] An α4β7 integrin inhibitor comprising, as an active ingredient, the sulfonamide derivative according to any one of [1] to [13] or a pharmaceutically acceptable salt thereof.

[17] A compound represented by any one of the following formulae or a pharmaceutically acceptable salt thereof:

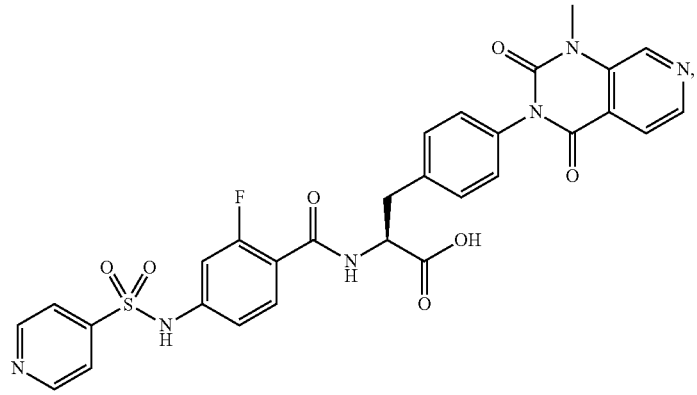

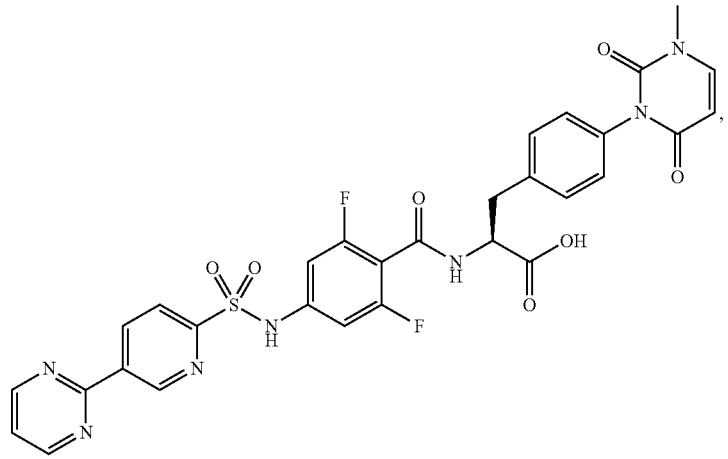

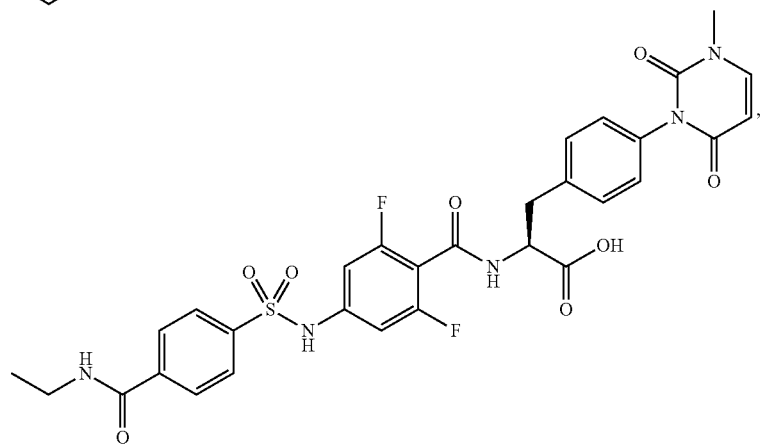

-continued
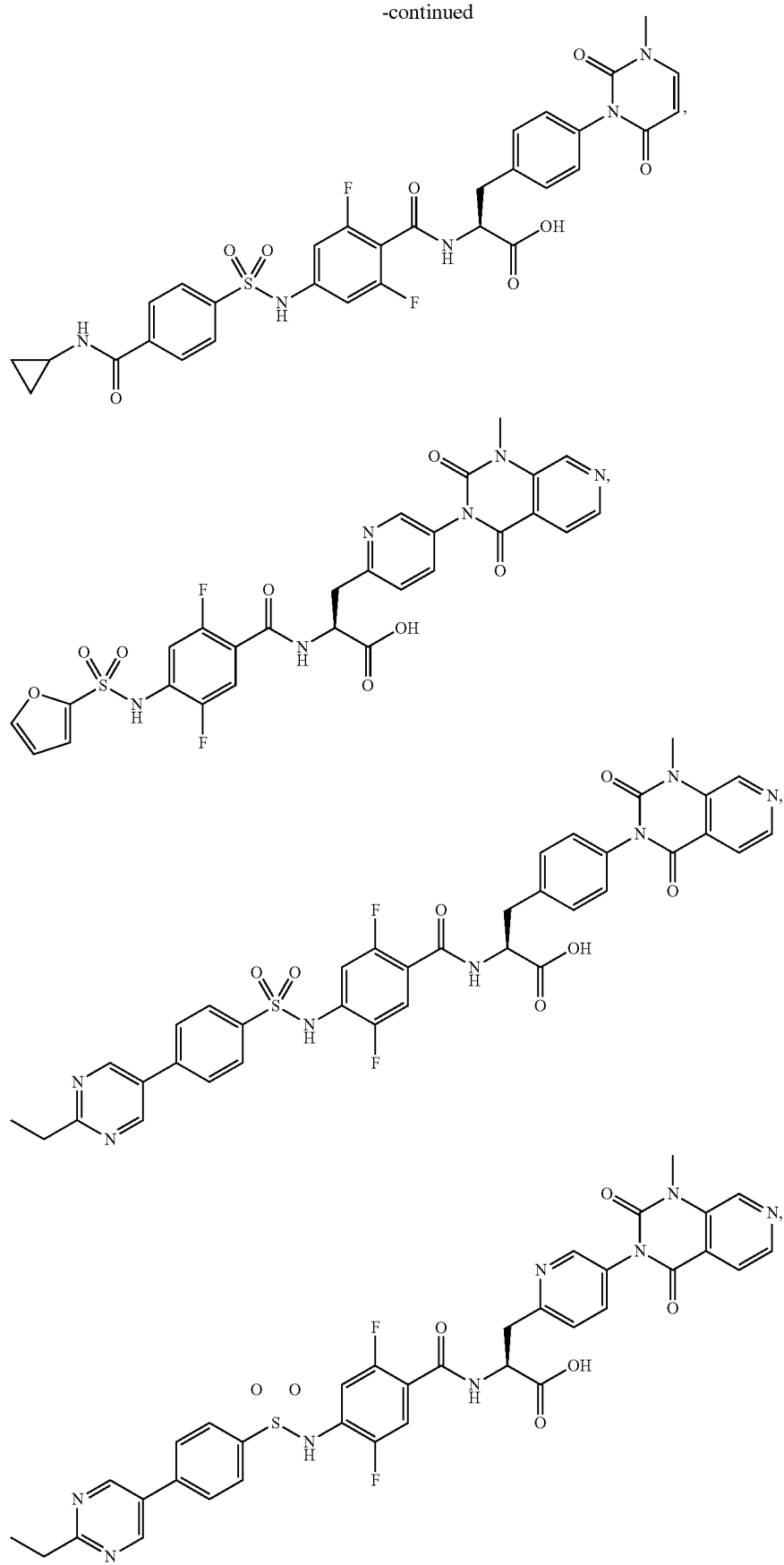

-continued

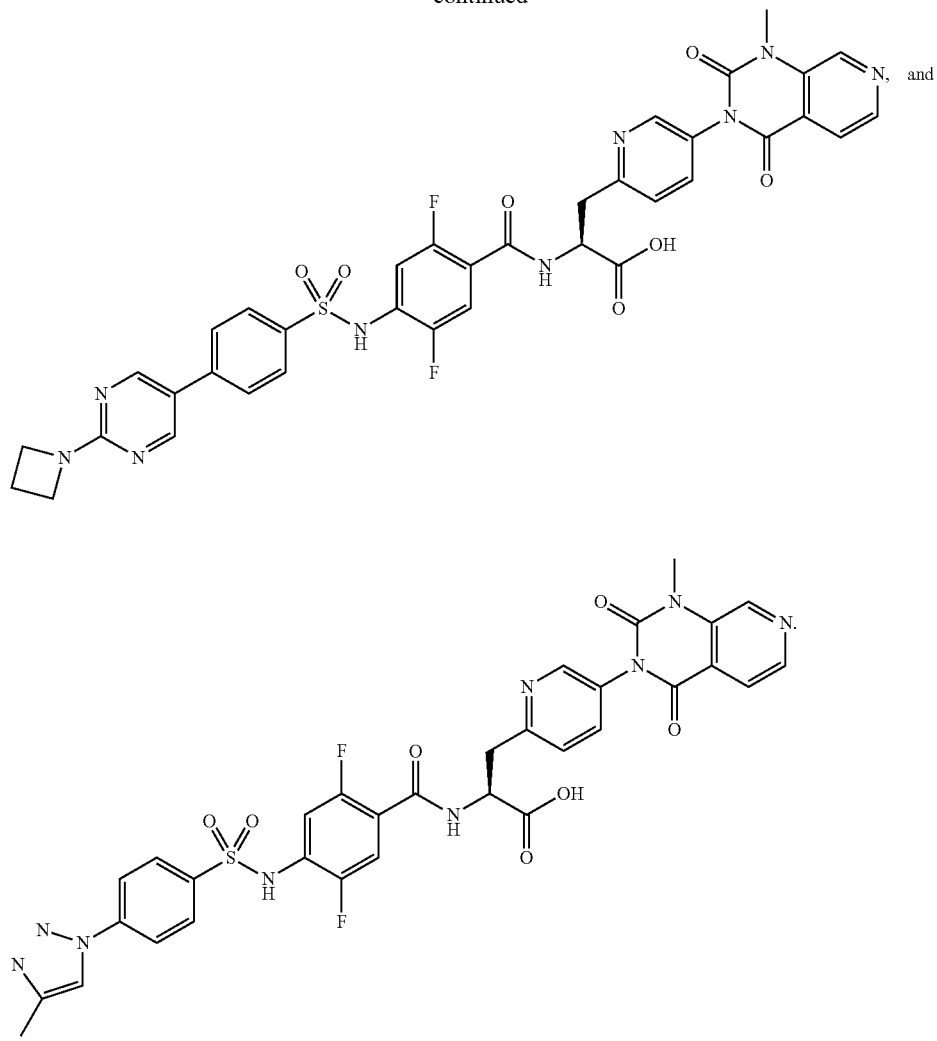

DESCRIPTION OF EMBODIMENTS

In this specification, the term "lower" in a lower alkyl group and the like means that the group has 1 to 6 carbon atoms, and preferably the number of carbon atoms is 1 to 4. An alkyl group, an alkenyl group, or an alkynyl group as a constituent in an alkyl group, an alkenyl group, an alkynyl group, an alkoxy group, an alkylthio group, an alkanoyl group, an alkylamino group, or the like may be linear, branched, or cyclic. Examples of the alkyl group include a methyl group, an ethyl group, a propyl group, an isopropyl group, a butyl group, a secondary butyl group, a tertiary butyl group, a pentyl group, a hexyl group, a cyclopropyl group, a cyclobutyl group, a cyclopentyl group, a cyclohexyl group, a cyclopropylmethyl group, a cyclopropylethyl group, and the like. The alkyl group preferably has 1 to 6 carbon atoms and more preferably has 1 to 4 carbon atoms. The alkenyl group may be a vinyl group, a propenyl group, a butenyl group, a pentenyl group, or the like, and preferably has 2 to 6 carbon atoms, and more preferably has 2 to 4 carbon atoms. The alkynyl group may be an ethynyl group, a propynyl group, a butynyl group, or the like, and preferably has 2 to 6 carbon atoms and more preferably has 2 to 4 carbon atoms.

The alkoxy group may be a methoxy group, an ethoxy group, a propyloxy group, an isopropyloxy group, or the like, and preferably has 1 to 6 carbon atoms, and more preferably has 1 to 4 carbon atoms. A hetero atom may be a nitrogen atom, an oxygen atom, a sulfur atom, or the like. A halogen atom represents a fluorine atom, a chlorine atom, a bromine atom, or an iodine atom. A halogenoalkyl group may be a chloromethyl group, a trichloromethyl group, a trifluoromethyl group, a trifluoroethyl group, a pentafluoromethyl group, or the like. A halogenoalkoxy group may be a trichloromethoxy group, a trifluoromethoxy group, or the like. A hydroxyalkyl group may be a hydroxymethyl group, a hydroxyethyl group, or the like.

In this specification, an aryl group means a substituted or unsubstituted aryl group, and may be a phenyl group, a 1-naphthyl group, a 2-naphthyl group, or the like. The aryl group is preferably a phenyl group or a substituted phenyl group. Here, halogen atoms, alkoxy groups, alkyl groups, hydroxyl groups, halogenoalkyl groups, and halogenoalkoxy groups are particularly preferable as the substituents. A heterocyclic group means a heteroatom-containing cyclic group which is constituted of carbon with nitrogen, oxygen, sulfur, and/or the like, and which is made of one to three 4- to 7-membered substituted or unsubstituted rings. Specific examples of the heterocyclic group include a pyridyl group, a dihydropyranyl group, a tetrahydropyranyl group, a pyridazyl group, a pyrimidyl group, a pyrazyl group, a pyrrolyl group, a furyl group, a thienyl group, a thiazolyl group, a triazolyl group, an isoxazolyl group, an isothiazolyl group, an oxazolyl group, an indolyl group, a quinolyl group, an isoquinolyl group, a benzoimidazolyl group, a pyrazolyl group, an imidazolyl group, a thiadiazolyl group, a pyrrolidyl group, a piperidyl group, a piperazyl group, a morpholyl group, an oxetanyl ring, an isoindolyl group, a benzofuryl group, an isobenzofuryl group, a benzothienyl group, a benzopyrazolyl group, a benzoimidazolyl group, a benzoxazolyl group, a benzothiazolyl group, and the like. The heterocyclic group is preferably a pyridyl group, a pyrazyl group, a pyrimidyl group, a furyl group, a thienyl group, a substituted pyridyl group, a substituted furyl group, a substituted thienyl group, or the like. Here, halogen atoms, alkoxy groups, alkyl groups, hydroxyl groups, halogenoalkyl groups, halogenoalkoxy groups are particularly preferable as the substituents.

In general formula (1) of the present invention, it is preferable that (i) D be a phenyl group optionally having a substituent(s) selected from the group consisting of lower alkyl groups, halogen atoms, hydroxyl groups, and lower alkoxy groups, or that (ii) D be a 6-membered aromatic heterocyclic group containing a nitrogen atom(s) as a ring-constituent atom(s) and optionally having a substituent(s) selected from the group consisting of lower alkyl groups, halogen atoms, and lower alkoxy groups. Here, the heterocyclic group represented by D is particularly preferably a pyridyl group or a pyrrole group.

Moreover, in general formula (1) of the present invention or in combination with the above-described (i) or (ii), E is preferably a 5- or 6-membered aromatic heterocyclic group containing 1, 2, 3, or 4 hetero atoms selected from oxygen atoms, sulfur atoms, and nitrogen atoms and optionally having a substituent(s) selected from the group consisting of lower alkyl groups, lower alkoxy groups, and halogen atoms. Here, the aromatic heterocyclic group is preferably selected from the group consisting of a pyridyl group, a pyridazyl group, a pyrimidyl group, a pyrazinyl group, a pyrrolyl group, a furanyl group, a thiophenyl group, a thiazolyl group, an oxazolyl group, a triazolyl group, and a tetrazole group.

Alternatively, in general formula (1) of the present invention or in combination with the above-described (i) or (ii), E is preferably an aminocarbonyl group or lower alkylaminoalkylene group optionally substituted with a lower alkyl, heterocyclic, or heterocycle-substituted lower alkyl group(s). Moreover, it is also preferable that E be a pyridyl group, pyrimidyl group, triazolyl group, or pyrrolyl group optionally having a lower alkyl group(s) and/or a 4- to 6-membered cyclic amino group(s), or an aminocarbonyl group optionally substituted with a lower alky or heterocycle-substituted lower alkyl group(s). Here the 4- to 6-membered cyclic amino group may be an azetidinyl group or the like, and the heterocycle-substituted lower alkyl group may be a tetrapyran lower alkyl group or the like.

In addition, when E represents a lower alkylcarbonyl group or a lower alkyloxycarbonyl group, a condensed ring formed by such a group bonded to the phenyl group of D may be a 1-oxoindanyl group, a 3-oxo-1H-isobenzofuranyl group, or the like.

Further, in general formula (1) of the present invention or in any one of the above-described preferred modes, R1, R11, and R21 are preferably lower alkyl groups.

Further, in general formula (1) of the present invention or in any one of the above-described preferred modes, Arm is preferably selected from the group consisting of a phenyl group, a pyridyl group, and an imidazolyl group.

Further, in general formula (1) of the present invention or in any one of the above-described preferred modes, it is preferable that one of R31, R32, R33, and R34 be a halogen atom, and the rest be hydrogen atoms, or that two of R31, R32, R33, and R34 be halogen atoms, and the rest be hydrogen atoms.

Further, in general formula (1) of the present invention or in any one of the above-described preferred modes, it is preferable that g be a carbon or nitrogen atom, and e be a carbon or nitrogen atom.

In the present invention, compounds represented by the following formulae and pharmaceutically acceptable salts thereof are particularly preferable. In addition, prodrugs of these compounds and pharmaceutically acceptable salts thereof are also preferable.

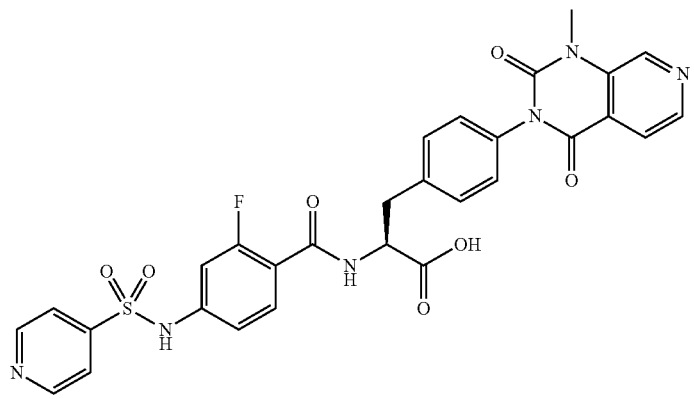

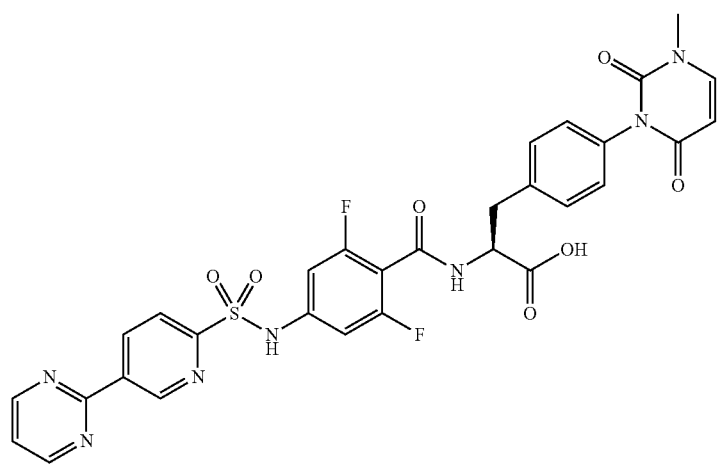
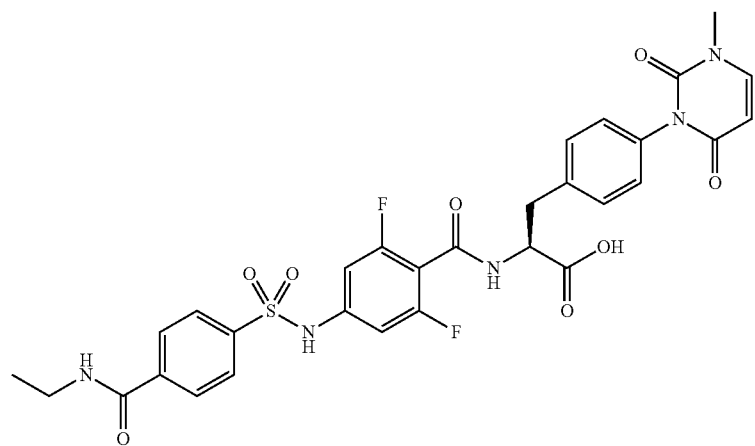
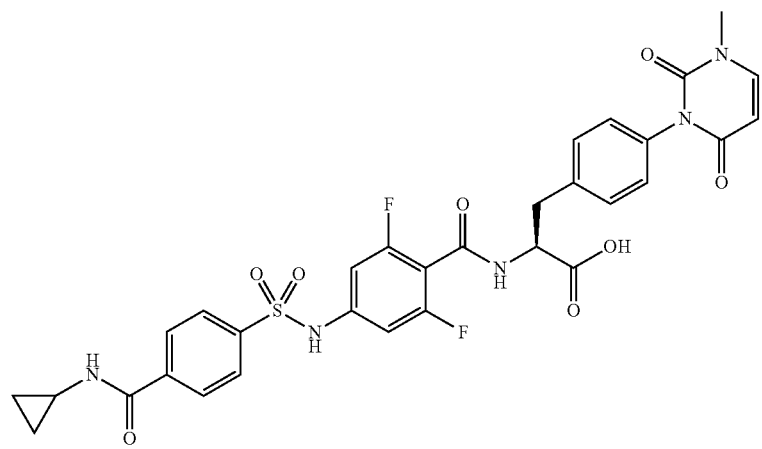

-continued
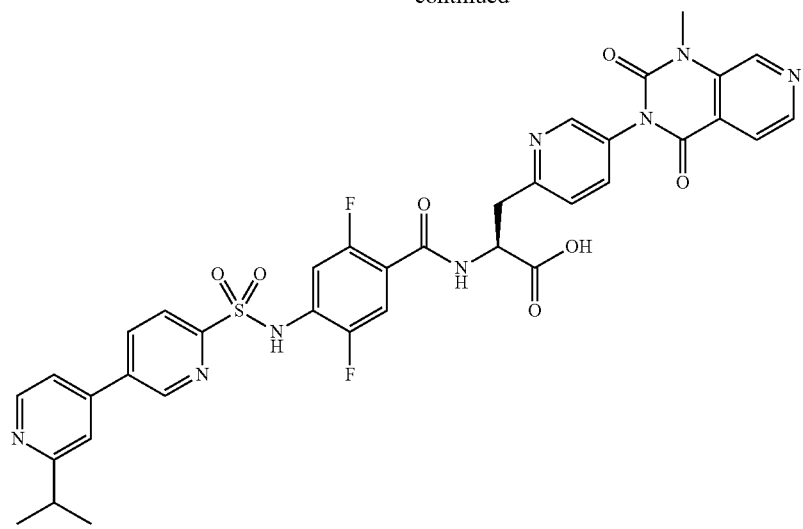
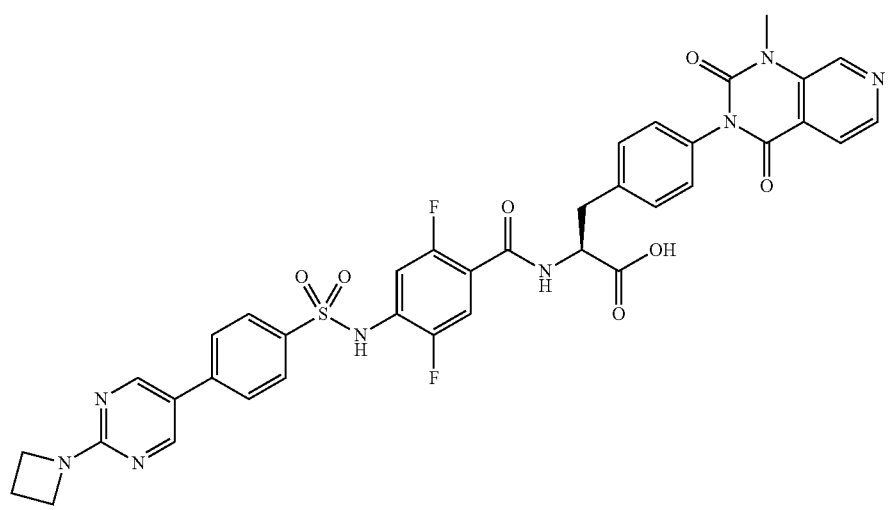
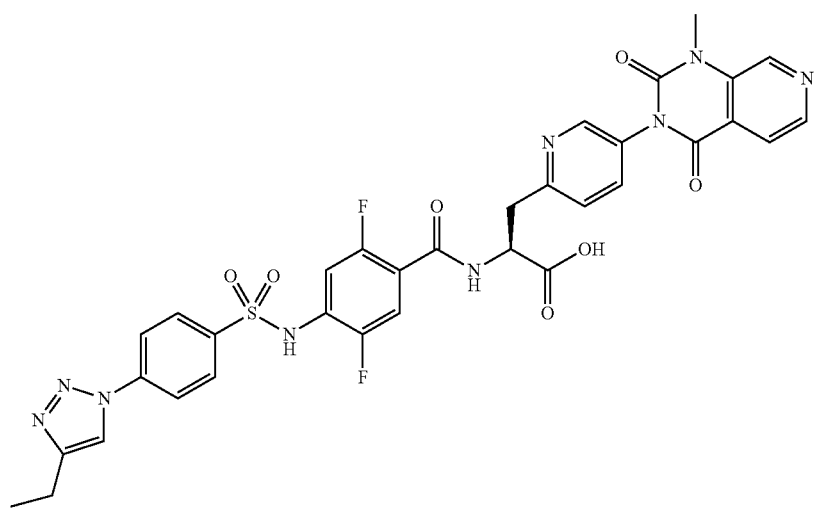

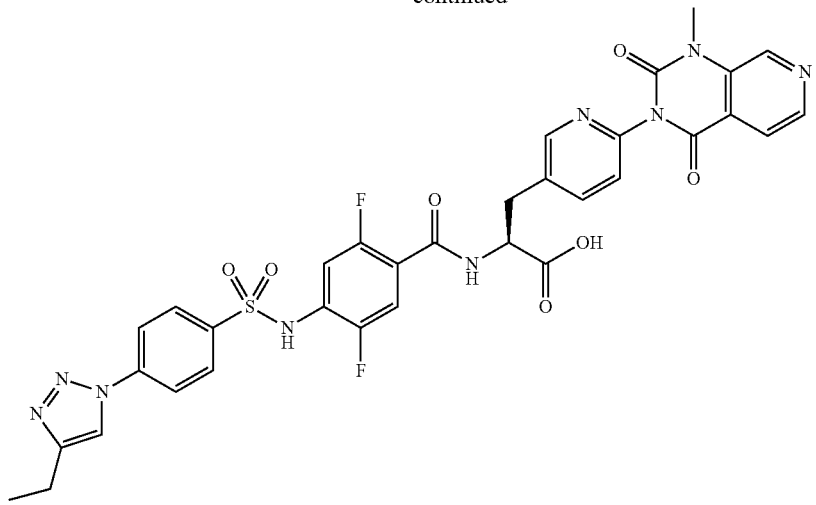

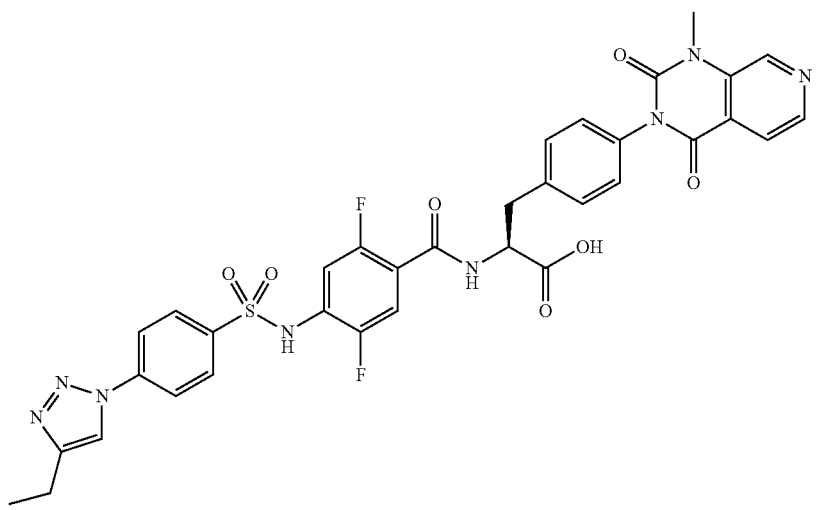

Furthermore, compounds of Examples 140, 237, 229, 232, 234, 246, 247, 248, 249, and 257 and salts and prodrugs thereof are also preferable.

When the compound represented by general formula (1) of the present invention can be in the form of a salt, the salt only needs to be pharmaceutically acceptable one. Examples of the salt for an acidic group such as a carboxyl group in the formula include ammonium salt, salts with alkali metals such as sodium and potassium, salts with alkaline earth metals such as calcium and magnesium, aluminum salt, zinc salt, salts with organic amines such as triethylamine, ethanolamine, morpholine, piperidine, and dicyclohexylamine, and salts with basic amino acids such as arginine and lysine. In a case where a basic group is present in the formula, examples of the salt for the basic group include salts with inorganic acids such as hydrochloric acid, sulfuric acid, and phosphoric acid, salts with organic carboxylic acids such as acetic acid, citric acid, benzoic acid, maleic acid, fumaric acid, tartaric acid, and succinic acid, and salts with organic sulfonic acids such as methanesulfonic acid and p-toluenesulfonic acid. A method for forming the salt may be a method in which the compound of general formula (1) is mixed with a necessary acid or base at an appropriate amount ratio in a solvent or a dispersion medium, or the salt can be obtained also by subjecting the compound of general formula (1) in the form of another salt to cation exchange or anion exchange.

The compound of the present invention may include solvates of the compound represented by general formula (1), such as a hydrate and alcohol adducts.

The compound of the present invention includes prodrug forms of the compound represented by general formula (1). A prodrug of the compound of the present invention refers to a compound which is converted to the compound represented by general formula (1) by a reaction due to an enzyme, gastric acid, or the like in a living organism under physiological conditions, namely, a compound which undergoes enzymatic oxidation, reduction, hydrolysis, or the like, and thus converted to the compound represented by general formula (1), or a compound which undergoes hydrolysis or the like due to gastric acid or the like, and thus converted to the compound represented by general formula (1). Examples of the prodrug of the compound represented by general formula (1) include compounds illustrated in Examples, but are not limited thereto. When the compound represented by general formula (1) has an amino, examples of compounds used as the prodrugs include compounds in which the amino is subjected to acylation, alkylation, or phosphorylation (for example, compounds in which the amino of the compound represented by general formula (1) is subjected to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, or tert-butylation), etc. When the compound represented by general formula (1) has a hydroxy, examples of compounds used as the prodrugs include compounds in which the hydroxy is subjected to acylation, alkylation, phosphorylation, or boration (for example, compounds in which the hydroxy of the compound represented by general formula (1) is subjected to acetylation, palmitoylation, propanoylation, pivaloylation, succinylation, fumarylation, alanylation, or dimethylaminomethylcarbonylation), etc. When the compound represented by general formula (1) has a carboxyl, examples of compounds used as the prodrugs include compounds in which the carboxyl is subjected to esterification or amidation (for example, compounds in which the carboxyl of the compound represented by general formula (1) is subjected to ethyl esterification, phenyl esterification, isopropyl esterification, isobutyl esterification, cyclopentyl esterification, cyclohexyl esterification, cycloheptyl esterification, cyclohexylmethyl esterification, normal-hexyl esterification, sec-butyl esterification, tert-butyl esterification, (4-tetrahydropyranyl)methyl esterification, (4-tetrahydropyranyl) esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methyl amidation), etc. These compounds can be produced from the compound represented by general formula (1) by methods known per se.

Moreover, the prodrug of compound (1) may be a compound which is converted to compound (1) under physiological conditions as described on Pages 163 to 198 of "IYAKUHIN NO KAIHATSU (Pharmaceutical Research and Development)," Vol. 7, BUNSHI SEKKEI (Molecular Design), published by HirokawaShoten., 1990.

The present invention includes all isotopically substituted forms of the compound represented by formula (1). An isotopically substituted form of the compound of the present invention refers to one in which at least one atom is replaced by an atom having the same atomic number (proton number) but having different mass number (the sum of the proton number and the neutron number). Examples of the isotopes contained in the compound of the present invention include hydrogen atoms, carbon atoms, nitrogen atoms, oxygen atoms, phosphorus atoms, sulfur atoms, fluorine atoms, chlorine atoms, and the like, and include $^2H$, $^3H$, $^{13}C$, $^{14}C$, $^{15}N$, $^{17}O$, $^{18}O$, $^{31}P$, $^{32}P$, $^{35}S$, $^{18}F$, $^{36}Cl$, and the like. Especially, radioisotopes such as $^3H$ and $^{14}C$, which are unstable and which exhibit radioactivity and release neutrons, are useful for a body tissue distribution test of drugs or compounds, and the like. Stable isotopes can be used safely, because they do not decay, undergo little change in the abundance, and do not have radioactivity. The isotope in the compound of the present invention can be introduced in a usual manner by replacing a reagent used for synthesis with a corresponding reagent containing the isotope.

The compound represented by general formula (1) of the present invention can be produced by, for example, a dehydration reaction between an intermediate being represented by general formula (M-I) and having an amino group at its terminal and an intermediate being represented by general formula (M-II) and having a carboxyl group at its terminal.

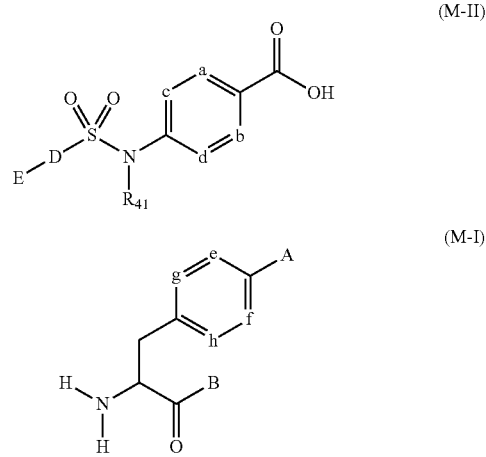

Of these intermediates, the intermediate being represented by general formula (M-II) and having a carboxyl group at its terminal can be produced by, for example, the following methods.

The following are methods for producing representative compounds among intermediates being represented by general formula (M-II) and having a carboxyl group at their terminal, which are compounds of the present invention. Note that, in the following description, the signs in the formulae are the same as those defined in formula (I) above, unless otherwise noted.

(1) Intermediate (S6) having a carboxyl group at its terminal and being represented by general formula (M-II), in which D is a phenyl group or pyridyl group optionally having a substituent(s) selected from the group consisting of lower alkyl groups and halogen atoms, and E is a 5-membered or 6-membered aromatic heterocyclic group containing 1, 2, 3, or 4 hetero atoms selected from oxygen atoms, sulfur atoms, and nitrogen atoms and optionally having a substituent(s) selected from lower alkyl groups and halogen atoms can be synthesize by employing, for example, one of the methods described below (production methods A, B, C, and D).

<Production Method A>

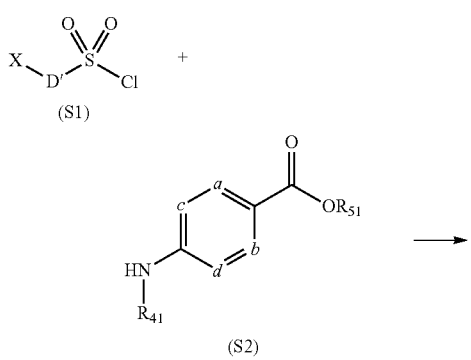

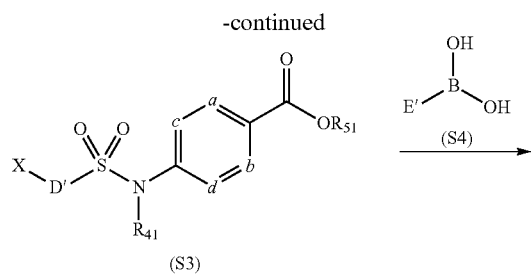

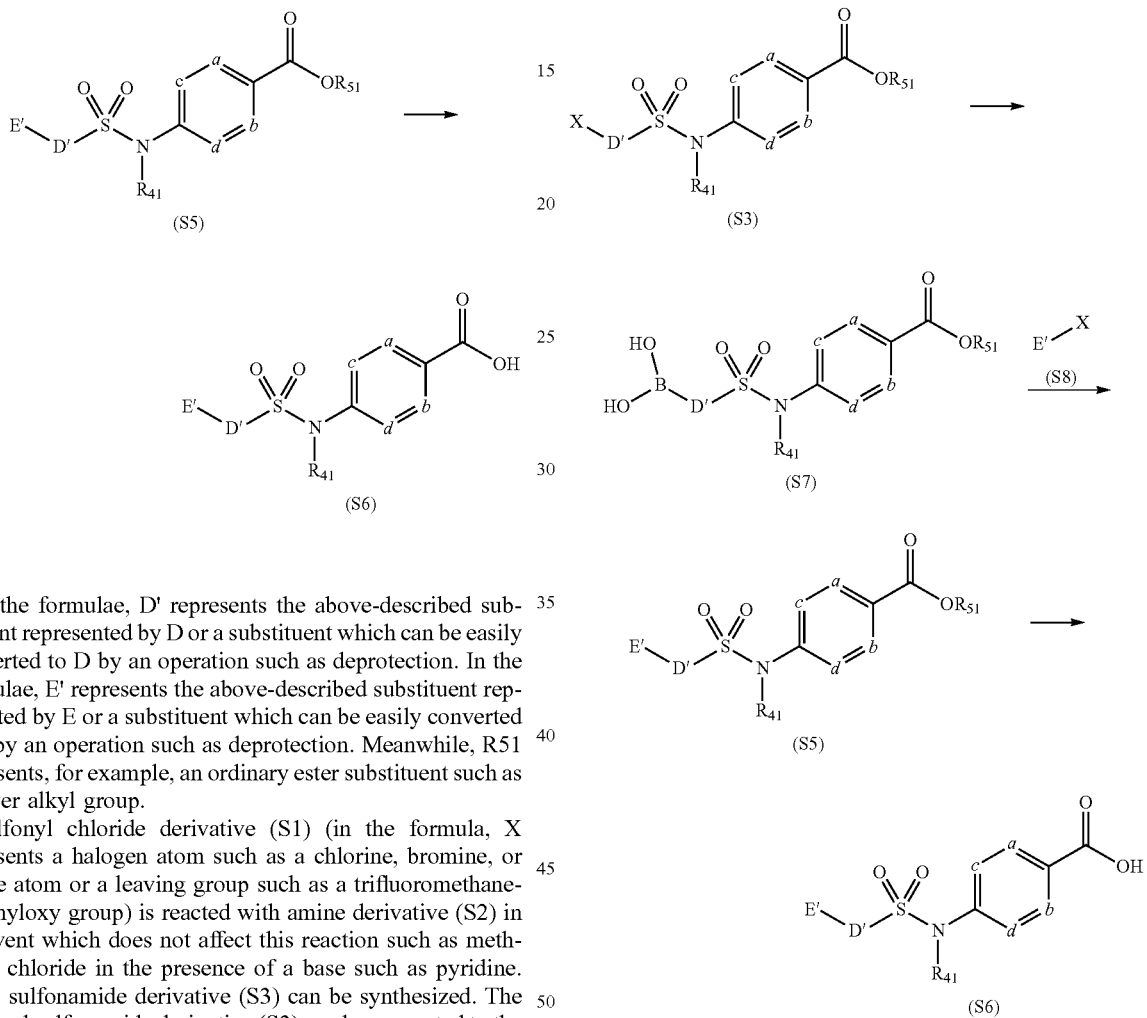

In the formulae, D' represents the above-described substituent represented by D or a substituent which can be easily converted to D by an operation such as deprotection. In the formulae, E' represents the above-described substituent represented by E or a substituent which can be easily converted to E by an operation such as deprotection. Meanwhile, R51 represents, for example, an ordinary ester substituent such as a lower alkyl group.

Sulfonyl chloride derivative (S1) (in the formula, X represents a halogen atom such as a chlorine, bromine, or iodine atom or a leaving group such as a trifluoromethanesulfonyloxy group) is reacted with amine derivative (S2) in a solvent which does not affect this reaction such as methylene chloride in the presence of a base such as pyridine. Thus, sulfonamide derivative (S3) can be synthesized. The obtained sulfonamide derivative (S3) can be converted to the corresponding sulfonamide derivative (S5) by the Suzuki coupling reaction with boronic acid derivative (S4). Subsequently, the obtained sulfonamide derivative (S5) is subjected to deprotection in a solvent which does not affect this reaction such as tetrahydrofuran, methanol, or ethanol, by alkali hydrolysis using a base such as sodium hydroxide, acid hydrolysis using, for example, hydrochloric acid or trifluoroacetic acid, or the like. Thus, the target intermediate (S6) having a carboxyl group at its terminal can be produced.

The Suzuki coupling reaction is known, and is carried out by reacting a boronic acid derivative or a boronic acid ester derivative with a halogen derivative, a trifluoromethanesulfonate, or a methanesulfonate in a solvent which does not affect this reaction such as 1,4-dioxane, tetrahydrofuran, toluene, dimethyl sulfoxide, or 1,2-dimethoxyethane in the presence or absence of a co-solvent such as water, by using a transition metal catalyst such as tetrakis(triphenylphosphine)palladium(0), [1,1'-bis(diphenylphosphino)ferrocene] dichloropalladium(II), or tris(dibenzylideneacetone)dipalladium(0) or using a transition metal catalyst such as palladium(II) acetate and a ligand such as triphenylphosphine, in the presence of a base such as potassium carbonate, sodium carbonate, potassium phosphate, sodium methoxide, or sodium hydroxide.

<Production Method B>

In the formulae, D' represents the above-described substituent represented by D or a substituent which can be easily converted to D by an operation such as deprotection. In the formulae, E' represents the above-described substituent represented by E or a substituent which can be easily converted to E by an operation such as deprotection. Meanwhile, R51 represents an ordinary ester substituent such as a lower alkyl group.

Sulfonamide derivative (S3), which is the intermediate described in <Production Method A>, and a borane derivative such as bis(pinacolato)diborane are converted to the corresponding boronic acid ester derivative by a coupling reaction in a solvent which does not affect this reaction such as N,N-dimethylformamide, in the presence of a base such as potassium acetate, using a metal catalyst such as [1,1'-bis(diphenylphosphino)ferrocene]dichloropalladium(II). Subsequently, the obtained boronic acid ester derivative is treated in a solvent which does not affect this reaction such as acetone by adding, for example, sodium periodate, ammonium acetate, and water to remove the boronic acid ester. Thus, the corresponding boronic acid derivative (S7) can be synthesized. The obtained boronic acid derivative (S7) can be converted to the corresponding sulfonamide derivative (S5) by the Suzuki coupling reaction (described above) with halogen derivative (S8) (in the formula, X represents a halogen atom such as a chlorine, bromine, or iodine atom or a leaving group such as a trifluoromethanesulfonyloxy group). By deprotecting sulfonamide derivative (S5) by hydrolysis or the like using the method described in <Production Method A>, the target intermediate (S6) having a carboxyl group at its terminal can be produced.

<Production Method C>

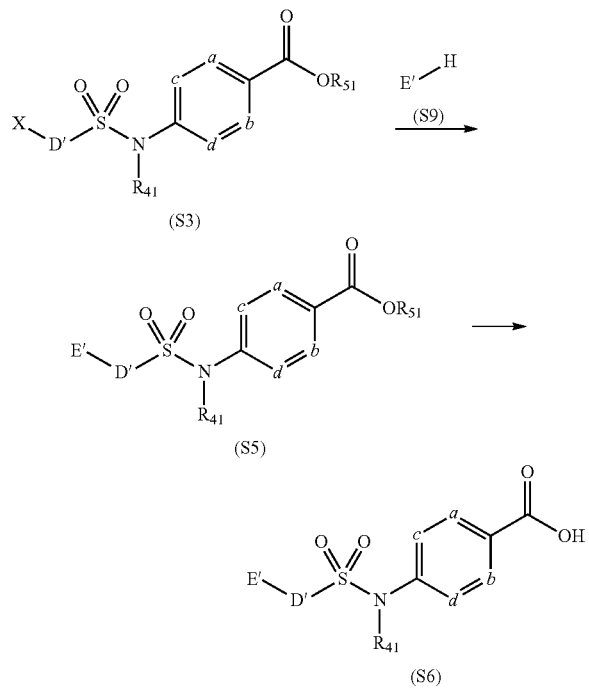

In the formulae, D' represents the above-described substituent represented by D or a substituent which can be easily converted to D by an operation such as deprotection. In the formulae, E' represents the above-described substituent represented by E or a substituent which can be easily converted to E by an operation such as deprotection. Meanwhile, R51 represents an ordinary ester substituent such as a lower alkyl group.

Sulfonamide derivative (S3), which is the intermediate described in <Production Method A>, (in the formula, X represents a halogen atom such as a chlorine, bromine, or iodine atom or a leaving group such as a trifluoromethanesulfonyloxy group) and aromatic heterocycle (S9) can be converted to the corresponding sulfonamide derivative (S5) by a coupling reaction in a solvent which does not affect this reaction such as N-methylpyrrolidone in the presence of a ligand generally used in organic synthesis such as trans-N,N'-dimethylcyclohexane-1,2-diamine and a base such as potassium phosphate by using a metal catalyst such as copper(I) iodide. Subsequently, the obtained sulfonamide derivative (S5) is deprotected by hydrolysis or the like by employing the method described in <Production Method A>. Thus, the target intermediate (S6) having a carboxyl group at its terminal can be produced.

<Production Method D>

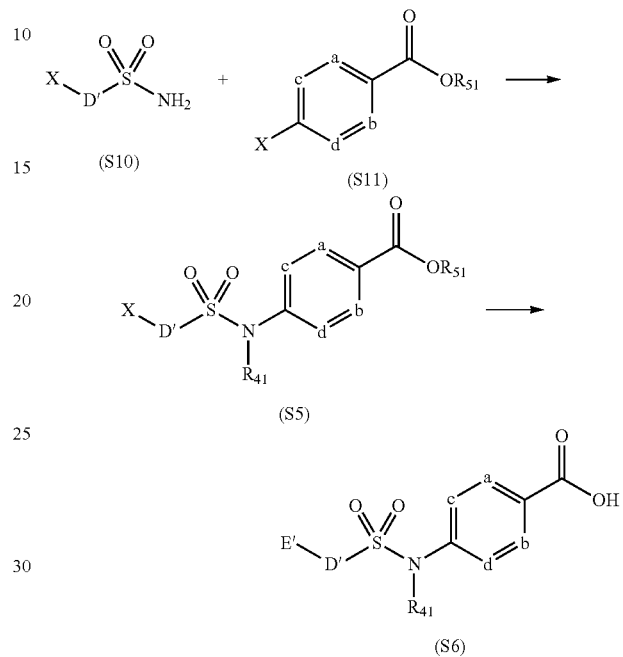

In the formulae, D' represents the above-described substituent represented by D or a substituent which can be easily converted to D by an operation such as deprotection. In the formulae, E' represents the above-described substituent represented by E or a substituent which can be easily converted to E by an operation such as deprotection. Meanwhile, R51 represents an ordinary ester substituent such as a lower alkyl group.

Sulfonamide derivative (S10) (in the formula, X represents a halogen atom such as a chlorine, bromine, or iodine atom or a leaving group such as a trifluoromethanesulfonyloxy group) and halogen derivative (S11) can be converted to the corresponding sulfonamide derivative (S5) by carrying out a coupling reaction in a solvent which does not affect this reaction such as 1,4-dioxane in the presence of a metal catalyst such as tris(dibenzylideneacetone)dipalladium(0), a ligand generally used inorganic synthesis such as XantPHOS, and a base such as cesium carbonate. Subsequently, the obtained sulfonamide derivative (S5) is deprotected by hydrolysis or the like by the method described in <Production Method A>. Thus, the target intermediate (S6) having a carboxyl group at its terminal can be produced.

The intermediate having a carboxyl group at its terminal and being represented by general formula (M-II), in which D is a phenyl group or pyridyl group optionally having a substituent(s) selected from the group consisting of lower alkyl groups and halogen atoms, and E is an aminocarbonyl group optionally substituted with lower alkyl, heterocycle, or heterocycle-substituted lower alkyl can be synthesized by employing the method described below (Production Method E).

27
<Production Method E>

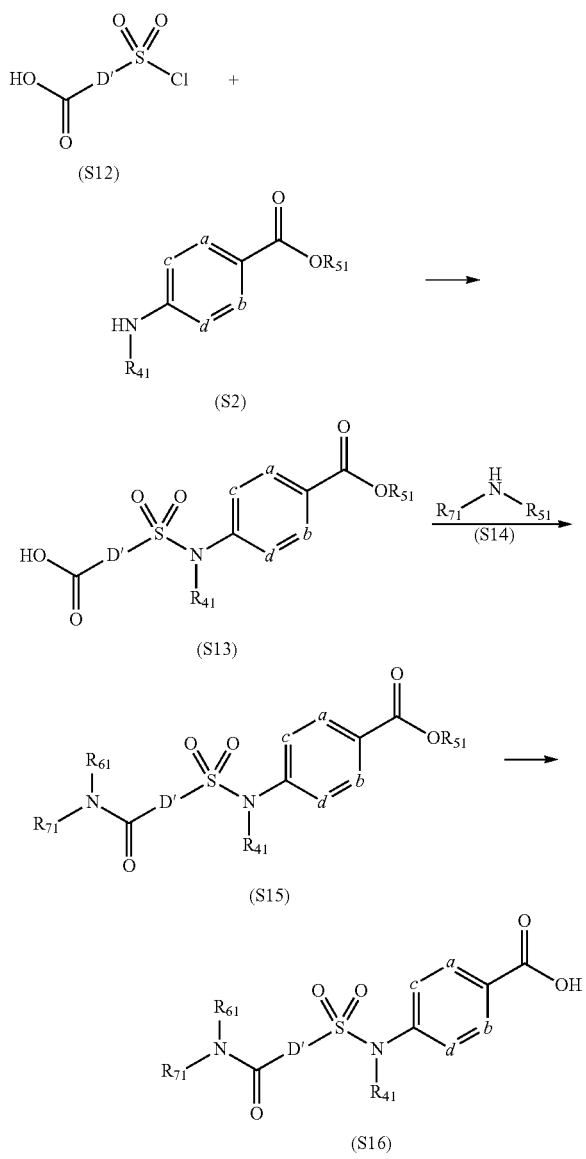

In the formulae, D' represents the above-described substituent represented by D or a substituent which can be easily converted to D by an operation such as deprotection. R51 represents an ordinary ester substituent such as a lower alkyl group. R61 and R71 each represent an ordinary substituent on an amine, such as a lower alkyl group, a heterocyclic group, or a heterocycle-substituted lower alkyl group.

Sulfonyl chloride derivative (S12) having a carboxylic acid or a substituent which can be easily converted to a carboxylic acid and amine derivative (S2) are reacted with each other in a solvent which does not affect this reaction such as methylene chloride in the presence of a base such as pyridine. Thus, the corresponding carboxylic acid derivative (S13) can be synthesized. By amidation between the obtained carboxylic acid derivative (S13) and amine derivative (S14), the corresponding amide derivative (S15) can be synthesized. Subsequently, the obtained amide derivative (S15) is deprotected by hydrolysis or the like by employing the method described in <Production Method A>. Thus, intermediate (S16) having a carboxyl group at its terminal can be produced.

The amidation reaction is known, and examples thereof include (1) a method using a condensation agent, (2) a method using an acid halide, and the like.

The method (1) using a condensation agent is carried out by a reaction between, for example, a carboxylic acid and an amine or a salt thereof in a solvent which does not affect this reaction such as dichloromethane, tetrahydrofuran, 1,4-dioxane, N,N-dimethylformamide, or acetonitrile in the presence or absence of abase such as pyridine, triethylamine, or N-ethyldiisopropylamine and in the presence or absence of a condensation aid such as 1-hydroxybenzotriazole (HOBt), 1-hydroxy-7-azabenzotriazole (HOAt), or N-hydroxysuccinimide (HOSu) by using a condensation agent such as 1-ethyl-3-(3'-dimethylaminopropyl)carbodiimide (WSC), 1,3-dicyclohexylcarbodiimide (DCC), or O-(benzotriazol-1-yl)-N,N,N',N'-tetramethyluronium hexafluorophosphate (HATU).

The method (2) using an acid halide is carried out by a reaction of an acid halide, which is obtained by a reaction of a carboxylic acid with, for example, thionyl chloride, oxalyl chloride, thionyl bromide, or the like in a solvent which does not affect this reaction such as dichloromethane or in the absent of any solvent in the presence or absence of a catalyst such as N,N-dimethylformamide, with an amine or a salt thereof in a solvent which does not affect this reaction such as dichloromethane or tetrahydrofuran in the presence of a base such as pyridine, triethylamine, or N-ethyldiisopropylamine.

In each step, the compound can be synthesized by using generally exchangeable reaction conditions, and the reaction conditions should be selected, as appropriate, according to the types of the raw material compounds and the like. Note that the compounds of the present invention obtained by the above-described methods can be purified by employing a method generally used in organic synthesis, such as extraction, distillation, crystallization, or column chromatography.

The intermediate having an amino group at its terminal and being represented by general formula (M-I), which is the compound of the present invention, can be synthesized by, for example, the method described in Patent Literature 1, a production method (Production Method F) shown below, or the like. Note that, in the following description, signs in the formulae have the same definitions as those in formula (I) described above, unless otherwise noted.

<Production Method F>

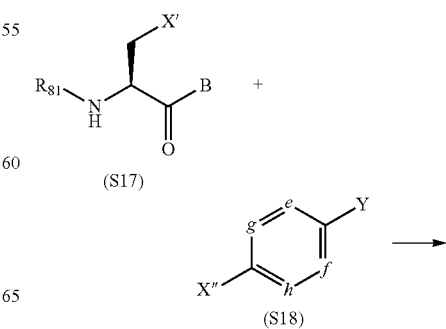

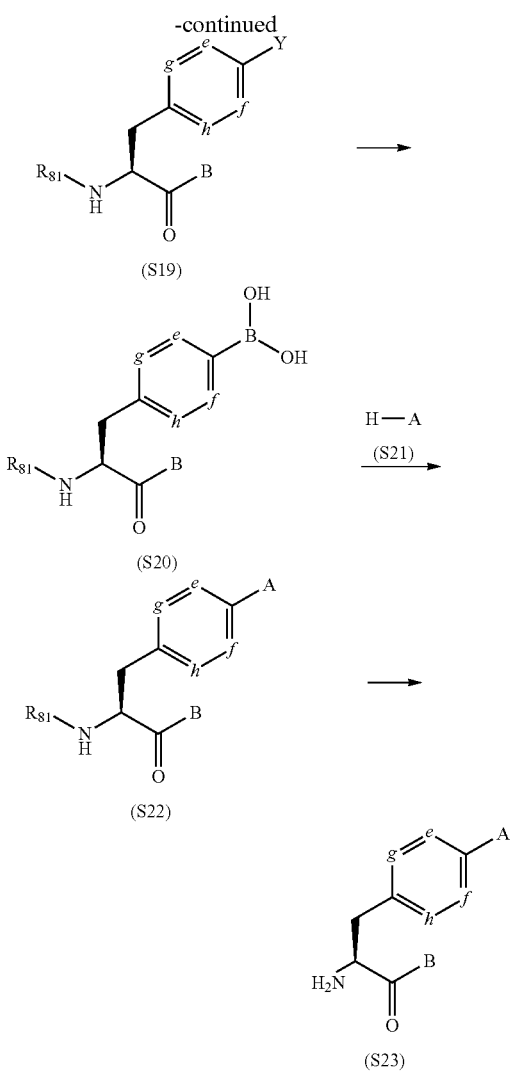

In the formulae, R81 represents an ordinary substituent on an amine such as a tert-butoxycarbonyl group or a benzyloxycarbonyl group, which can be removed by an operation such as deprotection. In the formulae, X', X", and Y each independently represent a halogen atom such as a chlorine, bromine, or iodine atom or a leaving group such as a trifluoromethanesulfonyloxy group.

Amino acid derivative (S17) and halogen derivative (S18) are converted to the corresponding amino acid derivative (S19) by a coupling reaction in a solvent which does not affect this reaction such as N,N-dimethylformamide in the presence of a metal such as zinc by using a metal catalyst such as tetrakis(triphenylphosphine) palladium. Subsequently, the obtained amino acid derivative (S19) is subjected to a coupling reaction with a boronic acid derivative such as bis(2,2,3,3-tetramethyl-2,3-butanedionato)diboron in a solvent which does not affect this reaction such as 1,4-dioxane in the presence of a base such as potassium acetate by using a metal catalyst such as [1,1'-bis(diphenylphosphino) ferrocene]dichloropalladium(II). Thus, the corresponding boronic acid derivative (S20) can be synthesized. The obtained boronic acid derivative (S20) is subjected to a coupling reaction with compound (S21) in a solvent which does not affect this reaction such as dichloromethane in the presence of a base such as triethylamine by using a metal catalyst such as copper(II) acetate. Thus, amino acid derivative (S22) can be produced. The obtained amino acid derivative (S22) is deprotected by acid hydrolysis using, for example, hydrochloric acid or trifluoroacetic acid, a hydrogenation reaction using a catalyst such as palladium carbon in the presence of hydrogen, or the like. Thus, the target intermediate (S23) having an amino group at its terminal can be produced.

The compound represented by general formula (1) or a salt thereof is administered as it is or in the forms of various pharmaceutical compositions. Examples of dosage forms of the pharmaceutical compositions include tablets, powders, pills, granules, capsules, suppositories, liquids, sugar-coated agents, depots, and syrups, which can be produced in a usual manner using ordinary excipients.

For example, the tablets can be obtained by mixing the sulfonamide derivative, which is an active ingredient of the present invention, with any of known auxiliary substances including inactive diluents such as lactose, calcium carbonate, and calcium phosphate; binders such as gum arabic, corn starch, and gelatin; bulking agents such as alginic acid, corn starch, and pregelatinized starch; sweeteners such as sucrose, lactose, or saccharin; flavoring agents such as peppermint, Gaultheria adenothrix oil, and cherry; lubricating and wetting agents such as magnesium stearate, talc, and carboxymethyl cellulose; vehicles for soft gelatin capsules or suppositories such as fats, waxes, semi-solid or liquid polyols, natural oils, and hydrogenated oils; and vehicles for solutions such as water, alcohol, glycerol, polyol, sucrose, inverted sugar syrup, glucose, and vegetable oil.

The inhibitor comprising, as an active ingredient, the compound represented by general formula (1) or a salt thereof can be used as an agent for treating or preventing any one of inflammatory diseases, rheumatoid arthritis, inflammatory bowel disease, systemic lupus erythematosus, multiple sclerosis, Sjögren's syndrome, asthma, psoriasis, allergy, diabetes mellitus, cardiovascular diseases, arteriosclerosis, restenosis, tumor growth, tumor metastasis, and transplant rejection, in which an α4 integrin-dependent adhesion process is associated with a pathological condition.

The administered amount of the compound represented by general formula (1) or a salt thereof used for the above-described purpose is determined according to the target therapeutic effect, the administration method, the treating period, the age, the body weight, and the like. The administered amount varies between oral routes and parenteral routes, and, in general, it is preferable that the amount administered to a human adult be 1 μg to 5 g per day for oral administration, and 0.01 μg to 1 g per day for parenteral administration.

EXAMPLES

The present invention will be described in detail with reference to the following Examples, which are preferred embodiments of the present invention. The present invention is not limited to these Examples.

Note that Examples 1 to 5, 97 to 103, and 186 to 188 show Synthesis Examples of intermediates represented by general formula (M-I) and having an amino group at their terminals, and Examples 6 to 38, 104 to 136, 189 to 210, and 240 to 245 show Synthesis Examples of intermediates represented by general formula (M-II) and having a carboxyl group at their terminals. Examples 39 to 96, 137 to 185, 211 to 239, and 246 to 257 are Synthesis Examples of compounds of the present invention. Of these, B-1 to B-5, B-7, B-9, B-10, B-12 to B-15, B-17 to B-20, B-22 to B-24, B-26 to B-32, and B-36 to B-40 in Examples 39 to 78, B-41 to B-54, B-56 to B-57, and B-59 to B-88 in Examples 79 to 96 and Examples 137 to 185, B-90 to B-113 and B-115 to B-118 in Examples 211 to 239, and B-119 to B-130 in Examples 246 to 257 show Synthesis Examples of prodrugs.

Example 1

Synthesis of M-1

(Step 1) Methyl N-(tert-Butoxycarbonyl)-4-(2,4-dioxo-1,4-dihydropyrido[3,4-d]pyrimidin-3(2H)-yl)-L-phenylalaninate

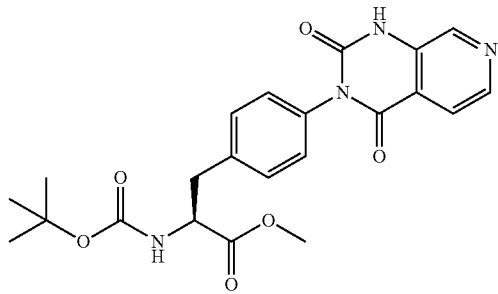 [SMILES: COC(=O)[C@H](Cc1ccc(-n2c(=O)[nH]c3cnccc3c2=O)cc1)NC(=O)OC(C)(C)C]

Methyl 3-aminoisonicotinate (10.0 g, 65.0 mmol) was dissolved in methylene chloride (100 ml), and diisopropylethylamine (17.0 g, 130 mmol) and triphosgene (6.40 g, 22.0 mmol) were added thereto, followed by stirring at 0° C. for 3 hours. To the solution, methyl 4-amino-N-(tert-butoxycarbonyl)-L-phenylalaninate (19.0 g, 65.0 mmol) was added, and the mixture was stirred for 12 hours, while the temperature was gradually raised from 0° C. to room temperature. After the reaction solution was concentrated under reduced pressure, ethyl acetate was added, and the mixture was washed with water and saturated aqueous sodium chloride and dried over anhydrous sodium sulfate. After the solvent was removed under reduced pressure, purification was conducted by silica gel column chromatography (petroleum ether/ethyl acetate=1:1). The obtained compound was dissolved in N,N-dimethylformamide (200 ml), and an aqueous solution of potassium carbonate (1.20 g, 8.70 mmol) was added, followed by stirring at room temperature for 3 hours. After the reaction solution was concentrated under reduced pressure, ethyl acetate was added, and the mixture was washed with water and saturated aqueous sodium chloride and dried over anhydrous sodium sulfate. After the solvent was removed under reduced pressure, purification was conducted by silica gel column chromatography (petroleum ether/ethyl acetate=1:1) to obtain the title compound (12.0 g, 43% over two steps).

1H NMR (CDCl3, 400 MHz): δ 10.07 (1H, s), 8.54 (d, J=5.2 Hz, 1H), 8.14 (s, 1H), 7.92 (d, J=8.8 Hz, 1H), 7.35 (d, J=7.6 Hz, 2H), 7.23 (d, J=8.0 Hz, 2H), 6.12-6.10 (m, 1H), 4.73-4.69 (m, 1H), 3.71 (s, 3H), 3.22-3.21 (m 2H), 1.44 (s, 9H).

(Step 2) Methyl N-(tert-Butoxycarbonyl)-4-(1-methyl-2,4-dioxo-1,4-dihydropyrido[3,4-d]pyrimidin-3(2H)-yl)-L-phenylalaninate

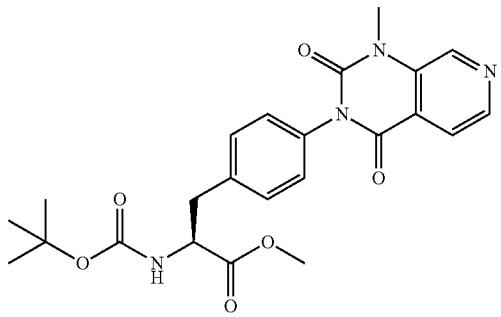 [SMILES: COC(=O)[C@H](Cc1ccc(-n2c(=O)c3ccncc3n(C)c2=O)cc1)NC(=O)OC(C)(C)C]

Methyl N-(tert-butoxycarbonyl)-4-(2,4-dioxo-1,4-dihydropyrido[3,4-d]pyrimidin-3(2H)-yl)-L-phenylalaninate (8.00 g, 18.5 mmol) was dissolved in N,N-dimethylformamide (100 ml), and potassium carbonate (5.10 g, 37.0 mmol) and methyl iodide (1.9 ml, 37 mmol) were added thereto, followed by stirring at room temperature for 3 hours. The suspension was filtered, and the filtrate was concentrated under reduced pressure. Then, purification was conducted by silica gel column chromatography (petroleum ether/ethyl acetate=1:1) to obtain the title compound (3.5 g, 43%).

1H NMR (CDCl3, 400 MHz): δ 8.81 (1H, s), 8.60 (d, J=4.8 Hz, 1H), 8.03 (d, J=4.8 Hz, 1H), 7.30 (d, J=8.0 Hz, 2H), 7.19 (d, J=8.4 Hz, 2H), 5.05-5.03 (m, 1H), 4.65-4.63 (m, 1H), 3.73 (s, 3H), 3.71 (s, 3H), 3.18-3.16 (m 2H), 1.44 (s, 9H).; MS (ESI) m/z 355 (M+H-Boc)+

(Step 3) Methyl 4-(1-Methyl-2,4-dioxo-1,4-dihydropyrido[3,4-d]pyrimidin-3(2H)-yl)-L-phenylalaninate (M-1)

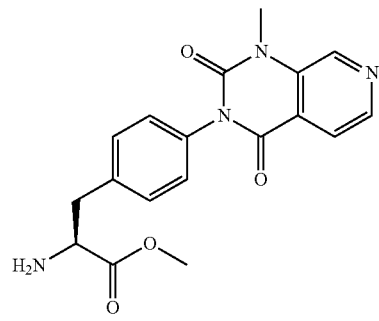

Methyl N-(tert-butoxycarbonyl)-4-(1-methyl-2,4-dioxo-1,4-dihydropyrido[3,4-d]pyrimidin-3(2H)-yl)-L-phenylalaninate (3.5 g, 7.7 mmol) was dissolved in a 4 N hydrogen chloride/ethyl acetate solution (40 ml), followed by stirring at room temperature for 1 hour. After the reaction liquid was filtered, the obtained solid was dried under reduced pressure to obtain the title compound (3.0 g, 94%).

1H NMR (CD3OD, 400 MHz): δ 9.28 (s, 1H), 8.76 (d, J=0.8 Hz, 1H), 8.56 (d, J=1.6 Hz, 1H), 7.51 (d, J=8.4 Hz, 2H), 7.41 (d, J=8.4 Hz, 2H), 4.48-4.44 (m, 1H), 3.90 (s, 3H), 3.76 (s, 3H), 3.49-3.44 (m 1H), 3.30-3.24 (m, 1H).; MS (ESI) m/z 355 (M+H)+

Example 2

Synthesis of M-2

(Step 1) Methyl N-(tert-Butoxycarbonyl)-O-[(trifluoromethyl)sulfonyl]-L-tyrosinate

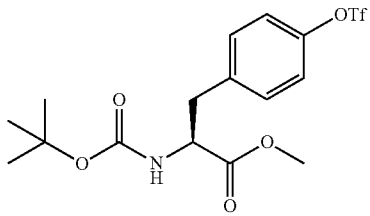 [SMILES: COC(=O)[C@H](Cc1ccc(OS(=O)(=O)C(F)(F)F)cc1)NC(=O)OC(C)(C)C]

Methyl N-(tert-butoxycarbonyl)-L-tyrosinate (60.0 g, 203 mmol) was dissolved in tetrahydrofuran, and N-phenyl bis(trifluoromethanesulfonamide) (79.8 g, 224 mmol) and diisopropylethylamine (90.0 g, 714 mmol) were added thereto, followed by stirring at room temperature for 12 hours. After the reaction solution was concentrated under reduced pressure, the obtained residue was purified by silica gel column chromatography (petroleum ether/ethyl acetate=3:1) to obtain the title compound (74 g, 85%).

1H NMR (CDCl3, 400 MHz): δ 7.25-7.19 (m, 4H), 5.08-5.06 (m, 1H), 4.61-4.59 (m, 1H), 3.71 (3H, s), 3.19-3.15 (m, 1H), 3.06-3.01 (m, 1H), 1.41 (s, 9H).; MS (ESI) m/z 328 (M+H-Boc)$^+$ (Step 2) Methyl N-(tert-Butoxycarbonyl)-4-(4,4,5,5-tetramethyl-1,3,2-dioxaborolan-2-yl)-L-phenylalaninate

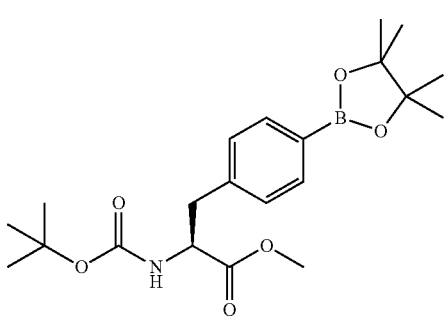 [SMILES: COC(=O)[C@H](Cc1ccc(B2OC(C)(C)C(C)(C)O2)cc1)NC(=O)OC(C)(C)C]

Methyl N-(tert-butoxycarbonyl)-O-[(trifluoromethyl)sulfonyl]-L-tyrosinate (74.0 g, 173 mmol) and bis(pinacolato)diborane (66.0 g, 260 mmol) were dissolved in N,N-dimethylformamide (1 L). To the solution, [1,1'-bis(diphenylphosphino) ferrocene]dichloropalladium(II) (13.6 g, 18.6 mmol) and potassium acetate (60.0 g, 612 mmol) were added, followed by stirring at 95° C. for 12 hours. After cooling to room temperature, the reaction solution was filtered through Celite, and the filtrate was concentrated under reduced pressure. The obtained residue was purified by silica gel column chromatography (petroleum ether/ethyl acetate=4:1) to obtain the title compound (45.0 g, 65%).

1H NMR (CDCl3, 400 MHz): δ 7.73 (d, J=8 Hz, 2H), 7.12 (d, J=8 Hz, 2H), 4.59-4.57 (m, 1H), 3.70 (3H, s), 3.11-3.06 (m, 2H), 1.41 (s, 9H), 1.13 (s, 12H).; MS (ESI) m/z 306 (M+H-Boc)$^+$ (Step 3) Methyl N-(tert-Butoxycarbonyl)-4-(dihydroxyboryl)-L-phenylalaninate

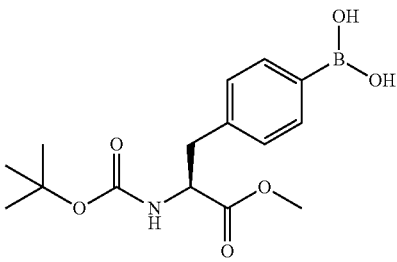 [SMILES: COC(=O)[C@H](Cc1ccc(B(O)O)cc1)NC(=O)OC(C)(C)C]

Methyl N-(tert-butoxycarbonyl)-4-(4,4,5,5-tetramethyl-1,3,2-dioxaborolan-2-yl)-L-phenylalaninate (67.0 g, 165 mmol) was dissolved in acetone (700 ml). To the solution, sodium periodate (71.0 g, 330 mmol), ammonium acetate (25.0 g, 330 mmol), and water (300 ml) were added, followed by stirring at room temperature for 55 hours. After the reaction solution was filtered, the filtrate was concentrated under reduced pressure, and ethyl acetate was added. The mixture was washed with water and saturated aqueous sodium chloride, and dried over anhydrous sodium sulfate. The solvent was removed under reduced pressure, and the precipitated solid was washed with a mixture solvent of petroleum ether/ethyl acetate (1:10) and dried to obtain the title compound (29 g, 55%).

1H NMR (CDCl3, 400 MHz): δ: 7.71-7.56 (m, 2H), 7.25-7.16 (m, 2H), 4.39-4.37 (m, 1H), 3.71 (s, 3H), 3.14-3.10 (m, 1H), 2.96-2.90 (m, 1H), 1.40 (s, 9H).; MS (ESI) m/z 224 (M+H-Boc)$^+$ (Step 4) Methyl N-(tert-Butoxycarbonyl)-4-(3-methyl-2,6-dioxo-3,6-dihydropyrimidin-1(2H)-yl)-L-phenylalaninate

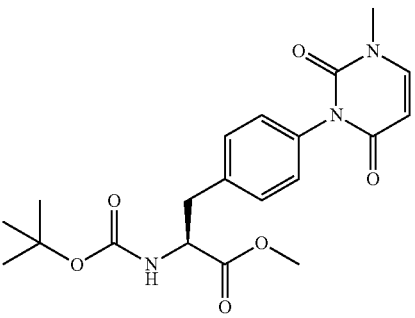

Pyrimidine-2,4(1H,3H)-dione (30.0 g, 268 mmol), 1,1,1,3,3,3-hexamethyldisilazane (550 ml), and trimethylchlorosilane (55 ml) were stirred at 130° C. for 5 hours. After the reaction solution was cooled to 60° C., methyl iodide (200 ml) was added, followed by stirring at 60° C. for 30 hours. The reaction solution was cooled to 0° C., and acetic acid (500 ml) was slowly added. Then, the solvent was removed under reduced pressure. To the residue, 2-propanol (1600 ml) was added, followed by vigorous stirring. Then, the obtained solid was filtered, and washed with water (500 ml) to obtain a white solid (22 g, 67%). Methyl N-(tert-butoxycarbonyl)-4-(dihydroxyboryl)-L-phenylalaninate (49.0 g, 152 mmol) was dissolved in methylene chloride (500 ml), and then the obtained white solid (22.0 g, 175 mmol) copper(II) acetate (18.0 g, 98.9 mmol), and triethylamine (40 ml) were added thereto, followed by stirring at room temperature for 60 hours. After the reaction solution was concentrated under reduced pressure, the obtained residue was purified by silica gel column chromatography (petroleum ether/ethyl acetate=1:1) to obtain the title compound (6.0 g, 10%) as white crystals.

1H NMR (d-DMSO, 400 MHz): δ 7.77 (d, J=8.0 Hz, 1H), 7.38 (d, J=8.0 Hz, 1H), 7.32 (d, J=8.8 Hz, 2H), 7.11 (d, J=8.4 Hz, 2H), 5.76 (d, J=8.0 Hz, 1H), 4.22-4.19 (m, 1H), 3.60 (s, 3H), 3.32 (s, 3H), 3.03-3.02 (m, 1H), 2.94-2.90 (m, 1H), 1.36 (s, 9H).; MS (ESI) m/z 421 (M+H+NH3)$^+$ (Step 5) Methyl 4-(3-Methyl-2,6-dioxo-3,6-dihydropyrimidin-1(2H)-yl)-L-phenylalaninate ((M-2)

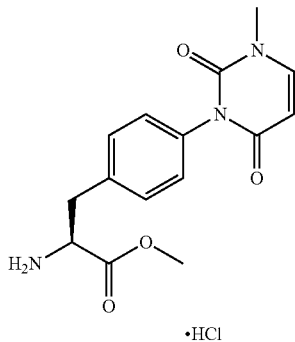 [SMILES: COC(=O)[C@@H](N)Cc1ccc(-n2c(=O)ccn(C)c2=O)cc1 ; Cl]

Methyl N-(tert-butoxycarbonyl)-4-(3-methyl-2,6-dioxo-3,6-dihydropyrimidin-1(2H)-yl)-L-phenylalaninate (6.00 g, 15.0 mmol) was dissolved in a 3 N hydrogen chloride/ethyl acetate solution (100 ml), followed by stirring at room temperature for 1 hour. After the solvent was removed under reduced pressure, ethyl acetate (50 ml) was added, followed by stirring at room temperature for further 0.5 hours. The suspension was filtered, and the obtained solid was dried to obtain the title compound (4.0 g, 80%) as a white solid.

1H NMR (CD3OD, 500 MHz): δ 7.72 (d, J=8 Hz, 1H), 7.45 (d, J=8 Hz, 2H), 7.29 (d, J=8 Hz, 2H), 5.85 (d, J=8 Hz, 1H), 4.44-4.41 (m, 1H), 3.91 (s, 3H), 3.49-3.45 (m, 4H), 3.23-3.17 (m, 1H).; MS (ESI) m/z 304 (M+H)$^+$

Example 3

Synthesis of M-3

(Step 1) 2-Chloro-5-nitroisonicotinic Acid

2-Chloro-4-methyl-5-nitropyridine (20.5 g, 119 mmol) was dissolved in concentrated sulfuric acid (200 ml), and chromium trioxide (40.0 g, 400 mmol) was added thereto, followed by stirring at 0° C. for 1 hour. Then, the temperature was gradually raised from 0° C. to room temperature, followed by stirring for 12 hours. The reaction solution was poured into ice-water (2000 ml), and the temperature was raised from 0° C. to room temperature. The precipitated solid was filtered and dried under reduced pressure to obtain the title compound (18 g, 750).

1H NMR (CD3OD, 400 MHz): δ 10.8 (1H, br, s), 9.13 (1H, s), 7.70 (1H, s).

(Step 2) Methyl 5-Amino-2-methoxyisonicotinate

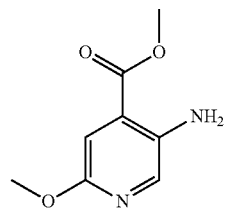

Potassium hydroxide (90 g) was dissolved in diethyl ether (300 ml) and water (30 ml), and N-methyl-N-nitrosourea (30.9 g, 300 mmol) was slowly added thereto. After stirring at 0° C. for 20 minutes, the organic layer (ether solution) was separated. 2-Chloro-5-nitroisonicotinic acid (20.2 g, 100 mmol) was dissolved in ethyl acetate (100 ml), and the mixture was cooled to 0° C. Then, the above-described ether solution was added to this mixture, followed by stirring for 1 hour. The solvent was removed under reduced pressure, and the obtained residue was purified by silica gel column chromatography (petroleum ether/ethyl acetate=6:1 to 2:1). The obtained compound (10.8 g, 50.0 mmol) was dissolved in methanol (100 ml), and sodium methoxide (8.10 g, 150 mmol) was added thereto, followed by stirring at 65° C. for 4 hours. After cooling to room temperature, the reaction solution was concentrated under reduced pressure, and the obtained residue was purified by silica gel column chromatography (petroleum ether/ethyl acetate=8:1 to 4:1). The obtained compound (8.0 g, 37 mmol) was dissolved in methanol (100 ml), and iron (10.6 g, 175 mmol) and a saturated aqueous ammonium chloride solution (50 ml) were added thereto, followed by stirring at 65° C. for 2 hours. After cooling to room temperature, the pH was adjusted to 7 or higher by adding a saturated aqueous sodium hydrogen carbonate solution. Then, ethyl acetate (100 ml×3) was added, and the organic layer was washed with water and saturated aqueous sodium chloride and dried over anhydrous sodium sulfate. After the solvent was removed under reduced pressure, the residue was purified by silica gel column chromatography (petroleum ether/ethyl acetate=4:1 to 1:1) to obtain the title compound (5.8 g, 58% over three steps).

1H NMR (CDCl3, 400 MHz): δ 7.80 (s, 1H), 7.15 (s, 1H), 5.10 (s, 2H), 3.90 (s, 3H), 3.84 (s, 3H).

(Step 3) Methyl N-(tert-Butoxycarbonyl)-4-[({[6-methoxy-4-(methoxycarbonyl) pyridin-3-yl]amino}carbonyl)amino]-L-phenylalaninate

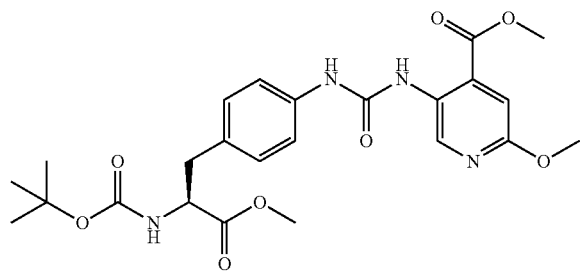 [SMILES: COC(=O)c1cc(OC)ncc1NC(=O)Nc1ccc(C[C@H](NC(=O)OC(C)(C)C)C(=O)OC)cc1]

Methyl 5-amino-2-methoxyisonicotinate (5.0 g, 27 mmol) was dissolved in methylene chloride (100 ml), and a solution of triphosgene (2.6 g, 9.0 mmol) in methylene chloride and diisopropylethylamine (10.0 g, 82.0 mmol) were added thereto, followed by stirring at 0° C. for 3 hours. Then, methyl 4-amino-N-(tert-butoxycarbonyl)-L-phenylalaninate (7.9 g, 27 mmol) was added thereto, followed by stirring at room temperature for 12 hours. After the solvent was removed under reduced pressure, ethyl acetate was added, and the mixture was washed with a saturated aqueous sodium hydrogen carbonate solution, water, and saturated aqueous sodium chloride and dried over anhydrous sodium sulfate. After the solvent was removed under reduced pressure, the residue was purified by silica gel column chromatography (petroleum ether/ethyl acetate=1:1) to obtain the title compound.
MS (ESI) m/z 503 (M+H)$^+$ (Step 4) Methyl 4-(6-Methoxy-1-methyl-2,4-dioxo-1,4-dihydropyrido[3,4-d]pyrimidin-3(2H)-yl)-L-phenylalaninate (M-3)

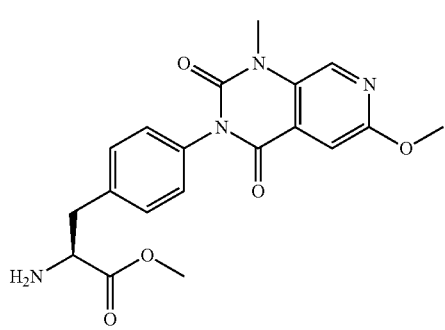

·2 HCl

Methyl N-(tert-butoxycarbonyl)-4-[({[6-methoxy-4-(methoxycarbonyl) pyridin-3-yl]amino}carbonyl)amino]-L-phenylalaninate was dissolved in N,N-dimethylformamide (20 ml), and an aqueous potassium carbonate solution (0.75 g, 5.3 mmol) was added thereto, followed by stirring at room temperature for 3 hours. To this reaction solution, methyl 4-methylbenzenesulfonate (5.5 g, 30 mmol) and potassium carbonate (7.5 g, 54 mmol) were added, followed by stirring at room temperature for 12 hours. The reaction solution was diluted with water (200 ml), followed by extraction with ethyl acetate. The extraction liquids were combined and dried over anhydrous sodium sulfate, and then the solvent was removed. The obtained residue was purified by silica gel column chromatography (petroleum ether/ethyl acetate=1:1).

The obtained compound (6.0 g, 12 mmol) was dissolved in a 3 N hydrogen chloride/ethyl acetate solution (30 ml), followed by stirring at room temperature for 1 hour. The precipitated solid was filtered and dried under reduced pressure to obtain the title compound (4.6 g, 45% over three steps).
1H NMR (CD3OD, 400 MHz): δ 8.50 (s, 1H), 7.48 (d, J=8.4 Hz, 2H), 7.42 (s, 1H) 7.36 (d, J=8.0 Hz, 2H), 4.69-4.35 (m, 1H), 4.01 (s, 3H), 3.91 (s, 3H), 3.67 (s, 3H), 3.49-3.44 (m 1H), 3.26-3.22 (m, 1H).; MS (ESI) m/z 385 (M+H)$^+$ Example 4

Synthesis of M-4

(Step 1) Methyl 2-[Bis(tert-butoxycarbonyl)amino]-5-hydroxybenzoate

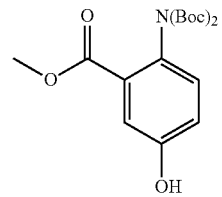

2-Amino-5-hydroxybenzoic acid (10.0 g, 65.3 mmol) was dissolved in methanol (200 ml). To the solution, concentrated sulfuric acid (10 ml) was slowly added dropwise, followed by stirring at 65° C. for 48 hours. After cooling to room temperature, the reaction solution was neutralized with sodium hydrogen carbonate, and concentrated under reduced pressure. Water (150 ml) was added to the obtained residue, and then the pH was adjusted to 7 or higher by adding sodium hydrogen carbonate. The precipitated solid was filtered, washed with water, and then dried under reduced pressure.

A portion (6.0 g, 36 mmol) of the obtained solid was dissolved in methylene chloride (300 ml), and di-tert-butyl-dicarbonate (18.8 g, 86.0 mmol) and N,N-dimethyl-4-aminopyridine (1.1 g, 8.7 mmol) were added thereto, followed by stirring at room temperature for 12 hours. After the reaction solution was concentrated under reduced pressure, the obtained residue was purified by silica gel column chromatography (petroleum ether/ethyl acetate=10:1 to 4:1) to obtain the title compound (8.1 g, 54% over two steps).
MS (ESI) m/z 368 (M+H)$^+$ (Step 2) Methyl 2-Amino-5-methoxybenzoate

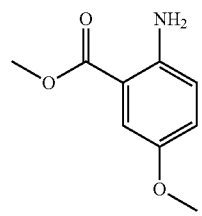

Methyl 2-[bis(tert-butoxycarbonyl)amino]-5-hydroxybenzoate (3.67 g, 10.0 mmol) was dissolved in tetrahydrofuran (50 ml), and 60% sodium hydride (667 mg, 27.8 mmol) and methyl iodide (2.9 ml, 46 mmol) were added thereto, followed by stirring at room temperature for 1 hour. Then, the temperature was raised to 65° C., followed by stirring for 3 hours. The reaction solution was cooled to room temperature, and diluted with an aqueous ammonium chloride solution, followed by extraction with ethyl acetate. The extraction liquids were combined and dried over anhydrous sodium sulfate, and then the solvent was removed. The obtained residue was purified by silica gel column chromatography (petroleum ether/ethyl acetate=6:1 to 2:1). The obtained compound (9.0 g, 23 mmol) was cooled to 0° C., and then a 3 N hydrogen chloride/ethyl acetate solution (100 ml) was added thereto, followed by stirring at room temperature for 1 hour. The reaction solution was concentrated under reduced pressure, and the obtained residue was diluted with a saturated aqueous sodium hydrogen carbonate solution, followed by extraction with ethyl acetate. The extraction liquids were combined, and dried over anhydrous sodium sulfate. Then, the solvent was removed to obtain the title compound (3.8 g, 70% over two steps).

MS (ESI) m/z 182 (M+H)$^+$ (Step 3) Methyl 4-(6-Methoxy-1-methyl-2,4-dioxo-1,4-dihydroquinazolin-3(2H)-yl)-L-phenylalaninate (M-4)

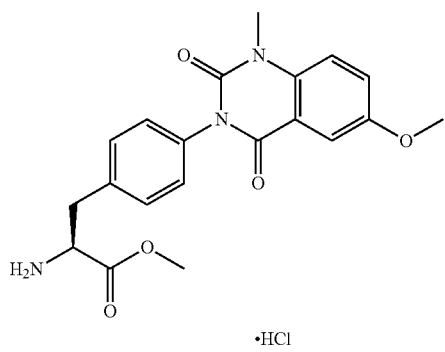 [SMILES: COC(=O)[C@@H](N)Cc1ccc(-n2c(=O)c3cc(OC)ccc3n(C)c2=O)cc1 ; Cl]

·HCl

Carbonyldiimidazole (5.1 g, 32 mmol) was dissolved in N,N-dimethylformamide (100 ml), and methyl 2-amino-5-methoxybenzoate (5.4 g, 30 mmol) and methyl 4-amino-N-(tert-butoxycarbonyl)-L-phenylalaninate (8.8 g, 30 mmol) were added thereto, followed by stirring at 50° C. for 2 hours. The reaction solution was diluted with ethyl acetate, then washed with a saturated aqueous sodium hydrogen carbonate solution and saturated aqueous sodium chloride, and dried over anhydrous sodium sulfate. The solvent was removed under reduced pressure, and the obtained residue was purified by silica gel column chromatography (petroleum ether/ethyl acetate=2:1 to 1:1). The obtained compound was dissolved in N,N-dimethylformamide (50 ml), and an aqueous solution of potassium carbonate (1.0 g, 7.2 mmol) was added thereto, followed by stirring at room temperature for 3 hours. To this reaction solution, methyl 4-methylbenzenesulfonate (7.7 g, 42 mmol) and potassium carbonate (7.5 g, 54 mmol) were added, followed by stirring at room temperature for 12 hours. The reaction solution was diluted with water (50 ml), followed by extraction with ethyl acetate. The extraction liquids were combined, and dried over anhydrous sodium sulfate, and then the solvent was removed. The obtained residue was purified by silica gel column chromatography (petroleum ether/ethyl acetate=1:1). Further, the obtained compound (9.6 g, 20 mmol) was dissolved in ethyl acetate, and a 3 N hydrogen chloride/ethyl acetate solution (50 ml) was added thereto, followed by stirring at room temperature for 1 hour. The precipitated solid was filtered, and dried under reduced pressure to obtain the title compound (7.0 g, 46% over four steps).

$^1$H NMR (CD$_3$OD, 400 MHz): δ 7.65 (d, J=2.8 Hz, 1H), 7.52-7.45 (m, 4H), 7.36 (d, J=8.4 Hz, 2H), 4.47-4.43 (m, 1H), 3.92 (s, 3H), 3.90 (s, 3H), 3.65 (s, 3H), 3.51-3.47 (m, 1H), 3.24-3.21 (m, 1H).; MS (ESI) m/z 384 (M+H)$^+$

Example 5

Synthesis of M-5

(Step 1)
1-Methyl-4-nitro-1H-imidazole-5-carboxylic Acid

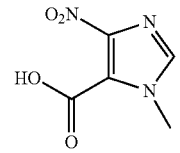

5-Chloro-1-methyl-4-nitro-1H-imidazole (3.21 g, 20.0 mmol) was suspended in ethanol (50 ml), and then potassium cyanide (3.91 g, 60.0 mmol) and potassium iodide (10.0 g, 60.0 mmol) were added thereto, followed by stirring at 70° C. for 16 hours. After cooling to room temperature, diethyl ether was added to the reaction solution, which was then washed with water and saturated aqueous sodium chloride, and then dried over anhydrous sodium sulfate. After the solvent was concentrated under reduced pressure, water (20 ml), concentrated sulfuric acid (20 ml), and sodium nitrite (1.38 g, 20.0 mmol) were added to the obtained residue, followed by stirring at 80° C. for 16 hours. After cooling to room temperature, water was added, and the precipitated solid was filtered to obtain the title compound (1.36 g, 45%).

MS (ESI) m/z 172 (M+H)$^+$ (Step 2) Isopropyl N-(tert-Butoxycarbonyl)-4-{[(1-methyl-4-nitro-1H-imidazol-5-yl)carbonyl]amino}-L-phenylalaninate

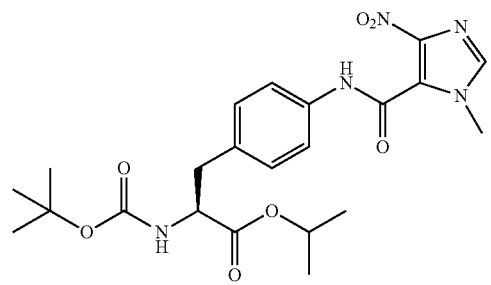 [SMILES: CC(C)OC(=O)[C@H](Cc1ccc(NC(=O)c2c([N+](=O)[O-])ncn2C)cc1)NC(=O)OC(C)(C)C]

1-Methyl-4-nitro-1H-imidazole-5-carboxylic acid (1.71 g, 10.0 mmol) was suspended in thionyl chloride (20 ml), followed by stirring at 60° C. for 6 hours. After concentration under reduced pressure, dichloromethane (20 ml), 3-(4-amino-phenyl)-2-tert-butoxycarbonylaminopropanoic acid isopropyl ester (3.22 g, 10.0 mmol), and triethylamine (2.8 ml, 20 mmol) were added to the obtained residue, followed by stirring at room temperature for 2 hours. After the solvent was removed under reduced pressure, ethyl acetate was added to the reaction solution, which was then washed with an aqueous sodium hydrogen carbonate solution, water, and saturated aqueous sodium chloride, and dried over anhydrous sodium sulfate. The solvent was removed by distillation under reduced pressure, and purification was conducted by reversed-phase HPLC ($H_2O$ containing 0.1% TFA/$CH_3CN$ system) to obtain the title compound (2.46 g, 52%).
MS (ESI) m/z 476 (M+H)$^+$ (Step 3) Isopropyl 4-(3,7-Dimethyl-2,6-dioxo-2,3,6,7-tetrahydro-1H-purin-1-yl)-L-phenylalaninate (M-5)

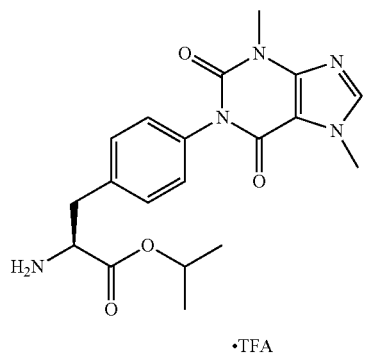 [SMILES: CC(C)OC(=O)[C@@H](N)Cc1ccc(-n2c(=O)c3c(ncn3C)n(C)c2=O)cc1]

·TFA

Isopropyl N-(tert-butoxycarbonyl)-4-{[(1-methyl-4-nitro-1H-imidazol-5-yl)carbonyl]amino}-L-phenylalaninate (2.38 g, 5.00 mmol) was dissolved in ethanol (100 mL), and reduction reaction of the nitro group was conducted in a hydrogenation reactor H-Cube (10% Pd/C catalyst, 40° C., hydrogen: 2.0 atm, flow rate: 1.0 ml/min). The solution was concentrated under reduced pressure, and then acetonitrile (20 mL) and carbonyldiimidazole (1.62 g, 10.0 mmol) were added thereto, followed by stirring at 60° C. for 6 hours. After the solvent was removed under reduced pressure, ethyl acetate was added to the reaction solution, which was then washed with an aqueous sodium hydrogen carbonate solution, water, and saturated aqueous sodium chloride, and dried over anhydrous sodium sulfate. After the solvent was concentrated under reduced pressure, dimethylformamide (20 mL), methyl iodide (1.42 g, 10.0 mmol), and potassium carbonate (2.07 g, 15.0 mmol) were added to the obtained residue, followed by stirring at room temperature for 2 hours. After the solvent was removed under reduced pressure, ethyl acetate was added to the reaction solution, which was then washed with an aqueous sodium hydrogen carbonate solution, water, and saturated aqueous sodium chloride, and dried over anhydrous sodium sulfate. After the solvent was concentrated under reduced pressure, TFA (5.0 mL) was added to the obtained residue, followed by stirring at room temperature for 1 hour. After removal of TFA under reduced pressure, purification was conducted by reversed-phase HPLC ($H_2O$ containing 0.1% TFA/$CH_3CN$ system) to obtain the TFA salt (1.20 g, 48%) of the title compound.
MS (ESI) m/z 386 (M+H)$^+$ Example 6

Synthesis of M-6

(Step 1) Pyridine-4-sulfonamide

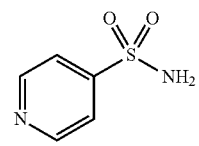

4-Pyridinethiol (16.7 g, 15.0 mmol) was dissolved in concentrated hydrochloric acid (110 ml) and water (30 ml). After cooling to 0° C., chlorine gas generated by adding concentrated hydrochloric acid (200 ml) to manganese dioxide (300 g) at room temperature was bubbled into the reaction liquid for 1 hour. After the reaction liquid was poured into ice-water (75 g), ammonia (600 mg) was added thereto, followed by stirring at room temperature for 12 hours. The reaction liquid was stored at 0° C. for 12 hours, and the obtained solid was filtered and dried under reduced pressure to obtain the title compound (10.6 g, 45%) as a yellow solid.
$^1$H NMR (d-DMSO, 400 MHz,) δ 8.85-8.38 (m, 2H), 7.78-7.77 (m, 4H).;
MS (ESI) m/z 159 (M+H)$^+$ (Step 2) 2-Fluoro-4-[(pyridin-4-yl-sulfonyl)amino]benzoic Acid (M-6)

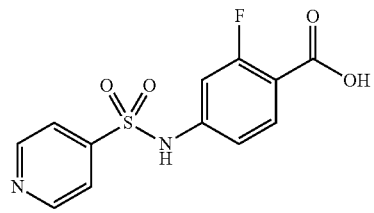 [SMILES: O=C(O)c1ccc(NS(=O)(=O)c2ccncc2)cc1F]

Pyridine-4-sulfonamide (14.0 g, 90.0 mmol) and methyl 4-bromo-2-fluorobenzoate (14.0 g, 60.0 mmol) were suspended in 1,4-dioxane (300 ml). To the solution, tris(dibenzylideneacetone)dipalladium(0) (2.84 g, 3.00 mmol), Xant-PHOS (3.42 g, 3.00 mmol), and cesium carbonate (38.0 g, 120 mmol) were added, followed by stirring at 100° C. for 16 hours in the presence of nitrogen gas. After cooling to room temperature, the reaction solution was filtered through Celite, and the filtrate was concentrated under reduced pressure. The obtained residue was purified by silica gel column chromatography (petroleum ether/ethyl acetate=5:1 to 1:1). A compound (9.30 g, 30.0 mmol) obtained by repeating the above-described process was dissolved in methanol (30 ml), and a 2 N aqueous sodium hydroxide solution (30 ml) was added thereto, followed by stirring at room temperature for 1 hour. The pH was adjusted to 4.0 by adding 2 N hydrochloric acid, and the precipitated solid was filtered, and then dried under reduced pressure to obtain the title compound (8.1 g, 36% over two steps).

¹H NMR (400 MHz, CD3OD) δ 8.82-8.80 (m, 2H), 7.88-7.82 (m, 3H), 7.05-7.00 (m, 2H).; MS (ESI) m/z 297 (M+H)⁺

Example 7

Synthesis of M-7

(Step 1) Methyl 4-{[(5-Bromopyridin-2-yl)sulfonyl]amino}-2,6-difluorobenzoate

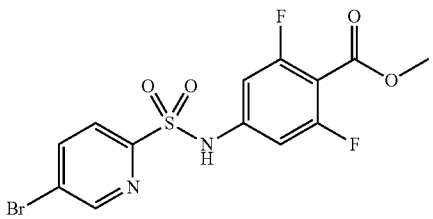

Phenylmethanethiol (80.0 g, 645 mmol) was dissolved in anhydrous tetrahydrofuran (600 ml), and 60% sodium hydride (45.0 g, 1.13 mol) was added thereto, followed by stirring at room temperature for 30 minutes. To this reaction solution, 5-bromo-2-chloropyridine (123 g, 640 mmol) was added, followed by stirring at room temperature for 3 hours. The reaction solution was diluted with water, followed by extraction with diethyl ether. The extraction liquids were combined, washed with a saturated aqueous sodium hydrogen carbonate solution and saturated aqueous sodium chloride, and dried over anhydrous sodium sulfate. Then, the solvent was removed. A compound (250 g, 0.90 mol) obtained by repeating the-above described process was suspended in a mixture solvent of acetic acid (2250 ml) and water (750 ml), and N-chlorosuccinimide (340 g, 2.60 mol) was added thereto, followed by stirring at room temperature for 2 hours. The reaction solution was diluted with water, followed by extraction with methylene chloride. The extraction liquids were combined, washed with a saturated aqueous sodium hydrogen carbonate solution and water, and dried over anhydrous sodium sulfate. Then, the solvent was removed. The obtained residue was purified by silica gel column chromatography (petroleum ether/ethyl acetate=30:1). The obtained compound (47.0 g, 185 mmol) and methyl 4-amino-2,6-difluorobenzoate (26.0 g, 139 mmol) were suspended in methylene chloride (1000 ml), and pyridine (30 ml) was added thereto, followed by stirring at room temperature for 12 hours. The reaction solution was concentrated under reduced pressure, and the obtained residue was purified by silica gel column chromatography (petroleum ether/ethyl acetate=4:1) to obtain the title compound (50 g, 15% over three steps).

¹H NMR (d-DMSO, 400 MHz): δ 8.92 (d, J=1.6 Hz, 1H), 8.41-8.38 (m, 1H), 8.07 (d, J=8.4 Hz, 1H), 6.93 (d, J=10 Hz, 2H), 3.81 (s, 3H).; MS (ESI) m/z 407 (M+H)⁺

(Step 2) [6-({[3,5-Difluoro-4-(methoxycarbonyl)phenyl]amino}sulfonyl)pyridin-3-yl]boronic Acid

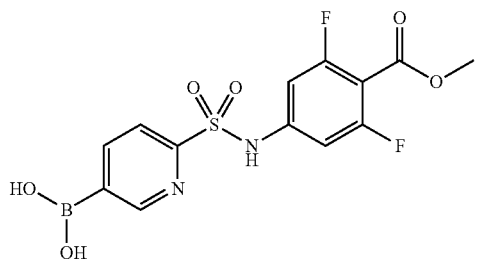 [SMILES: COC(=O)c1c(F)cc(NS(=O)(=O)c2ccc(B(O)O)cn2)cc1F]

Methyl 4-{[(5-bromopyridin-2-yl)sulfonyl]amino}-2,6-difluorobenzoate (25 g, 61.7 mmol) and bis(pinacolato)diborane (18.7 g, 73.6 mmol) were dissolved in N,N-dimethylformamide (500 ml). To the solution, [1,1'-bis(diphenylphosphino)ferrocene]dichloropalladium(II) (1.30 g, 1.80 mmol) and potassium acetate (18.0 g, 184 mmol) were added, followed by stirring at 90° C. for 12 hours in the presence of nitrogen gas. After cooling to room temperature, the reaction solution was diluted with water, followed by extraction with ethyl acetate. The extraction liquids were combined, washed with saturated aqueous sodium chloride, and dried over anhydrous sodium sulfate. Then, the solvent was removed. The obtained residue was purified by silica gel column chromatography (ethyl acetate) to obtain the title compound (11.0 g, 50%).

¹H NMR (CD3OD, 400 MHz): δ 8.91 (s, 1H), 8.33 (d, J=7.2 Hz, 1H), 8.04 (d, J=7.6 Hz, 1H), 6.93 (d, J=10 Hz, 2H), 3.87 (s, 3H).; MS (ESI) m/z 373 (M+H)⁺

(Step 3) 2,6-Difluoro-4-{[(5-pyrimidin-2-yl-pyridin-2-yl)sulfonyl]amino}benzoic Acid (M-7)

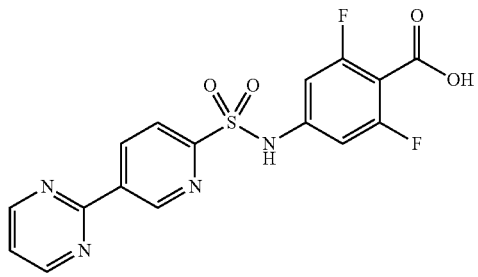 [SMILES: O=C(O)c1c(F)cc(NS(=O)(=O)c2ccc(-c3ncccn3)cn2)cc1F]

[6-({[3,5-Difluoro-4-(methoxycarbonyl)phenyl]amino}sulfonyl)pyridin-3-yl]boronic acid (11.0 g, 26.9 mmol) and 2-bromopyrimidine (9.40 g, 59.2 mmol) were dissolved in a mixture solvent of N,N-dimethylformamide (200 ml) and water (20 ml). To the solution, [1,1'-bis(diphenylphosphino)ferrocene]dichloropalladium(II) (650 mg, 0.89 mmol) and sodium carbonate (9.40 g, 88.8 mmol) were added, followed by stirring at 90° C. for 12 hours in the presence of nitrogen gas. After cooling to room temperature, the reaction solution was diluted with water, followed by extraction with ethyl acetate. The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:2 to 1:10).

The obtained compound (6.60 g, 16.2 mmol) was dissolved in methanol (300 ml), and a 6 N aqueous sodium hydroxide solution (300 ml) was added thereto, followed by stirring at room temperature for 30 minutes. The pH was adjusted to 4.0 by adding 4 N hydrochloric acid, and the precipitated solid was filtered and then dried under reduced pressure to obtain the title compound (5.8 g, 50% over two steps).

$^1$H NMR (CD3OD, 400 MHz): δ 9.65 (d, J=1.6 Hz, 1H), 9.01 (dd, J=8.4, 2.0 Hz, 1H), 8.94 (d, J=5.2 Hz, 2H), 8.23 (d, J=8.0 Hz, 1H), 7.49 (t, J=4.8 Hz, 1H), 6.97 (d, J=10.0 Hz, 2H).; MS (ESI) m/z 393 (M+H)$^+$

Example 8

Synthesis of M-8

(Step 1) Methyl 4-Amino-2,6-difluorobenzoate

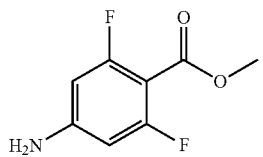

4-Bromo-2,6-difluorobenzoic acid (5.30 g, 23.7 mmol) was dissolved in methanol (35 ml). After cooling to 0° C., thionyl chloride (10 ml) was added dropwise thereto. The reaction solution was heated, and stirred at 95° C. for 12 hours. After the solvent was removed under reduced pressure, the obtained residue was dissolved in toluene (135 ml). To the solution, benzophenone imine (5.1 ml, 31 mmol), palladium(II) acetate (135 mg, 0.60 mmol), 2,2'-bis(diphenylphosphino)-1,1'-binaphthyl (500 mg, 0.80 mmol), and cesium carbonate (13.0 g, 40.0 mmol) were added. After purging with nitrogen gas, the mixture was stirred at 110° C. for 14 hours. After cooling to room temperature, the reaction solution was filtered through Celite, and the filtrate was concentrated under reduced pressure. The obtained residue was dissolved in a mixture solvent of tetrahydrofuran (80 ml) and water (30 ml), and concentrated hydrochloric acid (30 ml) was added thereto, followed by stirring at room temperature for 2 hours. The reaction solution was neutralized with an aqueous sodium hydrogen carbonate solution, followed by extraction with ethyl acetate. The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=6:1 to 2:1) to obtain the title compound (3.6 g, 81% over three steps).

(Step 2) Methyl 2,6-Difluoro-4-{[(4-iodophenyl) sulfonyl]amino}benzoate

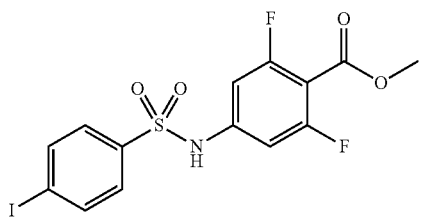 [SMILES: COC(=O)c1c(F)cc(NS(=O)(=O)c2ccc(I)cc2)cc1F]

Methyl 4-amino-2,6-difluorobenzoate (3.60 g, 19.2 mmol) was suspended in methylene chloride (1.5 L), and 4-iodobenzenesulfonyl chloride (7.50 g, 25.0 mmol) and pyridine (6.0 ml) were added thereto, followed by stirring at 80° C. for 12 hours. After the reaction solution was concentrated under reduced pressure, 4 N hydrochloric acid was added. After stirring for 10 minutes, the obtained suspension was filtered. The obtained solid was stirred in a mixture solvent of petroleum ether/ethyl acetate (8:1) for 1 hour, and then filtered and dried under reduced pressure to obtain the title compound (7.4 g, 85%) as a white solid.

(Step 3) [4-({[3,5-Difluoro-4-(methoxycarbonyl) phenyl]amino}sulfonyl)phenyl]boronic Acid

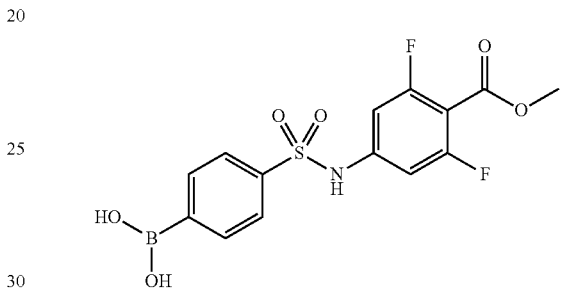

Methyl 2,6-difluoro-4-{[(4-iodophenyl)sulfonyl] amino}benzoate (6.00 g, 13.2 mmol) and bis(pinacolato) diborane (4.00 g, 16.1 mmol) were dissolved in N,N-dimethylformamide (100 ml). To the solution, [1,1'-bis (diphenylphosphino)ferrocene]dichloropalladium(II) (289 mg, 0.390 mmol) and potassium acetate (3.84 g, 39.1 mmol) were added, followed by stirring at 90° C. for 12 hours in the presence of nitrogen gas. After cooling to room temperature, the reaction solution was diluted with water, followed by extraction with ethyl acetate. The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=4:1 to 2:1).

The obtained compound was dissolved in acetone (30 ml), and sodium periodate (2.84 g, 13.2 mmol), ammonium acetate (1.00 g, 13.2 mmol), and water (10 ml) were added thereto, followed by stirring at room temperature for 55 hours. After the reaction solution was concentrated under reduced pressure, the residue was diluted with water, followed by extraction with ethyl acetate (500 ml×3). The extraction liquids were combined, washed with saturated aqueous sodium chloride, and dried over anhydrous sodium sulfate. Then, the solvent was removed. The obtained residue was washed with a mixture solvent of petroleum ether/ ethyl acetate (1/10), and dried under reduced pressure to obtain the title compound (2.5 g, 36% over two steps).

$^1$H NMR (d-DMSO, 400 MHz): δ 8.37 (s, 2H), 7.94 (d, J=8.0 Hz, 2H), 7.82 (d, J=8.4 Hz, 2H), 6.82 (d, J=10.4 Hz, 2H), 3.79 (s, 3H).; MS (ESI) m/z 372 (M+H)$^+$ (Step 4) 2,6-Difluoro-4-{[(4-pyrimidin-2-yl-phenyl) sulfonyl]amino}benzoic Acid (M-8)

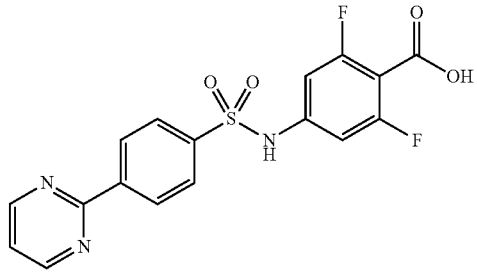 [SMILES: O=C(O)c1c(F)cc(NS(=O)(=O)c2ccc(-c3ncccn3)cc2)cc1F]

[4-({[3,5-Difluoro-4-(methoxycarbonyl)phenyl] amino}sulfonyl)phenyl]boronic acid (3.0 g, 8.1 mmol) and 2-bromopyrimidine (4.5 g, 28 mmol) were dissolved in a mixture solvent of N,N-dimethylformamide (100 ml) and water (10 ml). To the solution, [1,1'-bis(diphenylphosphino) ferrocene]dichloropalladium(II) (592 mg, 0.81 mmol) and sodium carbonate (2.5 g, 24 mmol) were added, followed by stirring at 90° C. for 12 hours in the presence of nitrogen gas. After cooling to room temperature, the reaction solution was diluted with water, followed by extraction with ethyl acetate. The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:1 to 1:4). The obtained compound (400 mg, 0.98 mmol) was dissolved in methanol (20 ml), and a 6 N aqueous sodium hydroxide solution (20 ml) was added thereto, followed by stirring at room temperature for 30 minutes. The pH was adjusted to 4.0 by adding 4 N hydrochloric acid, and the precipitated solid was filtered and then dried under reduced pressure to obtain the title compound (313 mg, 10% over two steps).

$^1$H NMR (CD3OD, 300 MHz): δ 8.88 (d, J=4.8 Hz, 2H), 8.59 (d, J=8.4 Hz, 2H), 8.0 (d, J=8.4 Hz, 2H), 7.40 (t, J=4.8 Hz, 1H), 6.84 (d, J=9.6 Hz, 2H).; MS (ESI) m/z 392 (M+H)$^+$

Example 9

Synthesis of M-9

(Step 1) Methyl 4-{[(6-Chloropyridin-3-yl)sulfonyl] amino}-2,6-difluorobenzoate

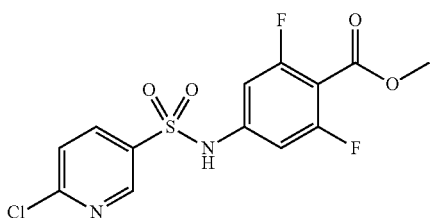 [SMILES: COC(=O)c1c(F)cc(NS(=O)(=O)c2ccc(Cl)nc2)cc1F]

6-Chloropyridine-3-sulfonyl chloride (10.0 g, 47.0 mmol) was dissolved in methylene chloride (300 ml), and methyl 4-amino-2,6-difluorobenzoate (7.5 g, 40 mmol) and pyridine (9.0 ml, 102 mmol) were added thereto, followed by stirring at room temperature for 12 hours. The reaction solution was washed with water and 2 N hydrochloric acid, followed by extraction with methylene chloride. The extraction liquids were combined, washed with saturated aqueous sodium chloride, and dried over anhydrous sodium sulfate. Then, the solvent was removed. The obtained residue was recrystallized from a mixture solvent of petroleum ether/ethyl acetate (1:2). The precipitated solid was filtered and then dried under reduced pressure to obtain the title compound (12.0 g, 83%) as a white solid.

$^1$H NMR (CD3OD, 300 MHz): δ 8.82 (d, J=2.4 Hz, 1H), 8.20 (dd, J=2.4 Hz, 8.7 Hz 1H), 7.86-7.82 (t, 1H), 7.04 (d, J=10 Hz, 2H), 3.86 (s, 3H)

(Step 2) 4-[(2,4'-Bipyridin-5-yl-sulfonyl)amino]-2, 6-difluorobenzoic Acid (M-9)

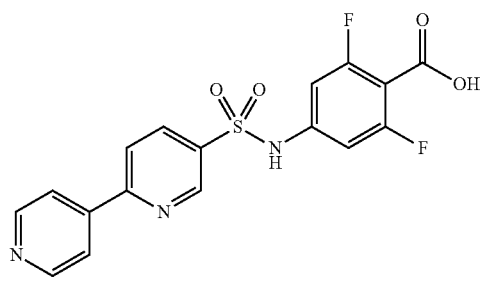 [SMILES: O=C(O)c1c(F)cc(NS(=O)(=O)c2ccc(-c3ccncc3)nc2)cc1F]

Methyl 4-{[(6-chloropyridin-3-yl)sulfonyl]amino}-2,6-difluorobenzoate (688 mg, 2.00 mmol) and 4-pyridylboronic acid (492 mg, 4.00 mmol) were dissolved in a mixture solvent of 1,4-dioxane (20 ml) and water (2.0 ml). To the solution, [1,1'-bis(diphenylphosphino) ferrocene]dichloropalladium(II) (162 mg, 0.20 mmol) and sodium carbonate (212 mg, 2.00 mmol) were added, followed by stirring at 130° C. for 30 minutes under microwave irradiation. After cooling to room temperature, the reaction solution was diluted with methanol and filtered through Celite. The filtrate was concentrated under reduced pressure, and the obtained residue was purified by silica gel column chromatography (petroleum ether/ethyl acetate=2:1 to 1:1). A compound (810 mg, 2.00 mmol) obtained by repeating the-above described process was dissolved in methanol (15 ml), and a 6 N aqueous sodium hydroxide solution (5.0 ml) was added thereto, followed by stirring at room temperature for 30 minutes. The pH was adjusted to 4.0 by adding 4 N hydrochloric acid. The precipitated solid was filtered and then dried under reduced pressure to obtain the title compound (620 mg, 47% over two steps) as a white solid.

$^1$H NMR (CD3OD, 400 MHz): δ 9.18 (d, J=2.4 Hz, 1H), 8.77-8.75 (m, 2H), 8.41 (d, J=2.0 Hz, 1H), 8.35 (d, J=8.4 Hz, 1H), 8.10-8.08 (m, 2H), 6.93 (d, J=10 Hz, 2H).; MS (ESI) m/z 392 (M+H)$^+$

Example 10

Synthesis of M-10

2,6-Difluoro-4-({[4-(1H-pyrrol-1-yl)phenyl]sulfonyl}amino)benzoic Acid (M-10)

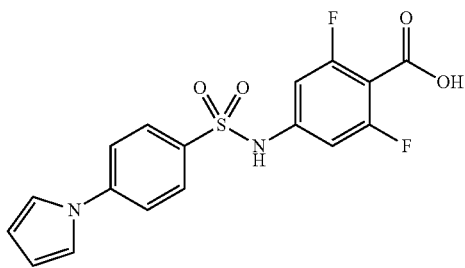 [SMILES: O=C(O)c1c(F)cc(NS(=O)(=O)c2ccc(-n3cccc3)cc2)cc1F]

Methyl 2,6-difluoro-4-{[(4-iodophenyl)sulfonyl]amino}benzoate (7.40 g, 16.3 mmol) was dissolved in N-methylpyrrolidone (30 ml), and copper (I) iodide (1.9 g, 9.8 mmol), potassium phosphate (8.6 g, 41 mmol), pyrrole (2.2 g, 33 mmol), and trans-N,N'-dimethylcyclohexane-1,2-diamine (1.2 g, 8.2 mmol) were added thereto, followed by stirring at 145° C. for 12 hours in the presence of nitrogen gas. After cooling to room temperature, the reaction solution was diluted with water, followed by extraction with methylene chloride (50 ml×2). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:1), followed by drying under reduced pressure to obtain a white solid. The obtained compound (1.3 g, 3.3 mmol) was dissolved in a mixture solvent of methanol (40 ml) and tetrahydrofuran (40 ml), and a 6 N aqueous sodium hydroxide solution (60 ml) was added thereto, followed by stirring at room temperature for 4 hours. The pH was adjusted to 4.0 by adding 4 N hydrochloric acid, and the precipitated solid was filtered and dried under reduced pressure to obtain the title compound (1.1 g, 18% over two steps) as a white solid.

1H NMR (CD$_3$OD, 400 MHz): δ 7.96 (d, J=8.8 Hz, 2H), 7.70 (d, J=8.8 Hz, 2H), 7.32 (s, 2H), 6.85 (d, J=9.6 Hz, 2H), 6.34 (s, 2H).; MS (ESI) m/z 379 (M+H)$^+$

Example 11

Synthesis of M-11

(Step 1) 4-({[3,5-Difluoro-4-(methoxycarbonyl)phenyl]amino}sulfonyl)benzoic Acid

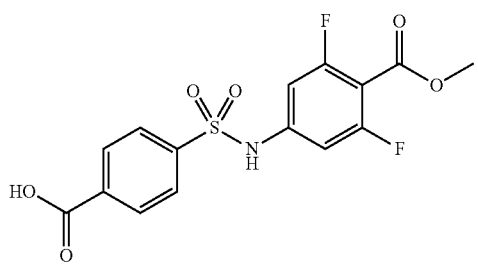 [SMILES: COC(=O)c1c(F)cc(NS(=O)(=O)c2ccc(C(=O)O)cc2)cc1F]

4-(Chlorosulfonyl)benzoic acid (25.0 g, 113 mmol) and methyl 4-amino-2,6-difluorobenzoate (19.0 g, 101 mmol) were dissolved in methylene chloride (500 ml), and pyridine (25.0 ml, 285 mmol) was added thereto, followed by stirring at room temperature for 12 hours. The reaction solution was concentrated under reduced pressure. The obtained residue was diluted with water, and then the pH was adjusted to 1.0 by adding 6 N hydrochloric acid. The precipitated solid was filtered, and washed with water. The obtained solid was resuspended in water, and washed with a saturated aqueous sodium hydrogen carbonate solution, followed by extraction with ethyl acetate (100 ml×2). The pH of the obtained aqueous layer was adjusted to 6.0 by adding 6 N hydrochloric acid thereto, followed by extraction with ethyl acetate (100 ml×2). The extraction liquids were combined, washed with saturated aqueous sodium chloride, and dried over anhydrous sodium sulfate. Then, the solvent was removed to obtain the title compound (15.0 g, 36%).

$^1$H NMR (d-DMSO, 400 MHz): δ 11.50 (s, 1H), 8.14 (d, J=8.4 Hz, 2H), 8.01 (d, J=8.4 Hz, 2H), 6.67 (d, J=10.4 Hz, 2H), 3.87 (s, 3H); MS (ESI) m/z 372 (M+H)$^+$ (Step 2) 4-[({4-[(Ethylamino)carbonyl]phenyl}sulfonyl)amino]-2,6-difluorobenzoic Acid (M-11)

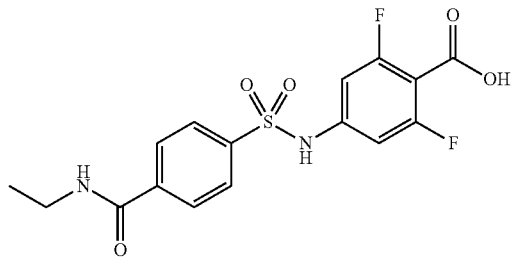 [SMILES: CCNC(=O)c1ccc(S(=O)(=O)Nc2cc(F)c(C(=O)O)c(F)c2)cc1]

4-({[3,5-Difluoro-4-(methoxycarbonyl)phenyl]amino}sulfonyl)benzoic acid (1.5 g, 4.0 mmol) was dissolved in thionyl chloride (40 ml), followed by stirring at 75° C. for 4 hours. The reaction solution was cooled to room temperature, and then concentrated under reduced pressure. The obtained residue was dissolved in methylene chloride (30 ml), and ethylamine hydrochloride (648 mg, 8.00 mmol) and triethylamine (808 mg, 8.00 mmol) were added thereto, followed by stirring at room temperature for 30 minutes. The solvent was removed under reduced pressure, and the obtained residue was purified by silica gel column chromatography (petroleum ether/ethyl acetate=2:1 to 1:1). The obtained compound (800 mg, 2.00 mmol) was dissolved in methanol (30 ml), and a 6 N aqueous sodium hydroxide solution (10 ml) was added thereto, followed by stirring at room temperature for 30 minutes. The pH was adjusted to 4.0 by adding 6 N hydrochloric acid. The precipitated solid was filtered and then dried under reduced pressure to obtain the title compound (691 mg, 50% over two steps) as a white solid.

1H NMR (CD3OD, 400 MHz): δ 7.98-7.92 (m, 4H), 6.80 (d, J=14.8 Hz, 2H), 3.43-3.40 (m, 2H), 1.23-1.14 (m, 3H).; MS (ESI) m/z 385 (M+H)$^+$

Example 12

Synthesis of M-12

4-[({4-[(Cyclopropylamino)carbonyl]phenyl}sulfonyl)amino]-2,6-difluorobenzoic Acid (M-12)

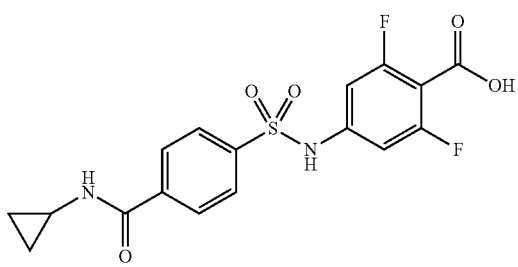 [SMILES: O=C(NC1CC1)c1ccc(S(=O)(=O)Nc2cc(F)c(C(=O)O)c(F)c2)cc1]

4-({[3,5-Difluoro-4-(methoxycarbonyl)phenyl]amino}sulfonyl)benzoic acid (1.5 g, 4.0 mmol) was dissolved in thionyl chloride (40 ml), followed by stirring at 75° C. for 4 hours. The reaction solution was cooled to room temperature, and then concentrated under reduced pressure. The obtained residue was dissolved in methylene chloride (30 ml), and cyclopropylamine (680 mg, 12.0 mmol) was added thereto, followed by stirring at room temperature for 30 minutes. The solvent was removed under reduced pressure, and the obtained residue was purified by silica gel column chromatography (petroleum ether/ethyl acetate=2:1 to 1:1). A portion (740 mg, 1.8 mmol) of the obtained compound was dissolved in methanol (15 ml), and a 3 N aqueous sodium hydroxide solution (5.0 ml) was added thereto, followed by stirring at room temperature for 30 minutes. The pH was adjusted to 4.0 by adding 6 N hydrochloric acid. The precipitated solid was filtered and then dried under reduced pressure to obtain the title compound (670 mg, 51% over two steps) as a white solid.

$^1$H NMR (d-DMSO, 400 MHz): δ 7.79-7.72 (m, 4H), 6.62 (d, J=10.0 Hz, 2H), 2.67-2.65 (m, 1H), 0.63-0.59 (m, 2H), 0.45-0.43 (m, 2H); MS (ESI) m/z 397 (M+H)$^+$

Example 13

Synthesis of M-13

2,6-Difluoro-4-({[4-(1H-1,2,4-triazol-1-yl)phenyl]sulfonyl}amino)benzoic Acid (M-13)

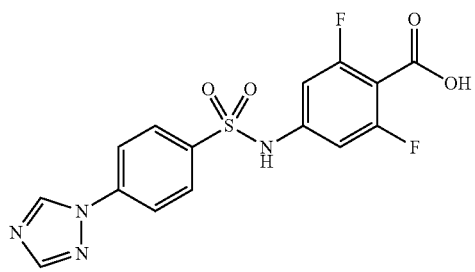 [SMILES: O=C(O)c1c(F)cc(NS(=O)(=O)c2ccc(-n3cncn3)cc2)cc1F]

Methyl 2,6-difluoro-4-{[(4-iodophenyl)sulfonyl]amino}benzoate (1.50 g, 3.30 mmol) was dissolved in N-methylpyrrolidone (15 ml), and copper(I) iodide (400 mg, 2.10 mmol), potassium phosphate (2.0 g, 9.4 mmol), 1,2,4-triazole (500 mg, 7.2 mmol), and trans-N,N'-dimethylcyclohexane-1,2-diamine (500 mg, 3.50 mmol) were added thereto, followed by stirring at 145° C. for 12 hours in the presence of nitrogen gas. After cooling to room temperature, the reaction solution was diluted with water, followed by extraction with methylene chloride (50 ml×2). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:1), followed by drying under reduced pressure to obtain a white solid. The obtained compound (230 mg, 0.580 mmol) was dissolved in methanol (10 ml), and a 6 N aqueous sodium hydroxide solution (10 ml) was added thereto, followed by stirring at room temperature for 30 minutes. The pH was adjusted to 4.0 by adding 3 N hydrochloric acid, and the precipitated solid was filtered and then dried under reduced pressure to obtain the title compound (165 mg, 14% over two steps) as a white solid.

$^1$H NMR (CD$_3$OD, 400 MHz): δ 9.10 (s, 1H), 8.01 (s, 1H), 7.96 (s, 4H), 6.73 (d, J=10.0 Hz, 2H).; MS (ESI) m/z 381 (M+H)$^+$

Example 14

Synthesis of M-14

2,6-Difluoro-4-({[4-(1H-imidazol-2-yl)phenyl]sulfonyl}amino)benzoic Acid (M-14)

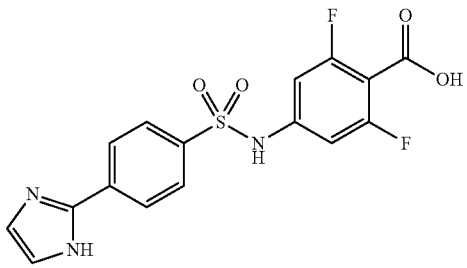 [SMILES: O=C(O)c1c(F)cc(NS(=O)(=O)c2ccc(-c3ncc[nH]3)cc2)cc1F]

Methyl 2,6-difluoro-4-{[(4-iodophenyl)sulfonyl]amino}benzoate (3.0 g, 6.6 mmol) was dissolved in N,N-dimethylformamide (50 ml), and copper(I) iodide (2.50 g, 13.2 mmol), palladium acetate (148 mg, 0.66 mmol), and imidazole (450 mg, 26.4 mmol) were added thereto, followed by stirring at 148° C. for 12 hours in the presence of nitrogen gas. After cooling to room temperature, the reaction solution was diluted with a saturated aqueous ammonium chloride solution, followed by extraction with ethyl acetate (50 ml×3). The extraction liquids were combined, washed with water and saturated aqueous sodium chloride, and dried over anhydrous sodium sulfate. Then, the solvent was removed. The obtained residue was purified by silica gel column chromatography (petroleum ether/ethyl acetate=2:1 to 1:1), followed by drying under reduced pressure to obtain a yellow solid. The obtained compound (450 mg, 1.15 mmol) was dissolved in methanol (20 ml), and a 6 N aqueous sodium hydroxide solution (20 ml) was added thereto, followed by stirring at room temperature for 30 minutes. The pH was adjusted to 4.0 by adding 4 N hydrochloric acid. The precipitated solid was filtered and then dried under reduced pressure to obtain the title compound (220 mg, 9% over two steps) as a white solid.

¹H NMR (CD3OD, 400 MHz): δ 8.01-7.95 (m, 4H), 7.53 (s, 2H), 6.73 (d, J=9.6 Hz, 2H).; MS (ESI) m/z 380 (M+H)⁺

Examples 15 to 18

Synthesis of M-15 to M-18

2,6-Difluoro-4-({[4-(1H-1,2,3-triazol-1-yl)phenyl]sulfonyl}amino)benzoic Acid (M-15)

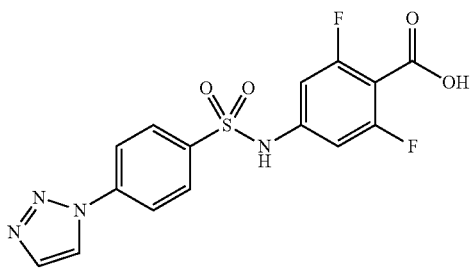 [SMILES: O=C(O)c1c(F)cc(NS(=O)(=O)c2ccc(-n3ccnn3)cc2)cc1F]

2,6-Difluoro-4-({[4-(2H-1,2,3-triazol-2-yl)phenyl]sulfonyl}amino)benzoic Acid (M-16)

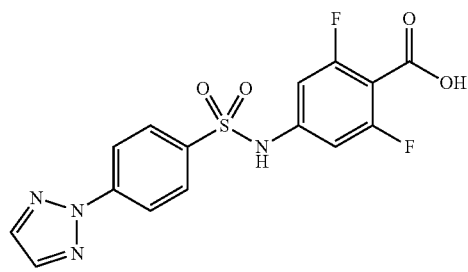 [SMILES: O=C(O)c1c(F)cc(NS(=O)(=O)c2ccc(-n3nccn3)cc2)cc1F]

Methyl 2,6-difluoro-4-{[(4-iodophenyl)sulfonyl]amino}benzoate (4.5 g, 9.9 mmol) was dissolved in N-methylpyrrolidone (90 ml), and 1,2,3-triazole (1.50 g, 21.7 mmol), copper(I) iodide (1.20 g, 6.30 mmol), potassium phosphate (6.0 g, 28 mmol), and trans-N,N'-dimethylcyclohexane-1,2-diamine (1.50 g, 10.5 mmol) were added thereto, followed by stirring at 145° C. for 12 hours in the presence of nitrogen gas. After cooling to room temperature, the reaction solution was diluted with water, followed by extraction with ethyl acetate (150 ml×5). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=2:1 to 1:1) to obtain methyl 2,6-difluoro-4-({[4-(1H-1,2,3-triazol-1-yl)phenyl]sulfonyl}amino)benzoate (M-17) (650 mg, 17%) and methyl 2,6-difluoro-4-({[4-(2H-1,2,3-triazol-2-yl)phenyl]sulfonyl}amino)benzoate (M-18) (800 mg, 20%).

¹H NMR (400 MHz, CD₃OD) for M-17: 8.63 (s, 1H), 8.12-8.07 (m, 4H), 7.91 (s, 1H), 6.85 (d, J=10.0 Hz, 2H), 3.84 (s, 3H).;
MS (ESI) m/z 395 (M+H)⁺

¹H NMR (400 MHz, CD₃OD) for M-18: 8.26 (d, J=8.8 Hz, 2H), 8.03 (d, J=8.8 Hz, 2H), 7.91 (s, 2H), 6.83 (d, J=10.0 Hz, 2H), 3.87 (s, 3H).; MS (ESI) m/z 395 (M+H)⁺

The obtained methyl 2,6-difluoro-4-({[4-(1H-1,2,3-triazol-1-yl)phenyl]sulfonyl}amino)benzoate (M-17) (650 mg, 1.60 mmol) was dissolved in methanol (30 ml), and a 6 N aqueous sodium hydroxide solution (30 ml) was added thereto, followed by stirring at room temperature for 12 hours. The pH was adjusted to 4.0 by adding 6 N hydrochloric acid, and the precipitated solid was filtered and then dried under reduced pressure to obtain the title compound (M-15, 470 mg, 75%).

¹H NMR (CD₃OD, 400 MHz) for M-15: δ 8.66 (d, J=1.2 Hz, 1H), 8.13-8.12 (m, 4H), 7.94 (d, J=1.2 Hz, 1H), 6.87 (d, J=10.0 Hz, 2H).; MS (ESI) m/z 381 (M+H)⁺

The title compound (M-16, 740 mg, 96%) was obtained by subjecting the obtained 2,6-difluoro-4-({[4-(2H-1,2,3-triazol-2-yl)phenyl]sulfonyl}amino)benzoate (M-18) to the same method.

¹H NMR (400 MHz, CD₃OD) for M-16: δ 8.31 (d, J=8.8 Hz, 2H), 8.06 (d, J=8.8 Hz, 2H), 8.00 (s, 2H), 6.86 (d, J=9.6 Hz, 2H).; MS (ESI) m/z 381 (M+H)⁺

Example 19

Synthesis of M-19

(Step 1) 4-({[3-Fluoro-4-(methoxycarbonyl)phenyl]amino}sulfonyl)benzoic Acid

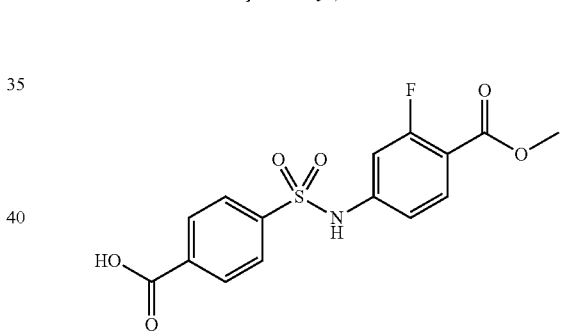

4-(Chlorosulfonyl)benzoic acid (17.0 g, 76.9 mmol) and methyl 4-amino-2-fluorobenzoate (10.0 g, 59.2 mmol) were dissolved in methylene chloride (250 ml), and pyridine (15.0 ml, 171 mmol) was added thereto, followed by stirring at room temperature for 12 hours. The reaction solution was concentrated under reduced pressure, and the obtained residue was diluted with water. Then, the pH was adjusted to 1.0 by adding 6 N hydrochloric acid. The precipitated solid was filtered, and washed with water. The obtained solid was resuspended in water, and washed with a saturated aqueous sodium hydrogen carbonate solution, followed by extraction with ethyl acetate (50 ml×2). The pH of the obtained aqueous layer was adjusted to 6.0 by adding 6 N hydrochloric acid thereto, followed by extraction with ethyl acetate (80 ml×3). The extraction liquids were combined, washed with saturated aqueous sodium chloride, and dried over anhydrous sodium sulfate. Then, the solvent was removed to obtain the title compound (5.0 g, 24%).

H NMR (CD₃OD, 400 MHz): δ 8.11 (d, J=11.2 Hz, 2H), 7.96 (d, J=11.6 Hz, 2H), 7.79-7.76 (m, 1H), 7.06-6.97 (m, 2H), 3.78 (s, 3H).

(Step 2) Methyl 2-Fluoro-4-({[4-(hydroxymethyl)phenyl]sulfonyl}amino)benzoate

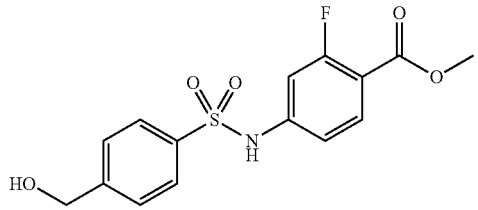 [SMILES: COC(=O)c1ccc(NS(=O)(=O)c2ccc(CO)cc2)cc1F]

4-({[3-Fluoro-4-(methoxycarbonyl)phenyl]amino}sulfonyl)benzoic acid was dissolved in a 1 N borane/tetrahydrofuran solution (25 ml) at 0° C., followed by stirring at room temperature for 15 minutes. To the reaction solution, water (20 ml) was slowly added dropwise. The precipitated solid was filtered, then washed with water, and dried under reduced pressure to obtain the title compound (4.3 g, 90%).

1H NMR (d-DMSO, 400 MHz): δ 11.11 (s, 1H), 7.84-7.76 (m, 3H), 7.52 (d, J=8.4 Hz, 2H), 7.05-6.96 (m, 2H), 5.40 (m, 1H), 4.55 (d, J=5.2 Hz, 2H), 3.79 (s, 3H).; MS (ESI) m/z 340 (M+H)$^+$ (Step 3) Methyl 2-Fluoro-4-[({4-[(methylamino)methyl]phenyl}sulfonyl)amino]benzoate

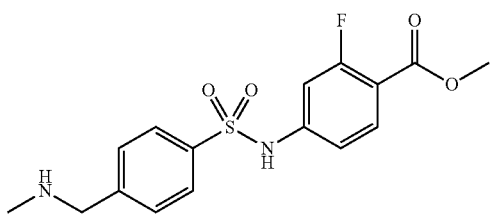

Methyl 2-fluoro-4-({[4-(hydroxymethyl)phenyl]sulfonyl}amino)benzoate (2.80 g, 8.30 mmol) and manganese dioxide (2.90 g, 33.0 mmol) were suspended in chloroform (35 ml), followed by stirring at 60° C. for 4 hours. The mixture was cooled to room temperature, and then filtered. The filtrate was concentrated under reduced pressure. The obtained residue was dissolved in tetrahydrofuran (50 ml), and a 2 N methylamine/tetrahydrofuran solution (7.0 ml) was added thereto, followed by stirring at room temperature for 5 minutes. To the reaction liquid, sodium cyanoborohydride (2.0 g, 32 mmol) was added, followed by stirring at room temperature for 20 hours. The reaction solution was filtered, and the filtrate was concentrated under reduced pressure. The obtained residue was dissolved in ethyl acetate (60 ml), and washed with a saturated aqueous ammonium chloride solution (50 ml×2). The organic layer was concentrated under reduced pressure to obtain the title compound (1.7 g, 60% over two steps).

MS (ESI) m/z 353 (M+H)$^+$ (Step 4) 4-{[(4-{[(tert-Butoxycarbonyl)(methyl)amino]methyl}phenyl)sulfonyl]amino}-2-fluorobenzoic Acid (M-19)

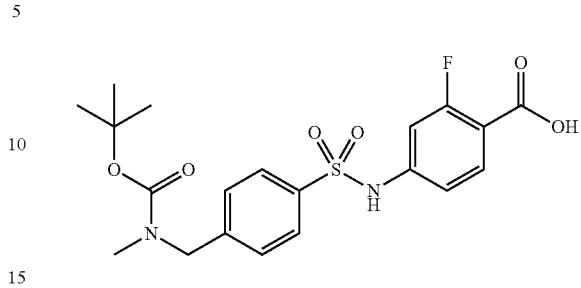

Methyl 2-fluoro-4-[({4-[(methylamino)methyl]phenyl}sulfonyl)amino]benzoate (1.7 g, 4.8 mmol) and N,N'-dimethyl-4-aminopyridine (0.20 g, 1.6 mmol) were dissolved in tetrahydrofuran (45 ml), followed by stirring at room temperature for 15 minutes. The reaction liquid was cooled to 5° C., and then triethylamine (1.0 ml) and di-tert-butyl dicarbonate (1.1 g, 5.3 mmol) were added thereto, followed by stirring for further 20 minutes. After the reaction liquid was concentrated under reduced pressure, the obtained residue was diluted with water (30 ml), followed by extraction with ethyl acetate (30 ml×3). The extraction liquids were combined, washed with saturated aqueous sodium chloride, and dried over anhydrous sodium sulfate. Then, the solvent was removed, followed by purification by silica gel column chromatography (methylene chloride/methanol=10:1). The obtained compound was dissolved in a 6 N aqueous lithium hydroxide solution (21 ml), followed by stirring at room temperature for 30 minutes. The pH was adjusted to 3.0 by adding citric acid. The precipitated solid was filtered, washed with water, and dried under reduced pressure to obtain the title compound (610 mg, 38% over two steps) as a white solid.

1H NMR (CD3OD, 400 MHz): δ 7.74 (d, J=8.4 Hz, 2H), 7.65 (d, J=8.4 Hz, 1H), 7.27 (d, J=8.0 Hz, 2H), 6.86-6.83 (m, 2H), 4.36 (s, 2H), 2.80-2.68 (m, 3H) 1.38-1.17 (m, 9H).; MS (ESI) m/z 339 (M+H-Boc)$^+$

Example 20

Synthesis of M-20

2,6-Difluoro-4-({[4-(3-thienyl)phenyl]sulfonyl}amino)benzoic Acid (M-20)

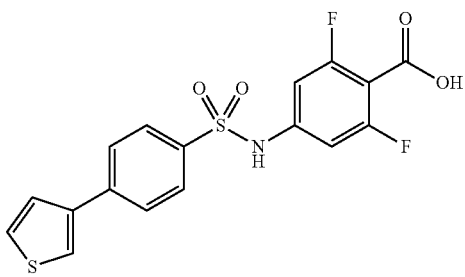

Methyl 2,6-difluoro-4-{[(4-iodophenyl)sulfonyl]amino}benzoate (3.00 g, 6.60 mmol) and 3-thienylboronic acid (1.70 g, 13.0 mmol) were dissolved in a mixture solvent of N,N-dimethylformamide (130 ml) and water (20 ml). To the solution, [1,1'-bis(diphenylphosphino)ferrocene]dichloropalladium(II) (0.76 g, 0.66 mmol) and sodium carbonate (2.1 g, 20 mmol) were added, followed by stirring at 110° C. for 12 hours in the presence of nitrogen gas. After cooling to room temperature, the reaction solution was diluted with water, followed by extraction with ethyl acetate. The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=5:1 to 1:4). The obtained compound (1.20 g, 2.90 mmol) was dissolved in a 6 N aqueous lithium hydroxide solution (20 ml), followed by stirring at room temperature for 30 minutes. The pH was adjusted to 3.0 by adding 6 N hydrochloric acid. The precipitated solid was filtered and then dried under reduced pressure to obtain the title compound (1.0 g, 86% over two steps).

1H NMR (CD$_3$OD, 400 MHz): δ 7.93-7.82 (m, 5H), 7.53 (t, J=1.2 Hz, 2H), 6.85 (d, J=10.0 Hz, 2H).; MS (ESI) m/z 394 (M−H)$^+$

Example 21

Synthesis of M-21

2,6-Difluoro-4-{[(5-pyrimidin-5-yl-pyridin-2-yl)sulfonyl]amino}benzoic Acid (M-21)

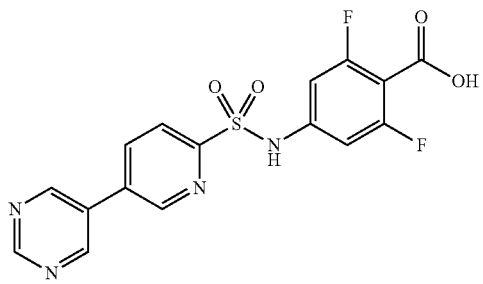 [SMILES: O=C(O)c1c(F)cc(NS(=O)(=O)c2ccc(-c3cncnc3)cn2)cc1F]

Methyl 4-{[(5-bromopyridin-2-yl)sulfonyl]amino}-2,6-difluorobenzoate (3.30 g, 8.10 mmol) and pyrimidin-5-yl-boronic acid (2.00 g, 16.3 mmol) were dissolved in a mixture solvent of N,N-dimethylformamide (50 ml) and water (20 ml). To the solution, [1,1'-bis(diphenylphosphino)ferrocene]dichloropalladium(II) (0.60 g, 0.81 mmol) and sodium carbonate (2.6 g, 24 mmol) were added, followed by stirring at 120° C. for 12 hours in the presence of nitrogen gas. After cooling to room temperature, the reaction solution was diluted with water (200 ml), followed by extraction with ethyl acetate (70 ml×10). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:1 to 1:2). The obtained compound (1.20 g, 3.00 mmol) was dissolved in methanol (40 ml) and tetrahydrofuran (40 ml), and a 6 N aqueous sodium hydroxide solution (60 ml) was added, followed by stirring at room temperature for 4 hours. The pH was adjusted to 4.0 by adding 4 N hydrochloric acid. The precipitated solid was filtered and then dried under reduced pressure to obtain the title compound (1.05 g, 33% over two steps).

$^1$H NMR (CD$_3$OD, 400 MHz): δ 9.26 (s, 1H), 9.20 (s, 2H), 9.08 (d, J=1.6 Hz, 1H), 8.45 (dd, J=8.4, 2.0 Hz, 1H), 8.26 (d, J=8.4 Hz, 1H), 6.97 (d, J=10.0 Hz, 2H).; MS (ESI) m/z 393 (M+H)$^+$

Example 22

Synthesis of M-22

2,6-Difluoro-4-({[6-(1H-1,2,4-triazol-1-yl)pyridin-3-yl]sulfonyl}amino)benzoic Acid (M-22)

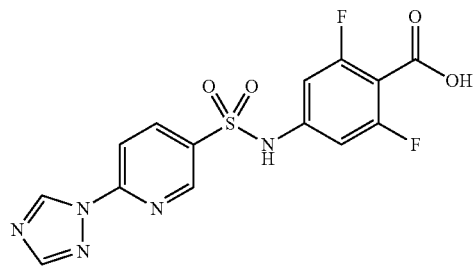

Methyl 4-{[(6-chloropyridin-3-yl)sulfonyl]amino}-2,6-difluorobenzoate (1.90 g, 5.00 mmol) was dissolved in N-methylpyrrolidone (30 ml), and 1,2,4-triazole (0.76 g, 11 mmol), copper(I) iodide (0.76 g, 4.0 mmol), potassium phosphate (3.0 g, 14 mmol), and trans-N,N'-dimethylcyclohexane-1,2-diamine (0.15 g, 1.0 mmol) were added thereto, followed by stirring at 145° C. for 12 hours in the presence of nitrogen gas. After cooling to room temperature, the reaction solution was diluted with water (50 ml), followed by extraction with ethyl acetate (50 ml×3). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=2:1 to 1:1). A portion (800 mg, 2.00 mmol) of the obtained compound was dissolved in methanol (15 ml), and a 6 N aqueous sodium hydroxide solution (5.0 ml) was added thereto, followed by stirring at room temperature for 1 hour. The pH was adjusted to 4.0 by adding 4 N hydrochloric acid, and the precipitated solid was filtered and then dried under reduced pressure to obtain the title compound (668 mg, 36% over two steps) as a white solid.

$^1$H NMR (d-DMSO, 400 MHz): δ 13.69 (s, 1H), 11.49 (s, 1H), 9.44 (d, J=6.4 Hz, 1H), 8.99 (d, J=2.0 Hz, 1H), 8.50-8.47 (m, 1H), 8.38 (s, 1H), 8.07 (d, J=8.4 Hz, 1H), 6.90 (d, J=9.6 Hz, 2H).; MS (ESI) m/z 382 (M+H)$^+$

Example 23

Synthesis of M-23

(Step 1) 5-Iodopyridine-2-sulfonyl Chloride

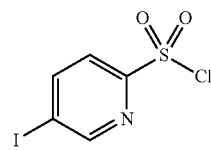 [SMILES: O=S(=O)(Cl)c1ccc(I)cn1]

Phenylmethanethiol (9.3 g, 75 mmol) was dissolved in dimethyl formaldehyde (120 ml). After cooling to 0° C., 60% sodium hydride (3.8 g, 95 mmol) was added thereto, followed by stirring at room temperature for 30 minutes. To this reaction solution, 2-chloro-5-iodopyridine (15 g, 63 mmol) was added, followed by stirring at room temperature for 1 hour. The reaction solution was diluted with water, followed by extraction with ethyl acetate (200 ml×2). The extraction liquids were combined, washed with saturated aqueous sodium chloride, and dried over anhydrous sodium sulfate. Then, the solvent was removed. A portion (11.3 g, 35.0 mmol) of the obtained compound was suspended in a mixture solvent of acetic acid (75 ml) and water (25 ml), and N-chlorosuccinimide (18.4 g, 138 mmol) was added thereto, followed by stirring at room temperature for 1 hour. The reaction solution was diluted with water, followed by extraction with methylene chloride (100 ml×2). The extraction liquids were combined, washed with a saturated aqueous sodium hydrogen carbonate solution and water, and dried over anhydrous sodium sulfate. Then, the solvent was removed. The obtained residue was purified by silica gel column chromatography (petroleum ether/ethyl acetate=30:1) to obtain the title compound (2.6 g, 23% over two steps) as a white solid.

(Step 2) Methyl 2,6-Difluoro-4-{[(5-iodopyridin-2-yl)sulfonyl]amino}benzoate

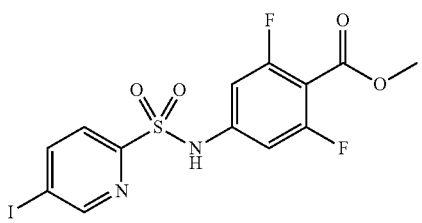 [SMILES: COC(=O)c1c(F)cc(NS(=O)(=O)c2ccc(I)cn2)cc1F]

5-Iodopyridine-2-sulfonyl chloride (5.1 g, 17 mmol) and methyl 4-amino-2,6-difluorobenzoate (2.5 g, 13 mmol) were dissolved in methylene chloride (25 ml), and pyridine (5.0 ml) was added thereto, followed by stirring at room temperature for 12 hours. The reaction solution was concentrated under reduced pressure. To the obtained residue, 6 N hydrochloric acid (100 ml) was added. The precipitated solid was filtered, and dried under reduced pressure to obtain the title compound (3.0 g, 69%).

$^1$H NMR (d-DMSO, 400 MHz): δ 11.58 (br, 1H), 9.00 (d, J=2.0 Hz, 1H), 8.54-8.51 (dd, J=8.4, 2.0 Hz, 1H), 7.92 (d, J=8.0 Hz, 1H), 6.94 (d, J=10.4 Hz, 2H), 3.81 (s, 3H).; MS (ESI) m/z 455 (M+H)$^+$ (Step 3) 2,6-Difluoro-4-({[5-(1H-1,2,4-triazol-1-yl)pyridin-2-yl]sulfonyl}amino)benzoic Acid (M-23)

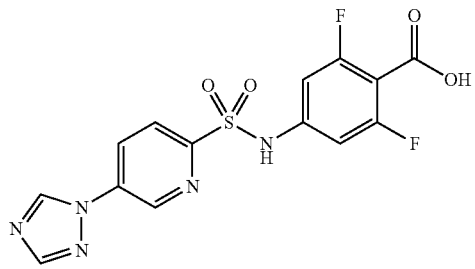

Methyl 2,6-difluoro-4-{[(5-iodopyridin-2-yl)sulfonyl]amino}benzoate (3.0 g, 6.6 mmol) was dissolved in N-methylpyrrolidone (20 ml), and 1,2,4-triazole (0.68 g, 9.9 mmol), copper(I) iodide (0.63 g, 3.3 mmol), potassium phosphate (2.8 g, 13 mmol), and trans-N,N'-dimethylcyclohexane-1,2-diamine (0.94 g, 6.6 mmol) were added thereto, followed by stirring at 145° C. for 12 hours in the presence of nitrogen gas. After cooling to room temperature, the reaction solution was diluted with water (40 ml), followed by extraction with ethyl acetate (50 ml×4). The extraction liquids were combined, washed with saturated aqueous sodium chloride, and dried over anhydrous sodium sulfate. Then, the solvent was removed. The obtained black residue was purified by silica gel column chromatography (petroleum ether/ethyl acetate=2:1). A portion (800 mg, 2.00 mmol) of the obtained compound was dissolved in methanol (50 ml), and a 4 N aqueous sodium hydroxide solution (5.0 ml) was added thereto, followed by stirring at room temperature for 12 hours. The pH was adjusted to 4.0 by adding 6 N hydrochloric acid. The precipitated solid was filtered and then dried under reduced pressure to obtain the title compound (0.49 g, 19% over two steps) as a white solid.

1H NMR (d6-DMSO, 400 MHz): δ 13.70 (br, 1H), 11.58 (br, 1H), 9.50 (s, 1H), 9.31 (d, J=2.0 Hz, 1H), 8.57-8.54 (m, 1H), 8.38-8.33 (m, 2H), 6.95 (d, J=10.0 Hz, 2H).; MS (ESI) m/z 382 (M+H)$^+$

Example 24

Synthesis of M-24

2,6-Difluoro-4-({[5-(1,3-thiazol-2-yl)pyridin-2-yl]sulfonyl}amino)benzoic Acid (M-24)

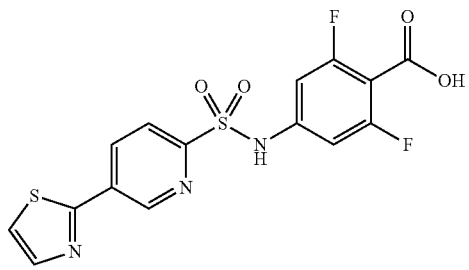 [SMILES: O=C(O)c1c(F)cc(NS(=O)(=O)c2ccc(-c3nccs3)cn2)cc1F]

[6-({[3,5-Difluoro-4-(methoxycarbonyl)phenyl]amino}sulfonyl)pyridin-3-yl]boronic acid (5.00 g, 13.4 mmol) and 2-bromo-1,3-thiazole (7.6 g, 47 mmol) were dissolved in a mixture solvent of N,N-dimethylformamide (100 ml) and water (40 ml). To the solution, [1,1'-bis(diphenylphosphino)ferrocene]dichloropalladium(II) (980 mg, 1.34 mmol) and sodium carbonate (4.30 g, 40.6 mmol) were added, followed by stirring at 120° C. for 12 hours in the presence of nitrogen gas. After cooling to room temperature, the reaction solution was diluted with water (200 ml), followed by extraction with ethyl acetate (80 ml×3). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:2). The obtained compound (1.20 g, 2.92 mmol) was dissolved in methanol (50 ml) and tetrahydrofuran (50 ml), and a 6 N aqueous sodium hydroxide solution (70 ml) was added thereto, followed by stirring at room temperature for 5 hours. The pH was adjusted to 4.0 by adding 4 N hydrochloric acid. The precipitated solid was filtered and then dried under reduced pressure to obtain the title compound (1.08 g, 20% over two steps) as a white solid.

$^1$H NMR (d-DMSO, 400 MHz): δ 13.6 (br, 1H), 11.60 (br, 1H), 9.29 (d, J=1.2 Hz, 1H), 8.64 (dd, J=8.0, 2.0 Hz, 1H), 8.24 (d, J=8.4 Hz, 1H), 8.10 (d, J=2.8 Hz, 1H), 8.03 (d, J=2.8 Hz, 1H), 6.95 (t, J=10.0 Hz, 2H).; MS (ESI) m/z 398 (M+H)$^+$

Example 25

Synthesis of M-25

2,6-Difluoro-4-{[(4-pyrimidin-5-yl-phenyl)sulfonyl]amino}benzoic Acid (M-25)

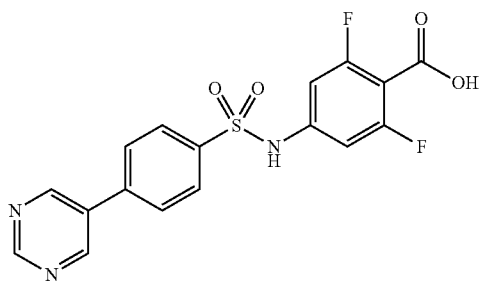 [SMILES: O=C(O)c1c(F)cc(NS(=O)(=O)c2ccc(-c3cncnc3)cc2)cc1F]

Methyl 2,6-difluoro-4-{[(4-iodophenyl)sulfonyl]amino}benzoate (3.0 g, 6.6 mmol) and pyrimidin-5-yl-boronic acid (0.89 g, 7.3 mmol) were dissolved in a mixture solvent of N,N-dimethylformamide (50 ml) and water (10 ml). To the solution, tetrakis(triphenylphosphine)palladium (0.76 g, 0.66 mmol) and sodium carbonate (2.00 g, 18.8 mmol) were added, followed by stirring at 100° C. for 12 hours in the presence of nitrogen gas. After cooling to room temperature, the reaction solution was diluted with water, followed by extraction with ethyl acetate. The extraction liquids were combined, washed with saturated aqueous sodium chloride, and dried over anhydrous sodium sulfate. Then, the solvent was removed under reduced pressure. The obtained residue was purified by silica gel column chromatography (petroleum ether/ethyl acetate=1:2 to 1:4). The obtained compound (640 mg, 1.58 mmol) was dissolved in methanol (15 ml), and a 6 N aqueous sodium hydroxide solution (5.0 ml) was added thereto, followed by stirring at room temperature for 30 minutes. The pH was adjusted to 4.0 by adding 4 N hydrochloric acid. The precipitated solid was filtered and then dried under reduced pressure to obtain the title compound (550 mg, 21% over two steps) as a white solid.

$^1$H NMR (CD$_3$OD, 400 MHz): δ 9.18 (s, 1H), 9.11 (s, 2H), 8.04 (d, J=8.0 Hz, 2H), 7.94 (d, J=8.4 Hz, 2H), 6.84 (d, J=9.6 Hz, 2H).; MS (ESI) m/z 392 (M+H)$^+$

Example 26

Synthesis of M-26

2,6-Difluoro-4-({[4-(1H-pyrazol-1-yl)phenyl]sulfonyl}amino)benzoic Acid (M-26)

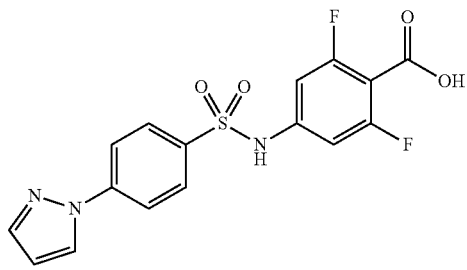

Methyl 2,6-difluoro-4-{[(4-iodophenyl)sulfonyl]amino}benzoate (3.0 g, 6.4 mmol) was dissolved in N-methylpyrrolidone (30 ml), and 1H-pyrazole (900 mg, 13.2 mmol), copper (I) iodide (0.84 g, 4.4 mmol), potassium phosphate (3.50 g, 16.5 mmol), and trans-N,N'-dimethylcyclohexane-1,2-diamine (0.28 g, 2.0 mmol) were added thereto, followed by stirring at 145° C. for 12 hours in the presence of nitrogen gas. After cooling to room temperature, the reaction solution was diluted with water (50 ml), followed by extraction with ethyl acetate (50 ml×3). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=2:1 to 1:1). The obtained compound (1.1 g, 2.8 mmol) was dissolved in methanol (20 ml), and a 6 N aqueous sodium hydroxide solution (5.0 ml) was added thereto, followed by stirring at room temperature for 1 hour. The pH was adjusted to 4.0 by adding 4 N hydrochloric acid. The precipitated solid was filtered and then dried under reduced pressure to obtain the title compound (960 mg, 40% over two steps) as a white solid.

1H NMR (CD$_3$OD, 400 MHz): δ 8.23 (d, J=3.2 Hz, 1H), 7.88 (s, 4H), 7.66 (d, J=1.6 Hz, 1H), 6.73 (d, J=10.0 Hz, 2H), 6.46-6.45 (m, 1H).; MS (ESI) m/z 380 (M+H)$^+$

Example 27

Synthesis of M-27

(Step 1) 2,6-Dimethyl-4-(4,4,5,5-tetramethyl-1,3,2-dioxaborolan-2-yl)pyridine

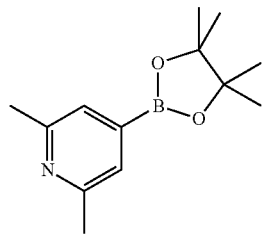

2,6-Dimethylpyridine (10 g, 93 mmol), 4,4'-bis(1,1'-tert-butyl)-2'-bipyridine (1.56 g, 5.80 mmol), 4,4,4',4',5,5,5',5'-octamethyl-2,2'-bi-1,3,2-dioxaborolane (25.4 g, 100 mmol), and (1,5-cyclooctadiene)(methoxy)iridium(I) dimer (1.96 g, 3.00 mmol) were dissolved in tetrahydrofuran (500 ml), followed by stirring at 65° C. for 16 hours in the presence of nitrogen gas. The reaction solution was concentrated under reduced pressure, and the obtained residue was purified by silica gel column chromatography (petroleum ether/ ethyl acetate=100:1) to obtain the title compound (15.0 g, 66%).

1H NMR (CDCl₃ 300 MHz): δ 7.38 (s, 2H), 2.53 (s, 6H), 1.37 (s, 12H).; MS (ESI) m/z 234 (M+H)⁺

(Step 2) 4-({[4-(2,6-Dimethylpyridin-4-yl)phenyl] sulfonyl}amino)-2,6-difluorobenzoic Acid (M-27)

Methyl 2,6-difluoro-4-{[(4-iodophenyl)sulfonyl] amino}benzoate (29.1 g, 64.3 mmol) and 2,6-dimethyl-4-(4,4,5,5-tetramethyl-1,3,2-dioxaborolan-2-yl)pyridine (18.0 g, 76.9 mmol) were dissolved in a mixture solvent of N,N-dimethylformamide (750 ml) and water (75 ml). To the solution, [1,1'-bis(diphenylphosphino)ferrocene]dichloropalladium(II) (1.7 g, 2.3 mmol) and sodium carbonate (24.4 g, 155 mmol) were added, followed by stirring at 90° C. for 12 hours in the presence of nitrogen gas. After cooling to room temperature, the reaction solution was diluted with water, followed by extraction with ethyl acetate. The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:2 to 1:10). The obtained compound (13.0 g, 30.0 mmol) was dissolved in methanol (90 ml), and a 6 N aqueous sodium hydroxide solution (30 ml) was added thereto, followed by stirring at room temperature for 30 minutes. The pH was adjusted to 4.0 by adding 4 N hydrochloric acid. The precipitated solid was filtered and then dried under reduced pressure to obtain the title compound (10.5 g, 39% over two steps) as a white solid.

¹H NMR (d-DMSO, 400 MHz): δ 8.02 (s, 4H), 7.57 (s, 2H), 6.88 (d, J=10.0 Hz, 2H), 2.53 (s, 6H).; MS (ESI) m/z 419 (M+H)⁺

Examples 28 to 31

Synthesis of M-28 to M-31

2,6-Difluoro-4-({[5-(1H-1,2,3-triazol-1-yl)pyridin-2-yl]sulfonyl}amino)benzoic Acid (M-28)

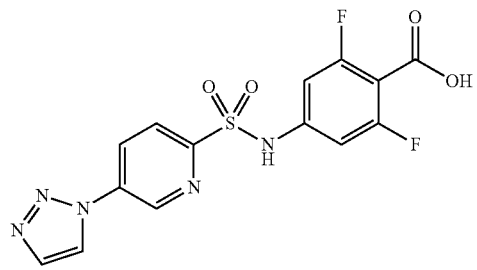 [SMILES: O=C(O)c1c(F)cc(NS(=O)(=O)c2ccc(-n3ccnn3)cn2)cc1F]

2,6-Difluoro-4-({[5-(2H-1,2,3-triazol-2-yl)pyridin-2-yl]sulfonyl}amino)benzoic Acid (M-29)

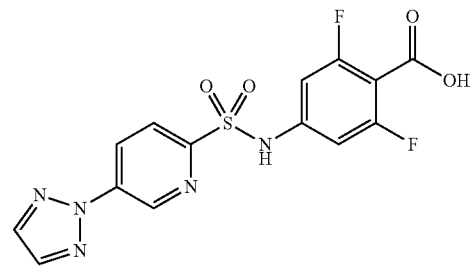 [SMILES: O=C(O)c1c(F)cc(NS(=O)(=O)c2ccc(-n3nccn3)cn2)cc1F]

Methyl 4-{[(5-bromopyridin-2-yl)sulfonyl]amino}-2,6-difluorobenzoate (8.0 g, 20 mmol) was dissolved in N-methylpyrrolidone (120 ml), and 1,2,3-triazole (2.0 g, 30 mmol), copper (I) iodide (1.9 g, 10 mmol), potassium phosphate (8.4 g, 40 mmol), and N, N-dimethylcyclohexylamine (2.8 g, 20 mmol) were added thereto, followed by stirring at 145° C. for 12 hours in the presence of nitrogen gas. After cooling to room temperature, the reaction solution was diluted with water (300 ml), followed by extraction with ethyl acetate (150 ml×5). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=2:1 to 1:1) to obtain methyl 2,6-difluoro-4-({[5-(1H-1,2,3-triazol-1-yl) pyridin-2-yl]sulfonyl}amino)benzoate (M-30: methyl ester of M-28) (1.5 g, 19%) and methyl 2,6-difluoro-4-({[5-(2H-1,2,3-triazol-2-yl)pyridin-2-yl]sulfonyl}amino)benzoate (M-31: methyl ester of M-29) (2.0 g, 25%).

The obtained methyl 2,6-difluoro-4-({[5-(1H-1,2,3-triazol-1-yl)pyridin-2-yl]sulfonyl}amino)benzoate (M-30) (800 mg, 2.00 mmol) was dissolved in methanol (50 ml), and a 4 N aqueous sodium hydroxide solution (50 ml) was added thereto, followed by stirring at room temperature for 12 hours. The pH was adjusted to 4.0 by adding 6 N hydrochloric acid. The precipitated solid was filtered and then dried under reduced pressure to obtain the title compound (M-28, 920 mg, 63%).

¹H NMR (CD₃OD, 400 MHz) for M-28: δ 9.30 (d, J=3.2 Hz, 1H), 8.76 (d, J=1.6 Hz, 1H), 8.62 (dd, J=11.6, 3.2 Hz, 1H), 8.33 (d, J=11.6 Hz, 1H), 7.99 (d, J=1.2 Hz, 1H), 6.98 (d, J=13.2 Hz, 2H).; MS (ESI) m/z 382 (M+H)⁺

The title compound (M-29, 910 mg, 46%) was obtained by subjecting the obtained methyl 2,6-difluoro-4-({[5-(2H-1,2,3-triazol-2-yl)pyridin-2-yl]sulfonyl}amino)benzoate (M-31) to the same method.

¹H NMR (d-DMSO, 400 MHz) for M-29: δ 13.58 (br, 1H), 11.72 (br, 1H), 9.38 (d, J=1.6 Hz, 1H), 8.65 (dd, J=8.4, 2.0 Hz, 1H), 8.30-8.27 (m, 3H), 6.95 (d, J=10.0 Hz, 2H).; MS (ESI) m/z 382 (M+H)⁺

Example 32

Synthesis of M-32

2,6-Difluoro-4-({[4-(2-methylpyridin-4-yl)phenyl]sulfonyl}amino)benzoic Acid (M-32)

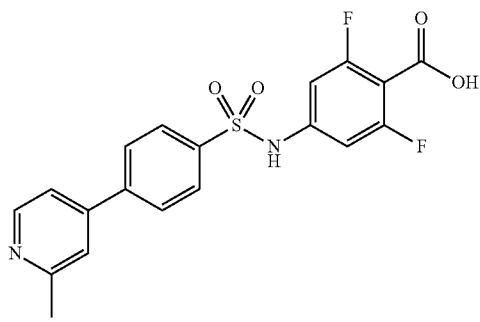

·TFA

Methyl 4-{[(4-bromophenyl)sulfonyl]amino}-2,6-difluorobenzoate (200 mg, 0.440 mmol) was dissolved in 1,4-dioxane (9.0 ml), and 2-methylpyridine-4-boronic acid (132 mg, 0.970 mmol), [1,1'-bis(diphenylphosphino)ferrocene]dichloropalladium(II) (32.0 mg, 44.0 μmol), and a 1 M aqueous sodium carbonate solution (3.0 ml) were added thereto. This solution was degassed under reduced pressure, and purged with argon gas. Then, the solution was stirred at 80° C. for 3 hours. After the stirring, the solvent was removed by distillation, and the obtained residue was suspended in methanol (3.0 ml). The suspension was filtered, and the solvent was removed by distillation from the obtained residue. To this residue, tetrahydrofuran (4.0 ml), water (1.0 ml), and a 2 N aqueous sodium hydroxide solution (2.0 ml) were added, followed by stirring at 60° C. for 3 hours. After the reaction liquid was concentrated under reduced pressure, purification was conducted by reversed-phase HPLC (H₂O containing 0.1% TFA/CH₃CN system) to obtain the TFA salt (85.0 mg, 0.210 mmol, 48%) of the title compound.

MS (ESI) m/z 405 (M+H)⁺

Example 33

Synthesis of M-33

2,6-Difluoro-4-({[4-(6-methylpyridin-3-yl)phenyl]sulfonyl}amino)benzoic Acid (M-33)

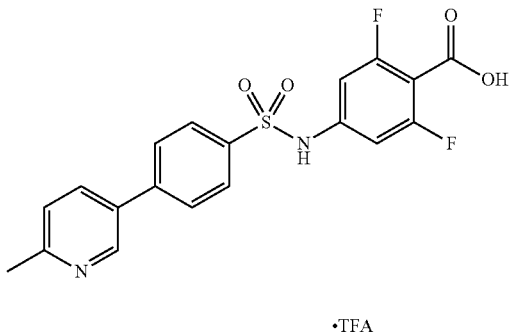 [SMILES: Cc1ccc(-c2ccc(S(=O)(=O)Nc3cc(F)c(C(=O)O)c(F)c3)cc2)cn1]

·TFA

Methyl 4-{[(4-bromophenyl)sulfonyl]amino}-2,6-difluorobenzoate (150 mg, 0.371 mmol) was dissolved in 1,4-dioxane (9.0 ml), and 2-picoline-5-boronic acid (120 mg, 0.777 mmol), [1,1'-bis(diphenylphosphino)ferrocene]dichloropalladium(II) (30.0 mg, 40.0 μmol), and a 1 M aqueous sodium carbonate solution (3.0 ml) were added thereto. This solution was degassed under reduced pressure, and purged with argon gas, followed by stirring at 80° C. for 3 hours. After the stirring, the solvent was removed by distillation, and the obtained residue was suspended in methanol (3.0 ml). The suspension was filtered, and the solvent was removed by distillation from the obtained residue. To this residue, tetrahydrofuran (4.0 ml), water (1.0 ml), and a 2 N aqueous sodium hydroxide solution (2.0 ml) were added, followed by stirring at 60° C. for 3 hours. After the reaction liquid was concentrated, purification was conducted by reversed-phase HPLC (H₂O containing 0.1% TFA/CH₃CN system) to obtain the TFA salt (112 mg, 0.277 mmol, 75%) of the title compound.

MS (ESI) m/z 405 (M+H)⁺

Example 34

Synthesis of M-34

2,6-Difluoro-4-({[4-(3-methylpyridin-4-yl)phenyl]sulfonyl}amino)benzoic Acid (M-34)

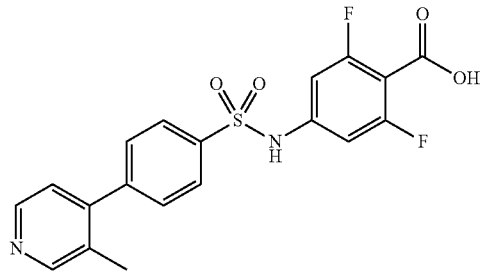

·TFA

Methyl 4-{[(4-bromophenyl)sulfonyl]amino}-2,6-difluorobenzoate (40.0 mg, 0.100 mmol) was dissolved in 1,4-dioxane (4.0 ml), and 3-picoline-4-boronic acid (30.0 mg, 0.219 mmol), [1,1'-bis(diphenylphosphino)ferrocene]dichloropalladium(II) (7.30 mg, 10.0 µmol), and a 1 M aqueous sodium carbonate solution (1.0 ml) were added thereto. This solution was degassed under reduced pressure, and purged with argon gas, followed by stirring at 80° C. for 3 hours. After the stirring, the solvent was removed by distillation from the reaction solution, and the obtained residue was suspended in methanol (3.0 ml). The suspension was filtered, and the solvent was removed by distillation from the obtained residue. To this residue, tetrahydrofuran (2.0 ml), water (0.5 ml), and a 2 N aqueous sodium hydroxide solution (1.0 ml) were added, followed by stirring at 50° C. for 3 hours. After the reaction liquid was concentrated, purification was conducted by reversed-phase HPLC ($H_2O$ containing 0.1% TFA/$CH_3CN$ system) to obtain the TFA salt (22.0 mg, 54.5 µmol, 55%) of the title compound.

MS (ESI) m/z 405 (M+H)$^+$

Example 35

Synthesis of M-35

2,6-Difluoro-4-({[4-(3-furyl)phenyl]sulfonyl}amino)benzoic Acid (M-35)

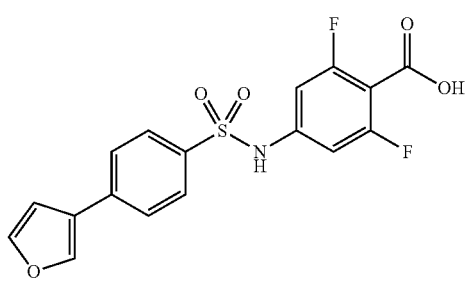 [SMILES: O=C(O)c1c(F)cc(NS(=O)(=O)c2ccc(-c3ccoc3)cc2)cc1F]

Methyl 4-{[(4-bromophenyl)sulfonyl]amino}-2,6-difluorobenzoate (150 mg, 0.372 mmol) was dissolved in 1,4-dioxane (15 ml), and 2-(furan-3-yl)-4,4,5,5-tetramethyl-1,3,2-dioxaborolane (158 mg, 0.814 mmol), [1,1'-bis(diphenylphosphino)ferrocene]dichloropalladium(II) (27.0 mg, 40.0 µmol), and a 1 M aqueous sodium carbonate solution (5.0 ml) were added thereto. This solution was degassed under reduced pressure, and purged with argon gas, followed by stirring at 85° C. for 3 hours. After the stirring, the solvent was removed by distillation, and the obtained residue was suspended in methanol (3.0 ml). The suspension was filtered, and the solvent was removed by distillation from the obtained residue. To this residue, tetrahydrofuran (4.0 ml), water (1.0 ml), and a 2 N aqueous sodium hydroxide solution (2.0 ml) were added, followed by stirring at 60° C. for 3 hours. After the reaction liquid was concentrated, purification was conducted by reversed-phase HPLC ($H_2O$ containing 0.1% TFA/$CH_3CN$ system) to obtain the title compound (100 mg, 0.264 mmol, 71%).

MS (ESI) m/z 380 (M+H)$^+$

Example 36

Synthesis of M-36

(Step 1) Methyl 4-{[(4-Bromophenyl)sulfonyl]amino}-2,6-difluorobenzoate

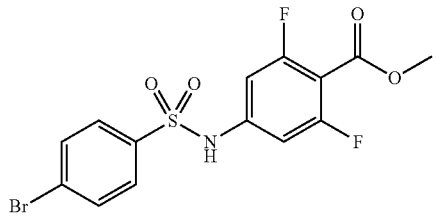 [SMILES: COC(=O)c1c(F)cc(NS(=O)(=O)c2ccc(Br)cc2)cc1F]

Methyl 4-amino-2,6-difluorobenzoate (5.00 g, 26.7 mmol) was dissolved in dichloromethane (100 ml), and p-bromobenzenesulfonyl chloride (7.50 g, 29.4 mmol) and pyridine (6.5 ml, 80 mmol) were added, followed by stirring at room temperature for 12 hours. The reaction solution was concentrated under reduced pressure, and purification was conducted by silica gel column chromatography (dichloromethane/methanol=95:5) to obtain the title compound (8.50 g, 21.0 mmol, 79%).

MS (ESI) m/z 406 (M+H)$^+$ (Step 2) 2,6-Difluoro-4-{[(4-pyridin-4-yl-phenyl)sulfonyl]amino}benzoic Acid (M-36)

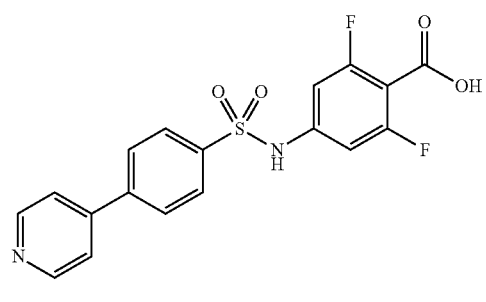

·TFA

Methyl 4-{[(4-bromophenyl)sulfonyl]amino}-2,6-difluorobenzoate (300 mg, 0.743 mmol) was dissolved in 1,4-dioxane (15 ml), and pyridine-4-boronic acid (200 mg, 1.63 mmol), [1,1'-bis(diphenylphosphino)ferrocene]dichloropalladium(II) (30.0 mg, 40.0 µmol), and a 1 M aqueous sodium carbonate solution (5.0 ml) were added. This solution was degassed under reduced pressure, and purged with argon gas, followed by stirring at 85° C. for 3 hours. After the stirring, the solvent was removed by distillation, and the obtained residue was suspended in methanol (3.0 ml). The suspension was filtered, and the solvent was removed by distillation from the obtained residue. To this residue, tetrahydrofuran (4.0 ml), water (1.0 ml), and a 2 N aqueous sodium hydroxide solution (2.0 ml) were added, followed by stirring at 60° C. for 3 hours. After the reaction liquid was concentrated under reduced pressure, purification was conducted by reversed-phase HPLC ($H_2O$ containing 0.1% TFA/$CH_3CN$ system) to obtain the TFA salt (182 mg, 0.467 mmol, 63%) of the title compound.

MS (ESI) m/z 391 (M+H)$^+$

Example 37

Synthesis of M-37

2,6-Difluoro-4-({[4-(2-fluoropyridin-4-yl)phenyl]sulfonyl}amino)benzoic Acid (M-37)

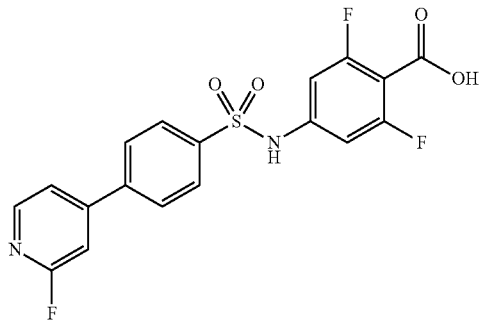

·TFA

Methyl 4-{[(4-bromophenyl)sulfonyl]amino}-2,6-difluorobenzoate (150 mg, 0.371 mmol) was dissolved in 1,4-dioxane (9.0 ml), and 2-fluoropyridine-4-boronic acid (110 mg, 0.777 mmol), [1,1'-bis(diphenylphosphino)ferrocene]dichloropalladium(II) (30.0 mg, 40.0 μmol), and a 1 M aqueous sodium carbonate solution (3.0 ml) were added thereto. This solution was degassed under reduced pressure, and purged with argon gas, followed by stirring at 80° C. for 3 hours. After the stirring, the solvent was removed by distillation, and the obtained residue was suspended in methanol (3.0 ml). The suspension was filtered, and the solvent was removed by distillation from the obtained residue. To this residue, tetrahydrofuran (4.0 ml), water (1.0 ml), and a 2 N aqueous sodium hydroxide solution (2.0 ml) were added, followed by stirring at 50° C. for 3 hours. After the reaction liquid was concentrated, purification was conducted by reversed-phase HPLC (H$_2$O containing 0.1% TFA/CH$_3$CN system) to obtain the TFA salt (114 mg, 0.279 mmol, 75%) of the title compound.

MS (ESI) m/z 409 (M+H)$^+$

Example 38

Synthesis of M-38

4-[({4-[1-(tert-Butoxycarbonyl)-1,2,3,6-tetrahydropyridin-4-yl]phenyl}sulfonyl)amino]-2,6-difluorobenzoic Acid (M-38)

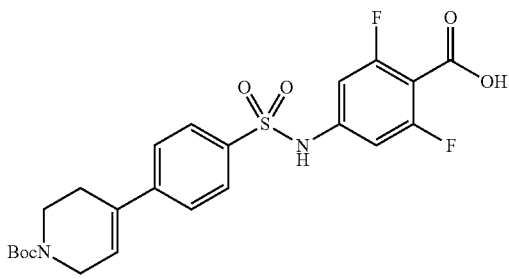 [SMILES: CC(C)(C)OC(=O)N1CC=C(c2ccc(S(=O)(=O)Nc3cc(F)c(C(=O)O)c(F)c3)cc2)CC1]

Methyl 4-{[(4-bromophenyl)sulfonyl]amino}-2,6-difluorobenzoate (150 mg, 0.371 mmol) was dissolved in 1,4-dioxane (9.0 ml), and 2-fluoropyridine-4-boronic acid (110 mg, 0.777 mmol), [1,1'-bis(diphenylphosphino) ferrocene] dichloropalladium(II) (30.0 mg, 40.0 μmol), and a 1 M aqueous sodium carbonate solution (3.0 ml) were added thereto. This solution was degassed under reduced pressure, and purged with argon gas, followed by stirring at 80° C. for 3 hours. After the stirring, the solvent was removed by distillation, and the obtained residue was suspended in methanol (3.0 ml). The suspension was filtered, and the solvent was removed by distillation from the obtained residue. To this residue, tetrahydrofuran (4.0 ml), water (1.0 ml), and a 2 N aqueous sodium hydroxide solution (2.0 ml) were added, followed by stirring at 50° C. for 3 hours. After the reaction liquid was concentrated, purification was conducted by reversed-phase HPLC (H$_2$O containing 0.1% TFA/CH$_3$CN system) to obtain the title compound (102 mg, 0.206 mmol, 56%).

MS (ESI) m/z 495 (M+H)$^+$

Example 39

Synthesis of A-1 and B-1

(Step 1) Methyl N-{2-Fluoro-4-[(pyridin-4-yl-sulfonyl)amino]benzoyl}-4-(1-methyl-2,4-dioxo-1,4-dihydropyrido[3,4-d]pyrimidin-3(2H)-yl)-L-phenylalaninate (B-1)

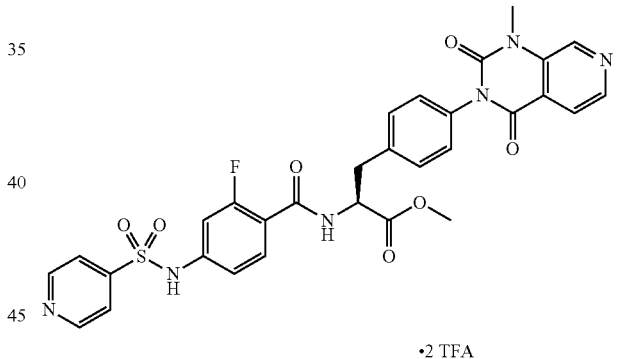

·2 TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2-fluoro-4-[(pyridin-4-yl-sulfonyl)amino]benzoic acid (M-6) (69.0 mg, 0.234 mmol) were suspended in methylene chloride (2.0 ml), and HATU (131 mg, 0.351 mmol) and diisopropylethylamine (0.160 ml, 0.920 mmol) were added thereto, followed by stirring at room temperature for 12 hours. After the reaction liquid was concentrated under reduced pressure, purification was conducted by reversed-phase HPLC (H$_2$O containing 0.1% TFA/CH$_3$CN system) to obtain the TFA salt (120 mg, 61%) of the title compound.

$^1$H NMR (d-DMSO, 400 MHz): δ 11.2 (s, 1H), 8.97 (s, 1H), 8.86 (dd, J=4.4, 1.6 Hz, 2H), 8.63 (dd, J=7.6, 2.0 Hz, 1H), 8.56 (d, J=4.8 Hz, 1H), 7.89 (dd, J=4.8, 0.4 Hz, 1H), 7.76 (dd, J=4.8, 1.6 Hz, 2H), 7.41 (t, J=8.0 Hz, 1H), 7.36 (d, J=8.4 Hz, 2H), 7.22 (d, J=8.4 Hz, 2H), 7.01-6.95 (m, 2H), 4.69-4.63 (m, 1H), 3.65 (s, 3H), 3.60 (s, 3H), 3.22-3.06 (m, 2H).; MS (ESI) m/z 633 (M+H)$^+$ (Step 2) N-{2-Fluoro-4-[(pyridin-4-yl-sulfonyl)amino]benzoyl}-4-(1-methyl-2,4-dioxo-1,4-dihydropyrido[3,4-d]pyrimidin-3(2H)-yl)-L-phenylalanine (A-1)

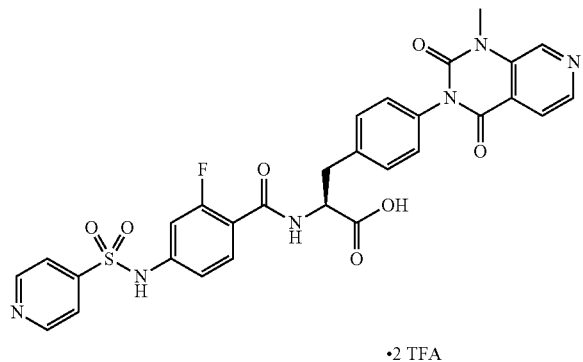 [SMILES: Cn1c(=O)n(-c2ccc(C[C@H](NC(=O)c3ccc(NS(=O)(=O)c4ccncc4)cc3F)C(=O)O)cc2)c(=O)c2ccncc21]

·2 TFA

To the TFA salt (60.0 mg, 70.0 μmol) of methyl N-{2-fluoro-4-[(pyridin-4-yl-sulfonyl)amino]benzoyl}-4-(1-methyl-2,4-dioxo-1,4-dihydropyrido[3,4-d]pyrimidin-3(2H)-yl)-L-phenylalaninate (B-1), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (45 mg, 76%) of the title compound.

¹H NMR (d-DMSO, 400 MHz): δ 11.1 (s, 1H), 8.90 (s, 1H), 8.79 (d, J=6.0 Hz, 2H), 8.49 (d, J=5.2 Hz, 1H), 8.38 (d, J=5.6 Hz, 1H), 7.82 (d, J=5.2 Hz, 1H), 7.69 (d, J=6.0 Hz, 2H), 7.36 (t, J=8.0 Hz, 1H), 7.30 (d, J=8.0 Hz, 2H), 7.14 (d, J=8.0 Hz, 2H), 6.94-6.88 (m, 2H), 4.57-4.52 (m, 1H), 3.53 (s, 3H), 3.17-3.00 (m, 2H).; MS (ESI) m/z 619 (M+H)⁺

Example 40

Synthesis of A-2 and B-2

(Step 1) Methyl N-(2,6-Difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalaninate (B-2)

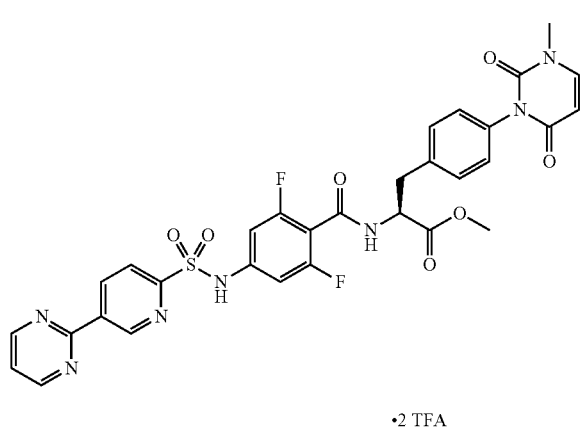 [SMILES: COC(=O)[C@H](Cc1ccc(-n2c(=O)ccn(C)c2=O)cc1)NC(=O)c1c(F)cc(NS(=O)(=O)c2ccc(-c3ncccn3)cn2)cc1F]

·2 TFA

Methyl 4-(3-methyl-2,6-dioxo-3,6-dihydropyrimidin-1(2H)-yl)-L-phenylalaninate (M-2) (80 mg, 0.24 mmol) and 2,6-difluoro-4-{[(5-pyrimidin-2-yl-pyridin-2-yl)sulfonyl]amino}benzoic acid (M-7) (103 mg, 0.240 mmol) were suspended in methylene chloride (2.0 ml), and HATU (137 mg, 0.360 mmol) and diisopropylethylamine (0.167 ml, 0.96 mmol) were added thereto, followed by stirring at room temperature for 2 hours. After the reaction liquid was concentrated under reduced pressure, purification was conducted by reversed-phase HPLC (H₂O containing 0.1% TFA/CH₃CN system) to obtain the TFA salt (80 mg, 37%) of the title compound as a white solid.

¹H NMR (d-DMSO, 400 MHz): δ 11.4 (s, 1H), 9.58 (dd, J=2.4, 0.8 Hz, 1H), 9.16 (d, J=7.6 Hz, 1H), 9.01 (d, J=4.8 Hz, 2H), 8.95 (dd, J=8.0, 2.0 Hz, 1H), 8.28 (dd, J=8.4, 0.8 Hz, 1H), 7.75 (d, J=8.0 Hz, 1H), 7.60 (t, J=4.8 Hz, 1H), 7.29 (d, J=8.4 Hz, 2H), 7.09 (d, J=8.0 Hz, 2H), 6.89 (d, J=9.2 Hz, 2H), 5.74 (d, J=7.6 Hz, 1H), 4.62-4.57 (m, 1H), 3.62 (s, 3H), 3.30 (s, 3H), 3.14-2.97 (m, 2H).; MS (ESI) m/z 678 (M+H)⁺

(Step 2) N-(2,6-Difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalanine (A-2)

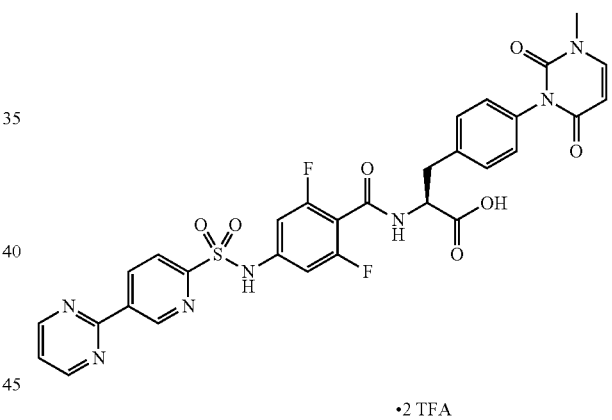

·2 TFA

To the TFA salt (60.0 mg, 66.0 μmol) of methyl N-(2,6-difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalaninate (B-2), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (42.3 mg, 72%) of the title compound as a white solid.

1H NMR (d-DMSO, 400 MHz): δ 11.46 (s, 1H), 9.64 (dd, J=2.1, 0.7 Hz, 1H), 9.09 (d, J=8.0 Hz, 1H), 9.06 (d, J=4.9 Hz, 2H), 9.01 (dd, J=8.2, 2.1 Hz, 1H), 8.33 (dd, J=8.2, 0.7 Hz, 1H), 7.81 (d, J=7.9 Hz, 1H), 7.66 (t, J=4.9 Hz, 1H), 7.36 (d, J=8.4 Hz, 2H), 7.14 (d, J=8.4 Hz, 2H), 6.94 (d, J=9.2 Hz, 2H), 5.80 (d, J=7.9 Hz, 1H), 4.68-4.55 (m, 1H), 3.36 (s, 3H), 3.19 (dd, J=14.2, 4.6 Hz, 1H), 3.02 (dd, J=14.2, 9.7 Hz, 1H).; MS (ESI) m/z 664 (M+H)⁺

Example 41

Synthesis of A-3 and B-3

(Step 1) Methyl N-(2,6-Difluoro-4-{[(4-pyrimidin-2-yl-phenyl)sulfonyl]amino}benzoyl)-4-(1-methyl-2,4-dioxo-1,4-dihydropyrido[3,4-d]pyrimidin-3(2H)-yl)-L-phenylalaninate (B-3)

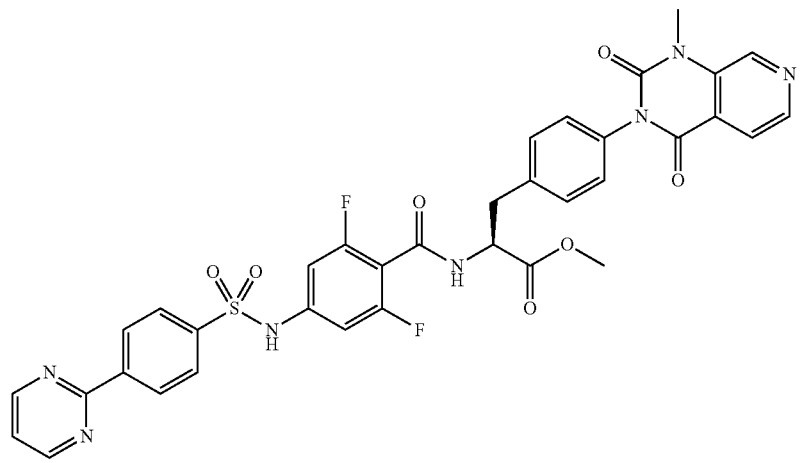

·2 TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-{[(4-pyrimidin-2-yl-phenyl)sulfonyl]amino}benzoic acid (M-8) (90.0 mg, 0.230 mmol) were suspended in methylene chloride (2.0 ml), and HATU (133 mg, 0.351 mmol) and diisopropylethylamine (0.160 ml, 0.920 mmol) were added thereto, followed by stirring at room temperature for 12 hours. After the reaction liquid was concentrated under reduced pressure, purification was conducted by reversed-phase HPLC (H₂O containing 0.1% TFA/CH₃CN system) to obtain the TFA salt (100 mg, 45%) of the title compound as a white solid.

$^1$H NMR (d-DMSO, 400 MHz): δ 11.2 (s, 1H), 9.16 (d, J=7.6 Hz, 1H), 8.97 (s, 2H), 8.95 (s, 1H), 8.59-8.02 (m, 3H), 8.03 (dd, J=6.8, 1.6 Hz, 2H), 7.88 (d, J=4.4 Hz, 1H), 7.54 (t, J=4.8 Hz, 1H), 7.33 (d, J=8.4 Hz, 2H), 7.20 (d, J=8.4 Hz, 2H), 6.82 (d, J=8.8 Hz, 2H), 4.65-4.59 (m, 1H), 3.63 (s, 3H), 3.59 (s, 3H), 3.17-2.98 (m, 2H).; MS (ESI) m/z 728 (M+H)$^+$ (Step 2) N-(2,6-Difluoro-4-{[(4-pyrimidin-2-yl-phenyl)sulfonyl]amino}benzoyl)-4-(1-methyl-2,4-dioxo-1,4-dihydropyrido[3,4-d]pyrimidin-3(2H)-yl)-L-phenylalanine (A-3)

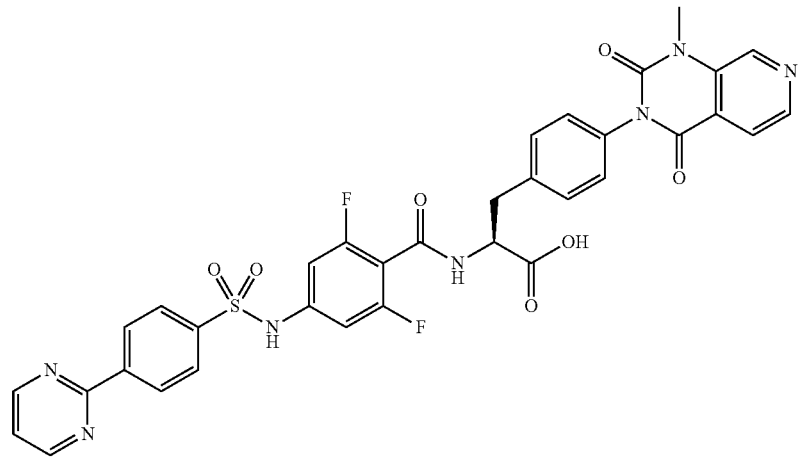

·2 TFA

To the TFA salt (80 mg, 84 μmol) of methyl N-(2,6-difluoro-4-{[(4-pyrimidin-2-yl-phenyl)sulfonyl]amino}benzoyl)-4-(1-methyl-2,4-dioxo-1,4-dihydropyrido[3,4-d]pyrimidin-3(2H)-yl)-L-phenylalaninate (B-3), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (52.7 mg, 67%) of the title compound.

1H NMR (d-DMSO, 400 MHz): δ 11.18 (s, 1H), 9.03 (d, J=7.9 Hz, 1H), 8.96 (d, J=4.9 Hz, 3H), 8.61-8.53 (m, 3H), 8.06-7.99 (m, 2H), 7.88 (dd, J=5.0, 0.6 Hz, 1H), 7.54 (t, J=4.9 Hz, 1H), 7.34 (d, J=8.4 Hz, 2H), 7.20 (d, J=8.4 Hz, 2H), 6.81 (d, J=9.1 Hz, 2H), 4.70-4.28 (m, 1H), 3.59 (s, 3H), 3.16 (dd, J=14.0, 4.7 Hz, 1H), 2.98 (dd, J=14.2, 9.8 Hz, 1H).; MS (ESI) m/z 714 (M+H)⁺

Example 42

Synthesis of A-4 and B-4

(Step 1) Methyl N-{4-[(2,4'-Bipyridin-5-yl-sulfonyl)amino]-2,6-difluorobenzoyl}-4-(1-methyl-2,4-dioxo-1,4-dihydropyrido[3,4-d]pyrimidin-3(2H)-yl)-L-phenylalaninate (B-4)

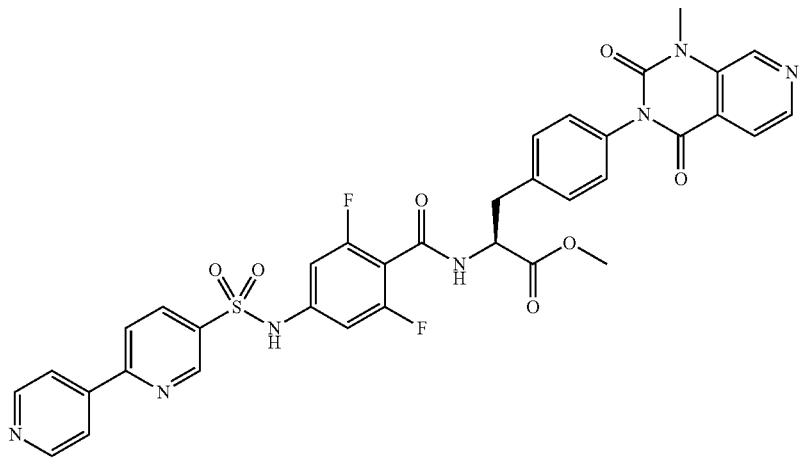

·3 TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 4-[(2,4'-bipyridin-5-yl-sulfonyl)amino]-2,6-difluorobenzoic acid (M-9) (90.0 mg, 0.230 mmol) were suspended in methylene chloride (1.0 ml), and HATU (133 mg, 0.351 mmol) and diisopropylethylamine (0.160 ml, 0.920 mmol) were added thereto, followed by stirring at room temperature for 2 hours. After the reaction liquid was concentrated under reduced pressure, purification was conducted by reversed-phase HPLC (H₂O containing 0.1% TFA/CH₃CN system) to obtain the TFA salt (105 mg, 43%) of the title compound as a white solid.

¹H NMR (d-DMSO, 400 MHz): δ 11.5 (s, 1H), 9.27-9.24 (m, 2H), 9.03 (s, 1H), 8.90 (dd, J=4.8, 1.6 Hz, 2H), 8.62 (d, J=4.8 Hz, 1H), 8.52-8.46 (m, 2H), 8.30 (dd, J=4.8, 1.2 Hz, 2H), 7.94 (dd, J=4.8, 0.4 Hz, 1H), 7.40 (d, J=8.4 Hz, 2H), 7.27 (d, J=8.4 Hz, 2H), 6.95 (d, J=8.8 Hz, 2H), 4.72-4.67 (m, 1H), 3.70 (s, 3H), 3.65 (s, 3H), 3.23-3.01 (m, 2H).; MS (ESI) m/z 728 (M+H)⁺

(Step 2) N-{4-[(2,4'-Bipyridin-5-yl-sulfonyl)amino]-2,6-difluorobenzoyl}-4-(1-methyl-2,4-dioxo-1,4-dihydropyrido[3,4-d]pyrimidin-3(2H)-yl)-L-phenylalanine (A-4)

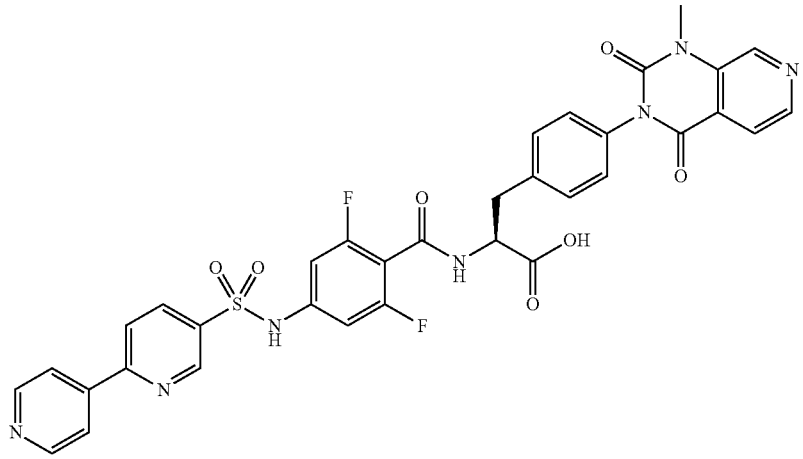

·3 TFA

To the TFA salt (85 mg, 79 μmol) of methyl N-{4-[(2,4'-bipyridin-5-yl-sulfonyl)amino]-2,6-difluorobenzoyl}-4-(1-methyl-2,4-dioxo-1,4-dihydropyrido[3,4-d]pyrimidin-3(2H)-yl)-L-phenylalaninate (B-4), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC ($H_2O$ containing 0.1% TFA/$CH_3CN$ system) to obtain the TFA salt (51.5 mg, 62%) of the title compound.

1H NMR (d-DMSO, 400 MHz): δ 11.34 (s, 1H), 9.16-9.06 (m, 1H), 9.00 (d, J=7.9 Hz, 1H), 8.90 (s, 1H), 8.81-8.70 (m, 2H), 8.49 (d, J=4.9 Hz, 1H), 8.42-8.29 (m, 2H), 8.25-8.09 (m, 2H), 7.81 (d, J=5.0 Hz, 1H), 7.28 (d, J=8.4 Hz, 2H), 7.13 (d, J=8.4 Hz, 2H), 6.81 (d, J=8.9 Hz, 2H), 4.58-4.43 (m, 1H), 4141414141413.53 (s, 3H), 3.10 (dd, J=14.2, 4.4 Hz, 1H), 2.92 (dd, J=14.2, 9.8 Hz, 1H).; MS (ESI) m/z 714 $(M+H)^+$

Example 43

Synthesis of A-5 and B-5

(Step 1) Methyl N-[2,6-difluoro-4-({[4-(1H-pyrrol-1-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-5)

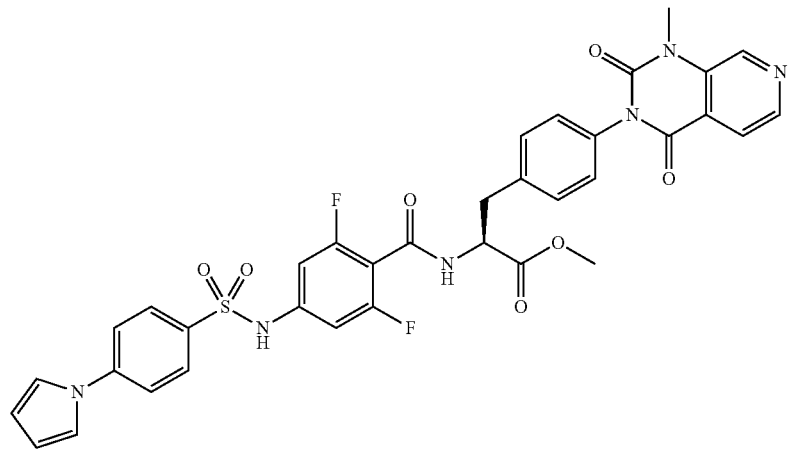

·TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-({[4-(1H-pyrrol-1-yl)phenyl]sulfonyl}amino)benzoic acid (M-10) (87.0 mg, 0.230 mmol) were suspended in methylene chloride (2.0 ml), and HATU (133 mg, 0.351 mmol) and diisopropylethylamine (0.160 ml, 0.920 mmol) were added thereto, followed by stirring at room temperature for 20 hours. After the reaction liquid was concentrated under reduced pressure, purification was conducted by reversed-phase HPLC (H$_2$O containing 0.1% TFA/CH$_3$CN system) to obtain the TFA salt (100 mg, 46%) of the title compound as a white solid.

$^1$H NMR (d-DMSO, 400 MHz): δ 11.1 (s, 1H), 9.17 (d, J=7.6 Hz, 1H), 8.97 (s, 1H), 8.55 (d, J=5.2 Hz, 1H), 7.92-7.88 (m, 3H), 7.83 (dd, J=6.8, 2.0 Hz, 2H), 7.50 (t, J=2.0 Hz, 2H), 7.33 (d, J=8.4 Hz, 2H), 7.21 (d, J=8.4 Hz, 2H), 6.82 (d, J=9.2 Hz, 2H), 6.32 (t, J=2.0 Hz, 2H), 4.65-4.60 (m, 1H), 3.63 (s, 3H), 3.60 (s, 3H), 3.16-2.99 (m, 2H).; MS (ESI) m/z 715 (M+H)$^+$ (Step 2) N-[2,6-Difluoro-4-({[4-(1H-pyrrol-1-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-5)

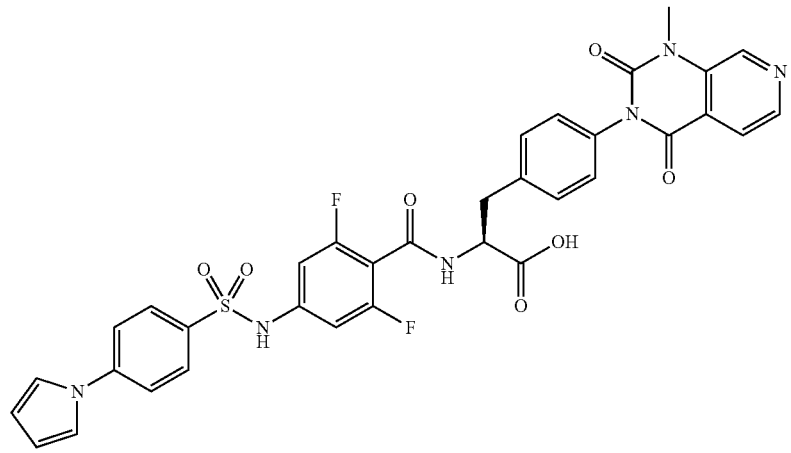

To the TFA salt (80 mg, 85 μmol) of methyl N-[2,6-difluoro-4-({[4-(1H-pyrrol-1-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-5), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H$_2$O containing 0.1% TFA/CH$_3$CN system) to obtain the TFA salt (41.0 mg, 52%) of the title compound.

1H NMR (d-DMSO, 400 MHz): δ 11.07 (s, 1H), 9.04 (d, J=7.9 Hz, 1H), 8.97 (s, 1H), 8.56 (d, J=4.9 Hz, 1H), 7.94-7.87 (m, 3H), 7.83 (d, J=8.9 Hz, 2H), 7.59-7.44 (m, 2H), 7.35 (d, J=8.3 Hz, 2H), 7.21 (d, J=8.3 Hz, 2H), 6.81 (d, J=9.1 Hz, 2H), 6.40-6.23 (m, 2H), 4.66-4.46 (m, 1H), 3.60 (s, 3H), 3.17 (dd, J=14.1, 4.3 Hz, 1H), 2.99 (dd, J=14.1, 9.9 Hz, 1H).; MS (ESI) m/z 701 (M+H)$^+$

Example 44

Synthesis of A-6

(Step 2) N-{4-[({4-[(Ethylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-6)

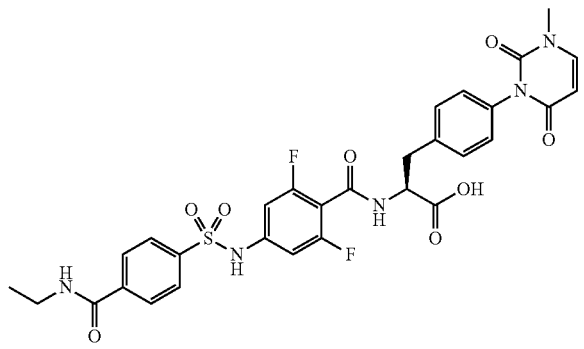 [SMILES: CCNC(=O)c1ccc(S(=O)(=O)Nc2cc(F)c(C(=O)N[C@@H](Cc3ccc(-n4c(=O)ccn(C)c4=O)cc3)C(=O)O)c(F)c2)cc1]

Methyl 4-(3-methyl-2,6-dioxo-3,6-dihydropyrimidin-1(2H)-yl)-L-phenylalaninate (M-2) (100 mg, 0.290 mmol) and 4-[({4-[(ethylamino)carbonyl]phenyl}sulfonyl)amino]-2,6-difluorobenzoic acid (M-11) (111 mg, 0.290 mmol) were suspended in methylene chloride (2.0 ml), and HATU (165 mg, 0.440 mmol) and diisopropylethylamine (0.202 ml, 1.16 mmol) were added thereto, followed by stirring at room temperature for 16 hours. After the reaction liquid was concentrated under reduced pressure, purification was conducted by reversed-phase HPLC (H$_2$O containing 0.1% TFA/CH$_3$CN system). To the obtained white solid, a 4 N hydrogen chloride/dioxane solution (3.0 ml) and water (2.0 ml) were added, followed by stirring at 80° C. for 1 hour. After the reaction liquid was concentrated under reduced pressure, purification was conducted by reversed-phase HPLC (H$_2$O containing 0.1% TFA/CH$_3$CN system) to obtain the title compound (80.0 mg, 42%) as a white solid.

1H NMR (d-DMSO, 400 MHz): δ 12.85 (s, 1H), 11.14 (s, 1H), 9.04 (d, J=7.8 Hz, 1H), 8.67 (d, J=5.4 Hz, 1H), 8.01-7.91 (m, 4H), 7.75 (d, J=7.9 Hz, 1H), 7.30 (d, J=8.4 Hz, 2H), 7.09 (d, J=8.4 Hz, 2H), 6.78 (d, J=9.1 Hz, 2H), 5.74 (d, J=7.9 Hz, 1H), 4.60-4.49 (m, 1H), 3.34-3.22 (m, 5H), 3.14 (dd, J=14.3, 4.6 Hz, 1H), 2.96 (dd, J=14.3, 9.7 Hz, 1H), 1.10 (t, J=7.2 Hz, 3H).; MS (ESI) m/z 656 (M+H)$^+$

Example 45

Synthesis of A-7 and B-7

(Step 1) Methyl N-{4-[({4-[(Cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (B-7)

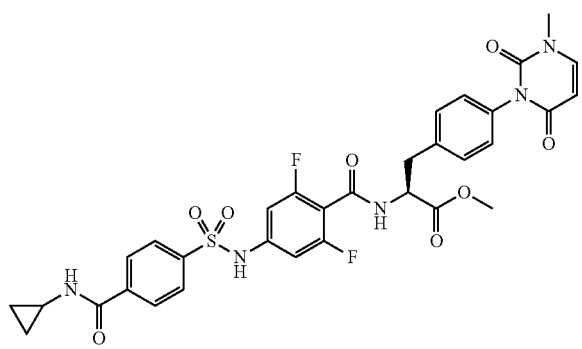 [SMILES: COC(=O)[C@H](Cc1ccc(-n2c(=O)ccn(C)c2=O)cc1)NC(=O)c1c(F)cc(NS(=O)(=O)c2ccc(C(=O)NC3CC3)cc2)cc1F]

Methyl 4-(3-methyl-2,6-dioxo-3,6-dihydropyrimidin-1(2H)-yl)-L-phenylalaninate (M-2) (77.0 mg, 0.230 mmol) and 4-[({4-[(cyclopropylamino)carbonyl]phenyl}sulfonyl)amino]-2,6-difluorobenzoic acid (M-12) (75.0 mg, 0.190 mmol) were suspended in methylene chloride (2.0 ml), and HATU (108 mg, 0.290 mmol) and diisopropylethylamine (0.132 ml, 0.760 mmol) were added, followed by stirring at room temperature for 20 hours. After the reaction liquid was concentrated under reduced pressure, purification was conducted by reversed-phase HPLC (H$_2$O containing 0.1% TFA/CH$_3$CN system) to obtain the TFA salt (80.0 mg, 62%) of the title compound as a white solid.

$^1$H NMR (d-DMSO, 400 MHz): δ 11.2 (s, 1H), 9.17 (d, J=7.6 Hz, 1H), 8.64 (d, J=4.4 Hz, 1H), 7.96-7.91 (m, 4H), 7.75 (d, J=8.0 Hz, 1H), 7.29 (d, J=8.4 Hz, 2H), 7.09 (d, J=8.4 Hz, 2H), 6.79 (d, J=9.2 Hz, 2H), 5.74 (d, J=8.0 Hz, 1H), 4.63-4.57 (m, 1H), 3.63 (s, 3H), 3.31 (s, 3H), 3.14-2.97 (m, 2H), 2.86-2.80 (m, 1H), 0.71-0.69 (m, 2H), 0.57-0.53 (m, 2H).; MS (ESI) m/z 682 (M+H)$^+$ (Step 2) N-{4-[({4-[(Cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-7)

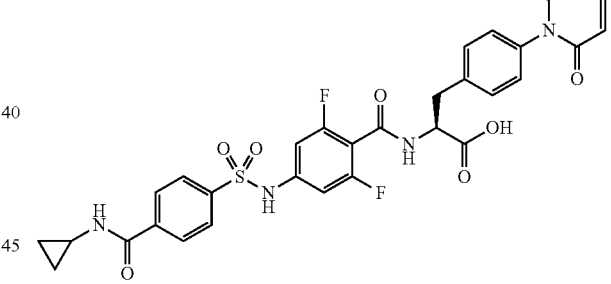

To the TFA salt (60 mg, 88 μmol) of methyl N-{4-[({4-[(cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (B-7), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H$_2$O containing 0.1% TFA/CH$_3$CN system) to obtain the title compound (32.4 mg, 55%).

1H NMR (d-DMSO, 400 MHz): δ 11.14 (s, 1H), 9.04 (d, J=7.8 Hz, 1H), 8.64 (d, J=4.3 Hz, 1H), 8.03-7.86 (m, 4H), 7.75 (d, J=7.9 Hz, 1H), 7.30 (d, J=8.3 Hz, 2H), 7.09 (d, J=8.3 Hz, 2H), 6.78 (d, J=9.0 Hz, 2H), 5.74 (d, J=7.9 Hz, 1H), 4.61-4.47 (m, 1H), 3.31 (s, 3H), 3.14 (dd, J=14.2, 4.5 Hz, 1H), 2.96 (dd, J=14.2, 9.8 Hz, 1H), 2.88-2.78 (m, 1H), 0.74-0.63 (m, 2H), 0.60-0.50 (m, 2H).; MS (ESI) m/z 668 (M+H)$^+$

Example 46

Synthesis of A-8

(Step 2) N-(2,6-Difluoro-4-{[(4-pyrimidin-2-yl-phenyl)sulfonyl]amino}benzoyl)-4-(6-methoxy-1-methyl-2,4-dioxo-1,4-dihydropyrido[3,4-d]pyrimidin-3(2H)-yl)-L-phenylalanine (A-8)

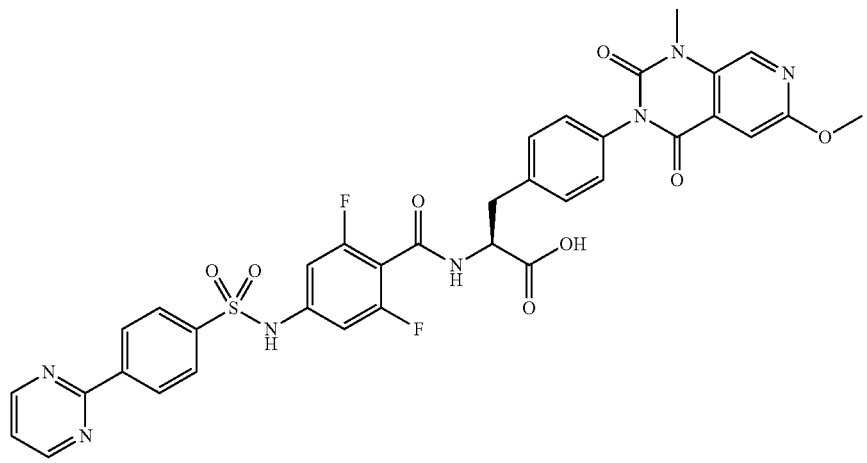

·2 TFA

Methyl 4-(6-methoxy-1-methyl-2,4-dioxo-1,4-dihydropyrido[3,4-d]pyrimidin-3(2H)-yl)-L-phenylalaninate (M-3) (100 mg, 0.220 mmol) and 2,6-difluoro-4-{[(4-pyrimidin-2-yl-phenyl)sulfonyl]amino}benzoic acid (M-8) (65.0 mg, 0.170 mmol) were suspended in methylene chloride (2.0 ml), and HATU (125 mg, 0.330 mmol) and diisopropylethylamine (0.153 ml, 0.880 mmol) were added thereto, followed by stirring at room temperature for 1 hour. After the reaction liquid was concentrated under reduced pressure, purification was conducted by reversed-phase HPLC ($H_2O$ containing 0.1% TFA/$CH_3CN$ system). To the obtained compound, a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC ($H_2O$ containing 0.1% TFA/$CH_3CN$ system) to obtain the TFA salt (18.0 mg, 11% over two steps) of the title compound as a white solid.

1H NMR (d-DMSO, 400 MHz): δ 11.18 (s, 1H), 9.03 (d, J=7.8 Hz, 1H), 8.96 (d, J=4.9 Hz, 2H), 8.58 (d, J=8.6 Hz, 2H), 8.53 (s, 1H), 8.02 (d, J=8.6 Hz, 2H), 7.53 (t, J=4.9 Hz, 1H), 7.33 (d, J=8.3 Hz, 2H), 7.26 (s, 1H), 7.19 (d, J=8.3 Hz, 2H), 6.82 (d, J=9.1 Hz, 2H), 4.64-4.45 (m, 1H), 3.93 (s, 3H), 3.54 (s, 3H), 3.16 (dd, J=14.2, 4.3 Hz, 1H), 2.98 (dd, J=14.1, 9.9 Hz, 1H).; MS (ESI) m/z 744 (M+H)$^+$

Example 47

Synthesis of A-9 and B-9

(Step 1) Methyl N-[2,6-Difluoro-4-({[4-(1H-1,2,4-triazol-1-yl)phenyl]sulfonyl}amino)benzoyl]-4-[6-(dimethylamino)-1-methyl-2,4-dioxo-1,4-dihydroquinazolin-3(2H)-yl]-L-phenylalaninate (B-9)

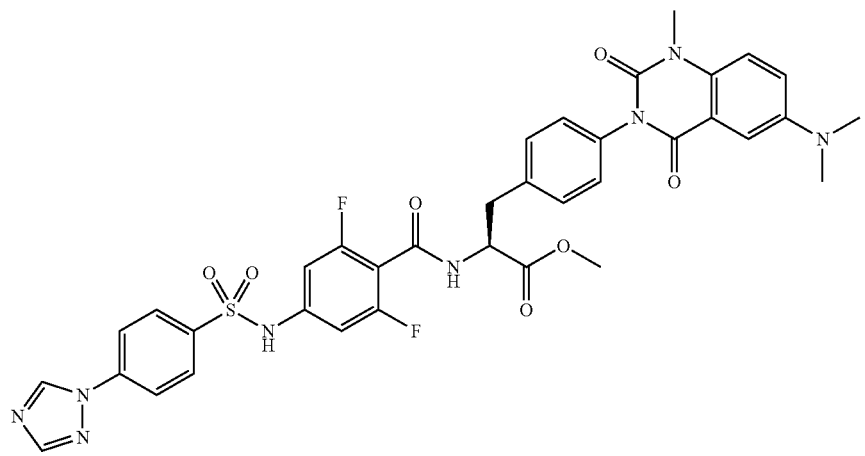

·2 TFA

Methyl 4-(3-methyl-2,6-dioxo-3,6-dihydropyrimidin-1 (2H)-yl)-L-phenylalaninate (80.0 mg, 0.170 mmol) and 2,6-difluoro-4-({[4-(1H-1,2,4-triazol-1-yl)phenyl]sulfonyl}amino)benzoic acid (M-13) (65.0 mg, 0.170 mmol) were suspended in methylene chloride (2.0 ml), and HATU (97.0 mg, 0.260 mmol) and diisopropylethylamine (0.118 ml, 0.680 mmol) were added thereto, followed by stirring at room temperature for 2 hours. After the reaction liquid was concentrated under reduced pressure, purification was conducted by reversed-phase HPLC (H$_2$O containing 0.1% TFA/CH$_3$CN system) to obtain the TFA salt (100 mg, 67%) of the title compound as a yellow solid.

$^1$H NMR (d-DMSO, 400 MHz): δ 11.2 (s, 1H), 9.41 (s, 1H), 9.19 (d, J=7.6 Hz, 1H), 8.30 (s, 1H), 8.11 (dd, J=6.8, 2.4 Hz, 2H), 8.05 (dd, J=6.8, 2.4 Hz, 2H), 7.41-7.27 (m, 5H), 7.17 (d, J=8.0 Hz, 2H), 6.83 (d, J=9.2 Hz, 2H), 4.65-4.60 (m, 1H), 3.63 (s, 3H), 3.49 (s, 3H), 3.16-2.99 (m, 2H), 2.95 (s, 6H).; MS (ESI) m/z 759 (M+H)$^+$ (Step 2) N-[2,6-Difluoro-4-({[4-(1H-1,2,4-triazol-1-yl)phenyl]sulfonyl}amino)benzoyl]-4-[6-(dimethylamino)-1-methyl-2,4-dioxo-1,4-dihydroquinazolin-3(2H)-yl]-L-phenylalanine (A-9)

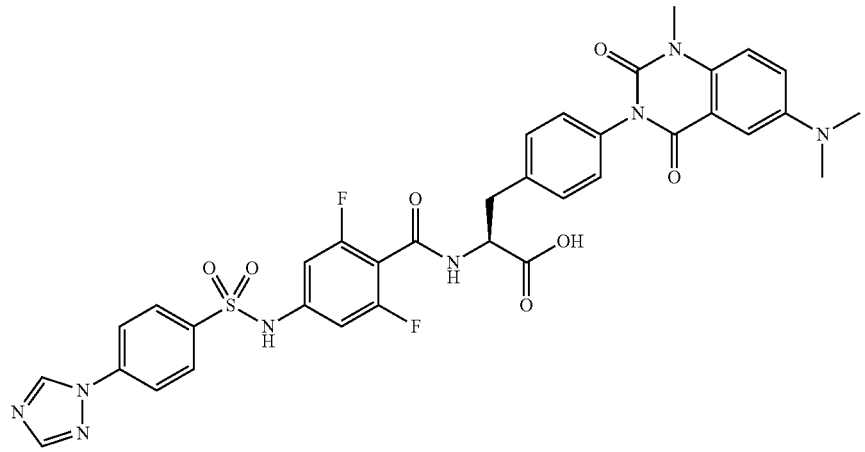

•2 TFA

To the TFA salt (80 mg, 92 μmol) of methyl N-[2,6-difluoro-4-({[4-(1H-1,2,4-triazol-1-yl)phenyl]sulfonyl}amino)benzoyl]-4-[6-(dimethylamino)-1-methyl-2,4-dioxo-1,4-dihydroquinazolin-3(2H)-yl]-L-phenylalaninate (B-9), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H$_2$O containing 0.1% TFA/CH$_3$CN system) to obtain the TFA salt (58.2 mg, 74%) of the title compound.

1H NMR (d-DMSO, 400 MHz): δ 11.18 (s, 1H), 9.40 (s, 1H), 9.06 (d, J=7.9 Hz, 1H), 8.30 (s, 1H), 8.16-8.08 (m, 2H), 8.08-8.00 (m, 2H), 7.45-7.30 (m, 5H), 7.17 (d, J=8.3 Hz, 2H), 6.83 (d, J=9.0 Hz, 2H), 4.69-4.44 (m, 1H), 3.50 (s, 3H), 3.16 (dd, J=14.2, 4.4 Hz, 1H), 3.05-2.93 (m, 7H).; MS (ESI) m/z 745 (M+H)$^+$

Example 48

Synthesis of A-10 and B-10

(Step 1) Methyl N-[2,6-Difluoro-4-({[4-(1H-imidazol-2-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-10)

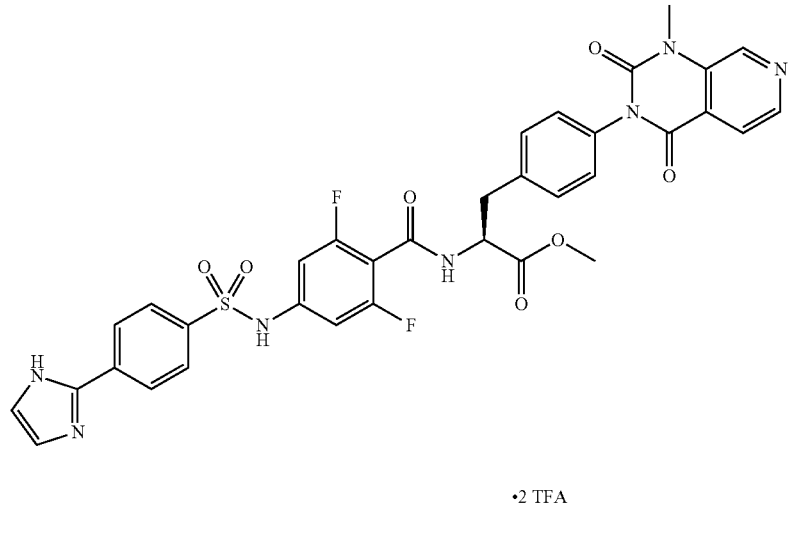 [SMILES: COC(=O)[C@H](Cc1ccc(-n2c(=O)c3ccncc3n(C)c2=O)cc1)NC(=O)c1c(F)cc(NS(=O)(=O)c2ccc(-c3ncc[nH]3)cc2)cc1F]

·2 TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-({[4-(1H-imidazol-2-yl)phenyl]sulfonyl}amino)benzoic acid (M-14) (87.0 mg, 0.234 mmol) were suspended in methylene chloride (2.0 ml), and HATU (133 mg, 0.351 mmol) and diisopropylethylamine (0.160 ml, 0.920 mmol) were added thereto, followed by stirring at room temperature for 17 hours. After the reaction liquid was concentrated under reduced pressure, purification was conducted by reversed-phase HPLC (H$_2$O containing 0.1% TFA/CH$_3$CN system) to obtain the TFA salt (120 mg, 55%) of the title compound as a white solid.

$^1$H NMR (d-DMSO, 400 MHz): δ 11.2 (s, 1H), 9.20 (d, J=7.6 Hz, 1H), 8.98 (s, 1H), 8.56 (d, J=4.8 Hz, 1H), 8.16 (d, J=8.8 Hz, 2H), 8.09 (d, J=8.4 Hz, 2H), 7.94 (d, J=8.4 Hz, 1H), 7.81-7.75 (m, 2H), 7.34 (d, J=8.4 Hz, 2H), 7.21 (d, J=8.4 Hz, 2H), 6.83 (d, J=9.2 Hz, 2H), 4.66-4.60 (m, 1H), 3.63 (s, 3H), 3.60 (s, 3H), 3.17-2.99 (m, 2H).; MS (ESI) m/z 716 (M+H)$^+$ (Step 2) N-[2,6-Difluoro-4-({[4-(1H-imidazol-2-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-10)

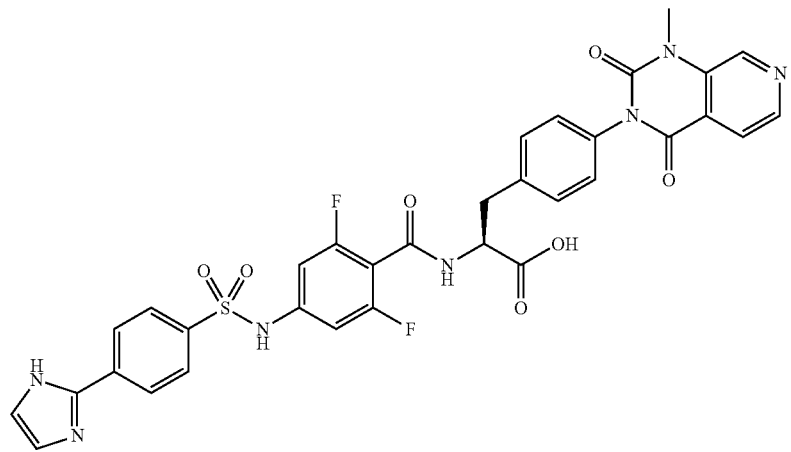

·2 TFA

To the TFA salt (100 mg, 0.110 mmol) of methyl N-[2,6-difluoro-4-({[4-(1H-imidazol-2-yl)phenyl]sulfonyl}amino)benzoyl]-4-(1-methyl-2,4-dioxo-1,4-dihydropyrido[3,4-d]pyrimidin-3(2H)-yl)-L-phenylalaninate (A-10), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (54.9 mg, 54%) of the title compound.

1H NMR (d-DMSO, 400 MHz): δ 11.24 (s, 1H), 9.07 (d, J=7.8 Hz, 1H), 8.97 (s, 1H), 8.56 (d, J=4.9 Hz, 1H), 8.16 (d, J=8.5 Hz, 2H), 8.09 (d, J=8.6 Hz, 2H), 7.88 (d, J=4.9 Hz, 1H), 7.76 (s, 2H), 7.35 (d, J=8.4 Hz, 2H), 7.20 (d, J=8.4 Hz, 2H), 6.82 (d, J=9.0 Hz, 2H), 4.62-4.51 (m, 1H), 3.60 (s, 3H), 3.14 (dd, J=15.2, 4.4 Hz, 1H), 2.99 (dd, J=14.2, 9.9 Hz, 1H).; MS (ESI) m/z 702 (M+H)⁺

Example 49

Synthesis of A-11

(Step 2) N-[2,6-Difluoro-4-({[4-(2-methylpyridin-4-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-11)

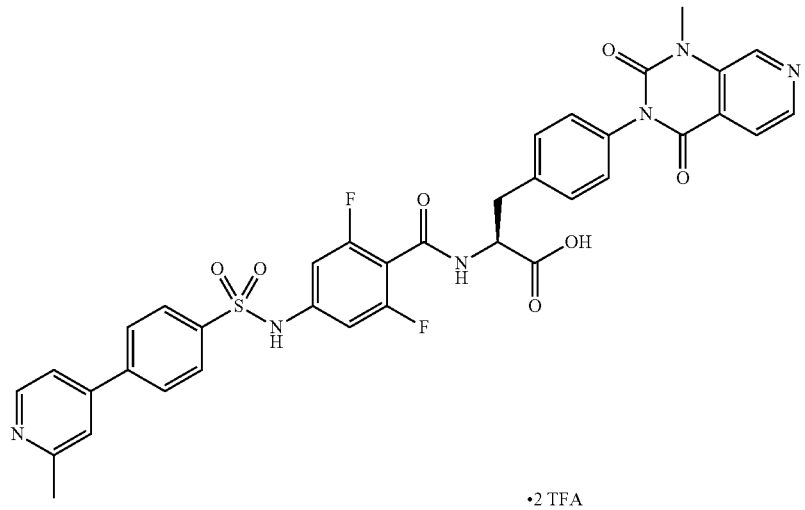 [SMILES: Cc1cc(-c2ccc(S(=O)(=O)Nc3cc(F)c(C(=O)N[C@@H](Cc4ccc(-n5c(=O)c6ccncc6n(C)c5=O)cc4)C(=O)O)c(F)c3)cc2)ccn1]

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-({[4-(2-methylpyridin-4-yl)phenyl]sulfonyl}amino)benzoic acid (M-32) (93.0 mg, 0.234 mmol) were suspended in methylene chloride (2.0 ml), and HATU (133 mg, 0.351 mmol) and diisopropylethylamine (0.160 ml, 0.920 mmol) were added thereto, followed by stirring at room temperature for 17 hours. After the reaction liquid was concentrated under reduced pressure, purification was conducted by reversed-phase HPLC (H₂O containing 0.1% TFA/CH₃CN system). To the obtained compound, a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (40.0 mg, 18%) of the title compound as a white solid.

1H NMR (d-DMSO, 400 MHz): δ 11.22 (s, 1H), 9.07 (d, J=7.9 Hz, 1H), 8.97 (s, 1H), 8.73 (d, J=5.7 Hz, 1H), 8.55 (d, J=4.9 Hz, 1H), 8.11 (d, J=8.6 Hz, 2H), 8.06-7.98 (m, 3H), 7.95-7.81 (m, 2H), 7.35 (d, J=8.4 Hz, 2H), 7.20 (d, J=8.4 Hz, 2H), 6.83 (d, J=9.0 Hz, 2H), 4.61-4.53 (m, 1H), 3.60 (s, 3H), 3.17 (dd, J=14.1, 4.4 Hz, 1H), 2.98 (dd, J=14.1, 9.9 Hz, 1H), 2.64 (s, 3H).; MS (ESI) m/z 727 (M+H)⁺

Example 50

Synthesis of A-12 and Synthesis of B-12

(Step 1) Methyl N-[2,6-Difluoro-4-({[4-(6-methyl-pyridin-3-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-12)

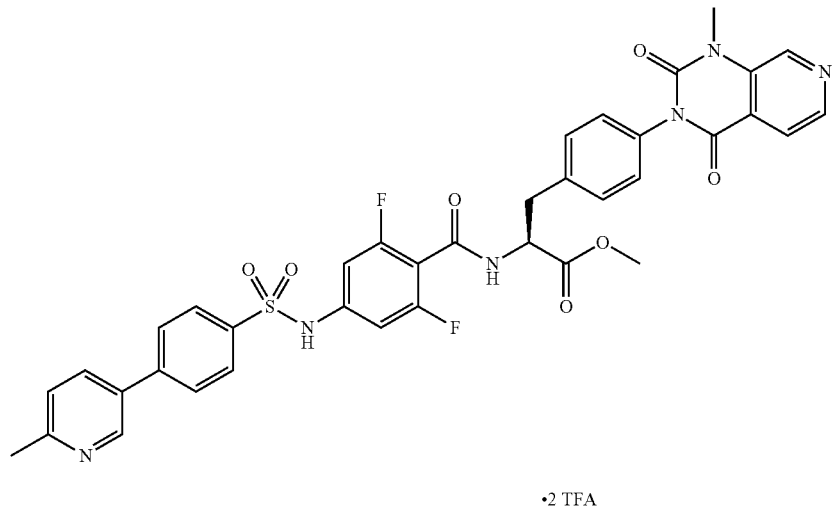 [SMILES: COC(=O)[C@H](Cc1ccc(-n2c(=O)c3ccncc3n(C)c2=O)cc1)NC(=O)c1c(F)cc(NS(=O)(=O)c2ccc(-c3ccc(C)nc3)cc2)cc1F]

•2 TFA

Methyl 4-(1-methyl-2,4-dioxo-1,4-dihydropyrido[3,4-d]pyrimidin-3(2H)-yl)-L-phenylalaninate (M-1) (75.0 mg, 0.180 mmol) and 2,6-difluoro-4-({[4-(6-methylpyridin-3-yl)phenyl]sulfonyl}amino)benzoic acid (M-33) (73.0 mg, 0.180 mmol) were suspended in methylene chloride (2.0 ml), and HATU (91.0 mg, 0.240 mmol) and diisopropylethylamine (0.111 ml, 0.640 mmol) were added thereto, followed by stirring at room temperature for 1 hour. After the reaction liquid was concentrated under reduced pressure, purification was conducted by reversed-phase HPLC (H$_2$O containing 0.1% TFA/CH$_3$CN system) to obtain the TFA salt (70.0 mg, 40%) of the title compound as a white solid.

$^1$H NMR (d-DMSO, 400 MHz): δ 11.2 (s, 1H), 9.14 (d, J=7.6 Hz, 1H), 8.90-8.88 (m, 2H), 8.49 (d, J=5.2 Hz, 1H), 8.27 (d, J=7.6 Hz, 1H), 7.95-7.91 (m, 4H), 7.82 (d, J=5.2 Hz, 1H), 7.56 (d, J=8.0 Hz, 1H), 7.27 (d, J=8.4 Hz, 2H), 7.14 (d, J=8.4 Hz, 2H), 6.78 (d, J=9.2 Hz, 2H), 4.59-4.53 (m, 1H), 3.57 (s, 3H), 3.53 (s, 3H), 3.10-2.92 (m, 2H), 2.54 (s, 3H).; MS (ESI) m/z 741 (M+H)$^+$ (Step 2) N-[2,6-Difluoro-4-({[4-(6-methylpyridin-3-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-12)

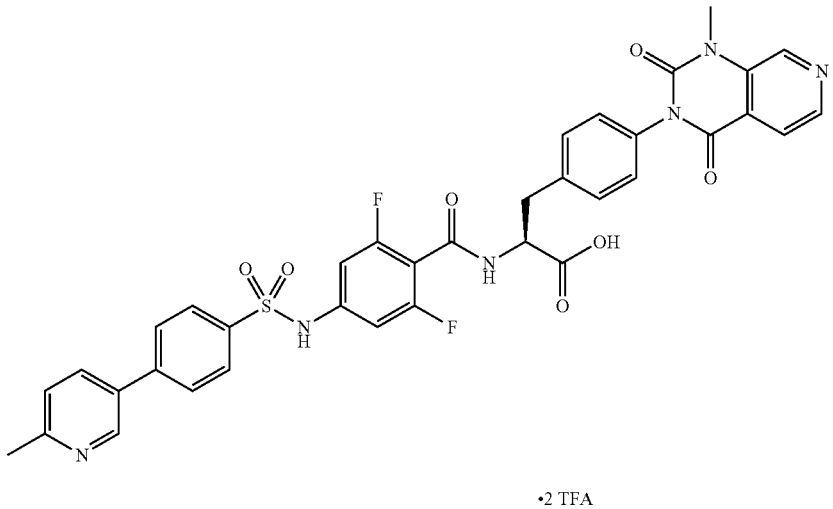 [SMILES: Cc1ccc(-c2ccc(S(=O)(=O)Nc3cc(F)c(C(=O)N[C@@H](Cc4ccc(-n5c(=O)c6ccncc6n(C)c5=O)cc4)C(=O)O)c(F)c3)cc2)cn1]

•2 TFA

To the TFA salt (50.0 mg, 52.0 μmol) of methyl N-[2,6-difluoro-4-({[4-(6-methylpyridin-3-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-12), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (30.8 mg, 62%) of the title compound.

1H NMR (d-DMSO, 400 MHz): δ 11.12 (s, 1H), 9.00 (d, J=7.9 Hz, 1H), 8.90 (s, 1H), 8.87 (s, 1H), 8.49 (d, J=4.9 Hz, 1H), 8.24 (d, J=8.3 Hz, 1H), 7.98-7.89 (m, 4H), 7.82 (d, J=4.9 Hz, 1H), 7.53 (d, J=8.0 Hz, 1H), 7.28 (d, J=8.3 Hz, 2H), 7.13 (d, J=8.4 Hz, 2H), 6.76 (d, J=9.1 Hz, 2H), 4.56-4.43 (m, 1H), 3.53 (s, 3H), 3.10 (dd, J=14.1, 4.4 Hz, 1H), 2.91 (dd, J=14.2, 9.9 Hz, 1H), 2.53 (s, 3H).; MS (ESI) m/z 727 (M+H)⁺

Example 51

Synthesis of A-13 and B-13

(Step 1) Isopropyl N-[2,6-Difluoro-4-({[4-(1H-1,2,3-triazol-1-yl)phenyl]sulfonyl}amino)benzoyl]-4-(6-methoxy-1-methyl-2,4-dioxo-1,4-dihydroquinazolin-3(2H)-yl)-L-phenylalaninate (B-13)

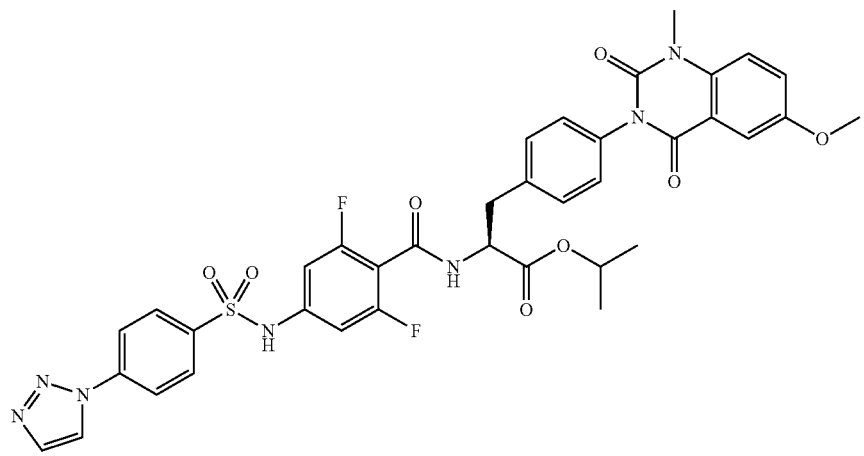

·TFA

Isopropyl 4-(6-methoxy-1-methyl-2,4-dioxo-1,4-dihydroquinazolin-3(2H)-yl)-L-phenylalaninate (M-4) (82.0 mg, 0.200 mmol) and 2,6-difluoro-4-({[4-(1H-1,2,3-triazol-1-yl)phenyl]sulfonyl}amino)benzoic acid (M-15) (76.0 mg, 0.200 mmol) were suspended in methylene chloride (2.0 ml), and HATU (111 mg, 0.290 mmol) and diisopropylethylamine (0.136 ml, 0.780 mmol) were added thereto, followed by stirring at room temperature for 18 hours. After the reaction liquid was concentrated under reduced pressure, purification was conducted by reversed-phase HPLC (H₂O containing 0.1% TFA/CH₃CN system) to obtain the TFA salt (80.0 mg, 52%) of the title compound.

¹H NMR (d-DMSO, 400 MHz): δ 11.2 (s, 1H), 9.16 (d, J=7.6 Hz, 1H), 8.94 (d, J=1.2 Hz, 1H), 8.18 (dd, J=6.8, 2.0 Hz, 2H), 8.09 (dd, J=6.8, 2.0 Hz, 2H), 8.02 (d, J=1.2 Hz, 1H), 7.49-7.42 (m, 3H), 7.33 (d, J=8.4 Hz, 2H), 7.18 (d, J=8.4 Hz, 2H), 6.85 (d, J=8.8 Hz, 2H), 4.91-4.85 (m, 1H), 4.56-4.51 (m, 1H), 3.83 (s, 3H), 3.51 (s, 3H), 3.12-2.99 (m, 2H), 1.17 (d, J=6.0 Hz, 3H), 1.12 (d, J=6.4 Hz, 3H).; MS (ESI) m/z 774 (M+H)+

(Step 2) N-[2,6-Difluoro-4-({[4-(1H-1,2,3-triazol-1-yl)phenyl]sulfonyl}amino)benzoyl]-4-(6-methoxy-1-methyl-2,4-dioxo-1,4-dihydroquinazolin-3(2H)-yl)-L-phenylalanine (A-13)

1H NMR (d-DMSO, 400 MHz): δ 11.21 (s, 1H), 9.06 (d, J=7.9 Hz, 1H), 8.93 (d, J=1.2 Hz, 1H), 8.22-8.14 (m, 2H), 8.12-8.05 (m, 2H), 8.01 (d, J=1.2 Hz, 1H), 7.51-7.41 (m, 3H), 7.33 (d, J=8.4 Hz, 2H), 7.18 (d, J=8.4 Hz, 2H), 6.83 (d, J=9.0 Hz, 2H), 4.62-4.53 (m, 1H), 3.83 (s, 3H), 3.51 (s, 3H), 3.20-3.14 (m, 1H), 2.98 (dd, J=14.2, 9.8 Hz, 1H).; MS (ESI) m/z 732 (M+H)+

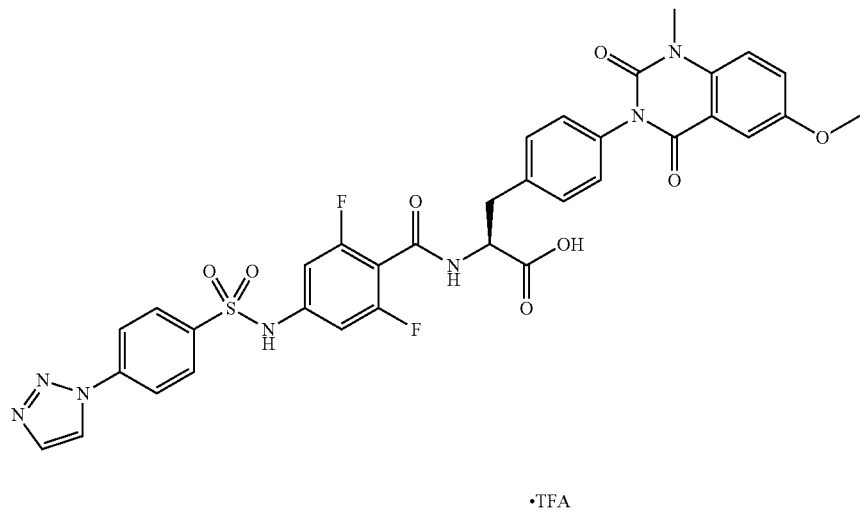 [SMILES: COc1ccc2c(c1)c(=O)n(-c1ccc(C[C@H](NC(=O)c3c(F)cc(NS(=O)(=O)c4ccc(-n5ccnn5)cc4)cc3F)C(=O)O)cc1)c(=O)n2C]

·TFA

To the TFA salt (20.0 mg, 26.0 μmol) of isopropyl N-[2,6-difluoro-4-({[4-(1H-1,2,3-triazol-1-yl)phenyl]sulfonyl}amino)benzoyl]-4-(6-methoxy-1-methyl-2,4-dioxo-1,4-dihydroquinazolin-3(2H)-yl)-L-phenylalaninate (B-13), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (11.9 mg, 63%) of the title compound.

Example 52

Synthesis of A-14 and B-14

(Step 1) Methyl N-{2-Fluoro-4-[({4-[(methylamino)methyl]phenyl}sulfonyl)amino]benzoyl}-4-(1-methyl-2,4-dioxo-1,4-dihydropyrido[3,4-d]pyrimidin-3(2H)-yl)-L-phenylalaninate (B-14)

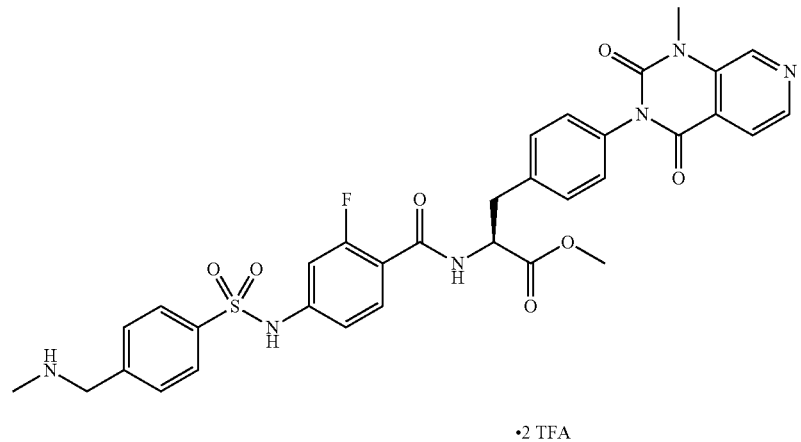 [SMILES: CNCc1ccc(S(=O)(=O)Nc2ccc(C(=O)N[C@@H](Cc3ccc(-n4c(=O)c5ccncc5n(C)c4=O)cc3)C(=O)OC)c(F)c2)cc1]

·2 TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 4-{[(4-{[(tert-butoxycarbonyl)(methyl)amino]methyl}phenyl)sulfonyl]amino}-2-fluorobenzoic acid (M-19) (101 mg, 0.230 mmol) were suspended in methylene chloride (2.0 ml), and HATU (131 mg, 0.350 mmol) and diisopropylethylamine (0.160 ml, 0.920 mmol) were added thereto, followed by stirring at room temperature for 19 hours. After the reaction liquid was concentrated under reduced pressure, trifluoroacetic acid (2.0 ml) was added thereto, followed by stirring at room temperature for 30 minutes. After the reaction liquid was concentrated under reduced pressure, purification was conducted by reversed-phase HPLC (H$_2$O containing 0.1% TFA/CH$_3$CN system) to obtain the TFA salt (120 mg, 58%) of the title compound as a white solid.

$^1$H NMR (d-DMSO, 400 MHz): δ 11.0 (s, 1H), 8.98 (s, 1H), 8.79 (br, 1H), 8.60 (dd, J=7.6, 2.0 Hz, 1H), 8.56 (d, J=4.8 Hz, 1H), 7.92 (d, J=8.0 Hz, 2H), 7.89 (d, J=4.8 Hz, 1H), 7.66 (d, J=8.4 Hz, 2H), 7.43-7.35 (m, 3H), 7.22 (d, J=8.4 Hz, 2H), 7.01-6.94 (m, 2H), 4.67-4.63 (m, 1H), 4.17 (t, J=5.6 Hz, 2H), 3.66 (s, 3H), 3.60 (s, 3H), 3.22-3.06 (m, 2H), 2.57 (t, J=5.2 Hz, 3H).; MS (ESI) m/z 675 (M+H)$^+$ (Step 2) N-{2-Fluoro-4-[({4-[(methylamino)methyl]phenyl}sulfonyl)amino]benzoyl}-4-(1-methyl-2,4-dioxo-1,4-dihydropyrido[3,4-d]pyrimidin-3(2H)-yl)-L-phenylalanine (A-14)

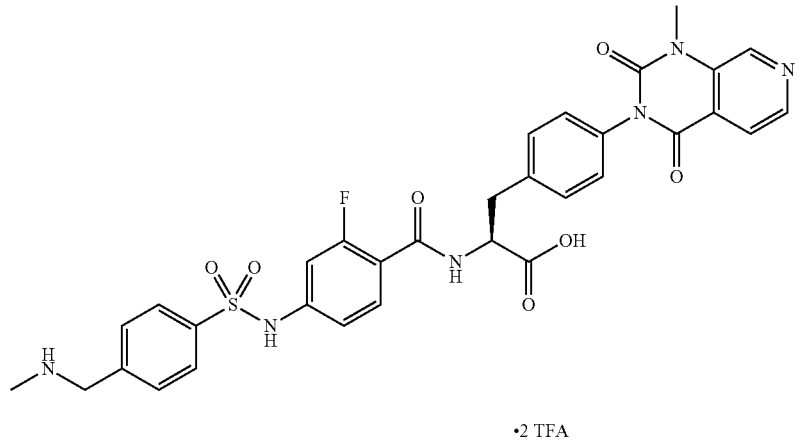 [SMILES: CNCc1ccc(S(=O)(=O)Nc2ccc(C(=O)N[C@@H](Cc3ccc(-n4c(=O)c5ccncc5n(C)c4=O)cc3)C(=O)O)c(F)c2)cc1]

•2 TFA

To the TFA salt (100 mg, 0.110 mmol) of methyl N-{2-fluoro-4-[({4-[(methylamino)methyl]phenyl}sulfonyl)amino]benzoyl}-4-(1-methyl-2,4-dioxo-1,4-dihydropyrido[3,4-d]pyrimidin-3(2H)-yl)-L-phenylalaninate (B-14), a 4 N hydrogen chloride/dioxane solution (2.0 ml) and water (2.0 ml) were added, followed by stirring at 70° C. for 2 hours. After the reaction liquid was concentrated under reduced pressure, purification was conducted by reversed-phase HPLC (H$_2$O containing 0.1% TFA/CH$_3$CN system) to obtain the TFA salt (89.5 mg, 92%) of the title compound as a white solid.

1H NMR (d-DMSO, 400 MHz): δ 11.03 (s, 1H), 8.98 (s, 1H), 8.87 (s, 2H), 8.56 (d, J=4.9 Hz, 1H), 8.41 (dd, J=7.8, 2.8 Hz, 1H), 7.96-7.83 (m, 3H), 7.66 (d, J=8.4 Hz, 2H), 7.42 (t, J=8.4 Hz, 1H), 7.37 (d, J=8.3 Hz, 2H), 7.22 (d, J=8.3 Hz, 2H), 7.04-6.92 (m, 2H), 4.66-4.55 (m, 1H), 4.17 (s, 2H), 3.60 (s, 3H), 3.22 (dd, J=14.0, 4.4 Hz, 1H), 3.08 (dd, J=14.0, 9.9 Hz, 1H), 2.57 (s, 3H).; MS (ESI) m/z 661 (M+H)$^+$

Example 53

Synthesis of A-15 and B-15

(Step 1) Methyl N-[2,6-Difluoro-4-({[4-(3-thienyl)phenyl]sulfonyl}amino)benzoyl]-4-(1-methyl-2,4-dioxo-1,4-dihydropyrido[3,4-d]pyrimidin-3(2H)-yl)-L-phenylalaninate (B-15)

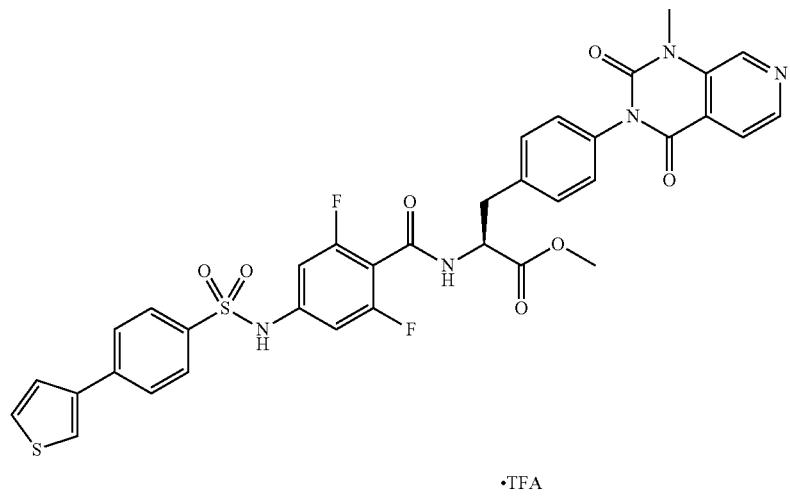 [SMILES: COC(=O)[C@H](Cc1ccc(-n2c(=O)c3ccncc3n(C)c2=O)cc1)NC(=O)c1c(F)cc(NS(=O)(=O)c2ccc(-c3ccsc3)cc2)cc1F]

·TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-({[4-(3-thienyl)phenyl]sulfonyl}amino)benzoic acid (M-20) (91.0 mg, 0.234 mmol) were suspended in methylene chloride (2.0 ml), and HATU (133 mg, 0.350 mmol) and diisopropylethylamine (0.160 ml, 0.920 mmol) were added thereto, followed by stirring at room temperature for 1 hour. After the reaction liquid was concentrated under reduced pressure, purification was conducted by reversed-phase HPLC (H₂O containing 0.1% TFA/CH₃CN system) to obtain the TFA salt (150 mg, 77%) of the title compound as a white solid.

$^1$H NMR (d-DMSO, 400 MHz): δ 11.2 (s, 1H), 9.23 (d, J=7.6 Hz, 1H), 9.03 (s, 1H), 9.26 (d, J=4.8 Hz, 1H), 8.14 (dd, J=2.8, 1.2 Hz, 1H), 8.02 (d, J=8.4 Hz, 2H), 7.95-7.93 (m, 3H), 7.76 (dd, J=4.8, 0.8 Hz, 1H), 7.68 (dd, J=4.8, 1.2 Hz, 1H), 7.39 (d, J=8.4 Hz, 2H), 7.27 (d, J=8.4 Hz, 2H), 6.88 (d, J=9.2 Hz, 2H), 4.71-4.65 (m, 1H), 3.69 (s, 3H), 3.66 (s, 3H), 3.17-3.04 (m, 2H).; MS (ESI) m/z 732 (M+H)⁺

(Step 2) N-[2,6-Difluoro-4-({[4-(3-thienyl)phenyl]sulfonyl}amino)benzoyl]-4-(1-methyl-2,4-dioxo-1,4-dihydropyrido[3,4-d]pyrimidin-3(2H)-yl)-L-phenylalanine (A-15)

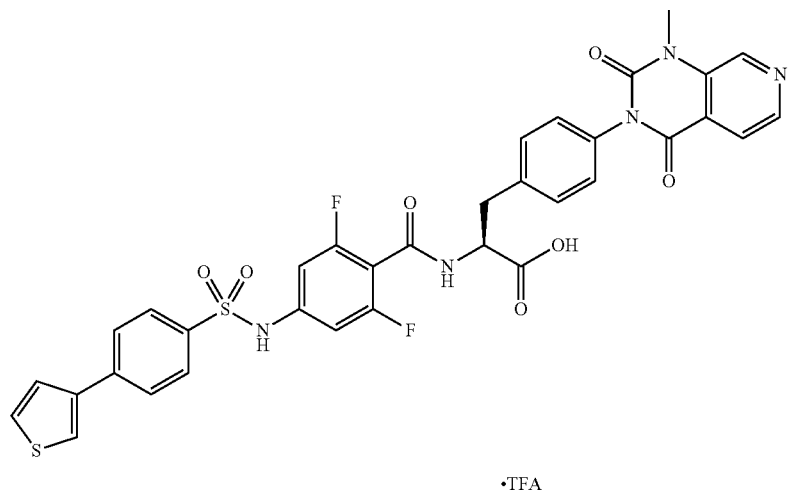 [SMILES: Cn1c(=O)n(-c2ccc(C[C@H](NC(=O)c3c(F)cc(NS(=O)(=O)c4ccc(-c5ccsc5)cc4)cc3F)C(=O)O)cc2)c(=O)c2ccncc21]

·TFA

To the TFA salt (130 mg, 0.150 mmol) of methyl N-[2,6-difluoro-4-({[4-(3-thienyl)phenyl]sulfonyl}amino)benzoyl]-4-(1-methyl-2,4-dioxo-1,4-dihydropyrido[3,4-d]pyrimidin-3 (2H)-yl)-L-phenylalaninate (B-15), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (95.6 mg, 73%) of the title compound.

1H NMR (d-DMSO, 400 MHz): δ 11.02 (s, 1H), 8.97 (d, J=7.9 Hz, 1H), 8.90 (s, 1H), 8.49 (d, J=4.9 Hz, 1H), 8.01 (dd, J=2.8, 1.3 Hz, 1H), 7.89 (d, J=8.6 Hz, 2H), 7.85-7.76 (m, 3H), 7.62 (dd, J=5.0, 2.9 Hz, 1H), 7.55 (dd, J=5.1, 1.2 Hz, 1H), 7.28 (d, J=8.3 Hz, 2H), 7.13 (d, J=8.3 Hz, 2H), 6.74 (d, J=9.1 Hz, 2H), 4.57-4.43 (m, 1H), 3.53 (s, 3H), 3.10 (dd, J=14.2, 4.4 Hz, 1H), 2.91 (dd, J=14.1, 9.9 Hz, 1H).; MS (ESI) m/z 718 (M+H)⁺

Example 54

Synthesis of A-16

(Step 2) N-(2,6-Difluoro-4-{[(5-pyrimidin-5-yl-pyridin-2-yl)sulfonyl]amino}benzoyl)-4-(1-methyl-2,4-dioxo-1,4-dihydropyrido[3,4-d]pyrimidin-3(2H)-yl)-L-phenylalanine (A-16)

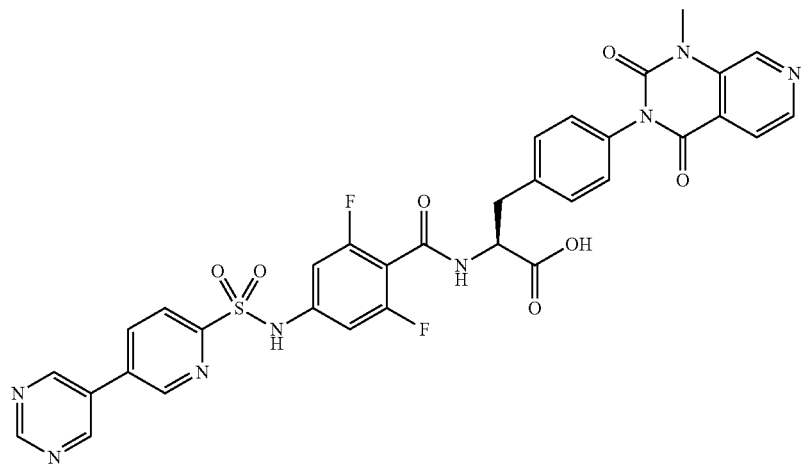

•3 TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-{[(5-pyrimidin-5-yl-pyridin-2-yl)sulfonyl]amino}benzoic acid (M-21) (99.0 mg, 0.234 mmol) were suspended in methylene chloride (2.0 ml), and HATU (133 mg, 0.350 mmol) and diisopropylethylamine (0.160 ml, 0.920 mmol) were added thereto, followed by stirring at room temperature for 3 days. After the reaction liquid was concentrated under reduced pressure, purification was conducted by reversed-phase HPLC (H₂O containing 0.1% TFA/CH₃CN system). To the obtained compound, a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (150 mg, 62%) of the title compound as a yellow solid.

1H NMR (d-DMSO, 400 MHz): δ 11.41 (s, 1H), 9.28 (d, J=1.3 Hz, 3H), 9.20 (dd, J=2.3, 0.7 Hz, 1H), 9.07 (d, J=7.9 Hz, 1H), 8.97 (s, 1H), 8.61-8.50 (m, 2H), 8.26 (dd, J=8.2, 0.7 Hz, 1H), 7.89 (dd, J=5.0, 0.5 Hz, 1H), 7.35 (d, J=8.4 Hz, 2H), 7.21 (d, J=8.4 Hz, 2H), 6.91 (d, J=9.2 Hz, 2H), 4.62-4.49 (m, 1H), 3.60 (s, 3H), 3.17 (dd, J=14.2, 4.3 Hz, 1H), 2.99 (dd, J=14.1, 9.9 Hz, 1H).; MS (ESI) m/z 715 (M+H)⁺

Example 55

Synthesis of A-17 and B-17

(Step 1) Methyl N-[2,6-Difluoro-4-({[6-(1H-1,2,4-triazol-1-yl)pyridin-3-yl]sulfonyl}amino)benzoyl]-4-(1-methyl-2,4-dioxo-1,4-dihydropyrido[3,4-d]pyrimidin-3(2H)-yl)-L-phenylalaninate (B-17)

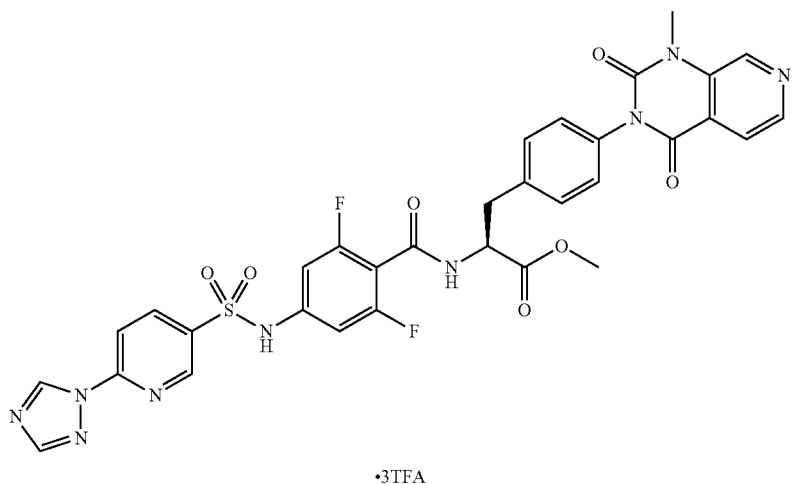 [SMILES: COC(=O)[C@H](Cc1ccc(-n2c(=O)c3ccncc3n(C)c2=O)cc1)NC(=O)c1c(F)cc(NS(=O)(=O)c2ccc(-n3cncn3)nc2)cc1F]

·3TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-({[6-(1H-1,2,4-triazol-1-yl)pyridin-3-yl]sulfonyl}amino)benzoic acid (M-22) (88.0 mg, 0.230 mmol) were suspended in methylene chloride (1.0 ml), and HATU (133 mg, 0.350 mmol) and diisopropylethylamine (0.160 ml, 0.920 mmol) were added thereto, followed by stirring at room temperature for 2 hours. After the reaction liquid was concentrated under reduced pressure, purification was conducted by reversed-phase HPLC ($H_2O$ containing 0.1% TFA/$CH_3CN$ system) to obtain the TFA salt (150 mg, 69%) of the title compound as a white solid.

$^1$H NMR (d-DMSO, 400 MHz): δ 11.4 (s, 1H), 9.51 (s, 1H), 9.26 (d, J=7.6 Hz, 1H), 9.03 (s, 2H), 8.62 (d, J=5.2 Hz, 1H), 8.55 (dd, J=8.8, 2.4 Hz, 1H), 8.44 (s, 1H), 8.14 (dd, J=8.8, 0.4 Hz, 1H), 7.95 (dd, J=5.2, 0.4 Hz, 1H), 7.40 (d, J=8.4 Hz, 2H), 7.27 (d, J=8.4 Hz, 2H), 6.93 (d, J=9.2 Hz, 2H), 4.73-4.67 (m, 1H), 3.70 (s, 3H), 3.66 (s, 3H), 3.21 (dd, J=14.0, 9.2 Hz, 1H), 3.09 (dd, J=14.4, 10.0 Hz, 1H).; MS (ESI) m/z 718 (M+H)$^+$ (Step 2) N-[2,6-Difluoro-4-({[6-(1H-1,2,4-triazol-1-yl)pyridin-3-yl]sulfonyl}amino)benzoyl]-4-(1-methyl-2,4-dioxo-1,4-dihydropyrido[3,4-d]pyrimidin-3(2H)-yl)-L-phenylalanine (A-17)

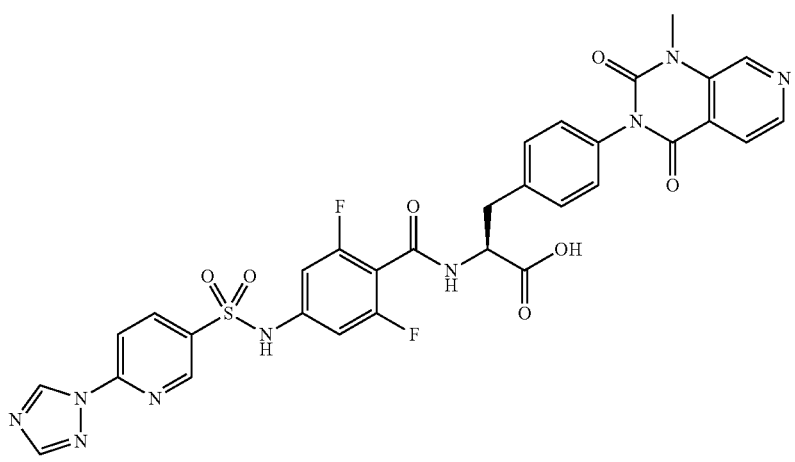

·3TFA

To the TFA salt (130 mg, 0.140 mmol) of methyl N-[2,6-difluoro-4-({[6-(1H-1,2,4-triazol-1-yl)pyridin-3-yl]sulfonyl}amino)benzoyl]-4-(1-methyl-2,4-dioxo-1,4-dihydropyrido[3,4-d]pyrimidin-3(2H)-yl)-L-phenylalaninate (B-17), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC ($H_2O$ containing 0.1% TFA/$CH_3CN$ system) to obtain the TFA salt (106 mg, 81%) of the title compound.

1H NMR (d-DMSO, 400 MHz): δ 11.28 (s, 1H), 9.38 (s, 1H), 9.00 (d, J=7.9 Hz, 1H), 8.95-8.84 (m, 2H), 8.49 (d, J=4.9 Hz, 1H), 8.42 (dd, J=8.7, 2.4 Hz, 1H), 8.31 (s, 1H), 8.01 (dd, J=8.7, 0.6 Hz, 1H), 7.82 (dd, J=5.0, 0.5 Hz, 1H), 7.28 (d, J=8.4 Hz, 2H), 7.13 (d, J=8.4 Hz, 2H), 6.79 (d, J=8.9 Hz, 2H), 4.59-4.45 (m, 1H), 3.53 (s, 3H), 3.10 (dd, J=14.2, 4.4 Hz, 1H), 2.92 (dd, J=14.2, 9.8 Hz, 1H).; MS (ESI) m/z 704 (M+H)+

Example 56

Synthesis of A-18 and B-18

(Step 1) Methyl N-[2,6-Difluoro-4-({[5-(1H-1,2,4-triazol-1-yl)pyridin-2-yl]sulfonyl}amino)benzoyl]-4-(3-methyl-2,6-dioxo-3,6-dihydropyrimidin-1(2H)-yl)-L-phenylalaninate (B-18)

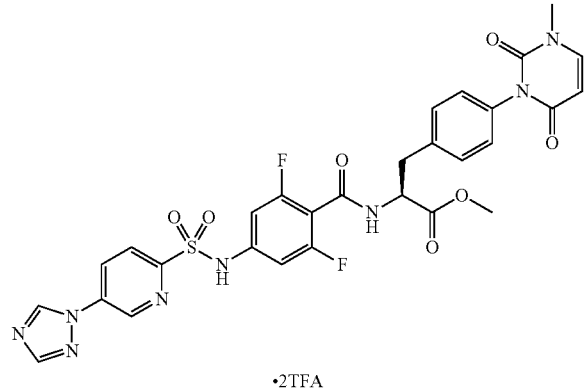 [SMILES: COC(=O)[C@H](Cc1ccc(-n2c(=O)ccn(C)c2=O)cc1)NC(=O)c1c(F)cc(NS(=O)(=O)c2ccc(-n3cncn3)cn2)cc1F]

•2TFA

Methyl 4-(3-methyl-2,6-dioxo-3,6-dihydropyrimidin-1(2H)-yl)-L-phenylalaninate (M-2) (80.0 mg, 0.240 mmol) and 2,6-difluoro-4-({[5-(1H-1,2,4-triazol-1-yl)pyridin-2-yl]sulfonyl}amino)benzoic acid (M-23) (91.0 mg, 0.240 mmol) were suspended in methylene chloride (2.0 ml), and HATU (137 mg, 0.360 mmol) and diisopropylethylamine (0.167 ml, 0.960 mmol) were added thereto, followed by stirring at room temperature for 20 hours. After the reaction liquid was concentrated under reduced pressure, purification was conducted by reversed-phase HPLC ($H_2O$ containing 0.1% TFA/$CH_3CN$ system) to obtain the TFA salt (38.0 mg, 26%) of the title compound as a white solid.

1H NMR (d-DMSO, 400 MHz): δ 11.3 (s, 1H), 9.41 (s, 1H), 9.22 (d, J=2.4 Hz, 1H), 9.11 (d, J=7.6 Hz, 1H), 8.48 (dd, J=8.8, 2.4 Hz, 1H), 8.30 (s, 1H), 8.25 (d, J=8.4 Hz, 1H), 7.68 (d, J=7.6 Hz, 1H), 7.23 (d, J=8.4 Hz, 2H), 7.03 (d, J=8.0 Hz, 2H), 6.83 (d, J=9.2 Hz, 2H), 5.67 (d, J=8.0 Hz, 1H), 4.60-4.51 (m, 1H), 3.56 (s, 3H), 3.24 (s, 3H), 3.08-2.91 (m, 2H).; MS (ESI) m/z 667 (M+H)+

(Step 2) N-[2,6-Difluoro-4-({[5-(1H-1,2,4-triazol-1-yl)pyridin-2-yl]sulfonyl}amino)benzoyl]-4-(3-methyl-2,6-dioxo-3,6-dihydropyrimidin-1(2H)-yl)-L-phenylalanine (A-18)

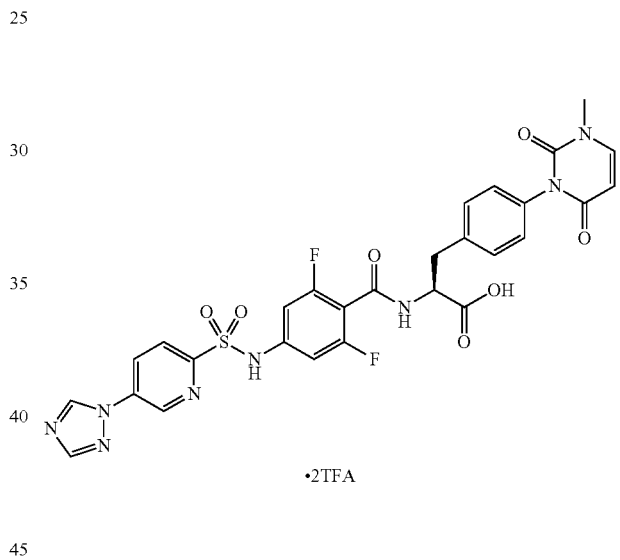

•2TFA

To the TFA salt (38 mg, 49 μmol) of methyl N-[2,6-difluoro-4-({[5-(1H-1,2,4-triazol-1-yl)pyridin-2-yl]sulfonyl}amino)benzoyl]-4-(3-methyl-2,6-dioxo-3,6-dihydropyrimidin-1(2H)-yl)-L-phenylalaninate (B-18), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC ($H_2O$ containing 0.1% TFA/$CH_3CN$ system) to obtain the TFA salt (22.9 mg, 61%) of the title compound.

1H NMR (d-DMSO, 400 MHz): δ 11.46 (s, 1H), 9.54 (s, 1H), 9.35 (d, J=1.9 Hz, 1H), 9.10 (d, J=7.8 Hz, 1H), 8.63-8.58 (m, 1H), 8.45-8.35 (m, 3H), 7.80 (d, J=7.9 Hz, 1H), 7.37 (d, J=8.3 Hz, 2H), 7.15 (d, J=8.3 Hz, 2H), 6.94 (d, J=9.2 Hz, 2H), 5.80 (d, J=7.9 Hz, 1H), 4.66-4.55 (m, 1H), 3.36 (s, 3H), 3.20 (dd, J=14.1, 4.4 Hz, 1H), 3.03 (dd, J=14.1, 9.8 Hz, 1H).; MS (ESI) m/z 653 (M+H)+

Example 57

Synthesis of A-19 and B-19

(Step 1) Methyl N-[2,6-Difluoro-4-({[5-(1H-1,2,4-triazol-1-yl)pyridin-2-yl]sulfonyl}amino)benzoyl]-4-(1-methyl-2,4-dioxo-1,4-dihydropyrido[3,4-d]pyrimidin-3(2H)-yl)-L-phenylalaninate (B-19)

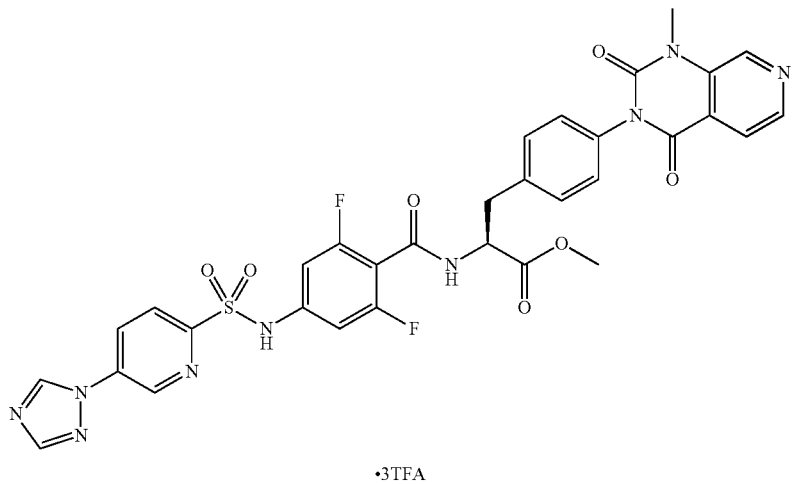

·3TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-({[5-(1H-1,2,4-triazol-1-yl)pyridin-2-yl]sulfonyl}amino)benzoic acid (M-23) (89.0 mg, 0.230 mmol) were suspended in methylene chloride (2.0 ml), and HATU (133 mg, 0.350 mmol) and diisopropylethylamine (0.160 ml, 0.920 mmol) were added thereto, followed by stirring at room temperature for 2 hours. After the reaction liquid was concentrated under reduced pressure, purification was conducted by reversed-phase HPLC (H$_2$O containing 0.1% TFA/CH$_3$CN system) to obtain the TFA salt (45.0 mg, 21%) of the title compound as a white solid.

$^1$H NMR (d-DMSO, 400 MHz): δ 11.4 (s, 1H), 9.49 (s, 1H), 9.30 (d, J=2.0 Hz, 1H), 9.19 (d, J=7.6 Hz, 1H), 8.97 (s, 1H), 8.56-8.54 (m, 2H), 8.37 (s, 1H), 8.33 (dd, J=8.4, 0.4 Hz, 1H), 7.89 (dd, J=4.8, 0.4 Hz, 1H), 7.34 (d, J=8.4 Hz, 2H), 7.21 (d, J=8.4 Hz, 2H), 6.90 (d, J=8.8 Hz, 2H), 4.67-4.61 (m, 1H), 3.69 (s, 3H), 3.60 (s, 3H), 3.17-3.00 (m, 2H).; MS (ESI) m/z 718 (M+H)$^+$ (Step 2) N-[2,6-Difluoro-4-({[5-(1H-1,2,4-triazol-1-yl)pyridin-2-yl]sulfonyl}amino)benzoyl]-4-(1-methyl-2,4-dioxo-1,4-dihydropyrido[3,4-d]pyrimidin-3(2H)-yl)-L-phenylalanine (A-19)

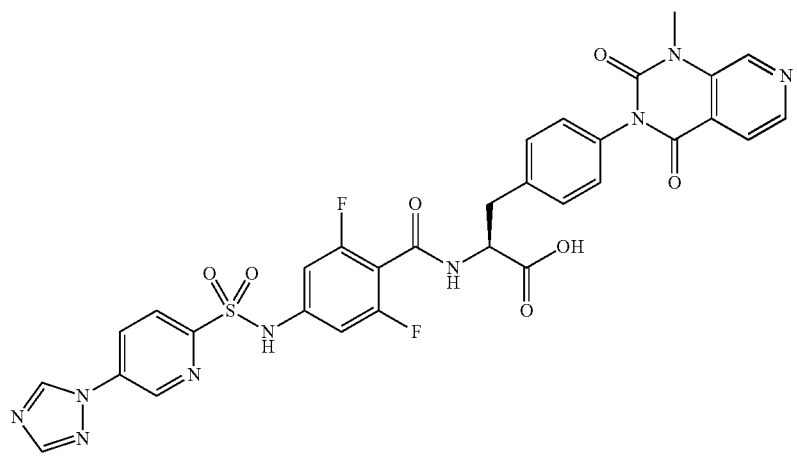

·3TFA

To the TFA salt (25.0 mg, 26.0 μmol) of methyl N-[2,6-difluoro-4-({[5-(1H-1,2,4-triazol-1-yl)pyridin-2-yl]sulfonyl}amino)benzoyl]-4-(1-methyl-2,4-dioxo-1,4-dihydropyrido[3,4-d]pyrimidin-3(2H)-yl)-L-phenylalaninate (B-19), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H$_2$O containing 0.1% TFA/CH$_3$CN system) to obtain the TFA salt (13.1 mg, 54%) of the title compound.

1H NMR (d-DMSO, 400 MHz): δ 11.40 (s, 1H), 9.48 (s, 1H), 9.30 (d, J=2.2 Hz, 1H), 9.05 (d, J=7.9 Hz, 1H), 8.97 (s, 1H), 8.61-8.50 (m, 2H), 8.37 (s, 1H), 8.32 (d, J=8.5 Hz, 1H), 7.89 (d, J=4.9 Hz, 1H), 7.35 (d, J=8.3 Hz, 2H), 7.21 (d, J=8.3 Hz, 2H), 6.89 (d, J=9.2 Hz, 2H), 4.63-4.53 (m, 1H), 3.60 (s, 3H), 3.17 (dd, J=14.2, 4.3 Hz, 1H), 2.99 (dd, J=14.1, 9.9 Hz, 1H).; MS (ESI) m/z 704 (M+H)$^+$

Example 58

Synthesis of A-20 and B-20

(Step 1) Methyl N-[2,6-Difluoro-4-({[4-(1H-1,2,3-triazol-1-yl)phenyl]sulfonyl}amino)benzoyl]-4-(3-methyl-2,6-dioxo-3,6-dihydropyrimidin-1(2H)-yl)-L-phenylalaninate (B-20)

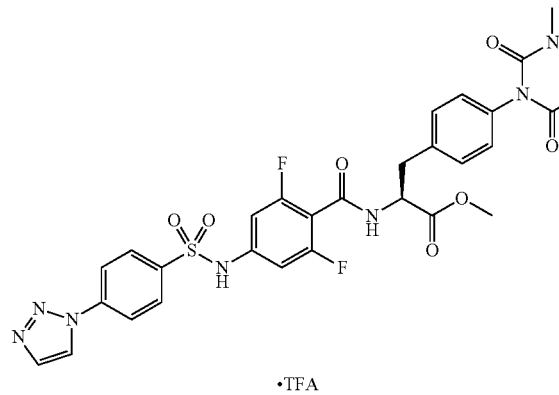

·TFA

Methyl 4-(3-methyl-2,6-dioxo-3,6-dihydropyrimidin-1(2H)-yl)-L-phenylalaninate (M-2) (80.0 mg, 0.240 mmol) and 2,6-difluoro-4-({[4-(1H-1,2,3-triazol-1-yl)phenyl]sulfonyl}amino)benzoic acid (M-15) (91.0 mg, 0.240 mmol) were suspended in methylene chloride (2.0 ml), and HATU (137 mg, 0.360 mmol) and diisopropylethylamine (0.167 ml, 0.960 mmol) were added thereto, followed by stirring at room temperature for 20 hours. After the reaction liquid was concentrated under reduced pressure, purification was conducted by reversed-phase HPLC (H$_2$O containing 0.1% TFA/CH$_3$CN system) to obtain the TFA salt (70.0 mg, 44%) of the title compound as a white solid.

$^1$H NMR (d-DMSO, 400 MHz): δ 11.2 (s, 1H), 9.17 (d, J=7.6 Hz, 1H), 8.93 (d, J=1.2 Hz, 1H), 8.18 (dd, J=7.2, 2.0 Hz, 2H), 8.08 (dd, J=6.8, 1.6 Hz, 2H), 8.02 (d, J=1.2 Hz, 1H), 7.75 (d, J=8.0 Hz, 1H), 7.29 (d, J=8.4 Hz, 2H), 7.09 (d, J=8.4 Hz, 2H), 6.83 (d, J=9.2 Hz, 2H), 5.74 (d, J=8.0 Hz, 1H), 4.63-4.57 (m, 1H), 3.62 (s, 3H), 3.30 (s, 3H), 3.14-2.97 (m, 2H) 4.67-4.61 (m, 1H), 3.69 (s, 3H), 3.60 (s, 3H), 3.17-3.00 (m, 2H).; MS (ESI) m/z 666 (M+H)$^+$ (Step 2) N-[2,6-Difluoro-4-({[4-(1H-1,2,3-triazol-1-yl)phenyl]sulfonyl}amino)benzoyl]-4-(3-methyl-2,6-dioxo-3,6-dihydropyrimidin-1(2H)-yl)-L-phenylalanine (A-20)

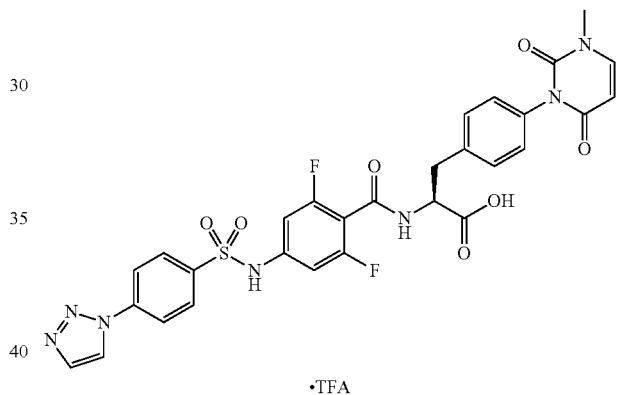

·TFA

To the TFA salt (50 mg, 75 μmol) of methyl N-[2,6-difluoro-4-({[4-(1H-1,2,3-triazol-1-yl)phenyl]sulfonyl}amino)benzoyl]-4-(3-methyl-2,6-dioxo-3,6-dihydropyrimidin-1(2H)-yl)-L-phenylalaninate (B-20), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H$_2$O containing 0.1% TFA/CH$_3$CN system) to obtain the TFA salt (34.7 mg, 71%) of the title compound as a white solid.

1H NMR (d-DMSO, 400 MHz): δ 11.14 (s, 1H), 8.97 (d, J=7.8 Hz, 1H), 8.85 (d, J=1.2 Hz, 1H), 8.16-8.05 (m, 2H), 8.05-7.97 (m, 2H), 7.95 (d, J=1.2 Hz, 1H), 7.67 (d, J=7.9 Hz, 1H), 7.23 (d, J=8.3 Hz, 2H), 7.02 (d, J=8.3 Hz, 2H), 6.76 (d, J=9.0 Hz, 2H), 5.67 (d, J=7.9 Hz, 1H), 4.54-4.42 (m, 1H), 3.23 (s, 3H), 3.07 (dd, J=14.2, 4.5 Hz, 1H), 2.90 (dd, J=14.2, 9.7 Hz, 1H).; MS (ESI) m/z 652 (M+H)$^+$

Example 59

Synthesis of A-21

(Step 2) N-[2,6-Difluoro-4-({[5-(1,3-thiazol-2-yl)pyridin-2-yl]sulfonyl}amino)benzoyl]-4-(1-methyl-2,4-dioxo-1,4-dihydropyrido[3,4-d]pyrimidin-3(2H)-yl)-L-phenylalanine (A-21)

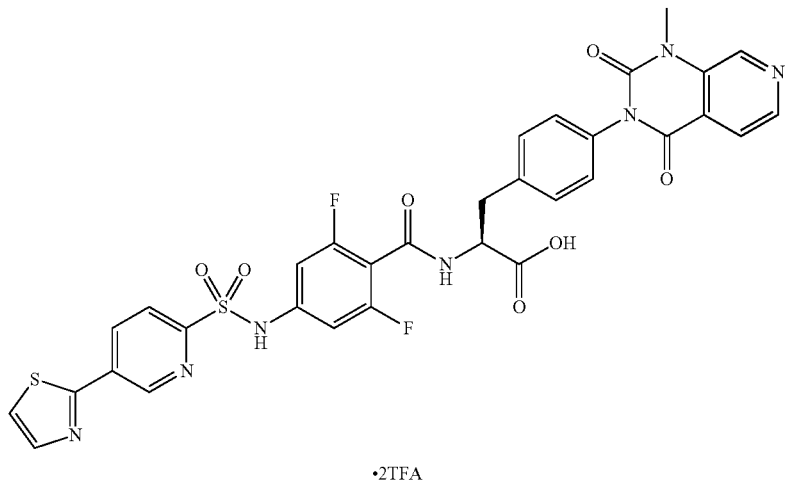 [SMILES: Cn1c(=O)n(-c2ccc(C[C@H](NC(=O)c3c(F)cc(NS(=O)(=O)c4ccc(-c5nccs5)cn4)cc3F)C(=O)O)cc2)c(=O)c2ccncc21]

•2TFA

Methyl 4-(1-methyl-2,4-dioxo-1,4-dihydropyrido[3,4-d]pyrimidin-3(2H)-yl)-L-phenylalaninate (M-1) (98.0 mg, 0.230 mmol) and 2,6-difluoro-4-({[5-(1,3-thiazol-2-yl)pyridin-2-yl]sulfonyl}amino)benzoic acid (M-24) (91.0 mg, 0.230 mmol) were suspended in methylene chloride (2.0 ml), and HATU (133 mg, 0.350 mmol) and diisopropylethylamine (0.160 ml, 0.920 mmol) were added thereto, followed by stirring at room temperature for 4 days. After the reaction liquid was concentrated under reduced pressure, purification was conducted by reversed-phase HPLC ($H_2O$ containing 0.1% $TFA/CH_3CN$ system). To the obtained compound, a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC ($H_2O$ containing 0.1% $TFA/CH_3CN$ system) to obtain the TFA salt (18.6 mg, 8% over two steps) of the title compound.

1H NMR (d-DMSO, 400 MHz): δ 12.85 (s, 1H), 11.39 (s, 1H), 9.29 (dd, J=2.2, 0.7 Hz, 1H), 9.04 (d, J=7.9 Hz, 1H), 8.97 (s, 1H), 8.61 (dd, J=8.2, 2.2 Hz, 1H), 8.55 (d, J=4.9 Hz, 1H), 8.22 (dd, J=8.3, 0.7 Hz, 1H), 8.08 (d, J=3.2 Hz, 1H), 8.02 (d, J=3.2 Hz, 1H), 7.88 (dd, J=5.0, 0.6 Hz, 1H), 7.35 (d, J=8.4 Hz, 2H), 7.20 (d, J=8.4 Hz, 2H), 6.88 (d, J=9.2 Hz, 2H), 4.62-4.52 (m, 1H), 3.60 (s, 3H), 3.17 (dd, J=14.2, 4.5 Hz, 1H), 2.99 (dd, J=14.1, 9.8 Hz, 1H).; MS (ESI) m/z 720 $(M+H)^+$

Example 60

Synthesis of A-22 and B-22

(Step 1) Methyl N-(2,6-Difluoro-4-{[(4-pyrimidin-5-yl-phenyl)sulfonyl]amino}benzoyl)-4-(3-methyl-2,6-dioxo-3,6-dihydropyrimidin-1(2H)-yl)-L-phenylalaninate (B-22)

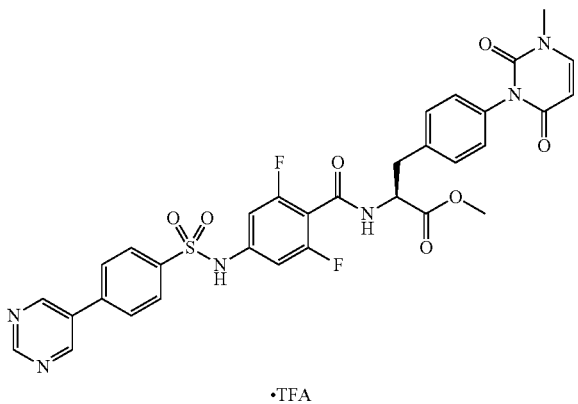 [SMILES: COC(=O)[C@H](Cc1ccc(-n2c(=O)ccn(C)c2=O)cc1)NC(=O)c1c(F)cc(NS(=O)(=O)c2ccc(-c3cncnc3)cc2)cc1F]

•TFA

Methyl 4-(3-methyl-2,6-dioxo-3,6-dihydropyrimidin-1(2H)-yl)-L-phenylalaninate (M-2) (80.0 mg, 0.240 mmol) and 2,6-difluoro-4-{[(4-pyrimidin-5-yl-phenyl)sulfonyl]amino}benzoic acid (M-25) (94.0 mg, 0.240 mmol) were suspended in methylene chloride (2.0 ml), and HATU (137 mg, 0.360 mmol) and diisopropylethylamine (0.167 ml, 0.960 mmol) were added thereto, followed by stirring at room temperature for 16 hours. After the reaction liquid was concentrated under reduced pressure, purification was conducted by reversed-phase HPLC (H$_2$O containing 0.1% TFA/CH$_3$CN system) to obtain the TFA salt (80.0 mg, 42%) of the title compound as a white solid.

$^1$H NMR (d-DMSO, 400 MHz): δ 11.2 (s, 1H), 9.24 (s, 1H), 9.20-9.15 (m, 3H), 8.06 (dd, J=6.8, 2.0 Hz, 2H), 8.01 (dd, J=6.8, 2.0 Hz, 2H), 7.75 (d, J=7.6 Hz, 1H), 7.29 (d, J=8.4 Hz, 2H), 7.09 (d, J=8.4 Hz, 2H), 6.84 (d, J=9.2 Hz, 2H), 5.74 (d, J=8.0 Hz, 1H), 4.63-4.57 (m, 1H), 3.62 (s, 3H), 3.30 (s, 3H), 3.17-2.97 (m, 2H).; MS (ESI) m/z 677 (M+H)$^+$ (Step 2) N-(2,6-Difluoro-4-{[(4-pyrimidin-5-yl-phenyl)sulfonyl]amino}benzoyl)-4-(3-methyl-2,6-dioxo-3,6-dihydropyrimidin-1 (2H)-yl)-L-phenylalanine (A-22)

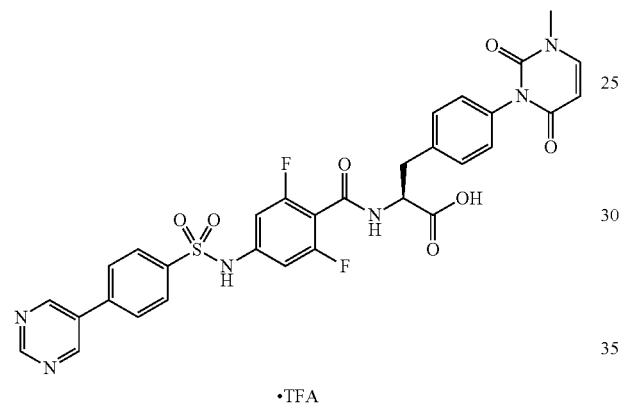

·TFA

To the TFA salt (60 mg, 76 μmol) of methyl N-(2,6-difluoro-4-{[(4-pyrimidin-5-yl-phenyl)sulfonyl] amino}benzoyl)-4-(3-methyl-2,6-dioxo-3,6-dihydropyrimidin-1(2H)-yl)-L-phenylalaninate (B-22), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H$_2$O containing 0.1% TFA/CH$_3$CN system) to obtain the TFA salt (34.8 mg, 59%) of the title compound as a white solid.

1H NMR (d-DMSO, 400 MHz): δ 11.22 (s, 1H), 9.22 (d, J=18.0 Hz, 3H), 9.05 (d, J=7.8 Hz, 1H), 8.06 (d, J=8.5 Hz, 2H), 8.01 (d, J=8.5 Hz, 2H), 7.75 (d, J=7.9 Hz, 1H), 7.30 (d, J=8.2 Hz, 2H), 7.08 (d, J=8.2 Hz, 2H), 6.83 (d, J=9.0 Hz, 2H), 5.74 (d, J=7.9 Hz, 1H), 4.61-4.49 (m, 1H), 3.30 (s, 3H), 3.14 (dd, J=14.2, 4.3 Hz, 1H), 2.96 (dd, J=14.1, 9.8 Hz, 1H).; MS (ESI) m/z 663 (M+H)$^+$

Example 61

Synthesis of A-23 and B-23

(Step 1) Methyl N-[2,6-Difluoro-4-({[4-(2H-1,2,3-triazol-2-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-23)

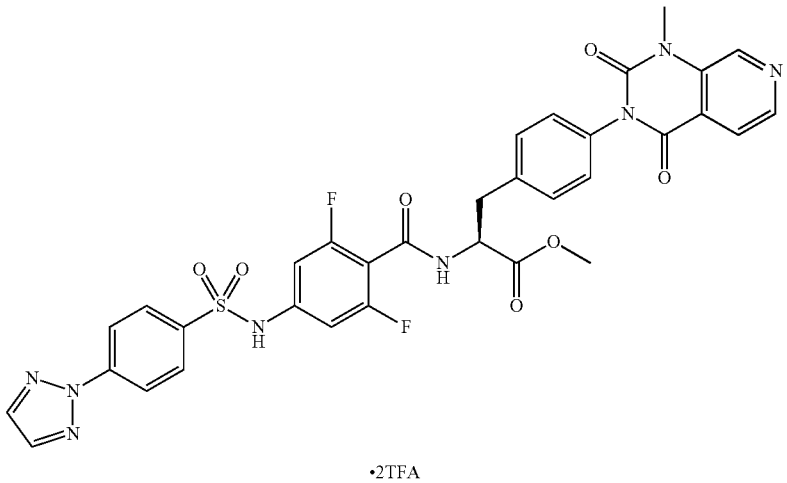 [SMILES: COC(=O)[C@H](Cc1ccc(-n2c(=O)c3ccncc3n(C)c2=O)cc1)NC(=O)c1c(F)cc(NS(=O)(=O)c2ccc(-n3nccn3)cc2)cc1F]

·2TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-({[4-(2H-1,2,3-triazol-2-yl)phenyl]sulfonyl}amino)benzoic acid (M-16) (87.0 mg, 0.230 mmol) were suspended in methylene chloride (2.0 ml), and HATU (133 mg, 0.350 mmol) and diisopropylethylamine (0.160 ml, 0.920 mmol) were added thereto, followed by stirring at room temperature for 17 hours. After the reaction liquid was concentrated under reduced pressure, purification was conducted by reversed-phase HPLC ($H_2O$ containing 0.1% TFA/$CH_3CN$ system) to obtain the TFA salt (120 mg, 63%) of the title compound as a white solid.

$^1$H NMR (d-DMSO, 400 MHz): δ 11.3 (s, 1H), 9.23 (d, J=7.6 Hz, 1H), 9.03 (s, 1H), 8.62 (d, J=5.2 Hz, 1H), 8.32-8.28 (m, 4H), 8.12 (dd, J=7.2, 2.0 Hz, 2H), 7.95 (d, J=4.8 Hz, 1H), 7.39 (d, J=8.4 Hz, 2H), 7.27 (d, J=8.4 Hz, 2H), 6.88 (d, J=9.2 Hz, 2H), 4.71-4.66 (m, 1H), 3.69 (s, 3H), 3.66 (s, 3H), 3.26-3.05 (m, 2H).; MS (ESI) m/z 717 (M+H)$^+$ (Step 2) N-[2,6-Difluoro-4-({[4-(2H-1,2,3-triazol-2-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-23)

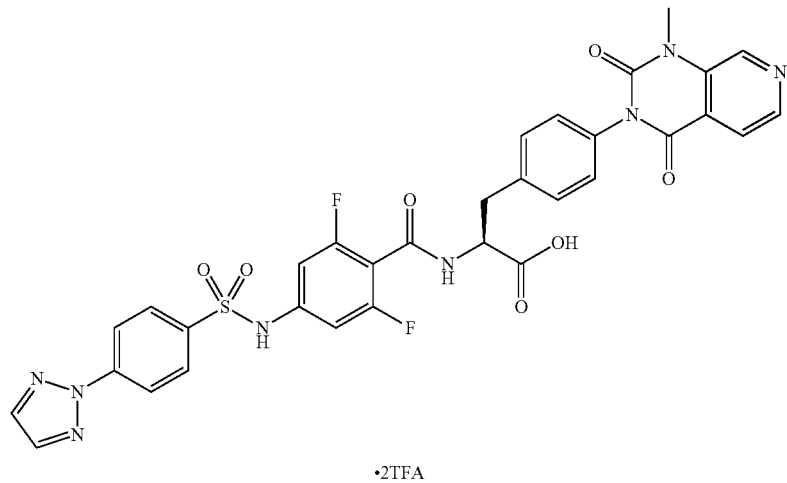 [SMILES: Cn1c(=O)n(-c2ccc(C[C@H](NC(=O)c3c(F)cc(NS(=O)(=O)c4ccc(-n5nccn5)cc4)cc3F)C(=O)O)cc2)c(=O)c2ccncc21]

•2TFA

To the TFA salt (100 mg, 0.120 mmol) of methyl N-[2,6-difluoro-4-({[4-(2H-1,2,3-triazol-2-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-23), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC ($H_2O$ containing 0.1% TFA/$CH_3CN$ system) to obtain the TFA salt (79.4 mg, 81%) of the title compound as a white solid.

1H NMR (d-DMSO, 400 MHz): δ 11.11 (s, 1H), 8.97 (d, J=7.9 Hz, 1H), 8.90 (s, 1H), 8.49 (d, J=4.9 Hz, 1H), 8.18 (d, J=8.9 Hz, 2H), 8.15 (s, 2H), 8.02-7.95 (m, 2H), 7.82 (d, J=4.9 Hz, 1H), 7.27 (d, J=8.3 Hz, 2H), 7.13 (d, J=8.3 Hz, 2H), 6.74 (d, J=9.0 Hz, 2H), 4.57-4.44 (m, 1H), 3.53 (s, 3H), 3.10 (dd, J=14.1, 4.4 Hz, 1H), 2.91 (dd, J=14.1, 9.8 Hz, 1H).; MS (ESI) m/z 703 (M+H)$^+$

Example 62

Synthesis of A-24 and B-24

(Step 1) Methyl N-[2,6-Difluoro-4-({[4-(1H-pyrazol-1-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-24)

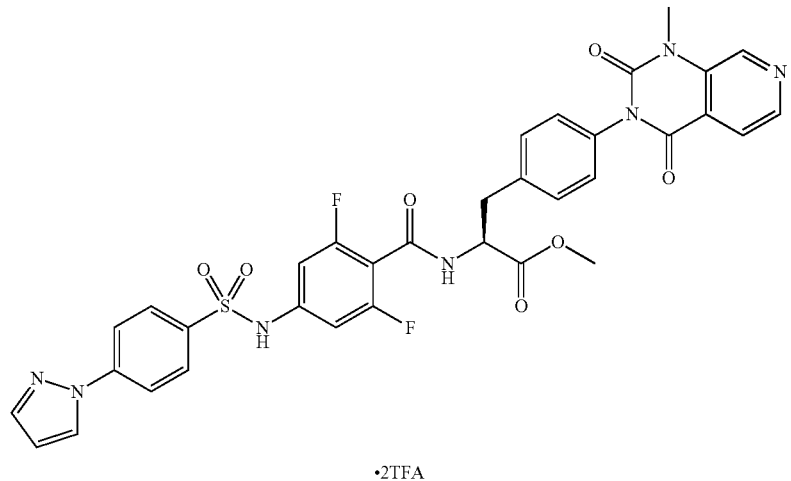 [SMILES: COC(=O)[C@H](Cc1ccc(-n2c(=O)c3ccncc3n(C)c2=O)cc1)NC(=O)c1c(F)cc(NS(=O)(=O)c2ccc(-n3cccn3)cc2)cc1F]

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-({[4-(1H-pyrazol-1-yl)phenyl]sulfonyl}amino)benzoic acid (M-26) (87.0 mg, 0.230 mmol) were suspended in methylene chloride (2.0 ml), and HATU (133 mg, 0.350 mmol) and diisopropylethylamine (0.160 ml, 0.920 mmol) were added thereto, followed by stirring at room temperature for 17 hours. After the reaction liquid was concentrated under reduced pressure, purification was conducted by reversed-phase HPLC (H$_2$O containing 0.1% TFA/CH$_3$CN system) to obtain the TFA salt (120 mg, 55%) of the title compound as a white solid.

$^1$H NMR (d-DMSO, 400 MHz): δ 11.1 (s, 1H), 9.16 (d, J=7.6 Hz, 1H), 8.97 (s, 1H), 8.61 (d, J=2.8 Hz, 1H), 8.56 (d, J=5.2 Hz, 1H), 8.08 (d, J=8.8 Hz, 2H), 7.97 (d, J=8.8 Hz, 2H), 7.89 (d, J=5.2 Hz, 1H), 7.83 (d, J=1.6 Hz, 1H), 7.33 (d, J=8.4 Hz, 2H), 7.21 (d, J=8.4 Hz, 2H), 6.82 (d, J=8.8 Hz, 2H), 6.61 (t, J=2.0 Hz 1H), 4.65-4.60 (m, 1H), 3.63 (s, 3H), 3.60 (s, 3H), 3.14 (dd, J=14.4, 5.2 Hz, 1H), 3.02 (dd, J=14.0, 9.6 Hz, 1H).; MS (ESI) m/z 716 (M+H)$^+$ (Step 2) N-[2,6-Difluoro-4-({[4-(1H-pyrazol-1-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-24)

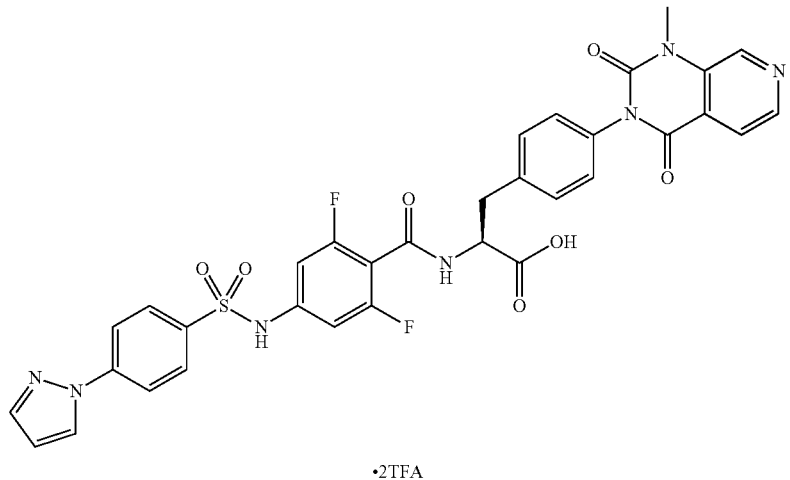 [SMILES: Cn1c(=O)n(-c2ccc(C[C@H](NC(=O)c3c(F)cc(NS(=O)(=O)c4ccc(-n5cccn5)cc4)cc3F)C(=O)O)cc2)c(=O)c2ccncc21]

To the TFA salt (100 mg, 0.110 mmol) of methyl N-[2,6-difluoro-4-({[4-(1H-pyrazol-1-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-24), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (77.6 mg, 76%) of the title compound as a white solid.

1H NMR (d-DMSO, 400 MHz): δ 11.03 (s, 1H), 8.96 (d, J=7.9 Hz, 1H), 8.90 (s, 1H), 8.54 (d, J=2.6 Hz, 1H), 8.49 (d, J=4.9 Hz, 1H), 8.01 (d, J=8.9 Hz, 2H), 7.90 (d, J=8.9 Hz, 2H), 7.82 (d, J=5.0 Hz, 1H), 7.76 (d, J=1.6 Hz, 1H), 7.28 (d, J=8.3 Hz, 2H), 7.13 (d, J=8.3 Hz, 2H), 6.74 (d, J=9.1 Hz, 2H), 6.54 (dd, J=2.5, 1.8 Hz, 1H), 4.57-4.43 (m, 1H), 3.53 (s, 3H), 3.10 (dd, J=14.2, 4.4 Hz, 1H), 2.91 (dd, J=14.1, 9.8 Hz, 1H).; MS (ESI) m/z 702 (M+H)⁺

Example 63

Synthesis of A-25

(Step 2) N-(2,6-Difluoro-4-{[(5-pyrimidin-5-yl-pyridin-2-yl)sulfonyl]amino}benzoyl)-4-(3-methyl-2,6-dioxo-3,6-dihydropyrimidin-1(2H)-yl)-L-phenylalanine (A-25)

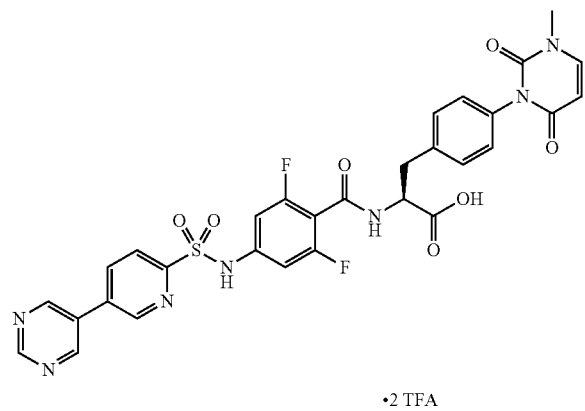 [SMILES: Cn1ccc(=O)n(-c2ccc(C[C@H](NC(=O)c3c(F)cc(NS(=O)(=O)c4ccc(-c5cncnc5)cn4)cc3F)C(=O)O)cc2)c1=O]

·2 TFA

Methyl 4-(3-methyl-2,6-dioxo-3,6-dihydropyrimidin-1(2H)-yl)-L-phenylalaninate (M-2) (100 mg, 0.290 mmol) and 2,6-difluoro-4-{[(5-pyrimidin-5-yl-pyridin-2-yl)sulfonyl]amino}benzoic acid (M-21) (124 mg, 0.290 mmol) were suspended in methylene chloride (2.0 ml), and HATU (165 mg, 0.440 mmol) and diisopropylethylamine (0.202 ml, 1.16 mmol) were added thereto, followed by stirring at room temperature for 3 days. After the reaction liquid was concentrated under reduced pressure, purification was conducted by reversed-phase HPLC (H₂O containing 0.1% TFA/CH₃CN system). To the obtained compound, a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H₂O containing 0.1% TFA/CH₃CN system) to obtain the TFA salt (120 mg, 46%) of the title compound.

1H NMR (d-DMSO, 400 MHz): δ 12.86 (s, 1H), 11.41 (s, 1H), 9.28 (s, 3H), 9.20 (dd, J=2.3, 0.7 Hz, 1H), 9.05 (d, J=7.8 Hz, 1H), 8.56 (dd, J=8.2, 2.3 Hz, 1H), 8.26 (dd, J=8.2, 0.6 Hz, 1H), 7.75 (d, J=7.9 Hz, 1H), 7.31 (d, J=8.4 Hz, 2H), 7.09 (d, J=8.4 Hz, 2H), 6.90 (d, J=9.2 Hz, 2H), 5.74 (d, J=7.9 Hz, 1H), 4.60-4.46 (m, 1H), 3.30 (s, 3H), 3.14 (dd, J=14.1, 4.4 Hz, 1H), 2.97 (dd, J=14.0, 9.7 Hz, 1H).; MS (ESI) m/z 664 (M+H)⁺

Example 64

Synthesis of A-26 and B-26

(Step 1) Methyl N-[2,6-Difluoro-4-({[4-(1H-pyrrol-1-yl)phenyl]sulfonyl}amino)benzoyl]-4-(3-methyl-2,6-dioxo-3,6-dihydropyrimidin-1(2H)-yl)-L-phenylalaninate (B-26)

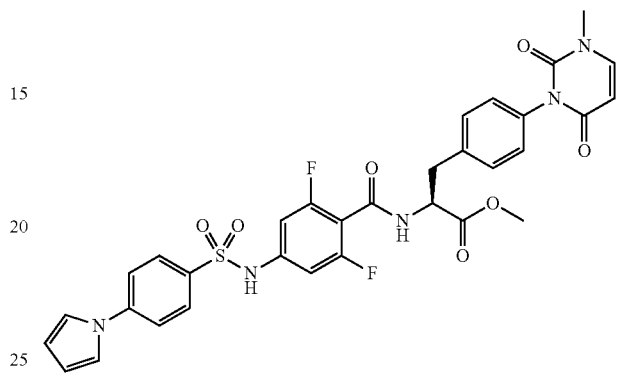

Methyl 4-(3-methyl-2,6-dioxo-3,6-dihydropyrimidin-1(2H)-yl)-L-phenylalaninate (M-2) (73.0 mg, 0.220 mmol) and 2,6-difluoro-4-({[4-(1H-pyrrol-1-yl)phenyl]sulfonyl}amino)benzoic acid (M-10) (69.0 mg, 0.180 mmol) were suspended in methylene chloride (2.0 ml), and HATU (103 mg, 0.270 mmol) and diisopropylethylamine (0.125 ml, 0.720 mmol) were added thereto, followed by stirring at room temperature for 2 hours. After the reaction liquid was concentrated under reduced pressure, purification was conducted by reversed-phase HPLC (H₂O containing 0.1% TFA/CH₃CN system) to obtain the title compound (70.0 mg, 59%) as a white solid.

¹H NMR (d-DMSO, 400 MHz): δ 11.1 (s, 1H), 9.16 (d, J=7.6 Hz, 1H), 7.90 (dd, J=7.2, 2.0 Hz, 2H), 7.82 (dd, J=7.2, 2.4 Hz, 2H), 7.75 (d, J=8.0 Hz, 1H), 7.49 (t, J=2.4 Hz, 2H), 7.29 (d, J=8.4 Hz, 2H), 7.09 (d, J=8.4 Hz, 2H), 6.81 (d, J=8.8 Hz, 2H), 6.32 (t, J=2.0 Hz, 2H), 5.74 (d, J=8.0 Hz, 1H), 4.62-4.57 (m, 1H), 3.62 (s, 3H), 3.30 (s, 3H), 3.14-2.96 (m, 2H).; MS (ESI) m/z 664 (M+H)⁺

(Step 2) N-[2,6-Difluoro-4-({[4-(1H-pyrrol-1-yl)phenyl]sulfonyl}amino)benzoyl]-4-(3-methyl-2,6-dioxo-3,6-dihydropyrimidin-1(2H)-yl)-L-phenylalanine (A-26)

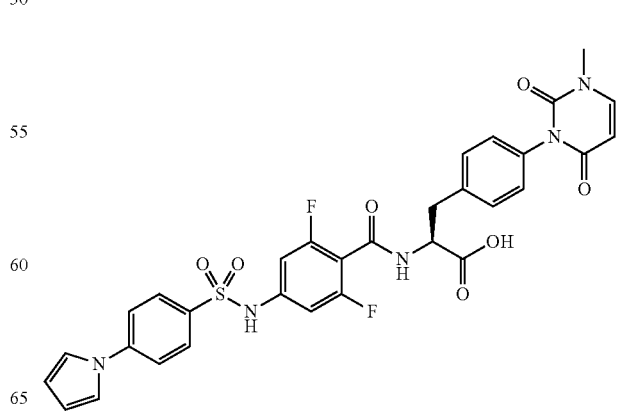

To the TFA salt (50 mg, 75 µmol) of methyl N-[2,6-difluoro-4-({[4-(1H-pyrrol-1-yl)phenyl]sulfonyl}amino)benzoyl]-4-(3-methyl-2,6-dioxo-3,6-dihydropyrimidin-1(2H)-yl)-L-phenylalaninate (B-26), a 4 N hydrogen chloride/dioxane solution (2.0 ml) and water (2.0 ml) were added, followed by stirring at 80° C. for 1 hour. After the reaction liquid was concentrated under reduced pressure, purification was conducted by reversed-phase HPLC (H$_2$O containing 0.1% TFA/CH$_3$CN system) to obtain the title compound (15.0 mg, 31%) as a white solid.

1H NMR (d-DMSO, 400 MHz): δ 12.78 (s, 1H), 10.99 (s, 1H), 8.96 (d, J=7.8 Hz, 1H), 7.83 (d, J=8.9 Hz, 2H), 7.75 (d, J=8.9 Hz, 2H), 7.68 (d, J=7.9 Hz, 1H), 7.46-7.39 (m, 2H), 7.23 (d, J=8.3 Hz, 2H), 7.02 (d, J=8.3 Hz, 2H), 6.73 (d, J=9.1 Hz, 2H), 6.32-6.18 (m, 2H), 5.67 (d, J=7.9 Hz, 1H), 4.55-4.41 (m, 1H), 3.23 (s, 3H), 3.06 (dd, J=14.1, 4.5 Hz, 1H), 2.89 (dd, J=14.2, 9.7 Hz, 1H).; MS (ESI) m/z 650 (M+H)$^+$

Example 65

Synthesis of A-27 and B-27

(Step 1) Methyl N-[2,6-Difluoro-4-({[4-(3-methylpyridin-4-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-27)

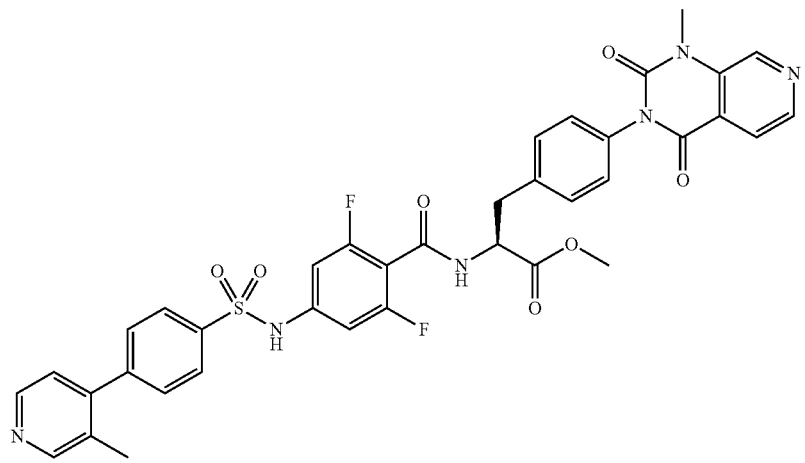

•2 TFA

Methyl 4-(1-methyl-2,4-dioxo-1,4-dihydropyrido[3,4-d]pyrimidin-3(2H)-yl)-L-phenylalaninate (M-1) (43.0 mg, 0.100 mmol) and 2,6-difluoro-4-({[4-(3-methylpyridin-4-yl)phenyl]sulfonyl}amino)benzoic acid (M-34) (40.0 mg, 77.2 µmol) were suspended in methylene chloride (4.0 ml), and HATU (53.0 mg, 0.140 mmol) and diisopropylethylamine (52 µl, 0.30 mmol) were added thereto, followed by stirring at room temperature for 3 hours. After the reaction liquid was concentrated under reduced pressure, purification was conducted by reversed-phase HPLC (H$_2$O containing 0.1% TFA/CH$_3$CN system) to obtain the TFA salt (32.0 mg, 42%) of the title compound as a white solid.

$^1$H NMR (d-DMSO, 400 MHz,) δ 11.2 (s, 1H), 9.22 (d, J=7.6 Hz 1H), 8.97 (s, 1H), 8.66 (s, 1H), 8.60 (d, J=5.2 Hz 1H), 8.55 (d, J=5.2 Hz 1H), 8.00 (d, J=8.4 Hz, 2H), 7.88 (d, J=4.8 Hz, 1H), 7.72 (d, J=8.4 Hz, 2H), 7.51 (d, J=5.2 Hz, 1H), 7.35 (d, J=8.4 Hz, 2H), 7.21 (d, J=8.4 Hz, 2H), 6.85 (d, J=9.2 Hz, 2H), 4.67-4.61 (m, 1H), 3.64 (s, 3H), 3.60 (s, 3H), 3.18-3.01 (m, 2H), 2.27 (s, 3H).; MS (ESI) m/z 741 (M+H)$^+$ (Step 2) N-[2,6-Difluoro-4-({[4-(3-methylpyridin-4-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-27)

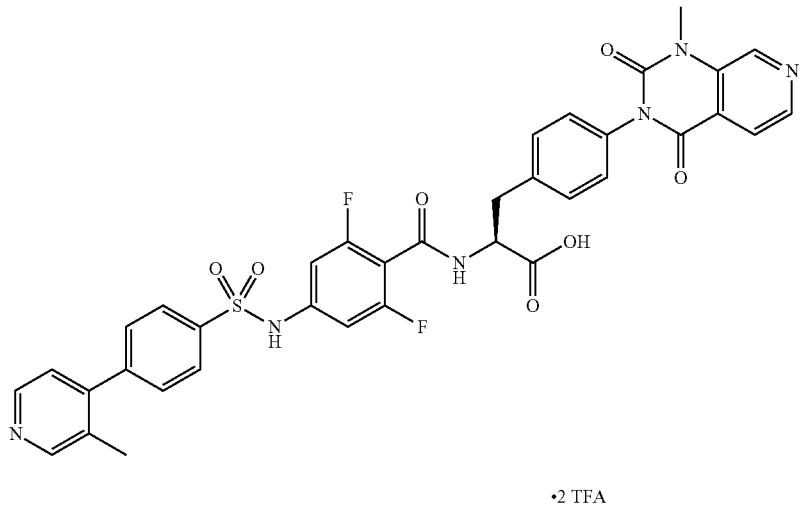 [SMILES: Cc1cnccc1-c1ccc(S(=O)(=O)Nc2cc(F)c(C(=O)N[C@@H](Cc3ccc(-n4c(=O)c5ccncc5n(C)c4=O)cc3)C(=O)O)c(F)c2)cc1]

·2 TFA

To the TFA salt (15.0 mg, 15.5 µmol) of methyl N-[2,6-difluoro-4-({[4-(3-methylpyridin-4-yl)phenyl]sulfonyl}amino)benzoyl]-4-(1-methyl-2,4-dihydropyrido[3,4-d]pyrimidin-3(2H)-yl)-L-phenylalaninate (B-27), a 4 N hydrogen chloride/dioxane solution (4.0 ml) and water (1.0 ml) were added, followed by stirring at 70° C. for 6 hours. After the reaction liquid was concentrated under reduced pressure, purification was conducted by reversed-phase HPLC (H₂O containing 0.1% TFA/CH₃CN system) to obtain the TFA salt (10.0 mg, 65%) of the title compound as a white solid.

$^1$H NMR (d-DMSO, 400 MHz) δ 11.2 (s, 1H), 9.08 (d, J=8.0 Hz 1H), 8.97 (s, 1H), 8.59 (s, 1H), 8.56-8.52 (m, 2H), 7.98 (d, J=8.4 Hz 2H), 7.88 (d, J=4.8 Hz 1H), 7.70 (d, J=8.4 Hz, 2H), 7.39-7.35 (m, 3H), 7.21 (d, J=8.4 Hz, 2H), 6.84 (d, J=8.8 Hz, 2H), 4.60-4.56 (m, 1H), 3.60 (s, 3H), 3.21-2.97 (m, 2H), 2.24 (s, 3H).; MS (ESI) m/z 727 (M+H)$^+$

Example 66

Synthesis of A-28 and B-28

(Step 1) Methyl N-[2,6-Difluoro-4-({[4-(3-furyl)phenyl]sulfonyl}amino)benzoyl]-4-(1-methyl-2,4-dioxo-1,4-dihydropyrido[3,4-d]pyrimidin-3(2H)-yl)-L-phenylalaninate (B-28)

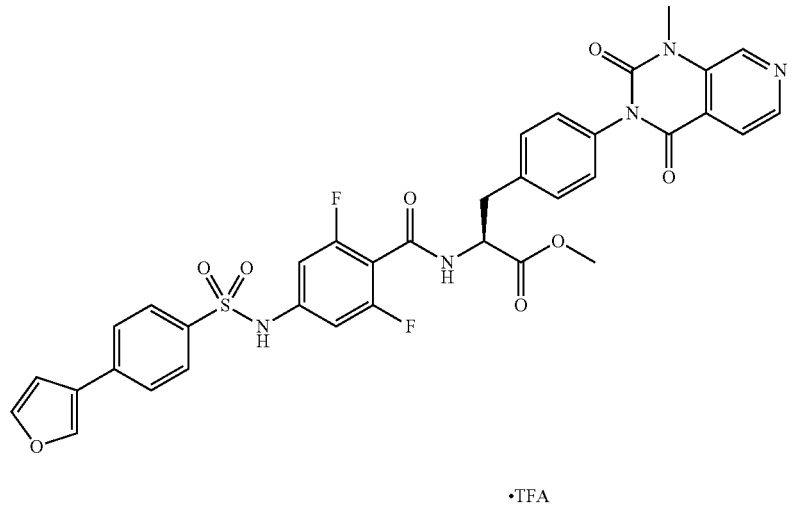 [SMILES: COC(=O)[C@H](Cc1ccc(-n2c(=O)c3ccncc3n(C)c2=O)cc1)NC(=O)c1c(F)cc(NS(=O)(=O)c2ccc(-c3ccoc3)cc2)cc1F]

·TFA

Methyl 4-(1-methyl-2,4-dioxo-1,4-dihydropyrido[3,4-d]pyrimidin-3(2H)-yl)-L-phenylalaninate (M-1) (122 mg, 0.286 mmol) and 2,6-difluoro-4-({[4-(3-furyl)phenyl]

sulfonyl}amino)benzoic acid (M-35) (100 mg, 0.264 mmol) were suspended in methylene chloride (4.0 ml), and HATU (138 mg, 0.364 mmol) and diisopropylethylamine (0.140 ml, 0.780 mmol) were added thereto, followed by stirring at room temperature for 3 hours. After the reaction liquid was concentrated under reduced pressure, purification was conducted by reversed-phase HPLC (H$_2$O containing 0.1% TFA/CH$_3$CN system) to obtain the TFA salt (64.0 mg, 34%) of the title compound as a white solid.

$^1$H NMR (d-DMSO, 400 MHz) δ 11.1 (s, 1H), 9.17 (d, J=7.6 Hz, 1H), 8.97 (s, 1H), 8.56 (d, J=5.2 Hz, 1H), 8.34 (s, 1H), 7.89 (d, J=4.8 Hz, 1H), 7.85-7.79 (m, 5H), 7.33 (d, J=8.4 2H), 7.21 (d, J=8.0 Hz, 2H), 7.03 (d, J=1.6, 1H), 6.81 (d, J=9.2 Hz, 2H), 4.65-4.60 (m, 1H), 3.63 (s, 3H), 3.60 (s, 3H), 3.19-2.99 (m, 2H).; MS (ESI) m/z 716 (M+H)$^+$ (Step 2) N-[2,6-Difluoro-4-({[4-(3-furyl)phenyl]sulfonyl}amino)benzoyl]-4-(1-methyl-2,4-dioxo-1,4-dihydropyrido[3,4-d]pyrimidin-3(2H)-yl)-L-phenylalanine (A-28)

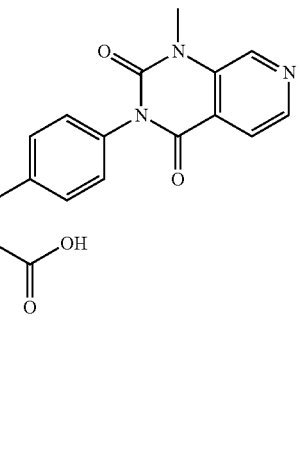

·TFA

To the TFA salt (20.0 mg, 24.0 μmol) of methyl N-[2,6-difluoro-4-({[4-(3-furyl)phenyl]sulfonyl}amino)benzoyl]-4-(1-methyl-2,4-dioxo-1,4-dihydropyrido[3,4-d]pyrimidin-3(2H)-yl)-L-phenylalaninate (B-28), a 4 N hydrogen chloride/dioxane solution (4.0 ml) and water (1.0 ml) were added, followed by stirring at room temperature for 6 hours. After the reaction liquid was concentrated under reduced pressure, purification was conducted by reversed-phase HPLC (H$_2$O containing 0.1% TFA/CH$_3$CN system) to obtain the TFA salt (12.0 mg, 61%) of the title compound as a white solid.

$^1$H NMR (d-DMSO, 400 MHz) δ 11.0 (s, 1H), 9.04 (d, J=7.6 Hz, 1H), 8.97 (s, 1H), 8.55 (d, J=4.8 Hz, 2H), 8.33 (s, 1H), 7.88 (d, J=4.8 Hz 1H), 7.79-7.85 (m, 5H), 7.34 (d, J=8.4 Hz, 2H), 7.20 (d, J=8.4 Hz, 2H), 7.02 (s, 1H), 6.80 (d, J=9.2 Hz, 2H), 4.53-4.59 (m, 1H), 3.60 (s, 3H), 2.95-3.23-2.88 (m, 2H);

MS (ESI) m/z 702 (M+H)$^+$

Example 67

Synthesis of A-29 and B-29

(Step 1) Methyl N-(2,6-Difluoro-4-{[(4-pyridin-4-yl-phenyl)sulfonyl]amino}benzoyl)-4-(1-methyl-2,4-dioxo-1,4-dihydropyrido[3,4-d]pyrimidin-3 (2H)-yl)-L-phenylalaninate (B-29)

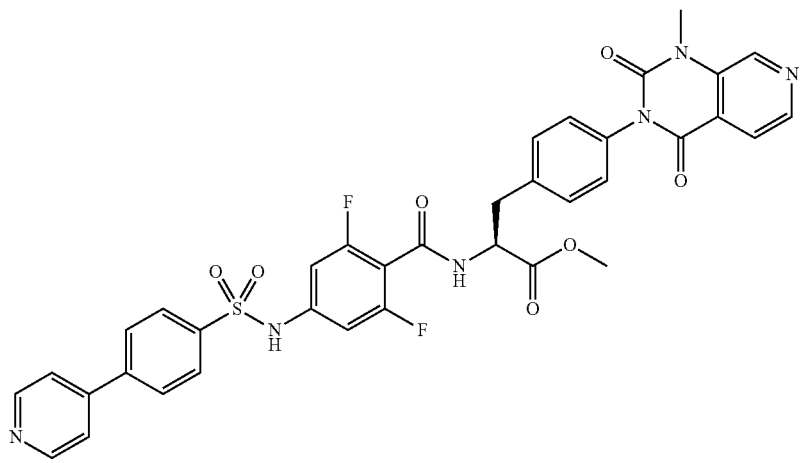

•2 TFA

Methyl 4-(1-methyl-2,4-dioxo-1,4-dihydropyrido[3,4-d]pyrimidin-3(2H)-yl)-L-phenylalaninate (M-1) (235 mg, 0.550 mmol) and 2,6-difluoro-4-{[(4-pyridin-4-yl-phenyl)sulfonyl]amino}benzoic acid (M-36) (195 mg, 0.500 mmol) were suspended in dimethylformamide (4.0 ml), and HATU (266 mg, 0.700 mmol) and diisopropylethylamine (0.350 ml, 2.00 mmol) were added thereto, followed by stirring at room temperature for 3 hours. After the reaction liquid was concentrated under reduced pressure, purification was conducted by reversed-phase HPLC (H$_2$O containing 0.1% TFA/CH$_3$CN system) to obtain the TFA salt (73.0 mg, 15%) of the title compound as a white solid.

$^1$H NMR (d-DMSO, 400 MHz) δ 11.2 (s, 1H), 9.19 (d, J=7.6 Hz, 1H), 8.99 (d, J=2.4 Hz, 1H), 8.97 (s, 1H), 8.67 (dd, J=4.8, 1.6 Hz 1H), 8.55 (d, J=4.8 Hz, 1H), 8.25 (d, J=7.6 Hz, 1H), 8.02-7.97 (m, 4H), 7.88 (d, J=4.8 Hz, 1H), 7.61 (dd, J=8.0, 4.8 Hz, 1H), 7.33 (d, J=8.4 2H), 7.21 (d, J=8.4, 2H), 6.84 (d, J=9.2 Hz, 2H), 4.66-4.60 (m, 1H), 3.63 (s, 3H), 3.59 (s, 3H), 3.17-2.99 (m, 2H).; MS (ESI) m/z 727 (M+H)$^+$ (Step 2) N-(2,6-Difluoro-4-{[(4-pyridin-4-yl-phenyl)sulfonyl]amino}benzoyl)-4-(1-methyl-2,4-dioxo-1,4-dihydropyrido[3,4-d]pyrimidin-3(2H)-yl)-L-phenylalanine (A-29)

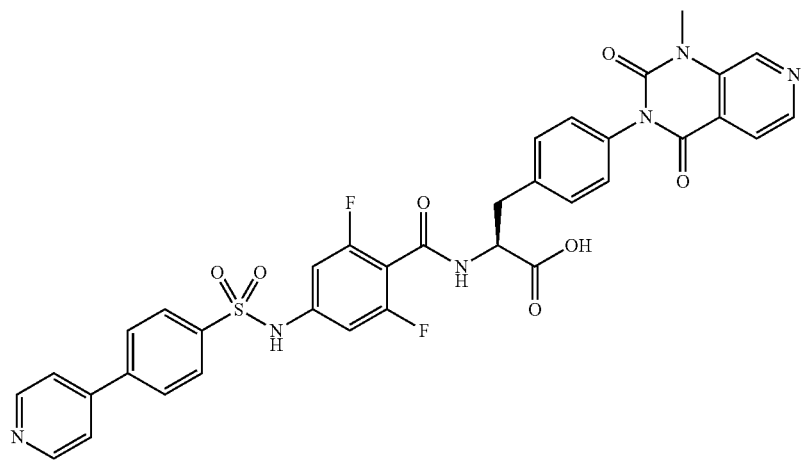

•2 TFA

To the TFA salt (50.0 mg, 52.4 μmol) of methyl N-(2,6-difluoro-4-{[(4-pyridin-4-yl-phenyl)sulfonyl]amino}benzoyl)-4-(1-methyl-2,4-dioxo-1,4-dihydropyrido[3,4-d]pyrimidin-3(2H)-yl)-L-phenylalaninate (B-29), a 4 N hydrogen chloride/dioxane solution (4.0 ml) and water (1.0 ml) were added, followed by stirring at 70° C. for 6 hours. After the reaction liquid was concentrated under reduced pressure, purification was conducted by reversed-phase HPLC ($H_2O$ containing 0.1% TFA/$CH_3CN$ system) to obtain the TFA salt (27.0 mg, 55%) of the title compound as a white solid.

$^1H$ NMR (d-DMSO, 400 MHz) δ 11.2 (s, 1H), 9.00 (d, J=7.6 Hz, 2H), 8.90 (s, 1H), 8.73 (d, J=6.4 Hz 2H), 8.49 (d, J=5.2 Hz, 1H), 8.04 (d, J=8.8 Hz, 2H), 7.96 (d, J=8.4 Hz, 2H), 7.81 (d, J=4.8 Hz, 1H), 7.93 (d, J=6.4 Hz, 2H), 7.28 (d, J=8.4 Hz, 2H), 7.13 (d, J=8.4 Hz, 2H), 6.77 (d, J=9.2 Hz, 2H), 4.53-4.48 (m, 1H), 3.12-2.88 (m, 2H).; MS (ESI) m/z 713 $(M+H)^+$

Example 68

Synthesis of A-30 and B-30

(Step 1) Methyl N-[2,6-Difluoro-4-({[4-(2-fluoropyridin-4-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-30)

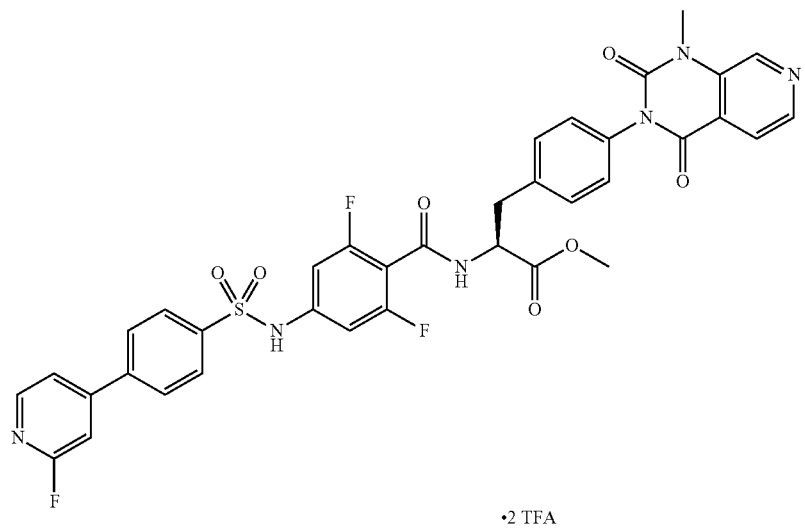 [SMILES: COC(=O)[C@H](Cc1ccc(-n2c(=O)c3ccncc3n(C)c2=O)cc1)NC(=O)c1c(F)cc(NS(=O)(=O)c2ccc(-c3ccnc(F)c3)cc2)cc1F]

·2 TFA

Methyl 4-(1-methyl-2,4-dioxo-1,4-dihydropyrido[3,4-d]pyrimidin-3(2H)-yl)-L-phenylalaninate (M-1) (100 mg, 0.234 mmol) and 2,6-difluoro-4-({[4-(2-fluoropyridin-4-yl)phenyl]sulfonyl}amino)benzoic acid (M-37) (94.0 mg, 0.230 mmol) were suspended in methylene chloride (2.0 ml), and HATU (133 mg, 0.350 mmol) and diisopropylethylamine (0.160 ml, 0.920 mmol) were added thereto, followed by stirring at room temperature for 16 hours. After the reaction liquid was concentrated under reduced pressure, purification was conducted by reversed-phase HPLC ($H_2O$ containing 0.1% TFA/$CH_3CN$ system) to obtain the TFA salt (30.0 mg, 13%) of the title compound as a white solid.

MS (ESI) m/z 745 $(M+H)^+$ (Step 2) N-[2,6-Difluoro-4-({[4-(2-fluoropyridin-4-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-30)

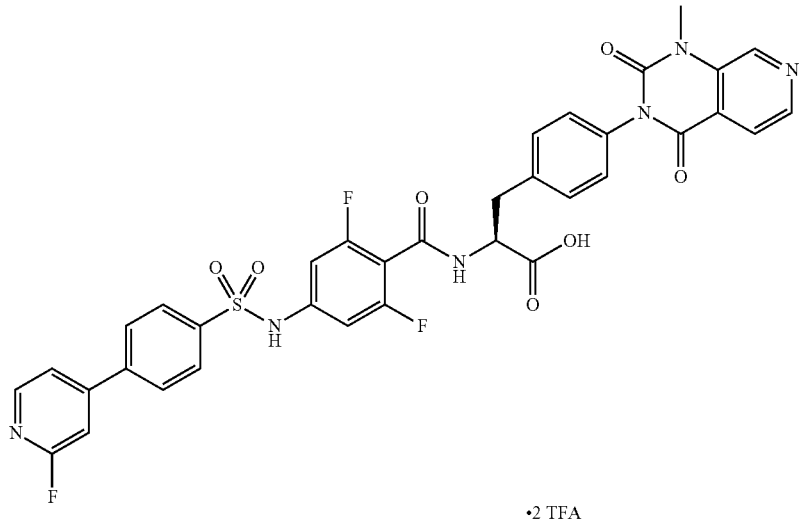 [SMILES: Cn1c(=O)n(-c2ccc(C[C@H](NC(=O)c3c(F)cc(NS(=O)(=O)c4ccc(-c5ccnc(F)c5)cc4)cc3F)C(=O)O)cc2)c(=O)c2ccncc21]

·2 TFA

To the TFA salt (20.0 mg, 20.6 μmol) of methyl N-[2,6-difluoro-4-({[4-(2-fluoropyridin-4-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-30), a 4 N hydrogen chloride/dioxane solution (4.0 ml) and water (1.0 ml) were added, followed by stirring at 70° C. for 6 hours. After the reaction liquid was concentrated under reduced pressure, purification was conducted by reversed-phase HPLC (H$_2$O containing 0.1% TFA/CH$_3$CN system) to obtain the TFA salt (11.0 mg, 56%) of the title compound as a white solid.

$^1$H NMR (d-DMSO, 400 MHz) δ 11.2 (s, 1H), 9.06 (d, J=7.6 Hz, 1H), 8.97 (s, 1H), 8.55 (d, J=5.2 Hz, 1H), 8.35 (d, J=5.2 Hz, 1H), 8.08 (d, J=8.8 Hz, 2H), 8.00 (d, J=8.4 Hz, 2H), 7.88 (d, J=4.8 Hz, 1H), 7.75 (d, J=5.2 Hz, 1H), 7.61 (s, 1H), 7.34 (d, J=8.4 Hz, 2H), 7.20 (d, J=8.4 Hz, 2H), 6.83 (d, J=9.2 Hz, 2H), 4.60-4.54 (m, 1H), 3.60 (s, 3H), 3.26-2.95 (m, 2H); MS (ESI) m/z 731 (M+H)$^+$

Example 69

Synthesis of A-31 and B-31

(Step 1) Methyl N-{4-[({4-[1-(tert-Butoxycarbonyl)-1,2,3,6-tetrahydropyridin-4-yl]phenyl}sulfonyl)amino]-2,6-difluorobenzoyl}-4-(1-methyl-2,4-dioxo-1,4-dihydropyrido[3,4-d]pyrimidin-3(2H)-yl)-L-phenylalaninate (B-31)

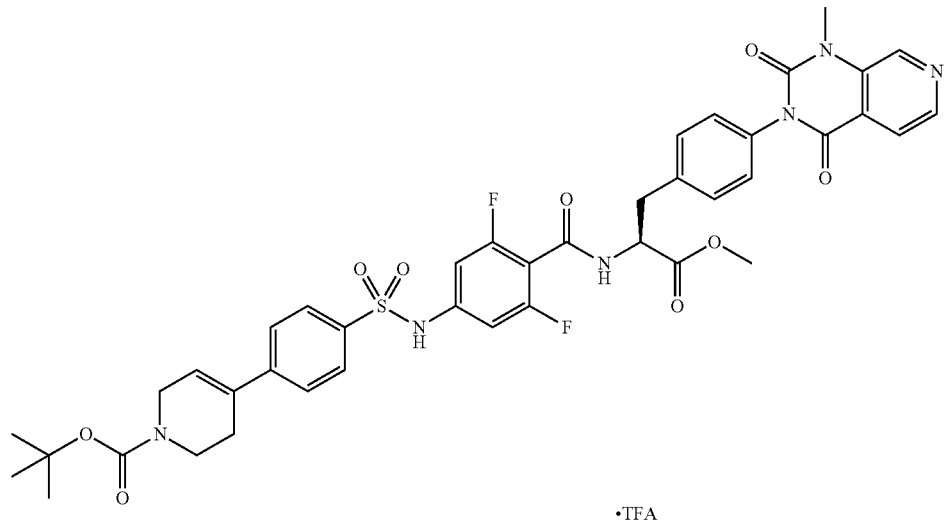 [SMILES: COC(=O)[C@H](Cc1ccc(-n2c(=O)c3ccncc3n(C)c2=O)cc1)NC(=O)c1c(F)cc(NS(=O)(=O)c2ccc(C3=CCN(C(=O)OC(C)(C)C)CC3)cc2)cc1F]

·TFA

Methyl 4-(1-methyl-2,4-dioxo-1,4-dihydropyrido[3,4-d]pyrimidin-3(2H)-yl)-L-phenylalaninate (M-1) (141 mg, 0.330 mmol) and 4-[({4-[1-(tert-butoxycarbonyl)-1,2,3,6-tetrahydropyridin-4-yl]phenyl}sulfonyl)amino]-2,6-difluorobenzoic acid (M-38) (130 mg, 0.300 mmol) were suspended in methylene chloride (5.0 ml), and HATU (160 mg, 0.420 mmol) and diisopropylethylamine (0.210 ml, 1.50 mmol) were added thereto, followed by stirring at room temperature for 3 hours. After the reaction liquid was concentrated under reduced pressure, purification was conducted by reversed-phase HPLC (H$_2$O containing 0.1% TFA/CH$_3$CN system) to obtain the TFA salt (22.0 mg, 8%) of the title compound as a white solid.

$^1$H NMR (d-DMSO, 400 MHz) δ 11.1 (s, 1H), 9.18 (d, J=6.4 Hz, 1H), 8.97 (s, 1H), 8.56 (d, J=4.8 Hz, 1H), 7.89 (d, J=4.4 Hz, 1H), 7.82 (d, J=8.4 Hz, 2H), 7.66 (d, J=8.4 Hz, 2H), 7.34 (d, J=8.4 Hz, 2H), 6.79 (d, J=9.2 Hz, 2H), 6.34 (br, 1H), 4.66-4.58 (m, 1H), 4.01 (br, 2H), 3.64 (s, 3H), 3.60 (s, 3H), 3.17-3.00 (m, 2H), 1.41 (s, 9H); MS (ESI) m/z 731 (M+H-Boc)$^+$ (Step 2) N-[2,6-Difluoro-4-({[4-(1,2,3,6-tetrahydropyridin-4-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-31)

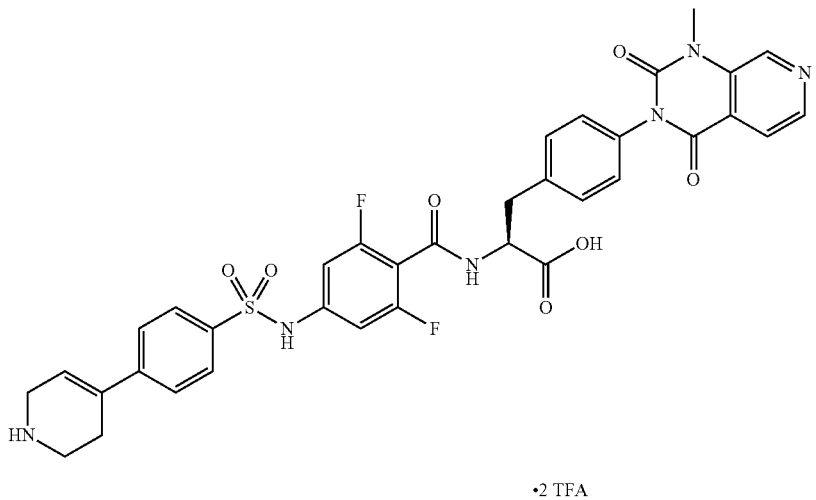 [SMILES: Cn1c(=O)n(-c2ccc(C[C@H](NC(=O)c3c(F)cc(NS(=O)(=O)c4ccc(C5=CCNCC5)cc4)cc3F)C(=O)O)cc2)c(=O)c2ccncc21]

•2 TFA

To the TFA salt (10.0 mg, 10.6 μmol) of methyl N-{4-[({4-[1-(tert-butoxycarbonyl)-1,2,3,6-tetrahydropyridin-4-yl]phenyl}sulfonyl)amino]-2,6-difluorobenzoyl}-4-(1-methyl-2,4-dioxo-1,4-dihydropyrido[3,4-d]pyrimidin-3(2H)-yl)-L-phenylalaninate (B-31), a 4 N hydrogen chloride/dioxane solution (4.0 ml) and water (1.0 ml) were added, followed by stirring at 70° C. for 6 hours. After the reaction liquid was concentrated under reduced pressure, purification was conducted by reversed-phase HPLC (H$_2$O containing 0.1% TFA/CH$_3$CN system) to obtain the TFA salt (6.0 mg, 59%) of the title compound as a white solid.

$^1$H NMR (d-DMSO, 400 MHz) δ 11.1 (s, 1H), 9.07 (d, J=8.0 Hz, 1H), 8.98 (s, 1H), 8.77 (br, 1H), 8.56 (d, J=5.2 Hz, 1H), 7.90 (d, J=4.4 Hz, 1H), 7.88 (d, J=5.6 Hz, 2H), 7.71 (d, J=8.4 Hz, 2H), 7.35 (d, J=8.4 Hz, 2H), 7.21 (d, J=8.4 Hz, 2H), 6.79 (d, J=9.2 Hz, 2H), 6.37 (br, 1H), 4.59-4.55 (m, 1H), 3.78 (br, 2H), 3.78 (s, 3H), 3.23-2.96 (m, 2H); MS (ESI) m/z 717 (M+H)$^+$

Example 70

Synthesis of A-32 and B-32

(Step 1) Methyl N-[4-({[4-(2,6-Dimethylpyridin-4-yl)phenyl]sulfonyl}amino)-2,6-difluorobenzoyl]-4-(1-methyl-2,4-dioxo-1,4-dihydropyrido[3,4-d]pyrimidin-3(2H)-yl)-L-phenylalaninate (B-32)

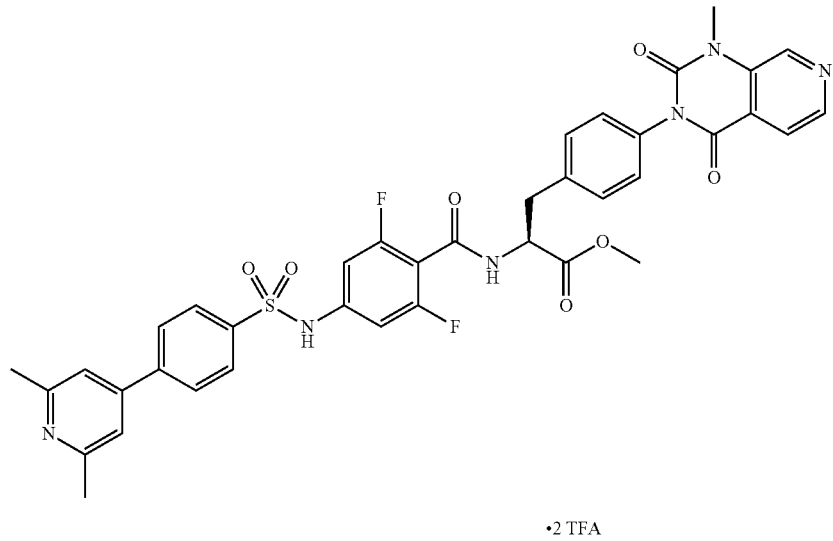 [SMILES: COC(=O)[C@H](Cc1ccc(-n2c(=O)c3ccncc3n(C)c2=O)cc1)NC(=O)c1c(F)cc(NS(=O)(=O)c2ccc(-c3cc(C)nc(C)c3)cc2)cc1F]

·2 TFA

Methyl 4-(1-methyl-2,4-dioxo-1,4-dihydropyrido[3,4-d]pyrimidin-3(2H)-yl)-L-phenylalaninate (M-1) (64.0 mg, 75.0 μmol) and 4-({[4-(2,6-dimethylpyridin-4-yl)phenyl]sulfonyl}amino)-2,6-difluorobenzoic acid (M-27) (63.0 mg, 0.118 mmol) were suspended in methylene chloride (4.0 ml), and HATU (80.0 mg, 0.165 mmol) and diisopropylethylamine (80 μL, 0.18 mmol) were added thereto, followed by stirring at room temperature for 3 hours. After the reaction liquid was concentrated under reduced pressure, purification was conducted by reversed-phase HPLC ($H_2O$ containing 0.1% TFA/$CH_3CN$ system) to obtain the TFA salt (40.0 mg, 34%) of the title compound as a white solid.

MS (ESI) m/z 755 (M+H)$^+$ (Step 2) N-[4-({[4-(2,6-Dimethylpyridin-4-yl)phenyl]sulfonyl}amino)-2,6-difluorobenzoyl]-4-(1-methyl-2,4-dioxo-1,4-dihydropyrido[3,4-d]pyrimidin-3(2H)-yl)-L-phenylalanine (A-32)

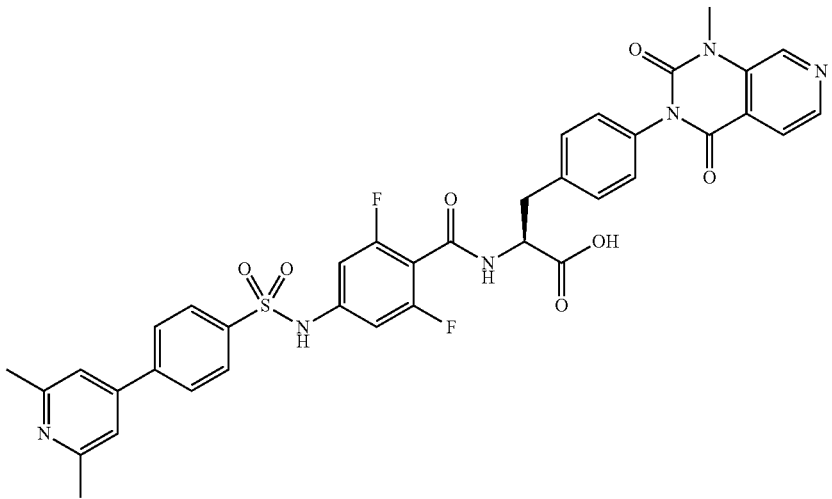

·2 TFA

To the TFA salt (20.0 mg, 20.6 μmol) of methyl N-[4-({[4-(2,6-dimethylpyridin-4-yl)phenyl]sulfonyl}amino)-2,6-difluorobenzoyl]-4-(1-methyl-2,4-dioxo-1,4-dihydropyrido[3,4-d]pyrimidin-3(2H)-yl)-L-phenylalaninate (B-32), a 4 N hydrogen chloride/dioxane solution (4.0 ml) and water (1.0 ml) were added, followed by stirring at 70° C. for 6 hours. After the reaction liquid was concentrated under reduced pressure, purification was conducted by reversed-phase HPLC (H₂O containing 0.1% TFA/CH₃CN system) to obtain the TFA salt (11.0 mg, 56%) of the title compound as a white solid.

¹H NMR (d-DMSO, 400 MHz) δ 11.2 (s, 1H), 9.07 (d, J=7.6 Hz, 1H), 8.97 (s, 1H), 8.56 (d, J=4.8 Hz, 1H), 8.10 (d, J=8.4 Hz, 2H), 8.05 (d, J=8.4 Hz, 2H), 7.94 (br, 2H), 7.88 (d, J=5.2 Hz, 1H), 7.35 (d, J=8.4 Hz, 2H), 7.20 (d, J=8.4 Hz, 2H), 6.83 (d, J=8.8 Hz, 2H), 4.60-4.54 (m, 1H), 3.60 (s, 3H), 3.19-2.98 (m, 2H), 2.65 (s, 6H).; MS (ESI) m/z 741 (M+H)⁺

Example 71

Synthesis of A-33

N-[2,6-Difluoro-4-({[5-(1H-1,2,3-triazol-1-yl)pyridin-2-yl]sulfonyl}amino)benzoyl]-4-(1-methyl-2,4-dioxo-1,4-dihydropyrido[3,4-d]pyrimidin-3(2H)-yl)-L-phenylalanine (A-33)

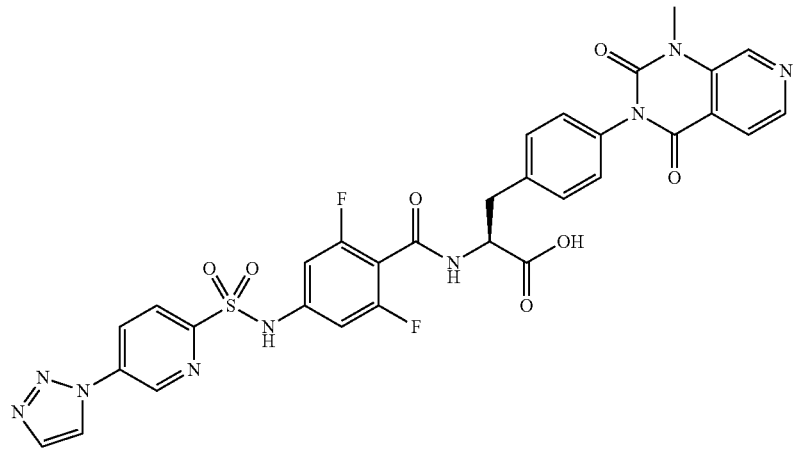

•3 TFA

¹H NMR (d-DMSO, 400 MHz) δ 11.4 (s, 1H), 9.35 (d, J=2.0 Hz, 1H), 9.06 (d, J=8.0 Hz, 1H), 9.02 (d, J=1.2 Hz, 1H), 8.98 (s, 1H), 8.66 (dd, J=2.8, 8.8 Hz, 1H), 8.56 (d, J=4.8 Hz, 1H), 8.36 (d, J=8.8 Hz, 1H), 8.07 (d, J=1.2 Hz, 1H), 7.89 (d, J=4.4 Hz, 1H), 7.36 (d, J=8.4 Hz, 2H), 7.21 (d, J=8.4 Hz, 2H), 6.91 (d, J=8.8 Hz, 2H), 4.61-4.56 (m, 1H), 3.60 (s, 3H), 3.22-2.99 (m, 2H).; MS (ESI) m/z 704 (M+H)⁺

Example 72

Synthesis of A-34

N-[2,6-Difluoro-4-({[5-(2H-1,2,3-triazol-2-yl)pyridin-2-yl]sulfonyl}amino)benzoyl]-4-(3-methyl-2,6-dioxo-3,6-dihydropyrimidin-1(2H)-yl)-L-phenylalanine (A-34)

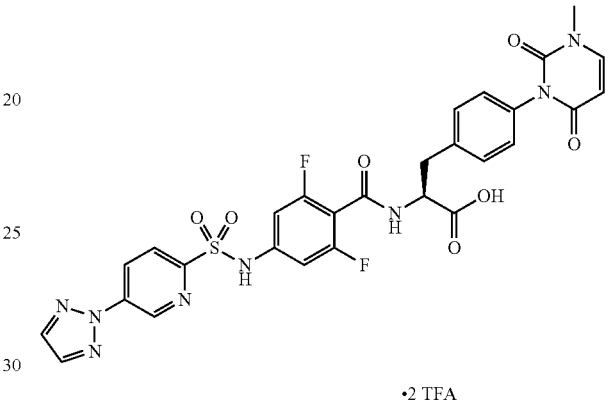

•2 TFA

Methyl 4-(1-methyl-2,4-dioxo-1,4-dihydropyrido[3,4-d]pyrimidin-3(2H)-yl)-L-phenylalaninate (M-1) (100 mg, 0.230 mmol) and 2,6-difluoro-4-({[5-(1H-1,2,3-triazol-1-yl)pyridin-2-yl]sulfonyl}amino)benzoic acid (M-28) (106 mg, 0.253 mmol) were suspended in methylene chloride (4.0 ml), and HATU (122 mg, 0.322 mmol) and diisopropylethylamine (0.120 ml, 0.690 mmol) were added thereto, followed by stirring at room temperature for 3 hours. After the reaction liquid was concentrated under reduced pressure, a 4 N hydrogen chloride/dioxane solution (4.0 ml) and water (1.0 ml) were added thereto, followed by stirring at 70° C. for 6 hours. After the reaction liquid was concentrated under reduced pressure, purification was conducted by reversed-phase HPLC (H₂O containing 0.1% TFA/CH₃CN system) to obtain the TFA salt (63.0 mg, 29%) of the title compound as a white solid.

Methyl 4-(3-methyl-2,6-dioxo-3,6-dihydropyrimidin-1(2H)-yl)-L-phenylalaninate (M-2) (100 mg, 0.290 mmol) and 2,6-difluoro-4-({[5-(2H-1,2,3-triazol-2-yl)pyridin-2-yl]sulfonyl}amino)benzoic acid (M-29) (133 mg, 0.319 mmol) were suspended in methylene chloride (4.0 ml), and HATU (154 mg, 0.406 mmol) and diisopropylethylamine (0.150 ml, 0.870 mmol) were added thereto, followed by stirring at room temperature for 3 hours. After the reaction liquid was concentrated under reduced pressure, a 4 N hydrogen chloride/dioxane solution (4.0 ml) and water (1.0 ml) were added thereto, followed by stirring at 70° C. for 6 hours. After the reaction liquid was concentrated under reduced pressure, purification was conducted by reversed-phase HPLC (H₂O containing 0.1% TFA/CH₃CN system) to obtain the TFA salt (78.0 mg, 35%) of the title compound as a white solid.

¹H NMR (d-DMSO, 400 MHz) δ11.4 (s, 1H), 9.38 (d, J=2.4 Hz, 1H), 9.03 (d, J=7.6 Hz, 1H), 8.65 (dd, J=2.8, 8.8 Hz, 1H), 8.32-8.30 (m, 3H), 7.75 (d, J=8.0 Hz, 1H), 7.31 (d, J=8.4 Hz, 2H), 7.09 (d, J=8.4 Hz, 2H), 6.88 (d, J=9.2 Hz, 2H), 5.74 (d, J=8.0 Hz, 1H), 4.58-4.52 (m, 1H), 3.31 (s, 3H), 3.17-2.94 (m, 2H).; MS (ESI) m/z 653 (M+H)⁺

Example 73

Synthesis of A-35

N-[2,6-Difluoro-4-({[5-(1H-1,2,3-triazol-1-yl)pyridin-2-yl]sulfonyl}amino)benzoyl]-4-(3-methyl-2,6-dioxo-3,6-dihydropyrimidin-1(2H)-yl)-L-phenylalanine (A-35)

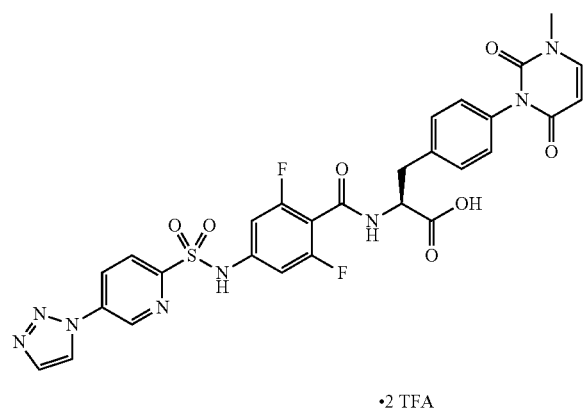 [SMILES: Cn1ccc(=O)n(-c2ccc(C[C@H](NC(=O)c3c(F)cc(NS(=O)(=O)c4ccc(-n5ccnn5)cn4)cc3F)C(=O)O)cc2)c1=O]

·2 TFA

Methyl 4-(3-methyl-2,6-dioxo-3,6-dihydropyrimidin-1 (2H)-yl)-L-phenylalaninate (M-2) (100 mg, 0.290 mmol) and 2,6-difluoro-4-({[5-(1H-1,2,3-triazol-1-yl)pyridin-2-yl]sulfonyl}amino)benzoic acid (M-28) (133 mg, 0.319 mmol) were suspended in methylene chloride (4.0 ml), and HATU (154 mg, 0.406 mmol) and diisopropylethylamine (0.150 ml, 0.870 mmol) were added thereto, followed by stirring at room temperature for 3 hours. After the reaction liquid was concentrated under reduced pressure, a 4 N hydrogen chloride/dioxane solution (4.0 ml) and water (1.0 ml) were added thereto, followed by stirring at 70° C. for 6 hours. After the reaction liquid was concentrated under reduced pressure, purification was conducted by reversed-phase HPLC (H₂O containing 0.1% TFA/CH₃CN system) to obtain the TFA salt (62.0 mg, 28%) of the title compound as a white solid.

¹H NMR (d-DMSO, 400 MHz) δ 11.4 (s, 1H), 9.34 (d, J=2.4 Hz, 1H), 9.05-9.02 (m, 2H), 8.66 (dd, J=2.8, 8.8 Hz, 1H), 8.36 (d, J=8.8 Hz, 1H), 8.07 (s, 1H), 7.75 (d, J=7.6 Hz, 1H), 7.31 (d, J=8.4 Hz, 2H), 7.09 (d, J=8.4 Hz, 2H), 6.90 (d, J=9.2 Hz, 2H), 5.74 (d, J=8.0 Hz, 1H), 4.58-4.53 (m, 1H), 3.31 (s, 3H), 3.17-2.95 (m, 2H).; MS (ESI) m/z 653 (M+H)⁺

Example 74

Synthesis of A-36 and B-36

(Step 1) Isopropyl N-[2,6-Difluoro-4-({[4-(2-methylpyridin-4-yl)phenyl]sulfonyl}amino)benzoyl]-4-(3,7-dimethyl-2,6-dioxo-2,3,6,7-tetrahydro-1H-purin-1-yl)-L-phenylalaninate (B-36)

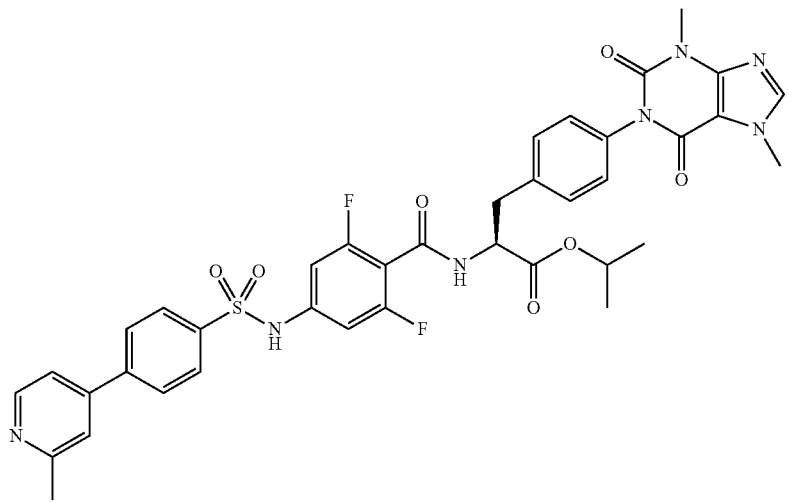

·TFA

Isopropyl 4-(3,7-dimethyl-2,6-dioxo-2,3,6,7-tetrahydro-1H-purin-1-yl)-L-phenylalaninate (M-5) (99.9 mg, 0.200 mmol) and 2,6-difluoro-4-({[4-(2-methylpyridin-4-yl)phenyl]sulfonyl}amino)benzoic acid (M-32) (80.9 mg, 0.200 mmol) were suspended in methylene chloride (4.0 ml), and HATU (114 mg, 0.300 mmol), HOAt (40.8 mg, 0.300 mmol), and triethylamine (70 μL, 0.50 mmol) were added thereto, followed by stirring at room temperature for 2 hours. After the reaction liquid was concentrated under reduced pressure, purification was conducted by reversed-phase HPLC (H$_2$O containing 0.1% TFA/CH$_3$CN system) to obtain the TFA salt (19.8 mg, 11%) of the title compound.

1H NMR (d-DMSO, 400 MHz): δ 11.24 (s, 1H), 9.17 (d, J=7.3 Hz, 1H), 8.70 (d, J=6.0 Hz, 1H), 8.12-8.01 (m, 5H), 7.96 (s, 1H), 7.86 (s, 1H), 7.31 (d, J=8.4 Hz, 2H), 7.13 (d, J=8.4 Hz, 2H), 6.85 (d, J=9.1 Hz, 2H), 4.91-4.85 (m, 1H), 4.57-4.47 (dd, J=14.2, 8.2 Hz, 1H), 3.86 (s, 3H), 3.42 (s, 3H), 3.12-2.97 (m, 2H), 2.63 (s, 3H), 1.17 (d, J=6.3 Hz, 3H), 1.11 (d, J=6.2 Hz, 3H).; MS (ESI) m/z 772 (M+H)$^+$ (Step 2) N-[2,6-Difluoro-4-({[4-(2-methylpyridin-4-yl)phenyl]sulfonyl}amino)benzoyl]-4-(3,7-dimethyl-2,6-dioxo-2,3,6,7-tetrahydro-1H-purin-1-yl)-L-phenylalanine (A-36)

·TFA

To the TFA salt (19.8 mg, 22.3 μmol) of isopropyl N-[2,6-difluoro-4-({[4-(2-methylpyridin-4-yl)phenyl]sulfonyl}amino)benzoyl]-4-(3,7-dimethyl-2,6-dioxo-2,3,6,7-tetrahydro-1H-purin-1-yl)-L-phenylalaninate (B-36), a 4 N hydrogen chloride/dioxane solution (2.0 ml) and water (4.0 ml) were added, followed by stirring at 70° C. for 6 hours. After the reaction liquid was concentrated under reduced pressure, purification was conducted by reversed-phase HPLC (H$_2$O containing 0.1% TFA/CH$_3$CN system) to obtain the TFA salt (4.7 mg, 25%) of the title compound.

1H NMR (d-DMSO, 400 MHz): δ 11.20 (s, 1H), 9.06 (d, J=7.9 Hz, 1H), 8.66 (d, J=4.8 Hz, 1H), 8.08-7.97 (m, 5H), 7.87 (s, 1H), 7.78 (s, 1H), 7.31 (d, J=8.4 Hz, 2H), 7.13 (d, J=8.3 Hz, 2H), 6.83 (d, J=9.0 Hz, 2H), 4.58-4.52 (m, 1H), 3.86 (s, 3H), 3.42 (s, 3H), 3.15 (dd, J=13.3, 3.2 Hz, 1H), 2.97 (dd, J=14.1, 9.6 Hz, 1H), 2.60 (s, 3H).; MS (ESI) m/z 730 (M+H)$^+$

Example 75

Synthesis of A-37 and B-37

(Step 1) Isopropyl N-(2,6-Difluoro-4-{[(4-pyridin-4-yl-phenyl)sulfonyl]amino}benzoyl)-4-(3,7-dimethyl-2,6-dioxo-2,3,6,7-tetrahydro-1H-purin-1-yl)-L-phenylalaninate (B-37)

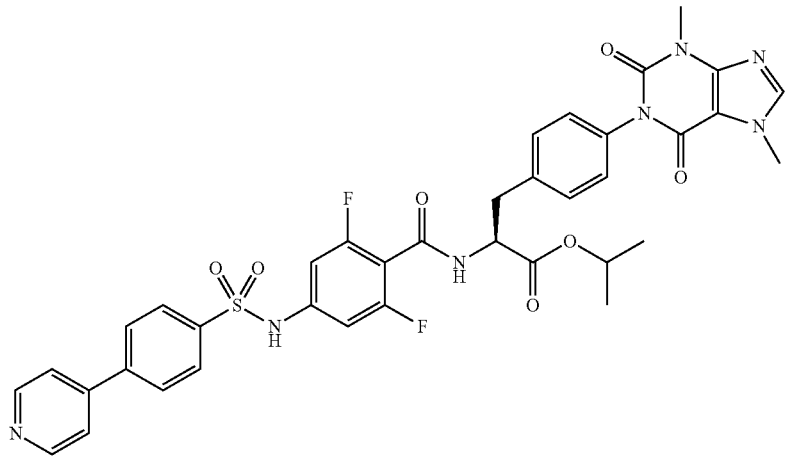

·TFA

Isopropyl 4-(3,7-dimethyl-2,6-dioxo-2,3,6,7-tetrahydro-1H-purin-1-yl)-L-phenylalaninate (M-5) (49.9 mg, 0.100 mmol) and 2,6-difluoro-4-{[(4-pyridin-4-yl-phenyl)sulfonyl]amino}benzoic acid (M-36) (39.0 mg, 0.100 mmol) were suspended in methylene chloride (2.0 ml), and HATU (57.0 mg, 0.150 mmol), HOAt (20.4 mg, 0.150 mmol), and triethylamine (28 μL, 0.20 mmol) were added thereto, followed by stirring at room temperature for 2 hours. After the reaction liquid was concentrated under reduced pressure, purification was conducted by reversed-phase HPLC ($H_2O$ containing 0.1% TFA/$CH_3CN$ system) to obtain the TFA salt (7.4 mg, 8%) of the title compound.

1H NMR (d-DMSO, 400 MHz): δ 11.23 (s, 1H), 9.16 (d, J=7.4 Hz, 1H), 8.73 (d, J=5.4 Hz, 2H), 8.10-8.04 (m, 3H), 8.01 (d, J=8.5 Hz, 2H), 7.85 (d, J=5.9 Hz, 2H), 7.31 (d, J=8.3 Hz, 2H), 7.13 (d, J=8.4 Hz, 2H), 6.85 (d, J=9.0 Hz, 2H), 4.91-4.84 (m, 1H), 4.54-4.49 (m, 1H), 3.85 (s, 3H), 3.42 (s, 3H), 3.14-2.97 (m, 2H), 1.17 (d, J=6.2 Hz, 3H), 1.11 (d, J=6.2 Hz, 3H);

MS (ESI) m/z 758 (M+H)$^+$ (Step 2) N-(2,6-Difluoro-4-{[(4-pyridin-4-yl-phenyl)sulfonyl]amino}benzoyl)-4-(3,7-dimethyl-2,6-dioxo-2,3,6,7-tetrahydro-1H-purin-1-yl)-L-phenylalanine (A-37)

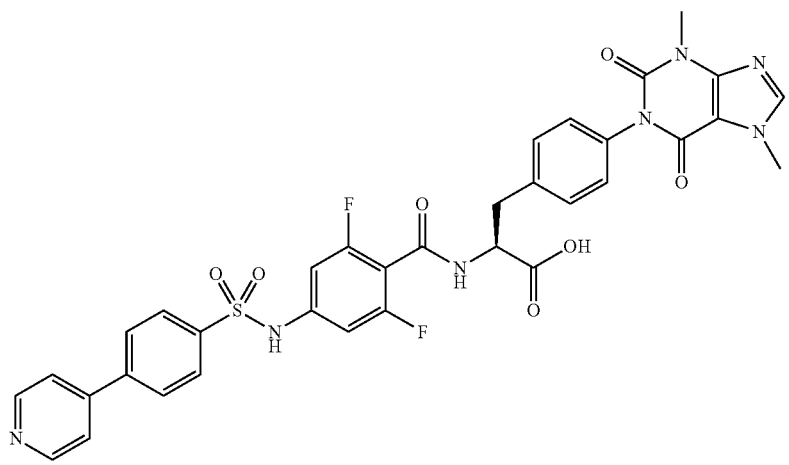

·TFA

To the TFA salt (7.4 mg, 8.5 μmol) of isopropyl N-(2,6-difluoro-4-{[(4-pyridin-4-yl-phenyl)sulfonyl]amino}benzoyl)-4-(3,7-dimethyl-2,6-dioxo-2,3,6,7-tetrahydro-1H-purin-1-yl)-L-phenylalaninate (B-37), a 4 N hydrogen chloride/dioxane solution (1.0 ml) and water (2.0 ml) were added, followed by stirring at 70° C. for 6 hours. After the reaction liquid was concentrated under reduced pressure, purification was conducted by reversed-phase HPLC (H₂O containing 0.1% TFA/CH₃CN system) to obtain the TFA salt (2.8 mg, 53%) of the title compound.

1H NMR (d-DMSO, 400 MHz): δ 11.20 (s, 1H), 9.05 (d, J=7.8 Hz, 1H), 8.73 (d, J=4.3 Hz, 2H), 8.08-8.05 (m, 3H), 8.00 (d, J=8.6 Hz, 2H), 7.85 (d, J=4.5 Hz, 2H), 7.31 (d, J=8.4 Hz, 2H), 7.13 (d, J=8.3 Hz, 2H), 6.83 (d, J=9.1 Hz, 2H), 4.62-4.48 (m, 1H), 3.85 (s, 3H), 3.42 (s, 3H), 3.15 (dd, J=13.8, 3.7 Hz, 1H), 2.97 (dd, J=15.5, 8.8 Hz, 1H); MS (ESI) m/z 716 (M+H)⁺

Example 76

Synthesis of A-38 and B-38

(Step 1) Isopropyl N-[2,6-Difluoro-4-({[4-(1H-pyrrol-1-yl)phenyl]sulfonyl}amino)benzoyl]-4-(3,7-dimethyl-2,6-dioxo-2,3,6,7-tetrahydro-1H-purin-1-yl)-L-phenylalaninate (B-38)

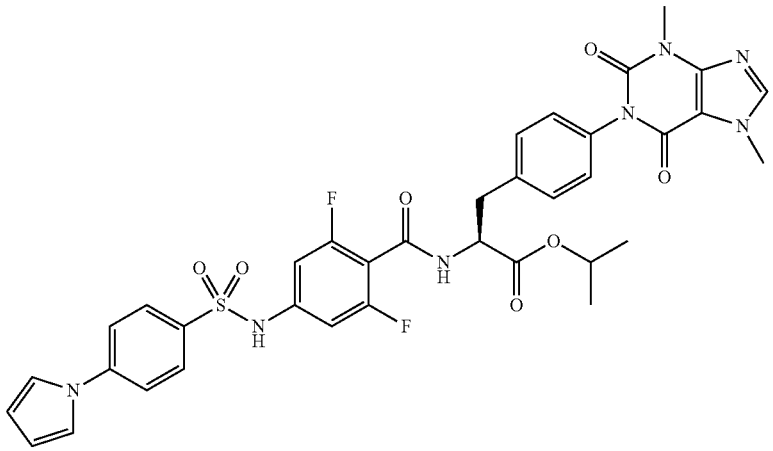 [SMILES: CC(C)OC(=O)[C@H](Cc1ccc(-n2c(=O)c3c(ncn3C)n(C)c2=O)cc1)NC(=O)c1c(F)cc(NS(=O)(=O)c2ccc(-n3cccc3)cc2)cc1F]

Isopropyl 4-(3,7-dimethyl-2,6-dioxo-2,3,6,7-tetrahydro-1H-purin-1-yl)-L-phenylalaninate (M-5) (99.9 mg, 0.200 mmol) and 2,6-difluoro-4-({[4-(1H-pyrrol-1-yl)phenyl]sulfonyl}amino)benzoic acid (M-10) (75.7 mg, 0.200 mmol) were suspended in methylene chloride (4.0 ml), and HATU (114 mg, 0.300 mmol), HOAt (40.8 mg, 0.300 mmol), and triethylamine (70 μL, 0.50 mmol) were added thereto, followed by stirring at room temperature for 2 hours. After the reaction liquid was concentrated under reduced pressure, purification was conducted by reversed-phase HPLC (H₂O containing 0.1% TFA/CH₃CN system) to obtain the title compound (27.8 mg, 16%).

1H NMR (d-DMSO, 400 MHz): δ 11.08 (s, 1H), 9.14 (d, J=7.3 Hz, 1H), 8.07 (s, 1H), 7.91 (d, J=9.0 Hz, 2H), 7.83 (d, J=9.0 Hz, 2H), 7.52-7.46 (m, 2H), 7.31 (d, J=8.3 Hz, 2H), 7.13 (d, J=8.4 Hz, 2H), 6.82 (d, J=9.0 Hz, 2H), 6.33-6.29 (m, 2H), 4.92-4.84 (m, 1H), 4.56-4.48 (m, 1H), 3.86 (s, 3H), 3.42 (s, 3H), 3.10-2.97 (m, 2H), 1.17 (d, J=6.2 Hz, 3H), 1.11 (d, J=6.2 Hz, 3H); MS (ESI) m/z 746 (M+H)⁺

(Step 2) N-[2,6-Difluoro-4-({[4-(1H-pyrrol-1-yl)phenyl]sulfonyl}amino)benzoyl]-4-(3,7-dimethyl-2,6-dioxo-2,3,6,7-tetrahydro-1H-purin-1-yl)-L-phenylalanine (A-38)

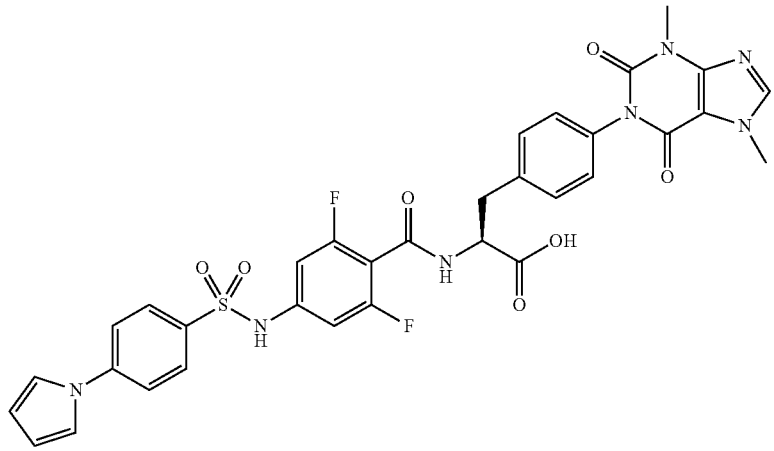 [SMILES: Cn1cnc2c1c(=O)n(-c1ccc(C[C@H](NC(=O)c3c(F)cc(NS(=O)(=O)c4ccc(-n5cccc5)cc4)cc3F)C(=O)O)cc1)c(=O)n2C]

To isopropyl N-[2,6-difluoro-4-({[4-(1H-pyrrol-1-yl)phenyl]sulfonyl}amino)benzoyl]-4-(3,7-dimethyl-2,6-dioxo-2,3,6,7-tetrahydro-1H-purin-1-yl)-L-phenylalaninate (B-38) (27.8 mg, 32.3 μmol), a 4 N hydrogen chloride/dioxane solution (2.0 ml) and water (4.0 ml) were added, followed by stirring at 70° C. for 6 hours. After the reaction liquid was concentrated under reduced pressure, purification was conducted by reversed-phase HPLC (H$_2$O containing 0.1% TFA/CH$_3$CN system) to obtain the title compound (7.6 mg, 29%).

1H NMR (d-DMSO, 400 MHz): δ 11.06 (s, 1H), 9.03 (d, J=7.8 Hz, 1H), 8.07 (d, J=0.5 Hz, 1H), 7.90 (d, J=8.9 Hz, 2H), 7.82 (d, J=8.9 Hz, 2H), 7.51-7.47 (m, 2H), 7.31 (d, J=8.4 Hz, 2H), 7.13 (d, J=8.4 Hz, 2H), 6.81 (d, J=9.1 Hz, 2H), 6.34-6.27 (m, 2H), 4.59-4.51 (m, 1H), 3.86 (s, 3H), 3.42 (s, 3H), 3.17-3.06 (m, 1H), 2.97 (dd, J=14.2, 9.7 Hz, 1H); MS (ESI) m/z 704 (M+H)$^+$

Example 77

Synthesis of A-39 and B-39

(Step 1) Isopropyl N-(2,6-Difluoro-4-{[(4-pyrimidin-2-yl-phenyl)sulfonyl]amino}benzoyl)-4-(3,7-dimethyl-2,6-dioxo-2,3,6,7-tetrahydro-1H-purin-1-yl)-L-phenylalaninate (B-39)

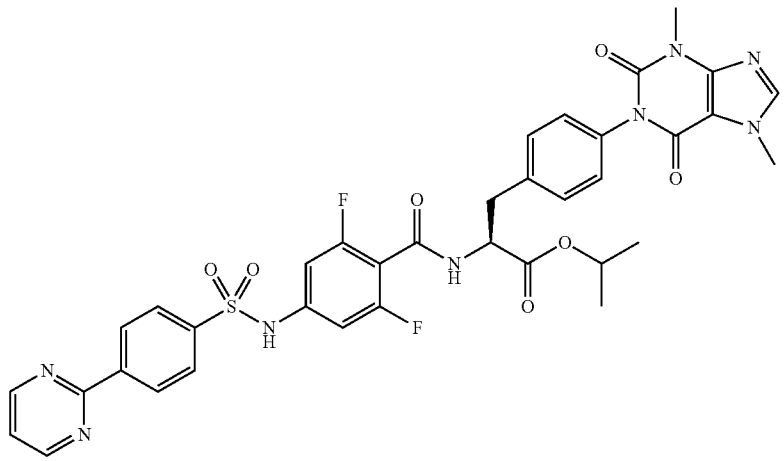

·TFA

Isopropyl 4-(3,7-dimethyl-2,6-dioxo-2,3,6,7-tetrahydro-1H-purin-1-yl)-L-phenylalaninate (M-5) (99.9 mg, 0.200 mmol) and 2,6-difluoro-4-{[(4-pyrimidin-2-yl-phenyl)sulfonyl]amino}benzoic acid (M-8) (78.3 mg, 0.200 mmol) were suspended in methylene chloride (4.0 ml), and HATU (114 mg, 0.300 mmol), HOAt (40.8 mg, 0.300 mmol), and triethylamine (70 µL, 0.50 mmol) were added thereto, followed by stirring at room temperature for 2 hours. After the reaction liquid was concentrated under reduced pressure, purification was conducted by reversed-phase HPLC ($H_2O$ containing 0.1% TFA/$CH_3CN$ system) to obtain the TFA salt (28.4 mg, 16%) of the title compound.

1H NMR (d-DMSO, 400 MHz): δ 11.19 (s, 1H), 9.14 (d, J=7.4 Hz, 1H), 8.96 (d, J=4.9 Hz, 2H), 8.64-8.53 (m, 2H), 8.10-7.97 (m, 3H), 7.54 (t, J=4.9 Hz, 1H), 7.30 (d, J=8.4 Hz, 2H), 7.13 (d, J=8.4 Hz, 2H), 6.83 (d, J=9.1 Hz, 2H), 4.95-4.78 (m, 1H), 4.59-4.44 (m, 1H), 3.86 (s, 3H), 3.42 (s, 3H), 3.12-2.96 (m, 2H), 1.16 (d, J=6.2 Hz, 3H), 1.11 (d, J=6.2 Hz, 3H);

MS (ESI) m/z 759 (M+H)$^+$ (Step 2) N-(2,6-Difluoro-4-{[(4-pyrimidin-2-yl-phenyl)sulfonyl]amino}benzoyl)-4-(3,7-dimethyl-2,6-dioxo-2,3,6,7-tetrahydro-1H-purin-1-yl)-L-phenylalanine (A-39)

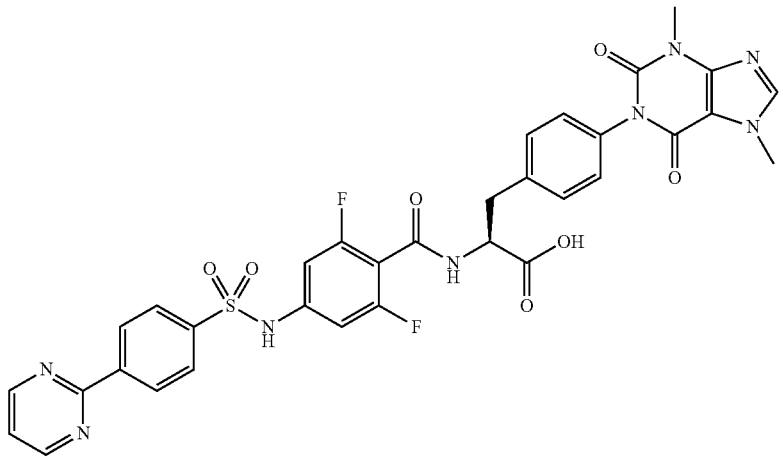

·TFA

To the TFA salt (28.4 mg, 32.5 µmol) of isopropyl N-(2,6-difluoro-4-{[(4-pyrimidin-2-yl-phenyl)sulfonyl]amino}benzoyl)-4-(3,7-dimethyl-2,6-dioxo-2,3,6,7-tetrahydro-1H-purin-1-yl)-L-phenylalaninate (B-39), a 4 N hydrogen chloride/dioxane solution (2.0 ml) and water (4.0 ml) were added, followed by stirring at 70° C. for 6 hours. After the reaction liquid was concentrated under reduced pressure, purification was conducted by reversed-phase HPLC ($H_2O$ containing 0.1% TFA/$CH_3CN$ system) to obtain the TFA salt (9.7 mg, 36%) of the title compound.

1H NMR (d-DMSO, 400 MHz): δ 11.17 (s, 1H), 9.03 (d, J=7.9 Hz, 1H), 8.96 (d, J=4.9 Hz, 2H), 8.58 (d, J=8.7 Hz, 2H), 8.06 (s, 1H), 8.02 (d, J=8.7 Hz, 2H), 7.53 (t, J=4.9 Hz, 1H), 7.31 (d, J=8.3 Hz, 2H), 7.12 (d, J=8.3 Hz, 2H), 6.81 (d, J=9.1 Hz, 2H), 4.57-4.51 (m, 1H), 3.86 (s, 3H), 3.42 (s, 3H), 3.14 (dd, J=14.4, 4.4 Hz, 1H), 2.96 (dd, J=13.9, 9.7 Hz, 1H);
MS (ESI) m/z 717 (M+H)$^+$

Example 78

Synthesis of A-40 and B-40

(Step 1) Isopropyl N-{4-[({4-[(Cyclopropylamino)carbonyl]phenyl}sulfonyl)amino]-2,6-difluorobenzoyl}-4-(6-methoxy-1-methyl-2,4-dioxo-1,4-dihydroquinazolin-3(2H)-yl)-L-phenylalaninate (B-40)

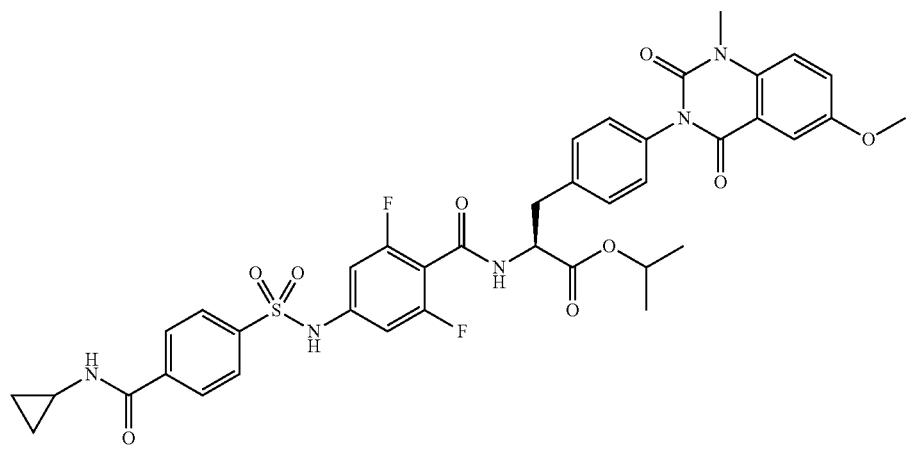 [SMILES: COc1ccc2c(c1)c(=O)n(-c1ccc(C[C@H](NC(=O)c3c(F)cc(NS(=O)(=O)c4ccc(C(=O)NC5CC5)cc4)cc3F)C(=O)OC(C)C)cc1)c(=O)n2C]

Isopropyl 4-(3,7-dimethyl-2,6-dioxo-2,3,6,7-tetrahydro-1H-purin-1-yl)-L-phenylalaninate (M-4) (105 mg, 0.200 mmol) and 4-[({4-[(cyclopropylamino)carbonyl]phenyl}sulfonyl)amino]-2,6-difluorobenzoic acid (M-12) (79.3 mg, 0.200 mmol) were suspended in methylene chloride (4.0 ml), and HATU (114 mg, 0.300 mmol), HOAt (40.8 mg, 0.300 mmol), and triethylamine (56 µL, 0.40 mmol) were added thereto, followed by stirring at room temperature for 2 hours. After the reaction liquid was concentrated under reduced pressure, purification was conducted by reversed-phase HPLC (H₂O containing 0.1% TFA/CH₃CN system) to obtain the title compound (24.2 mg, 15%).

1H NMR (d-DMSO, 400 MHz): δ 11.18 (s, 1H), 9.17 (d, J=7.4 Hz, 1H), 8.65 (d, J=4.3 Hz, 1H), 7.99-7.89 (m, 4H), 7.51-7.43 (m, 3H), 7.34 (d, J=8.3 Hz, 2H), 7.19 (d, J=8.3 Hz, 2H), 6.81 (d, J=9.0 Hz, 2H), 4.97-4.81 (m, 1H), 4.59-4.47 (m, 1H), 3.84 (s, 3H), 3.52 (s, 3H), 3.16-2.98 (m, 2H), 2.91-2.78 (m, 1H), 1.18 (d, J=6.2 Hz, 3H), 1.12 (d, J=6.2 Hz, 3H), 0.73-0.65 (m, 2H), 0.60-0.50 (m, 2H); MS (ESI) m/z 790 (M+H)⁺

(Step 2) N-{4-[({4-[(Cyclopropylamino)carbonyl]phenyl}sulfonyl)amino]-2,6-difluorobenzoyl}-4-(6-methoxy-1-methyl-2,4-dioxo-1,4-dihydroquinazolin-3(2H)-yl)-L-phenylalanine (A-40)

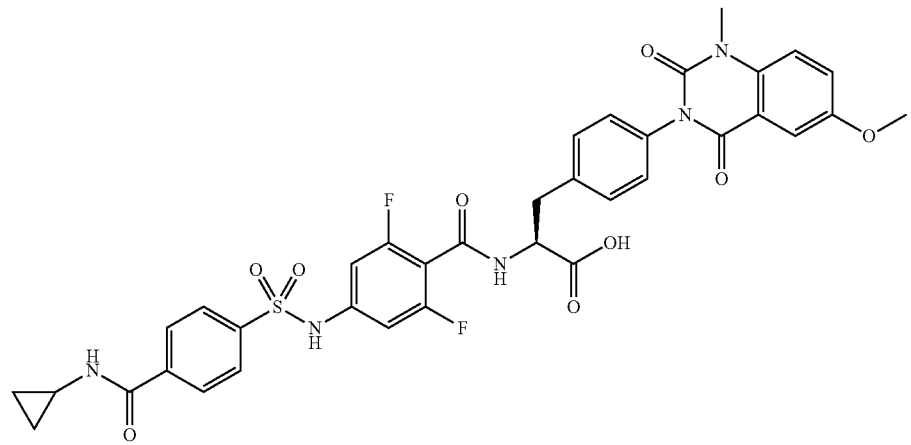 [SMILES: COc1ccc2c(c1)c(=O)n(-c1ccc(C[C@H](NC(=O)c3c(F)cc(NS(=O)(=O)c4ccc(C(=O)NC5CC5)cc4)cc3F)C(=O)O)cc1)c(=O)n2C]

To isopropyl N-{4-[({4-[(cyclopropylamino)carbonyl]phenyl}sulfonyl)amino]-2,6-difluorobenzoyl}-4-(6-methoxy-1-methyl-2,4-dioxo-1,4-dihydroquinazolin-3(2H)-yl)-L-phenylalaninate (B-40) (24.2 mg, 30.6 μmol), a 4 N hydrogen chloride/dioxane solution (2.0 ml) and water (4.0 ml) were added, followed by stirring at 70° C. for 6 hours. After the reaction liquid was concentrated under reduced pressure, purification was conducted by reversed-phase HPLC (H₂O containing 0.1% TFA/CH₃CN system) to obtain the title compound (10.3 mg, 45%).

1H NMR (d-DMSO, 400 MHz): δ 11.15 (s, 1H), 9.06 (d, J=7.7 Hz, 1H), 8.64 (d, J=4.1 Hz, 1H), 7.98-7.89 (m, 4H), 7.51-7.45 (m, 3H), 7.34 (d, J=8.2 Hz, 2H), 7.19 (d, J=8.2 Hz, 2H), 6.79 (d, J=9.0 Hz, 2H), 4.61-4.54 (m, 1H), 3.84 (s, 3H), 3.52 (s, 3H), 3.16-3.06 (m, 1H), 2.99 (dd, J=14.4, 9.5 Hz, 1H), 2.87-2.79 (m, 1H), 0.75-0.63 (m, 2H), 0.59-0.51 (m, 2H).; MS (ESI) m/z 748 (M+H)⁺

Example 79

Synthesis of C-1

Isopropyl N-{4-[(2,4'-Bipyridin-5-yl-sulfonyl)amino]-2,6-difluorobenzoyl}-4-(1-methyl-2,4-dioxo-1,4-dihydropyrido[3,4-d]pyrimidin-3 (2H)-yl)-L-phenylalaninate (C-1)

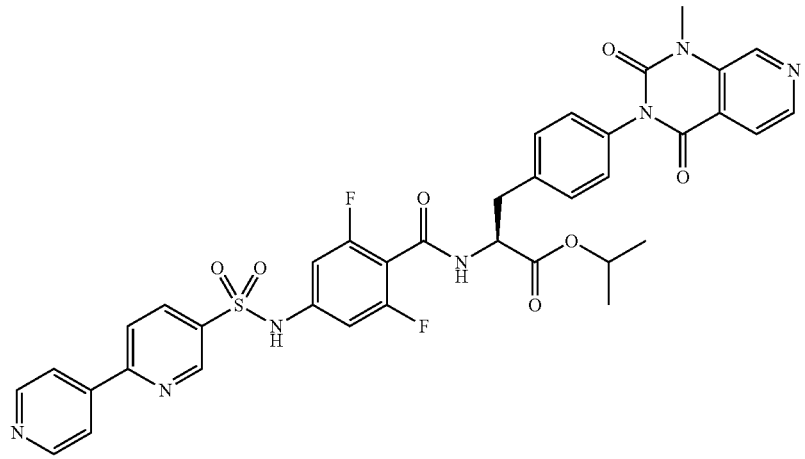

·3 TFA

N-{4-[(2,4'-Bipyridin-5-yl-sulfonyl)amino]-2,6-difluorobenzoyl}-4-(1-methyl-2,4-dioxo-1,4-dihydropyrido[3,4-d]pyrimidin-3(2H)-yl)-L-phenylalanine (A-4) (30.0 mg, 28.4 μmol) was dissolved in a 4 N hydrogen chloride/dioxane solution (2.0 ml), and isopropyl alcohol (1.0 ml) was added thereto, followed by stirring at 70° C. for 2 hours. After the reaction liquid was concentrated under reduced pressure, purification was conducted by reversed-phase HPLC (H₂O containing 0.1% TFA/CH₃CN system) to obtain the TFA salt (22.3 mg, 72%) of the title compound.

¹H NMR (d-DMSO, 400 MHz): δ 11.4 (s, 1H), 9.19-9.17 (m, 2H), 8.98 (s, 1H), 8.83 (dd, J=4.8, 1.2 Hz, 2H), 8.56 (d, J=4.8 Hz, 1H), 8.44-8.43 (m, 2H), 8.22 (d, J=6.0 Hz, 2H), 7.89 (d, J=4.8 Hz, 1H), 7.35 (d, J=8.0 Hz, 2H), 7.21 (d, J=8.4 Hz, 2H), 6.90 (d, J=8.8 Hz, 2H), 4.92-4.86 (m, 1H), 4.58-4.52 (m, 1H), 3.60 (s, 3H), 3.13-3.00 (m, 2H), 1.18 (d, J=6.0 Hz, 3H), 1.12 (d, J=6.4 Hz, 3H).; MS (ESI) m/z 756 (M+H)⁺

Example 80

Synthesis of C-2

2-Hydroxyethyl N-{4-[(2,4'-Bipyridin-5-yl-sulfonyl)amino]-2,6-difluorobenzoyl}-4-(1-methyl-2,4-dioxo-1,4-dihydropyrido[3,4-d]pyrimidin-3 (2H)-yl)-L-phenylalaninate (C-2)

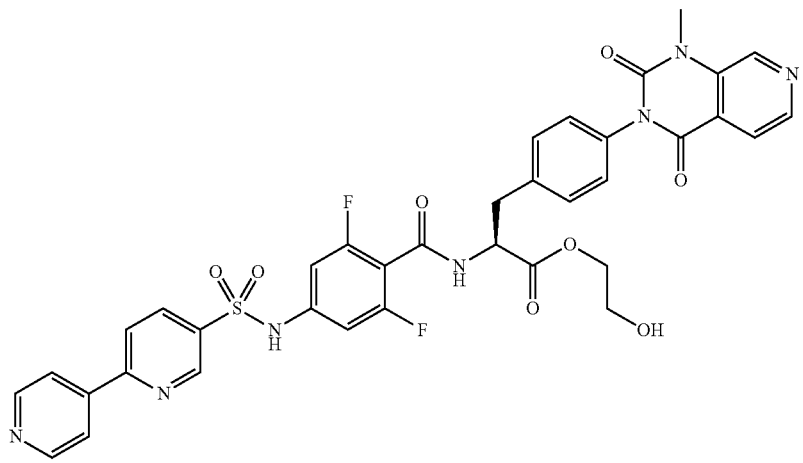

·3 TFA

The title compound was obtained by subjecting N-{4-[(2,4'-bipyridin-5-yl-sulfonyl)amino]-2,6-difluorobenzoyl}-4-(1-methyl-2,4-dioxo-1,4-dihydropyrido[3,4-d]pyrimidin-3 (2H)-yl)-L-phenylalanine (A-4) to the same method as described above.

$^1$H NMR (d-DMSO, 400 MHz): δ 11.4 (s, 1H), 9.13-9.11 (m, 2H), 8.90 (s, 1H), 8.79 (d, J=4.8 Hz, 2H), 8.49 (d, J=4.8 Hz, 1H), 8.40-8.35 (m, 2H), 8.21 (br, 2H), 7.81 (d, J=4.8 Hz, 1H), 7.28 (d, J=8.4 Hz, 2H), 7.14 (d, J=8.4 Hz, 2H), 6.82 (d, J=8.8 Hz, 2H), 4.62-4.56 (m, 1H), 4.01 (t, J=5.2 Hz, 2H), 3.53 (s, 3H), 3.14-2.93 (m, 2H).; MS (ESI) m/z 758 (M+H)$^+$

Example 81

Synthesis of C-3

2-(Diethylamino)ethyl N-{4-[(2,4'-Bipyridin-5-yl-sulfonyl)amino]-2,6-difluorobenzoyl}-4-(1-methyl-2,4-dioxo-1,4-dihydropyrido[3,4-d]pyrimidin-3(2H)-yl)-L-phenylalaninate (C-3)

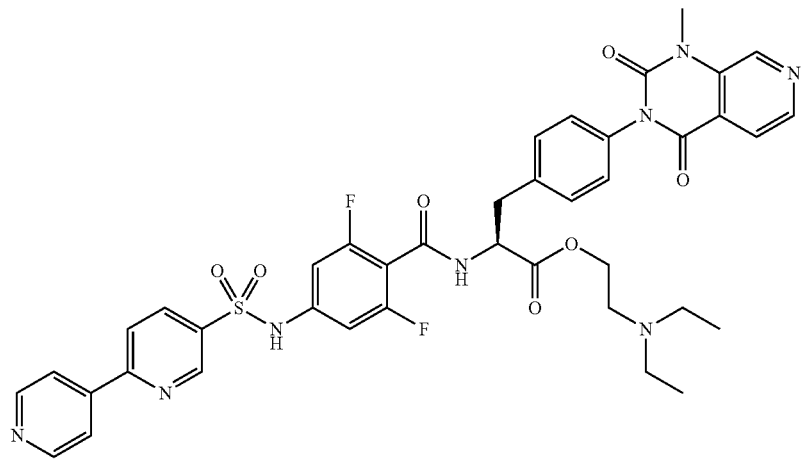

·4 TFA

The title compound was obtained by subjecting N-{4-[(2,4'-bipyridin-5-yl-sulfonyl)amino]-2,6-difluorobenzoyl}-4-(1-methyl-2,4-dioxo-1,4-dihydropyrido[3,4-d]pyrimidin-3(2H)-yl)-L-phenylalanine (A-4) to the same method as described above.

¹H NMR (d-DMSO, 400 MHz): δ 11.4 (s, 1H), 9.29 (d, J=7.2 Hz, 1H), 9.17 (d, J=2.0 Hz, 1H), 8.99 (s, 1H), 8.79 (dd, J=4.8, 1.6 Hz, 2H), 8.57 (d, J=4.8 Hz, 1H), 8.45-8.38 (m, 2H), 8.13 (dd, J=4.8, 1.6 Hz, 2H), 7.88 (d, J=5.2 Hz, 1H), 7.36 (d, J=8.4 Hz, 2H), 7.24 (d, J=8.4 Hz, 2H), 6.91 (d, J=9.2 Hz, 2H), 4.73-4.67 (m, 1H), 4.40-4.27 (m, 2H), 4.26 (s, 3H), 3.32 (br, 2H), 3.17-3.08 (m, 6H), 1.20-1.15 (m, 6H).; MS (ESI) m/z 813 (M+H)⁺

Example 82

Synthesis of C-4

Isobutyl N-{4-[(2,4'-Bipyridin-5-yl-sulfonyl)amino]-2,6-difluorobenzoyl}-4-(1-methyl-2,4-dioxo-1,4-dihydropyrido[3,4-d]pyrimidin-3(2H)-yl)-L-phenylalaninate (C-4)

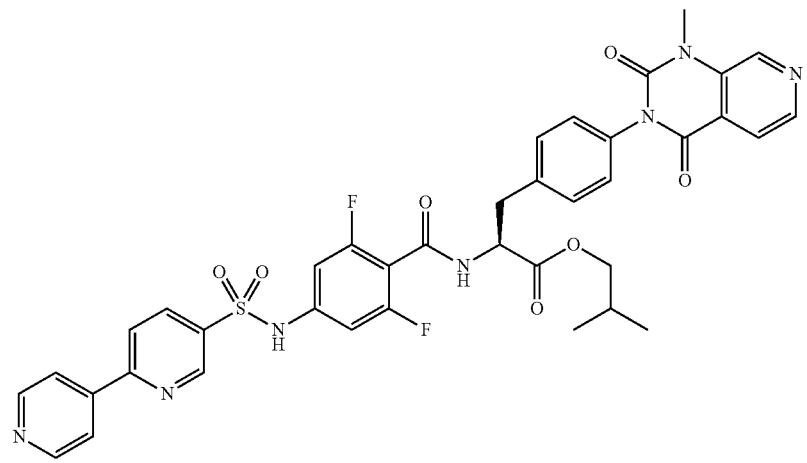

•3 TFA

The title compound was obtained by subjecting N-{4-[(2,4'-bipyridin-5-yl-sulfonyl)amino]-2,6-difluorobenzoyl}-4-(1-methyl-2,4-dioxo-1,4-dihydropyrido[3,4-d]pyrimidin-3(2H)-yl)-L-phenylalanine (A-4) to the same method as described above.

¹H NMR (d-DMSO, 400 MHz): δ 11.4 (s, 1H), 9.20-9.17 (m, 2H), 8.97 (s, 1H), 8.81 (dd, J=4.8, 1.6 Hz, 2H), 8.55 (d, J=5.2 Hz, 1H), 8.45-8.39 (m, 2H), 8.19 (dd, J=4.8, 1.6 Hz, 2H), 7.88 (dd, J=5.2, 0.4 Hz, 1H), 7.34 (d, J=8.4 Hz, 2H), 7.20 (d, J=8.4 Hz, 2H), 6.88 (d, J=8.8 Hz, 2H), 4.67-4.62 (m, 1H), 3.85 (d, J=5.6 Hz, 2H), 3.59 (s, 3H), 3.18-3.00 (m, 2H), 1.88-1.81 (m, 1H), 0.87 (d, J=6.8 Hz, 6H).; MS (ESI) m/z 770 (M+H)⁺

Example 83

Synthesis of C-5

Cyclohexylmethyl N-{4-[(2,4'-Bipyridin-5-yl-sulfonyl)amino]-2,6-difluorobenzoyl}-4-(1-methyl-2,4-dioxo-1,4-dihydropyrido[3,4-d]pyrimidin-3 (2H)-yl)-L-phenylalaninate (C-5)

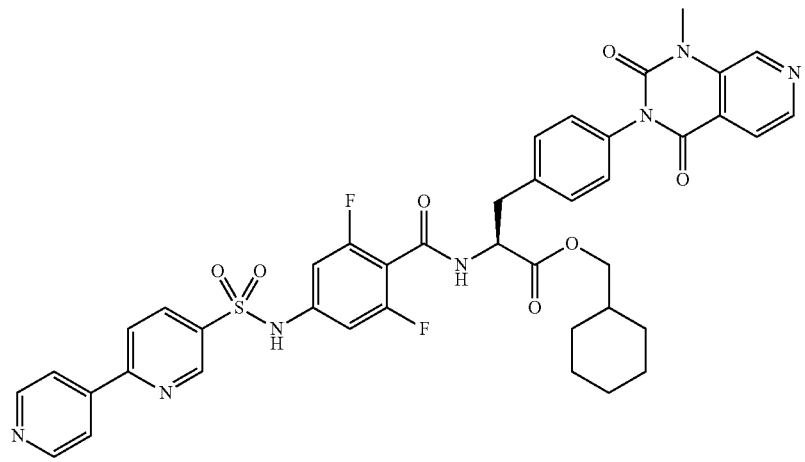

•3 TFA

The title compound was obtained by subjecting N-{4-[(2,4'-bipyridin-5-yl-sulfonyl)amino]-2,6-difluorobenzoyl}-4-(1-methyl-2,4-dioxo-1,4-dihydropyrido[3,4-d]pyrimidin-3 (2H)-yl)-L-phenylalanine (A-4) to the same method as described above.

$^1$H NMR (d-DMSO, 400 MHz): δ 11.4 (s, 1H), 9.12-9.10 (m, 2H), 8.90 (s, 1H), 8.76 (d, J=5.2 Hz, 2H), 8.49 (d, J=4.8 Hz, 1H), 8.39-8.33 (m, 2H), 8.16 (br, 2H), 7.81 (d, J=4.8 Hz, 1H), 7.27 (d, J=8.0 Hz, 2H), 7.14 (d, J=8.4 Hz, 2H), 6.82 (d, J=8.8 Hz, 2H), 4.58-4.54 (m, 1H), 3.80 (dd, J=6.4, 2.0 Hz, 2H), 3.52 (s, 3H), 3.12-2.92 (m, 2H), 1.60-1.47 (m, 6H), 1.16-1.01 (m, 3H), 0.89-0.76 (m, 2H).; MS (ESI) m/z 810 (M+H)$^+$

Example 84

Synthesis of C-6

Tetrahydro-2H-pyran-4-yl-methyl N-{4-[(2,4'-Bipyridin-5-yl-sulfonyl)amino]-2,6-difluorobenzoyl}-4-(1-methyl-2,4-dioxo-1,4-dihydropyrido[3,4-d]pyrimidin-3 (2H)-yl)-L-phenylalaninate (C-6)

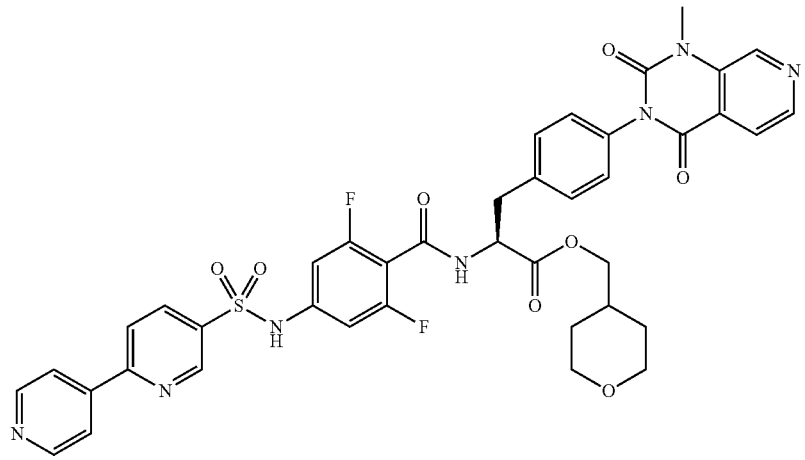

•3 TFA

The title compound was obtained by subjecting N-{4-[(2,4'-bipyridin-5-yl-sulfonyl)amino]-2,6-difluorobenzoyl}-4-(1-methyl-2,4-dioxo-1,4-dihydropyrido[3,4-d]pyrimidin-3(2H)-yl)-L-phenylalanine (A-4) to the same method as described above.

$^1$H NMR (d-DMSO, 400 MHz): δ 11.4 (s, 1H), 9.19-9.18 (m, 2H), 8.97 (s, 1H), 8.84 (dd, J=4.8, 1.6 Hz, 2H), 8.55 (d, J=5.2 Hz, 1H), 8.47-8.41 (m, 2H), 8.25 (dd, J=4.8, 1.2 Hz, 2H), 7.88 (dd, J=5.2, 0.4 Hz, 1H), 7.34 (d, J=8.4 Hz, 2H), 7.21 (d, J=8.4 Hz, 2H), 6.89 (d, J=8.8 Hz, 2H), 4.65-4.62 (m, 1H), 3.91 (d, J=6.4 Hz, 2H), 3.83-3.80 (m, 2H), 3.59 (s, 3H), 3.28-3.22 (m, 2H), 3.16-3.01 (m, 2H), 1.83-1.77 (m, 1H), 1.53-1.50 (m, 2H), 1.24-1.14 (m, 2H).; MS (ESI) m/z 812 (M+H)$^+$

Example 85

Synthesis of C-7

Isopropyl N-(2,6-Difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenyl-alaninate (C-7)

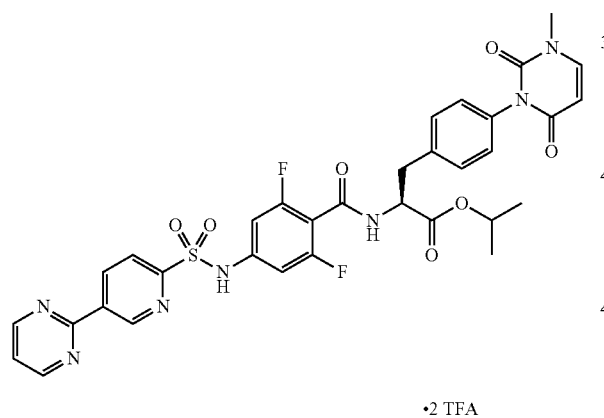

•2 TFA

The title compound was obtained by subjecting N-(2,6-difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalanine (A-2) to the same method as described above.

$^1$H NMR (d-DMSO, 400 MHz): δ 11.4 (s, 1H), 9.59 (dd, J=2.0, 0.8 Hz, 1H), 9.14 (d, J=7.2 Hz, 1H), 9.01 (d, J=4.8 Hz, 2H), 8.96 (dd, J=8.4, 2.0 Hz, 1H), 8.29 (dd, J=8.0, 0.4 Hz, 1H), 7.75 (d, J=8.0 Hz, 1H), 7.61 (t, J=4.8 Hz, 1H), 7.30 (d, J=8.4 Hz, 2H), 7.09 (d, J=8.4 Hz, 2H), 6.90 (d, J=9.2 Hz, 2H), 5.74 (d, J=8.0 Hz, 1H), 4.90-4.84 (m, 1H), 4.53-4.48 (m, 1H), 3.31 (s, 3H), 3.10-2.98 (m, 2H), 1.16 (d, J=6.4 Hz, 3H), 1.10 (d, J=6.0 Hz, 3H).; MS (ESI) m/z 706 (M+H)$^+$

Example 86

Synthesis of C-8

2-Hydroxyethyl N-(2,6-Difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalaninate (C-8)

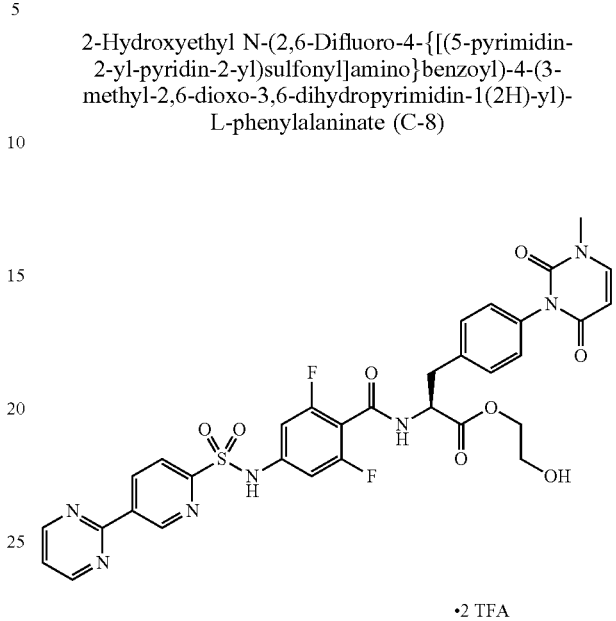

•2 TFA

The title compound was obtained by subjecting N-(2,6-difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalanine (A-2) to the same method as described above.

MS (ESI) m/z 708 (M+H)$^+$

Example 87

Synthesis of C-9

Isobutyl N-(2,6-Difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenyl-alaninate (C-9)

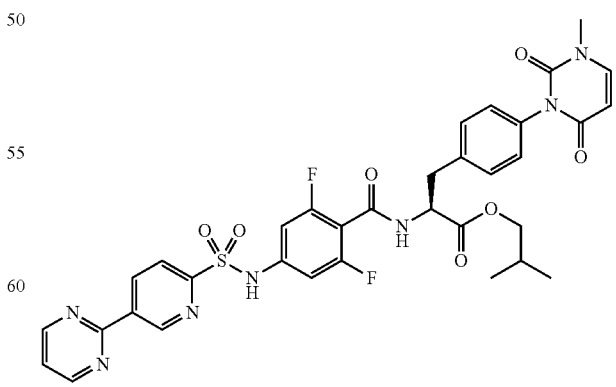

•2 TFA

The title compound was obtained by subjecting N-(2,6-difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalanine (A-2) to the same method as described above.

¹H NMR (d-DMSO, 400 MHz): δ 11.4 (s, 1H), 9.59 (d, J=1.6 Hz, 1H), 9.16 (d, J=7.6 Hz, 1H), 9.01 (d, J=5.2 Hz, 2H), 8.96 (dd, J=8.4, 2.0 Hz, 1H), 8.29 (d, J=8.0 Hz, 1H), 7.75 (d, J=8.0 Hz, 1H), 7.61 (t, J=5.2 Hz, 1H), 7.30 (d, J=8.4 Hz, 2H), 7.09 (d, J=8.4 Hz, 2H), 6.89 (d, J=9.2 Hz, 2H), 5.74 (d, J=8.0 Hz, 1H), 4.64-4.58 (m, 1H), 3.83 (dd, J=8.4, 6.8 Hz, 2H), 3.31 (s, 3H), 3.15-2.98 (m, 2H), 1.89-1.79 (m, 1H), 0.86 (d, J=6.8 Hz, 6H).; MS (ESI) m/z 720 (M+H)⁺

Example 88

Synthesis of C-10

Cyclohexylmethyl N-(2,6-Difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalaninate (C-10)

The title compound was obtained by subjecting N-(2,6-difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalanine (A-2) to the same method as described above.

¹H NMR (d-DMSO, 400 MHz): δ 11.4 (s, 1H), 9.51 (d, J=2.0 Hz, 1H), 9.07 (d, J=7.6 Hz, 1H), 8.94 (d, J=4.8 Hz, 2H), 8.88 (dd, J=8.0, 2.0 Hz, 1H), 8.21 (d, J=8.0 Hz, 1H), 7.68 (d, J=8.0 Hz, 1H), 7.53 (t, J=5.2 Hz, 1H), 7.23 (d, J=8.4 Hz, 2H), 7.02 (d, J=8.4 Hz, 2H), 6.82 (d, J=9.2 Hz, 2H), 5.67 (d, J=7.6 Hz, 1H), 4.54-4.52 (m, 1H), 3.80-3.76 (m, 1H), 3.23 (s, 3H), 3.08-2.90 (m, 2H), 1.59-1.47 (m, 6H), 1.11-1.03 (m, 3H), 0.88-0.83 (m, 2H).; MS (ESI) m/z 760 (M+H)⁺

Example 89

Synthesis of C-11

Tetrahydro-2H-pyran-4-yl-methyl N-(2,6-Difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalaninate (C-11)

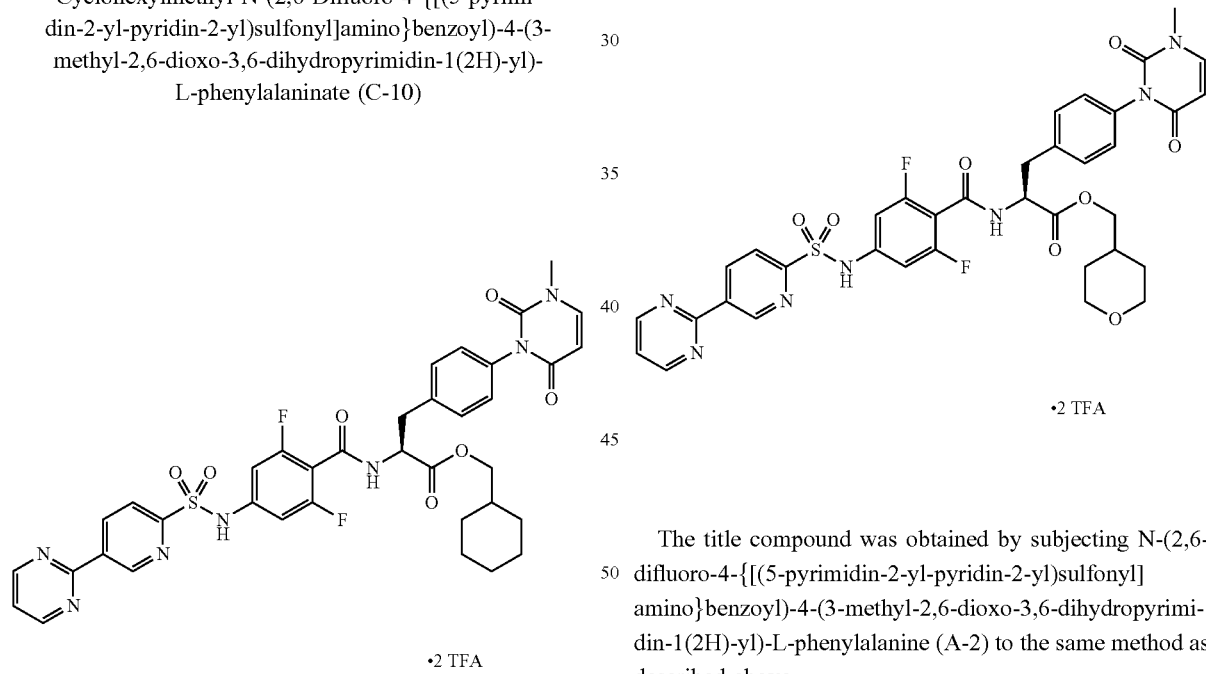

The title compound was obtained by subjecting N-(2,6-difluoro-4-{[(5-pyrimidin-2-yl-pyridin-2-yl)sulfonyl]amino}benzoyl)-4-(3-methyl-2,6-dioxo-3,6-dihydropyrimidin-1(2H)-yl)-L-phenylalanine (A-2) to the same method as described above.

¹H NMR (d-DMSO, 400 MHz): δ 11.4 (s, 1H), 9.59-9.59 (m, 1H), 9.17 (d, J=7.6 Hz, 1H), 9.01 (dd, J=5.2, 0.8 Hz, 2H), 8.96 (dd, J=8.4, 1.6 Hz, 1H), 8.29 (d, J=8.4 Hz, 1H), 7.75 (d, J=8.0 Hz, 1H), 7.61 (t, J=5.2 Hz, 1H), 7.30 (d, J=8.0 Hz, 2H), 7.10 (d, J=8.0 Hz, 2H), 6.90 (d, J=8.8 Hz, 2H), 5.74 (dd, J=8.0, 0.4 Hz, 1H), 4.63-4.57 (m, 1H), 3.90 (d, J=6.4 Hz, 2H), 3.81-3.79 (m, 2H), 3.31 (s, 3H), 3.27-3.21 (m, 2H), 3.14-2.98 (m, 2H), 1.83-1.76 (m, 1H), 1.52-1.49 (m, 2H), 1.23-1.13 (m, 2H).; MS (ESI) m/z 762 (M+H)⁺

Example 90

Synthesis of C-12

Ethyl N-{4-[({4-[(Cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (C-12)

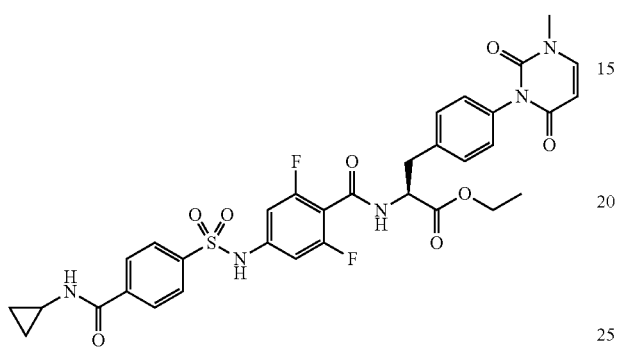

The title compound was obtained by subjecting N-{4-[({4-[(cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-7) to the same method as described above.

$^1$H NMR (d-DMSO, 400 MHz): δ 11.2 (s, 1H), 9.17 (br, 1H), 8.64 (s, 1H), 7.95 (br, 4H), 7.76 (dd, J=7.6, 4.4 Hz, 1H), 7.30 (d, J=3.6 Hz, 2H), 7.10 (d, J=4.0 Hz, 2H), 6.82-6.78 (m, 2H), 5.75 (dd, J=8.0, 5.2 Hz, 1H), 4.57 (br, 1H), 4.10-4.04 (m, 2H), 3.32 (s, 3H), 3.18-2.98 (m, 2H), 2.87-2.81 (m, 1H), 1.16-1.11 (m, 3H), 0.70 (br, 2H), 0.56 (br, 2H).; MS (ESI) m/z 696 (M+H)$^+$

Example 91

Synthesis of C-13

Isopropyl N-{4-[({4-[(Cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (C-13)

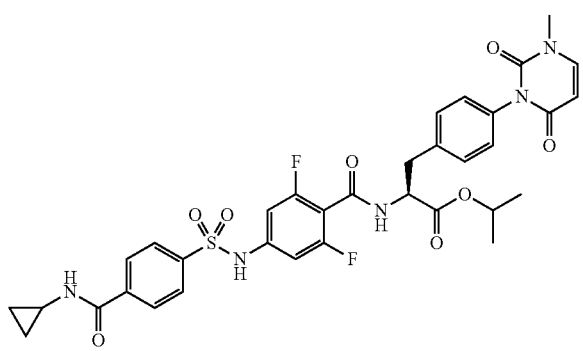 [SMILES: CC(C)OC(=O)[C@H](Cc1ccc(-n2c(=O)ccn(C)c2=O)cc1)NC(=O)c1c(F)cc(NS(=O)(=O)c2ccc(C(=O)NC3CC3)cc2)cc1F]

The title compound was obtained by subjecting N-{4-[({4-[(cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-7) to the same method as described above.

$^1$H NMR (d-DMSO, 400 MHz): δ 11.2 (s, 1H), 9.15 (d, J=7.2 Hz, 1H), 8.64 (d, J=4.0 Hz, 1H), 7.95 (dd, J=12.8, 8.8 Hz, 4H), 7.76 (d, J=8.0 Hz, 1H), 7.31 (d, J=8.0 Hz, 2H), 7.10 (d, J=8.0 Hz, 2H), 6.80 (d, J=9.2 Hz, 2H), 5.75 (d, J=8.0 Hz, 1H), 4.91-4.85 (m, 1H), 4.54-4.49 (m, 1H), 3.31 (s, 3H), 3.11-2.98 (m, 2H), 2.86-2.81 (m, 1H), 1.17 (d, J=6.0 Hz, 3H), 1.11 (d, J=6.4 Hz, 3H), 0.71-0.67 (m, 2H), 0.58-0.54 (m, 2H).;

MS (ESI) m/z 710 (M+H)$^+$

Example 92

Synthesis of C-14

2-Hydroxyethyl N-{4-[({4-[(Cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (C-14)

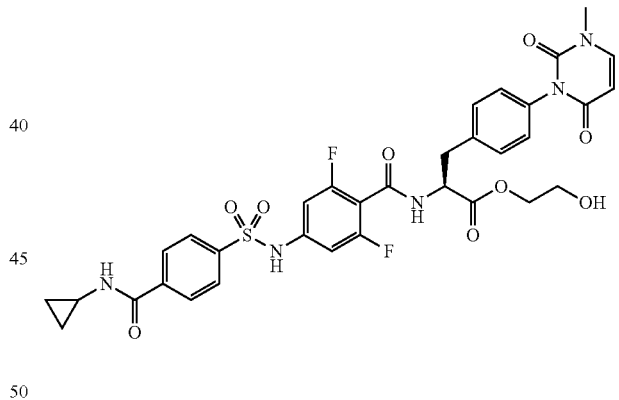

The title compound was obtained by subjecting N-{4-[({4-[(cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-7) to the same method as described above.

$^1$H NMR (d-DMSO, 400 MHz): δ 11.2 (s, 1H), 9.16 (d, J=7.6 Hz, 1H), 8.63 (d, J=4.4 Hz, 1H), 7.94 (dd, J=12.8, 8.8 Hz, 4H), 7.76 (d, J=7.6 Hz, 1H), 7.30 (d, J=8.0 Hz, 2H), 7.09 (d, J=8.4 Hz, 2H), 6.79 (dd, J=9.2, 2.0 Hz, 2H), 5.75 (d, J=7.6 Hz, 1H), 4.65-4.60 (m, 1H), 4.06 (t, J=5.2 Hz, 2H), 3.54 (t, J=6.0 Hz, 2H), 3.31 (s, 3H), 3.17-2.98 (m, 2H), 2.85-2.80 (m, 1H), 0.71-0.67 (m, 2H), 0.57-0.53 (m, 2H).;
MS (ESI) m/z 712 (M+H)$^+$

Example 93

Synthesis of C-15

2-(Diethylamino)ethyl N-{4-[({4-[(Cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (C-15)

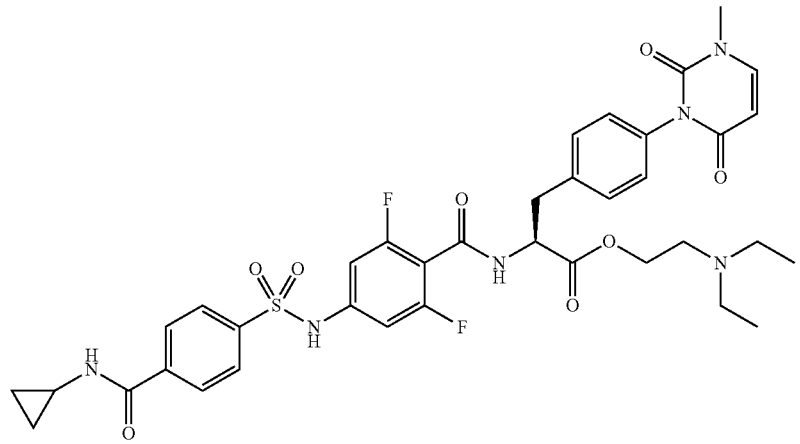

·TFA

The title compound was obtained by subjecting N-{4-[({4-[(cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-7) to the same method as described above.

$^1$H NMR (d-DMSO, 400 MHz): δ 11.2 (s, 1H), 9.26 (d, J=6.8 Hz, 1H), 8.64 (d, J=4.4 Hz, 1H), 7.94 (dd, J=14.4, 8.8 Hz, 4H), 7.77 (d, J=7.6 Hz, 1H), 7.31 (d, J=8.0 Hz, 2H), 7.13 (d, J=8.4 Hz, 2H), 6.81 (dd, J=9.2, 1.6 Hz, 2H), 5.76 (d, J=8.0 Hz, 1H), 4.69-4.63 (m, 1H), 4.39-4.33 (m, 1H), 4.29-4.23 (m, 1H), 3.35-3.27 (m, 5H), 3.14-3.07 (m, 6H), 2.87-2.80 (m, 1H), 1.18-1.14 (m, 6H), 0.71-0.68 (m, 2H), 0.57-0.54 (m, 2H).;
MS (ESI) m/z 767 (M+H)$^+$

The title compound was obtained by subjecting N-{4-[({4-[(cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-7) to the same method as described above.

$^1$H NMR (d-DMSO, 400 MHz): δ 11.2 (s, 1H), 9.17 (d, J=7.6 Hz, 1H), 8.64 (d, J=4.0 Hz, 1H), 7.94 (dd, J=12.0, 8.8 Hz, 4H), 7.76 (d, J=8.0 Hz, 1H), 7.31 (d, J=8.4 Hz, 2H), 7.10 (d, J=8.4 Hz, 2H), 6.79 (d, J=9.2 Hz, 2H), 5.75 (d, J=7.6 Hz, 1H), 4.65-4.59 (m, 1H), 3.84 (dd, J=6.8, 1.2 Hz, 2H), 3.31 (s, 3H), 3.16-2.98 (m, 2H), 2.86-2.81 (m, 1H), 1.88-1.81 (m, 1H), 0.86 (d, J=6.4 Hz, 6H), 0.72-0.67 (m, 2H), 0.57-0.53 (m, 2H).; MS (ESI) m/z 724 (M+H)$^+$

Example 94

Synthesis of C-16

Isobutyl N-{4-[({4-[(Cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (C-16)

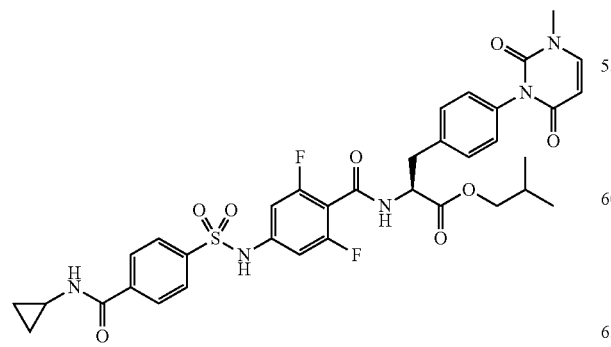

Example 95

Synthesis of C-17

Cyclohexylmethyl N-{4-[({4-[(Cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (C-17)

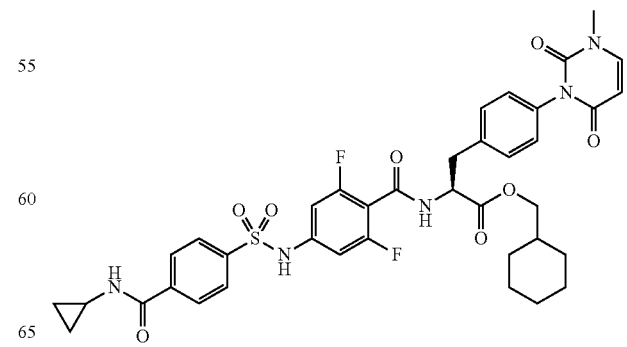

The title compound was obtained by subjecting N-{4-[({4-[(cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-7) to the same method as described above.

$^1$H NMR (d-DMSO, 400 MHz): δ 11.2 (s, 1H), 9.15 (d, J=7.6 Hz, 1H), 8.63 (d, J=4.4 Hz, 1H), 7.94 (dd, J=12.8, 8.8 Hz, 4H), 7.75 (d, J=8.0 Hz, 1H), 7.30 (d, J=8.0 Hz, 2H), 7.09 (d, J=8.4 Hz, 2H), 6.79 (d, J=9.2 Hz, 2H), 5.74 (d, J=8.0 Hz, 1H), 4.63-4.58 (m, 1H), 3.86 (d, J=4.8 Hz, 2H), 3.31 (s, 3H), 3.15-2.97 (m, 2H), 2.85-2.81 (m, 1H), 1.66-1.57 (m, 6H), 1.23-1.09 (m, 3H), 0.96-0.88 (m, 2H), 0.71-0.69 (m, 2H), 0.57-0.53 (m, 2H).; MS (ESI) m/z 764 (M+H)$^+$

Example 96

Synthesis of C-18

Tetrahydro-2H-pyran-4-yl-methyl N-{4-[({4-[(Cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (C-18)

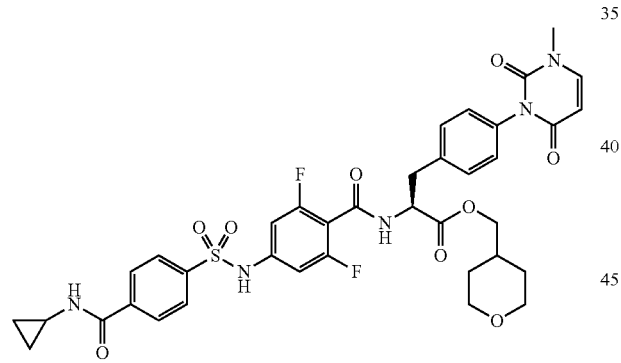

The title compound was obtained by subjecting N-{4-[({4-[(cyclopropylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-7) to the same method as described above.

$^1$H NMR (d-DMSO, 400 MHz): δ 11.2 (s, 1H), 9.18 (d, J=7.6 Hz, 1H), 8.64 (d, J=4.4 Hz, 1H), 7.94 (dd, J=12.8, 9.2 Hz, 4H), 7.76 (d, J=8.0 Hz, 1H), 7.30 (d, J=8.0 Hz, 2H), 7.10 (d, J=8.4 Hz, 2H), 6.80 (d, J=8.8 Hz, 2H), 5.75 (d, J=8.0 Hz, 1H), 4.64-4.58 (m, 1H), 3.90 (d, J=6.4 Hz, 2H), 3.82-3.81 (m, 2H), 3.31 (s, 3H), 3.28-3.23 (m, 2H), 3.14-2.99 (m, 2H), 2.87-2.80 (m, 1H), 1.84-1.76 (m, 1H), 1.53-1.50 (m, 2H), 1.24-1.14 (m, 2H), 0.72-0.69 (m, 2H), 0.57-0.54 (m, 2H).; MS (ESI) m/z 766 (M+H)$^+$

Example 97

Synthesis of M-39

(Step 1) Methyl N-(tert-Butoxycarbonyl)-3-iodo-L-alaninate

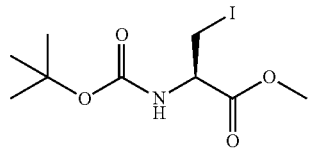

Triphenylphosphine (66.0 g, 0.250 mol) and imidazole (17.1 g, 0.250 mol) were dissolved in methylene chloride (900 ml). After cooling to 0° C., iodine (64.0 g, 0.250 mol) was added thereto, and the temperature was gradually raised from 0° C. to room temperature in the presence of nitrogen gas, followed by stirring for 10 minutes. After cooling to 0° C., a methylene chloride solution (100 of methyl N-(tert-butoxycarbonyl)-L-serinate (45.0 g, 0.200 mol) was slowly added dropwise over one hour, followed by stirring at room temperature for 2 hours. After the reaction solution was filtered, the filtrate was concentrated under reduced pressure. The obtained residue was purified by silica gel column chromatography (petroleum ether/ethyl acetate=1:1 to 1:2) to obtain the title compound (43.8 g, 65%).

1H NMR (CDCl3, 400 MHz): δ 5.36-5.34 (m, 1H), 4.53-4.51 (m, 1H), 3.80 (s, 3H), 3.61-3.53 (m, 2H), 1.46 (s, 9H).

(Step 2) Methyl 3-(5-Bromopyridin-2-yl)-N-(tert-butoxycarbonyl)-L-alaninate

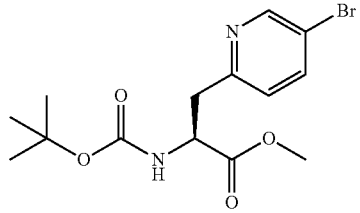 [SMILES: COC(=O)[C@H](Cc1ccc(Br)cn1)NC(=O)OC(C)(C)C]

An operation in which zinc (24.0 g, 0.360 mol) was heated at 200° C. for 30 minutes and cooled to room temperature was repeated three times, and then an N,N'-dimethylformamide solution (50 ml) of dibromoethane (3.40 g, 18.2 mmol) was added thereto. An operation in which the obtained reaction mixture was heated to 90° C. and then cooled to room temperature was repeated twice, and then chlorotrimethylsilane (0.400 g, 3.64 mmol) was added to the reaction mixture, followed by stirring at room temperature for 30 minutes. An N,N'-dimethylformamide solution (70 ml) of methyl N-(tert-butoxycarbonyl)-3-iodo-L-alaninate (20.0 g, 60.7 mmol) was added dropwise, followed by stirring at 35° C. for 2.5 hours. Then, 2,5-dibromopyridine (19.0 g, 80.7 mmol) and bis(triphenylphosphine)palladium (II) chloride (2.30 g, 3.30 mmol) were further added to the reaction solution, followed by stirring at 70° C. for 2 hours. After cooling to room temperature, the reaction solution was diluted with water, followed by extraction with ethyl acetate (200 ml×3). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:1 to 1:2) to obtain the title compound (11.7 g, 54%).

1H NMR (CDCl₃, 400 MHz): δ 8.61 (s, 1H), 7.98-7.96 (m, 1H), 7.29-7.25 (m, 2H), 4.45-4.39 (m, 1H), 3.60 (s, 3H), 3.12-2.97 (m, 2H), 1.32 (s, 9H).

(Step 3) Methyl N-(tert-Butoxycarbonyl)-3-{5-[(diphenylmethylene)amino]pyridin-2-yl}-L-alaninate

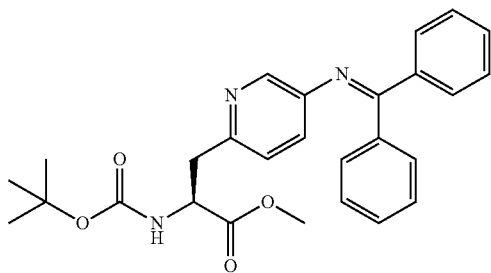 [SMILES: COC(=O)[C@H](Cc1ccc(N=C(c2ccccc2)c2ccccc2)cn1)NC(=O)OC(C)(C)C]

Methyl 3-(5-bromopyridin-2-yl)-N-(tert-butoxycarbonyl)-L-alaninate (15.0 g, 40.0 mmol) and BINAP (1.58 g, 2.40 mmol) were dissolved in toluene (150 ml). To the solution, palladium(II) acetate (537 mg, 2.40 mmol), cesium carbonate (27.0 g, 84.0 mmol), and benzophenone imine (11.0 g, 60.0 mmol) were added, followed by stirring at 110° C. for 10 hours. After cooling to room temperature, the liquid was filtered through Celite, followed by washing with ethyl acetate. The obtained filtrate was concentrated under reduced pressure, and the residue was purified by silica gel column chromatography (petroleum ether/ethyl acetate=1:1 to 1:2) to obtain the title compound (14.6 g, 76%).

1H NMR (DMSO-d₆, 400 MHz): δ 7.87 (s, 1H), 7.67-7.35 (m, 2H), 7.56-7.45 (m, 3H), 7.34-7.33 (m, 3H), 7.19-7.15 (m, 3H), 7.06 (s, 1H), 4.34-4.32 (m, 1H), 3.51 (s, 3H), 2.95-2.90 (m, 2H), 1.33 (s, 9H).; MS (ESI) m/z 460 (M+H)⁺

(Step 4) Methyl 3-(5-Aminopyridin-2-yl)-N-(tert-butoxycarbonyl-L-alaninate

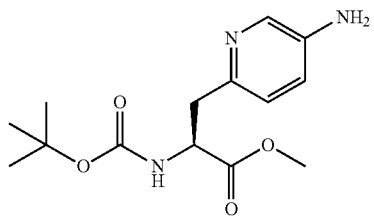 [SMILES: COC(=O)[C@H](Cc1ccc(N)cn1)NC(=O)OC(C)(C)C]

Methyl N-(tert-butoxycarbonyl)-3-{5-[(diphenylmethylene)amino]pyridin-2-yl}-L-alaninate (14.6 g, 32.0 mmol) and palladium hydroxide carbon (5.0 g, 7.0 mmol) were suspended in methanol (100 ml), and ammonium formate (2.0 g, 32 mmol) was added thereto, followed by stirring at 60° C. for 3 hours. After the reaction solution was filtered, the solvent was removed under reduced pressure. The obtained compound (14.6 g, 31.0 mmol) and palladium hydroxide carbon (5.0 g, 7.0 mmol) were suspended in methanol (100 ml), and ammonium formate (2.0 g, 32 mmol) was added thereto, followed by stirring at 60° C. for 6 hours. After the reaction solution was filtered, the filtrate was concentrated under reduced pressure. The obtained residue was purified by silica gel column chromatography (petroleum ether/ethyl acetate=1:1 to 1:2) to obtain the title compound (7.9 g, 84%).

MS (ESI) m/z 296 (M+H)⁺

(Step 5) Methyl N-(tert-Butoxycarbonyl)-3-[5-(2,4-dioxo-1,4-dihydropyrido[3,4-d]pyrimidin-3(2H)-yl)pyridin-2-yl]-L-alaninate

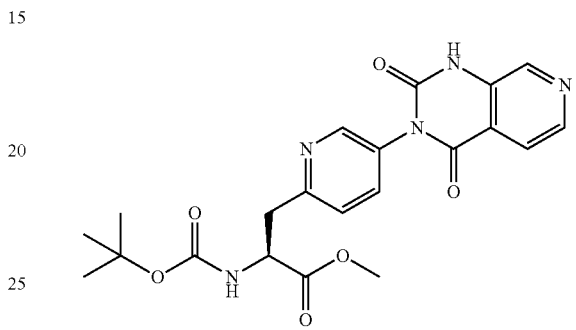

Methyl 3-aminoisonicotinate (4.80 g, 32.0 mmol) and diisopropylethylamine (8.20 g, 64.0 mmol) were dissolved in methylene chloride (100 ml), and a methylene chloride solution (20 ml) of triphosgene (3.10 g, 10.6 mmol) was added thereto, followed by stirring at 0° C. for 3 hours. To this solution, methyl 3-(5-aminopyridin-2-yl)-N-(tert-butoxycarbonyl-L-alaninate (7.90 g, 26.7 mmol) was added, followed by stirring at room temperature for further 12 hours. The reaction solution was concentrated under reduced pressure, and then ethyl acetate was added thereto. The mixture was washed with a saturated aqueous sodium hydrogen carbonate solution, water, and saturated aqueous sodium chloride, and dried over anhydrous sodium sulfate. The solvent was removed under reduced pressure, and the obtained residue was purified by silica gel column chromatography (petroleum ether/ethyl acetate=1:1 to 1:2) to obtain the title compound (7.6 g).

MS (ESI) m/z 442 (M+H)⁺

(Step 6) Methyl N-(tert-Butoxycarbonyl)-3-[5-(1-methyl-2,4-dioxo-1,4-dihydropyrido[3,4-d]pyrimidin-3(2H)-yl)pyridin-2-yl]-L-alaninate

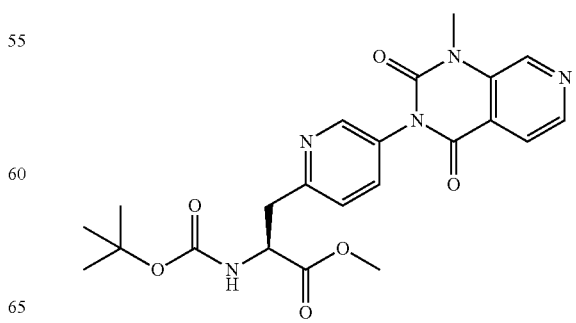

Methyl N-(tert-butoxycarbonyl)-3-[5-(2,4-dioxo-1,4-dihydropyrido[3,4-d]pyrimidin-3(2H)-yl)pyridin-2-yl]-L-alaninate (7.6 g) was dissolved in N,N'-dimethylformamide (60 ml), and an aqueous solution (4.0 ml) of potassium carbonate (0.60 g, 4.3 mmol) was added thereto, followed by stirring at room temperature for 3 hours. To this reaction solution, p-toluenesulfonic acid methyl ester (4.4 g, 24 mmol) and potassium carbonate (2.00 g, 14.4 mmol) were added, followed by stirring at room temperature for 12 hours. The reaction solution was diluted with water (100 ml), followed by extraction with ethyl acetate (100 ml×3). The extraction liquids were combined, washed with saturated aqueous sodium chloride, and dried over anhydrous sodium sulfate. Then, the solvent was removed under reduced pressure. The obtained residue was purified by silica gel column chromatography (petroleum ether/ethyl acetate=1:1) to obtain the title compound (6.0 g, 84%).

1H NMR (DMSO-$d_6$, 400 MHz): δ 8.99 (s, 1H), 8.58 (d, J=4.8 Hz, 1H), 8.45 (d, J=2.0 Hz, 1H), 7.92 (d, J=4.8 Hz, 1H), 7.73-7.71 (m, 1H), 7.42 (d, J=8.4 Hz, 1H), 7.34 (d, J=8.0 Hz, 1H), 4.55-4.49 (m, 1H), 3.19-3.15 (m, 2H), 3.71 (s, 3H), 3.52 (s, 3H), 1.35 (s, 9H).; MS (ESI) m/z 456 (M+H)+

(Step 7) Methyl 3-[5-(1-Methyl-2,4-dioxo-1,4-d-dihydropyrido[3,4-d]pyrimidin-3 (2H)-yl)pyridin-2-yl]-L-alaninate (M-39)

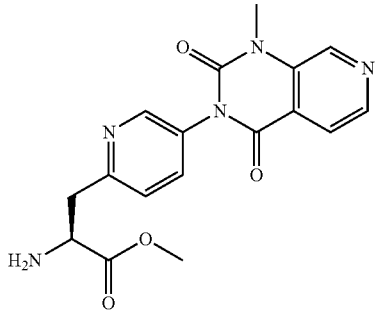 [SMILES: COC(=O)[C@@H](N)Cc1ccc(-n2c(=O)c3ccncc3n(C)c2=O)cn1]

To methyl N-(tert-butoxycarbonyl)-3-[5-(1-methyl-2,4-dioxo-1,4-dihydropyrido[3,4-d]pyrimidin-3(2H)-yl)pyridin-2-yl]-L-alaninate (6.00 g, 13.2 mmol), 4 N hydrogen chloride/ethyl acetate (50 ml) was added, followed by stirring at room temperature for 1 hour. The obtained white solid was filtered and dried under reduced pressure to obtain the title compound (M-39) (4.8 g, 93%).

$^1$H NMR (CD$_3$OD, 400 MHz): δ 9.25 (s, 1H), 8.71 (d, J=5.6 Hz, 1H), 8.66 (s, 1H), 8.54 (d, J=5.6 Hz, 1H), 8.08 (d, J=2.8 Hz, 1H), 7.78-7.58 (m, 1H), 4.65-4.62 (m, 1H), 3.78 (s, 3H), 3.71 (s, 3H), 3.62-3.61 (m 2H).; MS (ESI) m/z 356 (M+H)+

Example 98

Synthesis of M-40

(Step 1) Methyl 3-({[(5-Bromopyridin-2-yl)amino]carbonyl}amino)isonicotinate

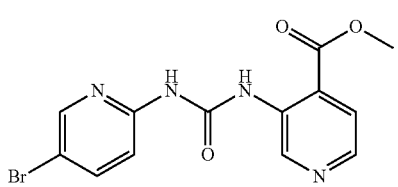

Methyl 3-aminoisonicotinate (4.80 g, 32.0 mmol) and diisopropylethylamine (8.20 g, 64.0 mmol) were dissolved in methylene chloride (100 ml), and a methylene chloride solution (20 ml) of triphosgene (3.10 g, 10.4 mmol) was added thereto, followed by stirring at 0° C. for 3 hours. To this solution, 5-bromopyridine-2-amine (4.60 g, 26.6 mmol) was added, followed by stirring at room temperature for further 12 hours. After the reaction solution was concentrated under reduced pressure, ethyl acetate was added. The mixture was washed with a saturated aqueous sodium hydrogen carbonate solution, water, and saturated aqueous sodium chloride, and dried over anhydrous sodium sulfate. The solvent was removed under reduced pressure, and the obtained residue was purified by silica gel column chromatography (petroleum ether/ethyl acetate=1:1 to 1:2) to obtain the title compound (6.2 g, 670).

$^1$H NMR (400 MHz, DMSO-$d_6$): δ 11.0 (s, 1H), 10.3 (s, 1H), 9.4 (s, 1H), 8.39 (d, J=5.2 Hz, 2H), 8.0 (d, J=8.8 Hz, 1H), 7.54 (d, J=4.8 Hz, 1H), 7.48 (d, J=8.8 Hz, 1H), 3.92 (s, 3H).

(Step 2) 3-(5-Bromopyridin-2-yl)-1-methylpyrido[3,4-d]pyrimidine-2,4(1H,3H)-dione

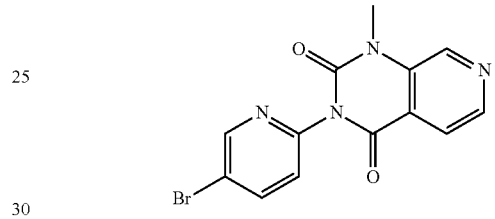

Methyl 3-({[(5-bromopyridin-2-yl)amino]carbonyl}amino)isonicotinate (6.20 g, 17.7 mmol) was dissolved in N,N'-dimethylformamide (60 ml), and an aqueous solution (4.0 ml) of potassium carbonate (600 mg, 4.34 mmol) was added thereto, followed by stirring at room temperature for 3 hours. To this reaction solution, p-toluenesulfonic acid methyl ester (4.40 g, 23.6 mmol) and potassium carbonate (3.00 g, 21.7 mmol) were added, followed by stirring at room temperature for 12 hours. The reaction solution was diluted with water (100 ml), followed by extraction with ethyl acetate (100 ml×3). The extraction liquids were combined, washed with saturated aqueous sodium chloride, and dried over anhydrous sodium sulfate. Then, the solvent was removed under reduced pressure. The obtained residue was purified by silica gel column chromatography (petroleum ether/ethyl acetate=1:1) to obtain the title compound (5.2 g, 88%).

$^1$H NMR (400 MHz, DMSO-$d_6$): δ 9.00 (s, 1H), 8.77 (d, J=2.4 Hz, 1H), 8.58 (d, J=4.8 Hz, 1H), 8.32-8.30 (m, 1H), 7.91 (d, J=4.8 Hz, 1H), 7.52 (d, J=8.8 Hz, 1H), 3.61 (s, 3H).

(Step 3) Methyl N-(tert-Butoxycarbonyl)-3-[6-(1-methyl-2,4-dioxo-1,4-dihydropyrido[3,4-d]pyrimidin-3(2H)-yl)pyridin-3-yl]-L-alaninate

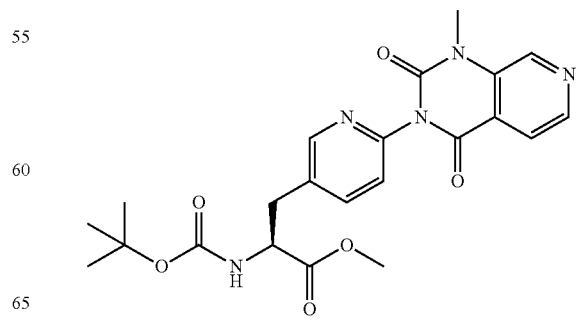

An operation in which zinc (2.40 g, 36.7 mmol) was heated at 200° C. for 30 minutes and cooled to room temperature was repeated three times, and then an N,N'-dimethylformamide solution (5.0 ml) of dibromoethane (0.340 g, 1.82 mmol) was added thereto. An operation in which the obtained reaction mixture was heated to 90° C. and then cooled to room temperature was repeated twice, and then chlorotrimethylsilane (40.0 mg, 0.364 mmol) was added to the reaction mixture, followed by stirring at room temperature for 30 minutes. An N,N'-dimethylformamide solution (5.0 ml) of methyl N-(tert-butoxycarbonyl)-3-iodo-L-alaninate (2.00 g, 6.08 mmol) was added dropwise, followed by stirring at 35° C. for 2.5 hours. Then, 3-(5-bromopyridin-2-yl)-1-methylpyrido[3,4-d]pyrimidine-2,4(1H,3H)-dione (2.60 g, 7.80 mmol) and bis(triphenylphosphine)palladium(II) chloride (230 mg, 0.328 mmol) were further added to the reaction solution, followed by stirring at 70° C. for 2 hours. After cooling to room temperature, the reaction solution was diluted with water, followed by extraction with ethyl acetate (20 ml×3). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:1 to 1:2) to obtain the title compound (300 mg, 11%).

$^1$H NMR (400 MHz, CDCl$_3$): δ 8.83 (s, 1H), 8.62 (d, J=3.6 Hz, 1H), 8.46 (s, 1H), 8.05 (d, J=3.2 Hz, 1H), 7.75 (d, J=4.4 Hz, 1H), 7.29-7.27 (m, 1H), 5.16-5.12 (m, 1H), 4.69-4.67 (m, 1H), 3.76 (s, 3H), 3.72 (s, 3H), 3.23-3.20 (m, 2H), 1.45 (s, 9H).

(Step 4) Methyl 3-[6-(1-Methyl-2,4-dioxo-1,4-dihydropyrido[3,4-d]pyrimidin-3(2H)-yl)pyridin-3-yl]-L-alaninate (M-40)

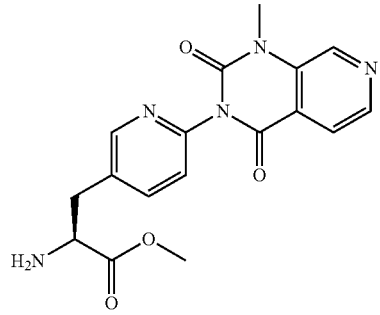 [SMILES: COC(=O)[C@@H](N)Cc1ccc(-n2c(=O)c3ccncc3n(C)c2=O)nc1]

To methyl N-(tert-butoxycarbonyl)-3-[6-(1-methyl-2,4-dioxo-1,4-dihydropyrido[3,4-d]pyrimidin-3(2H)-yl)pyridin-3-yl]-L-alaninate (300 mg, 0.659 mmol), 4 N hydrogen chloride/ethyl acetate (5.0 ml) was added, followed by stirring at room temperature for 1 hour. The obtained white solid was filtered and dried under reduced pressure to obtain a hydrochloride of the title compound (M-40) (253 mg, 98%).

$^1$H NMR (400 MHz, CD$_3$OD): δ 9.29 (s, 1H), 8.77 (d, J=6.0 Hz, 1H), 8.62 (d, J=2.0 Hz, 1H), 8.57 (d, J=5.6 Hz, 1H), 8.09 (dd, J=8.0, 2.0 Hz, 1H), 7.64 (dd, J=15.6, 8.0 Hz, 1H), 4.55-4.51 (m, 1H), 3.88 (s, 3H), 3.76 (s, 3H), 3.52-3.48 (m, 1H), 3.46-3.41 (m, 1H).; MS (ESI) m/z 356 (M+H)$^+$

Example 100

Synthesis of M-42

(Step 1) 1,6-Dimethylpyrimidine-2,4(1H,3H)-dione

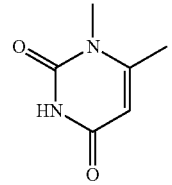

4-Methyleneaxetan-2-one (8.0 g, 95 mmol) and N-methylurea (5.0 g, 68 mmol) were dissolved in acetic acid (50 ml), followed by stirring at 120° C. for 12 hours. The solvent was removed under reduced pressure. To the obtained residue, ethyl acetate (50 ml) was added, followed by stirring for 30 minutes. After the precipitated solid was filtered, purification was conducted by reversed-phase HPLC (H2O containing 0.1% FTA/CH3CN system) to obtain the title compound (1.3 g, 14%).

$^1$H NMR (400 MHz, CD$_3$OD): δ 5.59 (s, 1H), 3.39 (s, 3H), 2.32 (s, 3H).

(Step 2) Methyl N-(tert-Butoxycarbonyl)-4-(3,4-dimethyl-2,6-dioxo-3,6-dihydropyrimidin-1(2H)-yl)-L-phenylalaninate

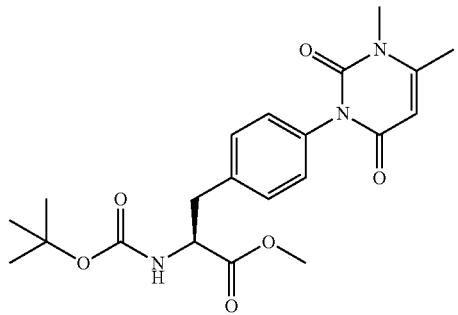 [SMILES: COC(=O)[C@H](Cc1ccc(-n2c(=O)cc(C)n(C)c2=O)cc1)NC(=O)OC(C)(C)C]

1,6-Dimethylpyrimidine-2,4(1H,3H)-dione (1.3 g, 9.3 mmol) and methyl N-(tert-butoxycarbonyl)-4-(dihydroxyboryl)-L-phenylalaninate (2.0 g, 6.2 mmol) were dissolved in methylene chloride (500 ml), and copper(II) acetate (3.0 g, 15 mmol) and triethylamine (6.0 ml) were added thereto, followed by stirring at room temperature for 2.5 days. The reaction liquid was concentrated under reduced pressure. The obtained residue was purified by silica gel column chromatography (petroleum ether/ethyl acetate=1:1) to obtain the title compound (250 mg, 9.7%) as a white solid.

$^1$H NMR (400 MHz, CD$_3$OD): δ 7.35 (d, J=8.0 Hz, 2H), 7.16 (d, J=8.0 Hz, 2H), 5.78 (s, 1H), 4.45-4.41 (m, 1H), 3.74 (s, 3H), 3.45 (s, 3H), 3.20-3.02 (m, 2H), 2.39 (s, 3H), 1.41 (s, 9H).

(Step 3) Methyl 4-(3,4-Dimethyl-2,6-dioxo-3,6-dihydropyrimidin-1(2H)-yl)-L-phenylalaninate (M-42)

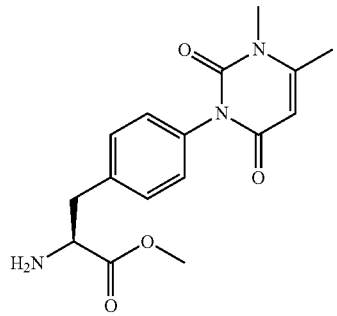 [SMILES: COC(=O)[C@@H](N)Cc1ccc(-n2c(=O)cc(C)n(C)c2=O)cc1]

To methyl N-(tert-butoxycarbonyl)-4-(3,4-dimethyl-2,6-dioxo-3,6-dihydropyrimidin-1(2H)-yl)-L-phenylalaninate (250 mg, 0.599 mmol), 3 N hydrogen chloride/ethyl acetate (5.0 ml) was added, followed by stirring at room temperature for 1 hour. The obtained white solid was filtered and dried under reduced pressure to obtain a hydrochloride of the title compound (M-42) (150 mg, 71%) as a white solid.

$^1$H NMR (400 MHz, CD$_3$OD): δ 7.36 (d, J=8.0 Hz, 2H), 7.21 (d, J=8.0 Hz, 2H), 5.75 (s, 1H), 4.35 (dd, J=8.4, 5.6 Hz, 1H), 3.84 (s, 3H), 3.40 (s, 3H), 3.42-3.37 (m, 1H), 3.15-3.09 (m, 1H), 2.34 (s, 3H).; MS (ESI) m/z 318 (M+H)$^+$

Example 101

Synthesis of M-43

(Step 1) 6-Isopropyl-1-methylpyrimidine-2,4(1H,3H)-dione

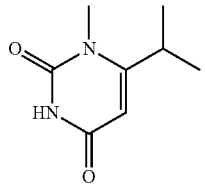

Methyl 4-methyl-3-oxopentanoate (5.0 g, 35 mmol) and N-methylurea (1.9 g, 26 mmol) were dissolved in acetic acid (50 ml), followed by stirring at 120° C. for 12 hours. The solvent was removed under reduced pressure, and the obtained residue was purified by silica gel column chromatography (methylene chloride/ethyl acetate=2:1 to 1:2) to obtain the title compound (1.5 g, 34%).

$^1$H NMR (400 MHz, CD$_3$OD): δ 9.96 (s, 1H), 3.34 (s, 3H), 2.66-2.60 (m, 1H), 1.26 (s, 3H), 1.25 (s, 3H).

(Step 2) Methyl N-(tert-Butoxycarbonyl)-4-(4-isopropyl-3-methyl-2,6-dioxo-3,6-dihydropyrimidin-1(2H)-yl)-L-phenylalaninate

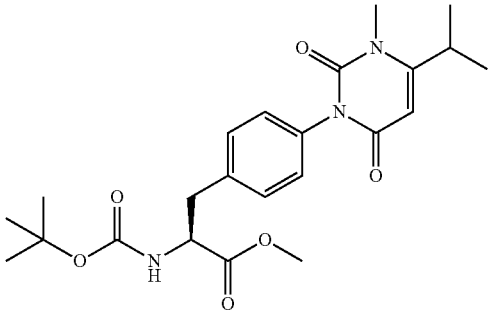 [SMILES: COC(=O)[C@H](Cc1ccc(-n2c(=O)cc(C(C)C)n(C)c2=O)cc1)NC(=O)OC(C)(C)C]

6-Isopropyl-1-methylpyrimidine-2,4(1H,3H)-dione (1.5 g, 8.9 mmol) and methyl N-(tert-butoxycarbonyl)-4-(dihydroxyboryl)-L-phenylalaninate (1.5 g, 4.6 mmol) were dissolved in methylene chloride (50 ml), and copper(II) acetate (3.0 g, 15 mmol) and triethylamine (3.0 ml) were added thereto, followed by stirring at room temperature for 2.5 days. The reaction liquid was concentrated under reduced pressure, and the obtained residue was purified by silica gel column chromatography (petroleum ether/ethyl acetate=1:1) to obtain the title compound (352 mg, 17%) as a white solid.

$^1$H NMR (400 MHz, CD$_3$OD): δ 7.37 (d, J=8.0 Hz, 2H), 7.22 (d, J=8.0 Hz, 2H), 5.60 (s, 1H), 4.43-4.40 (m, 1H), 3.79 (s, 3H), 3.38 (s, 3H), 3.19-3.01 (m, 2H), 2.67-2.62 (m, 1H), 1.42 (s, 9H). 1.26 (s, 3H), 1.25 (s, 3H).

(Step 3) Methyl 4-(4-Isopropyl-3-methyl-2,6-dioxo-3,6-dihydropyrimidin-1(2H)-yl)-L-phenylalaninate (M-43)

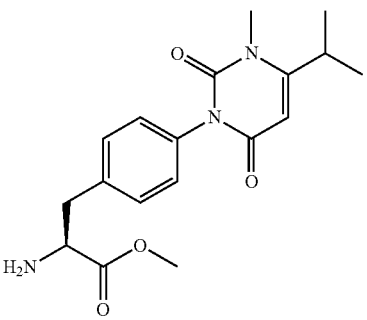 [SMILES: COC(=O)[C@@H](N)Cc1ccc(-n2c(=O)cc(C(C)C)n(C)c2=O)cc1]

To methyl N-(tert-butoxycarbonyl)-4-(4-isopropyl-3-methyl-2,6-dioxo-3,6-dihydropyrimidin-1(2H)-yl)-L-phenylalaninate (352 mg, 0.790 mmol), 3 N hydrogen chloride/ethyl acetate (10.0 ml) was added, followed by stirring at room temperature for 1 hour. The obtained white solid was filtered and dried under reduced pressure to obtain a hydrochloride of the title compound (M-43) (250 mg, 83%) as a white solid.

$^1$H NMR (400 MHz, CD$_3$OD): δ 7.33 (d, J=8.0 Hz, 2H), 7.18 (d, J=8.4 Hz, 2H), 5.72 (s, 1H), 4.32-4.31 (m, 1H), 3.81 (s, 3H), 3.38 (s, 3H), 3.42-3.34 (m, 1H), 3.11-3.03 (m, 2H), 1.25 (s, 3H), 1.23 (s, 3H).; MS (ESI) m/z 346 (M+H)$^+$

Example 102

Synthesis of M-44

(Step 1) Methyl 3-(5-Bromopyridin-2-yl)-N-(tert-butoxycarbonyl)-L-alaninate

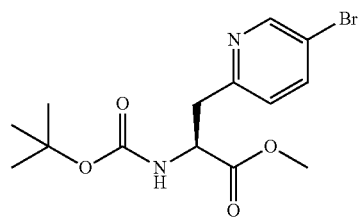 [SMILES: COC(=O)[C@H](Cc1ccc(Br)cn1)NC(=O)OC(C)(C)C]

An operation in which zinc (130 g, 2.00 mol) was heated at 200° C. for 30 minutes and cooled to room temperature was repeated three times, and then an N,N'-dimethylformamide solution (350 ml) of dibromoethane (10.0 ml, 0.11 mol) was added thereto. An operation in which the obtained reaction mixture was heated to 90° C. and then cooled to room temperature was repeated twice, and then chlorotrimethylsilane (3.00 ml, 23.5 mmol) was added thereto, followed by stirring at room temperature for 30 minutes. An N,N'-dimethylformamide solution (250 ml) of methyl N-(tert-butoxycarbonyl)-3-iodo-L-alaninate (110 g, 0.330 mol) was added dropwise, followed by stirring at 35° C. for 2.5 hours. Then, 2,5-dibromopyridine (100 g, 0.420 mol) and bis(triphenylphosphine)palladium(II) chloride (12.0 g, 17.0 mmol) were further added to the reaction solution, followed by stirring at 70° C. for 2 hours. After cooling to room temperature, the reaction solution was diluted with water, followed by extraction with ethyl acetate (200 ml×3). The extraction liquids were combined, washed with saturated aqueous sodium chloride, and dried over anhydrous sodium sulfate. Then, the solvent was removed. The obtained residue was purified by silica gel column chromatography (petroleum ether/ethyl acetate=1:1 to 1:2) to obtain the title compound (65 g, 54%).

1H NMR (CDCl$_3$, 400 MHz): δ 8.61 (s, 1H), 7.98-7.96 (m, 1H), 7.29-7.25 (m, 2H), 4.45-4.39 (m, 1H), 3.60 (s, 3H), 3.12-2.97 (m, 2H), 1.32 (s, 9H).

(Step 2) (6-{(2S)-2-[(tert-Butoxycarbonyl)amino]-3-methoxy-3-oxopropyl}pyridin-3-yl)boronic Acid

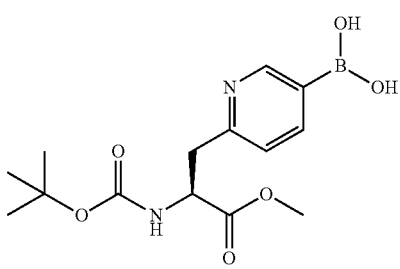 [SMILES: COC(=O)[C@H](Cc1ccc(B(O)O)cn1)NC(=O)OC(C)(C)C]

Methyl 3-(5-bromopyridin-2-yl)-N-(tert-butoxycarbonyl)-L-alaninate (55.0 g, 153 mmol) and bis(pinacolato)diborane (58.5 g, 230 mmol) were dissolved in N,N'-dimethylformamide (1.0 L), and [1,1'-bis(diphenylphosphino)ferrocene]dichloropalladium(II) (5.60 g, 7.68 mmol) and potassium acetate (45.1 g, 461 mol) were added thereto, followed by stirring at 95° C. for 12 hours in the presence of nitrogen gas. The reaction liquid was cooled to room temperature, and filtered through Celite. Then, the filtrate was concentrated under reduced pressure, and the obtained residue was purified by silica gel column chromatography (petroleum ether/ethyl acetate=4:1 to 1:1).

The obtained compound was dissolved in acetone (700 ml), and sodium periodate (71.0 g, 330 mmol), ammonium acetate (25.0 g, 330 mmol), and water (300 ml) were added thereto, followed by stirring at room temperature for 55 hours. After the reaction liquid was filtered, the solvent was removed under reduced pressure, and the obtained residue was diluted with water. After extraction with ethyl acetate (500 ml×3), the extraction liquids were combined, and dried over anhydrous sodium sulfate. After the solvent was removed under reduced pressure, the residue was washed with petroleum ether/ethyl acetate=10:1, and the obtained solid was filtered to obtain the title compound (42.0 g, 85%).

$^1$H NMR (400 MHz, CDCl$_3$): δ 8.90-8.84 (m, 1H), 8.39-8.28 (m, 1H), 7.27-7.15 (m, 2H), 5.95 (s, 1H), 4.66-4.59 (m, 1H), 3.68 (s, 3H), 3.22-3.15 (m, 2H), 1.45 (s, 9H).

(Step 3) Methyl N-(tert-Butoxycarbonyl)-3-[5-(3-methyl-2,6-dioxo-3,6-dihydropyrimidin-1(2H)-yl)pyridin-2-yl]-L-alaninate

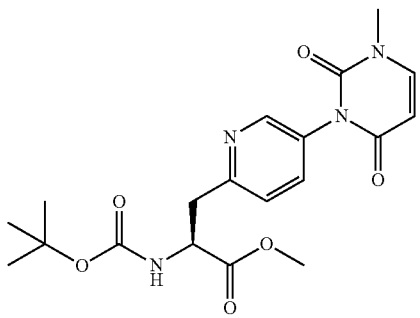 [SMILES: COC(=O)[C@H](Cc1ccc(-n2c(=O)ccn(C)c2=O)cn1)NC(=O)OC(C)(C)C]

1-Methylpyrimidine-2,4(1H,3H)-dione (15.5 g, 123 mmol) and (6-{(2S)-2-[(tert-butoxycarbonyl)amino]-3-methoxy-3-oxopropyl}pyridin-3-yl)boronic acid (40.0 g, 123 mmol) were dissolved in methylene chloride (800 ml), and copper(II) acetate (27.0 g, 148 mmol), 4A MS (30 g), and triethylamine (50 ml) were added thereto, followed by stirring at room temperature for 3 days. The reaction liquid was concentrated under reduced pressure, and the obtained residue was purified by silica gel column chromatography (petroleum ether/ethyl acetate=1:1) to obtain the title compound (9.94 g, 20%) as a white solid.

MS (ESI) m/z 405 (M+H)$^+$ (Step 4) Methyl 3-[5-(3-Methyl-2,6-dioxo-3,6-dihy-dropyrimidin-1 (2H)-yl)pyridin-2-yl]-L-alaninate (M-44)

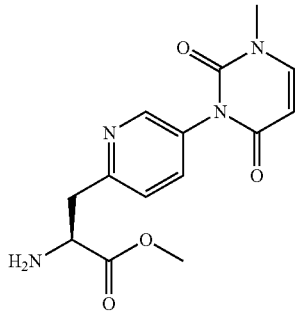 [SMILES: COC(=O)[C@@H](N)Cc1ccc(-n2c(=O)ccn(C)c2=O)cn1]

To methyl N-(tert-butoxycarbonyl)-3-[5-(3-methyl-2,6-dioxo-3,6-dihydropyrimidin-1(2H)-yl)pyridin-2-yl]-L-alaninate (4.20 g, 10.4 mmol), 4 N hydrogen chloride/ethyl acetate (30 ml) was added, followed by stirring at room temperature for 1 hour. The obtained white solid was filtered and dried under reduced pressure to obtain a hydrochloride of the title compound (M-44) (3.40 g, 95%) as a white solid.

$^1$H NMR (400 MHz, CD$_3$OD): δ 8.37 (s, 1H), 7.76 (d, J=8.4 Hz, 1H), 7.53 to 7.49 (m, 2H), 5.67 (d, J=8.0 Hz, 1H), 4.46 to 4.43 (m, 1H), 3.65 (s, 3H), 3.45 to 3.38 (m, 2H), 3.24 (s, 3H).;

MS (ESI) m/z 305 (M+H)$^+$

Example 103

Synthesis of M-45

(Step 1) Isopropyl L-Tyrosinate

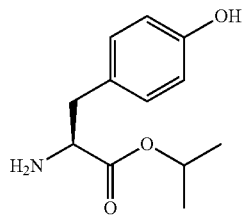 [SMILES: CC(C)OC(=O)[C@@H](N)Cc1ccc(O)cc1]

L-Tyrosine (100 g, 552 mmol) was dissolved in 2-propanol (1.00 L), and then concentrated sulfuric acid (60 ml) was added dropwise thereto, followed by stirring at 80° C. for 2 days. The reaction liquid was concentrated under reduced pressure, and then a saturated aqueous hydrogen carbonate solution was added to the residue, followed by stirring. The obtained solid was filtered and dried under reduced pressure to obtain the title compound (129 g, 85%) as a white solid.

$^1$H NMR (CD$_3$OD, 400 MHz): δ 7.01 (d, J=8.0 Hz, 2H), 6.71 (d, J=8.4 Hz, 2H), 4.96-4.90 (m, 1H), 3.62 (t, J=6.8 Hz, 1H), 2.91-2.80 (m, 2H), 1.15 (d, J=6.4 Hz, 6H).; MS (ESI) m/z 224 (M+H)$^+$ (Step 2) Isopropyl N-(tert-Butoxycarbonyl)-L-tyrosinate

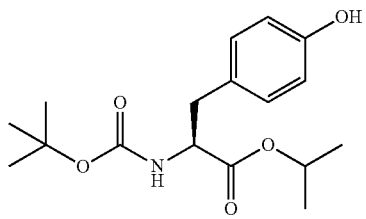 [SMILES: CC(C)OC(=O)[C@H](Cc1ccc(O)cc1)NC(=O)OC(C)(C)C]

Isopropyl L-tyrosinate (120 g, 538 mmol) was dissolved in tetrahydrofuran (1.3 L), and di-tert-butyl dicarbonate (123 g, 565 mmol) and triethylamine (80 ml) were added thereto, followed by stirring at room temperature for 2 hours. The reaction liquid was concentrated under reduced pressure to obtain the title compound (174 g, 91%).

MS (ESI) m/z 324 (M+H)$^+$ (Step 3) Isopropyl N-(tert-Butoxycarbonyl)-O-[(trifluoromethyl) sulfonyl]-L-tyrosinate

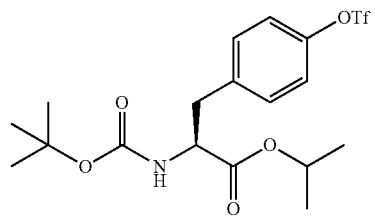 [SMILES: CC(C)OC(=O)[C@H](Cc1ccc(OS(=O)(=O)C(F)(F)F)cc1)NC(=O)OC(C)(C)C]

Isopropyl N-(tert-butoxycarbonyl)-L-tyrosinate (170 g, 526 mmol) was dissolved in methylene chloride (1.2 L). After the mixture was cooled to 0° C., trifluoromethanesulfonic anhydride (148 g, 526 mmol) and pyridine (200 ml) were added dropwise, followed by stirring at room temperature for 12 hours. The reaction liquid was diluted with water (800 ml), and then washed with a 0.5 N aqueous sodium hydroxide solution (800 ml), water (800 ml), 1 N hydrochloric acid (800 ml), and saturated aqueous sodium chloride, and dried over anhydrous sodium sulfate. Then, the solvent was removed under reduced pressure to obtain the title compound (214 g, 89%).

$^1$H NMR (CDCl$_3$, 400 MHz): δ 7.28-7.19 (m, 4H), 5.08-4.97 (m, 2H), 4.55-4.51 (m, 1H), 3.16-3.03 (m, 2H), 1.43 (s, 9H), 1.23 (q, J=8.4 Hz, 6H).; MS (ESI) m/z 456 (M+H)$^+$ (Step 4) Isopropyl N-(tert-Butoxycarbonyl)-4-(4,4,5,5-tetramethyl-1,3,2-dioxaborolan-2-yl)-L-phenylalaninate

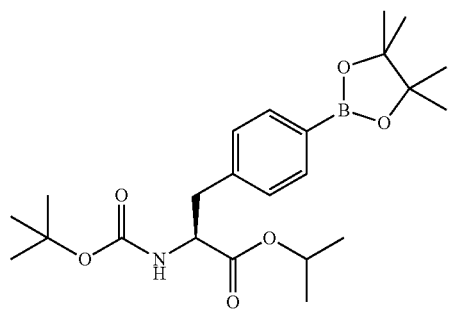 [SMILES: CC(C)OC(=O)[C@H](Cc1ccc(B2OC(C)(C)C(C)(C)O2)cc1)NC(=O)OC(C)(C)C]

Isopropyl N-(tert-butoxycarbonyl)-O-[(trifluoromethyl) sulfonyl]-L-tyrosinate (230 g, 505 mmol) and bis(pinacolato)diborane (192 g, 758 mmol) were dissolved in N,N'-dimethylformamide (1.0 L), and [1,1'-bis(diphenylphosphino)ferrocene]dichloropalladium(II) (18.5 g, 25.3 mmol) and potassium acetate (149 g, 1.52 mol) were added thereto, followed by stirring at 95° C. for 12 hours in the presence of nitrogen gas. The reaction liquid was cooled to room temperature, and then filtered through Celite. The filtrate was concentrated under reduced pressure, and the obtained residue was purified by silica gel column chromatography (petroleum ether/ethyl acetate=20:1) to obtain the title compound (180 g, 82%) as a yellow oil.

$^1$H NMR (CDCl$_3$, 400 MHz): δ 7.74 (d, J=8.4 Hz, 2H), 7.16 (d, J=7.6 Hz, 2H), 5.03-4.99 (m, 1H), 4.97 (d, J=8.4 Hz, 1H), 4.54-4.49 (m, 1H), 3.16-3.05 (m, 2H), 1.42 (s, 9H), 1.34 (s, 12H), 1.24 (t, J=6.0 Hz, 6H).; MS (ESI) m/z 434 (M+H)$^+$ (Step 5) Isopropyl N-(tert-Butoxycarbonyl)-4-(dihydroxyboryl)-L-phenylalaninate

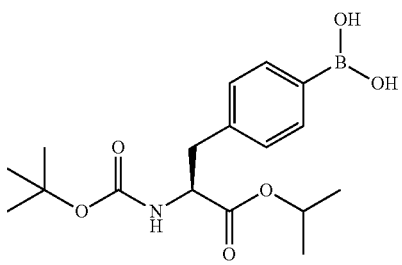 [SMILES: CC(C)OC(=O)[C@H](Cc1ccc(B(O)O)cc1)NC(=O)OC(C)(C)C]

Isopropyl N-(tert-butoxycarbonyl)-4-(4,4,5,5-tetramethyl-1,3,2-dioxaborolan-2-yl)-L-phenylalaninate (71.4 g, 165 mmol) was dissolved in acetone (700 ml), and sodium periodate (71.0 g, 330 mmol), ammonium acetate (25.0 g, 330 mmol), and water (300 ml) were added thereto, followed by stirring at room temperature for 72 hours. After the reaction liquid was filtered, the solvent was removed under reduced pressure, and the obtained residue was diluted with water. After extraction with ethyl acetate (500 ml×3), the extraction liquids were combined, and dried over anhydrous sodium sulfate. After the solvent was removed under reduced pressure, the residue was washed with petroleum ether/ethyl acetate=10:1, and the obtained solid was filtered to obtain the title compound (45.8 g, 79%).

$^1$H NMR (DMSO-d$_6$, 400 MHz): δ: 7.98 (s, 2H), 7.70 (d, J=7.6 Hz, 2H), 7.27 (d, J=7.6 Hz, 1H), 7.20 (d, J=8.0 Hz, 2H), 4.89-4.83 (m, 1H), 4.10-4.00 (m, 1H), 2.97-2.82 (m, 2H), 1.33 (s, 9H), 1.20-1.05 (m, 6H).; MS (ESI) m/z 252 (M+H-boc)$^+$ (Step 6) 1,5-Dimethylpyrimidine-2,4(1H,3H)-dione

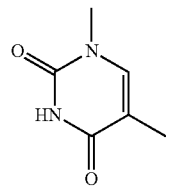

5-Methylpyrimidine-2,4(1H,3H)-dione (33.8 g, 268 mmol), bis(trimethylsilyl)amine (550 ml), and chlorotrimethylsilane (55.0 ml) were stirred at 130° C. for 5 hours. Then, the mixture was cooled to 60° C., and methyl iodide (200 ml, 3.2 mol) was added thereto, followed by stirring at 60° C. for further 30 hours. After cooling to 0° C., acetic acid (500 ml) was added, followed by stirring. The reaction liquid was concentrated under reduced pressure, and 2-propanol (1.6 L) was added thereto, followed by vigorous stirring. The solid obtained by filtration was purified by recrystallization from water (500 ml) to obtain the title compound (25.1 g, 67%) as a white solid.

$^1$H NMR (DMSO-d$_6$, 400 MHz): δ 11.24 (br, 1H), 7.51 (s, 1H), 3.19 (s, 3H), 1.74 (s, 3H).; MS (ESI) m/z 141 (M+H)$^+$ (Step 7) Isopropyl N-(tert-Butoxycarbonyl)-4-(3,5-dimethyl-2,6-dioxo-3,6-dihydropyrimidin-1(2H)-yl)-L-phenylalaninate

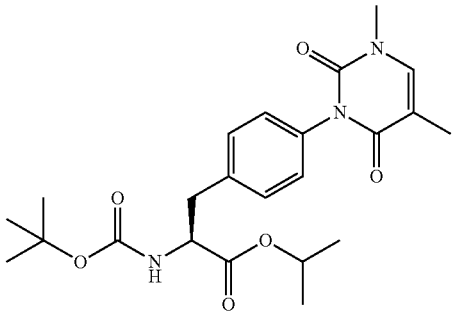 [SMILES: Cc1cn(C)c(=O)n(-c2ccc(C[C@H](NC(=O)OC(C)(C)C)C(=O)OC(C)C)cc2)c1=O]

1,5-Dimethylpyrimidine-2,4(1H,3H)-dione (15.0 g, 107 mmol) and methyl N-(tert-butoxycarbonyl)-4-(dihydroxyboryl)-L-phenylalaninate (37.6 g, 107 mmol) were dissolved in methylene chloride (500 ml), and copper(II) acetate (19.5 g, 107 mmol) and triethylamine (40 ml) were added thereto, followed by stirring at room temperature for 3 days. The reaction liquid was concentrated under reduced pressure, and the obtained residue was purified by silica gel column chromatography (petroleum ether/ethyl acetate=1:1) to obtain the title compound (3.4 g, 7%) as a yellow solid.

$^1$H NMR (CDCl$_3$, 400 MHz): δ 7.28 (d, J=6.4 Hz, 1H), 7.19 (d, J=5.6 Hz, 2H), 7.08 (s, 1H), 5.06 (d, J=8.4 Hz, 1H), 5.03-4.98 (m, 1H), 4.56 (d, J=4.0 Hz, 1H), 3.40 (s, 3H), 3.13-3.06 (m, 2H), 1.94 (s, 3H), 1.42 (s, 9H), 1.22 (t, J=6.8 Hz, 6H).; MS (ESI) m/z 363 (M+H+17 (NH3)-boc)$^+$ (Step 8) Isopropyl 4-(3,5-Dimethyl-2,6-dioxo-3,6-dihydropyrimidin-1(2H)-yl)-L-phenylalaninate (M-45)

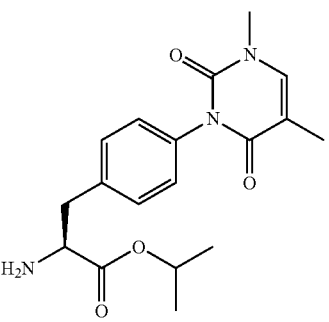 [SMILES: Cc1cn(C)c(=O)n(-c2ccc(C[C@H](N)C(=O)OC(C)C)cc2)c1=O]

To isopropyl N-(tert-butoxycarbonyl)-4-(3,5-dimethyl-2,6-dioxo-3,6-dihydropyrimidin-1(2H)-yl)-L-phenylalaninate (6.0 g, 15 mmol), 3 N hydrogen chloride/ethyl acetate (100 ml) was added, followed by stirring at room temperature for 1 hour. The obtained white solid was filtered and dried under reduced pressure to obtain a hydrochloride of the title compound (M-45) (2.66 g, 91%) as a white solid.

$^1$H NMR (CD$_3$OD, 400 MHz): δ 7.59 (s, 1H), 7.47 (d, J=8.4 Hz, 2H), 7.28 (d, J=8.0 Hz, 2H), 5.21-5.16 (m, 1H), 4.38-4.34 (m, 1H), 3.46-3.43 (m, 1H), 3.42 (s, 3H), 3.22-3.16 (m, 1H), 1.97 (s, 3H), 1.36 (t, J=4.8 Hz, 6H).; MS (ESI) m/z 346 (M+H)$^+$

Example 104

Synthesis of M-46

(Step 1) 4-Bromo-2,5-difluorobenzoic Acid

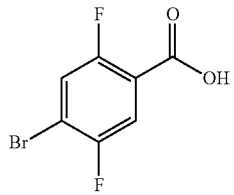 [SMILES: O=C(O)c1cc(F)c(Br)cc1F]

1,4-Dibromo-2,5-difluorobenzene (51.2 g, 188 mmol) was dissolved in 1,2-diethoxyethane (400 ml), and a 2.5 M n-butyllithium/hexane solution (76.0 ml, 190 mmol) was slowly added dropwise thereto at −78° C. in the presence of nitrogen gas.

After the reaction solution was stirred at −78° C. for 30 minutes, dry ice was added thereto, followed by stirring for further 30 minutes. After the temperature was gradually raised to room temperature, water (200 ml) was added to the reaction liquid. The reaction liquid was diluted with ethyl acetate, and washed with a 10% aqueous sodium carbonate solution (200 ml×2). Then, the obtained aqueous layers were combined, and made acidic by adjustment with 1 N hydrochloric acid. The precipitated yellow solid was filtered and dried to obtain the title compound (30.0 g, 67%).

$^1$H NMR (DMSO-d$_6$, 400 MHz): δ 7.90-7.87 (m, 1H), 7.79-7.75 (m, 1H).; MS (ESI) m/z 191 (M+H-44)$^+$ (Step 2) Methyl 4-Bromo-2,5-difluorobenzoate

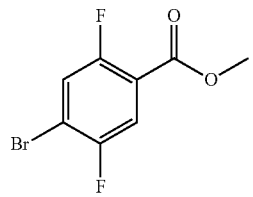

4-Bromo-2,5-difluorobenzoic acid (30.0 g, 127 mmol) was dissolved in ethyl acetate (500 ml). After the mixture was cooled to 0° C., an ether solution of diazomethane was added thereto. The reaction liquid was stirred at 0° C. for 1 hour, and the solvent was removed under reduced pressure. The obtained residue was purified by silica gel column chromatography (petroleum ether/ethyl acetate=6:1 to 2:1) to obtain the title compound (25.0 g, 78%).

$^1$H NMR (DMSO-d$_6$, 400 MHz): δ 7.93-7.89 (m, 1H), 7.80-7.77 (m, 1H), 3.86 (s, 3H).

(Step 3) Methyl 4-Amino-2,5-difluorobenzoate

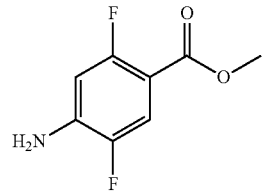

Methyl 4-bromo-2,5-difluorobenzoate (25.0 g, 99.6 mmol) and BINAP (1.86 g, 3.00 mmol) were dissolved in toluene (500 ml). To the solution, palladium(II) acetate (672 mg, 3.00 mmol), cesium carbonate (52.0 g, 160 mmol), and benzophenone imine (25.3 g, 140 mmol) were added, followed by stirring at 110° C. for 12 hours. After cooling to room temperature, the mixture was filtered through Celite, followed by washing with ethyl acetate. The obtained filtrate was concentrated under reduced pressure.

The obtained compound was dissolved in water (30 ml) and tetrahydrofuran (80 ml), and concentrated hydrochloric acid (30 ml) was added thereto, followed by stirring at room temperature for 2 hours. The precipitated solid was filtered to obtain a white solid. In addition, the filtrate was concentrated under reduced pressure, until a white solid precipitated. The obtained solid was filtered. These white solids were combined and dried to obtain the title compound (9.8 g, 53% over two steps).

$^1$H NMR (CD$_3$OD, 400 MHz): δ 7.53-7.49 (m, 1H), 6.60-6.56 (m, 1H), 3.85 (s, 3H).; MS (ESI) m/z 188 (M+H)$^+$ (Step 4) Methyl 2,5-Difluoro-4-[(phenylsulfonyl)amino]benzoate

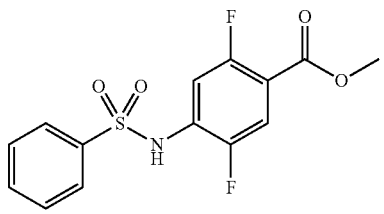 [SMILES: COC(=O)c1cc(F)c(NS(=O)(=O)c2ccccc2)cc1F]

Methyl 4-amino-2,5-difluorobenzoate (20.0 g, 107 mmol) was dissolved in methylene chloride (200 ml), and benzenesulfonyl chloride (37.8 g, 214 mmol) and pyridine (67.0 ml) were added thereto, followed by stirring at room temperature for 12 hours. The reaction liquid was concentrated under reduced pressure. Then, the pH of the obtained residue was adjusted to 1.0 by adding 6 N hydrochloric acid thereto. The obtained solid was filtered, washed with water and methylene chloride, and dried to obtain the title compound (21.0 g, 60%).

1H NMR (DMSO-d$_6$, 300 MHz): δ 11.1 (s, 1H), 7.87-7.84 (m, 2H), 7.67-7.58 (m, 4H), 7.29-7.23 (m, 1H), 3.80 (s, 3H).; MS (ESI) m/z 326 (M−1)

(Step 5) 2,5-Difluoro-4-[(phenylsulfonyl)amino]benzoic Acid (M-46)

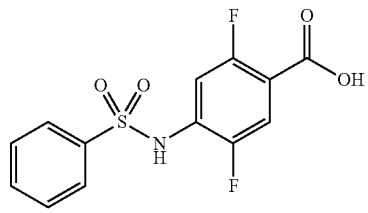 [SMILES: O=C(O)c1cc(F)c(NS(=O)(=O)c2ccccc2)cc1F]

Methyl 2,5-difluoro-4-[(phenylsulfonyl)amino]benzoate (21.0 g, 64.2 mmol) was dissolved in a saturated aqueous lithium hydroxide solution, followed by stirring at room temperature for 30 minutes. The pH of the reaction liquid was adjusted to lower than 6.0 by adding 8 N hydrochloric acid thereto, and the obtained white solid was filtered and dried to obtain the title compound (19.2 g, 95%).

$^1$H NMR (CD$_3$OD, 400 MHz): δ 7.92-7.90 (m, 2H), 7.67-7.64 (m, 1H), 7.60-7.50 (m, 3H), 7.40 (dd, J=11.6, 6.4 Hz, 1H).; MS (ESI) m/z 312 (M−1)

Example 105

Synthesis of M-47

(Step 1) Methyl 2,5-Difluoro-4-[(pyridin-2-ylsulfonyl)amino]benzoate

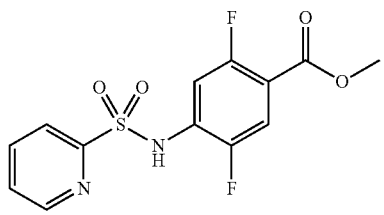 [SMILES: COC(=O)c1cc(F)c(NS(=O)(=O)c2ccccn2)cc1F]

Methyl 4-bromo-2,5-difluorobenzoate (500 mg, 1.99 mmol) <see (Step 3) of Example 104>, pyridine-2-sulfonamide (262 mg, 1.66 mmol), potassium carbonate (683 mg, 4.94 mmmol), diisopropylethylamine (72.0 mg, 0.82 mmol), and copper(I) iodide (26.0 mg, 0.140 mmol) were dissolved in acetonitrile, followed by stirring at 140° C. for 2 hours under microwave irradiation. The reaction liquid was cooled to room temperature and then filtered. The obtained filtrate was concentrated under reduced pressure, and the residue was purified by silica gel column chromatography (petroleum ether/ethyl acetate=2:1) to obtain the title compound (160 mg, 29%).

MS (ESI) m/z 327 (M−1)

(Step 2) 2,5-Difluoro-4-[(pyridin-2-ylsulfonyl)amino]benzoic Acid (M-47)

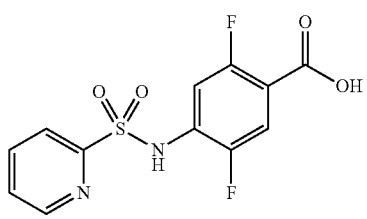 [SMILES: O=C(O)c1cc(F)c(NS(=O)(=O)c2ccccn2)cc1F]

Methyl 2,5-difluoro-4-[(pyridin-2-ylsulfonyl)amino]benzoate (2.30 g, 7.00 mmmol) was dissolved in methanol (30 ml), and a 6 N aqueous lithium hydroxide solution (20 ml) was added thereto, followed by stirring at room temperature for 30 minutes. The pH of the reaction liquid was adjusted to a range from 4.0 to 5.0 by adding 4 N hydrochloric acid thereto, and the precipitated yellow solid was filtered and dried to obtain the title compound (2.05 g, 93%).

$^1$H NMR (CD$_3$OD, 400 MHz): δ 8.56 (d, J=4.4 Hz, 1H), 7.97 (dd, J=6.4, 1.6 Hz, 2H), 7.54-7.41 (m, 3H).; MS (ESI) m/z 315 (M+H)$^+$

Example 106

Synthesis of M-48

(Step 1) Furan-2-sulfonyl Chloride

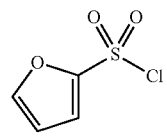

Furan (3.67 g, 53.9 mmol) was dissolved in diethyl ether (50 ml). After the solution was cooled to 0° C., a t-butyl-lithium/hexane solution (1.3 mol/l, 50 ml) was slowly added dropwise, followed by stirring for 15 minutes. Sulfur dioxide was added to the reaction liquid, followed by stirring for further 15 minutes. Subsequently, N-chlorosuccinimide (8.65 g, 64.8 mmol) was added thereto, followed by stirring at room temperature for 30 minutes. The reaction liquid was diluted with water. After extraction with ethyl acetate (100 ml×2), the extraction liquids were combined, and dried over anhydrous sodium sulfate. After the solvent was removed under reduced pressure, the residue was purified by silica gel column chromatography (petroleum ether/ethyl acetate=10:1 to 5:1) to obtain the title compound (3.2 g, 36%).

(Step 2) Methyl
2-Fluoro-4-[(2-furylsulfonyl)amino]benzoate

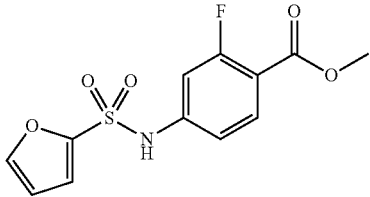 [SMILES: COC(=O)c1ccc(NS(=O)(=O)c2ccco2)cc1F]

The title compound was obtained by subjecting furan-2-sulfonyl chloride and methyl 4-amino-2-fluorobenzoate to the same method as in (Step 4) of Example 104.

$^1$H NMR (400 MHz, DMSO-d$_6$): δ 11.48 (s, 1H), 8.00 (d, J=0.8 Hz, 1H), 7.85-7.80 (m, 1H), 7.40-7.39 (m, 1H), 7.08-6.99 (m, 2H), 6.69-6.68 (m, 1H), 3.80 (s, 3H).

(Step 3) 2-Fluoro-4-[(2-furylsulfonyl)amino]benzoic
Acid (M-48)

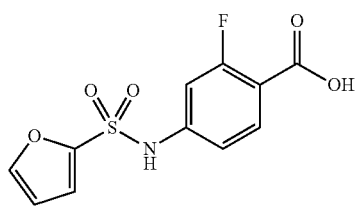 [SMILES: O=C(O)c1ccc(NS(=O)(=O)c2ccco2)cc1F]

The title compound (M-48) was obtained by subjecting methyl 2-fluoro-4-[(2-furylsulfonyl)amino]benzoate to the same method as in (Step 5) of Example 104.

$^1$H NMR (400 MHz, CD$_3$OD): δ 7.78 (t, J=8.8 Hz, 1H), 7.67 (d, J=0.8 Hz, 1H), 7.15-7.14 (m, 1H), 6.99-6.95 (m, 2H), 6.51 (dd, J=3.6, 2.0 Hz, 1H).

Example 107

Synthesis of M-49

(Step 1) Methyl
2,5-Difluoro-4-[(2-furylsulfonyl)amino]benzoate

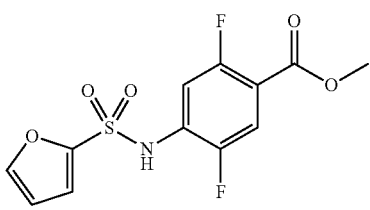 [SMILES: COC(=O)c1cc(F)c(NS(=O)(=O)c2ccco2)cc1F]

The title compound (800 mg, 34%) was obtained as a gray solid by subjecting methyl 4-amino-2,5-difluorobenzoate (1.40 g, 7.48 mmol) <see (Step 3) of Example 104> and furan-2-sulfonyl chloride (3.00 g, 18.0 mmol) <see (Step 1) of Example 106> to the same method as in (Step 4) of Example 104.

$^1$H NMR (DMSO-d$_6$, 400 MHz): δ 8.02 (s, 1H), 7.71-6.66 (m, 1H), 7.32-7.25 (m, 2H), 6.70-6.66 (m, 1H), 3.82 (s, 3H).;
MS (ESI) m/z 318 (M+H)$^+$ (Step 2) 2,5-Difluoro-4-[(2-furylsulfonyl)amino]
benzoic Acid (M-49)

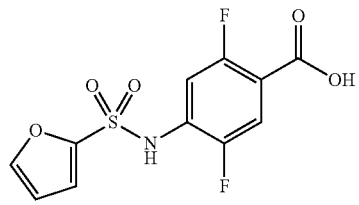

The title compound (M-49) (600 mg, 79%) was obtained by subjecting methyl 2,5-difluoro-4-[(2-furylsulfonyl)amino]benzoate (800 mg, 2.52 mmol) to the same method as in (Step 5) of Example 104.

$^1$H NMR (CD$_3$OD, 400 MHz): δ 7.74 (dd, J=2.4, 1.6 Hz, 1H), 7.61 (dd, J=14.4, 8.4 Hz, 1H), 7.38 (dd, J=15.6, 8.4 Hz, 1H), 7.18 (dd, J=4.8, 1.6 Hz, 1H), 6.58 (dd, J=4.8, 2.4 Hz, 1H).;
MS (ESI) m/z 304 (M+H)$^+$

Example 108

Synthesis of M-50

(Step 1) 4-{[(4-Acetylphenyl)sulfonyl]amino}-2,5-difluorobenzoic Acid (M-50)

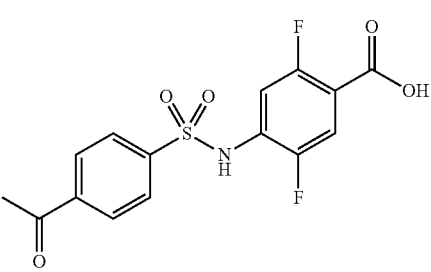 [SMILES: CC(=O)c1ccc(S(=O)(=O)Nc2cc(F)c(C(=O)O)cc2F)cc1]

To 4-acetylbenzenesulfonyl chloride (700 mg, 3.21 mmol) and methyl 4-amino-2,5-difluorobenzoate (600 mg, 3.21 mmol), dichloromethane (10 ml) and pyridine (5.2 ml) were added, followed by stirring at room temperature overnight. Water was added to the reaction solution, followed by extraction with ethyl acetate. The extraction liquid was washed with saturated aqueous sodium chloride, and dried over anhydrous magnesium sulfate. After concentration under reduced pressure, the residue was suspended in 1,4-dioxane (5.0 ml), and a 2 N aqueous lithium hydroxide solution (3.20 ml, 6.40 mmol) was added dropwise thereto, followed by stirring at room temperature overnight. The mixture was neutralized with 2 N hydrochloric acid, and concentrated under reduced pressure. Then, the obtained residue was purified by reversed-phase HPLC (H$_2$O containing 0.1% TFA/CH$_3$CN system), followed by freeze-drying, to obtain the title compound (390 mg, 34% over two steps).

Example 109

Synthesis of M-51

(Step 1) Methyl 2-Fluoro-4-[(pyridin-2-ylsulfonyl)amino]benzoate

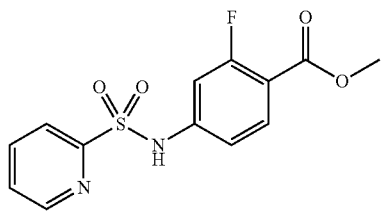 [SMILES: COC(=O)c1ccc(NS(=O)(=O)c2ccccn2)cc1F]

4-Pyridinethiol (16.7 g, 15.0 mmol) was dissolved in concentrated hydrochloric acid (110 ml) and water (30 ml). After the solution was cooled to 0° C., chlorine gas was injected for 1 hour. The reaction liquid was poured onto ice (80.0 g), and then neutralized slowly by adding sodium hydrogen carbonate. With the solution being cooled to 5 to 10° C., extraction was conducted with methylene chloride (150 ml×3), and the extraction liquids were combined and dried over anhydrous sodium sulfate. Then, with the combined liquid being cooled to 5 to 10° C., the solvent was removed under reduced pressure.

The obtained compound was dissolved in methylene chloride, and the solution was cooled to −10° C. Then, a methylene chloride solution (200 ml) of methyl 4-amino-2-fluorobenzoate (16.9 g, 100 mmol) and pyridine (10 ml) was added thereto, followed by stirring at room temperature for 2 hours. The reaction solution was washed with 0.1 N hydrochloric acid (200 ml×2). Then, the organic layers were combined and dried over anhydrous sodium sulfate, and the solvent was removed under reduced pressure. The obtained residue was purified by silica gel column chromatography (petroleum ether/ethyl acetate=2:1 to 1:1) to obtain the title compound (12.4 g, 40%).

MS (ESI) m/z 311 (M+H)$^+$ (Step 2) 2-Fluoro-4-[(pyridin-2-ylsulfonyl)amino] benzoic Acid (M-51)

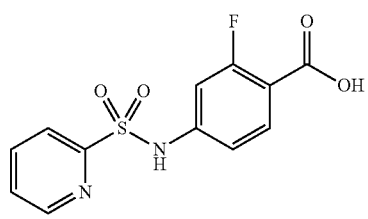 [SMILES: O=C(O)c1ccc(NS(=O)(=O)c2ccccn2)cc1F]

The title compound (M-51) (10.5 g, 92%) was obtained by subjecting methyl 2-fluoro-4-[(pyridin-2-ylsulfonyl) amino]benzoate (12.0 g, 38.7 mmol) to the same method as in (Step 5) of Example 104.

$^1$H NMR (400 MHz, CD$_3$OD): δ 8.66 (d, J=4.4 Hz, 1H), 8.08-8.01 (m, 2H), 7.79 (t, J=8.4 Hz, 1H), 7.61-7.57 (m, 1H), 7.10-7.02 (m, 2H).; MS (ESI) m/z 297 (M+H)$^+$

Example 110

Synthesis of M-52

(Step 1) 2,6-Difluoro-4-{[(2-methoxyphenyl)sulfonyl]amino}benzoic Acid (M-52)

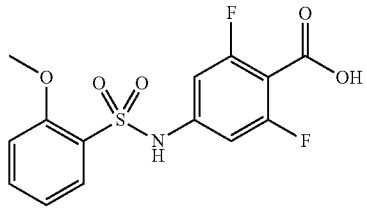 [SMILES: COc1ccccc1S(=O)(=O)Nc1cc(F)c(C(=O)O)c(F)c1]

To 5-bromo-2-methoxy-benzenesulfonyl chloride (500 mg, 1.76 mmol) and methyl 4-amino-2,6-difluorobenzoate (395 mg, 2.11 mmol), dichloromethane (12 ml) and pyridine (427 μl, 5.28 mmol) were added, followed by stirring at room temperature overnight. The reaction solution was concentrated under reduced pressure, diluted with dichloromethane, washed with 2 N hydrochloric acid, water, and saturated aqueous sodium chloride, dried over anhydrous sodium sulfate, and concentrated under reduced pressure. The obtained product was dissolved in ethanol (5.0 ml) and DMF (5.0 ml), and 10% Pd/C (50 mg) was added thereto, followed by stirring overnight in a hydrogen atmosphere at 3 atm. After filtration through Celite, the filtrate was concentrated under reduced pressure, and tetrahydrofuran (5.0 ml) and water (1.0 ml) were added thereto. Then, a 2 N aqueous sodium hydroxide solution (2.0 ml) was added dropwise thereto, followed by stirring at room temperature for 4 hours. The mixture was neutralized with 2 N hydrochloric acid, and concentrated under reduced pressure. Then, the obtained residue was purified by reversed-phase HPLC (H$_2$O containing 0.10 TFA/CH$_3$CN system), followed by freeze-drying, to obtain the title compound.

MS (ESI) m/z 344 (M+H)$^+$

Example 111

Synthesis of M-53

(Step 1) 2-Fluoro-4-{[(3-oxo-2,3-dihydro-1H-inden-5-yl)sulfonyl]amino}benzoic Acid (M-53)

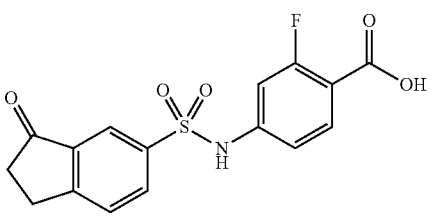 [SMILES: O=C(O)c1ccc(NS(=O)(=O)c2ccc3c(c2)C(=O)CC3)cc1F]

To 3-oxo-indane-5-sulfonyl chloride (500 mg, 2.17 mmol) and 4-amino-2-fluorobenzenecarboxylic acid (336 mg, 2.17 mmol), dichloromethane (10 ml) and pyridine (5.2 ml) were added, followed by stirring at room temperature for 12 hours. After the mixture was concentrated under reduced pressure, the obtained residue was purified by reversed-phase HPLC (H₂O containing 0.1% TFA/CH₃CN system), followed by freeze-drying, to obtain the title compound (412 mg, 54%).

Example 112

Synthesis of M-54

(Step 1) 2-Ethoxybenzenesulfonyl Chloride

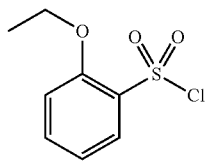

Tetramethylethylenediamine (15.2 ml, 101 mmol) was dissolved in diethyl ether (200 ml). After the solution was cooled to 0° C., n-butyllithium (2.5 mol/l, 40.0 ml, 100 mmol) was added thereto, followed by stirring for 5 minutes. To the reaction liquid, ethoxybenzene (11.0 ml, 87.1 mmol) was added, followed by stirring for further 1 hour. The reaction liquid was cooled to −78° C., and sulfur dioxide was added with a syringe over 30 minutes. After that, the temperature was raised to room temperature with stirring over 1 hour. To the reaction liquid, thionyl chloride (8.80 ml, 110 mmol) was added, followed by stirring at room temperature for 6 hours. The reaction liquid was diluted with diethyl ether, and washed with water and saturated aqueous sodium chloride. Then, the organic layer was dried over anhydrous sodium sulfate. The solvent was removed under reduced pressure to obtain the title compound (8.1 g, 42%).

(Step 2) Methyl 4-{[(2-Ethoxyphenyl)sulfonyl]amino}-2,6-difluorobenzoate

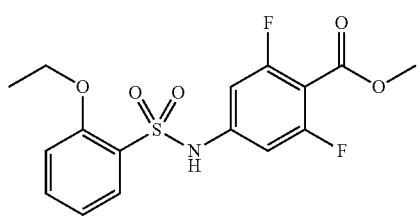 [SMILES: CCOc1ccccc1S(=O)(=O)Nc1cc(F)c(C(=O)OC)c(F)c1]

The title compound (1.4 g, 71%) was obtained by subjecting methyl 4-amino-2,6-difluorobenzoate (1.00 g, 5.34 mmol) and 2-ethoxybenzenesulfonyl chloride (3.00 g, 13.6 mmol) to the same method as in (Step 4) of Example 104.

¹H NMR (DMSO-d₆, 400 MHz): δ 10.97 (s, 1H), 7.93-7.91 (m, 1H), 7.64-7.60 (m, 1H), 7.22-7.20 (m, 1H), 7.13-7.09 (m, 1H), 6.81-6.78 (m, 2H), 4.21-4.16 (m, 2H), 3.79 (s, 3H), 1.27-1.24 (m, 3H).

(Step 3) 4-{[(2-Ethoxyphenyl)sulfonyl]amino}-2,6-difluorobenzoic Acid (M-54)

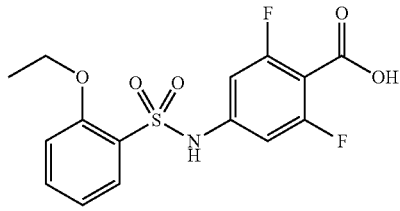 [SMILES: CCOc1ccccc1S(=O)(=O)Nc1cc(F)c(C(=O)O)c(F)c1]

The title compound (M-54) (1.05 g, 78%) was obtained as a yellow solid by subjecting methyl 4-{[(2-ethoxyphenyl)sulfonyl]amino}-2,6-difluorobenzoate (1.40 g, 3.77 mmol) to the same method as in (Step 5) of Example 104.

¹H NMR (CD₃OD, 400 MHz): δ 7.86 (dd, J=8.0, 1.6 Hz, 1H), 7.50-7.46 (m, 1H), 7.04 (d, J=8.4 Hz, 1H), 7.00-6.96 (m, 1H), 6.66 (d, J=10.4 Hz, 2H), 4.13 (q, J=6.8 Hz, 2H), 1.31 (t, J=6.8 Hz, 3H).; MS (ESI) m/z 356 (M−H)

Example 113

Synthesis of M-55

(Step 1) Methyl 2,6-Difluoro-4-[[4-(2-furyl)phenyl]sulfonylamino]benzoate

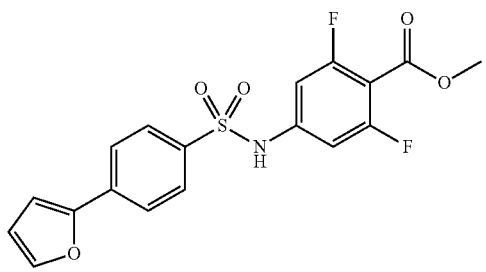 [SMILES: COC(=O)c1c(F)cc(NS(=O)(=O)c2ccc(-c3ccco3)cc2)cc1F]

The title compound (1.00 g, 77%) was obtained as a brown solid by subjecting methyl 2,6-difluoro-4-[(4-iodophenyl)sulfonylamino]benzoate <see (Step 2) of Example 8> (1.50 g, 3.31 mmol) and 2-furylboronic acid (556 mg, 4.97 mmol) to the same method as in Example 20.

¹H NMR (400 MHz, DMSO-d₆): δ 11.3 (s, 1H), 7.90 (s, 4H), 7.85 (d, J=1.2 Hz, 1H), 7.18 (d, J=3.2 Hz, 1H), 6.85 (d, J=10.0 Hz, 2H), 6.68-6.65 (m, 1H), 3.55 (s, 3H).

(Step 2) 2,6-Difluoro-4-[[4-(2-furyl)phenyl]sulfonylamino]benzoic Acid (M-55)

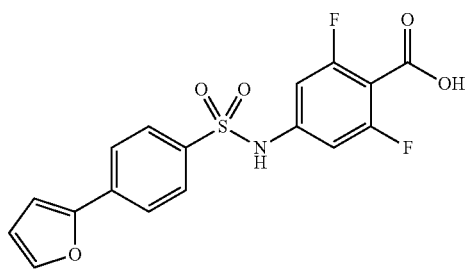 [SMILES: O=C(O)c1c(F)cc(NS(=O)(=O)c2ccc(-c3ccco3)cc2)cc1F]

The title compound (839 mg, 88%) was obtained as a white solid by subjecting methyl 2,6-difluoro-4-[[4-(2-furyl)phenyl]sulfonylamino]benzoate <see (Step 1)> (1.00 g, 2.50 mmol) to the same method as in (Step 5) of Example 104.

¹H NMR (400 MHz, CD₃OD): δ 7.84-7.78 (m, 4H), 7.57 (d, J=1.6 Hz, 1H), 6.92 (d, J=3.6 Hz, 1H), 6.76 (d, J=9.6 Hz, 2H), 6.51-6.49 (m, 1H).; MS (ESI) m/z 378 (M−1)

Example 114

Synthesis of M-56

(Step 1) 2,6-Difluoro-4-{[(6'-methyl-3,3'-bipyridin-6-yl)sulfonyl]amino}benzoic Acid (M-56)

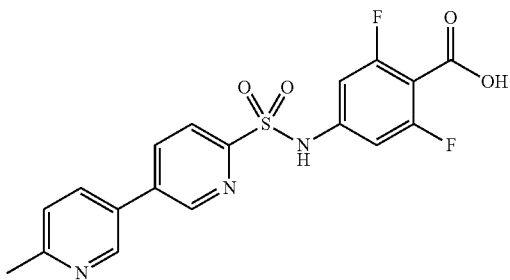 [SMILES: Cc1ccc(-c2ccc(S(=O)(=O)Nc3cc(F)c(C(=O)O)c(F)c3)nc2)cn1]

Methyl 2,6-difluoro-4-{[(5-iodopyridin-2-yl)sulfonyl]amino}benzoate (52 mg, 0.11 mmol) <see (Step 3) of Example 120>, 2-methyl-pyridine-5-boronic acid (34 mg, 0.22 mmol), Pd(dppf)Cl₂ (8 mg, 0.011 mmol), 1,4-dioxane (4.0 ml), and a 1 N aqueous sodium hydrogen carbonate solution (1.0 ml) were added sequentially. The reaction solution was degassed, and stirred at 80° C. overnight. The reaction solution was concentrated under reduced pressure, and tetrahydrofuran (2.0 ml) and water (0.50 ml) were added thereto. Then, a 2 N aqueous sodium hydroxide solution (0.50 ml) was added dropwise thereto, followed by stirring at 50° C. The mixture was neutralized with 2 N hydrochloric acid, and concentrated under reduced pressure. Then, the obtained residue was purified by reversed-phase HPLC (H₂O containing 0.1% TFA/CH₃CN system), followed by freeze-drying, to obtain a TFA salt (52 mg, 91% over two steps) of the title compound.

Example 115

Synthesis of M-57

(Step 1) Methyl 4-[({4-[(Ethylamino)carbonyl]phenyl}sulfonyl)amino]-2,6-difluorobenzoate

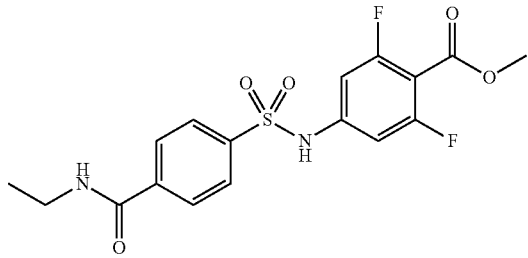 [SMILES: CCNC(=O)c1ccc(S(=O)(=O)Nc2cc(F)c(C(=O)OC)c(F)c2)cc1]

To 4-({[3,5-difluoro-4-(methoxycarbonyl)phenyl]amino}sulfonyl)benzoic acid (1.5 g, 4.0 mmol) <see (Step 1) of Example 11>, thionyl chloride (40 ml) was added, followed by stirring at 75° C. for 4 hours. The reaction liquid was concentrated under reduced pressure, and the concentrate was dissolved in methylene chloride (30 ml). Ethylamine hydrochloride (648 mg, 8.00 mmol) and triethylamine (8.00 ml) were added thereto, followed by stirring at room temperature for 30 minutes. The solvent was removed under reduced pressure, and the obtained residue was purified by silica gel column chromatography (petroleum ether/ethyl acetate=2:1 to 1:1) to obtain the title compound (0.85 g, 53%).

¹H NMR (CD₃OD, 400 MHz): δ 7.97-7.92 (m, 4H), 6.82 (d, J=9.6 Hz, 2H), 3.85 (s, 1H), 3.42-3.36 (m, 2H), 1.23-1.18 (m, 3H).;

MS (ESI) m/z 399 (M+H)⁺

(Step 2) 4-[({4-[(Ethylamino)carbonyl]phenyl}sulfonyl)amino]-2,6-difluorobenzoic Acid (M-57)

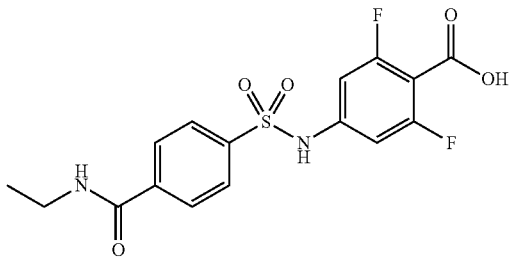 [SMILES: CCNC(=O)c1ccc(S(=O)(=O)Nc2cc(F)c(C(=O)O)c(F)c2)cc1]

The title compound (M-57) (1.12 g, 90%) was obtained by subjecting methyl 4-[({4-[(ethylamino)carbonyl]phenyl}sulfonyl)amino]-2,6-difluorobenzoate (1.30 g, 3.30 mmol) to the same method as in (Step 5) of Example 104.

¹H NMR (CD₃OD, 400 MHz): δ 7.98-7.92 (m, 4H), 6.80 (d, J=14.8 Hz, 2H), 3.43-3.40 (m, 2H), 1.23-1.14 (m, 3H).; MS (ESI) m/z 385 (M+H)⁺

Example 116

Synthesis of M-58

(Step 1) Methyl 5-Amino-3-fluoropyridine-2-carboxylate

The title compound (19.0 g, 49% over three steps) was obtained by subjecting 5-bromo-3-fluoropyridine-2-benzoic acid (50.0 g, 227 mmol) to the same methods as in (Step 1), (Step 2), and (Step 3) of Example 104.

(Step 2) Methyl 5-{[(5-Bromopyridin-2-yl)sulfonyl]amino}-3-fluoropyridine-2-carboxylate

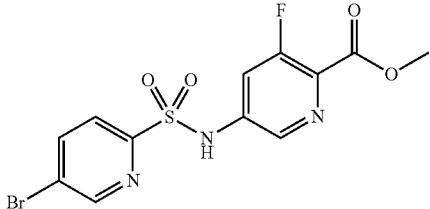

Methyl 5-amino-3-fluoropyridine-2-carboxylate (5.30 g, 31.2 mmol) and 5-bromopyridine-2-sulfonyl chloride (12.0 g, 46.8 mmol) <see (Step 1) of Example 7> were dissolved in methylene chloride (350 ml), and pyridine (20 ml) was added thereto, followed by stirring at room temperature for 12 hours. The reaction liquid was concentrated under reduced pressure, and the pH was adjusted to 4.0 by adding 4 N hydrochloric acid, followed by stirring for 10 minutes. Further, methylene chloride (100 ml) was added thereto, followed by stirring at room temperature for 1 hour. The obtained solid was filtered and dried to obtain the title compound (6.0 g, 49%) as a white solid.

MS (ESI) m/z 390 and 392 (M+H)+

(Step 3) [6-({[5-Fluoro-6-(methoxycarbonyl)pyridin-3-yl]amino}sulfonyl)pyridin-3-yl]boronic Acid

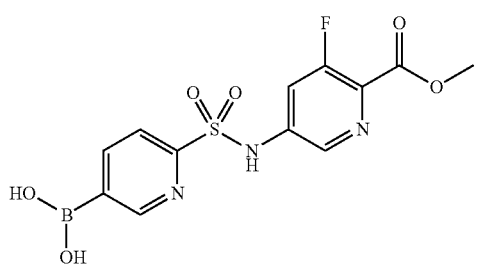 [SMILES: COC(=O)c1ncc(NS(=O)(=O)c2ccc(B(O)O)cn2)cc1F]

Methyl 5-{[(5-bromopyridin-2-yl)sulfonyl]amino}-3-fluoropyridine-2-carboxylate (6.00 g, 15.4 mmol) and bis(pinacolato)diborane (4.70 g, 18.5 mmol) were dissolved in N,N'-dimethylformamide (150 ml), and [1,1'-bis(diphenylphosphino)ferrocene]dichloropalladium(II) (338 mg, 0.460 mmol) and potassium acetate (4.50 g, 46.3 mmol) were added thereto, followed by stirring at 85° C. for 12 hours in the presence of nitrogen gas. The reaction liquid was cooled to room temperature, and diluted with water, followed by extraction with methylene chloride four times. The organic layers were combined, concentrated under reduced pressure, and then diluted with water. The obtained solid was filtered and dried to obtain the title compound (4.8 g, 88%).

1H NMR (CD3OD, 400 MHz): δ 8.83 (s, 1H), 8.28-8.26 (m, 2H), 8.03 (d, J=8.0 Hz, 1H), 7.72 (d, J=12.0 Hz, 1H), 3.91 (s, 3H).;

MS (ESI) m/z 356 (M+H)+

(Step 4) 3-Fluoro-5-{[(5-pyrimidin-2-ylpyridin-2-yl)sulfonyl]amino}pyridine-2-carboxylic Acid (M-58)

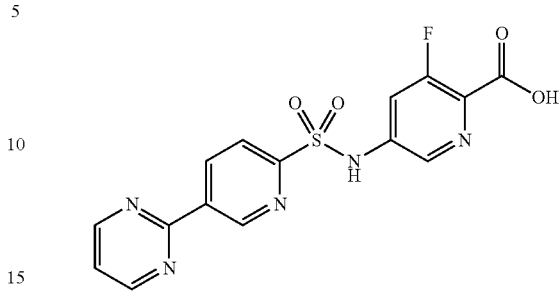

[6-({[5-Fluoro-6-(methoxycarbonyl)pyridin-3-yl]amino}sulfonyl)pyridin-3-yl]boronic acid (4.80 g, 13.5 mmol) and 2-bromopyrimidine (4.30 g, 27.0 mmol) were dissolved in N,N'-dimethylformamide (150 ml) and water (60 ml), and [1,1'-bis(diphenylphosphino)ferrocene]dichloropalladium(II) (989 mg, 1.35 mmol) and sodium carbonate (4.30 g, 40.6 mmol) were added thereto, followed by stirring at 95° C. for 12 hours in the presence of nitrogen gas. The reaction liquid was cooled to room temperature, and diluted with water. Then, the pH was adjusted to 5.0 by adding 6 N hydrochloric acid. The precipitated white solid was filtered and dried to obtain a hydrochloride (720 mg, 13%) of the title compound (M-58).

1H NMR (CD3OD, 400 MHz): δ 9.59 (s, 1H), 8.98 (d, J=8.0 Hz, 1H), 8.89 (d, J=4.8 Hz, 2H), 8.36 (s, 1H), 8.21 (d, J=8.0 Hz, 1H), 7.80 (d, J=12.0 Hz, 1H), 7.45 (t, J=4.8 Hz, 1H).;

MS (ESI) m/z 376 (M+H)+

Example 117

Synthesis of M-59

(Step 1) 4-{[(4-{[(Cyclopropylmethyl)amino]carbonyl}phenyl)sulfonyl]amino}-2,6-difluorobenzoic Acid

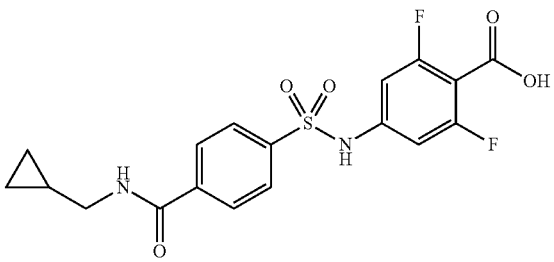 [SMILES: O=C(NCC1CC1)c1ccc(S(=O)(=O)Nc2cc(F)c(C(=O)O)c(F)c2)cc1]

4-({[3,5-Difluoro-4-(methoxycarbonyl)phenyl]amino}sulfonyl)benzoic acid <see (Step 1) of Example 11> (68 mg, 0.20 mmol) and cyclopropylmethylamine (7.1 mg, 0.10 mmol) were suspended in dichloromethane (3.0 ml), and HATU (57.0 mg, 0.150 mmol), HOAt (20.0 mg, 0.150 mmol), and triethylamine (28 µl, 0.20 mmol) were added thereto, followed by stirring at room temperature for 2 hours. The reaction liquid was concentrated under reduced pressure, and then a 4 N hydrochloric acid/1,4-dioxane solution (2.0 ml) and water (4.0 ml) were added thereto, Example 118

Synthesis of M-60

(Step 1) 4-(Chlorosulfonyl)-3-methylbenzoic Acid

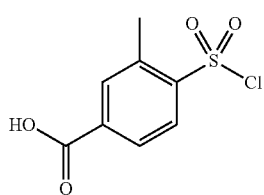

4-Amino-3-methylbenzoic acid (15.0 g, 0.933 mol) was dissolved in concentrated hydrochloric acid (60 ml) and glacial acetic acid (20 ml), and the solution was cooled to −10° C. Then, an aqueous solution (20 ml) of sodium nitrite (10.0 g, 0.149 mol) was added dropwise thereto, followed by stirring at −10° C. for 45 minutes, to obtain a diazonium salt. Another reaction vessel was filled with glacial acetic acid (480 ml), and sulfur dioxide (gas) was bubbled thereinto for 30 minutes. To the reaction liquid, copper(II) chloride (8.0 g) was added, and sulfur dioxide (gas) was bubbled for further 30 minutes. This reaction solution was cooled to −30° C., and the above-described solution of the diazonium salt was slowly added dropwise thereto, followed by stirring at room temperature for 1 hour. After the reaction, the mixture was diluted with water, and the precipitated solid was filtered and dried to obtain the title compound (5.1 g, 22%).

1H NMR (DMSO-$d_6$, 300 MHz): δ 8.23-8.13 (m, 3H), 2.89 (s, 3H).

(Step 2) 4-({[3,5-Difluoro-4-(methoxycarbonyl)phenyl]amino}sulfonyl)-3-methylbenzoic Acid

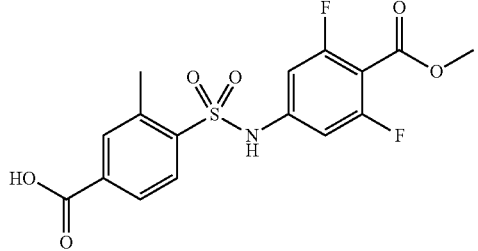 [SMILES: COC(=O)c1c(F)cc(NS(=O)(=O)c2ccc(C(=O)O)cc2C)cc1F]

The title compound (610 mg, 14%) was obtained by subjecting 4-(chlorosulfonyl)-3-methylbenzoic acid (4.17 g, 17.8 mmol) to the same method as in (Step 4) of Example 104.

MS (ESI) m/z 386 (M+H)$^+$ (Step 3) Methyl 4-[({4-[(tert-Butylamino)carbonyl]-2-methylphenyl}sulfonyl)amino]-2,6-difluorobenzoate

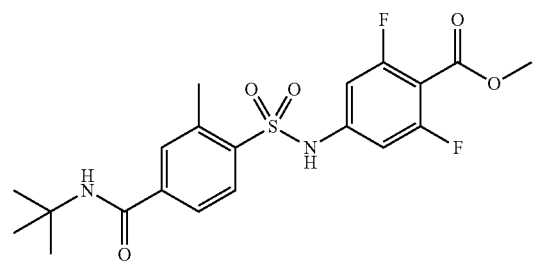 [SMILES: COC(=O)c1c(F)cc(NS(=O)(=O)c2ccc(C(=O)NC(C)(C)C)cc2C)cc1F]

4-({[3,5-Difluoro-4-(methoxycarbonyl)phenyl]amino}sulfonyl)-3-methylbenzoic acid (610 mg, 1.58 mmol) was dissolved in thionyl chloride (80 ml), followed by stirring at 100° C. for 3.5 hours. The reaction solvent was removed under reduced pressure, and the obtained residue was suspended in methylene chloride (anhydrous) (40 ml), and t-butylamine (10 ml) was added thereto, followed by stirring at room temperature for 12 hours. The obtained white solid was filtered, and further the solid was stirred in 6 N hydrochloric acid (50 ml) for 30 minutes, filtered, and dried to obtain the title compound (615 mg, 73%).

$^1$H NMR (DMSO-$d_6$, 400 MHz): δ 11.57 (s, 1H), 8.05 (d, J=8.8 Hz, 1H), 7.96 (s, 1H), 7.75-7.74 (m, 2H), 6.79 (d, J=10.4 Hz, 2H), 3.79 (s, 3H), 2.62 (s, 3H), 1.35 (s, 9H).; MS (ESI) m/z 441 (M+H)$^+$ (Step 4) 4-[({4-[(tert-Butylamino)carbonyl]-2-methylphenyl}sulfonyl)amino]-2,6-difluorobenzoic Acid (M-60)

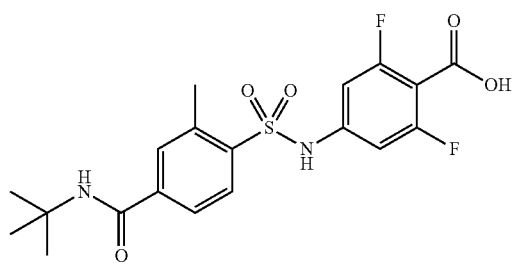 [SMILES: Cc1cc(C(=O)NC(C)(C)C)ccc1S(=O)(=O)Nc1cc(F)c(C(=O)O)c(F)c1]

The title compound (M-60) (483 mg, 96%) was obtained by subjecting methyl 4-[({4-[(tert-butylamino)carbonyl]-2-methylphenyl}sulfonyl)amino]-2,6-difluorobenzoate (615 mg, 1.17 mmol) to the same method as in (Step 5) of Example 104.

1H NMR (CD$_3$OD, 300 MHz): δ 8.10 (d, J=8.7 Hz, 1H), 7.69-7.67 (m, 2H), 6.74 (d, J=7.2 Hz, 2H), 2.70 (s, 3H), 1.43 (s, 9H).;

MS (ESI) m/z 425 (M−1)

Example 119

Synthesis of M-61

(Step 1) 2-Fluoro-4-({[4-(1H-1,2,3-triazol-1-yl)phenyl]sulfonyl}amino)benzoic Acid (M-61)

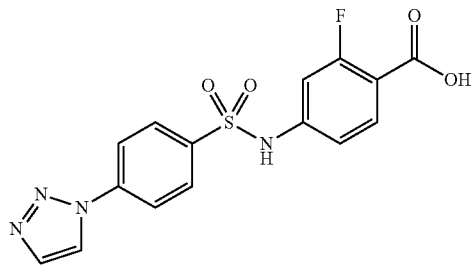 [SMILES: O=C(O)c1ccc(NS(=O)(=O)c2ccc(-n3ccnn3)cc2)cc1F]

The title compound (M-61) (1.2 g, 13%) was obtained by subjecting methyl 2-fluoro-4-{[(4-iodophenyl)sulfonyl]amino}benzoate (10.3 g, 23.1 mmol) to the same methods as in Examples 15 to 18.

$^1$H NMR (CD$_3$OD, 400 MHz): δ 8.64 (d, J=0.8 Hz, 2H), 8.10 (m, 4H), 7.93 (d, J=1.2 Hz, 1H), 7.83 (t, J=8.4 Hz, 1H), 7.06-7.00 (m, 2H).; MS (ESI) m/z 363.0 (M+H)$^+$

Example 120

Synthesis of M-62

(Step 1) 2-(Benzylthio)-5-iodopyridine

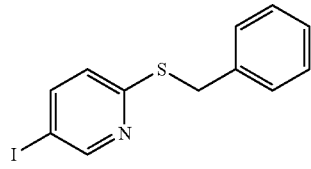 [SMILES: Ic1ccc(SCc2ccccc2)nc1]

2-Chloro-5-iodopyridine (9.30 g, 75.0 mmol) was dissolved in N,N'-dimethylformamide (120 ml). After the solution was cooled to 0° C., 60% sodium hydride (3.8 g, 95 mmol) was added thereto, followed by stirring at 0° C. for 30 minutes.

To this reaction liquid, an N,N'-dimethylformamide solution (30 ml) of phenylmethanethiol (15 g, 63 mmol) was added, followed by stirring at room temperature for 1 hour. After the reaction, the reaction liquid was diluted with water, followed by extraction with ethyl acetate (200 ml×2). The organic layers were combined and dried over anhydrous sodium sulfate. The solvent was removed under reduced pressure to obtain the title compound (18.4 g, 90%).

$^1$H NMR (CDCl$_3$, 400 MHz): δ 8.64 (d, J=1.6 Hz, 1H), 7.73-7.70 (m, 1H), 7.39 (d, J=7.6 Hz, 2H), 7.33-7.23 (m, 3H), 6.98-6.95 (m, 1H), 4.39 (s, 2H).; MS (ESI) m/z 328 (M+H)$^+$ (Step 2) 5-Iodopyridine-2-sulfonyl Chloride

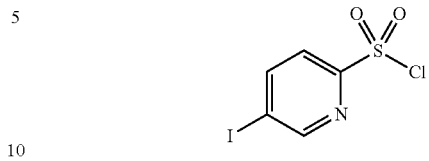

2-(Benzylthio)-5-iodopyridine (11.3 g, 35.0 mmol) was suspended in a mixture solvent of water (25 ml) and acetic acid (75 ml), and N-chlorosuccinimide (18.4 g, 138 mmol) was added thereto, followed by stirring at room temperature for 1 hour. The reaction liquid was diluted with water, followed by extraction with methylene chloride (100 ml×2). The organic layers were combined, then washed with a 3 N aqueous sodium hydroxide solution (80 ml) and saturated aqueous sodium chloride, and dried over anhydrous sodium sulfate. The solvent was removed under reduced pressure. The obtained residue was purified by silica gel column chromatography (petroleum ether/ethyl acetate=30:1) to obtain the title compound (2.6 g, 25%) as a white solid.

(Step 3) Methyl 2,6-Difluoro-4-{[(5-iodopyridin-2-yl)sulfonyl]amino}benzoate

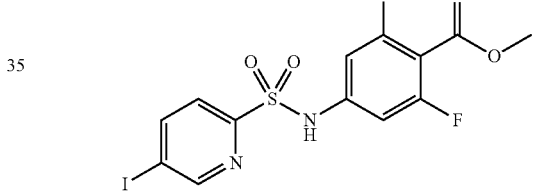

The title compound (3.0 g, 69%) was obtained by subjecting 5-iodopyridine-2-sulfonyl chloride (5.1 g, 17 mmol) to the same method as in (Step 4) of Example 104.

$^1$H NMR (DMSO-d$_6$, 400 MHz): δ 11.58 (br, 1H), 9.00 (d, J=2.0 Hz, 1H), 8.53 (dd, J=8.4, 2.0 Hz, 1H), 7.92 (d, J=8.0 Hz, 1H), 6.94 (d, J=10.4 Hz, 2H), 3.81 (s, 3H).; MS (ESI) m/z 455 (M+H)$^+$ (Step 4) Methyl 2,6-Difluoro-4-({[5-(1H-pyrrol-1-yl)pyridin-2-yl]sulfonyl}amino)benzoate

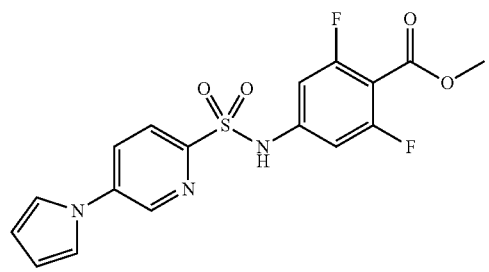 [SMILES: COC(=O)c1c(F)cc(NS(=O)(=O)c2ccc(-n3cccc3)cn2)cc1F]

The title compound (0.80 g, 31%) was obtained as a white solid by subjecting methyl 2,6-difluoro-4-{[(5-iodopyridin-2-yl)sulfonyl]amino}benzoate (3.0 g, 6.6 mmol) to the same method as in Example 10.

MS (ESI) m/z 394 (M+H)+

(Step 5) 2,6-Difluoro-4-({[5-(1H-pyrrol-1-yl)pyridin-2-yl]sulfonyl}amino)benzoic Acid (M-62)

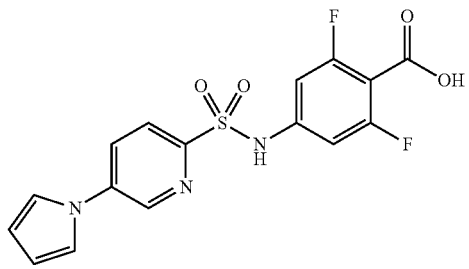

The title compound (M-62) (306 mg, 79%) was obtained by subjecting methyl 2,6-difluoro-4-({[5-(1H-pyrrol-1-yl)pyridin-2-yl]sulfonyl}amino)benzoate (400 mg, 1.01 mmol) to the same method as in (Step 5) of Example 104.

$^1$H NMR (CD$_3$OD, 300 MHz): δ 8.92 (s, 1H), 8.14 (d, J=1.2 Hz, 2H), 7.39 (t, J=1.8 Hz, 2H), 6.93 (d, J=9.9 Hz, 2H), 6.39 (d, J=1.8 Hz, 2H).; MS (ESI) m/z 378 (M−1)

Example 121

Synthesis of M-63

(Step 1) 2-(Benzylthio)-5-bromopyridine

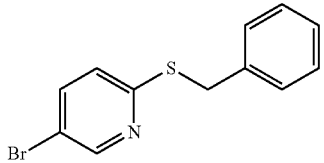 [SMILES: Brc1ccc(SCc2ccccc2)nc1]

The title compound (143 g, 80%) was obtained by subjecting 2-chloro-5-bromopyridine (123 g, 640 mmol) to the same method as in (Step 1) of Example 120.

(Step 2) 5-Bromopyridine-2-sulfonyl Chloride

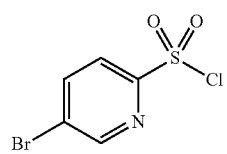 [SMILES: O=S(=O)(Cl)c1ccc(Br)cn1]

The title compound (4.70 g, 21%) was obtained by subjecting 2-(benzylthio)-5-bromopyridine (25.0 g, 90.0 mmol) to the same method as in (Step 2) of Example 120.

(Step 3) Methyl 4-{[(5-Bromopyridin-2-yl)sulfonyl]amino}-2-fluorobenzoate

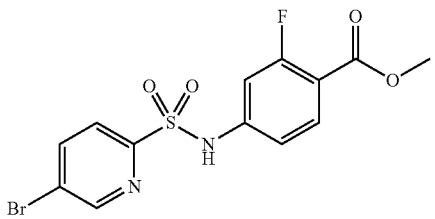 [SMILES: COC(=O)c1ccc(NS(=O)(=O)c2ccc(Br)cn2)cc1F]

The title compound (3.97 g, 85%) was obtained by subjecting 5-bromopyridine-2-sulfonyl chloride (4.70 g, 18.0 mmol) to the same method as in (Step 4) of Example 104.

$^1$H NMR (CDCl3, 300 MHz): δ 8.75 (d, J=2.1 Hz, 1H), 8.07-8.04 (m, 1H), 7.95 (d, J=7.8 Hz, 1H), 7.86-7.80 (m, 1H), 7.12 (dd, J=11.7, 2.1 Hz, 1H), 7.02 (dd, J=8.4, 2.1 Hz, 1H), 3.89 (s, 3H).; MS (ESI) m/z 389 (M+H)+

(Step 4) Methyl 2-Fluoro-4-{[(5-pyrimidin-5-ylpyridin-2-yl)sulfonyl]amino}benzoate

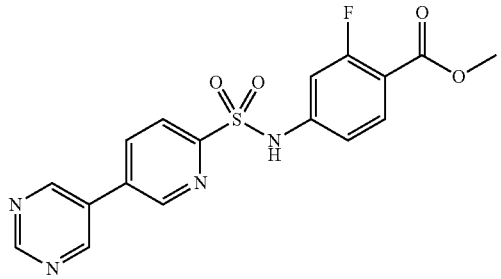 [SMILES: COC(=O)c1ccc(NS(=O)(=O)c2ccc(-c3cncnc3)cn2)cc1F]

Methyl 4-{[(5-bromopyridin-2-yl)sulfonyl]amino}-2-fluorobenzoate (4.20 g, 10.8 mmol) and pyrimidin-5-ylboronic acid (2.70 g, 17.8 mmol) were dissolved in N,N'-dimethylformamide (50 ml) and water (10 ml), and [1,1'-bis(diphenylphosphino)ferrocene]dichloropalladium(II) (366 mg, 0.500 mmol) and sodium carbonate (2.50 g, 23.6 mmol) were added thereto, followed by stirring at 90° C. for 12 hours in the presence of nitrogen gas. The reaction liquid was cooled to room temperature and diluted with water, and then ethyl acetate was added thereto for extraction. The organic layers were combined, washed with saturated aqueous sodium chloride, and dried over anhydrous sodium sulfate. Then, the solvent was removed under reduced pressure. The obtained residue was purified by silica gel column chromatography (petroleum ether/ethyl acetate=1:2 to 1:10) to obtain the title compound (2.3 g, 55%).

MS (ESI) m/z 389 (M+H)+

(Step 5) 2-Fluoro-4-{[(5-pyrimidin-5-ylpyridin-2-yl)sulfonyl]amino}benzoic Acid (M-63)

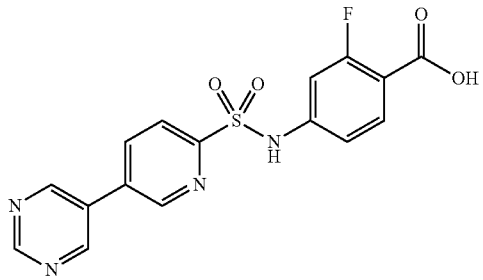

The title compound (M-63) (1.38 g, 90%) was obtained as a white solid by subjecting methyl 2-fluoro-4-{[(5-pyrimidin-5-ylpyridin-2-yl)sulfonyl]amino}benzoate (1.6 g, 4.1 mmol) to the same method as in (Step 5) of Example 104.

1H NMR (DMSO-$d_6$, 400 MHz): δ 11.47 (s, 1H), 9.27 (s, 3H), 9.18 (d, J=2.4 Hz, 1H), 8.56 (dd, J=10.8, 3.2 Hz, 1H), 8.25 (d, J=11.2 Hz, 1H), 7.77 (t, J=11.2 Hz, 1H), 7.12 (s, 1H), 7.08 (s, 1H).; MS (ESI) m/z 375 (M+H)$^+$

Example 122

Synthesis of M-64

(Step 1) Benzyl 4-Amino-2,6-difluorobenzoate

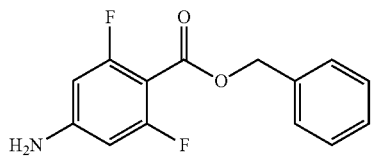 [SMILES: Nc1cc(F)c(C(=O)OCc2ccccc2)c(F)c1]

4-Amino-2,6-difluorobenzoic acid (101 g, 0.583 mol) was dissolved in acetonitrile (400 ml), and potassium carbonate (81.0 g, 0.586 mol) and benzyl bromide (100 g, 0.585 mol) were added thereto, followed by stirring at 80° C. for 2 hours. The reaction liquid was diluted with water, followed by extraction with ethyl acetate (150 ml). Then, the solvent was removed under reduced pressure to obtain the title compound (115 g, 75%).

$^1$H NMR (DMSO-$d_6$, 400 MHz): δ 7.46-7.27 (m, 5H), 6.18-6.13 (m, 2H), 5.35 (s, 2H), 4.23 (s, 2H).

(Step 2) Benzyl 4-{[(6-Chloropyridin-3-yl)sulfonyl]amino}-2,6-benzoate

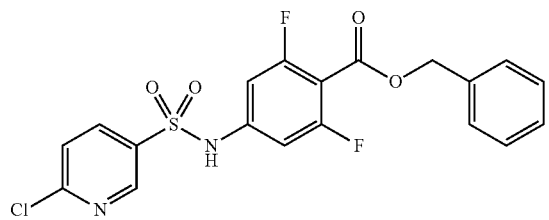 [SMILES: O=C(OCc1ccccc1)c1c(F)cc(NS(=O)(=O)c2ccc(Cl)nc2)cc1F]

The title compound (51.0 g, 64%) was obtained by subjecting benzyl 4-amino-2,6-difluorobenzoate (48.0 g, 0.182 mol) and 6-chloropyridine-3-sulfonyl chloride (57.0 g, 0.269 mol) to the same method as in (Step 4) of Example 104.

MS (ESI) m/z 439 (M+H)$^+$

(Step 3) Methyl 5-[({4-[(Benzyloxy)carbonyl]-3,5-difluorophenyl}amino)sulfonyl]pyridine-2-carboxylate

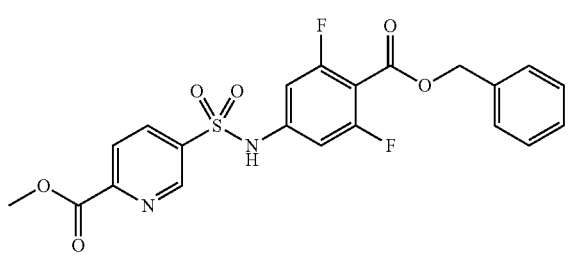 [SMILES: COC(=O)c1ccc(S(=O)(=O)Nc2cc(F)c(C(=O)OCc3ccccc3)c(F)c2)cn1]

Benzyl 4-{[(6-chloropyridin-3-yl)sulfonyl]amino}-2,6-benzoate (43.8 g, 99.8 mmol) was dissolved in methanol (200 ml), and trans-bis(benzonitrile)palladium(II) dichloride (4.80 g, 13.0 mmol), 1,3-bis(diphenylphosphino)propane (10.0 g, 25.0 mmol), and triethylamine (20.2 g, 0.200 mol) were added thereto, followed by stirring at 120° C. for 18 hours in the presence of carbon monoxide (80 psi). The reaction liquid was concentrated under reduced pressure, and the obtained residue was purified by silica gel column chromatography (petroleum ether/ethyl acetate=4:1 to 2:1) to obtain the title compound (27.0 g, 59%).

$^1$H NMR (DMSO-$d_6$, 400 MHz): δ 11.6 (s, 1H), 9.14 (d, J=2.0 Hz, 1H), 8.44-8.42 (m, 1H), 8.22 (d, J=8.4 Hz, 1H), 7.45-7.32 (m, 5H), 6.88 (d, J=10.4 Hz, 2H), 5.32 (s, 2H), 3.92 (s, 3H).;

MS (ESI) m/z 463 (M+H)$^+$

(Step 4) Benzyl 4-[({6-[(Ethylamino)carbonyl]pyridin-3-yl}sulfonyl)amino]-2,6-difluorobenzoate

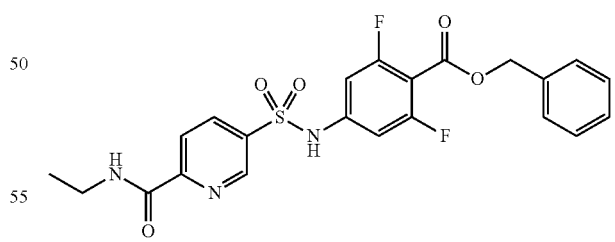

Methyl 5-[({4-[(benzyloxy)carbonyl]-3,5-difluorophenyl}amino)sulfonyl]pyridine-2-carboxylate (8.50 g, 18.4 mmol) was dissolved in tetrahydrofuran (40 ml), and a 2 N ethylamine tetrahydrofuran solution (27.6 ml) was added thereto, followed by stirring at room temperature for 72 hours. The solvent was removed under reduced pressure, and n-hexane (50 ml) was added to the residue. After stirring for 10 minutes, the obtained solid was filtered and dried to obtain the title compound (6.8 g, 78%).

¹H NMR (CD₃OD, 400 MHz): δ 9.03-9.02 (m, 1H), 8.35-8.33 (m, 1H), 8.15-8.13 (m, 1H), 7.42-7.29 (m, 5H), 6.58 (d, J=12.0 Hz, 2H), 5.29 (s, 2H), 3.48-3.42 (m, 2H), 1.30 (t, J=8.4 Hz, 3H).

(Step 5) 4-[({6-[(Ethylamino)carbonyl]pyridin-3-yl}sulfonyl)amino]-2,6-difluorobenzoic Acid (M-64)

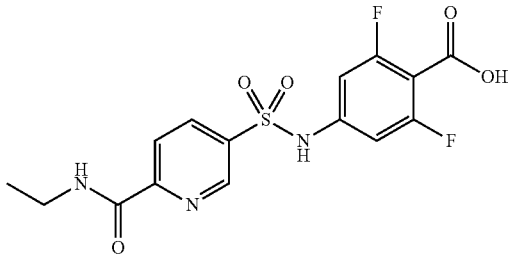 [SMILES: CCNC(=O)c1ccc(S(=O)(=O)Nc2cc(F)c(C(=O)O)c(F)c2)cn1]

Benzyl 4-[({6-[(ethylamino)carbonyl]pyridin-3-yl}sulfonyl)amino]-2,6-difluorobenzoate (6.80 g, 14.3 mmol) was dissolved in methanol (150 ml), and 10% palladium carbon (2.0 g) was added thereto, followed by stirring at room temperature for 4 days in the presence of hydrogen gas. The reaction liquid was filtered, and the filtrate was concentrated under reduced pressure. Then, n-hexane (30 ml) was added to the obtained residue, followed by stirring. The precipitated solid was filtered to obtain the title compound (M-64) (3.4 g, 62%).

¹H NMR (CD₃OD, 400 MHz): δ 9.06 (d, J=2.0 Hz, 1H), 8.43 (dd, J=8.0, 2.0 Hz, 1H), 8.26 (d, J=8.0 Hz, 1H), 6.89 (s, 1H), 6.87 (s, 1H), 3.46 (q, J=6.8 Hz, 2H), 1.24 (t, J=6.8 Hz, 3H).; MS (ESI) m/z 386 (M+H)⁺

Example 123

Synthesis of M-65

(Step 1) Methyl 4-[({4-[(Cyclopentylamino)carbonyl]phenyl}sulfonyl)amino]-2,6-difluorobenzoate

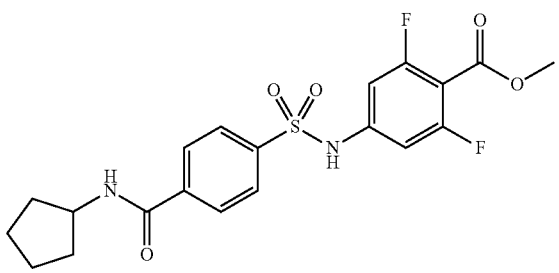 [SMILES: COC(=O)c1c(F)cc(NS(=O)(=O)c2ccc(C(=O)NC3CCCC3)cc2)cc1F]

The title compound (1.4 g, 47%) was obtained by subjecting 4-({[3,5-difluoro-4-(methoxycarbonyl)phenyl]amino}sulfonyl)benzoic acid <see (Step 1) of Example 11> (2.5 g, 4.0 mmol) to the same method as in (Step 2) of Example 11.

MS (ESI) m/z 439 (M+H)⁺

(Step 2) 4-[({4-[(Cyclopentylamino)carbonyl]phenyl}sulfonyl)amino]-2,6-difluorobenzoic Acid (M-65)

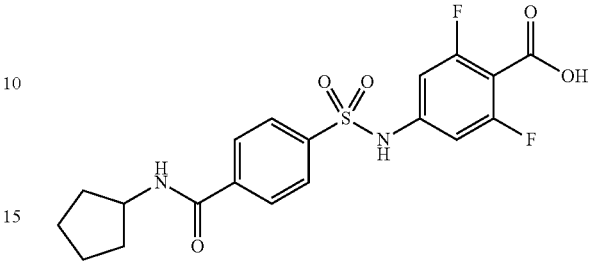

The title compound (M-65) (990 mg, 74%) was obtained as a white solid by subjecting methyl 4-[({4-[(cyclopentylamino)carbonyl]phenyl}sulfonyl)amino]-2,6-difluorobenzoate (1.4 g, 3.2 mmol) to the same method as in (Step 5) of Example 104.

¹H-NMR (CD₃OD, 400 MHz): δ 7.98-7.92 (m, 4H), 6.83 (d, J=10.0 Hz, 2H), 4.33-4.27 (m, 1H), 2.06-2.00 (m, 2H), 1.79-1.54 (m, 6H).; MS (ESI) m/z 425 (M+H)⁺

Example 124

Synthesis of M-66

(Step 1) 4-[({4-[(tert-Butylamino)carbonyl]phenyl}sulfonyl)amino]-2,6-difluorobenzoic Acid (M-66)

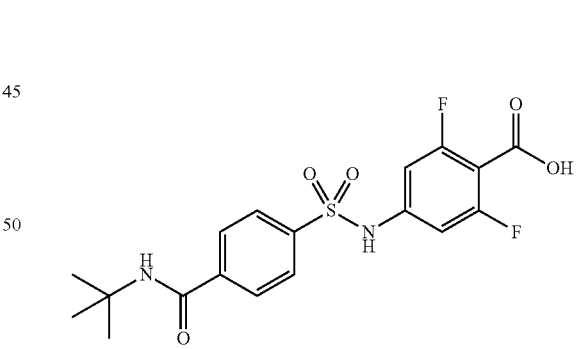

The title compound (M-66) (14.0 g, 74% over two steps) was obtained as a white solid by subjecting 4-({[3,5-difluoro-4-(methoxycarbonyl)phenyl]amino}sulfonyl)benzoic acid <see (Step 1) of Example 11> (17.0 g, 45.8 mmol) to a method including the same two steps as (Step 2) of Example 11 and (Step 5) of Example 104.

1H NMR (CD₃OD, 400 MHz): δ 7.95 (d, J=8.8 Hz, 2H), 7.87 (d, J=8.4 Hz, 2H), 6.82 (d, J=9.6 Hz, 2H), 1.44 (s, 9H).; MS (ESI) m/z 413 (M+H)⁺

Example 125

Synthesis of M-67

(Step 1) 4-[({4-[(Cyclohexylamino)carbonyl]phenyl}sulfonyl)amino]-2,6-difluorobenzoic Acid (M-67)

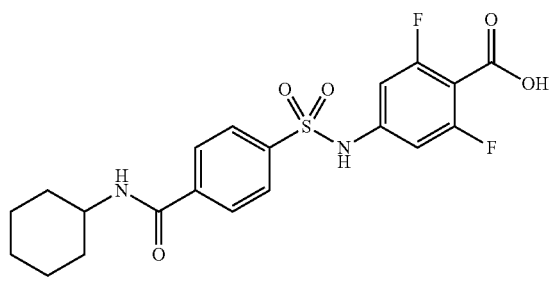 [SMILES: O=C(NC1CCCCC1)c1ccc(S(=O)(=O)Nc2cc(F)c(C(=O)O)c(F)c2)cc1]

The title compound (M-67) (600 mg, 34% over two steps) was obtained as a white solid by subjecting 4-({[3,5-difluoro-4-(methoxycarbonyl)phenyl]amino}sulfonyl)benzoic acid <see (Step 1) of Example 11> (1.5 g, 4.0 mmol) to a method including the same two steps as (Step 2) of Example 11 and (Step 5) of Example 104.

$^1$H-NMR (CD$_3$OD, 300 MHz): δ 7.97-7.90 (m, 4H), 6.84 (d, J=2.4 Hz, 1H), 6.80 (d, J=2.4 Hz, 1H), 3.33-3.10 (m, 1H), 1.96-1.92 (m, 2H), 1.82-1.78 (m, 3H), 1.42-1.30 (m, 5H).; MS (ESI) m/z 439 (M+H)$^+$

Example 126

Synthesis of M-68

(Step 1) 4-{[(4-{[(1-Ethylpropyl)amino]carbonyl}phenyl)sulfonyl]amino}-2,6-difluorobenzoic Acid (M-68)

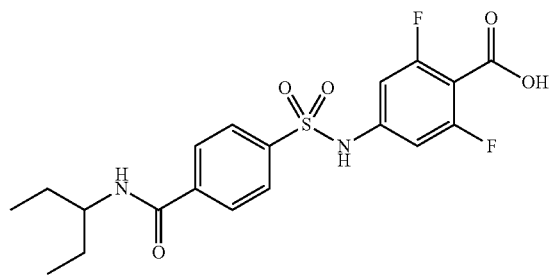 [SMILES: CCC(CC)NC(=O)c1ccc(S(=O)(=O)Nc2cc(F)c(C(=O)O)c(F)c2)cc1]

The title compound (M-68) (570 mg, 31% over two steps) was obtained as a white solid by subjecting 4-({[3,5-difluoro-4-(methoxycarbonyl)phenyl]amino}sulfonyl)benzoic acid <see (Step 1) of Example 11> (1.5 g, 4.0 mmol) to a method including the same two steps as (Step 2) of Example 11 and (Step 5) of Example 104.

$^1$H-NMR (CD$_3$OD, 400 MHz): δ 7.95-7.90 (m, 4H), 6.78 (d, J=9.2 Hz, 2H), 3.83-3.79 (m, 1H), 1.64-1.47 (m, 4H), 0.92 (t, J=7.2 Hz, 6H).; MS (ESI) m/z 427 (M+H)$^+$

Example 127

Synthesis of M-69

(Step 1) Methyl 2,6-Difluoro-4-[(pyridin-4-ylsulfonyl)amino]benzoate

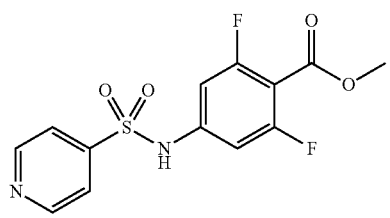 [SMILES: COC(=O)c1c(F)cc(NS(=O)(=O)c2ccncc2)cc1F]

Pyridine-4-thiol (16.7 g, 150 mmol) was dissolved in concentrated hydrochloric acid (110 ml) and water (30 ml). After cooling to 0° C., chlorine gas was bubbled for 1 hour. The reaction solution was diluted with ice-water (75 g), and neutralized by gradually adding sodium hydrogen carbonate. After extraction with methylene chloride (150 ml×3) cooled to 5 to 10° C., the organic layers were combined and dried over anhydrous sodium sulfate. Then, the solvent was removed under reduced pressure to obtain the corresponding sulfonyl chloride. In another reaction vessel, methyl 4-amino-2,6-difluorobenzoate (16.9 g, 90.3 mmol) and pyridine (10 ml) were dissolved in methylene chloride (200 ml). After cooling to −10° C., the above-described solution of the sulfonyl chloride in methylene chloride was added thereto, followed by stirring at room temperature for 6 hours. The organic layer was washed with 0.1 N hydrochloric acid (200 ml×2), and the solvent was removed under reduced pressure. The residue was purified by silica gel column chromatography (petroleum ether/ethyl acetate=2:1 to 1:1) to obtain the title compound (11.2 g, 38% over two steps).

MS (ESI) m/z 329 (M+H)$^+$ (Step 2) 2,6-Difluoro-4-[(pyridin-4-ylsulfonyl)amino]benzoic Acid (M-69)

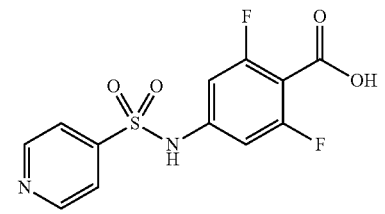 [SMILES: O=C(O)c1c(F)cc(NS(=O)(=O)c2ccncc2)cc1F]

The title compound (M-69) (790 mg, 90%) was obtained by subjecting methyl 2,6-difluoro-4-[(pyridin-4-ylsulfonyl)amino]benzoate (920 mg, 2.80 mmol) to the same method as in (Step 5) of Example 104.

$^1$H NMR (CD$_3$OD, 400 MHz): δ 8.99 (dd, J=5.2, 1.6 Hz, 2H), 8.27 (dd, J=5.2, 1.6 Hz, 2H), 6.83 (d, J=9.2 Hz, 2H).; MS (ESI) m/z 315 (M+H)$^+$

Example 128

Synthesis of M-70

(Step 1) 2,6-Difluoro-4-{[(4-{[(tetrahydro-2H-pyran-4-yl-methyl)amino]carbonyl}phenyl)sulfonyl]amino}benzoic Acid (M-70)

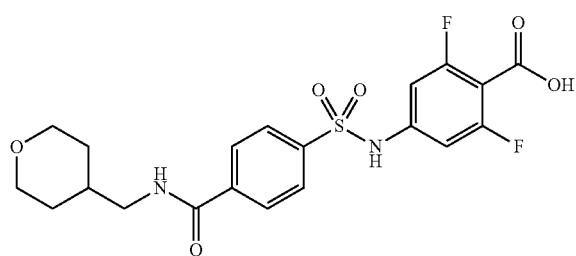 [SMILES: O=C(NCC1CCOCC1)c1ccc(S(=O)(=O)Nc2cc(F)c(C(=O)O)c(F)c2)cc1]

To 4-({[3,5-difluoro-4-(methoxycarbonyl)phenyl]amino}sulfonyl)benzoic acid <see (Step 1) of Example 11> (85 mg, 0.23 mmol), dichloromethane (5.0 ml) was added, and HATU (114 mg, 0.30 mmol), C-(tetrahydro-pyran-4-yl)-methylamine (32.0 μl, 0.280 mmol), and DIPEA (120 μl, 0.690 mmol) were added sequentially, followed by stirring at room temperature overnight. To the reaction solution, water was added, followed by extraction with ethyl acetate. The extraction liquid was washed with saturated aqueous sodium chloride, dried over anhydrous magnesium sulfate, and concentrated under reduced pressure. Then, tetrahydrofuran (2.0 ml) and water (0.50 ml) were added to the residue, and a 2 N aqueous sodium hydroxide solution (1.0 ml) was added dropwise thereto, followed by stirring at room temperature. The mixture was neutralized with 2 N hydrochloric acid, and concentrated under reduced pressure. Then, the obtained residue was purified by reversed-phase HPLC (H₂O containing 0.1% TFA/CH₃CN system), followed by freeze-drying, to obtain the title compound (58 mg, 57% over two steps).

Example 129

Synthesis of M-71

(Step 1) 5-[({4-[(Benzyloxy)carbonyl]-3,5-difluorophenyl}amino)sulfonyl]pyridine-2-benzoic Acid

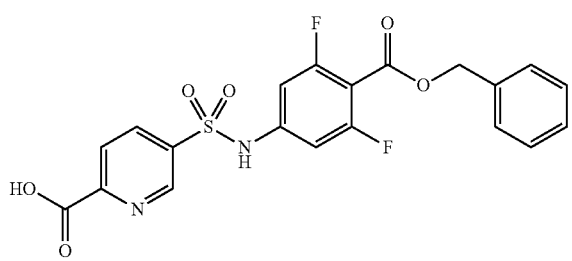 [SMILES: O=C(O)c1ccc(S(=O)(=O)Nc2cc(F)c(C(=O)OCc3ccccc3)c(F)c2)cn1]

The title compound (1.1 g, 57%) was obtained as a white solid by subjecting methyl 5-[({4-[(benzyloxy)carbonyl]-3,5-difluorophenyl}amino)sulfonyl]pyridine-2-carboxylate (2.0 g, 4.3 mmol) <see (Step 3) of Example 122> to the same method as in (Step 5) of Example 104.

MS (ESI) m/z 449 (M+H)⁺

(Step 2) Benzyl 4-[({6-[(tert-Butylamino)carbonyl]pyridin-3-yl}sulfonyl)amino]-2,6-difluorobenzoate

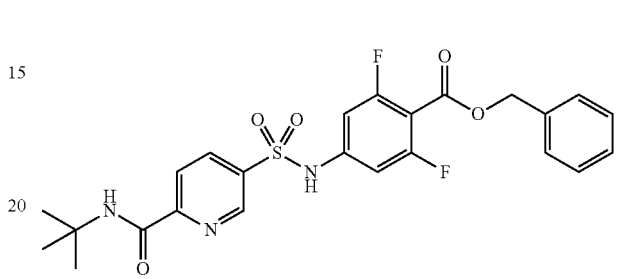

The title compound (749 mg, 61%) was obtained by subjecting 5-[({4-[(benzyloxy)carbonyl]-3,5-difluorophenyl}amino)sulfonyl]pyridine-2-benzoic acid (1.10 g, 2.45 mmol) to the same method as in (Step 2) of Example 11.

MS (ESI) m/z 504 (M+H)⁺

(Step 3) 4-[({6-[(tert-Butylamino)carbonyl]pyridin-3-yl}sulfonyl)amino]-2,6-difluorobenzoic Acid (M-71)

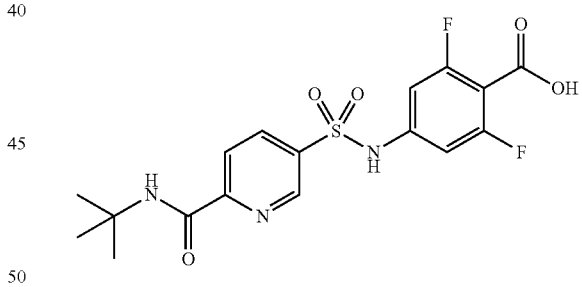

Benzyl 4-[({6-[(tert-butylamino)carbonyl]pyridin-3-yl}sulfonyl)amino]-2,6-difluorobenzoate (750 mg, 1.49 mmol) was dissolved in methanol (10 ml), and 10% palladium carbon (75.0 mg) was added thereto, followed by stirring at room temperature for 3 days in the presence of hydrogen gas (30 psi). The reaction solution was filtered, and the solvent was removed under reduced pressure. The residue was purified by reversed-phase HPLC (H2O/CH3CN system) to obtain the title compound (M-71) (110 mg, 18%).

¹H NMR (CD₃OD, 400 MHz): δ 8.91 (s, 1H), 8.29 (dd, J=8.4, 2.0 Hz, 1H), 8.10 (d, J=8.4 Hz, 1H), 6.82 (s, 1H), 6.75 (d, J=9.6 Hz, 1H), 1.35 (s, 9H).; MS (ESI) m/z 414 (M+H)⁺

Example 130

Synthesis of M-72

(Step 1) N-[4-(4-Chlorobutanoyl)phenyl]acetamide

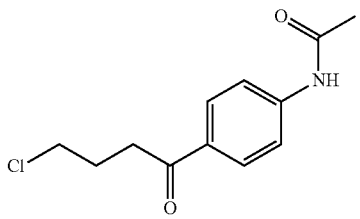 [SMILES: CC(=O)Nc1ccc(C(=O)CCCCl)cc1]

N-Phenylacetamide (10.0 g, 74.1 mmol) and 4-chlorobutanoyl chloride (18.8 g, 133 mmol) were dissolved in carbon disulfide (80 ml), and aluminum trichloride (26.9 g, 222 mmol) was gradually added thereto, followed by stirring at 60° C. for 5 hours. After cooling to room temperature, the reaction liquid was diluted with water. The precipitated solid was filtered, and purified by recrystallization from 95% ethanol to obtain the title compound (5.0 g, 28%) as a pink solid.

1H NMR (DMSO-$d_6$, 400 MHz): δ 10.28 (s, 1H), 7.93 (d, J=8.8 Hz, 2H), 7.71 (d, J=8.8 Hz, 2H), 3.70 (t, J=6.8 Hz, 2H), 3.12 (t, J=7.2 Hz, 2H), 2.08-2.02 (m, 5H).; MS (ESI) m/z 240 (M+H)$^+$ (Step 2) (4-Aminophenyl)(cyclopropyl)methanone

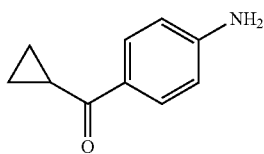 [SMILES: Nc1ccc(C(=O)C2CC2)cc1]

N-[4-(4-Chlorobutanoyl)phenyl]acetamide (5.00 g, 20.8 mmol) was suspended in ethanol (100 ml), and an 8 N aqueous sodium hydroxide solution (48 ml) was added thereto, followed by stirring at 95° C. for 1.5 hours. After cooling to room temperature, ethanol was removed under reduced pressure, and the obtained solid was filtered and dried to obtain the title compound (3.0 g, 90%) as a gray solid.

1H NMR (DMSO-$d_6$, 400 MHz): δ 7.77 (d, J=8.8 Hz, 2H), 6.57 (d, J=8.8 Hz, 2H), 6.02 (s, 2H), 2.72-2.69 (m, 1H), 0.90-0.87 (m, 4H).

(Step 3) 4-(Cyclopropylcarbonyl)benzenesulfonyl Chloride

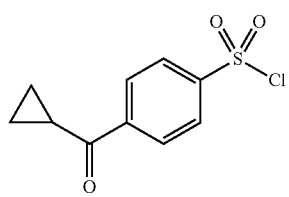 [SMILES: O=C(c1ccc(S(=O)(=O)Cl)cc1)C1CC1]

The title compound (2.60 g, 56%) was obtained by subjecting (4-aminophenyl)(cyclopropyl)methanone (3.00 g, 18.6 mmol) to the same method as in (Step 1) of Example 118. 1H NMR (DMSO-$d_6$, 400 MHz): δ 8.00 (d, J=8.0 Hz, 2H), 7.76 (d, J=8.0 Hz, 2H), 2.90-2.87 (m, 1H), 1.05-1.03 (m, 4H).; MS (ESI) m/z 225 (M+H)$^+$ (Step 4) Methyl 4-({[4-(Cyclopropylcarbonyl)phenyl]sulfonyl}amino)-2,6-difluorobenzoate

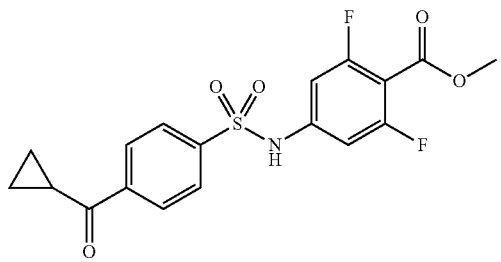 [SMILES: COC(=O)c1c(F)cc(NS(=O)(=O)c2ccc(C(=O)C3CC3)cc2)cc1F]

The title compound was obtained by subjecting 4-(cyclopropylcarbonyl)benzenesulfonyl chloride (2.60 g, 10.4 mmol) to the same method as in (Step 4) of Example 104. 1H NMR (DMSO-$d_6$, 400 MHz): δ 11.54 (s, 1H), 8.22 (d, J=8.4 Hz, 2H), 8.03 (d, J=8.4 Hz, 2H), 6.89 (d, J=10.0 Hz, 2H), 3.81 (s, 3H), 2.91-2.87 (m, 1H), 1.10-1.05 (m, 4H).

(Step 5) 4-({-[4-(Cyclopropylcarbonyl)phenyl]sulfonyl}amino)-2,6-difluorobenzoic Acid (M-72)

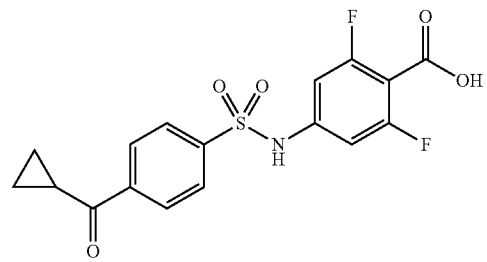 [SMILES: O=C(O)c1c(F)cc(NS(=O)(=O)c2ccc(C(=O)C3CC3)cc2)cc1F]

The title compound (M-72) (958 mg, 32% over two steps) was obtained by subjecting methyl 4-({-[4-(cyclopropylcarbonyl)phenyl]sulfonyl}amino)-2,6-difluorobenzoate to the same method as in (Step 5) of Example 104.

1H NMR (CD$_3$OD, 400 MHz): δ 8.20 (d, J=8.0 Hz, 2H), 8.03 (d, J=8.4 Hz, 2H), 6.85 (d, J=9.6 Hz, 2H), 2.87-2.81 (m, 1H), 1.21-1.20 (m, 4H).; MS (ESI) m/z 380 (M+H)$^+$

Example 131

Synthesis of M-73

(Step 1) 4-[({6-[(tert-Butylamino)carbonyl]pyridin-3-yl}sulfonyl)amino]-2-fluorobenzoic Acid (M-73)

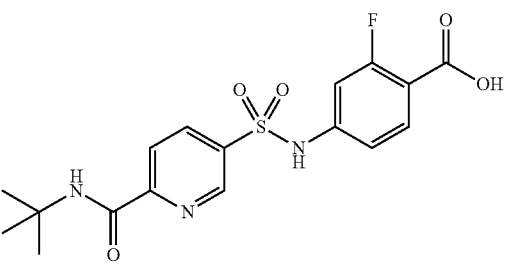 [SMILES: CC(C)(C)NC(=O)c1ccc(S(=O)(=O)Nc2ccc(C(=O)O)c(F)c2)cn1]

The title compound (M-73) was obtained by employing the same methods as in (Step 1), (Step 2), and (Step 3) of Example 129.

$^1$H NMR (CD$_3$OD, 400 MHz): δ 9.01 (s, 1H), 8.39 (d, J=10.8 Hz, 1H), 8.20 (d, J=10.8 Hz, 1H), 7.85-7.83 (m, 1H), 7.05-7.00 (m, 1H), 1.45 (s, 9H).; MS (ESI) m/z 396 (M+H)$^+$

Example 132

Synthesis of M-74

(Step 1) 4-({[3-Fluoro-4-(methoxycarbonyl)phenyl]amino}sulfonyl)-3-methylbenzoic Acid

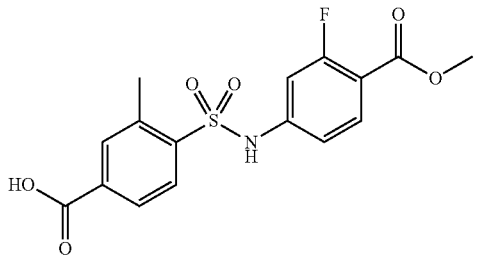

4-(Chlorosulfonyl)-3-methylbenzoic acid (2.71 g, 11.6 mmol) was dissolved in methylene chloride (300 ml), and methyl 4-amino-2-fluorobenzoate (4.17 g, 24.6 mmol) and pyridine (40 ml) were added thereto, followed by stirring at room temperature for 12 hours. The reaction liquid was concentrated under reduced pressure, and the residue was diluted with a saturated aqueous sodium hydrogen carbonate solution, followed by extraction with ethyl acetate (70 ml×2). The pH of the obtained aqueous layer was adjusted to lower than 5.0 with 6 N hydrochloric acid, and the precipitated solid was filtered and dried to obtain the title compound (610 mg, 14%) as a white solid.

MS (ESI) m/z 368 (M+H)$^+$ (Step 2) Methyl 2-Fluoro-4-({[4-(hydroxymethyl)-2-methylphenyl]sulfonyl}amino)benzoate

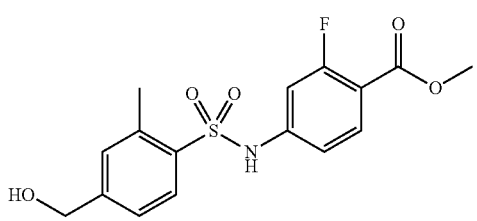

4-({[3-Fluoro-4-(methoxycarbonyl)phenyl]amino}sulfonyl)-3-methylbenzoic acid (13.0 g, 35.4 mmol) was dissolved in a 1 N borane/tetrahydrofuran solution (71 ml) at 0° C., followed by stirring at room temperature for 15 minutes. To the reaction solution, water (40 ml) was slowly added dropwise, and then the solvent was removed under reduced pressure. The precipitated solid was filtered, washed with water, and dried to obtain the title compound (11.0 g, 88%) as a white solid.

MS (ESI) m/z 354 (M+H)$^+$ (Step 3) Methyl 2-Fluoro-4-{[(4-formyl-2-methylphenyl)sulfonyl]amino}benzoate

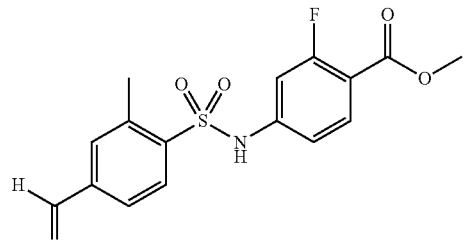

Methyl 2-fluoro-4-({[4-(hydroxymethyl)-2-methylphenyl]sulfonyl}amino)benzoate (2.80 g, 7.92 mmol) was dissolved in chloroform (35 ml), and manganese dioxide (2.90 g, 33.4 mmol) was added thereto, followed by stirring at 80° C. for 4 hours. After cooling to room temperature, the mixture was filtered, and the filtrate was concentrated under reduced pressure. The obtained residue was purified by silica gel column chromatography (petroleum ether/ethyl acetate=5:1) to obtain the title compound (1.77 g, 64%).

MS (ESI) m/z 352 (M+H)$^+$ (Step 4) Methyl 4-[({4-[(tert-Butylamino)methyl]-2-methylphenyl}sulfonyl)amino]-2-fluorobenzoate

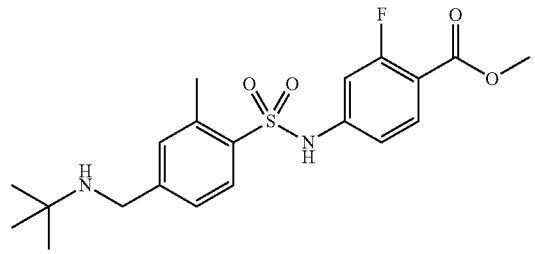 [SMILES: COC(=O)c1ccc(NS(=O)(=O)c2ccc(CNC(C)(C)C)cc2C)cc1F]

Methyl 2-fluoro-4-{[(4-formyl-2-methylphenyl)sulfonyl]amino}benzoate (1.00 g, 2.85 mmol) was dissolved in tetrahydrofuran (20 ml), and t-butylamine (416 mg, 5.69 mmol) was added thereto, followed by stirring at room temperature for 5 minutes. To the reaction liquid, sodium cyanoborohydride (718 mg, 11.4 mmol) was added, followed by stirring at room temperature for 12 hours. The reaction liquid was filtered, and the filtrate was concentrated under reduced pressure. The obtained residue was diluted with ethyl acetate (60 ml), washed with a saturated aqueous ammonium chloride solution (50 ml×2) and saturated aqueous sodium chloride, and dried over anhydrous sodium sulfate. Then, the solvent was removed under reduced pressure. The residue was purified by silica gel column chromatography (petroleum ether/ethyl acetate=3:1) to obtain the title compound (550 mg, 47%). MS (ESI) m/z 409 (M+H)$^+$ (Step 5) 4-[({4-[(tert-Butylamino)methyl]-2-methylphenyl}sulfonyl)amino]-2-fluorobenzoic Acid (M-74)

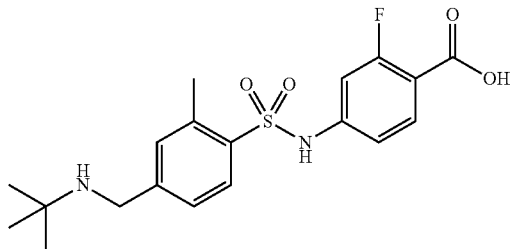 [SMILES: Cc1cc(CNC(C)(C)C)ccc1S(=O)(=O)Nc1ccc(C(=O)O)c(F)c1]

The title compound (M-74) (450 mg, 85%) was obtained as a white solid by subjecting methyl 4-[({4-[(tert-butylamino)methyl]-2-methylphenyl}sulfonyl)amino]-2-fluorobenzoate (550 mg, 1.35 mmol) to the same method as in (Step 5) of Example 104.

$^1$H NMR (400 MHz, CD$_3$OD): δ 8.05 (d, J=9.2 Hz, 1H), 7.68 (t, J=16.8 Hz, 1H), 7.43 (d, J=4.0 Hz, 2H), 6.84-6.78 (m, 2H), 4.10 (s, 2H), 2.61 (s, 3H), 1.33 (s, 9H).; MS (ESI) m/z 395 (M+H)$^+$

Example 133

Synthesis of M-75

(Step 1) 4-[({4-[(Cyclopentylamino)methyl]-2-methylphenyl}sulfonyl)amino]-2-fluorobenzoic Acid (M-75)

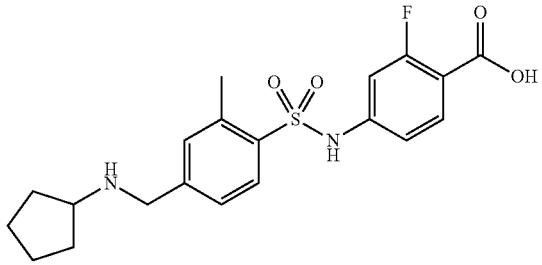 [SMILES: Cc1cc(CNC2CCCC2)ccc1S(=O)(=O)Nc1ccc(C(=O)O)c(F)c1]

The title compound (M-75) was obtained as a white solid by subjecting methyl 2-fluoro-4-{[(4-formyl-2-methylphenyl)sulfonyl]amino}benzoate <see (Step 3) of Example 132> and cyclopentylamine to the same methods as in (Step 4) and (Step 5) of Example 132.

$^1$H NMR (400 MHz, CD$_3$OD): δ 7.93 (d, J=8.4 Hz, 1H), 7.57-7.53 (m, 1H), 7.32-7.30 (m, 2H), 7.63-7.67 (m, 2H), 4.00 (s, 2H), 3.40-3.36 (m, 1H), 2.49 (s, 3H), 1.95-1.92 (m, 2H), 1.60-1.59 (m, 2H), 1.48-1.42 (m, 4H).; MS (ESI) m/z 407 (M+H)$^+$

Example 134

Synthesis of M-76

(Step 1) 1-(Phenylsulfonyl)-1H-pyrrole

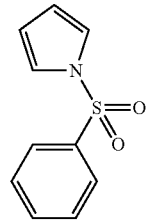 [SMILES: O=S(=O)(c1ccccc1)n1cccc1]

Pyrrole (3.48 ml, 50.0 mmol) was dissolved in tetrahydrofuran (anhydrous, 100 ml). After cooling to −70° C., 2.5 M n-butyllithium (52.5 mmol) was slowly added thereto over 20 minutes, followed by stirring for 10 minutes with the temperature kept at −70° C. After that, the temperature was raised to room temperature over 1 hour, and then the mixture was again cooled to −70° C. A solution (12 ml) of benzenesulfonyl chloride (6.41 ml, 50.0 mmol) in tetrahydrofuran was slowly added dropwise thereto, followed by stirring at room temperature for 12 hours. The reaction liquid was diluted with water (200 ml), followed by extraction with methylene chloride (100 ml×3). The organic layers were combined, washed with saturated aqueous sodium chloride, and then dried over anhydrous sodium sulfate. The solvent was removed under reduced pressure to obtain the title compound (9.8 g, 95%) as a cream-colored solid.

$^1$H NMR (CDCl$_3$, 400 MHz): δ 7.86-7.84 (m, 2H), 7.61-7.57 (m, 2H), 7.51-7.48 (m, 2H), 7.17-7.16 (m, 1H), 6.30-6.29 (m, 2H).

(Step 2) 1-(Phenylsulfonyl)-1H-pyrrole-2-sulfonyl Chloride

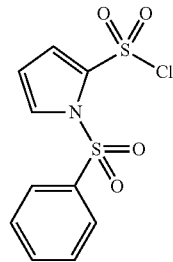 [SMILES: O=S(=O)(Cl)c1cccn1S(=O)(=O)c1ccccc1]

Diisopropylamine (12 g, 0.12 mol) was dissolved in dimethyl ether (500 ml). After cooling to −50° C., 2.5 M butyllithium (0.13 mol) and a solution (100 ml) of 1-(phenylsulfonyl)-1H-pyrrole (22.7 g, 0.110 mol) in dimethyl ether was slowly added dropwise, followed by stirring at 0° C. for 30 minutes. Subsequently, sulfur dioxide gas was bubbled into the reaction solution for 1 hour, and then the temperature was raised to room temperature. The solvent was removed under reduced pressure, and the residue was diluted with n-hexane (600 ml). The precipitated solid was filtered, washed with n-hexane, and dried. The obtained solid was dissolved in methylene chloride (500 ml), and N-chlorosuccinimide (18.6 g, 0.139 mol) was added thereto, followed by stirring at room temperature for 12 hours. The reaction liquid was washed with saturated aqueous sodium chloride, and dried over anhydrous sodium sulfate. The solvent was removed under reduced pressure, and the obtained residue was purified by silica gel column chromatography (petroleum ether/ethyl acetate=10:1 to 5:1) to obtain the title compound (25.0 g, 74%).

$^1$H NMR (CDCl$_3$, 400 MHz): δ 8.01 (d, J=7.6 Hz, 2H), 7.74-7.66 (m, 2H), 7.58-7.54 (m, 2H), 7.29-7.13 (m, 1H), 6.44-6.42 (m, 1H).

(Step 3) Methyl 2-Fluoro-4-({[1-(phenylsulfonyl)-1H-pyrrol-2-yl]sulfonyl}amino)benzoate

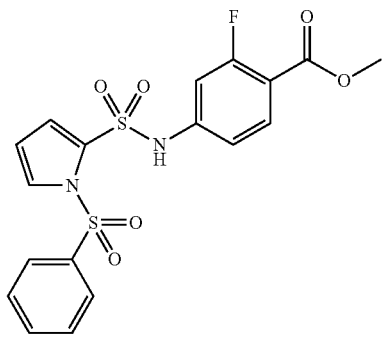 [SMILES: COC(=O)c1ccc(NS(=O)(=O)c2cccn2S(=O)(=O)c2ccccc2)cc1F]

The title compound (7.40 g, 68%) was obtained as a white solid by subjecting 1-(phenylsulfonyl)-1H-pyrrole-2-sulfonyl chloride (8.80 g, 29.0 mmol) to the same method as in (Step 4) of Example 104.

$^1$H NMR (DMSO-d$_6$, 400 MHz): δ 11.17 (s, 1H), 8.00 (d, J=7.6 Hz, 2H), 7.88 (d, J=2.0 Hz, 1H), 7.87-7.72 (m, 2H), 7.63-7.60 (m, 2H), 7.25-7.23 (m, 1H), 7.00 (dd, J=1.6 Hz, 1H), 6.87 (dd, J=1.2 Hz, 1H), 6.51-6.493 (m, 1H).

(Step 4) 2-Fluoro-4-[(1H-pyrrol-2-yl-sulfonyl) amino]benzoic Acid (M-76)

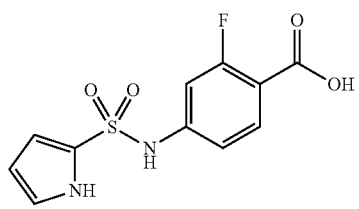 [SMILES: O=C(O)c1ccc(NS(=O)(=O)c2ccc[nH]2)cc1F]

The title compound (M-76) (5.36 g, 90%) was obtained as a white solid by subjecting methyl 2-fluoro-4-({[1-(phenylsulfonyl)-1H-pyrrol-2-yl]sulfonyl}amino)benzoate (9.20 g, 21.0 mmol) to the same method as in (Step 5) of Example 104.

$^1$H NMR (CD$_3$OD, 400 MHz): δ 7.72-7.68 (m, 1H), 6.90-6.83 (m, 3H), 6.65 (dd, J=4.0, 1.6 Hz, 1H), 6.08 (dd, J=3.6, 2.8 Hz, 1H).;

MS (ESI) m/z 285 (M+H)$^+$

Example 135

Synthesis of M-77

(Step 1) Methyl 3-Fluoro-5-[(2-furylsulfonyl) amino]pyridine-2-carboxylate

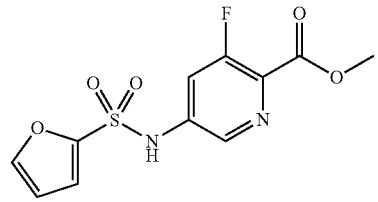 [SMILES: COC(=O)c1ncc(NS(=O)(=O)c2ccco2)cc1F]

The title compound (500 mg, 46%) was obtained as a white solid by subjecting methyl 5-amino-3-fluoropyridine-2-carboxylate (700 mg, 4.11 mmol) <see (Step 1) of Example 116> and furan-2-sulfonyl chloride (600 mg, 3.62 mmol) <see (Step 1) of Example 106> to the same method as in (Step 4) of Example 104.

$^1$H NMR (DMSO-d$_6$, 400 MHz): δ 11.8 (s, 1H), 8.30 (d, J=0.8 Hz, 1H), 8.02 (d, J=0.8 Hz, 1H), 7.51-7.48 (m, 2H), 6.71-6.70 (m, 2H), 3.84 (s, 3H).; MS (ESI) m/z 301 (M+H)$^+$ (Step 2) 3-Fluoro-5-[(2-furylsulfonyl)amino]pyridine-2-carboxylic Acid (M-77)

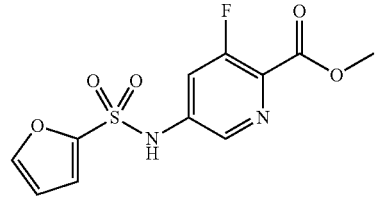 [SMILES: COC(=O)c1ncc(NS(=O)(=O)c2ccco2)cc1F]

The title compound (M-77) (360 mg, 75%) was obtained as a white solid by subjecting methyl 3-fluoro-5-[(2-furylsulfonyl)amino]pyridine-2-carboxylate (500 mg, 1.67 mmol) to the same method as in (Step 5) of Example 104.

$^1$H NMR (CD$_3$OD, 400 MHz): δ 8.16 (d, J=0.8 Hz, 1H), 7.66 (d, J=0.8 Hz, 1H), 7.48 (dd, J=11.6, 1.6 Hz, 1H), 7.18 (d, J=3.6 Hz, 1H), 6.50 (dd, J=3.6, 1.6 Hz, 1H).; MS (ESI) m/z 287 (M+H)$^+$

Example 136

Synthesis of M-78

(Step 1) Methyl 3-Fluoro-5-[(pyridin-4-yl-sulfonyl) amino]pyridine-2-carboxylate

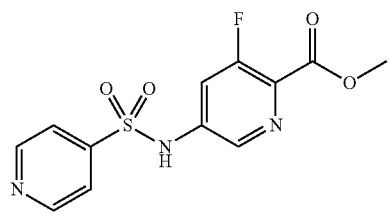 [SMILES: COC(=O)c1ncc(NS(=O)(=O)c2ccncc2)cc1F]

Methyl 5-bromo-3-fluoropyridine-2-carboxylate (2.00 g, 8.55 mmol) <see (Step 1) of Example 116> and pyridine-4-sulfonamide (2.00 g, 12.6 mmol) <see (Step 1) of Example 6> were dissolved in 1,4-dioxane (40 ml), and tris(dibenzylideneacetone)dipalladium(0) (391 mg, 0.427 mmol), Xantphos (204 mg, 0.353 mmol), and cesium carbonate (8.36 g, 25.7 mmol) were added thereto, followed by stirring at 110° C. for 12 hours in the presence of nitrogen gas. The reaction liquid was filtered, and the filtrate was diluted with water, followed by extraction with tetrahydrofuran (80 ml×5). The organic layers were combined, and the solvent was removed under reduced pressure. The obtained residue was purified by reversed-phase HPLC (H2O/CH3CN system) to obtain the title compound (263 mg, 9.9%).

MS (ESI) m/z 310 (M+H)+

(Step 2) 3-Fluoro-5-[(pyridin-4-yl-sulfonyl)amino]pyridine-2-carboxylic Acid (M-78)

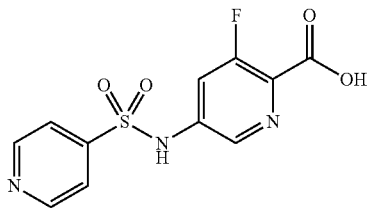 [SMILES: O=C(O)c1ncc(NS(=O)(=O)c2ccncc2)cc1F]

The title compound (M-78) (204 mg, 72%) was obtained by subjecting methyl 3-fluoro-5-[(pyridin-4-yl-sulfonyl)amino]pyridine-2-carboxylate (263 mg, 0.845 mmol) to the same method as in (Step 5) of Example 104.

$^1$H NMR (CD$_3$OD, 400 MHz): δ 8.84 (d, J=6.0 Hz, 2H), 8.24 (s, 1H), 7.87 (d, J=6.0 Hz, 2H), 7.65-7.61 (m, 1H).; MS (ESI) m/z 298 (M+H)+

The following group of compounds was synthesized by subjecting their corresponding intermediates among M-1 to M-78 to the same methods as in (Step 1) and (Step 2) of Example 39. Note that, in Examples 137 to 185 below, each compound was obtained as a TFA salt, unless otherwise noted.

Example 137

Synthesis of A-41 and B-41

(Step 1) N-{2,5-Difluoro-4-[(phenylsulfonyl)amino]benzoyl}-3-[5-(1-methyl-2,4-dioxo-1,4-dihydropyrido[3,4-d]pyrimidin-3(2H)-yl)pyridin-2-yl]-L-alanine (A-41)

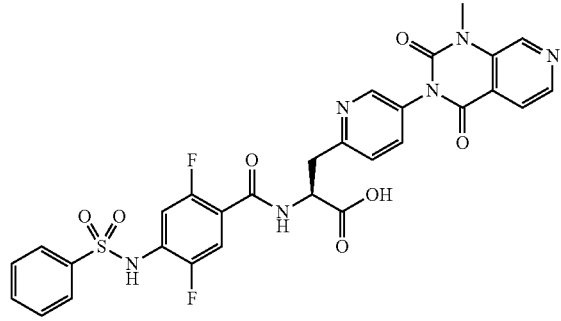 [SMILES: Cn1c(=O)n(-c2ccc(C[C@H](NC(=O)c3cc(F)c(NS(=O)(=O)c4ccccc4)cc3F)C(=O)O)nc2)c(=O)c2ccncc21]

$^1$H NMR (400 MHz, DMSO-d$_6$): δ 10.83 (s, 1H), 9.00 (d, J=3.9 Hz, 1H), 8.74 (s, 1H), 8.58 (d, J=4.9 Hz, 1H), 8.46 (s, 1H), 7.91 (s, 1H), 7.83 (s, 2H), 7.78-7.55 (m, 4H), 7.50-7.31 (m, 2H), 7.29-7.15 (m, 2H), 4.88 (s, 1H), 3.62 (s, 3H).; MS (ESI) m/z 637 (M+H)+

(Step 2) Cyclohexyl N-{2,5-Difluoro-4-[(phenylsulfonyl)amino]benzoyl}-3-[5-(1-methyl-2,4-dioxo-1,4-dihydropyrido[3,4-d]pyrimidin-3(2H)-yl)pyridin-2-yl]-L-alaninate (B-41)

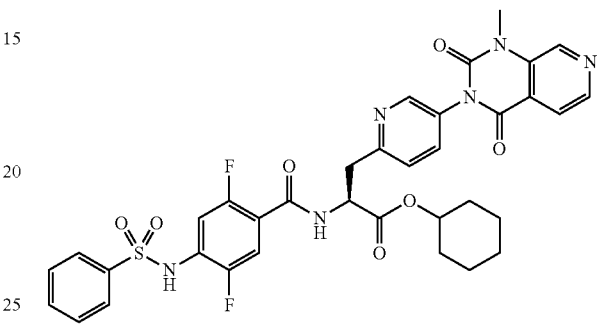

$^1$H NMR (400 MHz, DMSO-d$_6$): δ 10.84 (s, 1H), 9.00 (s, 1H), 8.85 (dd, J=7.4, 3.1 Hz, 1H), 8.58 (d, J=5.0 Hz, 1H), 8.45 (d, J=2.4 Hz, 1H), 7.91 (d, J=5.0 Hz, 1H), 7.83 (d, J=7.3 Hz, 2H), 7.73 (dd, J=8.2, 2.5 Hz, 1H), 7.70-7.64 (m, 1H), 7.63-7.55 (m, 2H), 7.45 (d, J=8.2 Hz, 1H), 7.35 (dd, J=10.4, 6.4 Hz, 1H), 7.21 (dd, J=11.2, 6.2 Hz, 1H), 4.91 (q, J=7.3 Hz, 1H), 4.75-4.60 (m, 1H), 3.62 (s, 3H), 1.84-1.11 (m, 10H).; MS (ESI) m/z 719 (M+H)+

Example 138

Synthesis of A-42 and Synthesis of B-42

(Step 1) N-{2,5-Difluoro-4-[(pyridin-2-yl-sulfonyl)amino]benzoyl}-3-[5-(1-methyl-2,4-dioxo-1,4-dihydropyrido[3,4-d]pyrimidin-3(2H)-yl)pyridin-2-yl]-L-alanine (A-42)

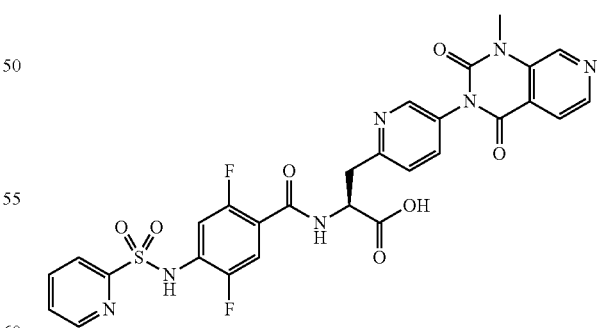

$^1$H NMR (400 MHz, DMSO-d$_6$): δ 10.97 (s, 1H), 9.00 (s, 1H), 8.74 (d, J=4.5 Hz, 2H), 8.58 (dd, J=4.9, 1.9 Hz, 1H), 8.46 (s, 1H), 8.12 (t, J=7.7 Hz, 1H), 8.02 (d, J=7.7 Hz, 1H), 7.91 (d, J=4.9 Hz, 1H), 7.80-7.65 (m, 2H), 7.46 (d, J=8.3 Hz, 1H), 7.41-7.29 (m, 2H), 4.95-4.82 (m, 1H), 3.62 (d, J=1.7 Hz, 3H).; MS (ESI) m/z 638 (M+H)+

223

(Step 2) Cyclohexyl N-{2,5-Difluoro-4-[(pyridin-2-yl-sulfonyl)amino]benzoyl}-3-[5-(1-methyl-2,4-dioxo-1,4-dihydropyrido[3,4-d]pyrimidin-3(2H)-yl)pyridin-2-yl]-L-alaninate (B-42)

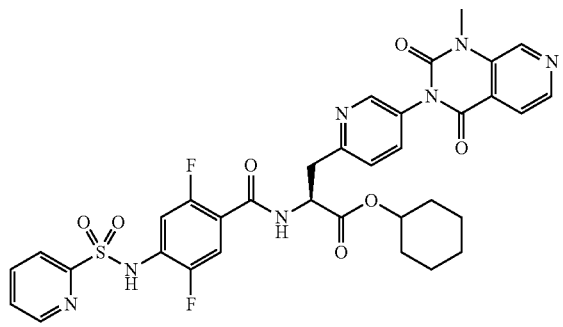 [SMILES: Cn1c(=O)n(-c2ccc(C[C@H](NC(=O)c3cc(F)c(NS(=O)(=O)c4ccccn4)cc3F)C(=O)OC3CCCCC3)nc2)c(=O)c2ccncc21]

$^1$H NMR (400 MHz, DMSO-d$_6$): δ 10.99 (s, 1H), 9.00 (s, 1H), 8.86 (dd, J=7.7, 3.3 Hz, 1H), 8.74 (ddd, J=4.7, 1.7, 0.9 Hz, 1H), 8.57 (d, J=4.9 Hz, 1H), 8.46 (d, J=1.8 Hz, 1H), 8.12 (td, J=7.8, 1.7 Hz, 1H), 8.02 (dt, J=7.9, 1.0 Hz, 1H), 7.91 (dd, J=5.0, 0.6 Hz, 1H), 7.76-7.66 (m, 2H), 7.46 (d, J=8.2 Hz, 1H), 7.41-7.32 (m, 2H), 4.92 (dd, J=13.7, 7.5 Hz, 1H), 4.74-4.63 (m, 1H), 3.62 (s, 3H), 1.79-1.17 (m, 10H).; MS (ESI) m/z 720 (M+H)$^+$

224

(Step 2) Cyclohexyl N-{2-Fluoro-4-[(2-furylsulfonyl)amino]benzoyl}-3-[5-(1-methyl-2,4-dioxo-1,4-dihydropyrido[3,4-d]pyrimidin-3(2H)-yl)pyridin-2-yl]-L-alaninate (B-43)

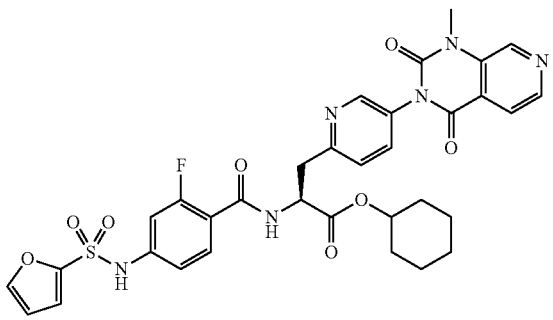 [SMILES: Cn1c(=O)n(-c2ccc(C[C@H](NC(=O)c3ccc(NS(=O)(=O)c4ccco4)cc3F)C(=O)OC3CCCCC3)nc2)c(=O)c2ccncc21]

$^1$H NMR (400 MHz, DMSO-d$_6$): δ 11.29 (s, 1H), 9.00 (s, 1H), 8.72 (dd, J=7.5, 3.7 Hz, 1H), 8.58 (d, J=4.9 Hz, 1H), 8.46 (d, J=2.4 Hz, 1H), 7.99 (dd, J=1.8, 0.9 Hz, 1H), 7.91 (d, J=4.9 Hz, 1H), 7.73 (dd, J=8.2, 2.5 Hz, 1H), 7.53 (t, J=8.4 Hz, 1H), 7.46 (d, J=8.2 Hz, 1H), 7.35 (dd, J=3.7, 0.8 Hz, 1H), 7.07-6.95 (m, 2H), 6.67 (dd, J=3.6, 1.8 Hz, 1H), 4.91 (q, J=7.1 Hz, 1H), 4.69 (m, 1H), 3.62 (s, 3H), 1.77-1.53 (m, 4H), 1.48-1.19 (m, 6H).; MS (ESI) m/z 691.4 (M+H)$^+$

Example 139

Synthesis of A-43 and Synthesis of B-43

(Step 1) N-{2-Fluoro-4-[(2-furylsulfonyl)amino]benzoyl}-3-[5-(1-methyl-2,4-dioxo-1,4-dihydropyrido[3,4-d]pyrimidin-3(2H)-yl)pyridin-2-yl]-L-alanine (A-43)

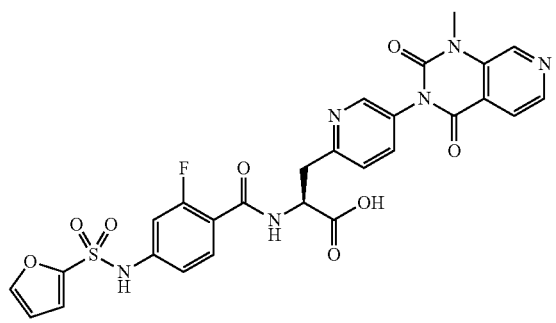

$^1$H NMR (400 MHz, DMSO-d$_6$): δ 11.28 (s, 1H), 9.00 (s, 1H), 8.67-8.54 (m, 2H), 8.46 (d, J=2.4 Hz, 1H), 8.02-7.93 (m, 1H), 7.91 (d, J=5.0 Hz, 1H), 7.73 (dd, J=8.2, 2.5 Hz, 1H), 7.53 (t, J=8.4 Hz, 1H), 7.46 (d, J=8.2 Hz, 1H), 7.34 (dd, J=3.5, 0.8 Hz, 1H), 7.09-6.91 (m, 2H), 6.66 (dd, J=3.6, 1.8 Hz, 1H), 4.88 (m, 1H), 3.62 (s, 3H), 3.35-3.23 (m, 2H).; MS (ESI) m/z 609.33 (M+H)$^+$

Example 140

Synthesis of A-44 and Synthesis of B-44

(Step 1) N-{2,5-Difluoro-4-[(2-furylsulfonyl)amino]benzoyl}-3-[5-(1-methyl-2,4-dioxo-1,4-dihydropyrido[3,4-d]pyrimidin-3(2H)-yl)pyridin-2-yl]-L-alanine (A-44)

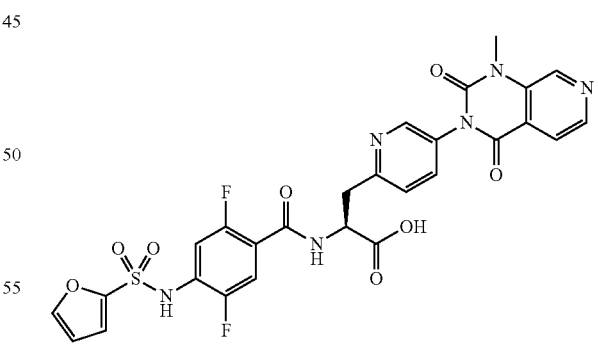

$^1$H NMR (400 MHz, DMSO-d$_6$): δ 11.14 (s, 1H), 9.00 (s, 1H), 8.79 (dd, J=7.9, 3.5 Hz, 1H), 8.58 (d, J=5.0 Hz, 1H), 8.48 (d, J=2.4 Hz, 1H), 8.02 (d, J=1.7 Hz, 1H), 7.99-7.83 (m, 1H), 7.76 (dd, J=8.2, 2.5 Hz, 1H), 7.49 (d, J=8.3 Hz, 1H), 7.40 (dd, J=10.2, 6.4 Hz, 1H), 7.28-7.16 (m, 2H), 6.68 (dd, J=3.6, 1.8 Hz, 1H), 4.99-4.82 (m, 1H), 3.62 (s, 3H), 3.42-3.25 (m, 2H).; MS (ESI) m/z 627.57 (M+H)$^+$ (Step 2) Cyclohexyl N-{2,5-Difluoro-4-[(2-furylsulfonyl)amino]benzoyl}-3-[5-(1-methyl-2,4-dioxo-1,4-dihydropyrido[3,4-d]pyrimidin-3(2H)-yl)pyridin-2-yl]-L-alaninate (B-44)

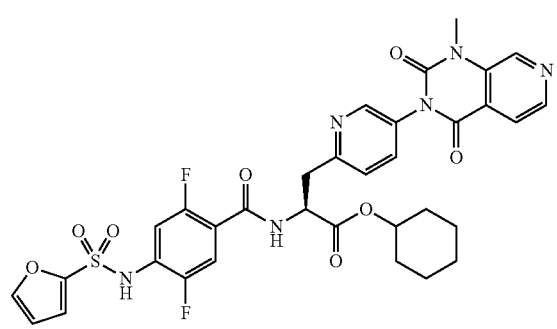

¹H NMR (400 MHz, DMSO-d₆): δ 11.15 (s, 1H), 9.00 (s, 1H), 8.91 (dd, J=7.6, 3.2 Hz, 1H), 8.58 (d, J=4.9 Hz, 1H), 8.46 (d, J=2.4 Hz, 1H), 8.05-7.99 (m, 1H), 7.91 (d, J=5.0 Hz, 1H), 7.74 (dd, J=8.2, 2.5 Hz, 1H), 7.47 (d, J=8.2 Hz, 1H), 7.40 (dd, J=10.1, 6.3 Hz, 1H), 7.28-7.19 (m, 2H), 6.68 (dd, J=3.5, 1.8 Hz, 1H), 4.93 (td, J=7.7, 6.0 Hz, 1H), 4.75-4.65 (m, 1H), 3.62 (s, 3H), 3.37-3.26 (m, 2H), 1.77-1.54 (m, 4H), 1.49-1.18 (m, 6H).; MS (ESI) m/z 709.42 (M+H)⁺

(Step 2) Cyclohexyl N-(4-{[(4-Acetylphenyl)sulfonyl]amino}-2,5-difluorobenzoyl)-3-[5-(1-methyl-2,4-dioxo-1,4-dihydropyrido[3,4-d]pyrimidin-3(2H)-yl)pyridin-2-yl]-L-alaninate (B-45)

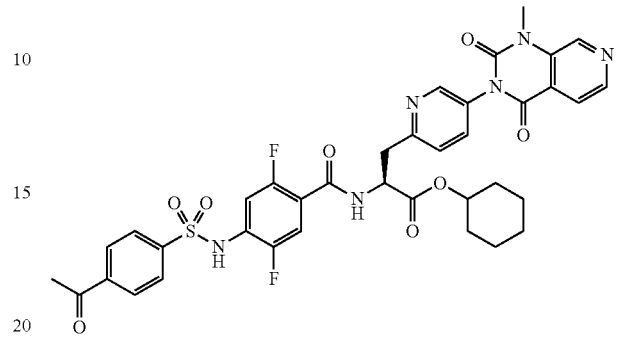

¹H NMR (400 MHz, DMSO-d₆): δ 11.03 (s, 1H), 9.00 (s, 1H), 8.86 (dd, J=7.6, 3.3 Hz, 1H), 8.58 (d, J=5.0 Hz, 1H), 8.47 (d, J=2.4 Hz, 1H), 8.17-8.09 (m, 2H), 8.00-7.93 (m, 2H), 7.91 (d, J=5.0 Hz, 1H), 7.75 (dd, J=8.2, 2.5 Hz, 1H), 7.48 (d, J=8.3 Hz, 1H), 7.37 (dd, J=10.3, 6.3 Hz, 1H), 7.25 (dd, J=11.1, 6.2 Hz, 1H), 4.97-4.87 (m, 1H), 4.73-4.64 (m, 1H), 3.62 (s, 3H), 3.40-3.25 (m, 2H), 2.61 (s, 3H), 1.79-1.53 (m, 4H), 1.46-1.19 (m, 6H).; MS (ESI) m/z 761.58 (M+H)⁺

Example 141

Synthesis of A-45 and Synthesis of B-45

(Step 1) N-(4-{[(4-Acetylphenyl)sulfonyl]amine}-2,5-difluorobenzoyl)-3-[5-(1-methyl-2,4-dioxo-1,4-dihydropyrido[3,4-d]pyrimidin-3(2H)-yl)pyridin-2-yl]-L-alanine (A-45)

Example 142

Synthesis of A-46 and Synthesis of B-46

(Step 1) N-{2-Fluoro-4-[(pyridin-2-yl-sulfonyl)amino]benzoyl}-3-[5-(1-methyl-2,4-dioxo-1,4-dihydropyrido[3,4-d]pyrimidin-3(2H)-yl)pyridin-2-yl]-L-alanine (A-46)

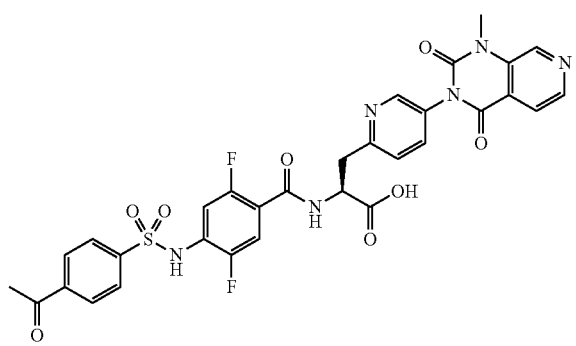 [SMILES: CC(=O)c1ccc(S(=O)(=O)Nc2cc(F)c(C(=O)N[C@@H](Cc3ccc(-n4c(=O)c5ccncc5n(C)c4=O)cn3)C(=O)O)cc2F)cc1]

¹H NMR (400 MHz, DMSO-d₆): δ 11.03 (s, 1H), 9.00 (s, 1H), 8.75 (dd, J=7.9, 3.7 Hz, 1H), 8.58 (d, J=5.0 Hz, 1H), 8.48 (d, J=2.4 Hz, 1H), 8.17-8.08 (m, 2H), 7.99-7.93 (m, 2H), 7.91 (d, J=4.8 Hz, 1H), 7.76 (dd, J=8.2, 2.5 Hz, 1H), 7.48 (d, J=8.3 Hz, 1H), 7.37 (dd, J=10.3, 6.4 Hz, 1H), 7.24 (dd, J=11.2, 6.2 Hz, 1H), 4.94-4.84 (m, 1H), 3.62 (s, 3H), 3.43-3.23 (m, 2H), 2.61 (s, 3H).; MS (ESI) m/z 679.34 (M+H)⁺

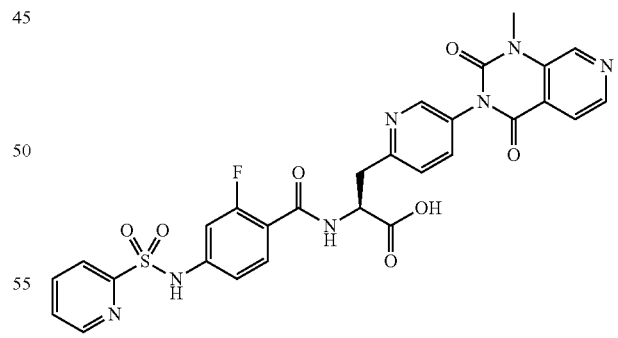

¹H NMR (400 MHz, DMSO-d₆): δ 11.15 (s, 1H), 9.00 (s, 1H), 8.75-8.70 (m, 1H), 8.58 (d, J=4.9 Hz, 1H), 8.54 (dd, J=7.8, 4.2 Hz, 1H), 8.45 (dd, J=2.5, 0.7 Hz, 1H), 8.14-8.04 (m, 2H), 7.91 (dd, J=5.0, 0.7 Hz, 1H), 7.72 (dd, J=8.2, 2.5 Hz, 1H), 7.67 (ddd, J=7.0, 4.7, 1.7 Hz, 1H), 7.51-7.42 (m, 2H), 7.06-6.99 (m, 2H), 4.90-4.82 (m, 1H), 3.62 (s, 3H), 3.31-3.22 (m, 2H).;

MS (ESI) m/z 620.35 (M+H)⁺

(Step 2) Cyclohexyl N-{2-Fluoro-4-[(pyridin-2-yl-sulfonyl)amino]benzoyl}-3-[5-(1-methyl-2,4-dioxo-1,4-dihydropyrido[3,4-d]pyrimidin-3(2H)-yl)pyridin-2-yl]-L-alaninate (B-46)

(Step 2) Cyclohexyl N-(2,6-Difluoro-4-{[(2-methoxyphenyl)sulfonyl]amino}benzoyl)-4-(1-methyl-2,4-dioxo-1,4-dihydropyrido[3,4-d]pyrimidin-3(2H)-yl)-L-phenylalaninate (B-47)

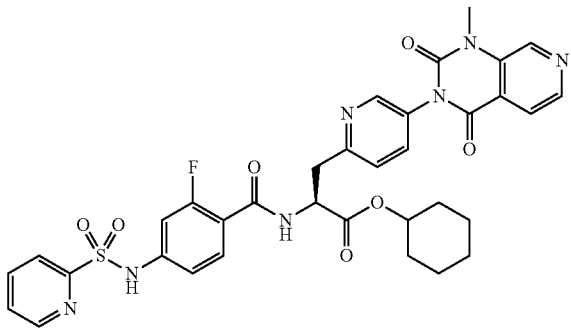 [SMILES: Cn1c(=O)n(-c2ccc(C[C@H](NC(=O)c3ccc(NS(=O)(=O)c4ccccn4)cc3F)C(=O)OC3CCCCC3)nc2)c(=O)c2ccncc21]

$^1$H NMR (400 MHz, DMSO-d$_6$): δ 11.16 (s, 1H), 9.00 (s, 1H), 8.74-8.70 (m, 1H), 8.67 (dd, J=7.6, 3.8 Hz, 1H), 8.58 (d, J=4.9 Hz, 1H), 8.45 (d, J=2.4 Hz, 1H), 8.16-8.05 (m, 2H), 7.91 (d, J=5.0 Hz, 1H), 7.73 (dd, J=8.2, 2.5 Hz, 1H), 7.68 (ddd, J=6.7, 4.7, 1.8 Hz, 1H), 7.53-7.42 (m, 2H), 7.07-7.00 (m, 2H), 4.94-4.84 (m, 1H), 4.71-4.65 (m, 2H), 3.62 (s, 3H), 1.76-1.51 (m, 4H), 1.48-1.17 (m, 6H).; MS (ESI) m/z 702.46 (M+H)$^+$ $^1$H NMR (400 MHz, DMSO-d$_6$): δ 10.80 (s, 1H), 9.14 (d, J=7.4 Hz, 1H), 8.97 (s, 1H), 8.55 (d, J=5.0 Hz, 1H), 7.96-7.81 (m, 2H), 7.63 (ddd, J=8.8, 7.4, 1.7 Hz, 1H), 7.41-7.30 (m, 2H), 7.28-7.17 (m, 3H), 7.11 (td, J=7.6, 1.0 Hz, 1H), 6.75 (d, J=9.3 Hz, 2H), 4.72-4.63 (m, 1H), 4.60-4.51 (m, 1H), 3.88 (s, 3H), 3.60 (s, 3H), 3.19-2.94 (m, 2H), 1.84-1.56 (m, 4H), 1.52-1.15 (m, 6H).; MS (ESI) m/z 748.52 (M+H)$^+$ Example 143

Synthesis of A-47 and Synthesis of B-47

Example 144

Synthesis of A-48 and Synthesis of B-48

(Step 1) N-(2,6-Difluoro-4-{[(2-methoxyphenyl)sulfonyl]amino}benzoyl)-4-(1-methyl-2,4-dioxo-1,4-dihydropyrido[3,4-d]pyrimidin-3(2H)-yl)-L-phenylalanine (A-47), Obtained as a Free Form (Step 1) N-(2-Fluoro-4-{[(3-oxo-2,3-dihydro-1H-inden-5-yl)sulfonyl]amino}benzoyl)-3-[5-(1-methyl-2,4-dioxo-1,4-dihydropyrido[3,4-d]pyrimidin-3(2H)-yl)pyridin-2-yl]-L-alanine (A-48)

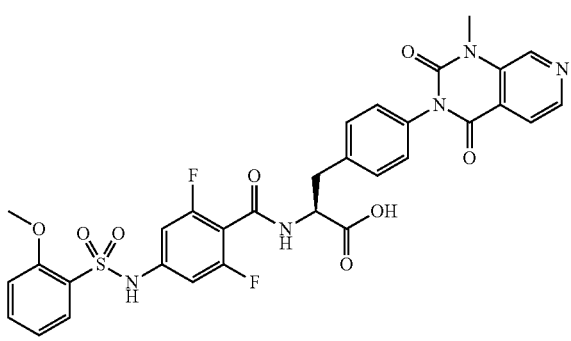 [SMILES: COc1ccccc1S(=O)(=O)Nc1cc(F)c(C(=O)N[C@@H](Cc2ccc(-n3c(=O)c4ccncc4n(C)c3=O)cc2)C(=O)O)c(F)c1]

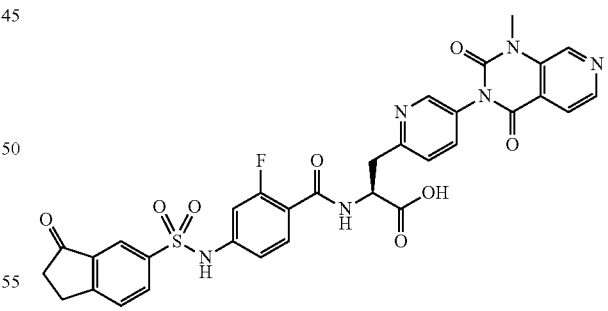

$^1$H NMR (400 MHz, DMSO-d$_6$): δ 10.78 (s, 1H), 9.03 (d, J=7.8 Hz, 1H), 8.97 (s, 1H), 8.56 (d, J=4.9 Hz, 1H), 7.94-7.83 (m, 2H), 7.63 (ddd, J=8.6, 7.5, 1.8 Hz, 1H), 7.39-7.28 (m, 2H), 7.27-7.16 (m, 3H), 7.11 (t, J=7.6 Hz, 1H), 6.74 (d, J=9.2 Hz, 2H), 4.63-4.49 (m, 1H), 3.88 (s, 3H), 3.60 (s, 3H), 3.22-2.92 (m, 2H).; MS (ESI) m/z 666.38 (M+H)$^+$ $^1$H NMR (400 MHz, DMSO-d$_6$): δ 11.02 (s, 1H), 9.00 (s, 1H), 8.61-8.52 (m, 2H), 8.46 (d, J=2.5 Hz, 1H), 8.07 (dd, J=8.0, 1.9 Hz, 1H), 7.99 (d, J=1.8 Hz, 1H), 7.91 (d, J=5.0 Hz, 1H), 7.79 (d, J=8.1 Hz, 1H), 7.74 (dd, J=8.2, 2.5 Hz, 1H), 7.53-7.42 (m, 2H), 7.04-6.91 (m, 2H), 4.91-4.80 (m, 1H), 3.62 (s, 3H), 3.31 (ddd, J=31.5, 14.7, 6.9 Hz, 2H), 3.19-3.10 (m, 2H), 2.72-2.64 (m, 2H).; MS (ESI) m/z 673.41 (M+H)$^+$ (Step 2) Cyclohexyl N-(2-fluoro-4-{[(3-oxo-2,3-dihydro-1H-inden-5-yl)sulfonyl]amino}benzoyl)-3-[5-(1-methyl-2,4-dioxo-1,4-dihydropyrido[3,4-d]pyrimidin-3(2H)-yl)pyridin-2-yl]-L-alaninate (B-48)

(Step 2) Cyclohexyl N-(2,6-difluoro-4-{[(2-methoxyphenyl)sulfonyl]amino}benzoyl)-3-[5-(1-methyl-2,4-dioxo-1,4-dihydropyrido[3,4-d]pyrimidin-3(2H)-yl)pyridin-2-yl]-L-alaninate (B-49)

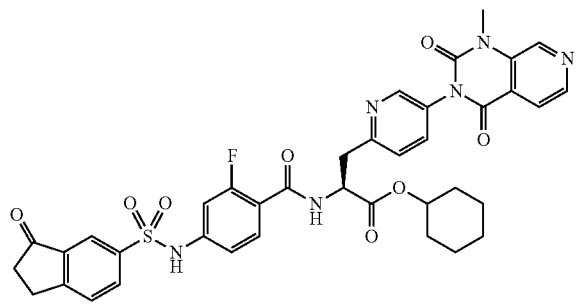 [SMILES: Cn1c(=O)n(-c2ccc(C[C@H](NC(=O)c3ccc(NS(=O)(=O)c4ccc5c(c4)C(=O)CC5)cc3F)C(=O)OC3CCCCC3)nc2)c(=O)c2ccncc21]

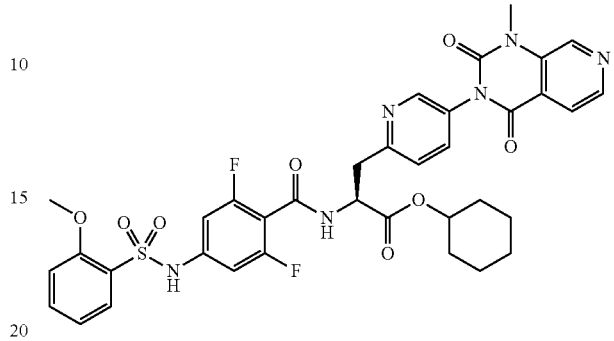

$^1$H NMR (400 MHz, DMSO-d$_6$): δ 11.03 (s, 1H), 9.00 (s, 1H), 8.69 (dd, J=7.6, 3.6 Hz, 1H), 8.58 (d, J=5.0 Hz, 1H), 8.47 (d, J=2.4 Hz, 1H), 8.08 (dd, J=8.1, 1.9 Hz, 1H), 7.99 (d, J=1.8 Hz, 1H), 7.92 (d, J=5.0 Hz, 1H), 7.80 (d, J=8.1 Hz, 1H), 7.76 (dd, J=8.2, 2.5 Hz, 1H), 7.53-7.44 (m, 2H), 7.05-6.92 (m, 2H), 4.94-4.84 (m, 1H), 4.72-4.63 (m, 1H), 3.62 (s, 3H), 3.31 (dd, J=6.8, 3.4 Hz, 2H), 3.15 (t, J=5.8 Hz, 2H), 2.68 (dd, J=7.9, 3.9 Hz, 2H), 1.75-1.52 (m, 4H), 1.47-1.18 (m, 6H).;

MS (ESI) m/z 755.54 (M+H)$^+$ $^1$H NMR (400 MHz, DMSO-d$_6$): δ 10.80 (s, 1H), 9.11 (d, J=7.6 Hz, 1H), 9.00 (s, 1H), 8.58 (d, J=5.0 Hz, 1H), 8.44 (d, J=2.4 Hz, 1H), 7.95-7.85 (m, 2H), 7.76-7.59 (m, 2H), 7.43 (d, J=8.2 Hz, 1H), 7.21 (d, J=8.4 Hz, 1H), 7.16-7.07 (m, 1H), 6.75 (d, J=9.3 Hz, 2H), 4.91-4.80 (m, 1H), 4.72-4.63 (m, 1H), 3.88 (s, 3H), 3.62 (s, 3H), 3.32-3.12 (m, 2H), 1.83-1.53 (m, 4H), 1.53-1.13 (m, 6H).; MS (ESI) m/z 749.47 (M+H)$^+$

Example 145

Synthesis of A-49 and Synthesis of B-49

(Step 1) N-(2,6-Difluoro-4-{[(2-methoxyphenyl)sulfonyl]amino}benzoyl)-3-[5-(1-methyl-2,4-dioxo-1,4-dihydropyrido[3,4-d]pyrimidin-3(2H)-yl)pyridin-2-yl]-L-alanine (A-49)

Example 146

Synthesis of A-50 and Synthesis of B-50

(Step 1) N-(4-{[(2-Ethoxyphenyl)sulfonyl]amino}-2,6-difluorobenzoyl)-3-[5-(1-methyl-2,4-dioxo-1,4-dihydropyrido[3,4-d]pyrimidin-3(2H)-yl)pyridin-2-yl]-L-alanine (A-50)

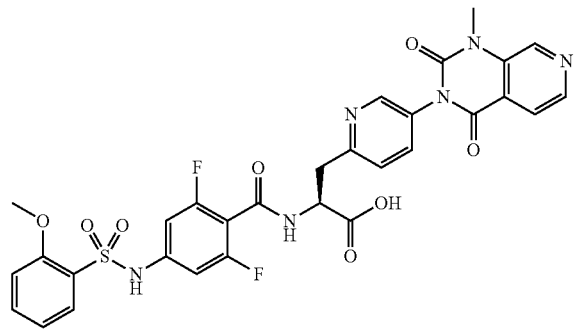 [SMILES: COc1ccccc1S(=O)(=O)Nc1cc(F)c(C(=O)N[C@@H](Cc2ccc(-n3c(=O)c4ccncc4n(C)c3=O)cn2)C(=O)O)c(F)c1]

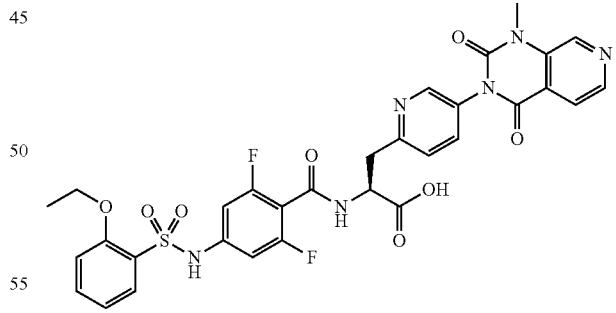

$^1$H NMR (400 MHz, DMSO-d$_6$): δ 10.78 (s, 1H), 9.00 (s, 1H), 8.98 (s, 1H), 8.58 (d, J=4.9 Hz, 1H), 8.47-8.41 (m, 2H), 7.95-7.84 (m, 2H), 7.75-7.58 (m, 2H), 7.40 (d, J=8.2 Hz, 1H), 7.20 (dd, J=8.6, 1.0 Hz, 1H), 7.11 (td, J=7.6, 0.9 Hz, 1H), 6.73 (d, J=9.3 Hz, 2H), 4.88-4.78 (m, 1H), 3.88 (s, 3H), 3.62 (s, 3H), 3.35-3.09 (m, 2H).; MS (ESI) m/z 667.36 (M+H)$^+$ $^1$H NMR (400 MHz, DMSO-d$_6$): δ 10.69 (s, 1H), 9.03-8.95 (m, 2H), 8.58 (d, J=4.9 Hz, 1H), 8.44 (d, J=2.5 Hz, 1H), 7.95-7.86 (m, 2H), 7.71 (dd, J=8.2, 2.5 Hz, 1H), 7.61 (ddd, J=8.7, 7.4, 1.8 Hz, 1H), 7.41 (d, J=8.3 Hz, 1H), 7.21 (d, J=8.4 Hz, 1H), 7.14-7.05 (m, 1H), 6.76-6.66 (m, 2H), 4.90-4.76 (m, 1H), 4.21 (q, J=7.0 Hz, 2H), 3.62 (s, 3H), 3.35-3.09 (m, 2H), 1.31 (t, J=7.0 Hz, 3H).; MS (ESI) m/z 681.41 (M+H)$^+$ (Step 2) Cyclohexyl N-(4-{[(2-Ethoxyphenyl)sulfonyl]amino}-2,6-difluorobenzoyl)-3-[5-(1-methyl-2,4-dioxo-1,4-dihydropyrido[3,4-d]pyrimidin-3(2H)-yl)pyridin-2-yl]-L-alaninate (B-50)

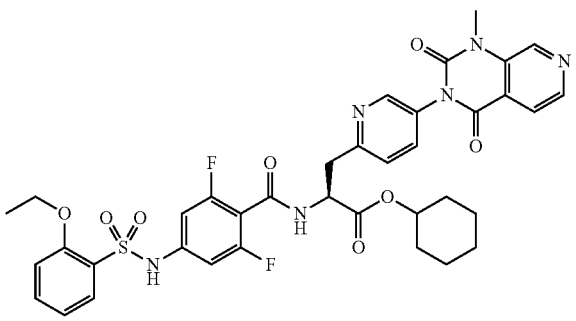

¹H NMR (400 MHz, DMSO-d₆): δ 10.71 (s, 1H), 9.10 (d, J=7.6 Hz, 1H), 9.00 (s, 1H), 8.58 (d, J=4.9 Hz, 1H), 8.44 (d, J=2.4 Hz, 1H), 7.95-7.87 (m, 2H), 7.71 (dd, J=8.2, 2.4 Hz, 1H), 7.61 (ddd, J=8.8, 7.4, 1.7 Hz, 1H), 7.42 (d, J=8.3 Hz, 1H), 7.21 (d, J=8.4 Hz, 1H), 7.14-7.05 (m, 1H), 6.73 (d, J=9.4 Hz, 2H), 4.90-4.79 (m, 1H), 4.73-4.62 (m, 1H), 4.21 (q, J=7.0 Hz, 2H), 3.62 (s, 3H), 3.31-3.13 (m, 2H), 1.79-1.55 (m, 4H), 1.52-1.16 (m, 9H).; MS (ESI) m/z 763.51 (M+H)⁺

Example 147

Synthesis of A-51 and Synthesis of B-51

(Step 1) N-{2-Fluoro-4-[(2-furylsulfonyl)amino]benzoyl}-4-(6-methoxy-1-methyl-2,4-dioxo-1,4-dihydropyrido[3,4-d]pyrimidin-3(2H)-yl)-L-phenylalanine (A-51), Obtained as a Free Form

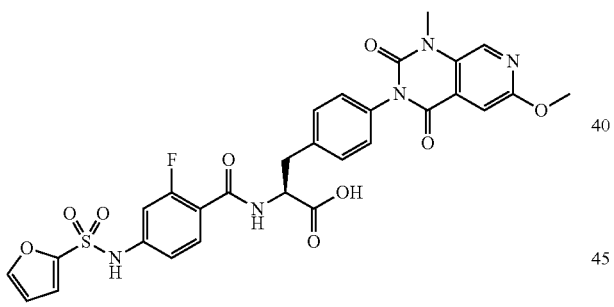

¹H NMR (400 MHz, DMSO-d₆): δ 12.86 (s, 1H), 11.25 (s, 1H), 8.54 (d, J=0.8 Hz, 1H), 8.43 (dd, J=7.7, 2.8 Hz, 1H), 7.98 (dd, J=1.8, 0.9 Hz, 1H), 7.49-7.31 (m, 4H), 7.27 (d, J=0.7 Hz, 1H), 7.24-7.17 (m, 2H), 7.06-6.92 (m, 2H), 6.67 (dd, J=3.6, 1.8 Hz, 1H), 4.67-4.57 (m, 1H), 3.92 (s, 3H), 3.55 (s, 3H), 3.26-3.03 (m, 2H).; MS (ESI) m/z 638.33 (M+H)⁺

(Step 2) Cyclohexyl N-{2-Fluoro-4-[(2-furylsulfonyl)amino]benzoyl}-4-(6-methoxy-1-methyl-2,4-dioxo-1,4-dihydropyrido[3,4-d]pyrimidin-3(2H)-yl)-L-phenylalaninate (B-51)

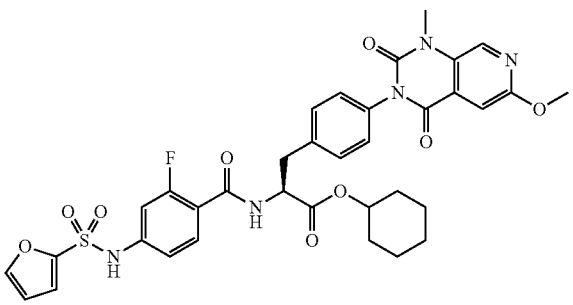 [SMILES: COc1cc2c(=O)n(-c3ccc(C[C@H](NC(=O)c4ccc(NS(=O)(=O)c5ccco5)cc4F)C(=O)OC4CCCCC4)cc3)c(=O)n(C)c2cn1]

¹H NMR (400 MHz, DMSO-d₆): δ 11.26 (s, 1H), 8.61-8.51 (m, 2H), 7.97 (s, 1H), 7.46-7.30 (m, 4H), 7.27 (d, J=0.8 Hz, 1H), 7.25-7.18 (m, 2H), 7.04-6.92 (m, 2H), 6.69-6.63 (m, 1H), 4.74-4.66 (m, 1H), 4.66-4.56 (m, 1H), 3.92 (s, 3H), 3.55 (s, 3H), 3.20-3.03 (m, 2H), 1.84-1.56 (m, 4H), 1.52-1.17 (m, 6H).;

MS (ESI) m/z 720.44 (M+H)⁺

Example 148

Synthesis of A-52 and Synthesis of B-52

(Step 1) N-[2,6-Difluoro-4-({[4-(2-furyl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alanine (A-52)

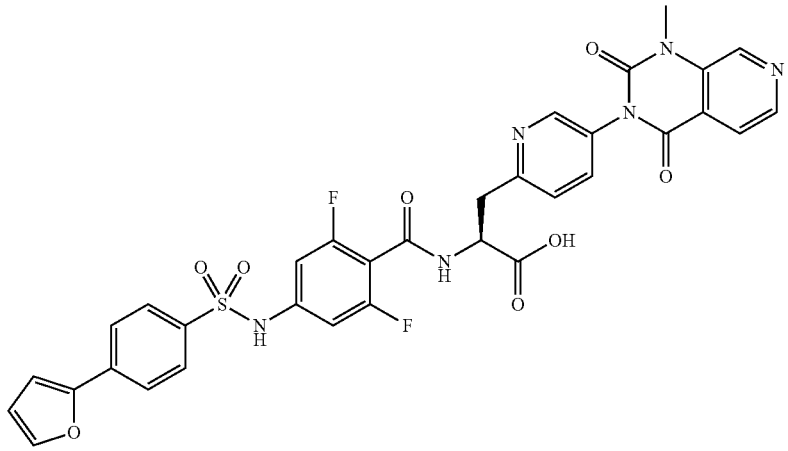 [SMILES: Cn1c(=O)n(-c2ccc(C[C@H](NC(=O)c3c(F)cc(NS(=O)(=O)c4ccc(-c5ccco5)cc4)cc3F)C(=O)O)nc2)c(=O)c2ccncc21]

¹H NMR (400 MHz, DMSO-d₆): δ 11.06 (s, 1H), 9.07-8.94 (m, 2H), 8.58 (d, J=5.0 Hz, 1H), 8.45 (d, J=2.5 Hz, 1H), 7.96-7.80 (m, 6H), 7.72 (dd, J=8.2, 2.5 Hz, 1H), 7.41 (d, J=8.2 Hz, 1H), 7.17 (d, J=3.5 Hz, 1H), 6.78 (d, J=8.9 Hz, 2H), 6.66 (dd, J=3.5, 1.8 Hz, 1H), 4.93-4.75 (m, 1H), 3.62 (s, 3H), 3.35-3.09 (m, 2H).; MS (ESI) m/z 703.36 (M+H)⁺

(Step 2) Cyclohexyl N-[2,6-Difluoro-4-({[4-(2-furyl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alaninate (B-52)

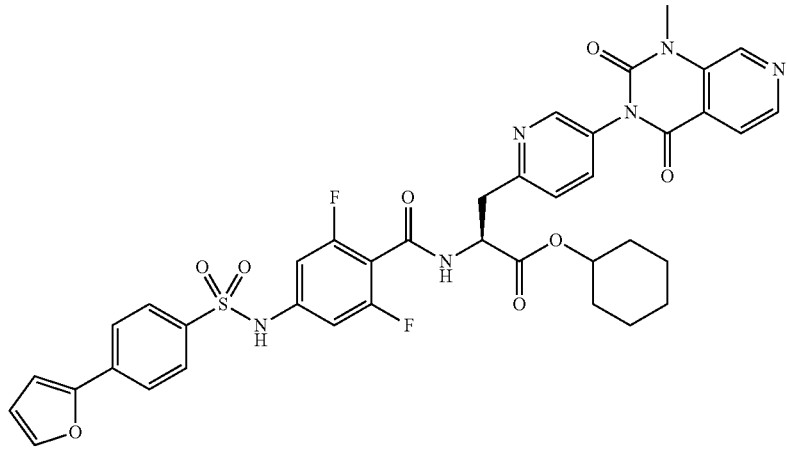 [SMILES: Cn1c(=O)n(-c2ccc(C[C@H](NC(=O)c3c(F)cc(NS(=O)(=O)c4ccc(-c5ccco5)cc4)cc3F)C(=O)OC3CCCCC3)nc2)c(=O)c2ccncc21]

¹H NMR (400 MHz, DMSO-d₅): δ 11.08 (s, 1H), 9.10 (d, J=7.6 Hz, 1H), 9.00 (s, 1H), 8.58 (d, J=5.0 Hz, 1H), 8.43 (d, J=2.5 Hz, 1H), 8.01-7.79 (m, 6H), 7.70 (dd, J=8.2, 2.5 Hz, 1H), 7.42 (d, J=8.3 Hz, 1H), 7.17 (d, J=3.4 Hz, 1H), 6.80 (d, J=8.9 Hz, 2H), 6.66 (dd, J=3.4, 1.8 Hz, 1H), 4.98-4.79 (m, 1H), 4.72-4.61 (m, 1H), 3.61 (s, 3H), 3.31-3.13 (m, 2H), 1.80-1.54 (m, 4H), 1.51-1.16 (m, 6H).; MS (ESI) m/z 785.54 (M+H)⁺

Example 149

Synthesis of A-53 and Synthesis of B-53

(Step 1) N-{2,5-Difluoro-4-[(2-furylsulfonyl)amino]benzoyl}-4-(1-methyl-2,4-dioxo-1,4-dihydropyrido[3,4-d]pyrimidin-3(2H)-yl)-L-phenylalanine (A-53), Obtained as a Free Form

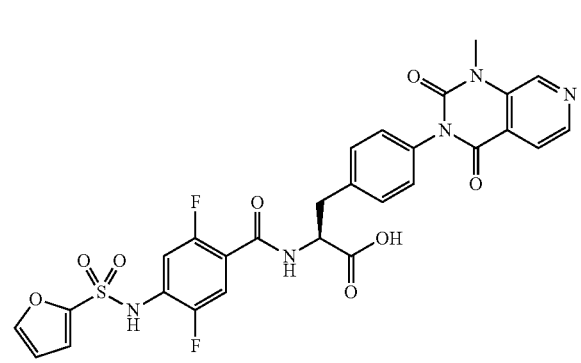

¹H NMR (400 MHz, DMSO-d₆): δ 11.12 (s, 1H), 8.97 (s, 1H), 8.67 (dd, J=7.9, 2.4 Hz, 1H), 8.55 (d, J=4.9 Hz, 1H), 8.05-7.99 (m, 1H), 7.90-7.87 (m, 1H), 7.41-7.36 (m, 2H), 7.33 (dd, J=10.1, 6.3 Hz, 1H), 7.25-7.18 (m, 4H), 6.68 (dd, J=3.6, 1.8 Hz, 1H), 4.69-4.60 (m, 1H), 3.60 (s, 3H), 3.27-3.03 (m, 2H).;

MS (ESI) m/z 626.33 (M+H)⁺

(Step 2) Cyclohexyl N-{2,5-Difluoro-4-[(2-furylsulfonyl)amino]benzoyl}-4-(1-methyl-2,4-dioxo-1,4-dihydropyrido[3,4-d]pyrimidin-3(2H)-yl)-L-phenylalaninate (B-53)

¹H NMR (400 MHz, DMSO-d₆): δ 11.12 (s, 1H), 8.97 (s, 1H), 8.83 (dd, J=7.6, 1.9 Hz, 1H), 8.55 (d, J=5.0 Hz, 1H), 8.07-7.98 (m, 1H), 7.92-7.86 (m, 1H), 7.41-7.35 (m, 2H), 7.32 (dd, J=10.0, 6.2 Hz, 1H), 7.27-7.17 (m, 4H), 6.69 (dd, J=3.5, 1.8 Hz, 1H), 4.75-4.60 (m, 2H), 3.60 (s, 3H), 3.23-3.06 (m, 2H), 1.83-1.54 (m, 4H), 1.51-1.19 (m, 6H).; MS (ESI) m/z 708.40 (M+H)+

Example 150

Synthesis of A-54 and Synthesis of B-54

(Step 1) N-{2,5-Difluoro-4-[(2-furylsulfonyl)amino]benzoyl}-3-[6-(1-methyl-2,4-dioxo-1,4-dihydropyrido[3,4-d]pyrimidin-3(2H)-yl)pyridin-3-yl]-L-alanine (A-54)

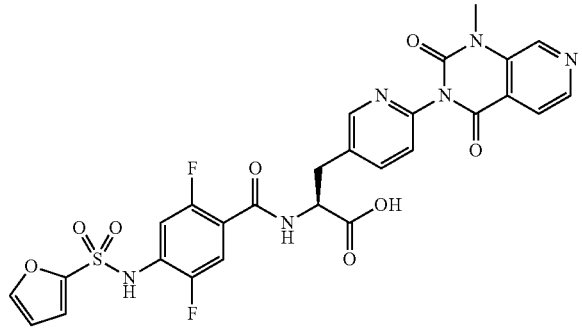 [SMILES: Cn1c(=O)n(-c2ccc(C[C@H](NC(=O)c3cc(F)c(NS(=O)(=O)c4ccco4)cc3F)C(=O)O)cn2)c(=O)c2ccncc21]

¹H NMR (400 MHz, DMSO-d₆): δ 11.11 (s, 1H), 8.99 (s, 1H), 8.75 (dd, J=8.1, 2.1 Hz, 1H), 8.57 (d, J=4.9 Hz, 1H), 8.48 (d, J=2.3 Hz, 1H), 8.05-7.99 (m, 1H), 7.95-7.85 (m, 2H), 7.41 (d, J=8.1 Hz, 1H), 7.31 (dd, J=10.1, 6.2 Hz, 1H), 7.27-7.14 (m, 2H), 6.68 (dd, J=3.5, 1.8 Hz, 1H), 4.75-4.64 (m, 1H), 3.60 (s, 3H), 3.30-3.03 (m, 2H).; MS (ESI) m/z 627.35 (M+H)+

(Step 2) Cyclohexyl N-{2,5-Difluoro-4-[(2-furylsulfonyl)amino]benzoyl}-3-[6-(1-methyl-2,4-dioxo-1,4-dihydropyrido[3,4-d]pyrimidin-3(2H)-yl)pyridin-3-yl]-L-alaninate (B-54)

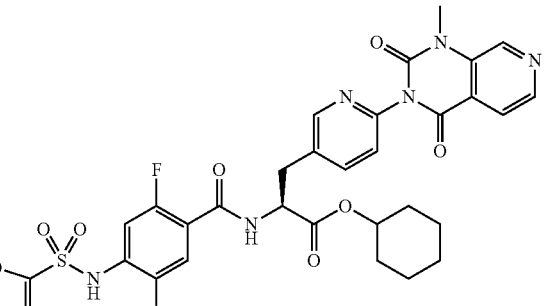

¹H NMR (400 MHz, DMSO-d₆): δ 11.12 (s, 1H), 8.99 (s, 1H), 8.90 (dd, J=7.9, 1.7 Hz, 1H), 8.57 (d, J=4.9 Hz, 1H), 8.48 (d, J=2.4 Hz, 1H), 8.07-7.98 (m, 1H), 7.98-7.86 (m, 2H), 7.42 (d, J=8.0 Hz, 1H), 7.30 (dd, J=10.0, 6.2 Hz, 1H), 7.26-7.19 (m, 2H), 6.69 (dd, J=3.5, 1.8 Hz, 1H), 4.77-4.66 (m, 2H), 3.61 (s, 3H), 3.31-3.09 (m, 2H), 1.81-1.58 (m, 4H), 1.51-1.19 (m, 6H).; MS (ESI) m/z 709.38 (M+H)+

Example 151

Synthesis of A-55

(Step 1) N-(2,6-Difluoro-4-{[(6'-methyl-3,3'-bipyridin-6-yl)sulfonyl]amino}benzoyl)-4-(1-methyl-2,4-dioxo-1,4-dihydropyrido[3,4-d]pyrimidin-3(2H)-yl)-L-phenylalanine (A-55)

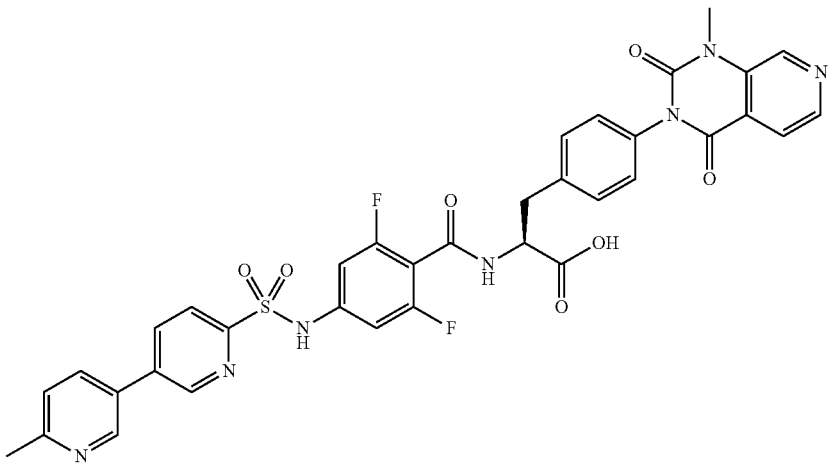 [SMILES: Cc1ccc(-c2ccc(S(=O)(=O)Nc3cc(F)c(C(=O)N[C@@H](Cc4ccc(-n5c(=O)c6ccncc6n(C)c5=O)cc4)C(=O)O)c(F)c3)nc2)cn1]

¹H NMR (400 MHz, DMSO-d₆): δ 11.37 (s, 1H), 9.14-9.10 (m, 1H), 9.06 (d, J=7.8 Hz, 1H), 8.97 (s, 1H), 8.95-8.92 (m, 1H), 8.55 (d, J=4.9 Hz, 1H), 8.46 (dd, J=8.3, 2.3 Hz, 1H), 8.28-8.19 (m, 2H), 7.89 (d, J=4.9 Hz, 1H), 7.50 (d, J=8.1 Hz, 1H), 7.35 (d, J=8.1 Hz, 2H), 7.21 (d, J=8.4 Hz, 2H), 6.90 (d, J=9.2 Hz, 2H), 4.62-4.53 (m, 1H), 3.60 (s, 3H), 3.25-2.94 (m, 2H), 2.56 (s, 3H).; MS (ESI) m/z 728 (M+H)+

Example 152

Synthesis of A-56 and Synthesis of B-56

(Step 1) 4-(3,7-Dimethyl-2,6-dioxo-2,3,6,7-tetra-hydro-1H-purin-1-yl)-N-{4-[({4-[(ethylamino)carbonyl]phenyl}sulfonyl)amino]-2,6-difluorobenzoyl}-L-phenylalanine (A-56), Obtained as a Free Form

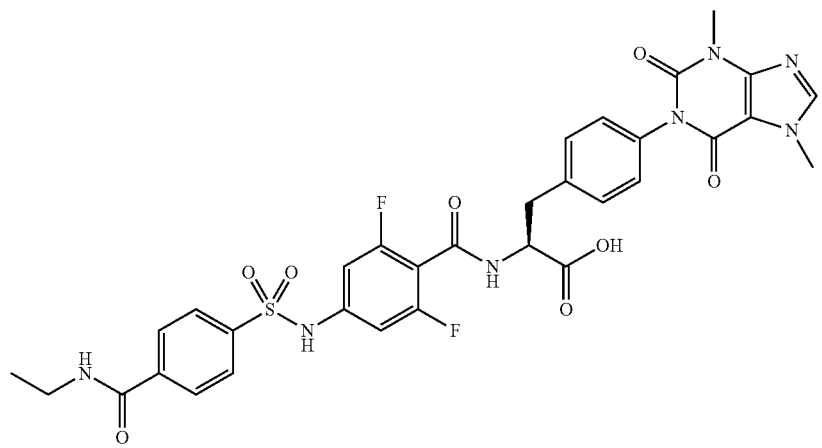 [SMILES: CCNC(=O)c1ccc(S(=O)(=O)Nc2cc(F)c(C(=O)N[C@@H](Cc3ccc(-n4c(=O)c5c(ncn5C)n(C)c4=O)cc3)C(=O)O)c(F)c2)cc1]

$^1$H NMR (400 MHz, DMSO-d$_6$): δ 11.15 (s, 1H), 9.05 (d, J=7.9 Hz, 1H), 8.66 (t, J=5.6 Hz, 1H), 8.07 (d, J=0.5 Hz, 1H), 8.01-7.91 (m, 4H), 7.32 (d, J=8.4 Hz, 2H), 7.13 (d, J=8.4 Hz, 2H), 6.79 (d, J=9.1 Hz, 2H), 4.61-4.50 (m, 1H), 3.86 (s, 3H), 3.43 (s, 3H), 3.30-3.23 (m, 2H), 3.15 (dd, J=14.1, 4.3 Hz, 1H), 2.97 (dd, J=14.3, 9.8 Hz, 1H), 1.10 (t, J=7.2 Hz, 3H).; MS (ESI) m/z 710 (M+H)$^+$ (Step 2) Isopropyl 4-(3,7-Dimethyl-2,6-dioxo-2,3,6,7-tetrahydro-1H-purin-1-yl)-N-{4-[({4-[(ethylamino)carbonyl]phenyl}sulfonyl)amino]-2,6-difluorobenzoyl}-L-phenylalaninate (B-56)

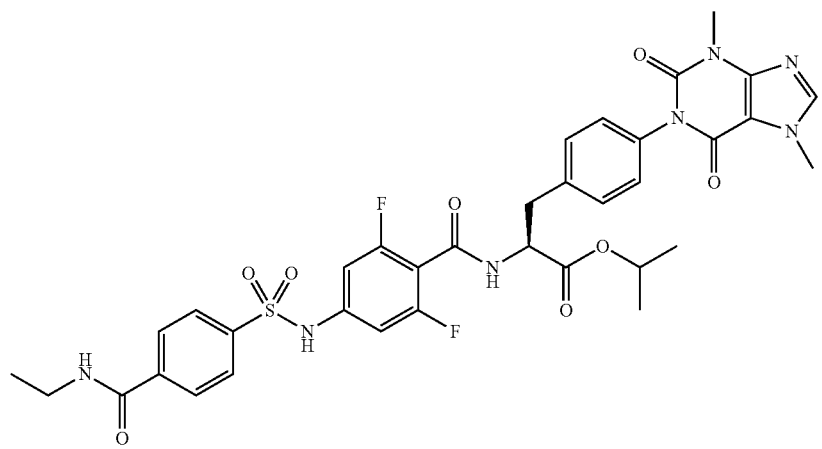 [SMILES: CCNC(=O)c1ccc(S(=O)(=O)Nc2cc(F)c(C(=O)N[C@@H](Cc3ccc(-n4c(=O)c5c(ncn5C)n(C)c4=O)cc3)C(=O)OC(C)C)c(F)c2)cc1]

$^1$H NMR (400 MHz, DMSO-d$_6$): δ 11.17 (s, 1H), 9.15 (d, J=7.4 Hz, 1H), 8.66 (t, J=5.6 Hz, 1H), 8.07 (s, 1H), 8.02-7.91 (m, 4H), 7.31 (d, J=8.3 Hz, 2H), 7.14 (d, J=8.3 Hz, 2H), 6.80 (d, J=9.1 Hz, 2H), 4.94-4.81 (m, 1H), 4.58-4.47 (m, 1H), 3.86 (s, 3H), 3.43 (s, 3H), 3.30-3.22 (m, 2H), 3.14-2.96 (m, 2H), 1.17 (d, J=6.2 Hz, 3H), 1.12-1.08 (m, 6H).; MS (ESI) m/z 752 (M+H)$^+$

Example 153

Synthesis of A-57 and Synthesis of B-57

(Step 1) N-(2,6-Difluoro-4-{[(5-pyrimidin-2-yl-pyridin-2-yl)sulfonyl]amino}benzoyl)-4-(3,7-dimethyl-2,6-dioxo-2,3,6,7-tetrahydro-1H-purin-1-yl)-L-phenylalanine (A-57)

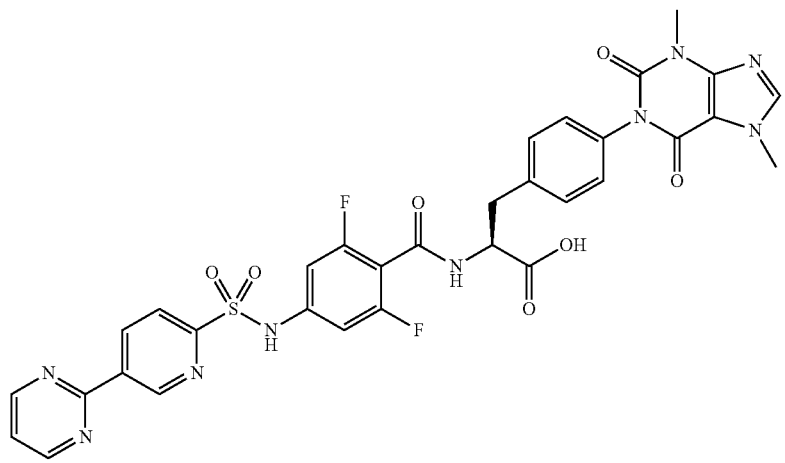 [SMILES: Cn1cnc2c1c(=O)n(-c1ccc(C[C@H](NC(=O)c3c(F)cc(NS(=O)(=O)c4ccc(-c5ncccn5)cn4)cc3F)C(=O)O)cc1)c(=O)n2C]

$^1$H NMR (400 MHz, DMSO-$d_6$): δ 11.40 (s, 1H), 9.58 (d, J=1.4 Hz, 1H), 9.03 (d, J=7.7 Hz, 1H), 9.00 (d, J=4.9 Hz, 2H), 8.95 (dd, J=8.2, 2.1 Hz, 1H), 8.28 (d, J=8.9 Hz, 1H), 8.07 (s, 1H), 7.60 (t, J=4.9 Hz, 1H), 7.31 (d, J=8.3 Hz, 2H), 7.13 (d, J=8.3 Hz, 2H), 6.88 (d, J=9.2 Hz, 2H), 4.59-4.51 (m, 1H), 3.86 (s, 3H), 3.42 (s, 3H), 3.14 (dd, J=13.8, 4.7 Hz, 1H), 2.97 (dd, J=14.1, 9.7 Hz, 1H).; MS (ESI) m/z 718.36 (M+H)$^+$ (Step 2) Isopropyl N-(2,6-Difluoro-4-{[(5-pyrimidin-2-yl-pyridin-2-yl)sulfonyl]amino}benzoyl)-4-(3,7-dimethyl-2,6-dioxo-2,3,6,7-tetrahydro-1H-purin-1-yl)-L-phenylalaninate (B-57)

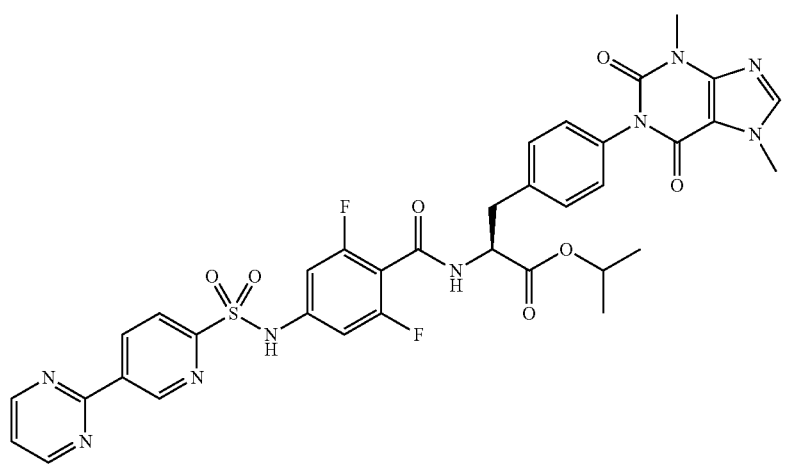 [SMILES: CC(C)OC(=O)[C@H](Cc1ccc(-n2c(=O)c3c(ncn3C)n(C)c2=O)cc1)NC(=O)c1c(F)cc(NS(=O)(=O)c2ccc(-c3ncccn3)cn2)cc1F]

$^1$H NMR (400 MHz, DMSO-$d_6$): δ 11.42 (s, 1H), 9.59 (dd, J=2.1, 0.7 Hz, 1H), 9.14 (d, J=7.4 Hz, 1H), 9.01 (d, J=4.9 Hz, 2H), 8.95 (dd, J=8.3, 2.1 Hz, 1H), 8.28 (dd, J=8.2, 0.7 Hz, 1H), 8.06 (s, 1H), 7.60 (t, J=4.9 Hz, 1H), 7.31 (d, J=8.4 Hz, 2H), 7.13 (d, J=8.3 Hz, 2H), 6.90 (d, J=9.2 Hz, 2H), 4.88 (dt, J=12.5, 6.2 Hz, 1H), 4.52 (dd, J=14.2, 8.1 Hz, 1H), 3.86 (s, 3H), 3.42 (s, 3H), 3.14-2.96 (m, 2H), 1.17 (d, J=6.3 Hz, 3H), 1.11 (d, J=6.2 Hz, 3H).; MS (ESI) m/z 760.33 (M+H)$^+$

Example 154

Synthesis of A-58 and Synthesis of B-58

(Step 1) N-[(3-Fluoro-5-{[(5-pyrimidin-2-yl-pyridin-2-yl)sulfonyl]amino}pyridin-2-yl)carbonyl]-4-(1-methyl-2,4-dioxo-1,4-dihydropyrido[3,4-d]pyrimidin-3(2H)-yl)-L-phenylalanine (A-58)

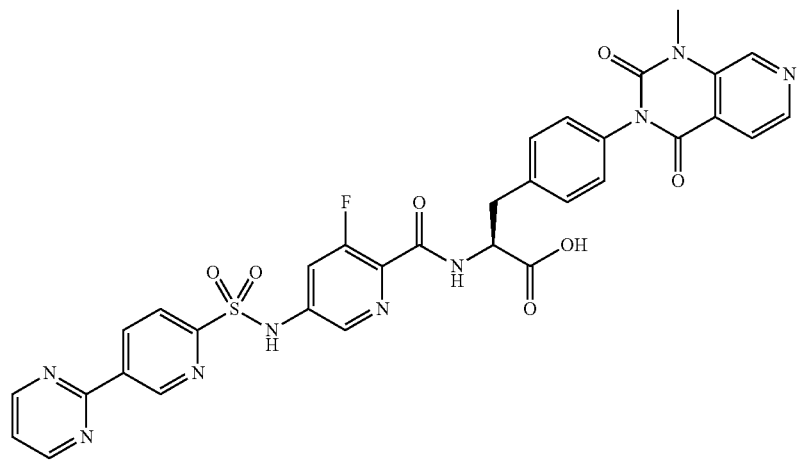 [SMILES: Cn1c(=O)n(-c2ccc(C[C@H](NC(=O)c3ncc(NS(=O)(=O)c4ccc(-c5ncccn5)cn4)cc3F)C(=O)O)cc2)c(=O)c2ccncc21]

$^1$H NMR (400 MHz, DMSO-d$_6$): δ 11.67 (s, 1H), 9.58 (dd, J=2.0, 0.8 Hz, 1H), 9.05-8.88 (m, 4H), 8.65 (d, J=8.0 Hz, 1H), 8.54 (d, J=4.9 Hz, 1H), 8.36-8.25 (m, 2H), 7.89-7.83 (m, 1H), 7.63-7.52 (m, 2H), 7.37-7.26 (m, 2H), 7.22-7.14 (m, 2H), 4.74-4.59 (m, 1H), 3.58 (s, 3H), 3.28-3.14 (m, 2H).; MS (ESI) m/z 698.26 (M+H)$^+$

Example 155

Synthesis of A-59 and Synthesis of B-59

(Step 1) 4-(3,4-Dimethyl-2,6-dioxo-3,6-dihydropyrimidin-1(2H)-yl)-N-{4-[({4-[(ethylamino)carbonyl]phenyl}sulfonyl)amino]-2,6-difluorobenzoyl}-L-phenylalanine (A-59), Obtained as a Free Form

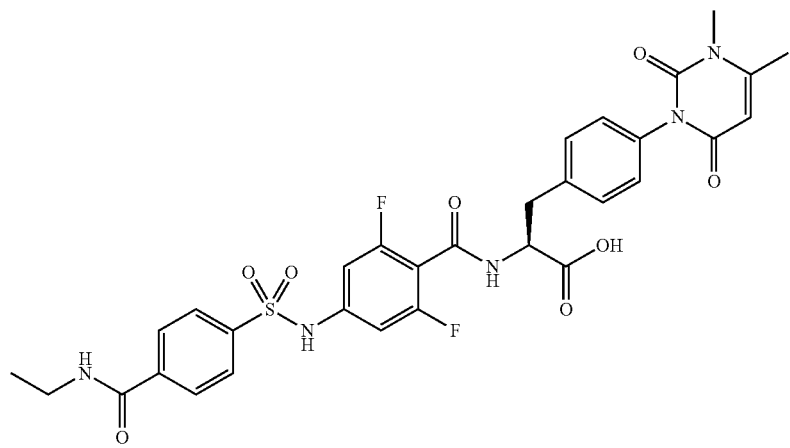 [SMILES: CCNC(=O)c1ccc(S(=O)(=O)Nc2cc(F)c(C(=O)N[C@@H](Cc3ccc(-n4c(=O)cc(C)n(C)c4=O)cc3)C(=O)O)c(F)c2)cc1]

$^1$H NMR (400 MHz, DMSO-d$_6$): δ 11.08 (s, 1H), 8.97 (d, J=7.8 Hz, 1H), 8.60 (t, J=5.6 Hz, 1H), 7.97-7.82 (m, 4H), 7.23 (d, J=7.9 Hz, 2H), 6.99 (d, J=8.1 Hz, 2H), 6.86-6.62 (m, 2H), 5.64 (s, 1H), 4.55-4.40 (m, 1H), 3.25 (s, 3H), 3.23-3.16 (m, 2H), 3.10-2.85 (m, 2H), 2.23 (s, 3H), 1.11-0.94 (m, 3H).; MS (ESI) m/z 670.25 (M+H)$^+$ (Step 2) Isopropyl 4-(3,4-Dimethyl-2,6-dioxo-3,6-dihydropyrimidin-1(2H)-yl)-N-{4-[({4-[(ethylamino)carbonyl]phenyl}sulfonyl)amino]-2,6-difluorobenzoyl}-L-phenylalaninate (B-59), Obtained as a Free Form

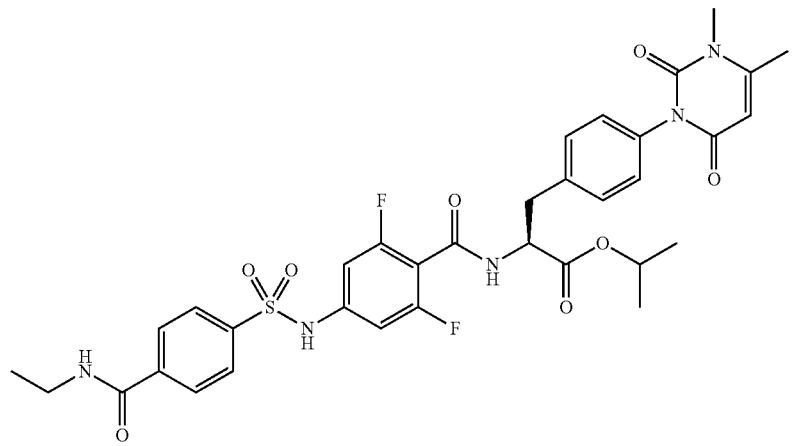 [SMILES: CCNC(=O)c1ccc(S(=O)(=O)Nc2cc(F)c(C(=O)N[C@@H](Cc3ccc(-n4c(=O)cc(C)n(C)c4=O)cc3)C(=O)OC(C)C)c(F)c2)cc1]

$^1$H NMR (400 MHz, DMSO-d$_6$): δ 11.12 (s, 1H), 9.08 (d, J=7.4 Hz, 1H), 8.60 (t, J=5.5 Hz, 1H), 7.89 (q, J=8.7 Hz, 4H), 7.23 (d, J=8.4 Hz, 2H), 7.05-6.94 (m, 2H), 6.73 (d, J=9.0 Hz, 2H), 5.64 (d, J=1.1 Hz, 1H), 4.85-4.71 (m, 1H), 4.50-4.35 (m, 1H), 3.25 (s, 3H), 3.23-3.16 (m, 2H), 2.96 (ddd, J=23.2, 14.1, 8.8 Hz, 2H), 2.26-2.18 (m, 3H), 1.10 (d, J=6.2 Hz, 3H), 1.07-0.97 (m, 6H).; MS (ESI) m/z 712.45 (M+H)$^+$ Example 156

Synthesis of A-60 and Synthesis of B-60

(Step 1) N-{4-[({4-[(Ethylamino)carbonyl]phenyl}sulfonyl)amino]-2,6-difluorobenzoyl}-4-(4-isopropyl-3-methyl-2,6-dioxo-3,6-dihydropyrimidin-1(2H)-yl)-L-phenylalanine (A-60), Obtained as a Free Form

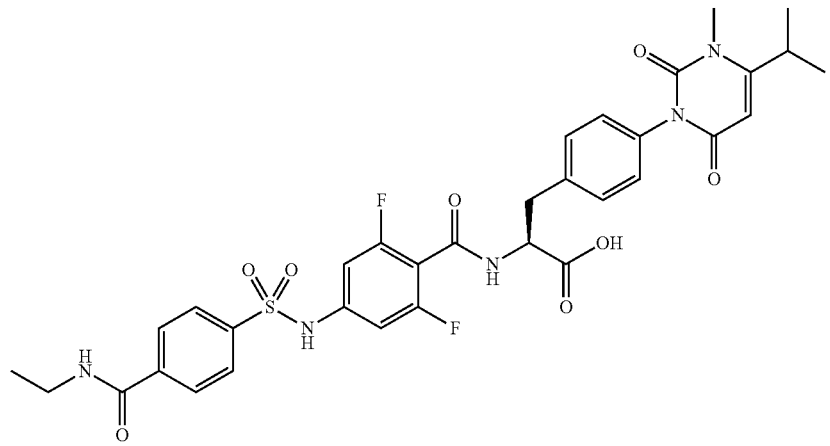 [SMILES: CCNC(=O)c1ccc(S(=O)(=O)Nc2cc(F)c(C(=O)N[C@@H](Cc3ccc(-n4c(=O)cc(C(C)C)n(C)c4=O)cc3)C(=O)O)c(F)c2)cc1]

$^1$H NMR (400 MHz, DMSO-d$_6$): δ 11.16 (s, 1H), 9.04 (d, J=7.8 Hz, 1H), 8.67 (t, J=5.5 Hz, 1H), 8.03-7.85 (m, 4H), 7.30 (d, J=8.0 Hz, 2H), 7.08 (d, J=7.9 Hz, 2H), 6.79 (d, J=8.9 Hz, 2H), 5.66 (s, 1H), 4.61-4.46 (m, 1H), 3.27 (dd, J=7.4, 5.7 Hz, 2H), 3.19-2.92 (m, 3H), 1.22 (d, J=6.6 Hz, 6H), 1.10 (t, J=7.2 Hz, 3H).; MS (ESI) m/z 698.30 (M+H)$^+$ (Step 2) Isopropyl N-{4-[({4-[(Ethylamino)carbonyl]phenyl}sulfonyl)amino]-2,6-difluorobenzoyl}-4-(4-isopropyl-3-methyl-2,6-dioxo-3,6-dihydropyrimidin-1(2H)-yl)-L-phenylalaninate (B-60), Obtained as a Free Form

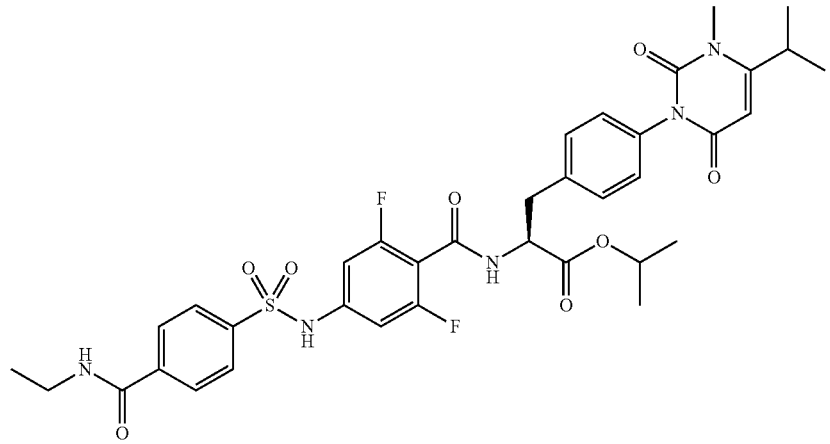 [SMILES: CCNC(=O)c1ccc(S(=O)(=O)Nc2cc(F)c(C(=O)N[C@@H](Cc3ccc(-n4c(=O)cc(C(C)C)n(C)c4=O)cc3)C(=O)OC(C)C)c(F)c2)cc1]

$^1$H NMR (400 MHz, DMSO-$d_6$): δ 11.10 (s, 1H), 9.08 (d, J=7.4 Hz, 1H), 8.60 (t, J=5.6 Hz, 1H), 8.04-7.77 (m, 4H), 7.23 (d, J=8.0 Hz, 2H), 7.02 (d, J=7.9 Hz, 2H), 6.73 (d, J=9.1 Hz, 2H), 5.58 (s, 1H), 4.86-4.75 (m, 1H), 4.52-4.34 (m, 1H), 3.20 (dt, J=12.6, 7.2 Hz, 2H), 3.05-2.88 (m, 3H), 1.14 (d, J=6.6 Hz, 6H), 1.10 (d, J=6.3 Hz, 3H), 1.07-0.99 (m, 6H).; MS (ESI) m/z 740.42 (M+H)$^+$

Example 157

Synthesis of A-61 and Synthesis of B-61

(Step 1) N-(4-{[(4-{[(Cyclopropylmethyl)amino]carbonyl}phenyl)sulfonyl]amino}-2,6-difluorobenzoyl)-4-(3-methyl-2,6-dioxo-3,6-dihydropyrimidin-1(2H)-yl)-L-phenylalanine (A-61), Obtained as a Free Form

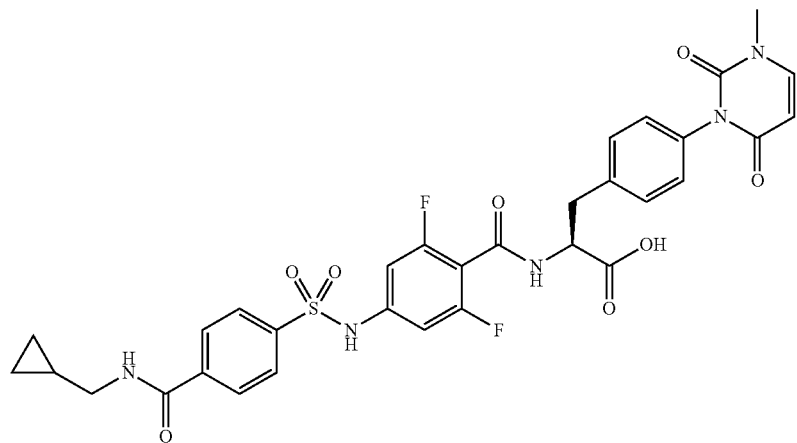 [SMILES: Cn1ccc(=O)n(-c2ccc(C[C@H](NC(=O)c3c(F)cc(NS(=O)(=O)c4ccc(C(=O)NCC5CC5)cc4)cc3F)C(=O)O)cc2)c1=O]

1H NMR (400 MHz, DMSO-$d_6$): δ 11.15 (s, 1H), 9.03 (d, J=7.8 Hz, 1H), 8.77 (t, J=5.7 Hz, 1H), 7.99 (d, J=8.7 Hz, 2H), 7.94 (d, J=8.7 Hz, 2H), 7.75 (d, J=7.9 Hz, 1H), 7.30 (d, J=8.4 Hz, 2H), 7.09 (d, J=8.4 Hz, 2H), 6.79 (d, J=9.1 Hz, 2H), 5.74 (d, J=7.9 Hz, 1H), 4.58-4.46 (m, 1H), 3.30 (s, 3H), 3.18-3.10 (m, 3H), 2.96 (dd, J=14.3, 9.7 Hz, 1H), 1.00 (dd, J=8.2, 3.5 Hz, 1H), 0.48-0.37 (m, 2H), 0.25-0.15 (m, 2H).; MS (ESI) m/z 682.25 (M+H)$^+$ (Step 2) Isopropyl N-(4-{[(4-{[(Cyclopropylmethyl)amino]carbonyl}phenyl)sulfonyl]amino}-2,6-difluorobenzoyl)-4-(3-methyl-2,6-dioxo-3,6-dihydropyrimidin-1(2H)-yl)-L-phenylalaninate (B-61), Obtained as a Free Form

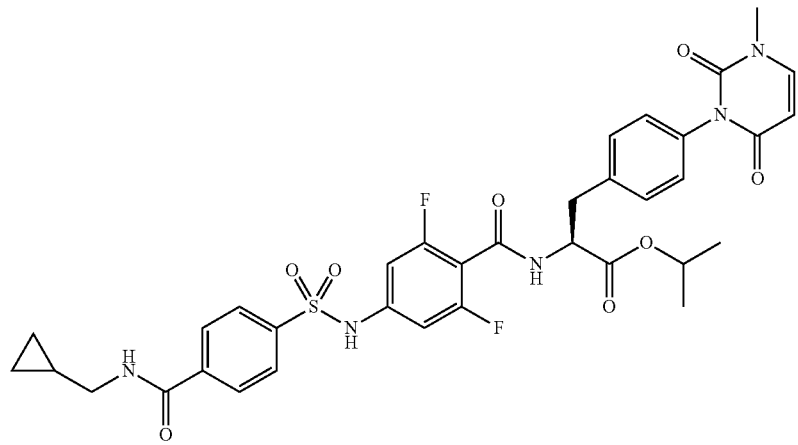 [SMILES: CC(C)OC(=O)[C@H](Cc1ccc(-n2c(=O)ccn(C)c2=O)cc1)NC(=O)c1c(F)cc(NS(=O)(=O)c2ccc(C(=O)NCC3CC3)cc2)cc1F]

¹H NMR (400 MHz, DMSO-d₆): δ 11.17 (s, 1H), 9.14 (d, J=7.3 Hz, 1H), 8.77 (t, J=5.4 Hz, 1H), 8.00 (d, J=8.4 Hz, 2H), 7.95 (d, J=8.4 Hz, 2H), 7.75 (d, J=7.9 Hz, 1H), 7.30 (d, J=8.1 Hz, 2H), 7.09 (d, J=8.1 Hz, 2H), 6.80 (d, J=9.0 Hz, 2H), 5.74 (d, J=7.9 Hz, 1H), 4.93-4.82 (m, 1H), 4.51 (dd, J=14.0, 8.4 Hz, 1H), 3.30 (s, 3H), 3.20-2.93 (m, 4H), 1.16 (d, J=6.2 Hz, 3H), 1.10 (d, J=6.2 Hz, 3H), 1.05-0.94 (m, 1H), 0.47-0.36 (m, 2H), 0.25-0.16 (m, 2H).; MS (ESI) m/z 724.41 (M+H)⁺

Example 158

Synthesis of A-62 and Synthesis of B-62

(Step 1) N-{4-[({4-[(tert-Butylamino)carbonyl]-2-methylphenyl}sulfonyl)amino]-2,6-difluorobenzoyl}-4-(3-methyl-2,6-dioxo-3,6-dihydropyrimidin-1(2H)-yl)-L-phenylalanine (A-62), Obtained as a Free Form

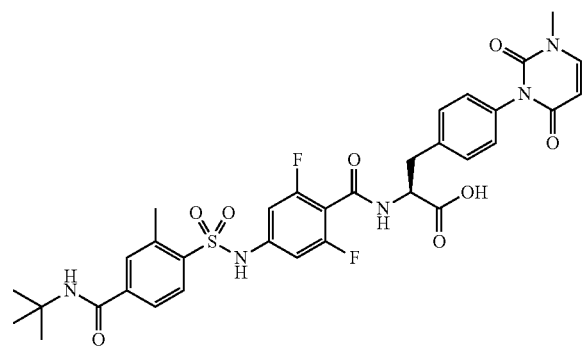

¹H NMR (400 MHz, DMSO-d₆): δ 11.28 (s, 1H), 9.01 (d, J=7.8 Hz, 1H), 8.03 (d, J=8.6 Hz, 1H), 7.98 (s, 1H), 7.78-7.70 (m, 3H), 7.33-7.28 (m, 2H), 7.12-7.06 (m, 2H), 6.73 (d, J=9.1 Hz, 2H), 5.74 (d, J=7.9 Hz, 1H), 4.58-4.49 (m, 1H), 3.31 (s, 3H), 3.18-2.90 (m, 2H), 2.63 (s, 3H), 1.35 (s, 9H).; MS (ESI) m/z 698.46 (M+H)⁺

(Step 2) Isopropyl N-{4-[({4-[(tert-Butylamino)carbonyl]-2-methylphenyl}sulfonyl)amino]-2,6-difluorobenzoyl}-4-(3-methyl-2,6-dioxo-3,6-dihydropyrimidin-1(2H)-yl)-L-phenylalaninate (B-62), Obtained as a Free Form

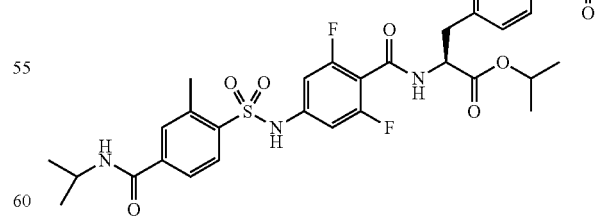

¹H NMR (400 MHz, DMSO-d₆): δ 11.30 (s, 1H), 9.12 (d, J=7.4 Hz, 1H), 8.04 (d, J=8.7 Hz, 1H), 7.98 (s, 1H), 7.78-7.72 (m, 3H), 7.29 (d, J=8.4 Hz, 2H), 7.09 (d, J=8.3 Hz, 2H), 6.74 (d, J=9.1 Hz, 2H), 5.74 (d, J=7.9 Hz, 1H), 4.92-4.81 (m, 1H), 4.55-4.44 (m, 1H), 3.30 (s, 3H), 3.12-

2.95 (m, 2H), 2.63 (s, 3H), 1.35 (s, 9H), 1.16 (d, J=6.2 Hz, 3H), 1.10 (d, J=6.2 Hz, 3H).; MS (ESI) m/z 740.54 (M+H)+

Example 159

Synthesis of A-63 and Synthesis of B-63

(Step 1) N-(2,6-Difluoro-4-{[(5-pyrimidin-2-yl-pyridin-2-yl)sulfonyl]amino}benzoyl)-3-[5-(3-methyl-2,6-dioxo-3,6-dihydropyrimidin-1(2H)-yl)pyridin-2-yl]-L-alanine (A-63)

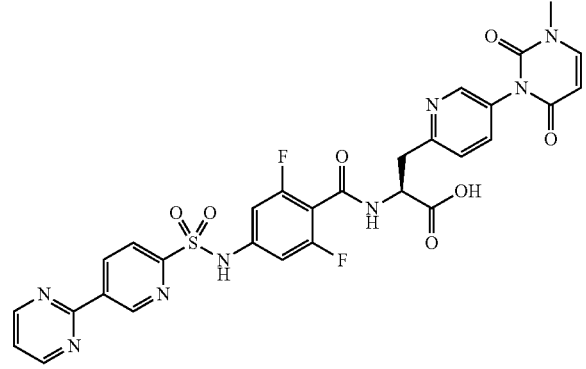 [SMILES: Cn1ccc(=O)n(-c2ccc(C[C@H](NC(=O)c3c(F)cc(NS(=O)(=O)c4ccc(-c5ncccn5)cn4)cc3F)C(=O)O)nc2)c1=O]

¹H NMR (400 MHz, DMSO-d₆): δ 11.39 (s, 1H), 9.58 (dd, J=2.1, 0.9 Hz, 1H), 9.05-8.90 (m, 4H), 8.38-8.31 (m, 1H), 8.27 (dd, J=8.3, 0.7 Hz, 1H), 7.79 (d, J=7.9 Hz, 1H), 7.69-7.55 (m, 2H), 7.37 (d, J=8.2 Hz, 1H), 6.86 (d, J=9.1 Hz, 2H), 5.79 (d, J=7.9 Hz, 1H), 4.87-4.75 (m, 2H), 4.41 (s, OH), 3.32 (s, 3H), 3.31-3.08 (m, 2H).; MS (ESI) m/z 665.45 (M+H)+

(Step 2) Isopropyl N-(2,6-Difluoro-4-{[(5-pyrimidin-2-yl-pyridin-2-yl)sulfonyl]amino}benzoyl)-3-[5-(3-methyl-2,6-dioxo-3,6-dihydropyrimidin-1(2H)-yl)pyridin-2-yl]-L-alaninate (B-63)

¹H NMR (400 MHz, DMSO-d₆): δ 11.41 (s, 1H), 9.58 (dd, J=2.2, 0.8 Hz, 1H), 9.09 (d, J=7.5 Hz, 1H), 9.01 (d, J=4.9 Hz, 2H), 8.95 (dd, J=8.3, 2.1 Hz, 1H), 8.33 (d, J=2.3 Hz, 1H), 8.28 (dd, J=8.4, 0.7 Hz, 1H), 7.79 (d, J=7.9 Hz, 1H), 7.67-7.56 (m, 2H), 7.37 (d, J=8.2 Hz, 1H), 6.96-6.81 (m, 2H), 5.78 (d, J=7.9 Hz, 1H), 4.86-4.77 (m, 2H), 3.32 (s, 3H), 3.28-3.09 (m, 2H), 1.87-1.68 (m, 2H), 1.65-1.43 (m, 6H), 1.35 (dt, J=13.5, 5.2 Hz, 4H).; MS (ESI) m/z 761.58 (M+H)+

Example 160

Synthesis of A-64 and Synthesis of B-64

(Step 1) N-{2-Fluoro-4-[({4-[(methylamino)methyl]phenyl}sulfonyl)amino]benzoyl}-4-(1-methyl-2,4-dioxo-1,4-dihydropyrido[3,4-d]pyrimidin-3(2H)-yl)-L-phenylalanine (A-64)

¹H NMR (400 MHz, DMSO-d₆): δ 11.03 (s, 1H), 8.98 (s, 1H), 8.86 (brs, 1H), 8.56 (d, J=5.0 Hz, 1H), 8.41 (dd, J=7.8, 3.0 Hz, 1H), 7.97-7.82 (m, 3H), 7.66 (d, J=8.1 Hz, 2H), 7.42 (t, J=8.3 Hz, 1H), 7.39-7.33 (m, 2H), 7.25-7.17 (m, 2H), 7.04-6.90 (m, 2H), 4.66-4.49 (m, 1H), 4.30-4.10 (m, 2H), 3.60 (s, 3H), 3.26-3.03 (m, 2H), 2.57 (s, 3H).; MS (ESI) m/z 661.24 (M+H)+

(Step 2) Methyl N-{2-Fluoro-4-[({4-[(methylamino)
methyl]phenyl}sulfonyl)amino]benzoyl}-4-(1-
methyl-2,4-dioxo-1,4-dihydropyrido[3,4-d]pyrimi-
din-3(2H)-yl)-L-phenylalaninate (B-64)

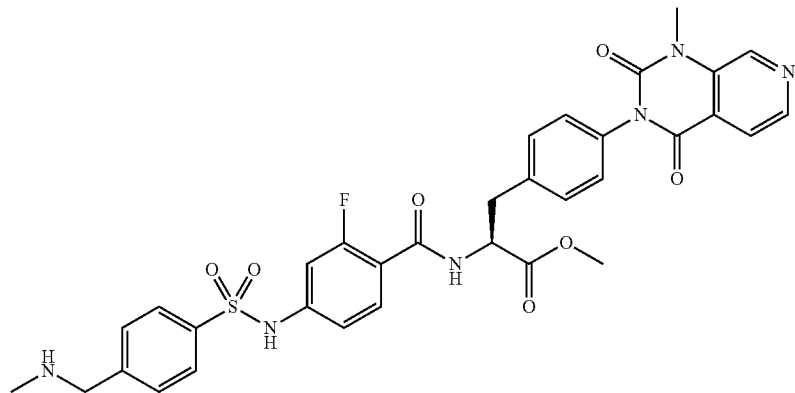 [SMILES: CNCc1ccc(S(=O)(=O)Nc2ccc(C(=O)N[C@@H](Cc3ccc(-n4c(=O)c5ccncc5n(C)c4=O)cc3)C(=O)OC)c(F)c2)cc1]

$^1$H NMR (400 MHz, DMSO-d$_6$): δ 11.03 (s, 1H), 8.98 (s, 1H), 8.79 (s, 1H), 8.60 (dd, J=7.6, 2.4 Hz, 1H), 8.56 (d, J=4.9 Hz, 1H), 7.95-7.90 (m, 2H), 7.89 (d, J=5.0 Hz, 1H), 7.69-7.62 (m, 2H), 7.41 (t, J=8.3 Hz, 1H), 7.38-7.33 (m, 2H), 7.25-7.19 (m, 2H), 7.03-6.93 (m, 2H), 4.71-4.60 (m, 1H), 4.22-4.12 (m, 2H), 3.65 (s, 3H), 3.60 (s, 3H), 3.23-3.05 (m, 2H), 2.60-2.54 (m, 3H).; MS (ESI) m/z 675.37 (M+H)$^+$

Example 161

Synthesis of A-65 and Synthesis of B-65

(Step 1) N-[2-Fluoro-4-({[4-(1H-1,2,3-triazol-1-yl)
phenyl]sulfonyl}amino)benzoyl]-4-(1-methyl-2,4-
dioxo-1,4-dihydropyrido[3,4-d]pyrimidin-3(2H)-yl)-
L-phenylalanine (A-65)

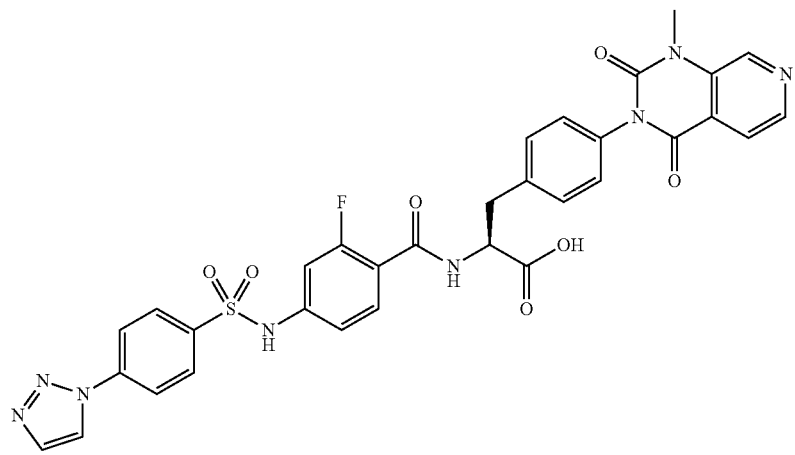 [SMILES: Cn1c(=O)n(-c2ccc(C[C@H](NC(=O)c3ccc(NS(=O)(=O)c4ccc(-n5ccnn5)cc4)cc3F)C(=O)O)cc2)c(=O)c2ccncc21]

$^1$H NMR (400 MHz, DMSO-d$_6$): δ 10.98 (s, 1H), 8.89 (s, 1H), 8.83 (d, J=1.2 Hz, 1H), 8.49 (d, J=5.0 Hz, 1H), 8.33 (dd, J=7.9, 2.9 Hz, 1H), 8.11-8.05 (m, 2H), 8.00-7.95 (m, 2H), 7.93 (d, J=0.8 Hz, 1H), 7.81 (d, J=4.9 Hz, 1H), 7.36 (t, J=8.3 Hz, 1H), 7.31-7.25 (m, 2H), 7.18-7.10 (m, 2H), 7.01-6.86 (m, 2H), 4.59-4.49 (m, 1H), 3.52 (s, 3H), 3.18-2.94 (m, 2H).; MS (ESI) m/z 685.36 (M+H)$^+$ (Step 2) Methyl N-[2-Fluoro-4-({[4-(1H-1,2,3-tri-azol-1-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-65)

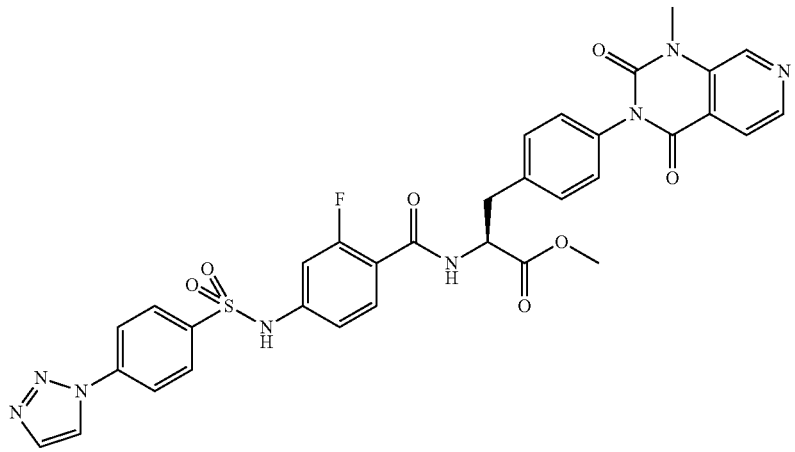 [SMILES: COC(=O)[C@H](Cc1ccc(-n2c(=O)c3ccncc3n(C)c2=O)cc1)NC(=O)c1ccc(NS(=O)(=O)c2ccc(-n3ccnn3)cc2)cc1F]

¹H NMR (400 MHz, DMSO-d₆): δ 11.05 (s, 1H), 8.97 (s, 1H), 8.92 (d, J=1.2 Hz, 1H), 8.59 (dd, J=7.7, 2.4 Hz, 1H), 8.55 (d, J=5.0 Hz, 1H), 8.20-8.12 (m, 2H), 8.09-8.02 (m, 2H), 8.01 (d, J=1.3 Hz, 1H), 7.88 (d, J=4.9 Hz, 1H), 7.41 (t, J=8.3 Hz, 1H), 7.38-7.31 (m, 2H), 7.25-7.17 (m, 2H), 7.05-6.96 (m, 2H), 4.69-4.61 (m, 1H), 3.64 (s, 3H), 3.59 (s, 3H), 3.23-3.03 (m, 2H).; MS (ESI) m/z 699. 32 (M+H)⁺

Example 162

Synthesis of A-66 and Synthesis of B-66

(Step 1) N-[2,6-Difluoro-4-({[5-(1H-pyrrol-1-yl)pyridin-2-yl]sulfonyl}amino)benzoyl]-4-(3-methyl-2,6-dioxo-3,6-dihydropyrimidin-1(2H)-yl)-L-phenylalanine (A-66), Obtained as a Free Form

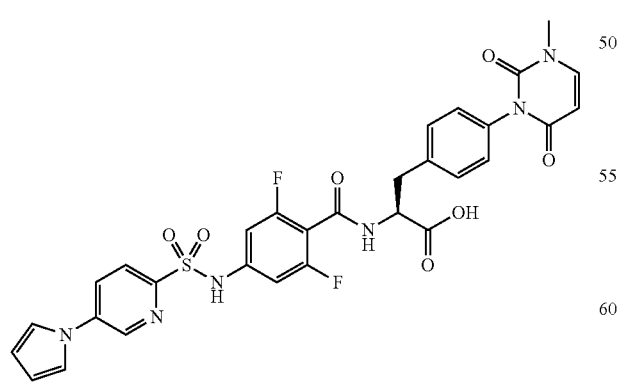

¹H NMR (400 MHz, DMSO-d₆): δ 11.28 (s, 1H), 9.09 (d, J=2.6 Hz, 1H), 9.02 (d, J=7.9 Hz, 1H), 8.30 (dd, J=8.7, 2.7 Hz, 1H), 8.16 (d, J=8.6 Hz, 1H), 7.75 (d, J=7.9 Hz, 1H), 7.61 (t, J=2.2 Hz, 2H), 7.38-7.26 (m, 2H), 7.15-7.03 (m, 2H), 6.93-6.78 (m, 2H), 6.37 (t, J=2.2 Hz, 2H), 5.74 (d, J=7.9 Hz, 1H), 4.62-4.46 (m, 1H), 3.30 (s, 3H), 3.18-2.92 (m, 2H).;
MS (ESI) m/z 651.37 (M+H)⁺

(Step 2) Isopropyl N-[2,6-Difluoro-4-({[5-(1H-pyrrol-1-yl)pyridin-2-yl]sulfonyl}amino)benzoyl]-4-(3-methyl-2,6-dioxo-3,6-dihydropyrimidin-1(2H)-yl)-L-phenylalaninate (B-66), Obtained as a Free Form

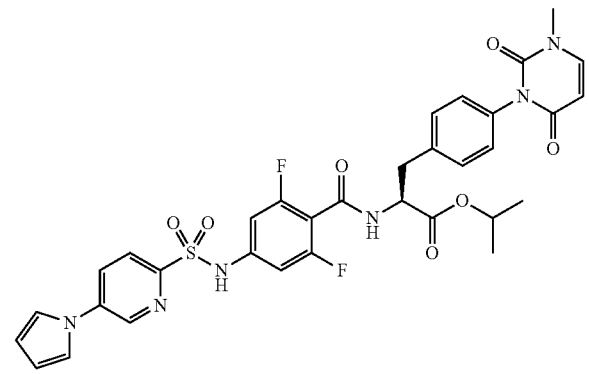 [SMILES: CC(C)OC(=O)[C@H](Cc1ccc(-n2c(=O)ccn(C)c2=O)cc1)NC(=O)c1c(F)cc(NS(=O)(=O)c2ccc(-n3cccc3)cn2)cc1F]

¹H NMR (400 MHz, DMSO-d₆): δ 11.22 (s, 1H), 9.06 (d, J=7.4 Hz, 1H), 9.02 (d, J=2.6 Hz, 1H), 8.23 (dd, J=8.7, 2.7 Hz, 1H), 8.10 (d, J=8.6 Hz, 1H), 7.68 (d, J=7.9 Hz, 1H), 7.54 (t, J=2.2 Hz, 2H), 7.26-7.20 (m, 2H), 7.06-6.99 (m, 2H), 6.87-6.78 (m, 2H), 6.30 (t, J=2.2 Hz, 2H), 5.67 (d, J=7.9 Hz, 1H), 4.86-4.75 (m, 1H), 4.50-4.40 (m, 1H), 3.24 (s, 3H), 3.05-2.89 (m, 2H), 1.10 (d, J=6.2 Hz, 3H), 1.04 (d, J=6.2 Hz, 3H).; MS (ESI) m/z 693.38 (M+H)⁺

Example 163

Synthesis of A-67 and Synthesis of B-67

(Step 1) N-(2-Fluoro-4-{[(5-pyrimidin-5-yl-pyridin-2-yl)sulfonyl]amino}benzoyl)-4-(1-methyl-2,4-dioxo-1,4-dihydropyrido[3,4-d]pyrimidin-3(2H)-yl)-L-phenylalanine (A-67)

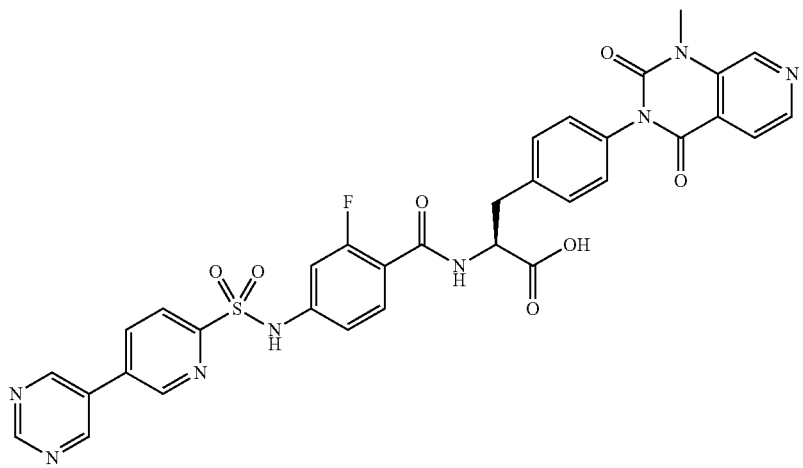 [SMILES: Cn1c(=O)n(-c2ccc(C[C@H](NC(=O)c3ccc(NS(=O)(=O)c4ccc(-c5cncnc5)cn4)cc3F)C(=O)O)cc2)c(=O)c2ccncc21]

$^1$H NMR (400 MHz, DMSO-$d_6$): δ 11.28 (s, 1H), 9.30-9.24 (m, 3H), 9.18 (d, J=2.3 Hz, 1H), 8.97 (s, 1H), 8.60-8.50 (m, 2H), 8.39 (dd, J=7.7, 3.1 Hz, 1H), 8.22 (d, J=8.3 Hz, 1H), 7.88 (d, J=4.9 Hz, 1H), 7.43 (t, J=8.3 Hz, 1H), 7.39-7.32 (m, 2H), 7.24-7.17 (m, 2H), 7.11-7.03 (m, 2H), 4.65-4.57 (m, 1H), 3.59 (s, 3H), 3.27-3.01 (m, 2H).; MS (ESI) m/z 697.28 (M+H)$^+$ (Step 2) Isopropyl N-(2-Fluoro-4-{[(5-pyrimidin-5-yl-pyridin-2-yl)sulfonyl]amino}benzoyl)-4-(1-methyl-2,4-dioxo-1,4-dihydropyrido[3,4-d]pyrimidin-3(2H)-yl)-L-phenylalanine (B-67)

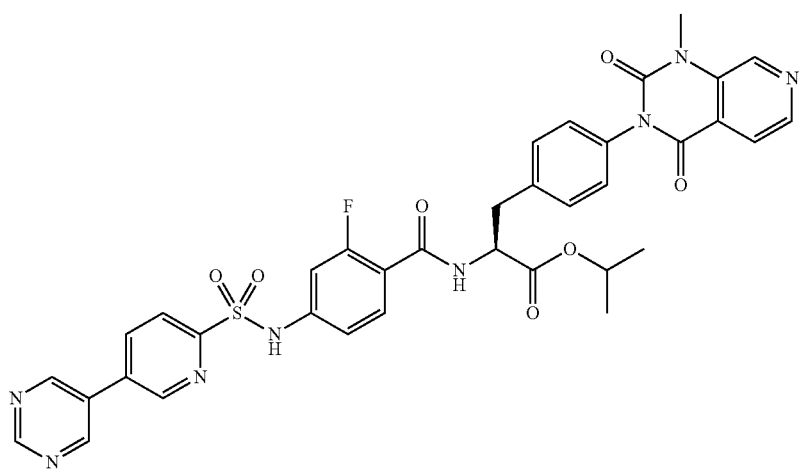 [SMILES: CC(C)OC(=O)[C@H](Cc1ccc(-n2c(=O)c3ccncc3n(C)c2=O)cc1)NC(=O)c1ccc(NS(=O)(=O)c2ccc(-c3cncnc3)cn2)cc1F]

$^1$H NMR (400 MHz, DMSO-$d_6$): δ 11.22 (s, 1H), 9.26-9.16 (m, 3H), 9.11 (d, J=2.3 Hz, 1H), 8.90 (s, 1H), 8.55-8.42 (m, 3H), 8.16 (d, J=8.2 Hz, 1H), 7.82 (d, J=5.0 Hz, 1H), 7.35 (t, J=8.2 Hz, 1H), 7.29 (d, J=8.0 Hz, 2H), 7.15 (d, J=8.1 Hz, 2H), 7.08-6.96 (m, 2H), 4.88-4.76 (m, 1H), 4.56-4.46 (m, 1H), 3.53 (s, 3H), 3.12-2.94 (m, 2H), 1.11 (d, J=6.2 Hz, 3H), 1.06 (d, J=6.2 Hz, 3H).; MS (ESI) m/z 739.54 (M+H)$^+$

Example 164

Synthesis of A-68 and Synthesis of B-68

(Step 1) N-{4-[({6-[(Ethylamino)carbonyl]pyridin-3-yl}sulfonyl)amino]-2,6-difluorobenzoyl}-4-(3-methyl-2,6-dioxo-3,6-dihydropyrimidin-1(2H)-yl)-L-phenylalanine (A-68), Obtained as a Free Form

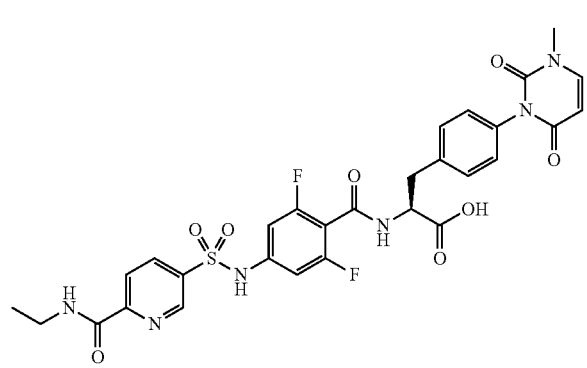

$^1$H NMR (400 MHz, DMSO-d$_6$): δ 11.42 (s, 1H), 9.11 (d, J=7.8 Hz, 1H), 9.08-9.01 (m, 2H), 8.48 (dd, J=8.3, 2.3 Hz, 1H), 8.27 (d, J=8.4 Hz, 1H), 7.81 (d, J=7.9 Hz, 1H), 7.37 (d, J=8.3 Hz, 2H), 7.23-7.09 (m, 2H), 6.89 (d, J=8.8 Hz, 2H), 5.80 (d, J=7.9 Hz, 1H), 4.67-4.56 (m, 1H), 3.37 (s, 3H), 3.25-2.98 (m, 2H), 1.16 (t, J=7.1 Hz, 3H).; MS (ESI) m/z 657.27 (M+H)$^+$ (Step 2) Isopropyl N-{4-[({6-[(Ethylamino)carbonyl]pyridin-3-yl}sulfonyl)amino]-2,6-difluorobenzoyl}-4-(3-methyl-2,6-dioxo-3,6-dihydropyrimidin-1(2H)-yl)-L-phenylalaninate (B-68)

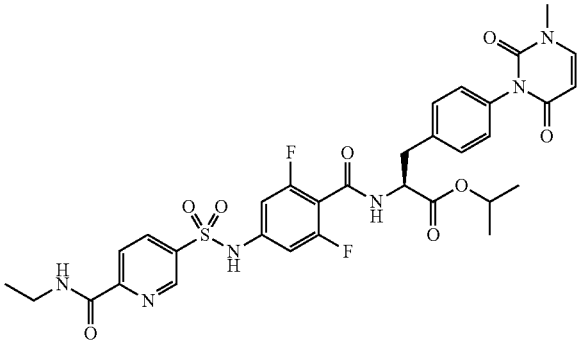 [SMILES: CCNC(=O)c1ccc(S(=O)(=O)Nc2cc(F)c(C(=O)N[C@@H](Cc3ccc(-n4c(=O)ccn(C)c4=O)cc3)C(=O)OC(C)C)c(F)c2)cn1]

$^1$H NMR (400 MHz, DMSO-d$_6$): δ 11.40 (s, 1H), 9.17 (d, J=7.5 Hz, 1H), 9.06-8.95 (m, 2H), 8.43 (d, J=8.2 Hz, 1H), 8.22 (d, J=8.4 Hz, 1H), 7.75 (d, J=8.0 Hz, 1H), 7.31 (d, J=7.9 Hz, 2H), 7.10 (d, J=7.9 Hz, 2H), 6.86 (d, J=9.3 Hz, 2H), 5.74 (d, J=7.9 Hz, 1H), 4.95-4.82 (m, 1H), 4.60-4.47 (m, 1H), 3.31 (s, 3H), 3.14-2.94 (m, 4H), 1.17 (d, J=6.5 Hz, 3H), 1.14-1.06 (m, 6H).; MS (ESI) m/z 699.28 (M+H)$^+$

Example 165

Synthesis of A-69 and Synthesis of B-69

(Step 1) N-{4-[({4-[(Cyclopentylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-69), Obtained as a Free Form

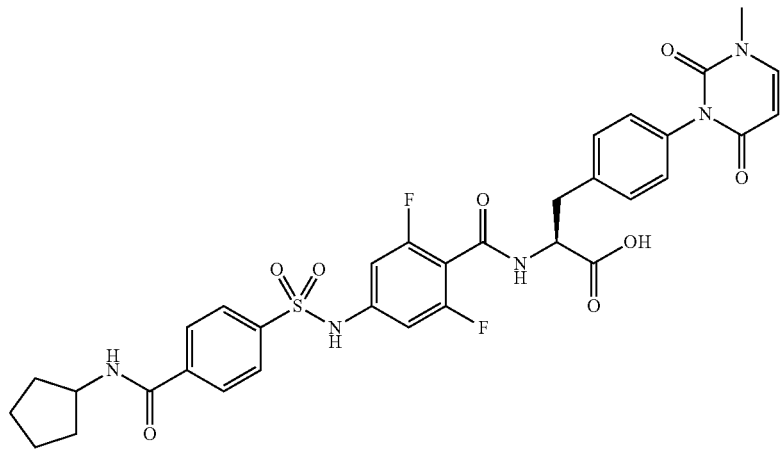 [SMILES: Cn1ccc(=O)n(-c2ccc(C[C@H](NC(=O)c3c(F)cc(NS(=O)(=O)c4ccc(C(=O)NC5CCCC5)cc4)cc3F)C(=O)O)cc2)c1=O]

$^1$H NMR (400 MHz, DMSO-d$_6$): δ 11.14 (s, 1H), 9.04 (d, J=7.8 Hz, 1H), 8.50 (d, J=7.3 Hz, 1H), 8.02-7.86 (m, 4H), 7.76 (d, J=7.8 Hz, 1H), 7.39-7.23 (m, 2H), 7.18-7.03 (m, 2H), 6.90-6.67 (m, 2H), 5.74 (d, J=7.9 Hz, 1H), 4.62-4.47 (m, 1H), 4.29-4.10 (m, 1H), 3.31 (s, 3H), 3.18-2.91 (m, 2H), 1.92-1.78 (m, 2H), 1.74-1.61 (m, 2H), 1.59-1.44 (m, 4H).; MS (ESI) m/z 696.25 (M+H)$^+$ (Step 2) Isopropyl N-{4-[({4-[(Cyclopentylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (B-69), Obtained as a Free Form

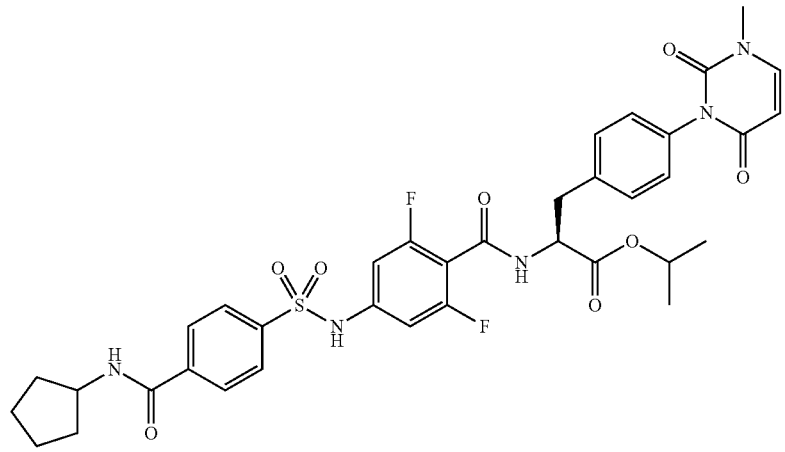 [SMILES: CC(C)OC(=O)[C@H](Cc1ccc(-n2c(=O)ccn(C)c2=O)cc1)NC(=O)c1c(F)cc(NS(=O)(=O)c2ccc(C(=O)NC3CCCC3)cc2)cc1F]

$^1$H NMR (400 MHz, DMSO-d$_6$): δ 11.11 (s, 1H), 9.08 (d, J=7.3 Hz, 1H), 8.44 (d, J=7.3 Hz, 1H), 7.98-7.81 (m, 4H), 7.68 (d, J=7.8 Hz, 1H), 7.23 (d, J=8.1 Hz, 2H), 7.02 (d, J=8.2 Hz, 2H), 6.73 (d, J=9.0 Hz, 2H), 5.67 (d, J=7.9 Hz, 1H), 4.90-4.73 (m, 1H), 4.51-4.37 (m, 1H), 4.21-4.01 (m, 1H), 3.24 (s, 3H), 3.06-2.89 (m, 2H), 1.85-1.74 (m, 2H), 1.68-1.53 (m, 2H), 1.53-1.37 (m, 4H), 1.09 (d, J=6.2 Hz, 3H), 1.04 (d, J=6.2 Hz, 3H).; MS (ESI) m/z 738.34 (M+H)$^+$

Example 166

Synthesis of A-70 and Synthesis of B-70

(Step 1) N-{4-[({4-[(Cyclopentylamino)carbonyl]phenyl}sulfonyl)amino]-2,6-difluorobenzoyl}-4-(1-methyl-2,4-dioxo-1,4-dihydropyrido[3,4-d]pyrimidin-3(2H)-yl)-L-phenylalanine (A-70), Obtained as a Free Form

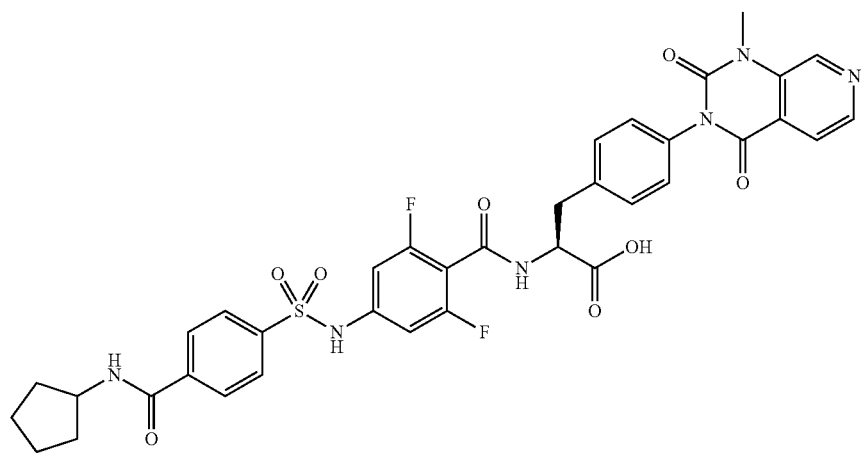 [SMILES: Cn1c(=O)n(-c2ccc(C[C@H](NC(=O)c3c(F)cc(NS(=O)(=O)c4ccc(C(=O)NC5CCCC5)cc4)cc3F)C(=O)O)cc2)c(=O)c2ccncc21]

$^1$H NMR (400 MHz, DMSO-d$_6$): δ 11.14 (s, 1H), 9.05 (d, J=7.9 Hz, 1H), 8.98 (s, 1H), 8.59-8.53 (m, 1H), 8.50 (dd, J=7.0, 3.8 Hz, 1H), 8.03-7.83 (m, 5H), 7.44-7.30 (m, 2H), 7.28-7.15 (m, 2H), 6.90-6.70 (m, 2H), 4.63-4.51 (m, 1H), 4.25-4.13 (m, 1H), 3.60 (s, 3H), 3.21-2.94 (m, 2H), 1.92-1.78 (m, 2H), 1.67 (q, J=3.8 Hz, 2H), 1.58-1.43 (m, 4H).; MS (ESI) m/z 747.27 (M+H)$^+$ (Step 2) Isopropyl N-{4-[({4-[(Cyclopentylamino)carbonyl]phenyl}sulfonyl)amino]-2,6-difluorobenzoyl}-4-(1-methyl-2,4-dioxo-1,4-dihydropyrido[3,4-d]pyrimidin-3(2H)-yl)-L-phenylalaninate (B-70)

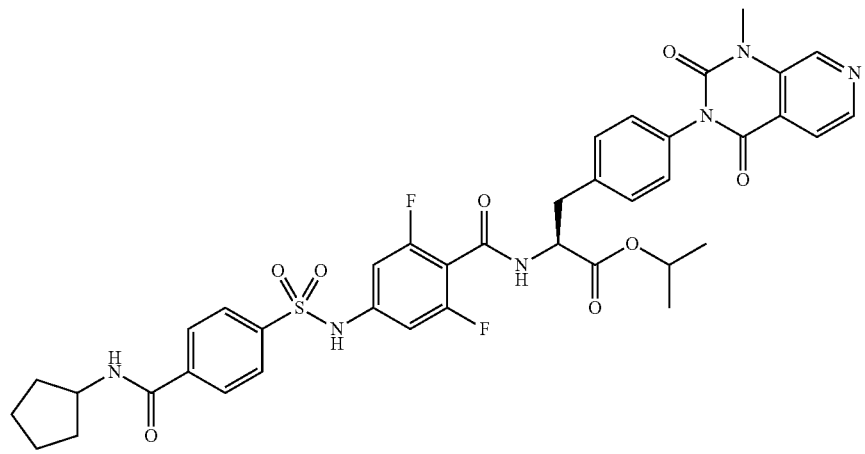 [SMILES: CC(C)OC(=O)[C@H](Cc1ccc(-n2c(=O)c3ccncc3n(C)c2=O)cc1)NC(=O)c1c(F)cc(NS(=O)(=O)c2ccc(C(=O)NC3CCCC3)cc2)cc1F]

$^1$H NMR (400 MHz, DMSO-d$_6$): δ 11.18 (s, 1H), 9.16 (d, J=7.4 Hz, 1H), 8.97 (s, 1H), 8.55 (d, J=4.9 Hz, 1H), 8.51 (d, J=7.1 Hz, 1H), 8.01-7.88 (m, 5H), 7.35 (d, J=8.3 Hz, 2H), 7.21 (d, J=8.2 Hz, 2H), 6.81 (d, J=9.0 Hz, 2H), 4.93-4.85 (m, 1H), 4.58-4.51 (m, 1H), 4.25-4.14 (m, 1H), 3.60 (s, 3H), 3.16-2.98 (m, 2H), 1.91-1.81 (m, 2H), 1.74-1.62 (m, 2H), 1.52 (td, J=6.8, 3.4 Hz, 4H), 1.17 (d, J=6.3 Hz, 3H), 1.12 (d, J=6.3 Hz, 3H).; MS (ESI) m/z 789.32 (M+H)$^+$

Example 167

Synthesis of A-71 and Synthesis of B-71

(Step 1) N-{4-[({4-[(tert-Butylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-71), Obtained as a Free Form

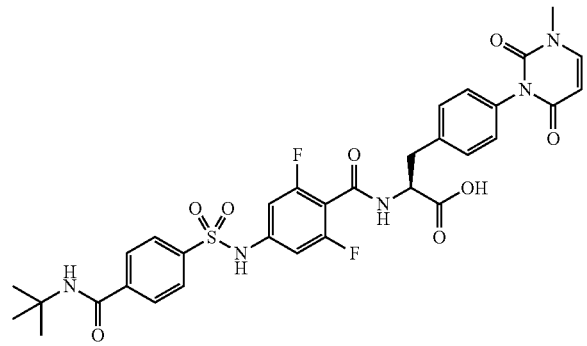 [SMILES: Cn1ccc(=O)n(-c2ccc(C[C@H](NC(=O)c3c(F)cc(NS(=O)(=O)c4ccc(C(=O)NC(C)(C)C)cc4)cc3F)C(=O)O)cc2)c1=O]

$^1$H NMR (400 MHz, DMSO-d$_6$): δ 11.14 (s, 1H), 9.04 (d, J=7.9 Hz, 1H), 8.02 (s, 1H), 7.97-7.86 (m, 4H), 7.75 (d, J=7.9 Hz, 1H), 7.35-7.25 (m, 2H), 7.15-7.05 (m, 2H), 6.78 (d, J=9.3 Hz, 2H), 5.74 (d, J=7.9 Hz, 1H), 4.60-4.49 (m, 1H), 3.31 (s, 3H), 3.17-2.92 (m, 2H), 1.35 (s, 9H).; MS (ESI) m/z 684.26 (M+H)$^+$ (Step 2) Isopropyl N-{4-[({4-[(tert-Butylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (B-71), obtained as a free form

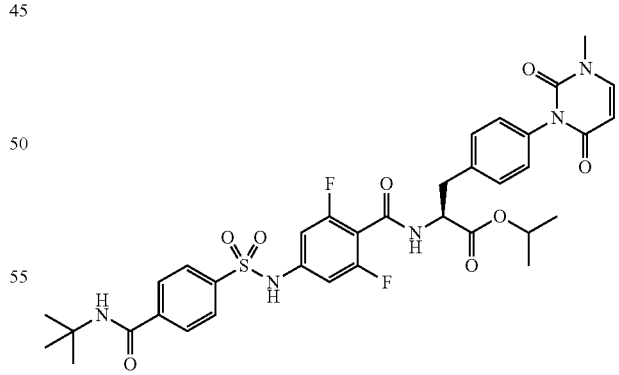

$^1$H NMR (400 MHz, DMSO-d$_6$): δ 11.10 (s, 1H), 9.08 (d, J=7.4 Hz, 1H), 7.95 (s, 1H), 7.90-7.79 (m, 4H), 7.68 (d, J=7.9 Hz, 1H), 7.27-7.20 (m, 2H), 7.07-6.99 (m, 2H), 6.73 (d, J=8.9 Hz, 2H), 5.67 (d, J=7.9 Hz, 1H), 4.91-4.75 (m, 1H), 4.52-4.37 (m, 1H), 3.23 (s, 3H), 3.08-2.88 (m, 2H), 1.28 (s, 9H), 1.09 (d, J=6.2 Hz, 3H), 1.04 (d, J=6.2 Hz, 3H).; MS (ESI) m/z 726.43 (M+H)$^+$

Example 168

Synthesis of A-72 and Synthesis of B-72

(Step 1) N-{4-[({4-[(tert-Butylamino)carbonyl]phenyl}sulfonyl)amino]-2,6-difluorobenzoyl}-4-(1-methyl-2,4-dioxo-1,4-dihydropyrido[3,4-d]pyrimidin-3(2H)-yl)-L-phenylalanine (A-72), Obtained as a Free Form

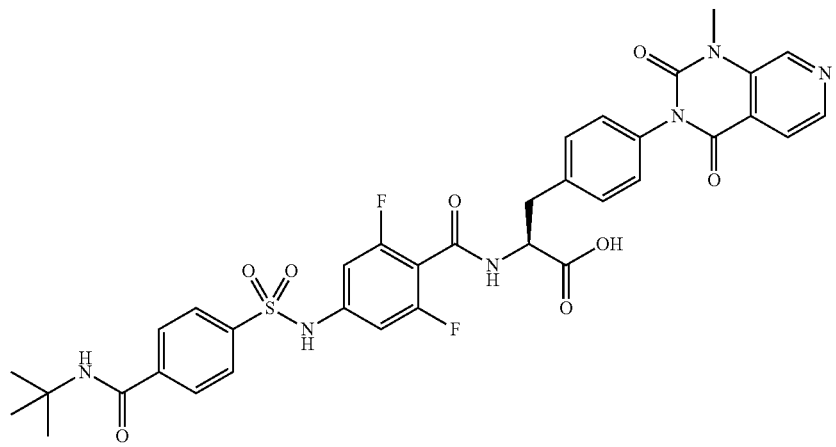 [SMILES: Cn1c(=O)n(-c2ccc(C[C@H](NC(=O)c3c(F)cc(NS(=O)(=O)c4ccc(C(=O)NC(C)(C)C)cc4)cc3F)C(=O)O)cc2)c(=O)c2ccncc21]

$^1$H NMR (400 MHz, DMSO-d$_6$): δ 11.14 (s, 1H), 9.05 (d, J=7.8 Hz, 1H), 8.97 (s, 1H), 8.55 (d, J=4.9 Hz, 1H), 8.03 (s, 1H), 7.95-7.86 (m, 5H), 7.37-7.32 (m, 2H), 7.23-7.17 (m, 2H), 6.79 (dd, J=9.1, 2.1 Hz, 2H), 4.61-4.53 (m, 1H), 3.60 (s, 3H), 3.23-2.94 (m, 2H), 1.35 (s, 9H).; MS (ESI) m/z 735.36 (M+H)$^+$ (Step 2) Isopropyl N-{4-[({4-[(tert-Butylamino)carbonyl]phenyl}sulfonyl)amino]-2,6-difluorobenzoyl}-4-(1-methyl-2,4-dioxo-1,4-dihydropyrido[3,4-d]pyrimidin-3(2H)-yl)-L-phenylalaninate (B-72)

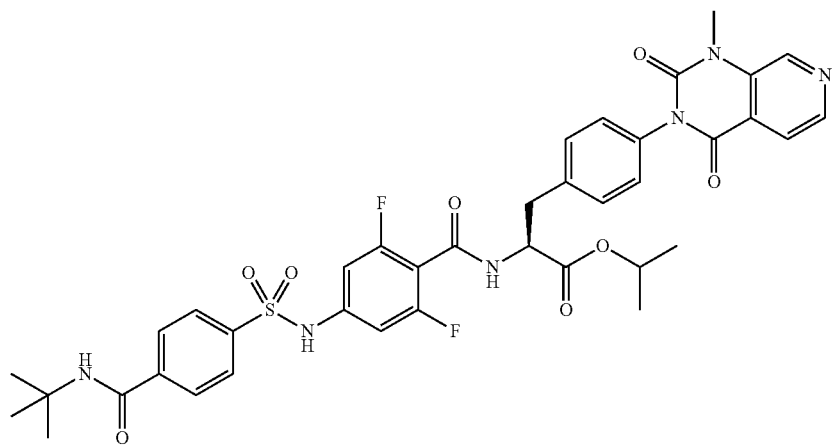 [SMILES: CC(C)OC(=O)[C@H](Cc1ccc(-n2c(=O)c3ccncc3n(C)c2=O)cc1)NC(=O)c1c(F)cc(NS(=O)(=O)c2ccc(C(=O)NC(C)(C)C)cc2)cc1F]

$^1$H NMR (400 MHz, DMSO-d$_6$): δ 11.17 (s, 1H), 9.17 (d, J=7.4 Hz, 1H), 8.97 (s, 1H), 8.56 (d, J=5.0 Hz, 1H), 8.03 (s, 1H), 7.99-7.82 (m, 5H), 7.35 (d, J=8.0 Hz, 2H), 7.22 (d, J=7.9 Hz, 2H), 6.81 (d, J=9.5 Hz, 2H), 4.97-4.84 (m, 1H), 4.61-4.49 (m, 1H), 3.60 (s, 3H), 3.18-2.98 (m, 2H), 1.36 (s, 9H), 1.18 (d, J=6.4 Hz, 3H), 1.12 (d, J=6.3 Hz, 3H).; MS (ESI) m/z 777.29 (M+H)$^+$

Example 169

Synthesis of A-73 and Synthesis of B-73

(Step 1) N-{4-[({4-[(Cyclohexylamino)carbonyl]phenyl}sulfonyl)amino]-2,6-difluorobenzoyl}-4-(3-methyl-2,6-dioxo-3,6-dihydropyrimidin-1(2H)-yl)-L-phenylalanine (A-73), Obtained as a Free Form

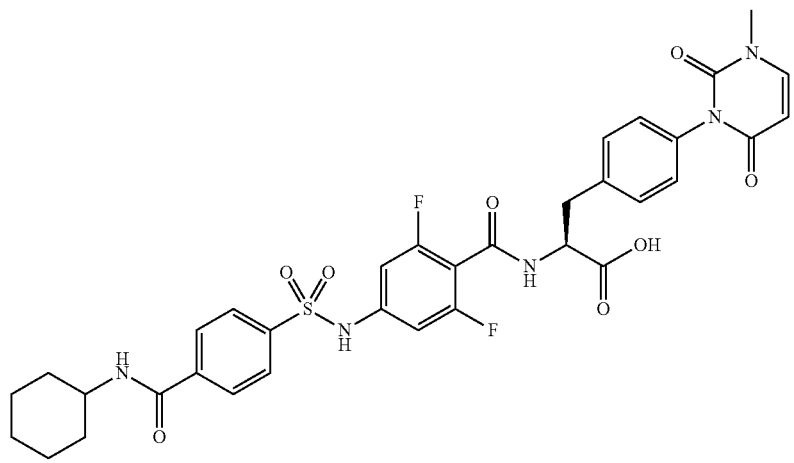 [SMILES: Cn1ccc(=O)n(-c2ccc(C[C@H](NC(=O)c3c(F)cc(NS(=O)(=O)c4ccc(C(=O)NC5CCCCC5)cc4)cc3F)C(=O)O)cc2)c1=O]

$^1$H NMR (400 MHz, DMSO-d$_6$): δ 11.14 (s, 1H), 9.04 (d, J=7.8 Hz, 1H), 8.43 (d, J=7.8 Hz, 1H), 8.03-7.85 (m, 4H), 7.75 (d, J=7.9 Hz, 1H), 7.37-7.27 (m, 2H), 7.13-7.01 (m, 2H), 6.78 (d, J=8.9 Hz, 2H), 5.74 (d, J=7.8 Hz, 1H), 4.60-4.46 (m, 1H), 3.80-3.66 (m, 1H), 3.31 (s, 3H), 3.18-2.91 (m, 2H), 1.83-1.76 (m, 2H), 1.76-1.67 (m, 2H), 1.63-1.54 (m, 1H), 1.34-1.20 (m, 4H), 1.19-1.07 (m, 1H).; MS (ESI) m/z 710.30 (M+H)$^+$ (Step 2) Isopropyl N-{4-[({4-[(Cyclohexylamino)carbonyl]phenyl}sulfonyl)amino]-2,6-difluorobenzoyl}-4-(3-methyl-2,6-dioxo-3,6-dihydropyrimidin-1(2H)-yl)-L-phenylalaninate (B-73), Obtained as a Free Form

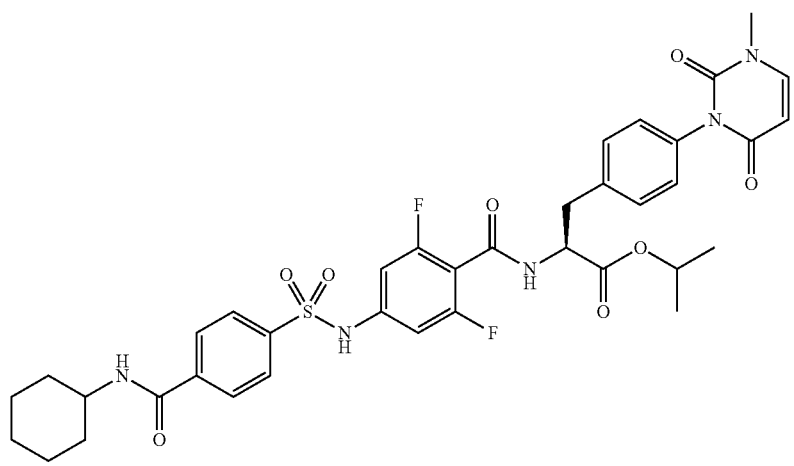 [SMILES: CC(C)OC(=O)[C@H](Cc1ccc(-n2c(=O)ccn(C)c2=O)cc1)NC(=O)c1c(F)cc(NS(=O)(=O)c2ccc(C(=O)NC3CCCCC3)cc2)cc1F]

$^1$H NMR (400 MHz, DMSO-d$_6$): δ 11.10 (s, 1H), 9.08 (d, J=7.4 Hz, 1H), 8.36 (d, J=7.9 Hz, 1H), 7.96-7.82 (m, 4H), 7.68 (d, J=7.9 Hz, 1H), 7.28-7.18 (m, 2H), 7.07-6.99 (m, 2H), 6.73 (d, J=8.9 Hz, 2H), 5.67 (d, J=7.9 Hz, 1H), 4.85-4.75 (m, 1H), 4.50-4.39 (m, 1H), 3.71-3.59 (m, 1H), 3.24 (s, 3H), 3.05-2.87 (m, 2H), 1.78-1.69 (m, 2H), 1.69-1.60 (m, 2H), 1.57-1.47 (m, 1H), 1.27-1.16 (m, 4H), 1.15-0.96 (m, 7H).; MS (ESI) m/z 752.31 (M+H)$^+$

Example 170

Synthesis of A-74 and Synthesis of B-74

(Step 1) N-(4-{[(4-{[(1-Ethylpropyl)amino]carbonyl}phenyl)sulfonyl]amino}-2,6-difluorobenzoyl)-4-(3-methyl-2,6-dioxo-3,6-dihydropyrimidin-1(2H)-yl)-L-phenylalanine (A-74), Obtained as a Free Form

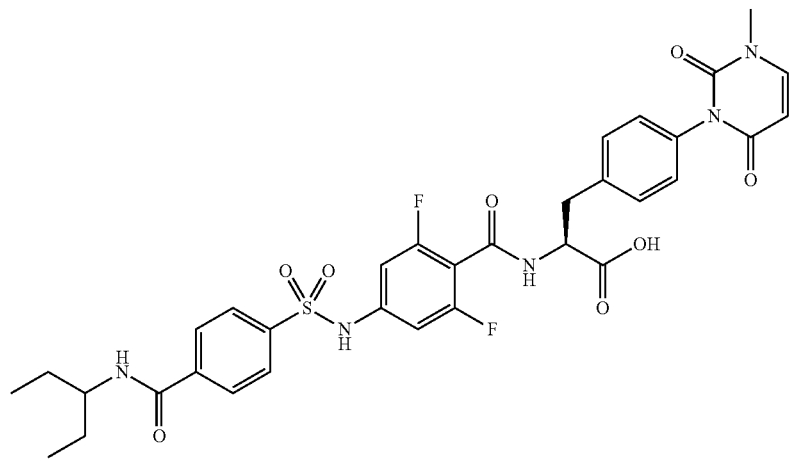 [SMILES: CCC(CC)NC(=O)c1ccc(S(=O)(=O)Nc2cc(F)c(C(=O)N[C@@H](Cc3ccc(-n4c(=O)ccn(C)c4=O)cc3)C(=O)O)c(F)c2)cc1]

$^1$H NMR (400 MHz, DMSO-$d_6$): δ 11.16 (s, 1H), 9.03 (d, J=7.9 Hz, 1H), 8.27 (d, J=8.6 Hz, 1H), 8.03-7.90 (m, 4H), 7.75 (d, J=7.9 Hz, 1H), 7.36-7.23 (m, 2H), 7.13-7.04 (m, 2H), 6.87-6.70 (m, 2H), 5.74 (d, J=7.9 Hz, 1H), 4.63-4.45 (m, 1H), 3.81-3.68 (m, 1H), 3.31 (s, 3H), 3.17-2.91 (m, 2H), 1.60-1.35 (m, 4H), 0.83 (t, J=7.4 Hz, 6H).; MS (ESI) m/z 698.38 (M+H)$^+$ (Step 2) Isopropyl N-(4-{[(4-{[(1-Ethylpropyl)amino]carbonyl}phenyl)sulfonyl]amino}-2,6-difluorobenzoyl)-4-(3-methyl-2,6-dioxo-3,6-dihydropyrimidin-1(2H)-yl)-L-phenylalaninate (B-74), Obtained as a Free Form

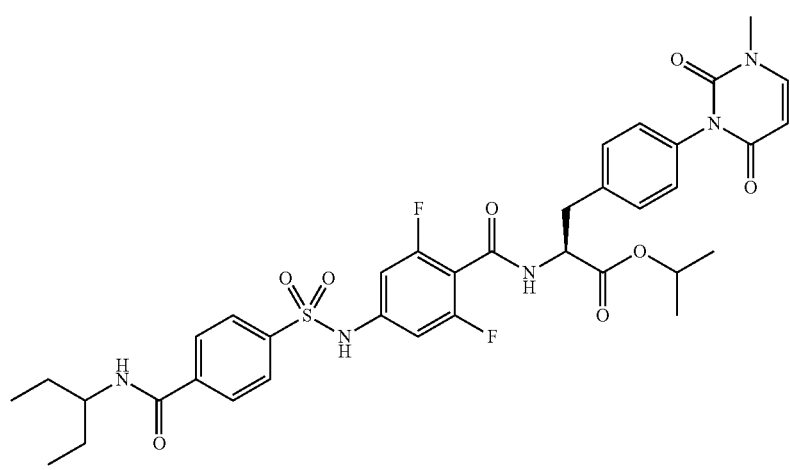 [SMILES: CCC(CC)NC(=O)c1ccc(S(=O)(=O)Nc2cc(F)c(C(=O)N[C@@H](Cc3ccc(-n4c(=O)ccn(C)c4=O)cc3)C(=O)OC(C)C)c(F)c2)cc1]

$^1$H NMR (400 MHz, DMSO-$d_6$): δ 11.12 (s, 1H), 9.08 (d, J=7.4 Hz, 1H), 8.20 (d, J=8.7 Hz, 1H), 7.98-7.80 (m, 4H), 7.68 (d, J=7.9 Hz, 1H), 7.31-7.19 (m, 2H), 7.07-6.93 (m, 2H), 6.80-6.61 (m, 2H), 5.67 (d, J=7.9 Hz, 1H), 4.92-4.71 (m, 1H), 4.51-4.32 (m, 1H), 3.79-3.58 (m, 1H), 3.24 (s, 3H), 3.07-2.88 (m, 2H), 1.54-1.27 (m, 4H), 1.09 (d, J=6.2 Hz, 3H), 1.03 (d, J=6.2 Hz, 3H), 0.77 (t, J=7.4 Hz, 6H).; MS (ESI) m/z 740.35 (M+H)$^+$

Example 171

Synthesis of A-75 and Synthesis of B-75

(Step 1) N-{2,6-Difluoro-4-[(pyridin-4-yl-sulfonyl)amino]benzoyl}-4-(3-methyl-2,6-dioxo-3,6-dihydro-pyrimidin-1(2H)-yl)-L-phenylalanine (A-75), Obtained as a Free Form

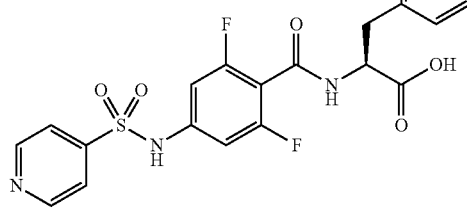

$^1$H NMR (400 MHz, DMSO-d$_6$): δ 11.39 (s, 1H), 9.07 (d, J=7.8 Hz, 1H), 8.96-8.82 (m, 2H), 7.80 (dd, J=4.4, 1.7 Hz, 2H), 7.76 (d, J=7.9 Hz, 1H), 7.37-7.29 (m, 2H), 7.13-7.05 (m, 2H), 6.81 (d, J=8.9 Hz, 2H), 5.75 (d, J=7.8 Hz, 1H), 4.62-4.51 (m, 1H), 3.31 (s, 3H), 3.19-2.93 (m, 2H).; MS (ESI) m/z 586.33 (M+H)$^+$ (Step 2) Isopropyl N-{2,6-Difluoro-4-[(pyridin-4-yl-sulfonyl)amino]benzoyl}-4-(3-methyl-2,6-dioxo-3,6-dihydropyrimidin-1(2H)-yl)-L-phenyl alaninate (B-75)

$^1$H NMR (400 MHz, DMSO-d$_6$): δ 11.34 (s, 1H), 9.11 (d, J=7.4 Hz, 1H), 8.82 (d, J=5.0 Hz, 2H), 7.74 (d, J=4.9 Hz, 2H), 7.68 (d, J=7.9 Hz, 1H), 7.24 (d, J=7.9 Hz, 2H), 7.03 (d, J=7.9 Hz, 2H), 6.76 (d, J=9.0 Hz, 2H), 5.67 (d, J=7.8 Hz, 1H), 4.90-4.72 (m, 1H), 4.53-4.37 (m, 1H), 3.24 (s, 3H), 3.08-2.89 (m, 2H), 1.10 (d, J=6.3 Hz, 3H), 1.04 (d, J=6.3 Hz, 3H).; MS (ESI) m/z 628.38 (M+H)$^+$

Example 172

Synthesis of A-76 and Synthesis of B-76

(Step 1) N-(2,6-Difluoro-4-{[(4-{[(tetrahydro-2H-pyran-4-yl-methyl)amino]carbonyl}phenyl)sulfonyl]amino}benzoyl)-4-(3-methyl-2,6-dioxo-3,6-dihydropyrimidin-1(2H)-yl)-L-phenylalanine (A-76), Obtained as a Free Form $^1$H NMR (400 MHz, DMSO-d$_6$): δ 11.17 (s, 1H), 9.04 (d, J=7.8 Hz, 1H), 8.69 (t, J=6.0 Hz, 1H), 8.02-7.84 (m, 4H), 7.75 (d, J=7.9 Hz, 1H), 7.31 (d, J=8.1 Hz, 2H), 7.09 (d, J=7.8 Hz, 2H), 6.79 (d, J=9.2 Hz, 2H), 5.75 (d, J=7.8 Hz, 1H), 4.62-4.48 (m, 1H), 3.91-3.75 (m, 4H), 3.33 (s, 3H), 3.28-3.20 (m, 2H), 3.19-2.92 (m, 2H), 1.74 (s, 1H), 1.56 (s, 2H), 1.19 (s, 2H).;
MS (ESI) m/z 726 (M+H)$^+$

Example 173

Synthesis of A-77 and Synthesis of B-77

(Step 1) N-{4-[({6-[(tert-Butylamino)carbonyl]pyridin-3-yl}sulfonyl)amino]-2,6-difluorobenzoyl}-4-(3-methyl-2,6-dioxo-3,6-dihydropyrimidin-1(2H)-yl)-L-phenylalanine (A-77), Obtained as a Free Form

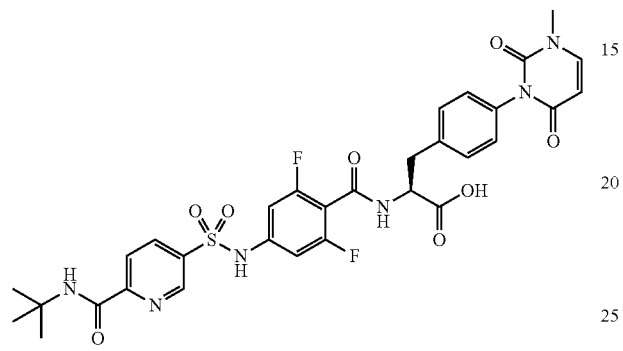

$^1$H NMR (400 MHz, DMSO-d$_6$): δ 11.38 (s, 1H), 9.04 (d, J=7.8 Hz, 1H), 9.01 (dd, J=2.4, 0.8 Hz, 1H), 8.42 (dd, J=8.3, 2.3 Hz, 1H), 8.20 (dd, J=8.4, 0.7 Hz, 1H), 8.11 (s, 1H), 7.75 (d, J=7.9 Hz, 1H), 7.35-7.27 (m, 2H), 7.13-7.04 (m, 2H), 6.83 (d, J=8.8 Hz, 2H), 5.74 (d, J=7.9 Hz, 1H), 4.61-4.50 (m, 1H), 3.30 (s, 3H), 3.18-2.92 (m, 2H), 1.38 (s, 9H).; MS (ESI) m/z 685.46 (M+H)$^+$ (Step 2) Isopropyl N-{4-[({6-[(tert-Butylamino)carbonyl]pyridin-3-yl}sulfonyl)amino]-2,6-difluorobenzoyl}-4-(3-methyl-2,6-dioxo-3,6-dihydropyrimidin-1(2H)-yl)-L-phenylalaninate (B-77)

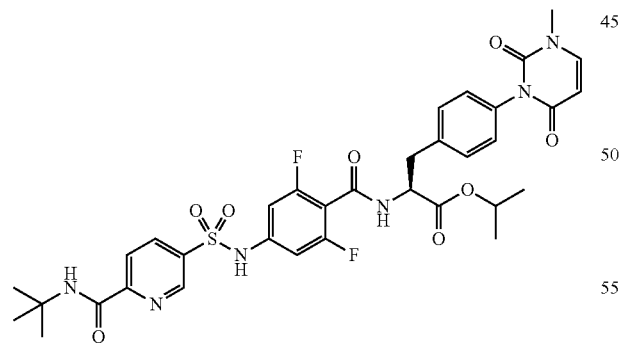

$^1$H NMR (400 MHz, DMSO-d$_6$): δ 11.40 (s, 1H), 9.15 (d, J=7.4 Hz, 1H), 9.08-8.96 (m, 1H), 8.43 (dd, J=8.3, 2.4 Hz, 1H), 8.23-8.17 (m, 1H), 8.11 (s, 1H), 7.75 (d, J=7.9 Hz, 1H), 7.37-7.24 (m, 2H), 7.13-7.05 (m, 2H), 6.84 (d, J=8.8 Hz, 2H), 5.74 (d, J=7.9 Hz, 1H), 4.99-4.78 (m, 1H), 4.62-4.40 (m, 1H), 3.31 (s, 3H), 3.12-2.95 (m, 2H), 1.39 (s, 9H), 1.17 (d, J=6.2 Hz, 3H), 1.11 (d, J=6.2 Hz, 3H).; MS (ESI) m/z 727.54 (M+H)$^+$

Example 174

Synthesis of A-78 and Synthesis of B-78

(Step 1) N-[4-({[4-(Cyclopropylcarbonyl)phenyl]sulfonyl}amino)-2,6-difluorobenzoyl]-4-(3-methyl-2,6-dioxo-3,6-dihydropyrimidin-1(2H)-yl)-L-phenylalanine (A-78), Obtained as a Free Form

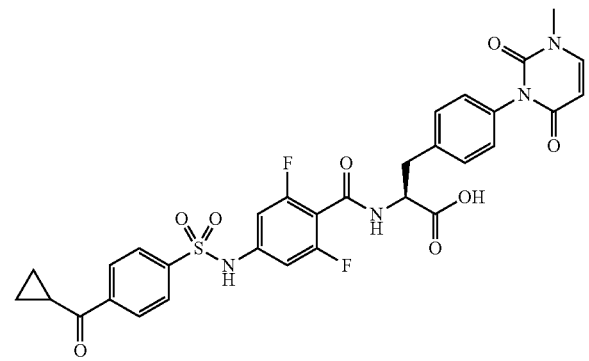 [SMILES: Cn1ccc(=O)n(-c2ccc(C[C@H](NC(=O)c3c(F)cc(NS(=O)(=O)c4ccc(C(=O)C5CC5)cc4)cc3F)C(=O)O)cc2)c1=O]

$^1$H NMR (400 MHz, DMSO-d$_6$): δ 11.23 (s, 1H), 9.03 (d, J=7.8 Hz, 1H), 8.29-8.14 (m, 2H), 8.06-7.94 (m, 2H), 7.75 (d, J=7.9 Hz, 1H), 7.40-7.25 (m, 2H), 7.14-7.03 (m, 2H), 6.79 (d, J=9.1 Hz, 2H), 5.74 (d, J=7.9 Hz, 1H), 4.62-4.45 (m, 1H), 3.31 (s, 3H), 3.17-2.93 (m, 2H), 2.91-2.85 (m, 1H), 1.12-1.02 (m, 4H).;

MS (ESI) m/z 653.41 (M+H)$^+$ (Step 2) Isopropyl N-[4-({[4-(Cyclopropylcarbonyl)phenyl]sulfonyl}amino)-2,6-difluorobenzoyl]-4-(3-methyl-2,6-dioxo-3,6-dihydropyrimidin-1(2H)-yl)-L-phenylalaninate (B-78), Obtained as a Free Form

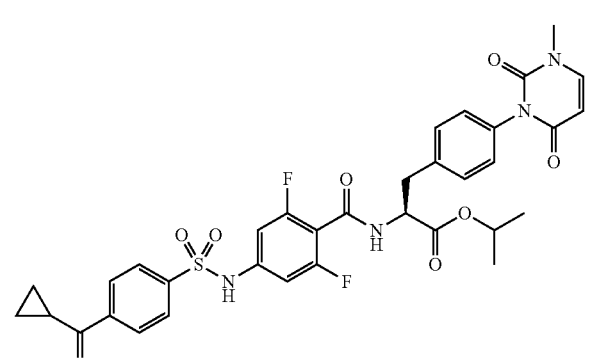

$^1$H NMR (400 MHz, DMSO-d$_6$): δ 11.19 (s, 1H), 9.07 (d, J=7.4 Hz, 1H) 8.18-8.12 (m, 2H), 7.98-7.90 (m, 2H), 7.68 (d, J=7.9 Hz, 1H) 7.27-7.20 (m, 2H), 7.06-6.98 (m, 2H), 6.74 (d, J=9.2 Hz, 2H) 5.67 (d, J=7.9 Hz, 1H), 4.88-4.74 (m, 1H), 4.51-4.36 (m, 1H), 3.24 (s, 3H), 3.06-2.89 (m, 2H), 2.86-2.77 (m, 1H), 1.09 (d, J=6.3 Hz, 3H), 1.06-0.95 (m, 7H).; MS (ESI) m/z 695.46 (M+H)$^+$

Example 175

Synthesis of A-79 and Synthesis of B-79

(Step 1) N-{4-[({6-[(tert-Butylamino)carbonyl]pyridin-3-yl}sulfonyl)amino]-2-fluorobenzoyl}-4-(3,5-dimethyl-2,6-dioxo-3,6-dihydropyrimidin-1(2H)-yl)-L-phenylalanine (A-79), Obtained as a Free Form

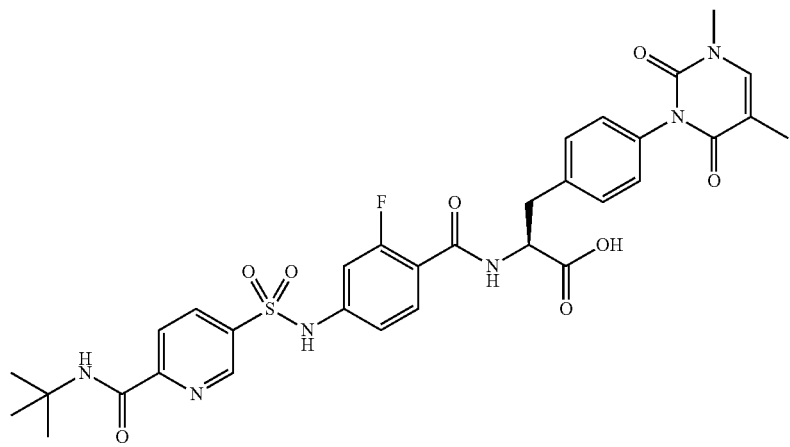 [SMILES: Cc1cn(C)c(=O)n(-c2ccc(C[C@H](NC(=O)c3ccc(NS(=O)(=O)c4ccc(C(=O)NC(C)(C)C)nc4)cc3F)C(=O)O)cc2)c1=O]

$^1$H NMR (400 MHz, DMSO-d$_6$): δ 11.21 (s, 1H), 8.96 (dd, J=2.3, 0.8 Hz, 1H), 8.45-8.35 (m, 2H), 8.18 (dd, J=8.3, 0.8 Hz, 1H), 8.09 (s, 1H), 7.66 (q, J=1.0 Hz, 1H), 7.43 (t, J=8.2 Hz, 1H), 7.35-7.25 (m, 2H), 7.12-7.05 (m, 2H), 7.04-6.91 (m, 2H), 4.64-4.52 (m, 1H), 3.28 (s, 3H), 3.23-2.99 (m, 2H), 1.82 (d, J=1.2 Hz, 3H), 1.38 (s, 9H).; MS (ESI) m/z 681.54 (M+H)$^+$ (Step 2) Isopropyl N-{4-[({6-[(tert-Butylamino)carbonyl]pyridin-3-yl}sulfonyl)amino]-2-fluorobenzoyl}-4-(3,5-dimethyl-2,6-dioxo-3,6-dihydropyrimidin-1(2H)-yl)-L-phenylalaninate (B-79)

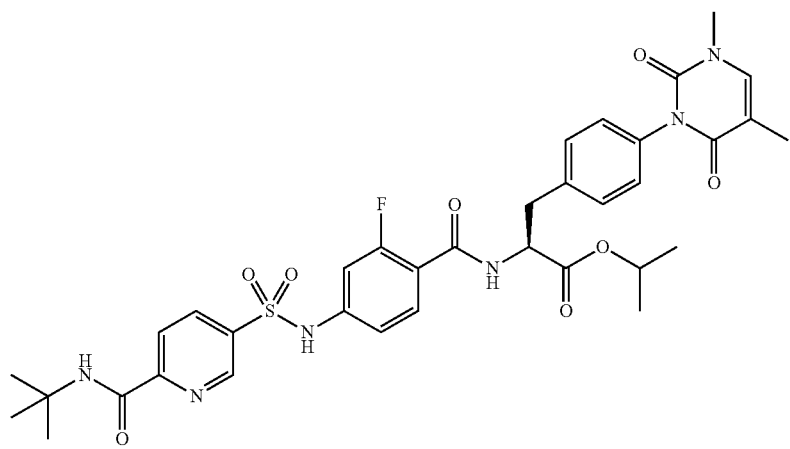 [SMILES: Cc1cn(C)c(=O)n(-c2ccc(C[C@H](NC(=O)c3ccc(NS(=O)(=O)c4ccc(C(=O)NC(C)(C)C)nc4)cc3F)C(=O)OC(C)C)cc2)c1=O]

$^1$H NMR (400 MHz, DMSO-d$_6$): δ 11.23 (s, 1H), 8.97 (dd, J=2.4, 0.8 Hz, 1H), 8.57 (dd, J=7.5, 2.2 Hz, 1H), 8.39 (dd, J=8.3, 2.3 Hz, 1H), 8.18 (dd, J=8.3, 0.8 Hz, 1H), 8.09 (s, 1H), 7.66 (q, J=1.0 Hz, 1H), 7.41 (t, J=8.4 Hz, 1H), 7.36-7.26 (m, 2H), 7.14-7.04 (m, 2H), 7.04-6.94 (m, 2H), 4.88 (dt, J=12.5, 6.2 Hz, 1H), 4.61-4.49 (m, 1H), 3.28 (s, 3H), 3.16-3.02 (m, 2H), 1.82 (d, J=1.2 Hz, 3H), 1.38 (s, 9H), 1.17 (d, J=6.2 Hz, 3H), 1.12 (d, J=6.2 Hz, 3H).; MS (ESI) m/z 723.54 (M+H)$^+$

Example 176

Synthesis of A-80 and Synthesis of B-80

(Step 1) tert-Butyl 4-Bromo-2,6-difluorobenzoate, Obtained as a Free Form

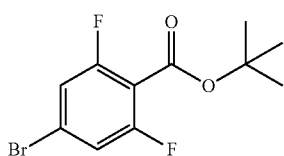 [SMILES: CC(C)(C)OC(=O)c1c(F)cc(Br)cc1F]

To 4-Bromo-2,6-difluoro-benzene carboxylic acid (2.37 g, 10.0 mmol), tert-butanol (20 ml), (Boc)$_2$O (6.55 g, 30.0 mmol), and DMAP (122 mg, 1.00 mmol) were added, followed by stirring at 40° C. for 16 hours. The reaction liquid was concentrated under reduced pressure, and then petroleum ether (100 ml) was added thereto, followed by filtration. The mother liquor was washed with water and then concentrated to obtain the title compound (2.12 g, 72%).

(Step 2) tert-Butyl 4-Amino-2,6-difluorobenzoate

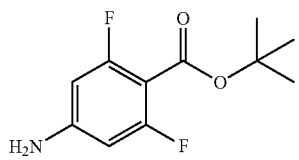

To tert-butyl 4-bromo-2,6-difluorobenzoate (1.47 g, 5.00 mmol), DMA (10 ml), copper(I) chloride (990 mg, 10.0 mmol), triethylamine (1.74 ml, 12.5 mmol), and TMSN3 (1.32 ml, 10.0 mmol) were added, followed by stirring at 100° C. for 16 hours. To the reaction liquid, water was added, followed by extraction with ethyl acetate (10 ml×3). After concentration under reduced pressure, the residue was purified by reversed-phase HPLC (H$_2$O containing 0.1% TFA/CH$_3$CN system), followed by freeze-drying, to obtain a TFA salt (810 mg, 71%) of the title compound.

MS (ESI) m/z 230 (M+H)$^+$ (Step 3) 2,6-Difluoro-4-{[(4-formylphenyl)sulfonyl]amino}benzoic Acid, Obtained as a Free Form

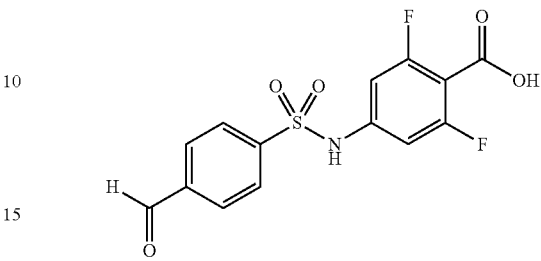

To tert-butyl 4-amino-2,6-difluorobenzoate (229 mg, 1.00 mmol), dichloromethane (10.0 ml), 4-formyl-benzenesulfonyl chloride (205 mg, 1.00 mmol), and pyridine (243 µl, 3.00 mmol) were added, followed by stirring at room temperature for 16 hours. After the mixture was concentrated under reduced pressure, trifluoroacetic acid (5.0 ml) was added thereto, followed by stirring at room temperature for 1 hour. Then, purification was conducted by reversed-phase HPLC (H$_2$O containing 0.1% TFA/CH$_3$CN system), followed by freeze-drying, to obtain the title compound (90.0 mg, 26% over two steps).

MS (ESI) m/z 342 (M+H)$^+$ (Step 4) Methyl N-(2,6-Difluoro-4-{[(4-formylphenyl)sulfonyl]amino}benzoyl)-4-(3-methyl-2,6-dioxo-3,6-dihydropyrimidin-1(2H)-yl)-L-phenylalaninate, Obtained as a Free Form

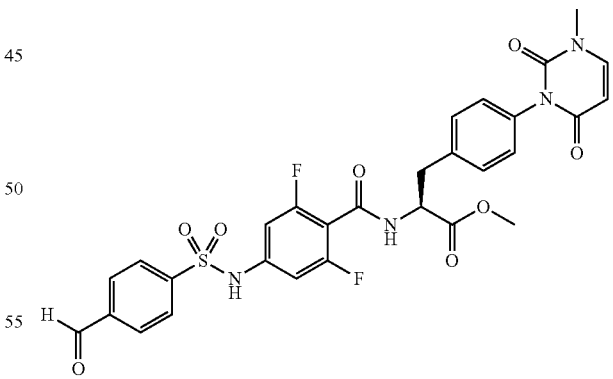

2-Amino-3-[4-(3-methyl-2,6-dioxo-3,6-dihydro-2H-pyrimidin-1-yl)-phenyl]-propionic acid methyl ester (68 mg, 0.20 mmol) and 2,6-difluoro-4-{[(4-formylphenyl)sulfonyl]amino}benzoic acid (61 mg, 0.20 mmol) were suspended in dichloromethane (5.0 ml), and HATU (114 mg, 0.300 mmol), HOAt (41 mg, 0.30 mmol), and triethylamine (56 µl, 0.40 mmol) were added thereto, followed by stirring at room temperature for 2 hours. After the reaction liquid was concentrated under reduced pressure, purification was conducted by reversed-phase HPLC (H₂O containing 0.1% TFA/CH₃CN system), followed by freeze-drying, to obtain the title compound (32 mg, 25%).

MS (ESI) m/z 627 (M+H)⁺

(Step 5) Methyl N-{2,6-Difluoro-4-[({4-[(methylamino)methyl]phenyl}sulfonyl)amino]benzoyl}-4-(3-methyl-2,6-dioxo-3,6-dihydropyrimidin-1 (2H)-yl)-L-phenylalaninate

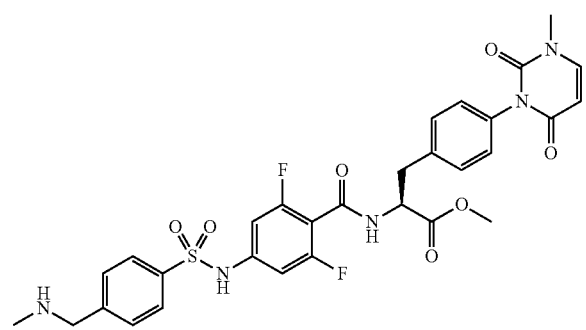 [SMILES: CNCc1ccc(S(=O)(=O)Nc2cc(F)c(C(=O)N[C@@H](Cc3ccc(-n4c(=O)ccn(C)c4=O)cc3)C(=O)OC)c(F)c2)cc1]

To methyl N-(2,6-difluoro-4-{[(4-formylphenyl)sulfonyl]amino}benzoyl)-4-(3-methyl-2,6-dioxo-3,6-dihydropyrimidin-1(2H)-yl)-L-phenylalaninate (31.3 mg, 0.050 mmol), ethanol (3.0 ml), acetic acid (6.0 mg, 0.10 mmol), a 40% aqueous methylamine solution (7.80 mg, 0.100 mmol), and NaCNBH₄ (15.7 mg, 0.250 mmol) were added, followed by stirring at room temperature for 2 hours. After water (5.0 ml) was added thereto, purification was conducted by reversed-phase HPLC (H₂O containing 0.1% TFA/CH₃CN system), followed by freeze-drying, to obtain a TFA salt (10.0 mg, 27%) of the title compound.

MS (ESI) m/z 642 (M+H)⁺

(Step 6) N-{2,6-Difluoro-4-[({4-[(methylamino)methyl]phenyl}sulfonyl)amino]benzoyl}-4-(3-methyl-2,6-dioxo-3,6-dihydropyrimidin-1(2H)-yl)-L-phenylalanine (A-80), Obtained as a Free Form

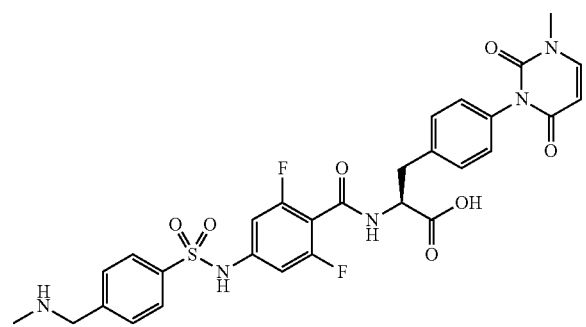 [SMILES: CNCc1ccc(S(=O)(=O)Nc2cc(F)c(C(=O)N[C@@H](Cc3ccc(-n4c(=O)ccn(C)c4=O)cc3)C(=O)O)c(F)c2)cc1]

To methyl N-{2,6-difluoro-4-[({4-[(methylamino)methyl]phenyl}sulfonyl)amino]benzoyl}-4-(3-methyl-2,6-dioxo-3,6-dihydropyrimidin-1(2H)-yl)-L-phenylalaninate <see (Step 5)>, a 4 N hydrochloric acid/1,4-dioxane solution (2.0 ml) and water (4.0 ml) were added, followed by stirring at 50° C. for 6 hours. After the reaction liquid was concentrated under reduced pressure, purification was conducted by reversed-phase HPLC (H₂O containing 0.1% TFA/CH₃CN system), followed by freeze-drying, to obtain the title compound (5.0 mg, 51%).

¹H NMR (400 MHz, DMSO-d₆): δ 11.16 (s, 1H), 9.07 (d, J=7.9 Hz, 1H), 8.76 (s, 1H), 7.94 (d, J=8.5 Hz, 2H), 7.76 (d, J=7.9 Hz, 1H), 7.67 (d, J=8.5 Hz, 2H), 7.31 (d, J=8.4 Hz, 2H), 7.09 (d, J=8.4 Hz, 2H), 6.78 (d, J=9.1 Hz, 2H), 5.74 (d, J=7.9 Hz, 1H), 4.59-4.49 (m, 1H), 4.18 (s, 2H), 3.31 (s, 3H), 3.16-3.10 (m, 1H), 2.98 (dd, J=10.2, 3.9 Hz, 1H), 2.58 (s, 3H).; MS (ESI) m/z 628.38 (M+H)⁺

(Step 7) Cyclohexylmethyl N-{2,6-Difluoro-4-[({4-[(methylamino)methyl]phenyl}sulfonyl)amino]benzoyl}-4-(3-methyl-2,6-dioxo-3,6-dihydropyrimidin-1 (2H)-yl)-L-phenylalaninate (B-80)

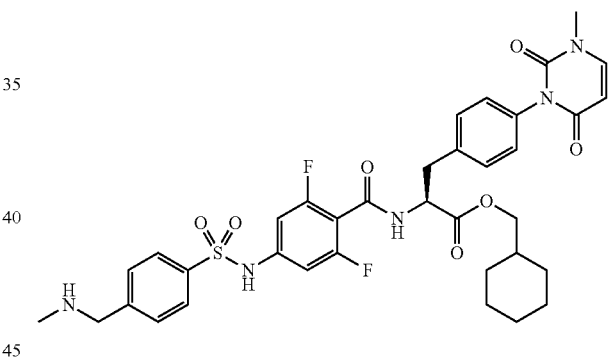

To N-{2,6-difluoro-4-[({4-[(methylamino)methyl]phenyl}sulfonyl)amino]benzoyl}-4-(3-methyl-2,6-dioxo-3,6-dihydropyrimidin-1(2H)-yl)-L-phenylalanine (A-80) (3.2 mg, 0.005 mmol), a 4 N hydrochloric acid/1,4-dioxane solution (2.0 ml) and cyclohexanemethanol (4.0 ml) were added, followed by stirring at 70° C. for 6 hours. After the reaction liquid was concentrated under reduced pressure, purification was conducted by reversed-phase HPLC (H₂O containing 0.1% TFA/CH₃CN system), followed by freeze-drying, to obtain a TFA salt (1.6 mg, 38%) of the title compound.

¹H NMR (400 MHz, DMSO-d₆): δ 11.18 (s, 1H), 9.19 (d, J=7.6 Hz, 1H), 8.77 (s, 1H), 7.94 (d, J=8.4 Hz, 2H), 7.75 (d, J=7.9 Hz, 1H), 7.67 (d, J=8.4 Hz, 2H), 7.30 (d, J=8.4 Hz, 2H), 7.10 (d, J=8.4 Hz, 2H), 6.79 (d, J=9.1 Hz, 2H), 5.74 (d, J=7.9 Hz, 1H), 4.65-4.56 (m, 1H), 4.18 (s, 2H), 3.87 (dd, J=6.4, 1.4 Hz, 2H), 3.31 (s, 3H), 3.13 (dd, J=14.2, 5.1 Hz, 1H), 3.00 (dd, J=14.2, 9.6 Hz, 1H), 2.58 (s, 3H), 1.62 (m, 5H), 1.32-1.02 (m, 4H), 1.00-0.85 (m, 2H).; MS (ESI) m/z 724.58 (M+H)⁺

Example 177

Synthesis of A-81 and Synthesis of B-81

(Step 1) N-{2-Fluoro-4-[({4-[(methylamino)methyl]phenyl}sulfonyl)amino]benzoyl}-3-[5-(1-methyl-2,4-dioxo-1,4-dihydropyrido[3,4-d]pyrimidin-3(2H)-yl)pyridin-2-yl]-L-alanine (A-81)

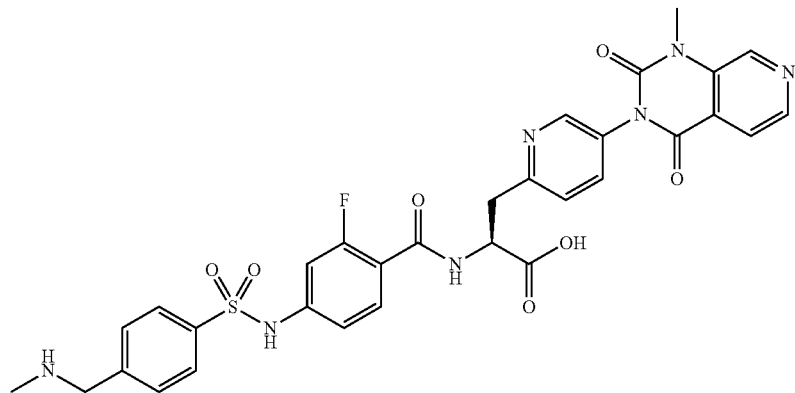 [SMILES: CNCc1ccc(S(=O)(=O)Nc2ccc(C(=O)N[C@@H](Cc3ccc(-n4c(=O)c5ccncc5n(C)c4=O)cn3)C(=O)O)c(F)c2)cc1]

$^1$H NMR (400 MHz, DMSO-$d_6$): δ 11.02 (s, 1H), 9.01 (s, 1H), 8.73 (s, 1H), 8.61-8.54 (m, 2H), 8.45 (d, J=2.4 Hz, 1H), 7.94-7.88 (m, 3H), 7.72 (dd, J=8.2, 2.5 Hz, 1H), 7.68-7.62 (m, 2H), 7.51 (t, J=8.4 Hz, 1H), 7.44 (d, J=8.3 Hz, 1H), 7.05-6.92 (m, 2H), 4.92-4.82 (m, 1H), 4.17 (t, J=6.1 Hz, 2H), 3.62 (s, 3H), 2.56 (t, J=5.4 Hz, 3H).; MS (ESI) m/z 662.41 (M+H)$^+$ (Step 2) Isopropyl N-{2-Fluoro-4-[({4-[(methylamino)methyl]phenyl}sulfonyl)amino]benzoyl}-3-[5-(1-methyl-2,4-dioxo-1,4-dihydropyrido[3,4-d]pyrimidin-3(2H)-yl)pyridin-2-yl]-L-alaninate (B-81)

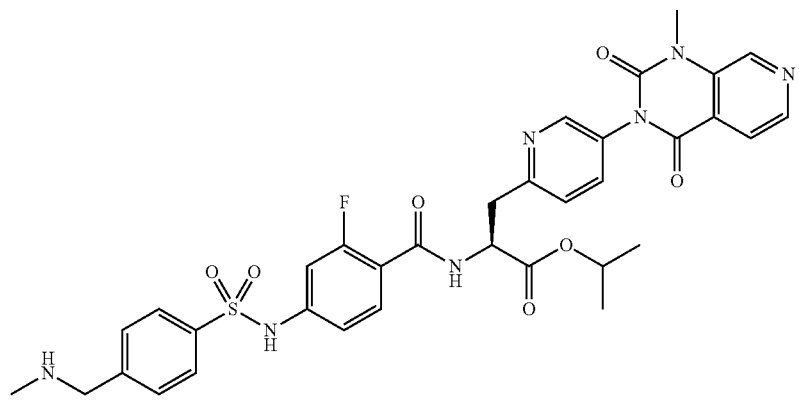 [SMILES: CNCc1ccc(S(=O)(=O)Nc2ccc(C(=O)N[C@@H](Cc3ccc(-n4c(=O)c5ccncc5n(C)c4=O)cn3)C(=O)OC(C)C)c(F)c2)cc1]

MS (ESI) m/z 704.74 (M+H)$^+$

Example 178

Synthesis of A-82 and Synthesis of B-82

(Step 1) N-[2,6-Difluoro-4-({[4-(3-thienyl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alanine (A-82)

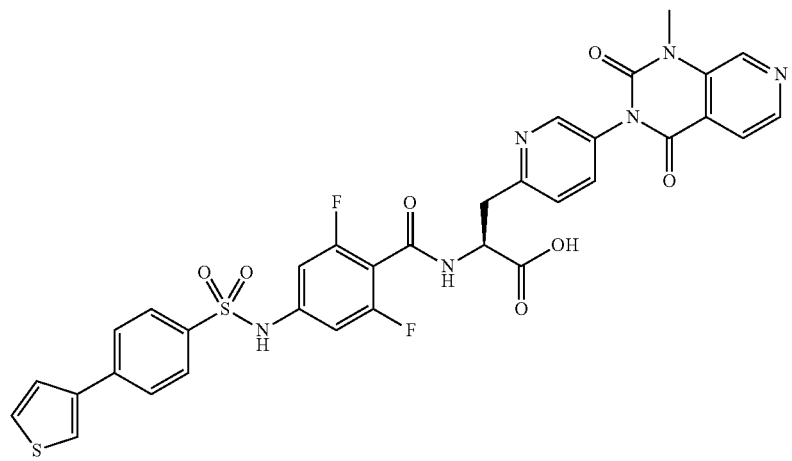 [SMILES: Cn1c(=O)n(-c2ccc(C[C@H](NC(=O)c3c(F)cc(NS(=O)(=O)c4ccc(-c5ccsc5)cc4)cc3F)C(=O)O)nc2)c(=O)c2ccncc21]

$^1$H NMR (400 MHz, DMSO-$d_6$): δ 11.07 (s, 1H), 9.04-8.97 (m, 2H), 8.58 (d, J=4.9 Hz, 1H), 8.45 (d, J=2.4 Hz, 1H), 8.08 (dd, J=2.9, 1.3 Hz, 1H), 7.99-7.93 (m, 2H), 7.91 (d, J=5.0 Hz, 1H), 7.89-7.83 (m, 2H), 7.76-7.66 (m, 2H), 7.62 (dd, J=5.1, 1.4 Hz, 1H), 7.42 (d, J=8.3 Hz, 1H), 6.80 (d, J=9.1 Hz, 2H), 4.89-4.79 (m, 1H), 3.61 (s, 3H), 3.32 (dd, J=14.5, 5.0 Hz, 1H), 3.14 (dd, J=14.5, 9.4 Hz, 1H).; MS (ESI) m/z 719.33 (M+H)$^+$ (Step 2) Cyclohexyl N-[2,6-Difluoro-4-({[4-(3-thienyl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alaninate (B-82)

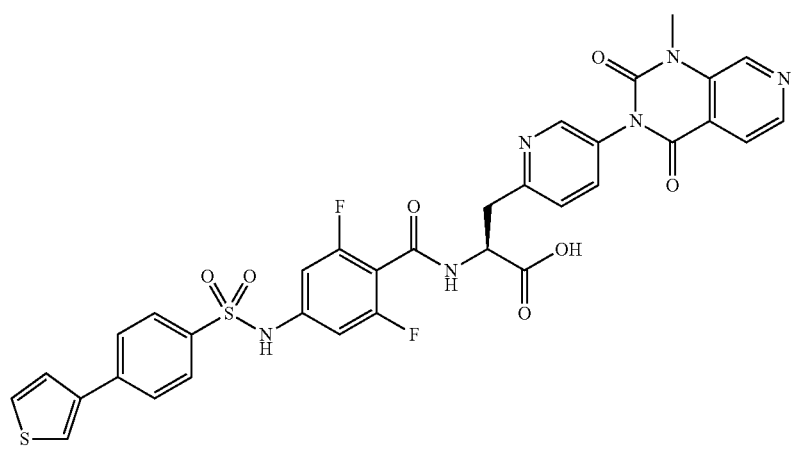 [SMILES: Cn1c(=O)n(-c2ccc(C[C@H](NC(=O)c3c(F)cc(NS(=O)(=O)c4ccc(-c5ccsc5)cc4)cc3F)C(=O)O)nc2)c(=O)c2ccncc21]

$^1$H NMR (400 MHz, DMSO-$d_6$): δ 11.09 (s, 1H), 9.11 (d, J=7.6 Hz, 1H), 9.00 (s, 1H), 8.58 (d, J=4.9 Hz, 1H), 8.44 (d, J=2.4 Hz, 1H), 8.08 (dd, J=2.9, 1.3 Hz, 1H), 7.99-7.93 (m, 2H), 7.93-7.84 (m, 3H), 7.75-7.66 (m, 2H), 7.62 (dd, J=5.2, 1.3 Hz, 1H), 7.42 (d, J=8.3 Hz, 1H), 6.81 (d, J=9.1 Hz, 2H), 4.91-4.81 (m, 1H), 4.72-4.63 (m, 1H), 3.61 (s, 3H), 3.33-3.12 (m, 2H), 1.77-1.56 (m, 4H), 1.52-1.11 (m, 6H).; MS (ESI) m/z 801.59 (M+H)$^+$

Example 179

Synthesis of A-83 and Synthesis of B-83

(Step 1) (2S)-2-[[2-Fluoro-4-[(1-oxidopyridin-1-ium-4-yl)sulfonylamino]benzoyl]amino]-3-[4-(1-methyl-7-oxido-2,4-dioxo-pyrido[3,4-d]pyrimidin-7-ium-3-yl)phenyl]propanoic Acid (A-83), Obtained as a Free Form

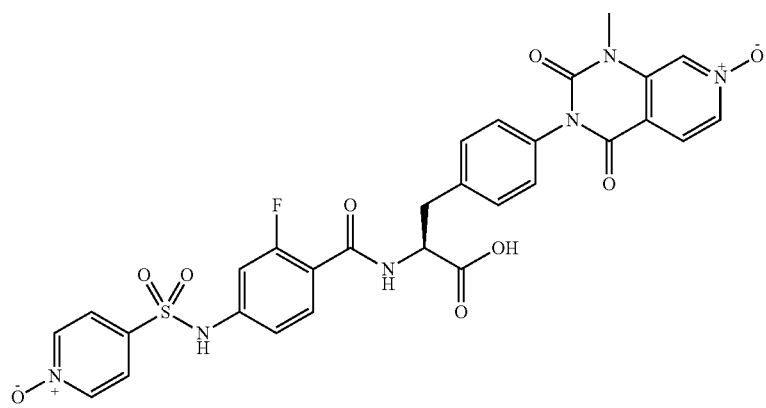

2-[2-Fluoro-4-(pyridine-4-sulfonylamino)-benzoylamino]-3-[4-(1-methyl-2,4-dioxo-1,4-dihydro-2H-pyrido[3,4-d]pyrimidin-3-yl)-phenyl]-propionic acid (30.0 mg, 0.0354 mmol) was dissolved in dichloromethane (3.0 ml), and m-chloroperoxybenzoic acid (21.0 mg, 0.124 mmol) was added thereto, followed by stirring at room temperature overnight. The residue was purified by reversed-phase HPLC (H$_2$O containing 0.1% TFA/CH$_3$CN system), followed by freeze-drying, to obtain the compound (A-83) (4.90 mg, 21%).

$^1$H NMR (400 MHz, DMSO-d$_6$): δ 11.09 (s, 1H), 8.62 (s, 1H), 8.49-8.40 (m, 0H), 8.33 (d, J=6.5 Hz, 2H), 8.10 (d, J=6.7 Hz, 1H), 7.89 (d, J=6.6 Hz, 1H), 7.73 (d, J=6.4 Hz, 2H), 7.50-7.30 (m, 3H), 7.20 (d, J=7.9 Hz, 2H), 7.06-6.88 (m, 2H), 4.62 (s, 1H), 3.46 (s, 3H), 3.14-2.99 (m, 1H).; MS (ESI) m/z 651 (M+H)$^+$ (Step 2) Isopropyl (2S)-2-[[2-Fluoro-4-[(1-oxidopyridin-1-ium-4-yl)sulfonylamino]benzoyl]amino]-3-[4-(1-methyl-7-oxido-2,4-dioxo-pyrido[3,4-d]pyrimidin-7-ium-3-yl)phenyl]propanoate (B-83), Obtained as a Free Form

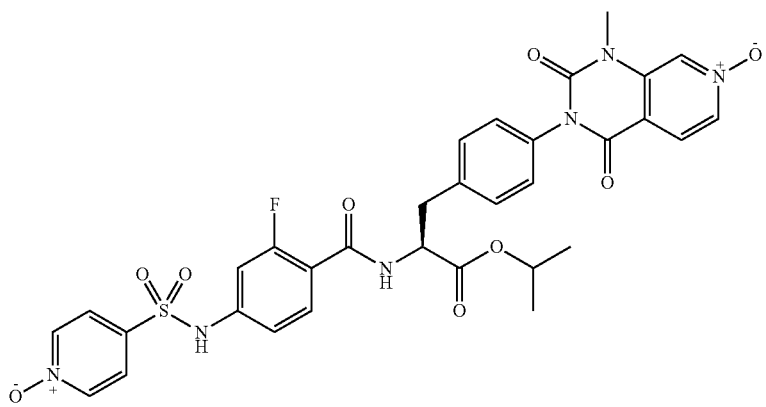

To (2S)-2-[[2-fluoro-4-[(1-oxidopyridin-1-ium-4-yl)sulfonylamino]benzoyl]amino]-3-[4-(1-methyl-7-oxido-2,4-dioxo-pyrido[3,4-d]pyrimidin-7-ium-3-yl)phenyl]propanoic acid (A-83), a 4 N hydrochloric acid/1,4-dioxane solution (3.0 ml) and isopropyl alcohol (1.0 ml) were added, followed by stirring at 60° C. for 5 hours. After the reaction liquid was concentrated under reduced pressure, purification was conducted by reversed-phase HPLC (H$_2$O containing 0.1% TFA/CH$_3$CN system), followed by freeze-drying, to obtain the title compound (B-83) (7.6 mg, 27% over two steps).

$^1$H NMR (400 MHz, DMSO-d$_6$): δ 11.10 (s, 1H), 8.68-8.54 (m, 2H), 8.41-8.26 (m, 2H), 8.10 (dd, J=6.7, 1.6 Hz, 1H), 7.89 (d, J=6.6 Hz, 1H), 7.80-7.69 (m, 2H), 7.43 (t, J=8.3 Hz, 1H), 7.36 (d, J=8.4 Hz, 2H), 7.20 (d, J=8.4 Hz, 2H), 7.06-6.91 (m, 2H), 4.89 (dt, J=12.3, 6.1 Hz, 1H), 4.64-4.50 (m, 1H), 3.46 (s, 3H), 3.19-3.05 (m, 2H), 1.16 (dd, J=22.9, 6.2 Hz, 6H).;

MS (ESI) m/z 693 (M+H)$^+$

Example 180

Synthesis of A-84 and Synthesis of B-84

(Step 1) N-{4-[({4-[(tert-Butylamino)methyl]-2-methylphenyl}sulfonyl)amino]-2-fluorobenzoyl}-4-(1-methyl-2,4-dioxo-1,4-dihydropyrido[3,4-d]pyrimidin-3(2H)-yl)-L-phenylalanine (A-84), Obtained as a Free Form

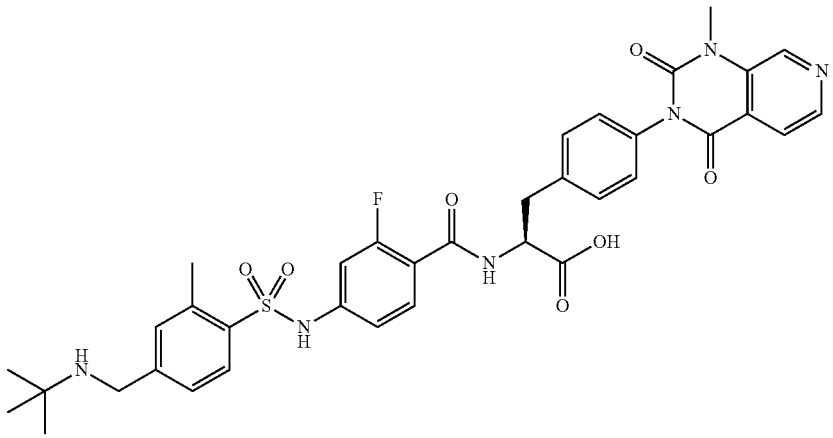 [SMILES: Cc1cc(CNC(C)(C)C)ccc1S(=O)(=O)Nc1ccc(C(=O)N[C@@H](Cc2ccc(-n3c(=O)c4ccncc4n(C)c3=O)cc2)C(=O)O)c(F)c1]

$^1$H NMR (400 MHz, DMSO-d$_6$): δ 11.18 (s, 1H), 8.98 (s, 1H), 8.62 (s, 1H), 8.56 (d, J=4.9 Hz, 1H), 8.38 (dd, J=8.0, 2.9 Hz, 1H), 8.08 (d, J=8.0 Hz, 1H), 7.88 (dd, J=5.1, 0.7 Hz, 1H), 7.54 (d, J=1.7 Hz, 1H), 7.51 (s, 1H), 7.41 (t, J=8.4 Hz, 1H), 7.38-7.33 (m, 2H), 7.24-7.18 (m, 2H), 6.97 (dd, J=8.6, 2.1 Hz, 1H), 6.90 (dd, J=12.4, 2.1 Hz, 1H), 4.65-4.57 (m, 1H), 4.16-4.09 (m, 2H), 3.60 (s, 3H), 3.27-3.01 (m, 2H), 2.63 (s, 3H), 1.32 (s, 9H).; MS (ESI) m/z 717.48 (M+H)$^+$ (Step 2) Cyclohexyl N-{4-[({4-[(tert-Butylamino)methyl]-2-methylphenyl}sulfonyl)amino]-2-fluorobenzoyl}-4-(1-methyl-2,4-dioxo-1,4-dihydropyrido[3,4-d]pyrimidin-3(2H)-yl)-L-phenylalaninate (B-84)

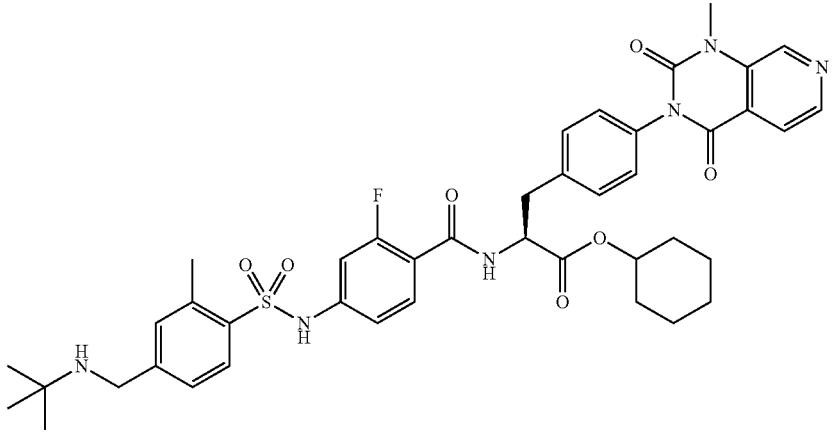 [SMILES: Cc1cc(CNC(C)(C)C)ccc1S(=O)(=O)Nc1ccc(C(=O)N[C@@H](Cc2ccc(-n3c(=O)c4ccncc4n(C)c3=O)cc2)C(=O)OC2CCCCC2)c(F)c1]

¹H NMR (400 MHz, DMSO-d₆): δ 11.19 (s, 1H), 8.98 (s, 1H), 8.63 (s, 1H), 8.58-8.52 (m, 2H), 8.09 (d, J=8.1 Hz, 1H), 7.88 (d, J=4.9 Hz, 1H), 7.56-7.50 (m, 2H), 7.43-7.32 (m, 3H), 7.24-7.19 (m, 2H), 7.00-6.87 (m, 2H), 4.73-4.64 (m, 1H), 4.64-4.56 (m, 1H), 4.17-4.08 (m, 2H), 3.60 (s, 3H), 3.21-3.04 (m, 2H), 2.63 (s, 3H), 1.80-1.56 (m, 4H), 1.48-1.27 (m, 15H).; MS (ESI) m/z 799.55 (M+H)⁺

Example 181

Synthesis of A-85 and Synthesis of B-85

(Step 1) N-{4-[({4-[(Cyclopentylamino)methyl]-2-methylphenyl}sulfonyl)amino]-2-fluorobenzoyl}-4-(1-methyl-2,4-dioxo-1,4-dihydropyrido[3,4-d]pyrimidin-3(2H)-yl)-L-phenylalanine (A-85), Obtained as a Free Form

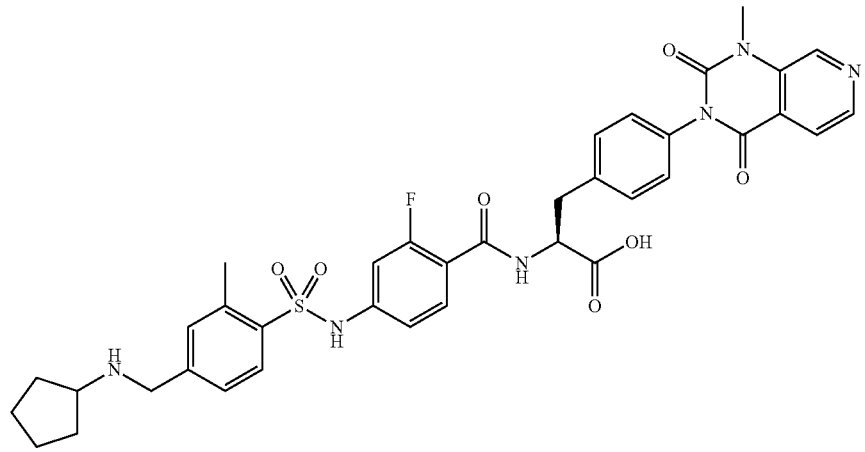 [SMILES: Cc1cc(CNC2CCCC2)ccc1S(=O)(=O)Nc1ccc(C(=O)N[C@@H](Cc2ccc(-n3c(=O)c4ccncc4n(C)c3=O)cc2)C(=O)O)c(F)c1]

¹H NMR (400 MHz, DMSO-d₆): δ 11.17 (s, 1H), 8.98 (s, 1H), 8.77 (brs, 2H), 8.56 (d, J=4.9 Hz, 1H), 8.37 (dd, J=7.9, 3.2 Hz, 1H), 8.06 (d, J=8.6 Hz, 1H), 7.88 (d, J=5.0 Hz, 1H), 7.57-7.47 (m, 2H), 7.41 (t, J=8.4 Hz, 1H), 7.38-7.33 (m, 2H), 7.24-7.18 (m, 2H), 7.00-6.86 (m, 2H), 4.66-4.55 (m, 1H), 4.19-4.11 (m, 2H), 3.60 (s, 3H), 3.27-3.01 (m, 2H), 2.62 (s, 3H), 1.96 (dt, J=9.8, 5.0 Hz, 2H), 1.72-1.46 (m, 6H).; MS (ESI) m/z 729.44 (M+H)⁺

(Step 2) Cyclohexyl N-{4-[({4-[(Cyclopentylamino)methyl]-2-methylphenyl}sulfonyl)amino]-2-fluorobenzoyl}-4-(1-methyl-2,4-dioxo-1,4-dihydropyrido[3,4-d]pyrimidin-3(2H)-yl)-L-phenylalaninate (B-85)

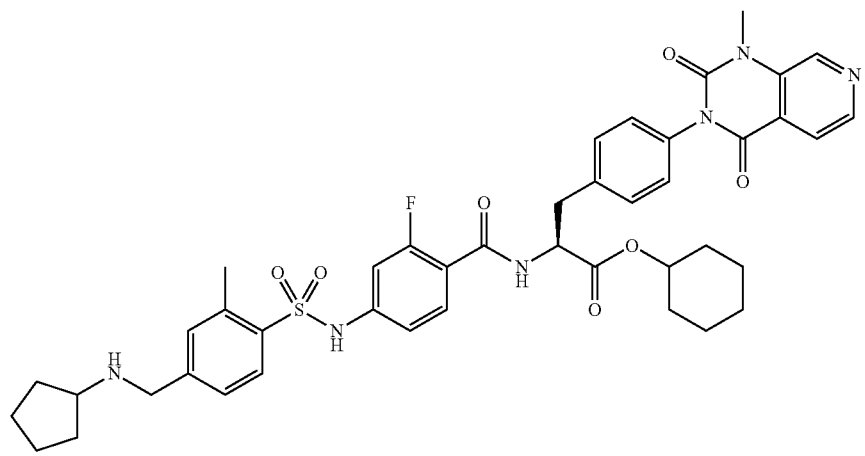 [SMILES: Cc1cc(CNC2CCCC2)ccc1S(=O)(=O)Nc1ccc(C(=O)N[C@@H](Cc2ccc(-n3c(=O)c4ccncc4n(C)c3=O)cc2)C(=O)OC2CCCCC2)c(F)c1]

¹H NMR (400 MHz, DMSO-d₆): δ 11.17 (s, 1H), 8.98 (s, 1H), 8.77 (brs, 2H), 8.63-8.49 (m, 2H), 8.07 (d, J=8.7 Hz, 1H), 7.88 (d, J=5.0 Hz, 1H), 7.55-7.48 (m, 2H), 7.44-7.31 (m, 3H), 7.25-7.16 (m, 2H), 7.02-6.84 (m, 2H), 4.74-4.55 (m, 2H), 4.18-4.10 (m, 2H), 3.60 (s, 3H), 3.21-3.03 (m, 2H), 2.62 (s, 3H), 1.96 (dd, J=11.5, 5.8 Hz, 2H), 1.83-1.17 (m, 16H).; MS (ESI) m/z 811.59 (M+H)⁺

Example 182

Synthesis of A-86 and Synthesis of B-86

(Step 1) N-{2-Fluoro-4-[(1H-pyrrol-2-yl-sulfonyl)amino]benzoyl}-3-[5-(1-methyl-2,4-dioxo-1,4-dihydropyrido[3,4-d]pyrimidin-3(2H)-yl)pyridin-2-yl]-L-alanine (A-86)

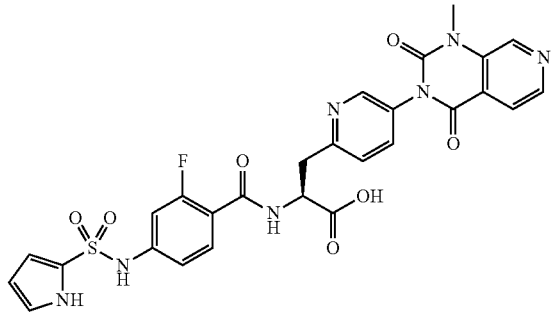 [SMILES: Cn1c(=O)n(-c2ccc(C[C@H](NC(=O)c3ccc(NS(=O)(=O)c4ccc[nH]4)cc3F)C(=O)O)nc2)c(=O)c2ccncc21]

¹H NMR (400 MHz, DMSO-d₆): δ 12.14 (s, 1H), 10.67 (s, 1H), 9.00 (s, 1H), 8.58 (d, J=4.9 Hz, 1H), 8.53 (dd, J=7.7, 4.5 Hz, 1H), 8.46 (d, J=2.4 Hz, 1H), 7.91 (d, J=5.0 Hz, 1H), 7.76-7.71 (m, 1H), 7.50 (t, J=8.6 Hz, 1H), 7.46 (d, J=8.3 Hz, 1H), 7.04-6.94 (m, 3H), 6.82-6.62 (m, 1H), 6.20-6.13 (m, 1H), 4.91-4.84 (m, 1H), 3.62 (s, 3H), 3.35-3.25 (m, 2H).; MS (ESI) m/z 608.35 (M+H)⁺

(Step 2) Cyclohexyl N-{2-Fluoro-4-[(1H-pyrrol-2-yl-sulfonyl)amino]benzoyl}-3-[5-(1-methyl-2,4-dioxo-1,4-dihydropyrido[3,4-d]pyrimidin-3(2H)-yl)pyridin-2-yl]-L-alaninate (B-86)

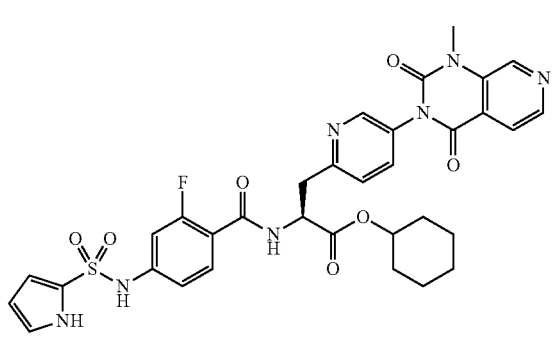 [SMILES: Cn1c(=O)n(-c2ccc(C[C@H](NC(=O)c3ccc(NS(=O)(=O)c4ccc[nH]4)cc3F)C(=O)OC3CCCCC3)nc2)c(=O)c2ccncc21]

¹H NMR (400 MHz, DMSO-d₆): δ 12.14 (d, J=2.9 Hz, 1H), 10.69 (s, 1H), 9.00 (s, 1H), 8.66 (dd, J=7.6, 4.1 Hz, 1H), 8.58 (d, J=5.0 Hz, 1H), 8.49-8.44 (m, 1H), 7.91 (dd, J=5.2, 0.7 Hz, 1H), 7.73 (dd, J=8.2, 2.5 Hz, 1H), 7.54-7.43 (m, 2H), 7.03-6.94 (m, 3H), 6.70 (ddd, J=3.8, 2.4, 1.5 Hz, 1H), 6.18-6.14 (m, 1H), 4.95-4.85 (m, 1H), 4.72-4.63 (m, 1H), 3.62 (s, 3H), 1.76-1.51 (m, 4H), 1.48-1.17 (m, 6H).; MS (ESI) m/z 690.50 (M+H)⁺

Example 183

Synthesis of A-87 and Synthesis of B-87

(Step 1) N-({3-Fluoro-5-[(2-furylsulfonyl)amino]pyridin-2-yl}carbonyl)-4-(1-methyl-2,4-dioxo-1,4-dihydropyrido[3,4-d]pyrimidin-3(2H)-yl)-L-phenylalanine (A-87)

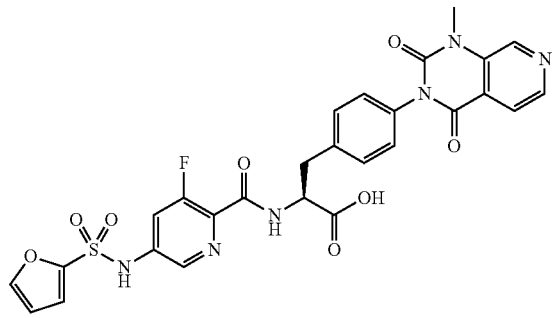 [SMILES: Cn1c(=O)n(-c2ccc(C[C@H](NC(=O)c3ncc(NS(=O)(=O)c4ccco4)cc3F)C(=O)O)cc2)c(=O)c2ccncc21]

¹H NMR (400 MHz, DMSO-d₆): δ 11.71 (s, 1H), 8.97 (s, 1H), 8.68 (d, J=8.0 Hz, 1H), 8.55 (d, J=5.0 Hz, 1H), 8.27 (d, J=1.9 Hz, 1H), 8.05-7.99 (m, 1H), 7.88 (d, J=5.0 Hz, 1H), 7.52-7.43 (m, 2H), 7.38-7.30 (m, 2H), 7.24-7.16 (m, 2H), 6.70 (dd, J=3.6, 1.8 Hz, 1H), 4.74-4.64 (m, 1H), 3.59 (s, 3H), 3.30-3.16 (m, 2H).; MS (ESI) m/z 609.41 (M+H)⁺

(Step 2) Cyclohexyl N-({3-Fluoro-5-[(2-furylsulfonyl)amino]pyridin-2-yl}carbonyl)-4-(1-methyl-2,4-dioxo-1,4-dihydropyrido[3,4-d]pyrimidin-3(2H)-yl)-L-phenylalaninate (B-87)

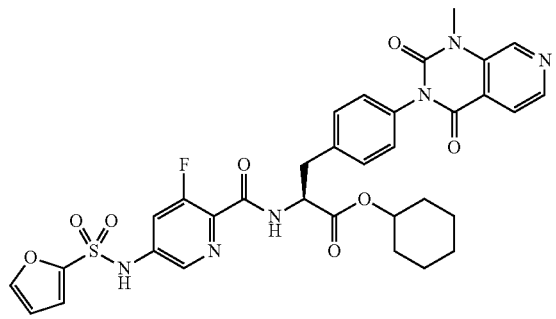 [SMILES: Cn1c(=O)n(-c2ccc(C[C@H](NC(=O)c3ncc(NS(=O)(=O)c4ccco4)cc3F)C(=O)OC3CCCCC3)cc2)c(=O)c2ccncc21]

¹H NMR (400 MHz, DMSO-d₆): δ 11.72 (s, 1H), 8.96 (s, 1H), 8.82 (d, J=7.8 Hz, 1H), 8.55 (d, J=5.0 Hz, 1H), 8.28 (d, J=1.9 Hz, 1H), 8.05-7.99 (m, 1H), 7.88 (d, J=4.9 Hz, 1H), 7.52-7.44 (m, 2H), 7.40-7.31 (m, 2H), 7.25-7.17 (m, 2H), 6.70 (dd, J=3.6, 1.8 Hz, 1H), 4.75-4.64 (m, 2H), 3.59 (s, 3H), 3.30-3.16 (m, 2H), 1.79-1.57 (m, 4H), 1.50-1.19 (m, 6H).; MS (ESI) m/z 691.50 (M+H)⁺

Example 184

Synthesis of A-88 and Synthesis of B-88

(Step 1) N-({3-Fluoro-5-[(pyridin-4-yl-sulfonyl)amino]pyridin-2-yl}carbonyl)-4-(1-methyl-2,4-dioxo-1,4-dihydropyrido[3,4-d]pyrimidin-3(2H)-yl)-L-phenylalanine (A-88)

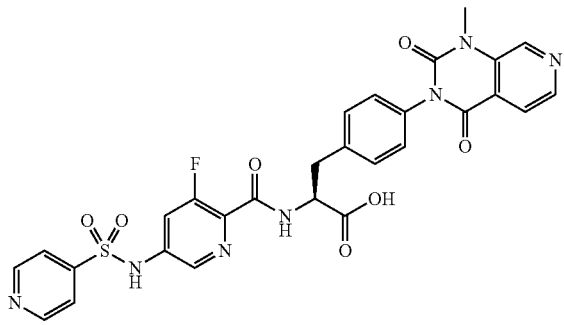 [SMILES: Cn1c(=O)n(-c2ccc(C[C@H](NC(=O)c3ncc(NS(=O)(=O)c4ccncc4)cc3F)C(=O)O)cc2)c(=O)c2ccncc21]

$^1$H NMR (400 MHz, DMSO-d$_6$): δ 11.64 (s, 1H), 8.97 (s, 1H), 8.91-8.84 (m, 2H), 8.67 (d, J=8.0 Hz, 1H), 8.55 (d, J=5.0 Hz, 1H), 8.22 (d, J=1.9 Hz, 1H), 7.88 (d, J=5.0 Hz, 1H), 7.85-7.78 (m, 2H), 7.51 (dd, J=12.1, 2.0 Hz, 1H), 7.37-7.29 (m, 2H), 7.24-7.15 (m, 2H), 4.74-4.63 (m, 1H), 3.59 (s, 3H), 3.30-3.14 (m, 2H).; MS (ESI) m/z 620.37 (M+H)$^+$ (Step 2) Cyclohexyl N-({3-Fluoro-5-[(pyridin-4-yl-sulfonyl)amino]pyridin-2-yl}carbonyl)-4-(1-methyl-2,4-dioxo-1,4-dihydropyrido[3,4-d]pyrimidin-3(2H)-yl)-L-phenylalaninate (B-88)

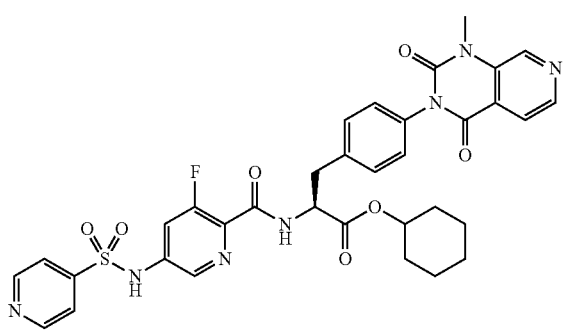 [SMILES: Cn1c(=O)n(-c2ccc(C[C@H](NC(=O)c3ncc(NS(=O)(=O)c4ccncc4)cc3F)C(=O)OC3CCCCC3)cc2)c(=O)c2ccncc21]

$^1$H NMR (400 MHz, DMSO-d$_6$): δ 8.96 (s, 1H), 8.90-8.84 (m, 2H), 8.81 (d, J=7.7 Hz, 1H), 8.55 (d, J=4.9 Hz, 1H), 8.22 (t, J=1.5 Hz, 1H), 7.88 (d, J=4.9 Hz, 1H), 7.85-7.78 (m, 2H), 7.51 (dd, J=11.9, 2.1 Hz, 1H), 7.34 (d, J=8.3 Hz, 2H), 7.20 (d, J=8.2 Hz, 2H), 4.74-4.63 (m, 2H), 3.59 (s, 3H), 3.28-3.13 (m, 2H), 1.84-1.54 (m, 4H), 1.49-1.18 (m, 6H).; MS (ESI) m/z 702.46 (M+H)$^+$

Example 185

Synthesis of Synthesis of A-89

(Step 1) N-(2,6-Difluoro-4-{[(2-hydroxyphenyl)sulfonyl]amino}benzoyl)-3-[5-(1-methyl-2,4-dioxo-1,4-dihydropyrido[3,4-d]pyrimidin-3(2H)-yl)pyridin-2-yl]-L-alanine (A-89)

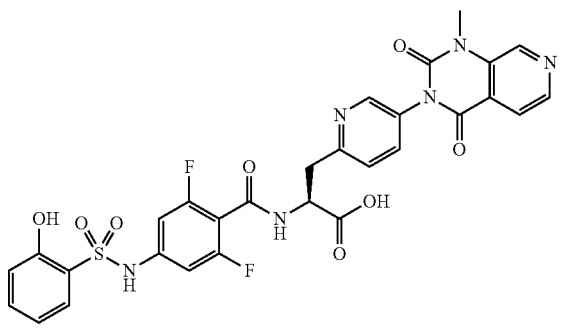 [SMILES: Cn1c(=O)n(-c2ccc(C[C@H](NC(=O)c3c(F)cc(NS(=O)(=O)c4ccccc4O)cc3F)C(=O)O)nc2)c(=O)c2ccncc21]

To N-(2,6-difluoro-4-{[(2-methoxyphenyl)sulfonyl]amino}benzoyl)-3-[5-(1-methyl-2,4-dioxo-1,4-dihydropyrido[3,4-d]pyrimidin-3(2H)-yl)pyridin-2-yl]-L-alanine <synthesized by the same method as in (Step 1) of Example 143> (20.0 mg, 0.0220 mmol), dichloromethane (2.0 ml) was added, and a 1 M BBr$_3$/dichloromethane solution (224 μl, 0.220 mmol) was added dropwise thereto, followed by stirring at room temperature overnight. Further, a 1 M BBr$_3$/dichloromethane solution (448 ul, 0.440 mmol) was added thereto, followed by stirring at room temperature for 3 hours. Water was added thereto, followed by stirring for 5 minutes. Then, the mixture was concentrated under reduced pressure, and the obtained residue was purified by reversed-phase HPLC (H$_2$O containing 0.1% TFA/CH$_3$CN system), followed by freeze-drying, to obtain a TFA salt (7.20 mg, 52%) of the title compound.

$^1$H NMR (400 MHz, DMSO-d$_6$): δ 11.04 (d, J=9.1 Hz, 1H), 10.65 (s, 1H), 9.00-8.84 (m, 2H), 8.51 (d, J=5.1 Hz, 1H), 8.37 (s, 1H), 7.85 (d, J=5.2 Hz, 1H), 7.72 (s, 1H), 7.65 (s, 1H), 7.48-7.29 (m, 2H), 6.95-6.81 (m, 2H), 6.75-6.59 (m, 2H), 4.83-4.70 (m, 1H), 3.55 (s, 3H).; MS (ESI) m/z 653.28 (M+H)$^+$

Example 186

Synthesis of M-79

(Step 1) Methyl 3-[(5-Bromo-2-pyridyl)carbamoylamino]pyridine-4-carboxylate

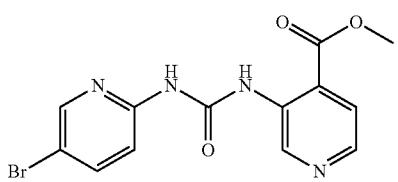 [SMILES: COC(=O)c1ccncc1NC(=O)Nc1ccc(Br)cn1]

Methyl 3-aminopyridine-4-carboxylate (31.8 g, 209 mmol) was dissolved in methylene chloride (1.1 L), and a solution (50 ml) of triphosgene (20.7 g, 69.8 mmol) in methylene chloride was added thereto, followed by stirring at 0° C. for 3 hours. To this reaction solution, a solution (50 ml) of 5-bromopyridine-2-amine (30.0 g, 174 mmol) in methylene chloride was added, followed by stirring at room temperature for 12 hours. The precipitated solid was filtered, washed with methylene chloride, and then dried under reduced pressure to obtain the title compound (30 g, 49%).

$^1$H NMR (400 MHz, DMSO-$d_6$): δ 11.02 (s, 1H), 10.36 (s, 1H), 9.44 (s, 1H), 8.39 (s, 2H), 7.98 (d, J=8.0 Hz, 1H), 7.74-7.73 (m, 1H), 7.48 (d, J=8.0 Hz, 1H), 3.92 (s, 3H).

(Step 2) 3-(5-Bromo-2-pyridyl)-1-methyl-pyrido[3,4-d]pyrimidine-2,4-dione

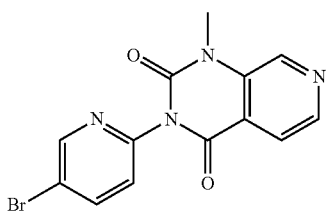 [SMILES: Cn1c(=O)n(-c2ccc(Br)cn2)c(=O)c2ccncc21]

Methyl 3-[(5-bromo-2-pyridyl)carbamoylamino]pyridine-4-carboxylate <see (Step 1)> (30 g, 85.7 mmol) was dissolved in N,N-dimethylformamide (600 ml), and an aqueous solution (80 ml) of potassium carbonate (23.7 g, 171 mmol) was added thereto, followed by stirring at room temperature for 3 hours. To this solution, potassium carbonate (23.7 g, 171 mmol) and p-toluenesulfonic acid methyl ester (31.9 g, 171 mmol) were further added, followed by stirring at room temperature for 90 minutes. The reaction solution was cooled to 0° C., and diluted with water, followed by extraction with ethyl acetate (100 ml×4). The extraction liquids were combined, washed with saturated aqueous sodium chloride, and dried over anhydrous sodium sulfate. Then, the solvent was removed under reduced pressure. The obtained residue was stirred in petroleum ether for 20 minutes, and the obtained solid was filtered and dried under reduced pressure to obtain the title compound (9.8 g, 34%).

$^1$H NMR (400 MHz, DMSO-$d_6$): δ 9.00 (s, 1H), 8.77 (m, 1H), 8.58 (d, J=4.8 Hz, 1H), 8.32-8.29 (m, 1H), 7.91 (d, J=4.8 Hz, 1H), 7.52 (d, J=8.4 Hz, 1H), 3.61 (s, 3H).

(Step 3) Cyclohexyl (2S)-3-Benzyloxy-2-(tert-butoxycarbonylamino)propanoate

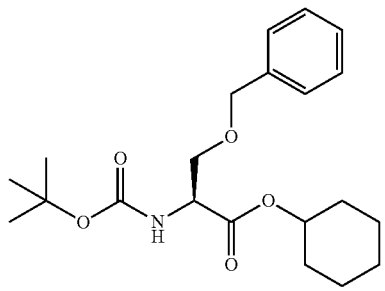 [SMILES: CC(C)(C)OC(=O)N[C@@H](COCc1ccccc1)C(=O)OC1CCCCC1]

(2S)-3-Benzyloxy-2-(tert-butoxycarbonylamino)propionic acid (300 g, 1.02 mol) was dissolved in N,N-dimethylformamide (2.0 L), and EDCL (189 g, 1.22 mmol), cyclohexanol (210 g, 2.10 mol), and N,N-dimethyl-4-aminopyridine (12.4 g, 102 mmol) were added thereto, followed by stirring at room temperature for 90 minutes in the presence of nitrogen gas. The reaction solution was diluted with water (5.0 L), followed by extraction with ethyl acetate (1.0 L×2). The extraction liquids were combined, washed with water (1.0 L), 1 N hydrochloric acid (900 ml), a saturated aqueous sodium hydrogen carbonate solution (1.0 L), and saturated aqueous sodium chloride (900 ml), and dried over anhydrous sodium sulfate. Then the solvent was removed under reduced pressure to obtain the title compound (360 g, 94%).

$^1$H NMR (400 MHz, DMSO-$d_6$): δ 7.35-7.25 (m, 5H), 7.06 (d, J=8.4 Hz, 1H), 4.73-4.69 (m, 1H), 4.51-4.39 (m, 2H), 4.26-4.21 (m, 1H), 3.73-3.64 (m, 2H), 1.47-1.10 (m, 19H).

(Step 4) Cyclohexyl (2S)-2-(tert-Butoxycarbonylamino)-3-hydroxy-propanoate

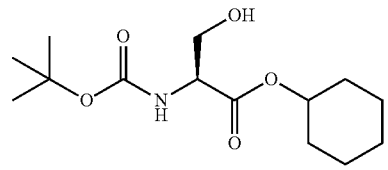 [SMILES: CC(C)(C)OC(=O)N[C@@H](CO)C(=O)OC1CCCCC1]

Cyclohexyl(2S)-2-(tert-butoxycarbonylamino)-3-hydroxy-propanoate (360 g, 954 mmol) <see (Step 3)> was dissolved in ethanol (1.6 L), and 20% palladium hydroxide/carbon (40 g) was added thereto, followed by stirring at 70° C. for 3 days in the presence of hydrogen gas (50 psi). The reaction solution was filtered, and the obtained filtrate was concentrated and then dried under reduced pressure to obtain the title compound (250 g, 91%).

$^1$H NMR (400 MHz, DMSO-$d_6$): δ 6.80 (d, J=8.0 Hz, 1H), 4.82 (s, 1H), 4.72-4.67 (m, 1H), 4.37 (s, 1H), 4.01-3.99 (m, 1H), 3.46-3.38 (m, 1H), 1.48-1.35 (m, 19H).

(Step 5) Cyclohexyl (2R)-2-(tert-Butoxycarbonylamino)-3-iodo-propanoate

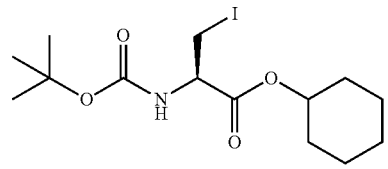 [SMILES: CC(C)(C)OC(=O)N[C@@H](CI)C(=O)OC1CCCCC1]

Triphenylphosphine (275 g, 1.05 mol) and imidazole (75.0 g, 1.05 mol) were dissolved in methylene chloride (3.0 L). After cooling to 0° C., iodine (270 g, 1.05 mol) was added thereto, followed by stirring at room temperature for 30 minutes in the presence of nitrogen gas. After the reaction solution was cooled to 0° C., a solution (500 ml) of cyclohexyl(2S)-2-(tert-butoxycarbonylamino)-3-hydroxy-propanoate <see (Step 4)> (250 g, 871 mmol) in methylene chloride was slowly added dropwise over 1 hour. Then, the reaction liquid was stirred at room temperature for 2 hours.

The reaction liquid was filtered, followed by washing with hexane/diethyl ether (1:1). The obtained filtrate was purified by silica gel column chromatography (petroleum ether/ethyl acetate=1:1 to 1:2) to obtain the title compound (200 g, 580).

¹H NMR (400 MHz, DMSO-d₆): δ 7.24 (d, J=8.0 Hz, 1H), 4.75-4.69 (m, 1H), 4.21-4.16 (m, 1H), 3.51-3.47 (m, 1H), 3.36-3.33 (m, 1H), 1.75-1.10 (m, 19H).

(Step 6) Cyclohexyl (2S)-2-(tert-Butoxycarbonylamino)-3-[6-(1-methyl-2,4-dioxo-pyrido[3,4-d]pyrimidin-3-yl)-3-pyridyl]propanoate

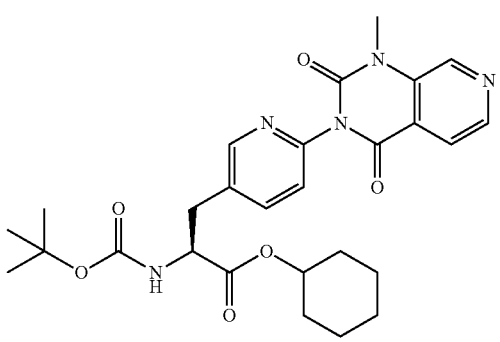 [SMILES: Cn1c(=O)n(-c2ccc(C[C@H](NC(=O)OC(C)(C)C)C(=O)OC3CCCCC3)cn2)c(=O)c2ccncc21]

Zinc (9.50 g, 146 mmol) was heated at 210° C. for 10 minutes, and cooled to 70° C. Then, the zinc was again heated to 210° C., and stirred for 10 minutes. After cooling to room temperature, N,N-dimethylformamide (20 ml) and a solution (5.0 ml) of dibromoethane (2, 10 g, 11.2 mmol) in N,N-dimethylformamide was added thereto, followed by stirring at 90° C. for 30 minutes. After cooling to room temperature, trimethylsilyl chloride (243 mg, 2.25 mmol) was added, followed by stirring at room temperature for 10 minutes. A solution (15 ml) of cyclohexyl(2R)-2-(tert-butoxycarbonylamino)-3-iodo-propanoate <see (Step 5)> (8.90 g, 22.5 mmol) in N,N-dimethylformamide was added to the reaction liquid, followed by stirring at 35° C. for 90 minutes. This zinc derivative was added to a solution in which 3-(5-bromo-2-pyridyl)-1-methyl-pyrido[3,4-d]pyrimidine-2,4-dione <see (Step 2)> (2.50 g, 7.49 mmol) and Pd(PPh3)2Cl2 (788 mg, 1.12 mmol) were suspended in N,N-dimethylformamide (20 ml), followed by stirring at 80° C. for 2 hours in the presence of nitrogen gas. After cooling to room temperature, the reaction solution was filtered, and the obtained filtrate was diluted with water (150 ml), followed by extraction with ethyl acetate (100 ml×3). The extraction liquids were combined, washed with saturated aqueous sodium chloride, and dried over anhydrous sodium sulfate. Then, the solvent was removed under reduced pressure, and the obtained residue was purified by silica gel column chromatography (petroleum ether/ethyl acetate=1:1 to 1:2) to obtain the title compound (1.88 g, 48%).

¹H NMR (400 MHz, DMSO-d₆): δ 8.99 (s, 1H), 8.56 (d, J=4.8 Hz, 1H), 8.46-8.45 (m, 1H), 7.92-7.89 (m, 2H), 7.43-7.40 (m, 2H), 4.69-4.67 (m, 1H), 4.26-4.21 (m, 1H), 3.60 (s, 3H), 3.13-2.96 (m, 2H), 1.76-1.20 (m, 19H).

(Step 7) Cyclohexyl 3-[6-(1-Methyl-2,4-dioxo-1,4-dihydropyrido[3,4-d]pyrimidin-3(2H)-yl)pyridin-3-yl]-L-alaninate (M-79)

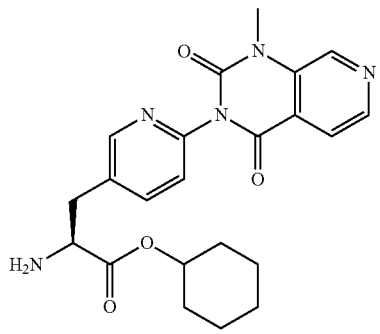 [SMILES: Cn1c(=O)n(-c2ccc(C[C@H](N)C(=O)OC3CCCCC3)cn2)c(=O)c2ccncc21]

Cyclohexyl(2S)-2-(tert-butoxycarbonylamino)-3-[6-(1-methyl-2,4-dioxo-pyrido[3,4-d]pyrimidin-3-yl)-3-pyridyl]propanoate <see (Step 6)> (7.50 g, 14.3 mmol) was dissolved in ethyl acetate (20 ml), and 4 N hydrogen chloride/ethyl acetate (25 ml) was added, followed by stirring at room temperature for 1 hour. After the solvent was removed under reduced pressure, ethyl acetate (30 ml) was added thereto, followed by stirring for 5 minutes. The obtained white solid was filtered and dried under reduced pressure to obtain the title compound (5.77 g, 87%) as a hydrochloride.

¹H NMR (400 MHz, CD₃OD): δ 9.29 (s, 1H), 8.75 (d, J=6.0 Hz, 1H), 8.61 (d, J=2.0 Hz, 1H), 8.58 (d, J=5.6 Hz, 1H), 8.11 (dd, J=8.0, 2.4 Hz, 1H), 7.61 (d, J=8.0 Hz, 1H), 4.87-4.83 (m, 1H), 4.47 (t, J=7.6 Hz, 1H), 3.73 (s, 3H), 3.40-3.38 (m, 2H), 1.87-1.29 (m, 10H).; MS (ESI) m/z 424 (M+H)⁺

Example 187

Synthesis of M-80

(Step 1) 6-Bromopyridine-3-amine

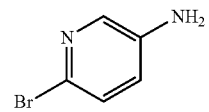

2-Bromo-5-nitro-pyridine (202 g, 1.0 mol) was dissolved in methanol (2.0 L), and a saturated aqueous ammonium chloride solution (2.0 L) was added thereto, followed by stirring at 50° C. Then, iron (224 g, 4.0 mol) was slowly added thereto, followed by stirring at 50° C. for 6 hours. The reaction solution was cooled to room temperature and then filtered, followed by washing with ethyl acetate. The filtrate was diluted with water, followed by extraction with ethyl acetate (1.0 L×6). The extraction liquids were combined, washed with a saturated aqueous sodium hydrogen carbonate solution (2.0 L) and saturated aqueous sodium chloride, and dried over anhydrous sodium sulfate. Then, the solvent was removed under reduced pressure, and the obtained residue was purified by silica gel column chromatography (petroleum ether/ethyl acetate=1:1) to obtain the title compound (126 g, 73%).

1H NMR (400 MHz, DMSO-$d_6$): δ 7.69 (d, J=2.8 Hz, 1H), 7.19 (d, J=8.4 Hz, 1H), 6.90 (dd, J=8.4 Hz, 2.8 Hz, 1H), 5.50 (s, 2H).

(Step 2) 3-(6-Bromo-3-pyridyl)-1-methyl-pyrido[3,4-d]pyrimidine-2,4-dione

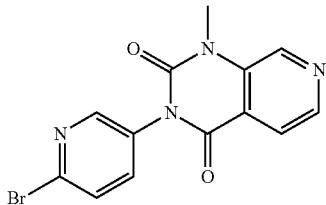

The title compound (32.5 g, over two steps 24.8%) was obtained by subjecting 6-bromopyridine-3-amine <see (Step 1)> (67.7 g, 394 mmol) to the same methods as in (Step 1) and (Step 2) of Example 186.

1H NMR (400 MHz, DMSO-$d_6$): δ 9.00 (s, 1H), 8.59 (d, J=8.8 Hz, 1H), 8.41 (d, J=4.8 Hz, 1H), 7.92 (d, J=4.8 Hz, 1H), 7.86 (d, J=8.0 Hz, 1H), 7.80 (dd, J=8.4 Hz, 2.0 Hz, 1H), 3.62 (s, 3H).

(Step 3) Cyclohexyl (2S)-2-(tert-Butoxycarbonylamino)-3-[5-(1-methyl-2,4-dioxo-pyrido[3,4-d]pyrimidin-3-yl)-2-pyridyl]propanoate

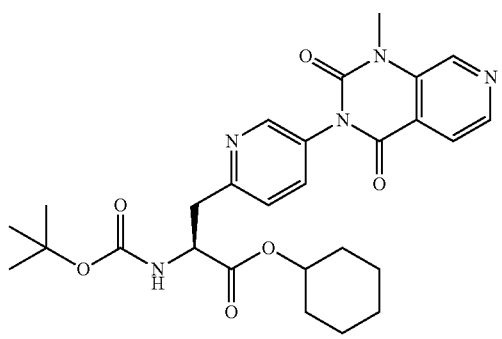 [SMILES: Cn1c(=O)n(-c2ccc(C[C@H](NC(=O)OC(C)(C)C)C(=O)OC3CCCCC3)nc2)c(=O)c2ccncc21]

The title compound (21.7 g, 60%) was obtained by subjecting 3-(6-bromo-3-pyridyl)-1-methyl-pyrido[3,4-d]pyrimidine-2,4-dione <see (Step 2)> (23.0 g, 69.2 mmol) to the same method as in (Step 6) of Example 186.

1H NMR (400 MHz, DMSO-$d_6$): δ 8.99 (s, 1H), 8.56 (d, J=4.8 Hz, 1H), 8.46 (d, J=1.6 Hz, 1H), 7.91 (d, J=5.2 Hz, 1H), 7.72 (dd, J=8.0, 2.4 Hz, 1H), 7.42 (d, J=8.0 Hz, 1H), 7.31 (d, J=8.0 Hz, 1H), 4.67-4.65 (m, 1H), 4.48-4.47 (m, 1H), 3.61 (s, 3H), 3.17-3.13 (m, 2H), 1.71-1.25 (m, 19H).

(Step 4) Cyclohexyl 3-[5-(1-Methyl-2,4-dioxo-1,4-dihydropyrido[3,4-d]pyrimidin-3(2H)-yl)pyridin-2-yl]-L-alaninate (M-80)

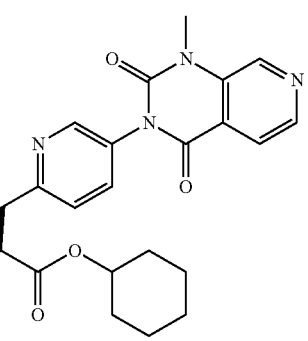

The title compound (27.9 g, 91%) was obtained as a hydrochloride by subjecting cyclohexyl(2S)-2-(tert-butoxycarbonylamino)-3-[5-(1-methyl-2,4-dioxo-pyrido[3,4-d]pyrimidin-3-yl)-2-pyridyl]propanoate <see (Step 3)> (35.0 g, 66.9 mmol) to the same method as in (Step 7) of Example 186.

$^1$H NMR (400 MHz, CD$_3$OD): δ 9.16 (s, 1H), 8.65 (d, J=5.6 Hz, 1H), 8.52 (d, J=2.0 Hz, 1H), 8.44 (d, J=5.6 Hz, 1H), 7.89 (dd, J=8.4, 2.4 Hz, 1H), 7.61 (d, J=8.4 Hz, 1H); 4.80 (m, 1H), 4.54 (t, J=6.0 Hz, 1H), 3.65 (s, 3H), 3.46-3.59 (m, 2H), 1.70-1.20 (m, 10H).; MS (ESI) m/z 424 (M+H)$^+$

Example 188

Synthesis of M-81

(Step 1) Methyl 3-Aminopyridine-2-carboxylate

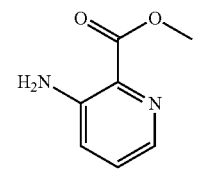

3-Aminopyridine-2-carboxylic acid (10.0 g, 72.5 mmol) was dissolved in methanol (100 ml). After cooling to 0° C., concentrated hydrochloric acid (25 ml) was added dropwise thereto, and the reaction solution was stirred at 85° C. for 12 hours. After the solvent was removed under reduced pressure, water and sodium hydrogen carbonate (10 g) were added to the obtained residue, followed by stirring and extraction with ethyl acetate (80 ml×4). The extraction liquids were combined, washed with saturated aqueous sodium chloride, and dried over anhydrous sodium sulfate. Then, the solvent was removed under reduced pressure. The residue was stirred in petroleum ether/ethyl acetate=8:1, and the obtained solid was filtered and dried under reduced pressure to obtain the title compound (4.50 g, 41%).

$^1$H-NMR (400 MHz, DMSO-d$_6$): δ 7.85-7.83 (m, 1H), 7.27-7.20 (m, 2H), 6.66 (s, 2H), 3.80 (s, 3H).; MS (ESI) m/z 153 (M+H)$^+$ (Step 2) 3-(6-Bromo-3-pyridyl)-1-methyl-pyrido[3,2-d]pyrimidine-2,4-dione

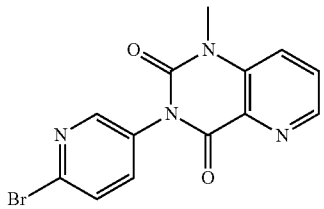 [SMILES: Cn1c(=O)n(-c2ccc(Br)nc2)c(=O)c2ncccc21]

The title compound (1.5 g, 18%) was obtained by subjecting methyl 3-aminopyridine-2-carboxylate <see (Step 1)> (4.50 g, 29.6 mmol) to the same method as in (Step 2) of Example 187.

$^1$H NMR (400 MHz, DMSO-d$_6$): δ 8.60-8.59 (m, 1H), 8.41 (d, J=2.4 Hz, 1H), 8.05-8.03 (m, 1H), 7.87-7.79 (m, 3H), 3.53 (s, 3H).;
MS (ESI) m/z 333, 335 (M+H)$^+$ (Step 3) Methyl (2S)-2-(tert-Butoxycarbonylamino)-3-[5-(1-methyl-2,4-dioxo-pyrido[3,2-d]pyrimidin-3-yl)-2-pyridyl]propanoate

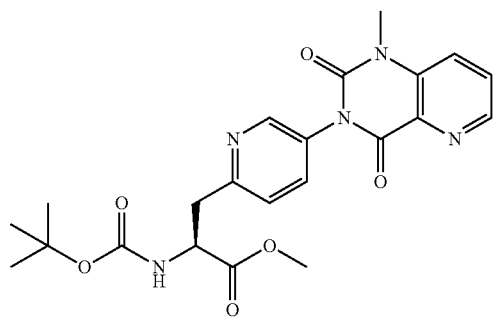 [SMILES: COC(=O)[C@H](Cc1ccc(-n2c(=O)c3ncccc3n(C)c2=O)cn1)NC(=O)OC(C)(C)C]

The title compound (0.9 g, 44%) was obtained by subjecting 3-(6-bromo-3-pyridyl)-1-methyl-pyrido[3,2-d]pyrimidine-2,4-dione <see (Step 2)> (1.50 g, 4.50 mmol) and methyl(2R)-2-(tert-butoxycarbonylamino)-3-iodo-propanoate <see (Step 1) of Example 97> to the same method as in (Step 6) of Example 186.

$^1$H NMR (400 MHz, DMSO-d$_6$): δ 8.59-8.58 (m, 1H), 8.45-8.44 (m, 1H), 8.04-8.02 (m, 1H), 7.85-7.81 (m, 1H), 7.73-7.71 (m, 1H), 7.43-7.41 (m, 1H), 7.36-7.34 (m, 1H), 4.53-4.51 (m, 1H), 3.63 (s, 3H), 3.53 (s, 3H), 3.19-3.09 (m, 2H), 1.36 (s, 9H).; MS (ESI) m/z 456 (M+H)$^+$ (Step 4) Methyl 3-[5-(1-Methyl-2,4-dioxo-1,4-dihydropyrido[3,2-d]pyrimidin-3(2H)-yl)pyridin-2-yl]-L-alaninate (M-81)

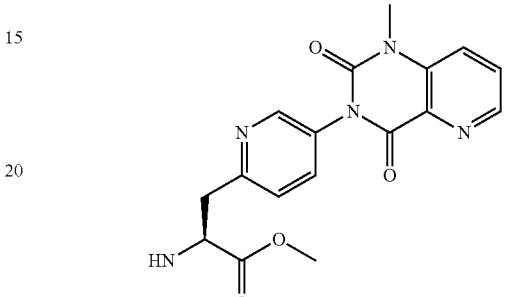

The title compound (614 mg, 79%) was obtained as a hydrochloride by subjecting methyl(2S)-2-(tert-butoxycarbonylamino)-3-[5-(1-methyl-2,4-dioxo-pyrido[3,2-d]pyrimidin-3-yl)-2-pyridyl]propanoate <see (Step 3)> (900 mg, 1.98 mmol) to the same method as in (Step 7) of Example 186.

$^1$H NMR (400 MHz, CD$_3$OD): δ 8.63-8.60 (m, 2H), 8.38 (d, J=8.4 Hz, 1H), 8.06 (dd, J=8.8, 4.8 Hz, 1H), 8.00 (dd, J=8.4, 2.4 Hz, 1H), 7.69 (d, J=8.4 Hz, 1H), 4.58 (t, J=6.8 Hz, 1H), 3.74 (s, 3H), 3.62 (s, 3H), 3.56-3.54 (m, 2H).; MS (ESI) m/z 356 (M+H)$^+$

Example 189

Synthesis of M-82

(Step 1) Methyl 4-[(4-Bromophenyl)sulfonylamino]-2,5-difluoro-benzoate

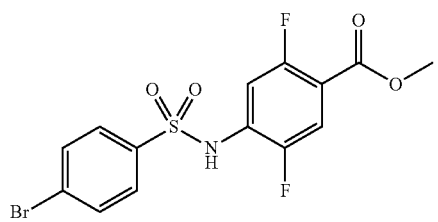 [SMILES: COC(=O)c1cc(F)c(NS(=O)(=O)c2ccc(Br)cc2)cc1F]

The title compound (8.0 g, 91%) was obtained as a yellow solid by subjecting methyl 4-amino-2,5-difluoro-benzoate <see (Step 3) of Example 104> (4.00 g, 21.4 mmol) and 4-bromobenzenesulfonyl chloride (10.9 g, 42.8 mmol) to the same method as in (Step 4) of Example 104.

MS (ESI) m/z 406 (M+H)$^+$ (Step 2) [4-[(2,5-Difluoro-4-methoxycarbonyl-phenyl)sulfamoyl]phenyl]boronic Acid

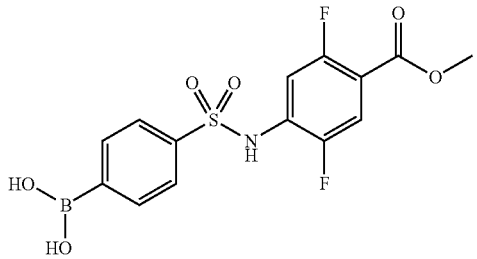 [SMILES: COC(=O)c1cc(F)c(NS(=O)(=O)c2ccc(B(O)O)cc2)cc1F]

The title compound (1.5 g, 61% over two steps) was obtained by subjecting methyl 4-[(4-bromophenyl)sulfonylamino]-2,5-difluoro-benzoate <see (Step 1)> (4.00 g, 9.83 mmol) to the same two steps as in (Step 3) of Example 8.

1H NMR: (400 MHz, DMSO-d$_6$): δ 11.05 (s, 1H), 8.37 (s, 2H), 7.94 (d, J=8.4 Hz, 2H), 7.81 (d, J=8.0 Hz, 2H), 7.65-7.61 (m, 1H), 7.27-7.23 (m, 1H), 3.80 (s, 3H).; MS (ESI) m/z 372 (M+H)$^+$ (Step 3) Methyl 2,5-Difluoro-4-[(4-pyrimidin-2-ylphenyl)sulfonylamino]benzoate

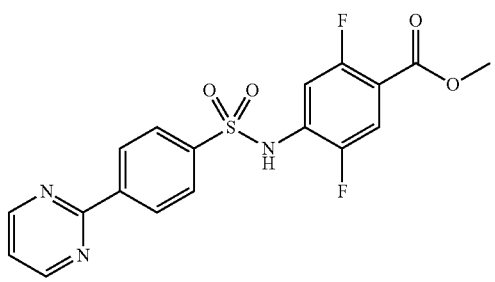 [SMILES: COC(=O)c1cc(F)c(NS(=O)(=O)c2ccc(-c3ncccn3)cc2)cc1F]

The title compound (465 mg, 29%) was obtained by subjecting [4-[(2,5-difluoro-4-methoxycarbonyl-phenyl)sulfamoyl]phenyl]boronic acid <see (Step 2)> (1.50 g, 4.40 mmol) to the same method as in (Step 4) of Example 8.

$^1$H NMR (DMSO-d$_6$, 400 MHz): δ 11.15 (s, 1H), 8.96 (d, J=4.4 Hz, 2H), 8.56-8.55 (m, 2H), 8.01-7.96 (m, 2H), 7.68-7.62 (m, 1H), 7.55-7.53 (m, 1H), 7.32-7.27 (m, 1H), 3.80 (s, 3H).; MS (ESI) m/z 406 (M+H)$^+$ (Step 4) 2,5-Difluoro-4-{[(4-pyrimidin-2-ylphenyl)sulfonyl]amino}benzoic Acid (M-82)

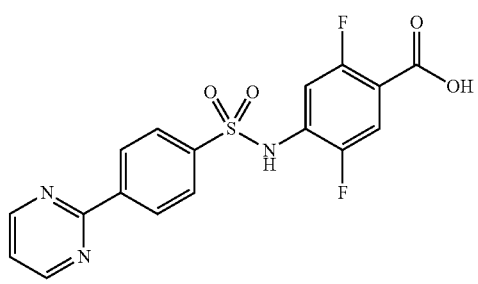

The title compound (413 mg, 92%) was obtained by subjecting methyl 2,5-difluoro-4-[(4-pyrimidin-2-ylphenyl)sulfonylamino]benzoate <see (Step 3)> (465 mg, 1.15 mmol) to the same method as in (Step 5) of Example 104.

$^1$H NMR: (400 MHz, CD$_3$OD): δ 8.90 (d, J=4.8 Hz, 2H), 8.60 (d, J=8.8 Hz, 2H), 8.03 (d, J=8.4 Hz, 2H), 7.60 (dd, J=10.8, 6.4 Hz, 1H), 7.48-7.43 (m, 2H).; MS (ESI) m/z 392 (M+H)$^+$

Example 190

Synthesis of M-83

(Step 1) Methyl 2,5-Difluoro-4-(2-thienylsulfonylamino)benzoate

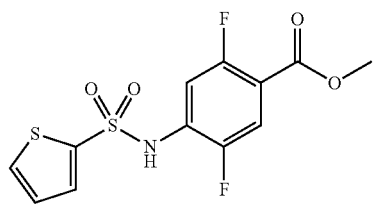 [SMILES: COC(=O)c1cc(F)c(NS(=O)(=O)c2cccs2)cc1F]

The title compound (1.6 g, 44%) was obtained as a yellow solid by subjecting methyl 4-amino-2,5-difluorobenzoate <see (Step 3) of Example 104> (2.0 g, 11 mmol) and thiophene-2-sulfonyl chloride (2.9 g, 16 mmol) to the same method as in (Step 4) of Example 104.

$^1$H NMR (400 MHz, DMSO-d$_6$): δ 11.2 (s, 1H), 8.00 (d, J=4.4 Hz, 1H), 7.71-7.66 (m, 2H), 7.34-7.30 (m, 1H), 7.19-7.17 (m, 1H), 3.88 (s, 3H).

(Step 2) 2,5-Difluoro-4-[(2-thienylsulfonyl)amino]benzoic Acid (M-83)

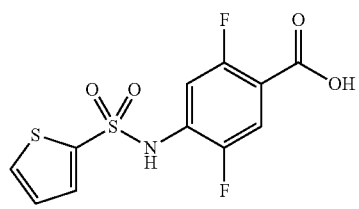 [SMILES: O=C(O)c1cc(F)c(NS(=O)(=O)c2cccs2)cc1F]

The title compound (1.2 g, 80%) was obtained by subjecting methyl 2,5-difluoro-4-(2-thienylsulfonylamino)benzoate <see (Step 1)> (1.6 g, 4.8 mmol) to the same method as in (Step 5) of Example 104.

$^1$H NMR (400 MHz, CD$_3$OD): δ 7.83 (dd, J=5.2, 1.2 Hz, 1H), 7.70 (dd, J=4.0, 1.6 Hz, 1H), 7.63 (dd, J=10.8, 6.4 Hz, 1H), 7.46 (dd, J=12.0, 6.4 Hz, 1H), 7.15 (dd, J=5.2, 4.0 Hz, 1H).

Example 191

Synthesis of M-84

(Step 1) 2-Ethoxybenzenesulfonyl Chloride

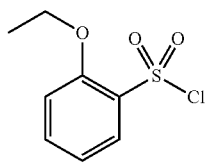

TMEDA (15.2 ml, 101 mmol) was added to diethyl ether (200 ml). After cooling to 0° C., n-butyllithium (2.5 mol/l, 40 ml, 100 mmol) was added thereto, followed by stirring for 5 minutes. To the reaction solution, ethoxybenzene (11.0 ml, 87.1 mmol) was added, followed by stirring for 1 hour. Then, after cooling to −78° C., sulfur dioxide gas was injected for 30 minutes, and then the temperature was gradually raised to room temperature over 1 hour. To the reaction liquid, thionyl chloride (8.80 ml, 110 ml) was added, followed by stirring at room temperature for 6 hours. The reaction liquid was diluted with water, followed by extraction with diethyl ether. The extraction liquids were combined, washed with saturated aqueous sodium chloride, and dried over anhydrous sodium sulfate. Then, the solvent was removed under reduced pressure to obtain the title compound (8.10 g, 42%).

(Step 2) Methyl 4-[(2-Ethoxyphenyl)sulfonylamino]-2,6-difluoro-benzoate

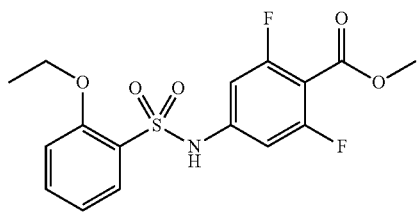 [SMILES: CCOc1ccccc1S(=O)(=O)Nc1cc(F)c(C(=O)OC)c(F)c1]

The title compound (1.4 g, 71%) was obtained as a white solid by subjecting 2-ethoxybenzenesulfonyl chloride <see (Step 1)> (1.00 g, 5.34 mmol) to the same method as in (Step 4) of Example 104.

$^1$H NMR (400 MHz, DMSO-$d_6$): δ 10.97 (s, 1H), 7.93-7.91 (m, 1H), 7.64-7.60 (m, 1H), 7.22-7.20 (m, 1H), 7.13-7.09 (m, 1H), 6.81-6.78 (m, 2H), 4.21-4.16 (m, 2H), 3.79 (s, 3H), 1.27-1.24 (m, 3H).; MS (ESI) m/z 372 (M+H)$^+$ (Step 3) 4-{[(2-Ethoxyphenyl)sulfonyl]amino}-2,6-difluorobenzoic Acid (M-84)

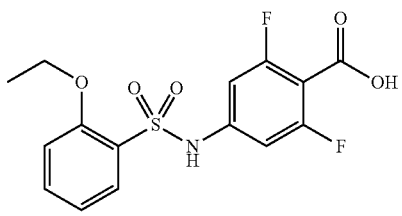 [SMILES: CCOc1ccccc1S(=O)(=O)Nc1cc(F)c(C(=O)O)c(F)c1]

The title compound (1.05 g, 78%) was obtained as a yellow solid by subjecting methyl 4-[(2-ethoxyphenyl)sulfonylamino]-2,6-difluoro-benzoate <see (Step 2)> (1.40 g, 3.77 mmol) to the same method as in (Step 5) of Example 104.

$^1$H NMR (400 MHz, CD$_3$OD): δ 7.86 (dd, J=8.0, 2.0 Hz, 1H), 7.50-7.46 (m, 1H), 7.04 (d, J=8.4 Hz, 1H), 7.00-6.96 (m, 1H), 6.65 (d, J=10.4 Hz, 2H), 4.13 (q, J=6.8 Hz, 2H), 1.31 (t, J=6.8 Hz, 3H).; MS (ESI) m/z 356 (M−1)

Example 192

Synthesis of M-85

(Step 1) Methyl 2,5-Difluoro-4-[(4-pyrimidin-5-ylphenyl)sulfonylamino]benzoate

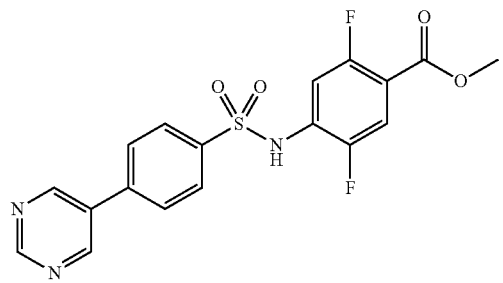

The title compound (5.50 g, 69%) was obtained as a yellow solid by subjecting methyl 4-[(4-bromophenyl)sulfonylamino]-2,5-difluoro-benzoate <see (Step 1) of Example 189> (8.00 g, 19.8 mmol) to the same method as in Example 25.

MS (ESI) m/z 406 (M+H)$^+$ (Step 2) 2,5-Difluoro-4-{[(4-pyrimidin-5-ylphenyl)sulfonyl]amino}benzoic Acid (M-85)

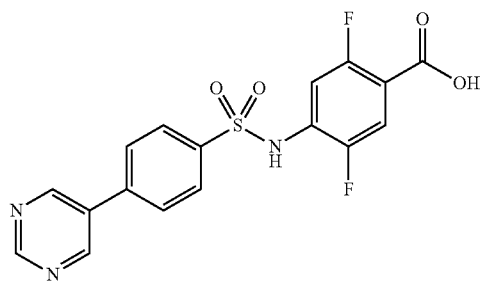 [SMILES: O=C(O)c1cc(F)c(NS(=O)(=O)c2ccc(-c3cncnc3)cc2)cc1F]

The title compound (4.8 g, 90%) was obtained by subjecting methyl 2,5-difluoro-4-[(4-pyrimidin-5-ylphenyl)sulfonylamino]benzoate <see (Step 1)> (5.50 g, 13.6 mmol) to the same method as in (Step 5) of Example 104.

$^1$H NMR (400 MHz, CD$_3$OD): δ 9.09 (s, 1H), 9.02 (s, 2H), 7.95 (dd, J=7.2, 2.0 Hz, 2H), 7.83 (dd, J=7.2, 2.0 Hz, 2H), 7.48 (dd, J=11.2, 6.8 Hz, 1H), 7.34 (dd, J=12.0, 6.8 Hz, 1H).; MS (ESI) m/z 392 (M+H)$^+$

Example 193

Synthesis of M-86

(Step 1) Methyl 2,5-Difluoro-4-[(5-iodo-2-pyridyl)sulfonylamino]benzoate

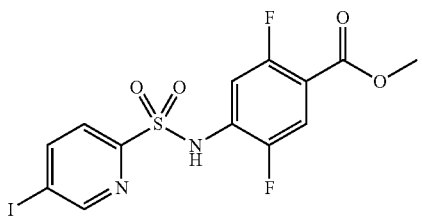 [SMILES: COC(=O)c1cc(F)c(NS(=O)(=O)c2ccc(I)cn2)cc1F]

The title compound (12.0 g, 86%) was obtained by subjecting methyl 4-amino-2,5-difluoro-benzoate <see (Step 3) of Example 104> (5.80 g, 31.0 mmol) and 5-iodopyridine-2-sulfonyl chloride <see (Step 2) of Example 120> (20.0 g, 65.8 mmol) to the same method as in (Step 4) of Example 104.

$^1$H NMR (400 MHz, DMSO-$d_6$): δ 8.99-8.98 (m, 1H), 8.53-8.50 (m, 1H), 7.82 (d, J=8.4 Hz, 1H), 7.66-7.64 (m, 1H), 7.42-7.36 (m, 1H), 3.83 (s, 3H).; MS (ESI) m/z 455 (M+H)$^+$ (Step 2) Methyl 2,5-Difluoro-4-[[5-(1,2,4-triazol-1-yl)-2-pyridyl]sulfonylamino]benzoate

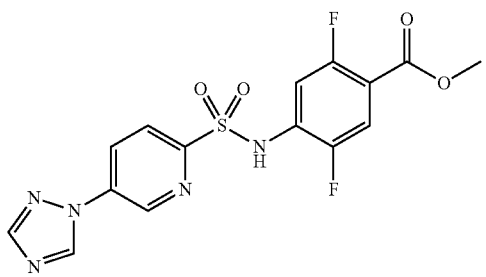 [SMILES: COC(=O)c1cc(F)c(NS(=O)(=O)c2ccc(-n3cncn3)cn2)cc1F]

The title compound (410 mg, 15%) was obtained as a white solid by subjecting methyl 2,5-difluoro-4-[(5-iodo-2-pyridyl)sulfonylamino]benzoate <see (Step 1)> (3.0 g, 6.6 mmol) to the same method as in (Step 3) of Example 23.

$^1$H NMR (300 MHz, DMSO-$d_6$): δ 9.48 (s, 1H), 9.26-9.25 (m, $^1$H), 8.56-8.52 (m, 1H), 8.37 (s, 1H), 8.26-8.23 (m, 1H), 7.69-7.63 (m, 1H), 7.49-7.43 (m, 1H), 3.81 (s, 3H).; MS (ESI) m/z 396 (M+H)$^+$ (Step 3) 2,5-Difluoro-4-({[5-(1H-1,2,4-triazol-1-yl)pyridin-2-yl]sulfonyl}amino)benzoic Acid (M-86)

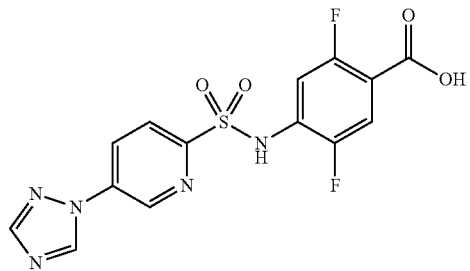 [SMILES: O=C(O)c1cc(F)c(NS(=O)(=O)c2ccc(-n3cncn3)cn2)cc1F]

The title compound (289 mg, 73%) was obtained by subjecting methyl 2,5-difluoro-4-[[5-(1,2,4-triazol-1-yl)-2-pyridyl]sulfonylamino]benzoate <see (Step 2)> (410 mg, 1.04 mmol) to the same method as in (Step 5) of Example 104.

$^1$H NMR (300 MHz, DMSO-$d_6$): δ 13.43-13.37 (s, 1H), 11.29-11.26 (m, 1H), 9.52-9.50 (m, 1H), 9.30 (d, J=2.4 Hz, 1H), 8.55 (dd, J=8.7, 2.7 Hz, 1H), 8.38 (s, 1H), 8.27-8.23 (m, 1H), 7.62 (m, 1H), 7.42 (m, 1H).; MS (ESI) m/z 382 (M+H)$^+$

Example 194

Synthesis of M-87

(Step 1) Methyl 2,5-Difluoro-4-[(4-nitrophenyl)sulfonylamino]benzoate

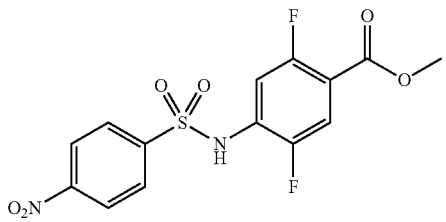

The title compound (5.60 g, 71%) was obtained as a yellow solid by subjecting methyl 4-amino-2,5-difluorobenzoate <see (Step 3) of Example 104> (4.00 g, 21.0 mmol) and 4-nitrobenzenesulfonyl chloride (7.10 g, 32.0 mmol) to the same method as in (Step 4) of Example 104.

$^1$H NMR (400 MHz, CD$_3$OD): δ 8.42 (d, J=8.8 Hz, 2H), 8.15 (d, J=8.8 Hz, 2H), 7.65-7.61 (m, 1H), 7.49-7.44 (m, 1H), 3.89 (s, 3H).; MS (ESI) m/z 373 (M+H)$^+$ (Step 2) Methyl 4-[(4-Aminophenyl)sulfonylamino]-2,5-difluoro-benzoate

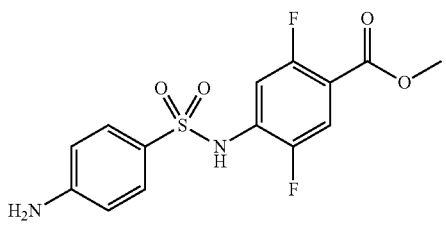 [SMILES: COC(=O)c1cc(F)c(NS(=O)(=O)c2ccc([N+](=O)[O-])cc2)cc1F]

Methyl 2,5-difluoro-4-[(4-nitrophenyl)sulfonylamino]benzoate <see (Step 1)> (5.0 g, 13 mmol) was dissolved in methanol (20 ml), and 10% palladium/carbon (500 mg) was added thereto, followed by stirring at room temperature for 6 hours in the presence of hydrogen gas. The reaction solution was filtered, and the obtained filtrate was concentrated and then dried under reduced pressure to obtain the title compound (3.5 g, 78%) as a yellow solid.

MS (ESI) m/z 343 (M+H)$^+$ (Step 3) Methyl 2,5-Difluoro-4-[[4-(tetrazol-1-yl)phenyl]sulfonylamino]benzoate

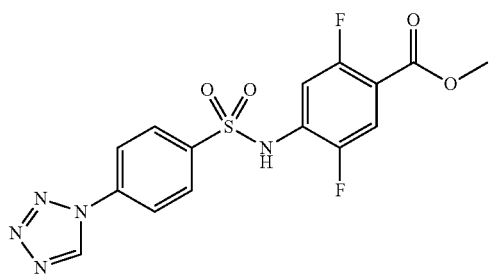

Methyl 4-[(4-aminophenyl)sulfonylamino]-2,5-difluorobenzoate <see (Step 2)> (1.5 g, 4.4 mmol) was dissolved in acetic acid (50 ml), and sodium azide (329 mg, 4.80 mmol) and triethyl orthoformate (2.00 g, 13.2 mmol) were added thereto, followed by stirring at 100° C. for 2 hours. After cooling to room temperature, concentrated hydrochloric acid (5.0 ml) and water (250 ml) were added, and the precipitated solid was filtered. The obtained solid was dried under reduced pressure to obtain the title compound (1.1 g, 64%).

$^1$H NMR (400 MHz, CD$_3$OD): δ 9.55 (s, 1H), 7.96-7.90 (m, 4H), 7.42-7.38 (m, 1H), 7.29-7.25 (m, 1H), 3.66 (s, 3H).; MS (ESI) m/z 396 (M+H)$^+$ (Step 4) 2,5-Difluoro-4-({[4-(1H-tetrazol-1-yl)phenyl]sulfonyl}amino)benzoic Acid (M-87)

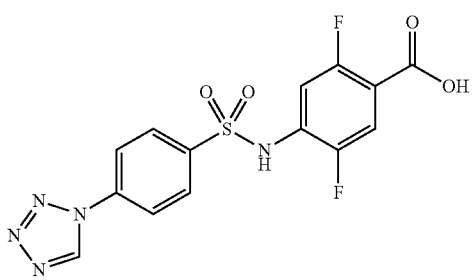 [SMILES: O=C(O)c1cc(F)c(NS(=O)(=O)c2ccc(-n3cnnn3)cc2)cc1F]

The title compound (910 mg, 86%) was obtained as a white solid by subjecting methyl 2,5-difluoro-4-[[4-(tetrazol-1-yl)phenyl]sulfonylamino]benzoate <see (Step 3)> (1.1 g, 2.8 mmol) to the same method as in (Step 5) of Example 104.

$^1$H NMR (400 MHz, DMSO-d$_6$): δ 9.74 (s, 1H), 8.05-7.99 (m, 4H), 7.48 (dd, J=10.8, 6.4 Hz, 1H), 7.35 (dd, J=12.0, 6.4 Hz, 1H).

Example 195

Synthesis of M-88

(Step 1) Methyl 2,5-Difluoro-4-[[4-(1,2,4-triazol-4-yl)phenyl]sulfonylamino]benzoate

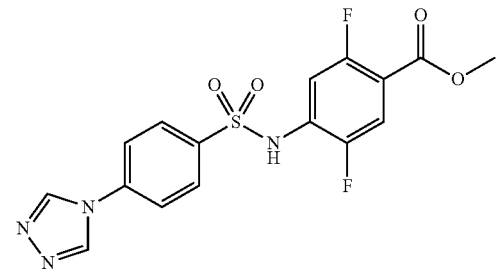 [SMILES: COC(=O)c1cc(F)c(NS(=O)(=O)c2ccc(-n3cnnc3)cc2)cc1F]

Methyl 4-[(4-aminophenyl)sulfonylamino]-2,5-difluorobenzoate <see (Step 2) of Example 194> (1.5 g, 4.4 mmol) was dissolved in pyridine, and N,N'-diformylhydrazine (1.20 g, 13.6 mmol), chlorotrimethylsilane (7.20 g, 66.0 mmol), and triethylamine (3.10 g, 31.0 mmol) were added dropwise thereto, followed by stirring at 100° C. for 12 hours. After cooling to room temperature, the reaction solution was concentrated under reduced pressure. Methanol was added to the obtained residue, followed by stirring at room temperature for 30 minutes. The precipitated solid was filtered and dried under reduced pressure to obtain the title compound (850 mg, 49%).

$^1$H NMR (400 MHz, CD$_3$OD): δ 8.86 (s, 2H), 7.88-7.86 (m, 2H), 7.66-7.64 (m, 2H), 7.40-7.35 (m, 1H), 7.26-7.22 (m, 1H), 3.64 (s, 3H).; MS (ESI) m/z 395 (M+H)$^+$ (Step 2) 2,5-Difluoro-4-({[4-(4H-1,2,4-triazol-4-yl)phenyl]sulfonyl}amino)benzoic Acid (M-88)

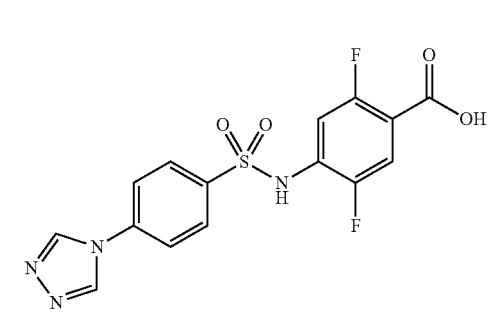 [SMILES: O=C(O)c1cc(F)c(NS(=O)(=O)c2ccc(-n3cnnc3)cc2)cc1F]

The title compound (810 mg, 84%) was obtained as a yellow solid by subjecting methyl 2,5-difluoro-4-[[4-(1,2,4-triazol-4-yl)phenyl]sulfonylamino]benzoate <see (Step 1)> (1.00 g, 2.54 mmol) to the same method as in (Step 5) of Example 104.

¹H NMR (400 MHz, DMSO-d₆): δ 13.42-13.41 (m, 1H), 11.12 (br s, 1H), 9.23 (s, 2H), 8.05 (d, J=8.8 Hz, 2H), 7.97 (d, J=8.8 Hz, 2H), 7.62 (dd, J=10.8, 6.8 Hz, 1H), 7.29 (dd, J=11.6, 6.4 Hz, 1H).; MS (ESI) m/z 381 (M+H)⁺

Example 196

Synthesis of M-89

(Step 1) Methyl 4-[(5-Bromo-2-pyridyl)sulfonylamino]-2,5-difluoro-benzoate

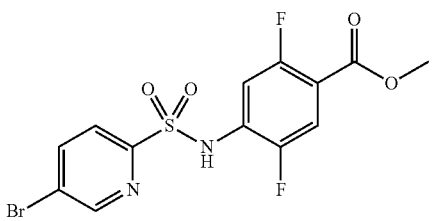

The title compound (20.0 g, 84%) was obtained by subjecting methyl 4-amino-2,5-difluoro-benzoate <see (Step 3) of Example 104> (10.9 g, 58.3 mmol) and 5-bromopyridine-2-sulfonyl chloride <see (Step 2) of Example 121> (30.0 g, 118 mmol) to the same method as in (Step 4) of Example 104.

¹H NMR (400 MHz, DMSO-d₆): δ 11.30 (s, 1H), 8.91 (d, J=2.0 Hz, 1H), 8.40 (dd, J=8.4, 2.4 Hz, 1H), 8.00 (d, J=8.4 Hz, 1H), 7.69-7.65 (m, 1H), 7.45-7.39 (m, 1H), 3.83 (s, 3H).; MS (ESI) m/z 407, 409 (M+H)⁺

(Step 2) Methyl 2,5-Difluoro-4-[(5-pyrimidin-5-yl-2-pyridyl)sulfonylamino]benzoate

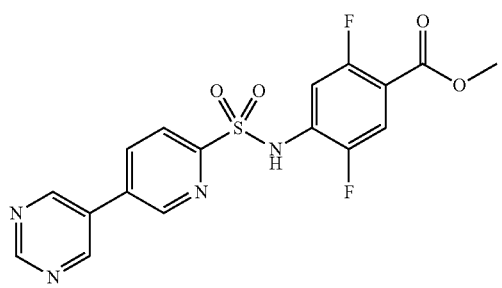 [SMILES: COC(=O)c1cc(F)c(NS(=O)(=O)c2ccc(-c3cncnc3)cn2)cc1F]

The title compound (2.70 g, 34%) was obtained as a red solid by subjecting methyl 4-[(5-bromo-2-pyridyl)sulfonylamino]-2,5-difluoro-benzoate <see (Step 1)>(8.00 g, 19.7 mmol) to the same method as in Example 25.

¹H NMR (400 MHz, DMSO-d₆): δ 11.36 (s, 1H), 9.29 (s, 3H), 9.19 (d, J=2.0 Hz, 1H), 8.58 (dd, J=8.0, 1.6 Hz, 1H), 8.20 (d, J=8.0 Hz, 1H), 7.68-7.63 (m, 1H), 7.52-7.48 (m, 1H), 3.82 (s, 3H).

(Step 3) 2,5-Difluoro-4-{[(5-pyrimidin-5-ylpyridin-2-yl)sulfonyl]amino}benzoic Acid (M-89)

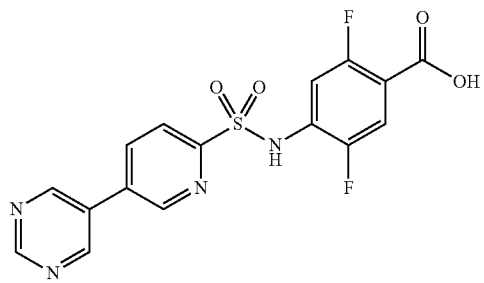 [SMILES: O=C(O)c1cc(F)c(NS(=O)(=O)c2ccc(-c3cncnc3)cn2)cc1F]

The title compound (2.5 g, 96%) was obtained as a red solid by subjecting methyl 2,5-difluoro-4-[(5-pyrimidin-5-yl-2-pyridyl)sulfonylamino]benzoate <see (Step 2)> (2.70 g, 6.70 mmol) to the same method as in (Step 5) of Example 104.

¹H NMR (400 MHz, DMSO-d₆): δ 13.40-13.33 (m, 1H), 11.28-11.24 (m, 1H), 9.32-9.29 (m, 3H), 9.21 (d, J=2.0 Hz, 1H), 8.57 (dd, J=8.4, 2.4 Hz, 1H), 8.20 (d, J=8.4 Hz, 1H), 7.63 (dd, J=10.8, 6.8 Hz, 1H), 7.47 (dd, J=12.0, 6.4 Hz, 1H).; MS (ESI) m/z 393 (M+H)⁺

Example 197

Synthesis of M-90

(Step 1) Methyl 2,5-Difluoro-4-[(4-iodophenyl)sulfonylamino]benzoate

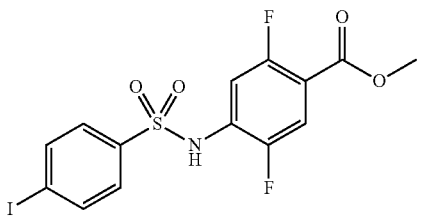

The title compound (14.0 g, 89%) was obtained as a yellow solid by subjecting methyl 4-amino-2,5-difluoro-benzoate <see (Step 3) of Example 104> (6.50 g, 34.8 mmol) and 4-iodobenzenesulfonyl chloride (21.0 g, 69.5 mmol) to the same method as in (Step 4) of Example 104.
MS (ESI) m/z 452 (M−1)

(Step 2) Methyl 2,5-Difluoro-4-[[4-(1,2,4-triazol-1-yl)phenyl]sulfonylamino]benzoate

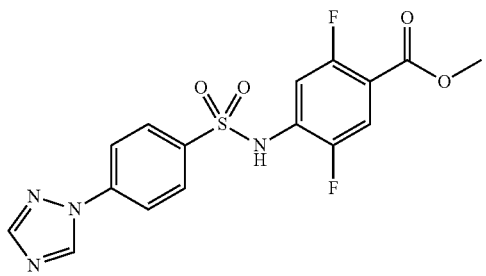 [SMILES: COC(=O)c1cc(F)c(NS(=O)(=O)c2ccc(-n3cncn3)cc2)cc1F]

The title compound (6.50 g, 53%) was obtained as a white solid by subjecting methyl 2,5-difluoro-4-[(4-iodophenyl)sulfonylamino]benzoate <see (Step 1)> (14.0 g, 31.0 mmol) to the same method as in (Step 3) of Example 23.

¹H NMR (400 MHz, CD₃OD): δ 9.18 (s, 1H), 8.19 (s, 1H), 8.09 (m, 2H), 7.98 (m, 2H), 7.47-7.42 (m, 1H), 7.15-7.10 (m, 1H), 3.83 (s, 3H).

(Step 3) 2,5-Difluoro-4-({[4-(1H-1,2,4-triazol-1-yl)phenyl]sulfonyl}amino)benzoic Acid (M-90)

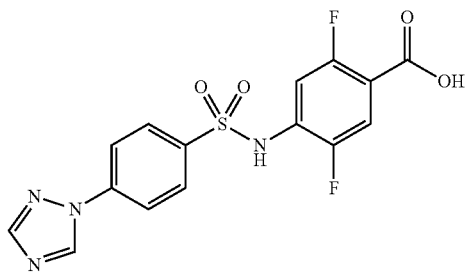 [SMILES: O=C(O)c1cc(F)c(NS(=O)(=O)c2ccc(-n3cncn3)cc2)cc1F]

The title compound (5.00 g, 79%) was obtained by subjecting methyl 2,5-difluoro-4-[[4-(1,2,4-triazol-1-yl)phenyl]sulfonylamino]benzoate <see (Step 2)> (6.50 g, 16.5 mmol) to the same method as in (Step 5) of Example 104.

¹H NMR (CD₃OD, 400 MHz): δ 9.13 (br s, 1H), 8.11 (s, 1H), 7.96 (s, 4H), 7.48 (d, J=10.8, 6.4 Hz, 1H), 7.34 (dd, J=12.0, 6.4 Hz, 1H).; MS (ESI) m/z 381 (M+H)⁺

Example 198

Synthesis of M-91

(Step 1) [6-[(2,5-Difluoro-4-methoxycarbonyl-phenyl)sulfamoyl]-3-pyridyl]boronic Acid

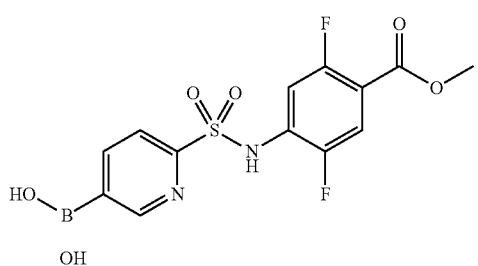

The title compound was obtained by subjecting methyl 4-[(5-bromo-2-pyridyl)sulfonylamino]-2,5-difluoro-benzoate <see (Step 1) of Example 196> (4.10 g, 10.1 mmol) to the same method as in (Step 3) of Example 7.

MS (ESI) m/z 371 (M−1)

(Step 2) Methyl 2,5-Difluoro-4-[(5-pyrimidin-2-yl-2-pyridyl)sulfonylamino]benzoate

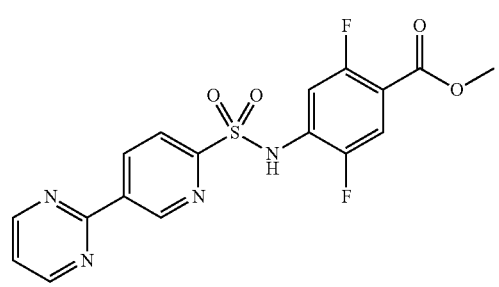

The title compound (1.3 g, 32% over two steps) was obtained by subjecting 6-[(2,5-difluoro-4-methoxycarbonyl-phenyl)sulfamoyl]-3-pyridyl]boronic acid <see (Step 1)> (3.00 g) to the same method as in (Step 4) of Example 7.

MS (ESI) m/z 405 (M−1)

(Step 3) 2,5-Difluoro-4-{[(5-pyrimidin-2-ylpyridin-2-yl)sulfonyl]amino}benzoic Acid (M-91)

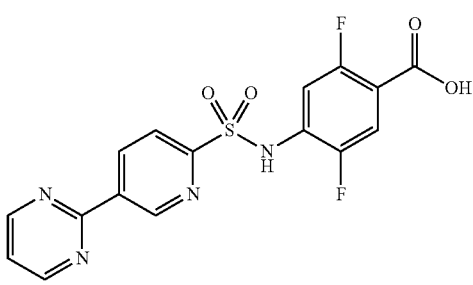 [SMILES: O=C(O)c1cc(F)c(NS(=O)(=O)c2ccc(-c3ncccn3)cn2)cc1F]

The title compound (800 mg, 62%) was obtained as a brown solid by subjecting methyl 2,5-difluoro-4-[(5-pyrimidin-2-yl-2-pyridyl)sulfonylamino]benzoate <see (Step 2)> (1.30 g, 3.30 mmol) to the same method as in (Step 5) of Example 104.

¹H NMR (400 MHz, DMSO-d₆): δ 13.39 (br s, 1H), 11.26 (br s, 1H), 9.59 (d, J=1.2 Hz, 1H), 9.02 (d, J=5.2 Hz, 2H), 8.96 (dd, J=8.0, 2.0 Hz, 1H), 8.21 (d, J=8.4 Hz, 1H), 7.65-7.60 (m, 2H), 7.41 (dd, J=12.0, 6.4 Hz, 1H).; MS (ESI) m/z 393 (M+H)⁺

Example 199

Synthesis of M-92

(Step 1) Methyl 4-[[4-(Cyclopropanecarbonyl)phenyl]sulfonylamino]-2,5-difluoro-benzoate

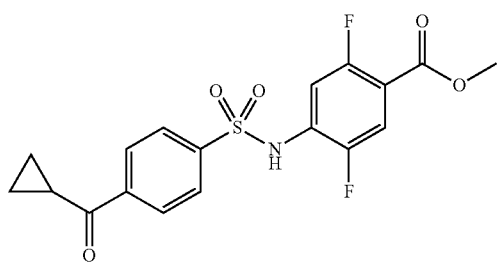 [SMILES: COC(=O)c1cc(F)c(NS(=O)(=O)c2ccc(C(=O)C3CC3)cc2)cc1F]

The title compound (600 mg, 19%) was obtained by subjecting methyl 4-amino-2,5-difluoro-benzoate <see (Step 3) of Example 104>(1.50 g, 8.02 mmol) and 4-(cyclopropanecarbonyl)benzenesulfonyl chloride <see (Step 3) of Example 130>(2.60 g, 8.02 mmol) to the same method as in (Step 4) of Example 104.

¹H NMR (400 MHz, CD₃OD): δ 8.22 (d, 2H), 8.00 (d, 2H), 7.67 (m, 1H), 7.32 (m, 1H), 3.80 (s, 3H), 2.86-2.82 (m, 1H), 1.10-1.06 (m, 4H).

(Step 2) 4-({-[4-(Cyclopropylcarbonyl)phenyl]sulfonyl}amino)-2,5-difluorobenzoic Acid (M-92)

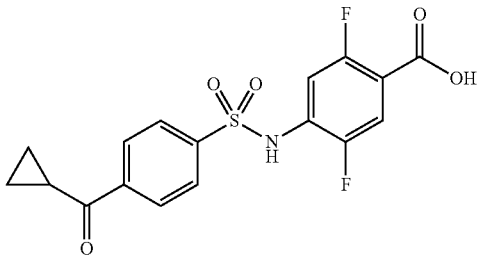 [SMILES: O=C(O)c1cc(F)c(NS(=O)(=O)c2ccc(C(=O)C3CC3)cc2)cc1F]

The title compound (231 mg, 40%) was obtained by subjecting methyl 4-[[4-(cyclopropanecarbonyl)phenyl]sulfonylamino]-2,5-difluoro-benzoate <see (Step 1)>(600 mg, 1.52 mmol) to the same method as in (Step 5) of Example 104.

$^1$H NMR (400 MHz, CD$_3$OD): δ 8.20 (d, J=8.4 Hz, 2H), 8.03 (d, J=8.4 Hz, 2H), 7.61 (dd, J=10.8, 6.4 Hz, 1H), 7.44 (dd, J=11.6, 6.8 Hz, 1H), 2.86-2.82 (m, 1H), 1.20-1.14 (m, 4H).

Example 200

Synthesis of M-93

(Step 1) Methyl 2,5-Difluoro-4-[[4-(triazol-1-yl)phenyl]sulfonylamino]benzoate

M-93-a

M-93-b

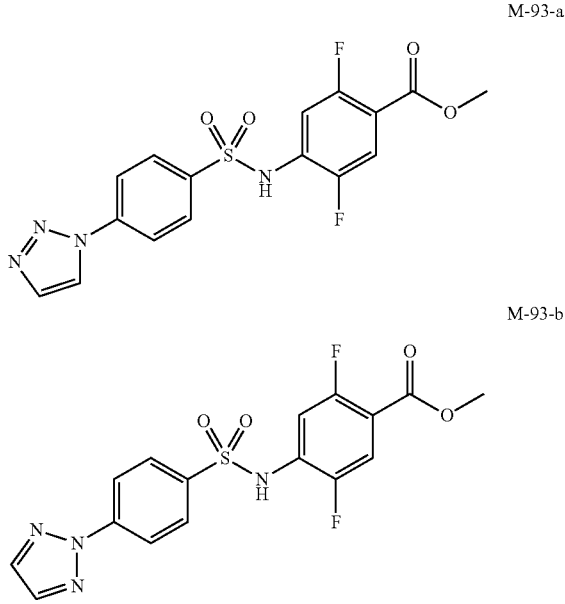

The title compound (M-93-a, 530 mg) was obtained as a gray solid by subjecting methyl 2,5-difluoro-4-[(4-iodophenyl)sulfonylamino]benzoate <(Step 1) of Example 197> (6.50 g, 14.0 mmol) to the same methods as in Examples 15 to 18. At the same time, a regioisomer methyl 2,5-difluoro-4-[[4-(triazol-2-yl)phenyl]sulfonylamino]benzoate (M-93-b, 1.71 g) was also obtained.

$^1$H NMR (400 MHz, DMSO-d$_6$) for M-93-a: δ 11.1 (s, 1H), 8.25-8.21 (m, 4H), 8.06-8.02 (m, 2H), 7.67-7.63 (m, 1H), 7.34-7.29 (m, 1H), 3.80 (s, 3H).

$^1$H NMR (400 MHz, DMSO-d$_6$) for M-93-b: δ 11.2 (s, 1H), 8.95 (d, J=1.2 Hz, 1H), 8.19-8.16 (m, 2H), 8.09-8.01 (m, 3H), 7.68-7.64 (m, 1H), 7.35-7.31 (m, 1H), 3.81 (s, 3H).

(Step 2) 2,5-Difluoro-4-({[4-(1H-1,2,3-triazol-1-yl)phenyl]sulfonyl}amino)benzoic Acid (M-93)

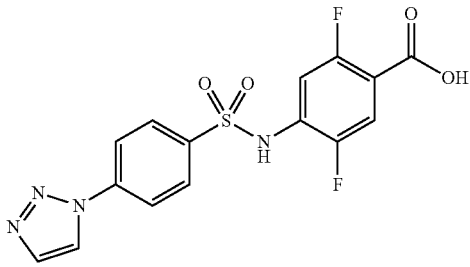 [SMILES: O=C(O)c1cc(F)c(NS(=O)(=O)c2ccc(-n3ccnn3)cc2)cc1F]

The title compound (454 mg, 89%) was obtained as a yellow solid by subjecting methyl 2,5-difluoro-4-[[4-(triazol-1-yl)phenyl]sulfonylamino]benzoate <see (Step 1)> (530 mg, 1.35 mmol) to the same method as in (Step 5) of Example 104.

$^1$H NMR (400 MHz, CD$_3$OD): δ 8.54 (d, J=0.8 Hz, 1H), 8.00 (s, 4H), 7.82 (d, J=0.8 Hz, 1H), 7.48 (dd, J=10.8, 6.4 Hz, 1H), 7.34 (dd, J=12.0, 6.4 Hz, 1H).; MS (ESI) m/z 381 (M+H)$^+$

Example 201

Synthesis of M-94

(Step 1) Methyl 4-[[5-(2,6-Dimethyl-4-pyridyl)-2-pyridyl]sulfonylamino]-2,5-difluoro-benzoate

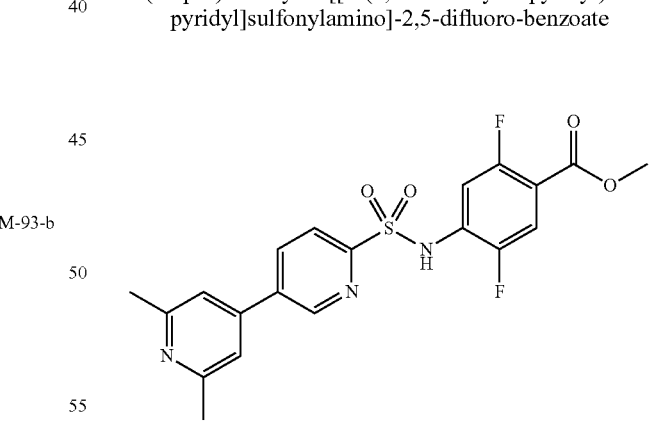

The title compound (11.0 g, 49%) was obtained by subjecting methyl 4-[(5-bromo-2-pyridyl)sulfonylamino]-2,5-difluoro-benzoate <see (Step 1) of Example 196>(21.0 g, 51.6 mmol) and 2,6-dimethyl-4-(4,4,5,5-tetramethyl-1,3,2-dioxaborolan-2-yl) pyridine <see (Step 1) of Example 27> (15.6 g, 67.1 mmol) to the same method as in (Step 2) of Example 27.

$^1$H NMR (400 MHz, CD$_3$OD): δ 9.16 (d, J=1.6 Hz, 1H), 8.59 (dd, J=8.4, 2.4 Hz, 1H), 8.31 (d, J=8.4 Hz, 1H), 8.07 (s, 2H), 7.67-7.62 (m, 2H), 3.90 (s, 3H), 2.81 (s, 6H).

(Step 2) 4-{[(2',6'-Dimethyl-3,4'-bipyridin-6-yl)sulfonyl]amino}-2,5-difluorobenzoic Acid (M-94)

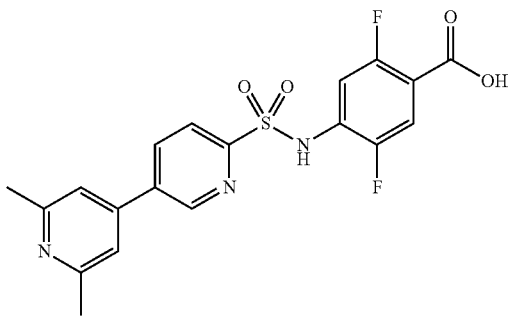 [SMILES: Cc1cc(-c2ccc(S(=O)(=O)Nc3cc(F)c(C(=O)O)cc3F)nc2)cc(C)n1]

The title compound (9.57 g, 90%) was obtained as a white solid by subjecting methyl 4-[[5-(2,6-dimethyl-4-pyridyl)-2-pyridyl]sulfonylamino]-2,5-difluoro-benzoate <see (Step 1)>(11.0 g, 25.4 mmol) to the same method as in (Step 5) of Example 104.

$^1$H NMR (400 MHz, CD$_3$OD): δ 9.19 (d, J=1.6 Hz, 1H), 8.59 (dd, J=8.0, 2.4 Hz, 1H), 8.31 (d, J=8.4 Hz, 1H), 8.15 (s, 2H), 7.65-7.59 (m, 2H), 2.85 (s, 6H).; MS (ESI) m/z 420 (M+H)$^+$

Example 202

Synthesis of M-95

(Step 1) 2,5-Difluoro-4-({[4-(2-methoxypyrimidin-5-yl)phenyl]sulfonyl}amino)benzoic Acid (M-95)

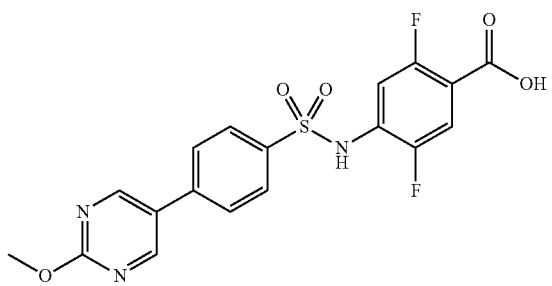 [SMILES: COc1ncc(-c2ccc(S(=O)(=O)Nc3cc(F)c(C(=O)O)cc3F)cc2)cn1]

2,5-Difluoro-4-[(4-iodophenyl)sulfonylamino]benzoate <(Step 1) of Example 197>(453 mg, 1.00 mmol), 4,4,5,5-tetramethyl-2-(4,4,5,5-tetramethyl-1,3,2-dioxaboran-2-yl)-1,3,2-dioxaborane (304 mg, 1.20 mmol), potassium acetate (147 mg, 1.50 mmol), and PdCl2(dppf) (36 mg, 0.050 mmol) were dissolved in N,N-dimethylformamide (3.0 ml), followed by stirring at 90° C. for 5 hours. After the insoluble matters were separated by filtration, the filtrate was diluted with ethyl acetate, and washed with water, 1 N-hydrochloric acid, and saturated aqueous sodium chloride. The extraction liquid was dried over sodium sulfate, and then the solvent was removed under reduced pressure. Purification was conducted by preparative HPLC to obtain a crude product (110 mg, 0.240 mmol) of [4-[(2,5-difluoro-4-methoxycarbonyl-phenyl)sulfamoyl]phenyl]boronic acid. Dioxane (1.0 ml) and water (0.3 ml) were added to the obtained crude product (42 mg, 0.11 mmol) of [4-[(2,5-difluoro-4-methoxycarbonyl-phenyl)sulfamoyl]phenyl]boronic acid, 4-bromo-2-methoxypyrimidine (32 mg, 0.17 mmol), PdCl2(dppf) (4.0 mg, 5.4 μmol), and sodium carbonate (36 mg, 0.34 mmol), followed by stirring at 120° C. for 20 minutes in microwave reactor. After the solvent was removed under reduced pressure, the residue was roughly purified by silica gel column chromatography. The obtained crude product (42 mg) was dissolved in tetrahydrofuran (2.0 ml), methanol (1.0 ml), and water (1.0 ml), and lithium hydroxide monohydrate (12 mg, 0.28 mmol) was added thereto. After stirring at room temperature for 12 hours, lithium hydroxide (12 mg, 0.28 mmol) was added, followed by stirring at room temperature for further 12 hours. The pH of the reaction liquid was made acidic by adding 1 N-hydrochloric acid thereto, and then the solution was freeze dried to obtain the title compound (M-95).

Example 203

Synthesis of M-96

(Step 1) 5-Bromo-2-ethyl-pyrimidine

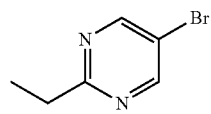

5-Bromo-2-iodo-pyrimidine (50.0 g, 176 mmol) was dissolved in tetrahydrofuran (1.0 L), and Pd(PPh3)4 (10.2 g, 9.00 mmol) was added thereto. After cooling to 0° C., diethylzinc (250 ml, 250 mmol) was added dropwise, followed by stirring for 30 minutes in the presence of nitrogen gas. The reaction solution was diluted with ethyl acetate (500 ml), and then washed with a saturated aqueous ammonium chloride solution, a saturated aqueous sodium hydrogen carbonate solution, and saturated aqueous sodium chloride. After the extraction liquid was dried over sodium sulfate, the solvent was removed under reduced pressure. The obtained residue was purified by silica gel column chromatography (petroleum ether/ethyl acetate=10:1 to 5:1) to obtain the title compound (24.0 g, 73%).

1H NMR (400 MHz, DMSO-d$_6$): δ 8.86 (s, 4H), 2.89-2.81 (m, 2H), 1.26-1.21 (t, 3H).

(Step 2) Methyl 4-[[4-(2-Ethylpyrimidin-5-yl)phenyl]sulfonylamino]-2,5-difluoro-benzoate

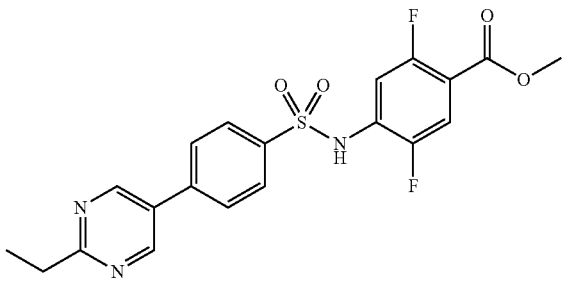

The title compound (24.6 g, 49%) was obtained by subjecting [4-[(2,5-difluoro-4-methoxycarbonyl-phenyl)sulfamoyl]phenyl]boronic acid <see (Step 2) of Example 189>

(43.1 g, 116 mmol) and 5-bromo-2-ethyl-pyrimidine <see (Step 1)>(24.0 g, 128 mmol) to the same method as in (Step 4) of Example 8.

1H NMR (400 MHz, DMSO-$d_6$): δ 11.26 (s, 1H), 9.10 (s, 2H), 8.06-4.96 (m, 4H), 7.68-7.64 (m, 1H), 7.36-7.31 (m, 1H), 3.80 (s, 3H), 2.96-2.92 (m, 2H), 1.32-1.29 (t, 3H).

(Step 3) 4-({[4-(2-Ethylpyrimidin-5-yl)phenyl]sulfonyl}amino)-2,5-difluorobenzoic Acid (M-96)

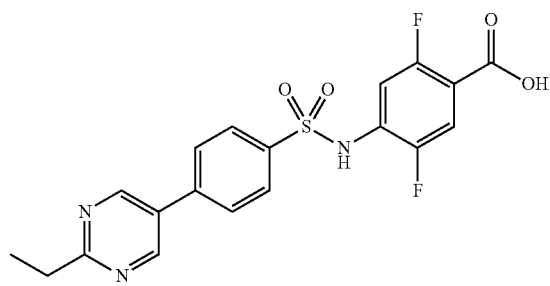

The title compound (712 mg, 92%) was obtained as a white solid by subjecting methyl 4-[[4-(2-ethylpyrimidin-5-yl)phenyl]sulfonylamino]-2,5-difluoro-benzoate <see (Step 2)>(800 mg, 1.84 mmol) to the same method as in (Step 5) of Example 104.

1H NMR (400 MHz, $CD_3OD$): δ 9.05 (s, 2H), 8.07-8.05 (m, 2H), 7.93 (dd, J=6.8, 2.0 Hz, 2H), 7.60 (dd, J=11.2, 6.8 Hz, 1H), 7.47 (dd, J=12.0, 6.8 Hz, 1H), 3.03 (q, J=7.6 Hz, 2H), 1.40 (t, J=7.6 Hz, 3H).; MS (ESI) m/z 420 (M+H)$^+$

Example 204

Synthesis of M-97

(Step 1) 4-Bromo-2-ethoxy-1-nitro-benzene

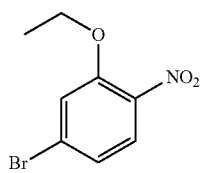

4-Bromo-2-fluoro-1-nitro-benzene (15.0 g, 68.2 mmol) was dissolved in ethanol (150 ml), and sodium ethoxide (14.0 g, 205 mmol) was added thereto, followed by stirring at room temperature for 2 hours. The reaction liquid was concentrated under reduced pressure, and then diluted with water. The precipitated solid was filtered and dried under reduced pressure to obtain the title compound (16.0 g, 95%).

$^1$H NMR (400 MHz, $CDCl_3$): δ 7.72 (d, J=8.4 Hz, 1H), 7.21 (d, J=1.6 Hz, 1H), 7.15 (dd, J=8.8, 2.0 Hz, 1H), 4.18 (q, J=7.2 Hz, 2H), 1.48 (t, J=7.2 Hz, 3H).

(Step 2) 4-Bromo-2-ethoxy-aniline

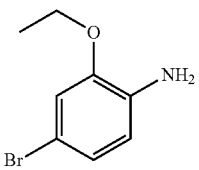

4-Bromo-2-ethoxy-1-nitro-benzene <see (Step 1)> (16.0 g, 65.0 mmol) was dissolved in methanol (150 ml) and a saturated aqueous ammonium chloride solution (50 ml), and iron (18.2 g, 325 mmol) was added thereto, followed by stirring at 50° C. for 2 hours. After cooling to room temperature, the reaction liquid was filtered and diluted with water. After extraction with ethyl acetate (50 ml×6), the extraction liquids were combined, washed with a saturated aqueous sodium hydrogen carbonate solution (100 ml) and saturated aqueous sodium chloride, and dried over sodium sulfate. Then, the solvent was removed under reduced pressure to obtain the title compound (12.0 g, 86%).

MS (ESI) m/z 216 (M+H)$^+$ (Step 3) 4-Bromo-2-ethoxy-benzenesulfonyl Chloride

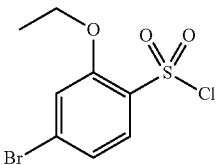

The title compound (2.4 g, 28%) was obtained by subjecting 4-bromo-2-ethoxy-aniline <see (Step 2)> (6.00 g, 27.8 mmol) to the same method as in (Step 1) of Example 118.

1H NMR (300 MHz, $CDCl_3$): δ 7.81 (d, J=11.2 Hz, 1H), 7.26-7.22 (m, 2H), 4.29 (q, J=11.2 Hz, 2H), 1.57 (t, J=11.2H).

(Step 4) Methyl 4-[(4-Bromo-2-ethoxy-phenyl)sulfonylamino]-2,6-difluoro-benzoate

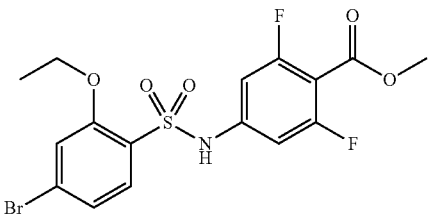 [SMILES: CCOc1cc(Br)ccc1S(=O)(=O)Nc1cc(F)c(C(=O)OC)c(F)c1]

The title compound (0.89 g, 31%) was obtained as a yellow solid by subjecting methyl 4-amino-2,5-difluoro-benzoate <see (Step 3) of Example 104> (1.20 g, 6.40 mmol) and 4-bromo-2-ethoxy-benzenesulfonyl chloride <see (Step 3)> (2.40 g, 8.00 mmol) to the same method as in (Step 4) of Example 104.

¹H NMR (300 MHz, CDCl₃): δ 7.79 (d, J=8.4 Hz, 1H), 7.24-7.20 (m, 1H), 7.16-7.15 (m, 1H), 6.73-6.66 (m, 2H), 4.26 (q, J=7.2 Hz, 2H), 3.90 (s, 3H), 1.56 (t, J=7.2 Hz, 3H).; MS (ESI) m/z 450, 452 (M+H)⁺

(Step 5) [4-[(3,5-Difluoro-4-methoxycarbonyl-phenyl)sulfamoyl]-3-ethoxy-phenyl]boronic Acid

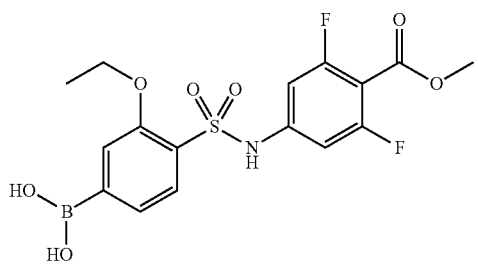 [SMILES: CCOc1cc(B(O)O)ccc1S(=O)(=O)Nc1cc(F)c(C(=O)OC)c(F)c1]

The title compound (1.65 g, 77% over two steps) was obtained by subjecting methyl 4-[(4-bromo-2-ethoxy-phenyl)sulfonylamino]-2,6-difluoro-benzoate <see (Step 4)> (2.30 g, 5.12 mmol) to the same two steps as in (Step 3) of Example 8.

¹H NMR (DMSO-d₆, 300 MHz): δ 8.38 (s, 2H), 7.88-7.85 (m, 1H), 7.52 (s, 1H), 7.46-7.43 (m, 1H), 6.79-6.75 (m, 2H), 4.21-4.14 (m, 2H), 3.78 (s, 3H), 1.26 (t, J=6.9 Hz, 3H).; MS (ESI) m/z 414 (M−1)

(Step 6) Methyl 4-[(2-Ethoxy-4-pyrimidin-2-yl-phenyl)sulfonylamino]-2,6-difluoro-benzoate

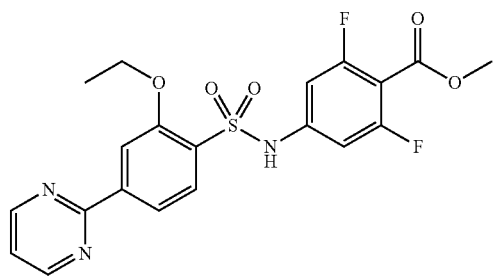 [SMILES: CCOc1cc(-c2ncccn2)ccc1S(=O)(=O)Nc1cc(F)c(C(=O)OC)c(F)c1]

The title compound (165 mg, 28%) was obtained by subjecting [4-[(3,5-difluoro-4-methoxycarbonyl-phenyl)sulfamoyl]-3-ethoxy-phenyl]boronic acid <see (Step 5)> (550 mg, 1.33 mmol) to the same method as in (Step 4) of Example 8.

¹H NMR (400 MHz, CDCl₃): δ 8.82 (d, J=4.4 Hz, 2H), 8.17-8.15 (m, 2H), 8.04-8.02 (m, 1H), 7.33 (s, 1H), 7.28-7.26 (m, 1H), 6.73-6.71 (m, 2H), 4.44-4.39 (m, 2H), 3.85 (s, 3H), 1.61-1.57 (m, 3H).; MS (ESI) m/z 448 (M−1)

(Step 7) 4-{[(2-Ethoxy-4-pyrimidin-2-ylphenyl)sulfonyl]amino}-2,6-difluorobenzoic Acid (M-97)

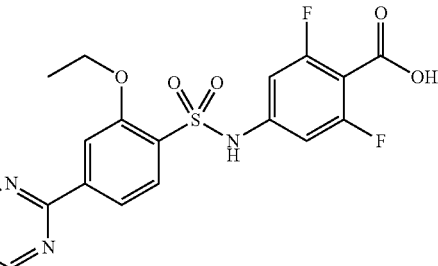

The title compound (115 mg, 76%) was obtained as a white solid by subjecting methyl 4-[(2-ethoxy-4-pyrimidin-2-yl-phenyl)sulfonylamino]-2,6-difluoro-benzoate <see (Step 6)> (155 mg, 0.345 mmol) to the same method as in (Step 5) of Example 104.

¹H NMR (400 MHz, CD₃OD): δ 8.77 (d, J=5.2 Hz, 2H), 8.07-7.97 (m, 3H), 7.33-7.31 (m, 1H), 6.70-6.68 (m, 2H), 4.25 (q, J=7.2 Hz, 2H), 1.36 (t, J=7.2 Hz, 3H).; MS (ESI) m/z 436 (M+H)⁺

Example 205

Synthesis of M-98

(Step 1) 2-(Azetidin-1-yl)-5-bromo-pyrimidine

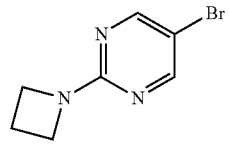 [SMILES: Brc1cnc(N2CCC2)nc1]

5-Bromo-2-chloro-pyrimidine (29.9 g, 150 mmol) was dissolved in N,N-dimethylformamide (300 ml), and azetidine (11.4 g, 500 mmol) and potassium carbonate (42.5 g, 310 mmol) were added thereto, followed by stirring at 50° C. for 12 hours. After cooling to room temperature, the reaction solution was diluted with water, followed by extraction with diethyl ether (300 ml×3). The extraction liquids were combined, washed with saturated aqueous sodium chloride, and dried over sodium sulfate. The solvent was removed under reduced pressure to obtain the title compound (30.0 g, 93%).

¹H NMR (400 MHz, CDCl₃): δ 8.26 (s, 2H), 4.12 (t, J=7.4 Hz, 4H), 2.40-2.33 (m, 2H).

(Step 2) Methyl 4-[[4-[2-(Azetidin-1-yl)pyrimidin-5-yl]phenyl]sulfonylamino]-2,5-difluoro-benzoate

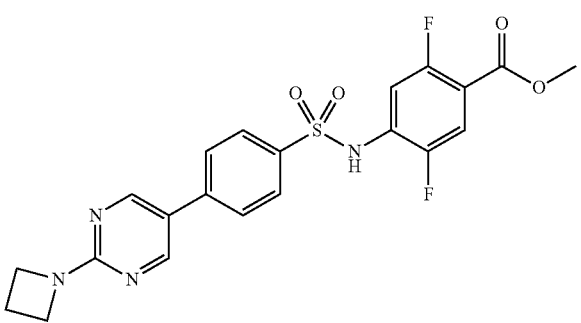 [SMILES: COC(=O)c1cc(F)c(NS(=O)(=O)c2ccc(-c3cnc(N4CCC4)nc3)cc2)cc1F]

The title compound (15 g, 64%) was obtained by subjecting 2-(azetidin-1-yl)-5-bromo-pyrimidine <see (Step 1)> (10.7 mg, 50.4 mmol) and [4-[(2,5-difluoro-4-methoxycarbonyl-phenyl)sulfamoyl]phenyl]boronic acid <see (Step 2) of Example 189> to the same method as in (Step 4) of Example 8.

MS (ESI) m/z 461 (M+H)+

(Step 3) 4-({[4-(2-Azetidin-1-ylpyrimidin-5-yl)phenyl]sulfonyl}amino)-2,5-difluorobenzoic Acid (M-98)

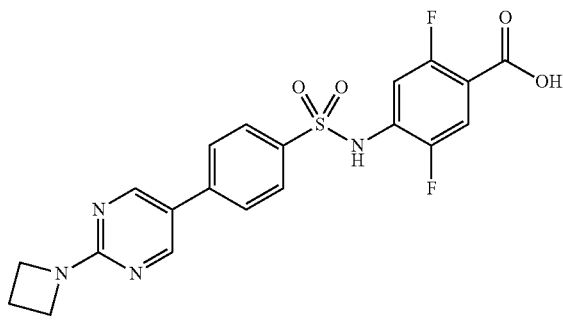 [SMILES: O=C(O)c1cc(F)c(NS(=O)(=O)c2ccc(-c3cnc(N4CCC4)nc3)cc2)cc1F]

The title compound (10.0 g, 69%) was obtained as a white solid by subjecting methyl 4-[[4-[2-(azetidin-1-yl)pyrimidin-5-yl]phenyl]sulfonylamino]-2,5-difluoro-benzoate <see (Step 2)> (15.0 g, 32.6 mmol) to the same method as in (Step 5) of Example 104.

$^1$H NMR (400 MHz, DMSO-d$_6$): δ 13.41 (s, 1H), 11.10 (s, 1H), 8.78 (s, 2H), 7.98-7.88 (m, 4H), 7.64-7.60 (m, 1H), 7.31-7.27 (m, 1H), 4.12 (t, J=7.2 Hz, 4H), 2.52-2.32 (m, 2H).; MS (ESI) m/z 447 (M+H)+

Example 206

Synthesis of M-99

(Step 1) 6-Nitro-3H-isobenzofuran-1-one

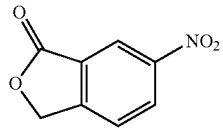 [SMILES: O=C1OCc2ccc([N+](=O)[O-])cc21]

3H-Isobenzofuran-1-one (4.00 g, 29.8 mmol) was dissolved in concentrated sulfuric acid (5.0 ml) at 0° C., and a solution of potassium nitrate (3.0 g, 30 mmol) in concentrated sulfuric acid (8.0 ml) was added dropwise thereto. After stirring at room temperature for 5 hours, the reaction solution was diluted with water. The precipitated solid was filtered and recrystallized from ethanol (20 ml) to obtain the title compound (2.0 g, 37%).

1H NMR (400 MHz, DMSO-d$_6$): δ 8.62-8.59 (m, 1H), 8.53 (d, J=2.8 Hz, 1H), 7.72 (d, J=8.0 Hz, 1H), 5.57 (s, 2H).

(Step 2) 6-Amino-3H-isobenzofuran-1-one

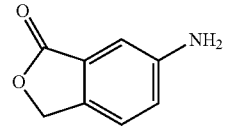 [SMILES: Nc1ccc2c(c1)C(=O)OC2]

6-Nitro-3H-isobenzofuran-1-one <see (Step 1)> (2.00 g, 11.1 mmol) was dissolved in methanol (25 ml), and 20% palladium/carbon (200 mg) was added thereto, followed by stirring at room temperature for 12 hours in the presence of hydrogen gas (50 psi). The reaction solution was filtered and concentrated under reduced pressure to obtain the title compound (1.43 g, 86%).

1H NMR (400 MHz, DMSO-d$_6$): δ 7.30 (d, J=8.0 Hz, 1H), 6.96 (dd, J=8.0, 2.0 Hz, 1H), 6.91 (d, J=4.0 Hz, 1H), 5.56 (s, 2H), 5.21 (s, 2H).

(Step 3) 3-Oxo-1H-isobenzofuran-5-sulfonyl Chloride

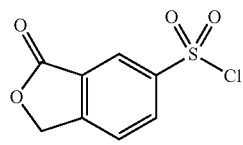 [SMILES: O=C1OCc2ccc(S(=O)(=O)Cl)cc21]

The title compound (0.95 g, 44%) was obtained by subjecting 6-amino-3H-isobenzofuran-1-one <see (Step 2)> (1.40 g, 9.39 mmol) to the same method as in (Step 1) of Example 118.

1H NMR (400 MHz, CDCl$_3$): δ 8.61 (d, J=1.2 Hz, 1H), 8.38 (dd, J=8.0, 1.6 Hz, 1H), 7.83 (d, J=8.0 Hz, 1H), 5.48 (s, 2H).

(Step 4) Methyl 2,5-Difluoro-4-[(3-oxo-1H-isobenzofuran-5-yl)sulfonylamino]benzoate

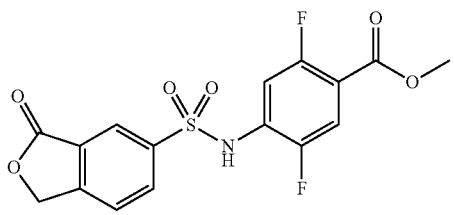 [SMILES: COC(=O)c1cc(F)c(NS(=O)(=O)c2ccc3c(c2)C(=O)OC3)cc1F]

The title compound (919 mg, 88%) was obtained as a yellow solid by subjecting 3-oxo-1H-isobenzofuran-5-sulfonyl chloride <see (Step 3)> (0.95 g, 4.1 mmol) and methyl 4-amino-2,5-difluoro-benzoate <see (Step 3) of Example 104> (0.51 g, 2.7 mmol) to the same method as in (Step 4) of Example 104.

1H NMR (400 MHz, DMSO-d$_6$): δ 11.31 (s, 1H), 8.24-8.21 (m, 2H), 7.92 (d, J=8.0 Hz, 1H), 7.68-7.64 (m, 1H), 7.35-7.31 (m, 1H), 5.51 (s, 2H), 3.81 (s, 3H).

(Step 5) 2,5-Difluoro-4-{[(3-oxo-1,3-dihydro-2-benzofuran-5-yl)sulfonyl]amino}benzoic Acid (M-99)

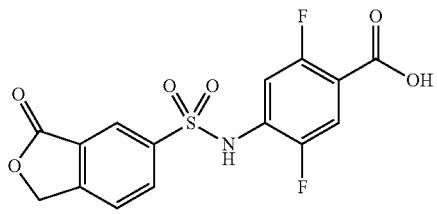 [SMILES: O=C(O)c1cc(F)c(NS(=O)(=O)c2ccc3c(c2)C(=O)OC3)cc1F]

The title compound (671 mg, 91%) was obtained as a white solid by subjecting methyl 2,5-difluoro-4-[(3-oxo-1H-isobenzofuran-5-yl)sulfonylamino]benzoate <see (Step 4)> (766 mg, 2.00 mmol) to the same method as in (Step 5) of Example 104.

1H NMR (400 MHz, CD$_3$OD): δ 8.37 (d, J=0.8 Hz, 1H), 8.23 (dd, J=8.0, 1.6 Hz, 1H), 7.83 (dd, J=8.0, 0.8 Hz, 1H), 7.59 (dd, J=10.8, 6.4 Hz, 1H), 7.46 (dd, J=11.6, 6.4 Hz, 1H), 5.47 (s, 2H).; MS (ESI) m/z 387 (M+NH4)$^+$

Example 207

Synthesis of M-100

(Step 1) Methyl 2,5-Difluoro-4-[[4-(4-methyltriazol-1-yl)phenyl]sulfonylamino]benzoate

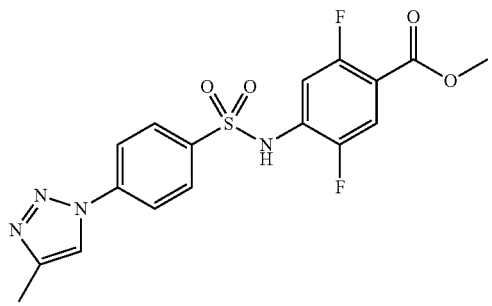 [SMILES: COC(=O)c1cc(F)c(NS(=O)(=O)c2ccc(-n3cc(C)nn3)cc2)cc1F]

The title compound (252 mg, 4%) was obtained as a white solid by subjecting methyl 2,5-difluoro-4-[(4-iodophenyl)sulfonylamino]benzoate <see (Step 4) of Example 197> (7.00 g, 15.5 mmol) and 4-methyl-1H-triazole (2.50 g, 30.1 mmol) to the same methods as in Examples 15 to 18.

1H NMR (400 MHz, DMSO-d$_6$): δ 11.18 (s, 1H), 8.67 (s, 1H), 8.15 (m, 2H), 8.06 (m, 2H), 7.68-7.63 (m, 1H), 7.34-7.29 (m, 1H), 3.80 (s, 3H), 2.33 (s, 3H).

(Step 2) 2,5-Difluoro-4-({[4-(4-methyl-1H-1,2,3-triazol-1-yl)phenyl]sulfonyl}amino)benzoic Acid (M-100)

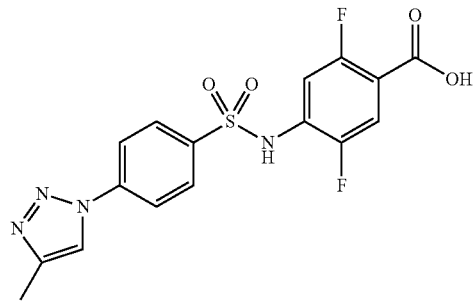 [SMILES: Cc1cn(-c2ccc(S(=O)(=O)Nc3cc(F)c(C(=O)O)cc3F)cc2)nn1]

The title compound (219 mg, 90%) was obtained by subjecting methyl 2,5-difluoro-4-[[4-(4-methyltriazol-1-yl)phenyl]sulfonylamino]benzoate <see (Step 1)> (252 mg, 0.60 mmol) to the same method as in (Step 5) of Example 104.

1H NMR (400 MHz, CD$_3$OD): δ 8.39 (s, 1H), 8.11-8.06 (m, 4H), 7.63-7.59 (m, 1H), 7.49-7.44 (m, 1H), 2.42 (s, 3H).; MS (ESI) m/z 395 (M+H)$^+$

Example 208

Synthesis of M-101

(Step 1) 4-{[(3',5'-Difluorobiphenyl-4-yl)sulfonyl]amino}-2,5-difluorobenzoic Acid (M-101)

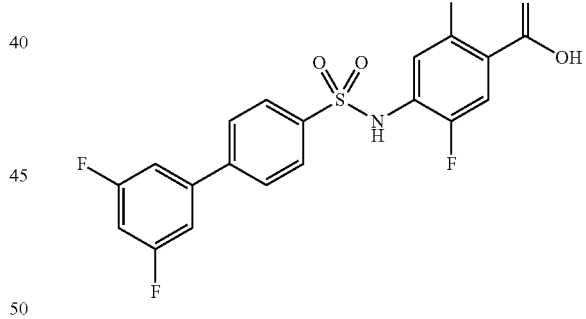

Methyl 2,5-difluoro-4-[(4-iodophenyl)sulfonylamino]benzoate (200 mg, 0.440 mmol) <see (Step 1) of Example 197> was dissolved in 1,4-dioxane (4.0 ml), and a 1 M aqueous sodium carbonate solution (1.0 ml), 3,5-difluorophenylboronic acid (50% in THF, 278 μl, 0.880 mmol), and PdCl2(dppf) (20 mg, 0.020 mmol) were added thereto, followed by stirring at 90° C. for 5 hours. After cooling to room temperature, the mixture was filtered through Celite, and the solvent was removed under reduced pressure. To the obtained residue, tetrahydrofuran (3.0 ml), water (1.0 ml), and a 2 N aqueous sodium hydroxide solution (2.0 ml) were added, followed by stirring at 50° C. for 2 hours. After cooling to room temperature, the solvent was removed under reduced pressure, followed by drying, to obtain the title compound (M-101).

MS (ESI) m/z 426.20 (M+H)$^+$

Example 209

Synthesis of M-102

(Step 1) Methyl 4-[[5-(2-Ethylpyrimidin-5-yl)-2-pyridyl]sulfonylamino]-2,5-difluoro-benzoate

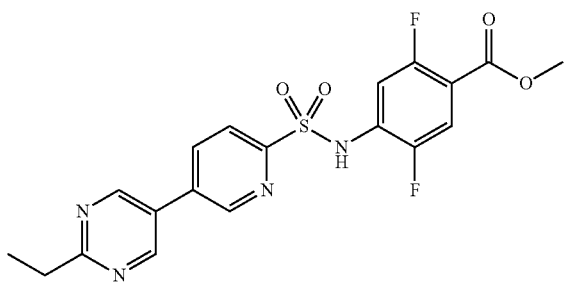

The title compound (531 mg, 49%) was obtained by subjecting [6-[(2,5-difluoro-4-methoxycarbonyl-phenyl)sulfamoyl]-3-pyridyl]boronic acid <see (Step 1) of Example 198> (930 mg, 2.50 mmol) and 5-bromo-2-ethyl-pyrimidine <see (Step 1) of Example 203> (467 mg, 2.50 mmol) to the same method as in (Step 4) of Example 8.
MS (ESI) m/z 435 (M+H)$^+$ (Step 2) 4-({[5-(2-Ethylpyrimidin-5-yl)pyridin-2-yl]sulfonyl}amino)-2,5-difluorobenzoic Acid (M-102)

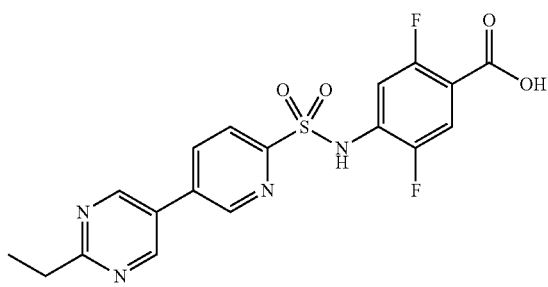 [SMILES: CCc1ncc(-c2ccc(S(=O)(=O)Nc3cc(F)c(C(=O)O)cc3F)nc2)cn1]

The title compound (378 mg, 90%) was obtained as a white solid by subjecting methyl 4-[[5-(2-ethylpyrimidin-5-yl)-2-pyridyl]sulfonylamino]-2,5-difluoro-benzoate <see (Step 1)> (434 mg, 1.00 mmol) to the same method as in (Step 5) of Example 104.
$^1$H NMR (400 MHz, DMSO-d$_6$): δ 11.31 (br s, 1H), 9.20-9.19 (m, 3H), 8.56 (dd, J=8.0, 2.4 Hz, 1H), 8.20 (d, J=8.4 Hz, 1H), 7.66-7.62 (m, 1H), 7.50-7.45 (m, 1H), 3.00 (q, J=7.6 Hz, 2H), 1.32 (t, J=7.6 Hz, 3H).; MS (ESI) m/z 421 (M+H)$^+$

Example 210

Synthesis of M-103

(Step 1) 5-Bromo-2-cyclopropyl-pyrimidine

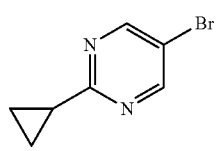

5-Bromo-2-iodo-pyrimidine (5.00 g, 17.6 mmol) and tetrakis(triphenylphosphine)palladium(0) (5.70 mg, 5.00 mmol) were dissolved in tetrahydrofuran (80 ml), and cyclopropylmagnesium bromide (0.5 mol/L in THF, 70.0 ml, 35.0 mmol) was slowly added dropwise thereto in the presence of nitrogen gas. The reaction liquid was stirred at 70° C. for 2 hours, and then diluted with water (20 ml), followed by extraction with ethyl acetate (50 ml×3). The extraction liquids were combined and dried over sodium sulfate. The solvent was removed under reduced pressure, and the obtained residue was purified by silica gel column chromatography (petroleum ether/ethyl acetate=50:1) to obtain the title compound (1.20 g, 35%).
$^1$H NMR (400 MHz, CDCl$_3$): δ 8.51 (s, 2H), 2.17-2.11 (m, 1H), 1.04-1.02 (m, 4H).; MS (ESI) m/z 199 (M+H)$^+$ (Step 2) Methyl 4-[[4-(2-Cyclopropylpyrimidin-5-yl)phenyl]sulfonylamino]-2,5-difluoro-benzoate

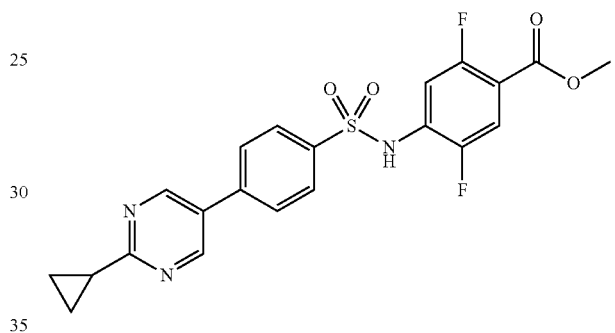

The title compound (400 mg, 22%) was obtained by subjecting 5-bromo-2-cyclopropyl-pyrimidine <see (Step 1)> (800 mg, 4.00 mmol) and [4-[(2,5-difluoro-4-methoxycarbonyl-phenyl)sulfamoyl]phenyl]boronic acid <see (Step 2) of Example 189> (1.83 g, 4.04 mmol) to the same method as in (Step 4) of Example 8.
$^1$H NMR (400 MHz, CD$_3$OD): δ 8.81 (s, 2H), 7.92-7.90 (m, 2H), 7.77 (d, J=8.8 Hz, 2H), 7.48-7.44 (m, 1H), 7.35-7.31 (m, 1H), 3.80 (s, 3H), 2.28-2.24 (m, 1H), 1.15-1.12 (m, 4H).

(Step 3) 4-({[4-(2-Cyclopropylpyrimidin-5-yl)phenyl]sulfonyl}amino)-2,5-difluorobenzoic Acid (M-103)

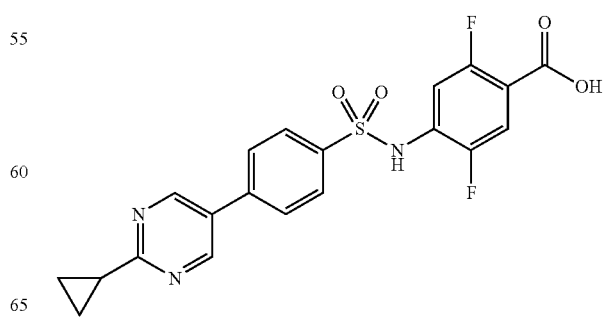

The title compound (110 mg, 75%) was obtained as a white solid by subjecting methyl 4-[[4-(2-cyclopropylpyrimidin-5-yl)phenyl]sulfonylamino]-2,5-difluoro-benzoate <see (Step 2)> (150 mg, 0.340 mmol) to the same method as in (Step 5) of Example 104.

$^1$H NMR (400 MHz, CD$_3$OD): δ 8.81 (s, 2H), 7.92-7.90 (m, 2H), 7.77 (d, J=8.8 Hz, 2H), 7.48-7.44 (m, 1H), 7.35-7.31 (m, 1H), 2.19-2.15 (m, 1H), 1.06-1.02 (m, 4H).; MS (ESI) m/z 432 (M+H)$^+$

The following group of compounds was synthesized by subjecting their corresponding intermediates among M-1 to M-103 to the same methods as in (Step 1) and (Step 2) of Example 39. Note that, in Examples 211 to 239 below, each compound was obtained as a TFA salt, unless otherwise noted.

Example 211

Synthesis of A-90 and Synthesis of B-90

(Step 1) N-(2,5-Difluoro-4-{[(4-pyrimidin-2-ylphenyl)sulfonyl]amino}benzoyl)-3-[5-(1-methyl-2,4-dioxo-1,4-dihydropyrido[3,4-d]pyrimidin-3(2H)-yl)pyridin-2-yl]-L-alanine (A-90)

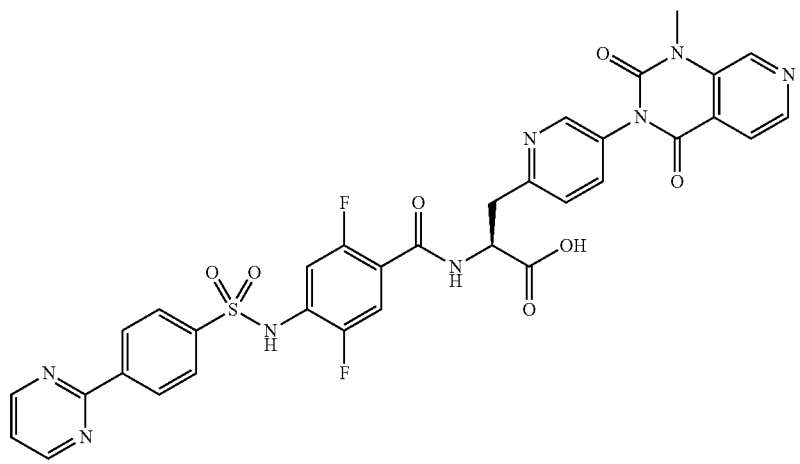 [SMILES: Cn1c(=O)n(-c2ccc(C[C@H](NC(=O)c3cc(F)c(NS(=O)(=O)c4ccc(-c5ncccn5)cc4)cc3F)C(=O)O)nc2)c(=O)c2ccncc21]

$^1$H NMR (400 MHz, DMSO-d$_6$): δ 10.93 (s, 1H), 9.00 (s, 1H), 8.96 (d, J=4.9 Hz, 2H), 8.73 (dd, J=7.7, 3.7 Hz, 1H), 8.61-8.52 (m, 3H), 8.50-8.43 (m, 1H), 8.01-7.93 (m, 2H), 7.93-7.87 (m, 1H), 7.78-7.70 (m, 1H), 7.54 (t, J=4.9 Hz, 1H), 7.50-7.43 (m, 1H), 7.35 (dd, J=10.3, 6.3 Hz, 1H), 7.24 (dd, J=11.2, 6.3 Hz, 1H), 4.93-4.83 (m, 1H), 3.61 (s, 3H), 3.42-3.25 (m, 2H).;
MS (ESI) m/z 715.40 (M+H)$^+$ (Step 2) Cyclohexyl N-(2,5-Difluoro-4-{[(4-pyrimidin-2-ylphenyl)sulfonyl]amino}benzoyl)-3-[5-(1-methyl-2,4-dioxo-1,4-dihydropyrido[3,4-d]pyrimidin-3(2H)-yl)pyridin-2-yl]-L-alaninate (B-90)

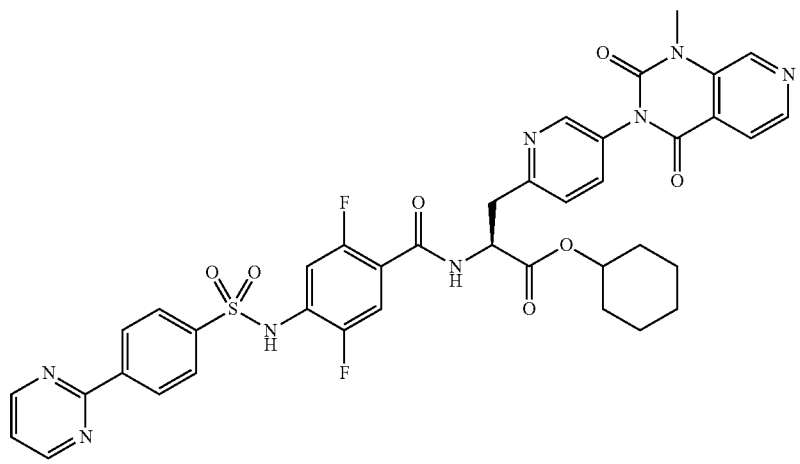 [SMILES: Cn1c(=O)n(-c2ccc(C[C@H](NC(=O)c3cc(F)c(NS(=O)(=O)c4ccc(-c5ncccn5)cc4)cc3F)C(=O)OC3CCCCC3)nc2)c(=O)c2ccncc21]

¹H NMR (400 MHz, DMSO-d₆): δ 10.94 (s, 1H), 9.02-8.98 (m, 1H), 8.96 (d, J=4.8 Hz, 2H), 8.85 (dd, J=7.6, 3.2 Hz, 1H), 8.61-8.52 (m, 3H), 8.48-8.42 (m, 1H), 8.02-7.94 (m, 2H), 7.94-7.86 (m, 1H), 7.77-7.69 (m, 1H), 7.54 (t, J=4.9 Hz, 1H), 7.50-7.42 (m, 1H), 7.35 (dd, J=10.2, 6.4 Hz, 1H), 7.25 (dd, J=11.2, 6.2 Hz, 1H), 4.96-4.86 (m, 1H), 4.73-4.62 (m, 1H), 3.61 (s, 3H), 3.39-3.23 (m, 2H), 1.76-1.50 (m, 4H), 1.44-1.08 (m, 6H).; MS (ESI) m/z 797.50 (M+H)⁺

Example 212

Synthesis of A-91 and Synthesis of B-91

(Step 1) N-{2,5-Difluoro-4-[(phenylsulfonyl)amino]benzoyl}-4-(1-methyl-2,4-dioxo-1,4-dihydropyrido[3,4-d]pyrimidin-3(2H)-yl)-L-phenylalanine (A-91), Obtained as a Free Form

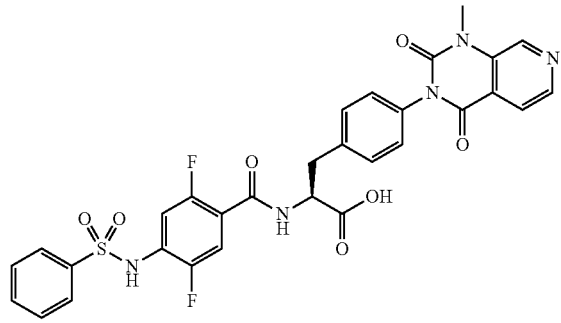 [SMILES: Cn1c(=O)n(-c2ccc(C[C@H](NC(=O)c3cc(F)c(NS(=O)(=O)c4ccccc4)cc3F)C(=O)O)cc2)c(=O)c2ccncc21]

¹H NMR (400 MHz, DMSO-d₆): δ 10.81 (s, 1H), 8.97 (s, 1H), 8.64-8.52 (m, 2H), 7.88 (d, J=5.0 Hz, 1H), 7.86-7.79 (m, 2H), 7.72-7.64 (m, 1H), 7.64-7.55 (m, 2H), 7.40-7.33 (m, 2H), 7.28 (dd, J=10.3, 6.3 Hz, 1H), 7.24-7.15 (m, 3H), 4.67-4.57 (m, 1H), 3.60 (s, 3H), 3.22 (dd, J=14.1, 4.6 Hz, 1H), 3.06 (dd, J=14.0, 9.9 Hz, 1H).; MS (ESI) m/z 636.40 (M+H)⁺

(Step 2) Cyclohexyl N-{2,5-Difluoro-4-[(phenylsulfonyl)amino]benzoyl}-4-(1-methyl-2,4-dioxo-1,4-dihydropyrido[3,4-d]pyrimidin-3(2H)-yl)-L-phenylalaninate (B-91)

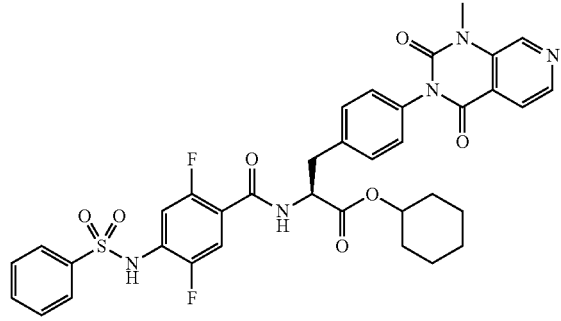 [SMILES: Cn1c(=O)n(-c2ccc(C[C@H](NC(=O)c3cc(F)c(NS(=O)(=O)c4ccccc4)cc3F)C(=O)OC3CCCCC3)cc2)c(=O)c2ccncc21]

¹H NMR (400 MHz, DMSO-d₆): δ 10.83 (s, 1H), 8.97 (s, 1H), 8.76 (dd, J=7.6, 2.0 Hz, 1H), 8.55 (d, J=5.0 Hz, 1H), 7.89 (d, J=4.9 Hz, 1H), 7.84 (dt, J=7.1, 1.3 Hz, 2H), 7.72-7.64 (m, 1H), 7.64-7.56 (m, 3H), 7.40-7.33 (m, 2H), 7.28 (dd, J=10.2, 6.2 Hz, 1H), 7.25-7.16 (m, 3H), 4.74-4.66 (m, 1H), 4.66-4.57 (m, 1H), 3.60 (s, 3H), 3.22-3.04 (m, 2H), 1.81-1.55 (m, 4H), 1.48-1.20 (m, 6H).; MS (ESI) m/z 718.47 (M+H)⁺

Example 213

Synthesis of A-92 and Synthesis of B-92

(Step 1) N-{2,5-Difluoro-4-[(2-thienylsulfonyl)amino]benzoyl}-4-(1-methyl-2,4-dioxo-1,4-dihydropyrido[3,4-d]pyrimidin-3(2H)-yl)-L-phenylalanine (A-92), Obtained as a Free Form

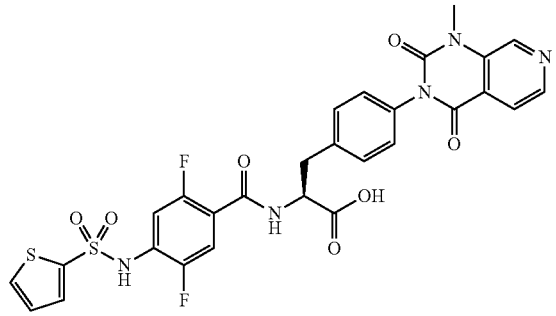

¹H NMR (400 MHz, DMSO-d₆): δ 10.95 (s, 1H), 8.97 (s, 1H), 8.65 (dd, J=7.9, 2.5 Hz, 1H), 8.55 (d, J=5.0 Hz, 1H), 7.98 (dd, J=5.0, 1.4 Hz, 1H), 7.89 (d, J=5.0 Hz, 1H), 7.64 (dd, J=3.8, 1.4 Hz, 1H), 7.42-7.36 (m, 2H), 7.32 (dd, J=10.2, 6.3 Hz, 1H), 7.28-7.19 (m, 3H), 7.17 (dd, J=5.0, 3.8 Hz, 1H), 4.69-4.58 (m, 1H), 3.60 (s, 3H), 3.24 (dd, J=14.0, 4.6 Hz, 1H), 3.08 (dd, J=14.0, 9.8 Hz, 1H).; MS (ESI) m/z 642.38 (M+H)⁺

(Step 2) Cyclohexyl N-{2,5-Difluoro-4-[(2-thienylsulfonyl)amino]benzoyl}-4-(1-methyl-2,4-dioxo-1,4-dihydropyrido[3,4-d]pyrimidin-3(2H)-yl)-L-phenylalaninate (B-92)

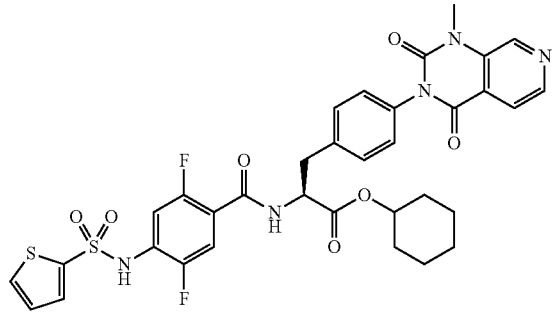

¹H NMR (400 MHz, DMSO-d₆): δ 10.97 (s, 1H), 8.97 (s, 1H), 8.80 (d, J=7.5 Hz, 1H), 8.55 (d, J=4.9 Hz, 1H), 7.98 (dd, J=5.0, 1.4 Hz, 1H), 7.89 (dd, J=5.0, 0.8 Hz, 1H), 7.65 (dd, J=3.8, 1.4 Hz, 1H), 7.41-7.35 (m, 2H), 7.32 (dd, J=10.2, 6.2 Hz, 1H), 7.28-7.20 (m, 3H), 7.17 (dd, J=5.0, 3.8 Hz, 1H), 4.75-4.68 (m, 1H), 4.68-4.58 (m, 1H), 3.60 (s, 3H), 3.23-3.05 (m, 2H), 1.82-1.57 (m, 4H), 1.48-1.20 (m, 6H).; MS (ESI) m/z 724.45 (M+H)⁺

Example 214

Synthesis of A-93 and Synthesis of B-93

(Step 1) N-(4-{[(2-Ethoxyphenyl)sulfonyl]amino}-2,6-difluorobenzoyl)-4-(1-methyl-2,4-dioxo-1,4-dihydropyrido[3,4-d]pyrimidin-3(2H)-yl)-L-phenylalanine (A-93), Obtained as a Free Form

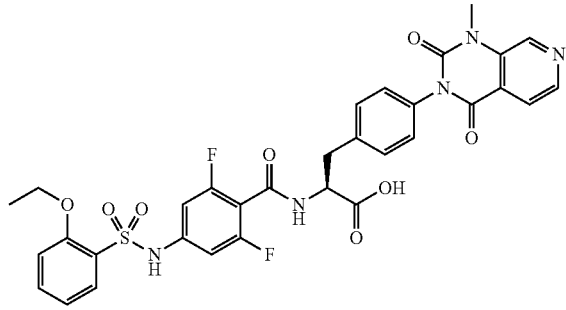

$^1$H NMR (400 MHz, DMSO-d$_6$): δ 10.70 (s, 1H), 9.02 (d, J=7.9 Hz, 1H), 8.97 (s, 1H), 8.56 (d, J=4.9 Hz, 1H), 7.94-7.86 (m, 2H), 7.61 (ddd, J=8.8, 7.5, 1.8 Hz, 1H), 7.38-7.31 (m, 2H), 7.21 (d, J=8.1 Hz, 3H), 7.10 (t, J=7.5 Hz, 1H), 6.73 (d, J=9.3 Hz, 2H), 4.61-4.50 (m, 1H), 4.21 (q, J=7.0 Hz, 2H), 3.60 (s, 3H), 3.16 (dd, J=14.2, 4.6 Hz, 1H), 2.98 (dd, J=14.2, 9.8 Hz, 1H), 1.32 (t, J=7.0 Hz, 3H).; MS (ESI) m/z 680.58 (M+H)$^+$ (Step 2) Cyclohexyl N-(4-{[(2-Ethoxyphenyl)sulfonyl]amino}-2,6-difluorobenzoyl)-4-(1-methyl-2,4-dioxo-1,4-dihydropyrido[3,4-d]pyrimidin-3(2H)-yl)-L-phenylalaninate (B-93)

$^1$H NMR (400 MHz, DMSO-d$_6$): δ 10.71 (s, 1H), 9.13 (d, J=7.4 Hz, 1H), 8.97 (s, 1H), 8.55 (d, J=4.9 Hz, 1H), 7.95-7.86 (m, 2H), 7.66-7.56 (m, 1H), 7.38-7.31 (m, 2H), 7.21 (dd, J=8.4, 1.5 Hz, 3H), 7.15-7.05 (m, 1H), 6.74 (d, J=9.4 Hz, 2H), 4.72-4.61 (m, 1H), 4.61-4.51 (m, 1H), 4.22 (q, J=7.0 Hz, 2H), 3.60 (s, 3H), 3.16-2.97 (m, 2H), 1.79-1.58 (m, 4H), 1.51-1.15 (m, 9H).; MS (ESI) m/z 762.70 (M+H)$^+$

Example 215

Synthesis of A-94 and Synthesis of B-94

(Step 1) N-(2,5-Difluoro-4-{[(4-pyrimidin-5-ylphenyl)sulfonyl]amino}benzoyl)-3-[5-(1-methyl-2,4-dioxo-1,4-dihydropyrido[3,4-d]pyrimidin-3(2H)-yl)pyridin-2-yl]-L-alanine (A-94)

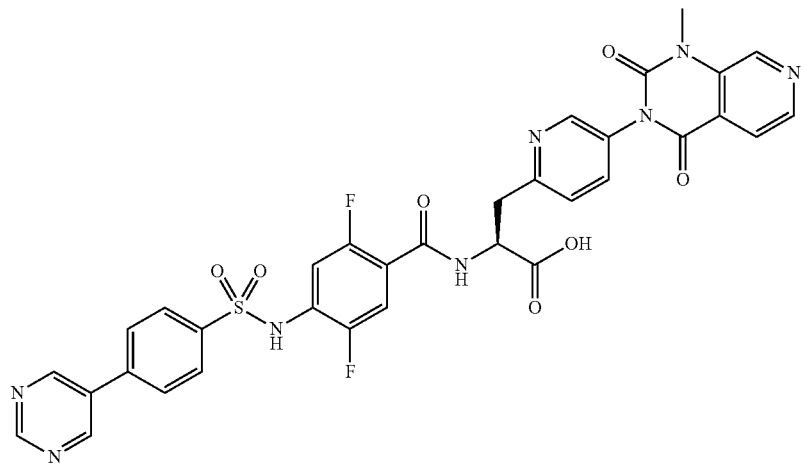

$^1$H NMR (400 MHz, DMSO-d$_6$): δ 11.00 (s, 1H), 9.24 (s, 1H), 9.20 (s, 2H), 9.00 (s, 1H), 8.74 (dd, J=7.8, 3.8 Hz, 1H), 8.57 (d, J=5.0 Hz, 1H), 8.46 (d, J=2.4 Hz, 1H), 8.09-8.02 (m, 2H), 8.02-7.94 (m, 2H), 7.90 (d, J=4.9 Hz, 1H), 7.73 (dd, J=8.2, 2.5 Hz, 1H), 7.46 (d, J=8.2 Hz, 1H), 7.38 (dd, J=10.3, 6.4 Hz, 1H), 7.28 (dd, J=11.4, 6.2 Hz, 1H), 4.94-4.83 (m, 1H), 3.61 (s, 3H), 3.38-3.22 (m, 2H).; MS (ESI) m/z 715.58 (M+H)$^+$ (Step 2) Cyclohexyl N-(2,5-Difluoro-4-{[(4-pyrimidin-5-ylphenyl)sulfonyl]amino}benzoyl)-3-[5-(1-methyl-2,4-dioxo-1,4-dihydropyrido[3,4-d]pyrimidin-3(2H)-yl)pyridin-2-yl]-L-alaninate (B-94)

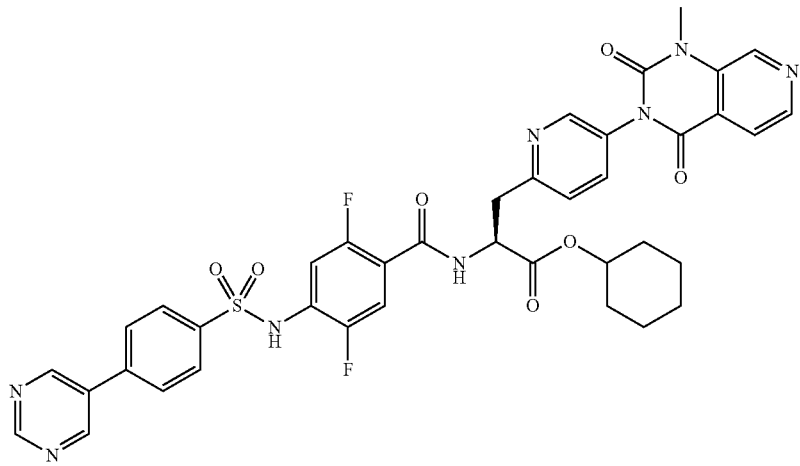 [SMILES: Cn1c(=O)n(-c2ccc(C[C@H](NC(=O)c3cc(F)c(NS(=O)(=O)c4ccc(-c5cncnc5)cc4)cc3F)C(=O)OC3CCCCC3)nc2)c(=O)c2ccncc21]

$^1$H NMR (400 MHz, DMSO-d$_6$): δ 11.01 (s, 1H), 9.24 (s, 1H), 9.20 (s, 2H), 8.99 (s, 1H), 8.86 (dd, J=7.7, 3.3 Hz, 1H), 8.57 (d, J=4.9 Hz, 1H), 8.48-8.42 (m, 1H), 8.09-8.02 (m, 2H), 8.02-7.95 (m, 2H), 7.90 (dd, J=5.1, 0.7 Hz, 1H), 7.76-7.69 (m, 1H), 7.46 (d, J=8.1 Hz, 1H), 7.38 (dd, J=10.3, 6.4 Hz, 1H), 7.29 (dd, J=11.2, 6.3 Hz, 1H), 4.97-4.86 (m, 1H), 4.72-4.62 (m, 1H), 3.61 (s, 3H), 3.35-3.24 (m, 2H), 1.77-1.51 (m, 4H), 1.47-1.15 (m, 6H).; MS (ESI) m/z 797.55 (M+H)$^+$

Example 216

Synthesis of A-95 and Synthesis of B-95

(Step 1) N-(2,5-Difluoro-4-{[(4-pyrimidin-5-ylphenyl)sulfonyl]amino}benzoyl)-4-(3-methyl-2,6-dioxo-3,6-dihydropyrimidin-1(2H)-yl)-L-phenylalanine (A-95), Obtained as a Free Form

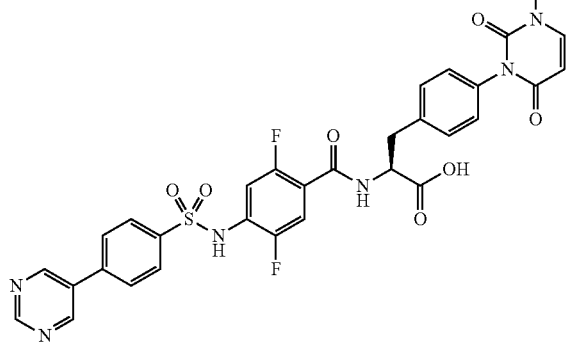

$^1$H NMR (400 MHz, DMSO-d$_6$): δ 10.97 (s, 1H), 9.24 (s, 1H), 9.20 (s, 2H), 8.58 (dd, J=7.8, 2.6 Hz, 1H), 8.10-8.01 (m, 2H), 8.01-7.94 (m, 2H), 7.74 (d, J=7.9 Hz, 1H), 7.35-7.22 (m, 4H), 7.13-7.05 (m, 2H), 5.74 (d, J=7.9 Hz, 1H), 4.60 (ddd, J=9.9, 7.8, 4.6 Hz, 1H), 3.29 (s, 3H), 3.19 (dd, J=14.5, 4.8 Hz, 1H), 3.04 (dd, J=14.1, 9.8 Hz, 1H).; MS (ESI) m/z 663.45 (M+H)$^+$ (Step 2) Cyclohexyl N-(2,5-Difluoro-4-{[(4-pyrimidin-5-ylphenyl)sulfonyl]amino}benzoyl)-4-(3-methyl-2,6-dioxo-3,6-dihydropyrimidin-1 (2H)-yl)-L-phenylalaninate (B-95)

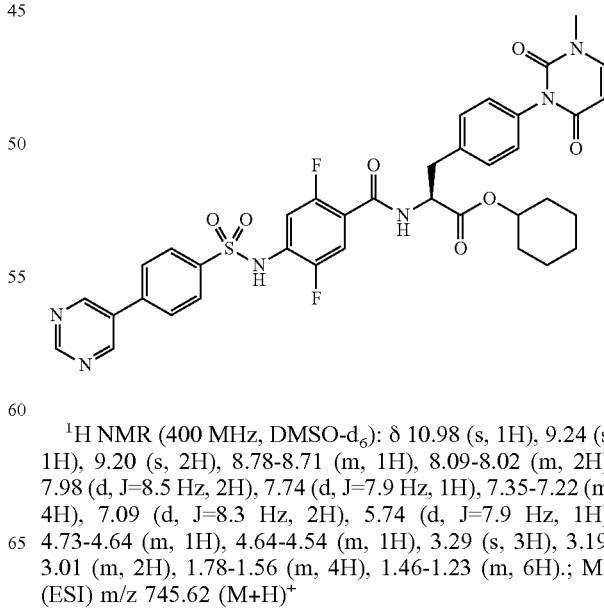

$^1$H NMR (400 MHz, DMSO-d$_6$): δ 10.98 (s, 1H), 9.24 (s, 1H), 9.20 (s, 2H), 8.78-8.71 (m, 1H), 8.09-8.02 (m, 2H), 7.98 (d, J=8.5 Hz, 2H), 7.74 (d, J=7.9 Hz, 1H), 7.35-7.22 (m, 4H), 7.09 (d, J=8.3 Hz, 2H), 5.74 (d, J=7.9 Hz, 1H), 4.73-4.64 (m, 1H), 4.64-4.54 (m, 1H), 3.29 (s, 3H), 3.19-3.01 (m, 2H), 1.78-1.56 (m, 4H), 1.46-1.23 (m, 6H).; MS (ESI) m/z 745.62 (M+H)$^+$

Example 217

Synthesis of A-96 and Synthesis of B-96

(Step 1) N-[2,5-Difluoro-4-({[5-(1H-1,2,4-triazol-1-yl)pyridin-2-yl]sulfonyl}amino)benzoyl]-3-[5-(1-methyl-2,4-dioxo-1,4-dihydropyrido[3,4-d]pyrimidin-3(2H)-yl)pyridin-2-yl]-L-alanine (A-96)

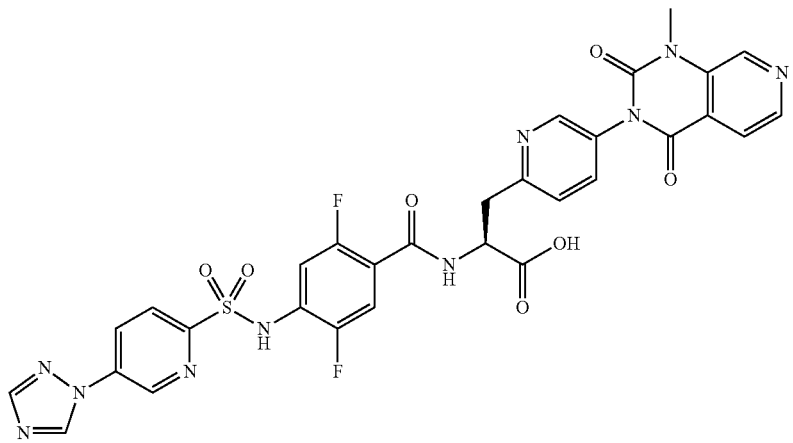 [SMILES: Cn1c(=O)n(-c2ccc(C[C@H](NC(=O)c3cc(F)c(NS(=O)(=O)c4ccc(-n5cncn5)cn4)cc3F)C(=O)O)nc2)c(=O)c2ccncc21]

$^1$H NMR (400 MHz, DMSO-d$_6$): δ 11.12 (s, 1H), 9.49 (s, 1H), 9.32-9.27 (m, 1H), 9.00 (s, 1H), 8.75 (dd, J=7.9, 3.9 Hz, 1H), 8.58 (d, J=5.0 Hz, 1H), 8.54 (dd, J=8.6, 2.5 Hz, 1H), 8.47 (d, J=2.4 Hz, 1H), 8.37 (s, 1H), 8.21 (d, J=8.6 Hz, 1H), 7.90 (d, J=4.9 Hz, 1H), 7.74 (dd, J=8.2, 2.5 Hz, 1H), 7.47 (d, J=8.2 Hz, 1H), 7.39 (dd, J=10.8, 6.3 Hz, 2H), 4.95-4.85 (m, 1H), 3.61 (s, 3H), 3.39-3.24 (m, 2H).; MS (ESI) m/z 705.54 (M+H)$^+$ (Step 2) Cyclohexyl N-[2,5-Difluoro-4-({[5-(1H-1,2,4-triazol-1-yl)pyridin-2-yl]sulfonyl}amino)benzoyl]-3-[5-(1-methyl-2,4-dioxo-1,4-dihydropyrido[3,4-d]pyrimidin-3(2H)-yl)pyridin-2-yl]-L-alaninate (B-96)

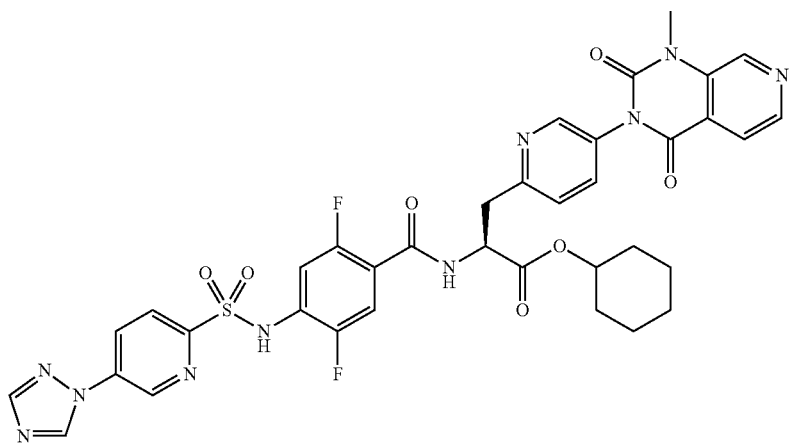 [SMILES: Cn1c(=O)n(-c2ccc(C[C@H](NC(=O)c3cc(F)c(NS(=O)(=O)c4ccc(-n5cncn5)cn4)cc3F)C(=O)OC3CCCCC3)nc2)c(=O)c2ccncc21]

$^1$H NMR (400 MHz, DMSO-d$_6$): δ 11.13 (s, 1H), 9.50 (s, 1H), 9.30 (d, J=2.5 Hz, 1H), 9.00 (s, 1H), 8.87 (dd, J=7.6, 3.4 Hz, 1H), 8.57 (d, J=5.0 Hz, 1H), 8.54 (dd, J=8.6, 2.5 Hz, 1H), 8.47 (d, J=2.4 Hz, 1H), 8.38 (s, 1H), 8.22 (d, J=8.6 Hz, 1H), 7.91 (d, J=4.9 Hz, 1H), 7.75 (dd, J=8.2, 2.5 Hz, 1H), 7.48 (d, J=8.2 Hz, 1H), 7.44-7.35 (m, 2H), 4.98-4.88 (m, 1H), 4.73-4.63 (m, 1H), 3.61 (s, 3H), 3.40-3.25 (m, 2H), 1.74-1.53 (m, 4H), 1.47-1.25 (m, 6H).; MS (ESI) m/z 787.60 (M+H)$^+$

Example 218

Synthesis of A-97 and Synthesis of B-97

(Step 1) N-[2,5-Difluoro-4-({[4-(1H-tetrazol-1-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alanine (A-97)

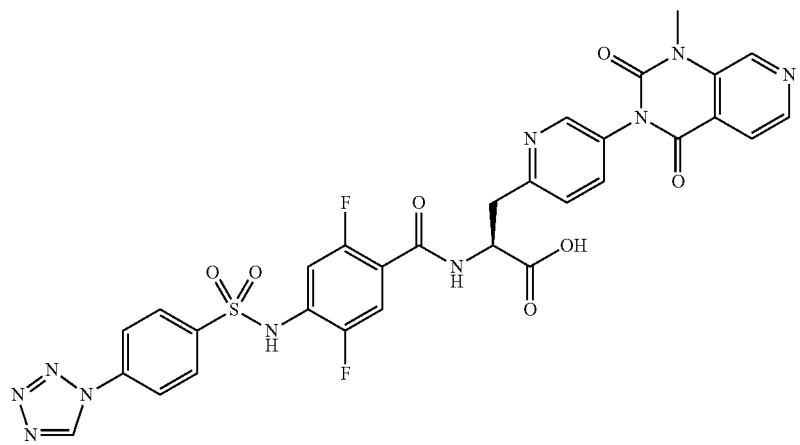 [SMILES: Cn1c(=O)n(-c2ccc(C[C@H](NC(=O)c3cc(F)c(NS(=O)(=O)c4ccc(-n5cnnn5)cc4)cc3F)C(=O)O)nc2)c(=O)c2ccncc21]

$^1$H NMR (400 MHz, DMSO-d$_6$): δ 11.13 (s, 1H), 9.50 (s, 1H), 9.30 (d, J=2.5 Hz, 1H), 9.00 (s, 1H), 8.87 (dd, J=7.6, 3.4 Hz, 1H), 8.57 (d, J=5.0 Hz, 1H), 8.54 (dd, J=8.6, 2.5 Hz, 1H), 8.47 (d, J=2.4 Hz, 1H), 8.38 (s, 1H), 8.22 (d, J=8.6 Hz, 1H), 7.91 (d, J=4.9 Hz, 1H), 7.75 (dd, J=8.2, 2.5 Hz, 1H), 7.48 (d, J=8.2 Hz, 1H), 7.44-7.35 (m, 2H), 4.98-4.88 (m, 1H), 4.73-4.63 (m, 1H), 3.61 (s, 3H), 3.40-3.25 (m, 2H), 1.74-1.53 (m, 4H), 1.47-1.25 (m, 6H).; MS (ESI) m/z 705.46 (M+H)$^+$ (Step 2) Cyclohexyl N-[2,5-Difluoro-4-({[4-(1H-tetrazol-1-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alaninate (B-97)

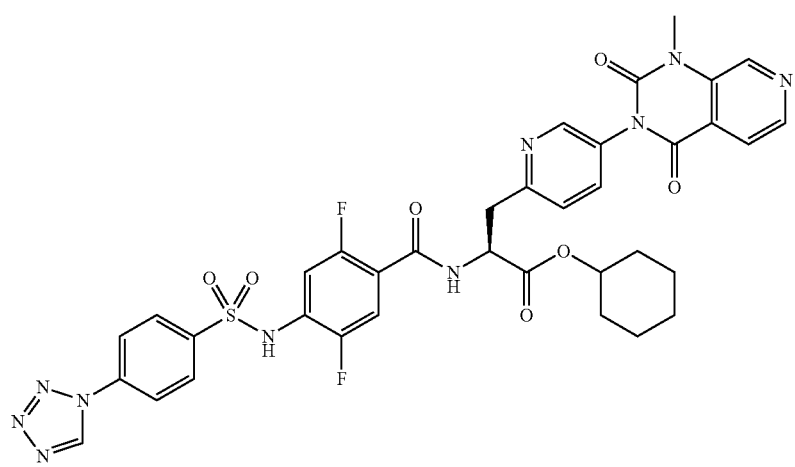 [SMILES: Cn1c(=O)n(-c2ccc(C[C@H](NC(=O)c3cc(F)c(NS(=O)(=O)c4ccc(-n5cnnn5)cc4)cc3F)C(=O)OC3CCCCC3)nc2)c(=O)c2ccncc21]

$^1$H NMR (400 MHz, DMSO-d$_6$): δ 11.04 (s, 1H), 10.19 (s, 1H), 9.00 (s, 1H), 8.86 (dd, J=7.7, 3.3 Hz, 1H), 8.57 (d, J=4.9 Hz, 1H), 8.45 (dd, J=2.5, 0.7 Hz, 1H), 8.21-8.13 (m, 2H), 8.13-8.06 (m, 2H), 7.90 (dd, J=5.0, 0.7 Hz, 1H), 7.73 (dd, J=8.2, 2.5 Hz, 1H), 7.46 (d, J=8.2 Hz, 1H), 7.38 (dd, J=10.2, 6.3 Hz, 1H), 7.29 (dd, J=11.1, 6.2 Hz, 1H), 4.97-4.87 (m, 1H), 4.72-4.63 (m, 1H), 3.61 (s, 3H), 3.35-3.28 (m, 2H), 1.72-1.55 (m, 4H), 1.46-1.24 (m, 6H).; MS (ESI) m/z 787.59 (M+H)$^+$

Example 219

Synthesis of A-98 and Synthesis of B-98

(Step 1) N-[2,5-Difluoro-4-({[4-(4H-1,2,4-triazol-4-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alanine (A-98)

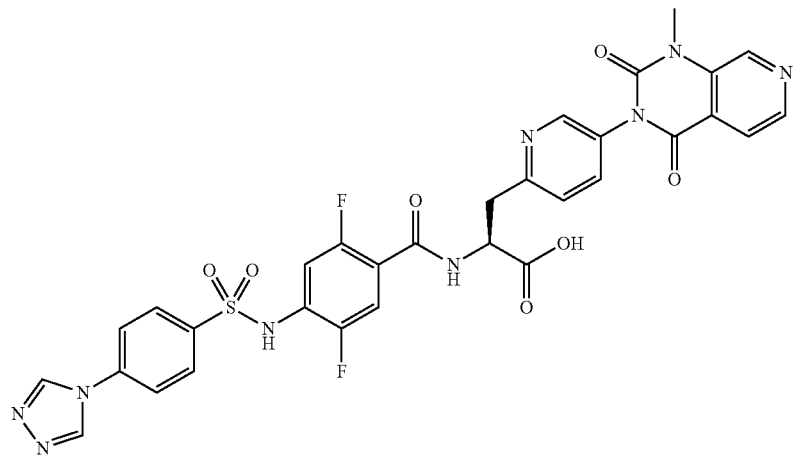 [SMILES: Cn1c(=O)n(-c2ccc(C[C@H](NC(=O)c3cc(F)c(NS(=O)(=O)c4ccc(-n5cnnc5)cc4)cc3F)C(=O)O)nc2)c(=O)c2ccncc21]

$^1$H NMR (400 MHz, DMSO-d$_6$): δ 10.97 (s, 1H), 9.23 (s, 2H), 9.00 (s, 1H), 8.74 (dd, J=7.9, 3.9 Hz, 1H), 8.58 (d, J=4.9 Hz, 1H), 8.46 (d, J=2.4 Hz, 1H), 8.04-7.98 (m, 2H), 7.98-7.92 (m, 2H), 7.90 (d, J=4.9 Hz, 1H), 7.73 (dd, J=8.2, 2.5 Hz, 1H), 7.46 (d, J=8.2 Hz, 1H), 7.38 (dd, J=10.4, 6.3 Hz, 1H), 7.28 (dd, J=11.4, 6.0 Hz, 1H), 4.93-4.84 (m, 1H), 3.61 (s, 3H), 3.38-3.26 (m, 2H).; MS (ESI) m/z 704.58 (M+H)$^+$ (Step 2) Cyclohexyl N-[2,5-Difluoro-4-({[4-(4H-1,2,4-triazol-4-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alaninate (B-98)

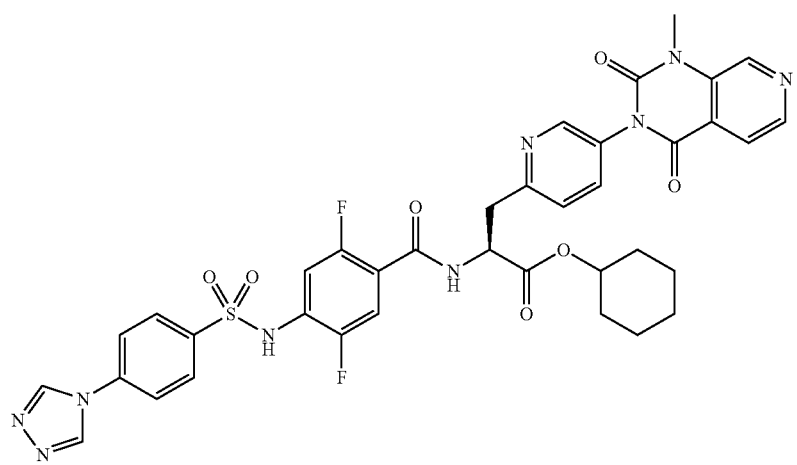 [SMILES: Cn1c(=O)n(-c2ccc(C[C@H](NC(=O)c3cc(F)c(NS(=O)(=O)c4ccc(-n5cnnc5)cc4)cc3F)C(=O)OC3CCCCC3)nc2)c(=O)c2ccncc21]

$^1$H NMR (400 MHz, DMSO-d$_6$): δ 10.98 (s, 1H), 9.22 (s, 2H), 9.00 (s, 1H), 8.85 (dd, J=7.6, 3.4 Hz, 1H), 8.57 (d, J=4.9 Hz, 1H), 8.45 (d, J=2.4 Hz, 1H), 8.05-7.99 (m, 2H), 7.99-7.93 (m, 2H), 7.90 (d, J=4.9 Hz, 1H), 7.73 (dd, J=8.2, 2.5 Hz, 1H), 7.45 (d, J=8.3 Hz, 1H), 7.38 (dd, J=10.3, 6.4 Hz, 1H), 7.28 (dd, J=11.2, 6.3 Hz, 1H), 4.97-4.87 (m, 1H), 4.67 (dt, J=11.9, 3.7 Hz, 1H), 3.61 (s, 3H), 3.39-3.24 (m, 2H), 1.80-1.50 (m, 4H), 1.48-1.18 (m, 6H).; MS (ESI) m/z 786.35 (M+H)$^+$

Example 220

Synthesis of A-99 and Synthesis of B-99

(Step 1) N-(2,5-Difluoro-4-{[(5-pyrimidin-5-ylpyridin-2-yl)sulfonyl]amino}benzoyl)-3-[5-(1-methyl-2,4-dioxo-1,4-dihydropyrido[3,4-d]pyrimidin-3(2H)-yl)pyridin-2-yl]-L-alanine (A-99)

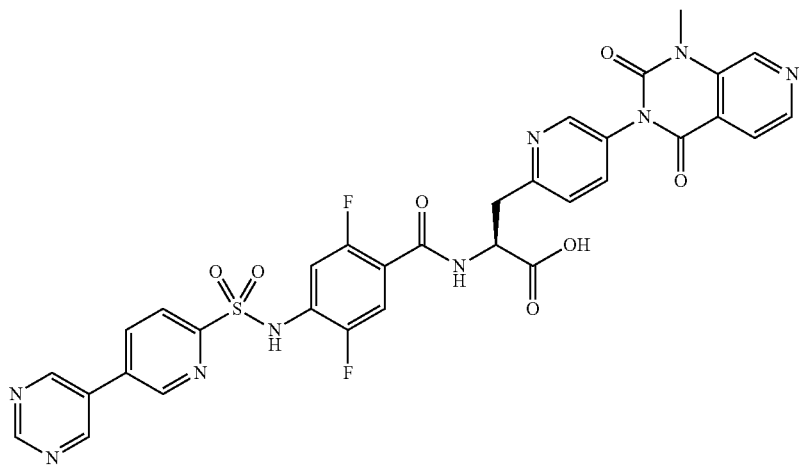 [SMILES: Cn1c(=O)n(-c2ccc(C[C@H](NC(=O)c3cc(F)c(NS(=O)(=O)c4ccc(-c5cncnc5)cn4)cc3F)C(=O)O)nc2)c(=O)c2ccncc21]

$^1$H NMR (400 MHz, DMSO-$d_6$): δ 11.14 (s, 1H), 9.32-9.26 (m, 3H), 9.20 (d, J=2.2 Hz, 1H), 9.00 (s, 1H), 8.74 (dd, J=7.9, 3.9 Hz, 1H), 8.60-8.52 (m, 2H), 8.47 (d, J=2.4 Hz, 1H), 8.16 (d, J=8.2 Hz, 1H), 7.90 (d, J=5.0 Hz, 1H), 7.74 (dd, J=8.2, 2.5 Hz, 1H), 7.50-7.36 (m, 3H), 4.95-4.85 (m, 1H), 3.61 (s, 3H), 3.42-3.24 (m, 2H).; MS (ESI) m/z 716.29 (M+H)$^+$ (Step 2) Cyclohexyl N-(2,5-Difluoro-4-{[(5-pyrimidin-5-ylpyridin-2-yl)sulfonyl]amino}benzoyl)-3-[5-(1-methyl-2,4-dioxo-1,4-dihydropyrido[3,4-d]pyrimidine-3(2H)-yl)pyridin-2-yl]-L-alaninate (B-99)

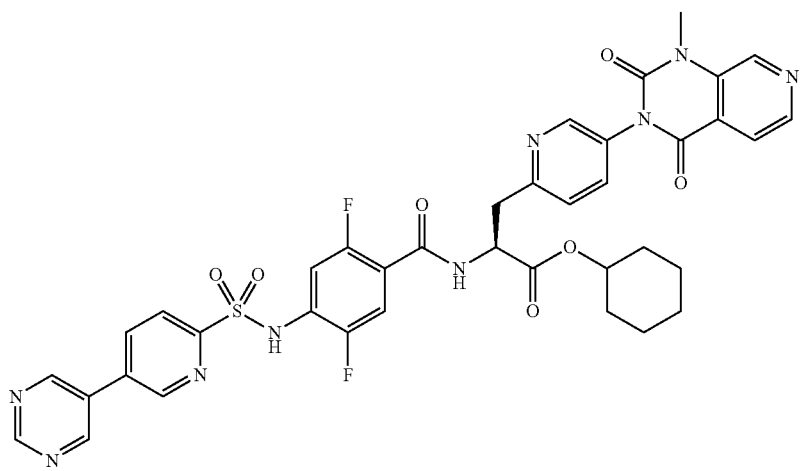 [SMILES: Cn1c(=O)n(-c2ccc(C[C@H](NC(=O)c3cc(F)c(NS(=O)(=O)c4ccc(-c5cncnc5)cn4)cc3F)C(=O)OC3CCCCC3)nc2)c(=O)c2ccncc21]

$^1$H NMR (400 MHz, DMSO-$d_6$): δ 11.15 (s, 1H), 9.31-9.26 (m, 3H), 9.20 (d, J=2.2 Hz, 1H), 9.00 (s, 1H), 8.87 (dd, J=7.6, 3.5 Hz, 1H), 8.60-8.52 (m, 2H), 8.46 (d, J=2.4 Hz, 1H), 8.17 (d, J=8.2 Hz, 1H), 7.90 (d, J=5.0 Hz, 1H), 7.74 (dd, J=8.2, 2.5 Hz, 1H), 7.50-7.36 (m, 3H), 4.98-4.88 (m, 1H), 4.73-4.64 (m, 1H), 3.61 (s, 3H), 3.40-3.25 (m, 2H), 1.78-1.52 (m, 4H), 1.47-1.19 (m, 6H).; MS (ESI) m/z 798.59 (M+H)$^+$

Example 221

Synthesis of A-100 and Synthesis of B-100

(Step 1) N-[2,5-Difluoro-4-({[4-(1H-1,2,4-triazol-1-yl)phenyl]sulfonyl}amino)benzoyl]-3-[6-(1-methyl-2,4-dioxo-1,4-dihydropyrido[3,4-d]pyrimidin-3(2H)-yl)pyridin-3-yl]-L-alanine (A-100)

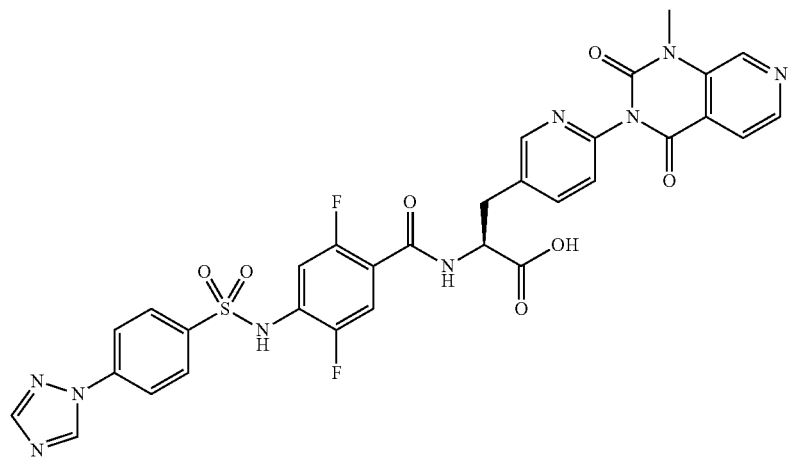 [SMILES: Cn1c(=O)n(-c2ccc(C[C@H](NC(=O)c3cc(F)c(NS(=O)(=O)c4ccc(-n5cncn5)cc4)cc3F)C(=O)O)cn2)c(=O)c2ccncc21]

$^1$H NMR (400 MHz, DMSO-d$_6$): δ 10.91 (s, 1H), 9.41 (s, 1H), 8.99 (s, 1H), 8.69 (dd, J=8.0, 2.2 Hz, 1H), 8.57 (d, J=4.9 Hz, 1H), 8.46 (d, J=2.3 Hz, 1H), 8.30 (s, 1H), 8.14-8.06 (m, 2H), 8.04-7.96 (m, 2H), 7.94-7.85 (m, 2H), 7.40 (d, J=8.1 Hz, 1H), 7.26 (ddd, J=12.4, 10.6, 6.3 Hz, 2H), 4.74-4.63 (m, 1H), 3.59 (s, 3H), 3.29 (dd, J=14.1, 4.6 Hz, 1H), 3.09 (dd, J=14.0, 10.2 Hz, 1H).; MS (ESI) m/z 704.30 (M+H)$^+$ (Step 2) Cyclohexyl N-[2,5-Difluoro-4-({[4-(1H-1,2,4-triazol-1-yl)phenyl]sulfonyl}amino)benzoyl]-3-[6-(1-methyl-2,4-dioxo-1,4-dihydropyrido[3,4-d]pyrimidin-3(2H)-yl)pyridin-3-yl]-L-alaninate (B-100)

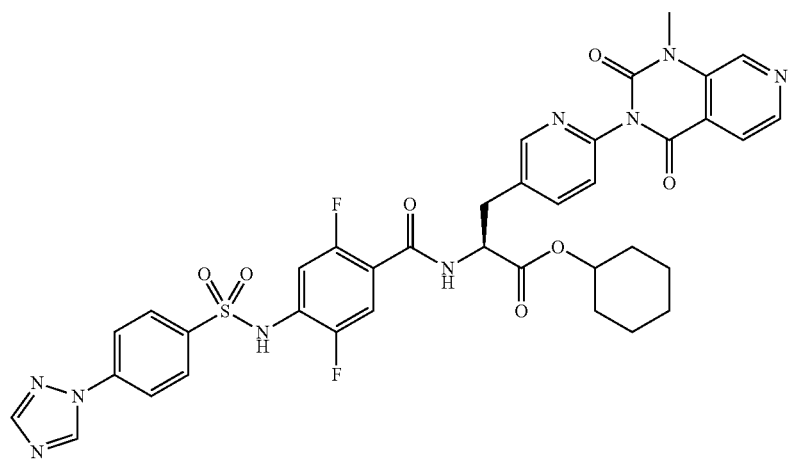 [SMILES: Cn1c(=O)n(-c2ccc(C[C@H](NC(=O)c3cc(F)c(NS(=O)(=O)c4ccc(-n5cncn5)cc4)cc3F)C(=O)OC3CCCCC3)cn2)c(=O)c2ccncc21]

$^1$H NMR (400 MHz, DMSO-d$_6$): δ 10.92 (s, 1H), 9.42 (s, 1H), 8.99 (s, 1H), 8.84 (dd, J=7.8, 1.9 Hz, 1H), 8.57 (d, J=5.0 Hz, 1H), 8.46 (d, J=2.3 Hz, 1H), 8.30 (s, 1H), 8.14-8.06 (m, 2H), 8.05-7.97 (m, 2H), 7.96-7.85 (m, 2H), 7.40 (d, J=8.1 Hz, 1H), 7.32-7.21 (m, 2H), 4.75-4.66 (m, 2H), 3.59 (s, 3H), 3.29-3.19 (m, 1H), 3.12 (dd, J=14.1, 9.7 Hz, 1H), 1.78-1.56 (m, 4H), 1.49-1.19 (m, 6H).; MS (ESI) m/z 786.46 (M+H)$^+$

Example 222

Synthesis of A-101 and Synthesis of B-101

(Step 1) N-(2,5-Difluoro-4-{[(5-pyrimidin-2-ylpyridin-2-yl)sulfonyl]amino}benzoyl)-3-[5-(1-methyl-2,4-dioxo-1,4-dihydropyrido[3,4-d]pyrimidin-3(2H)-yl)pyridin-2-yl]-L-alanine (A-101)

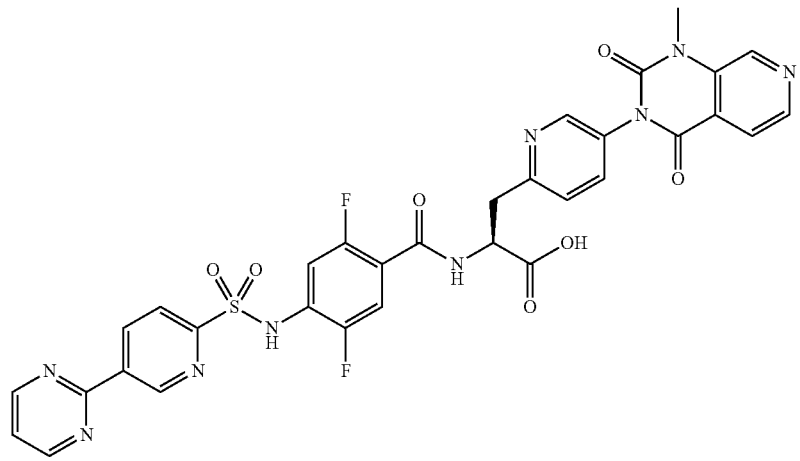

$^1$H NMR (400 MHz, DMSO-d$_6$): δ 9.58 (d, J=2.0 Hz, 1H), 9.03-8.97 (m, 3H), 8.94 (dd, J=8.3, 2.1 Hz, 1H), 8.75 (dd, J=7.8, 3.7 Hz, 1H), 8.57 (d, J=5.0 Hz, 1H), 8.45 (d, J=2.4 Hz, 1H), 8.17 (d, J=8.2 Hz, 1H), 7.90 (d, J=5.0 Hz, 1H), 7.73 (dd, J=8.2, 2.5 Hz, 1H), 7.59 (t, J=4.9 Hz, 1H), 7.46 (d, J=8.2 Hz, 1H), 7.41-7.32 (m, 2H), 4.94-4.84 (m, 1H), 3.60 (s, 3H), 3.38-3.25 (m, 2H).; MS (ESI) m/z 716.54 (M+H)$^+$ (Step 2) Cyclohexyl N-(2,5-Difluoro-4-{[(5-pyrimidin-2-ylpyridin-2-yl)sulfonyl]amino}benzoyl)-3-[5-(1-methyl-2,4-dioxo-1,4-dihydropyrido[3,4-d]pyrimidin-3(2H)-yl)pyridin-2-yl]-L-alaninate (B-101)

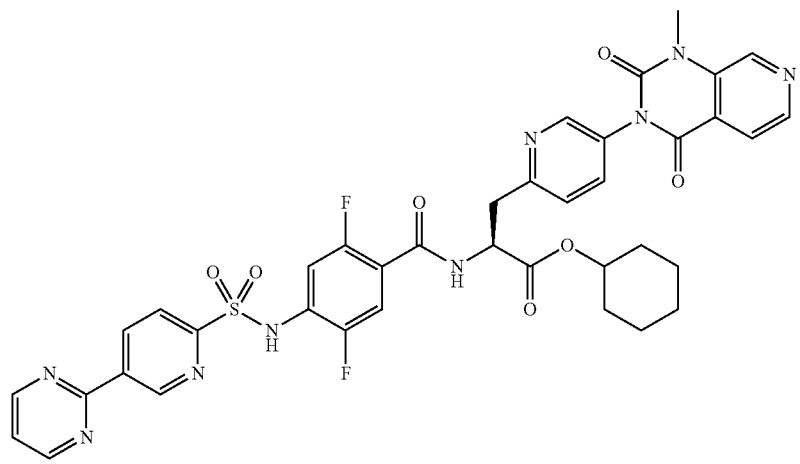

$^1$H NMR (400 MHz, DMSO-d$_6$): δ 9.58 (dd, J=2.1, 0.8 Hz, 1H), 9.04-8.97 (m, 3H), 8.95 (dd, J=8.3, 2.1 Hz, 1H), 8.88 (dd, J=7.7, 3.3 Hz, 1H), 8.57 (d, J=5.0 Hz, 1H), 8.46 (d, J=2.3 Hz, 1H), 8.18 (dd, J=8.3, 0.8 Hz, 1H), 7.90 (d, J=4.9 Hz, 1H), 7.78-7.69 (m, 1H), 7.60 (t, J=4.9 Hz, 1H), 7.47 (d, J=8.2 Hz, 1H), 7.42-7.33 (m, 2H), 4.92 (dd, J=14.1, 6.9 Hz, 1H), 4.74-4.63 (m, 1H), 3.61 (s, 3H), 3.40-3.28 (m, 2H), 1.76-1.52 (m, 4H), 1.48-1.07 (m, 6H).; MS (ESI) m/z 798.63 (M+H)$^+$

Example 223

Synthesis of A-102 and Synthesis of B-102

(Step 1) N-[4-({[4-(Cyclopropylcarbonyl)phenyl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alanine (A-102)

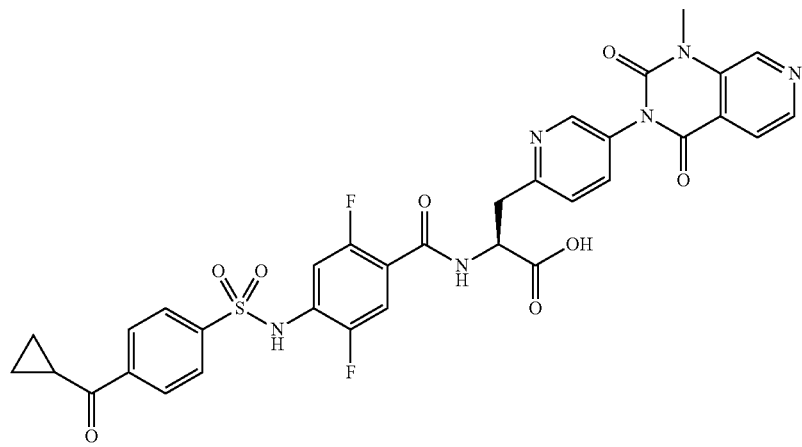 [SMILES: Cn1c(=O)n(-c2ccc(C[C@H](NC(=O)c3cc(F)c(NS(=O)(=O)c4ccc(C(=O)C5CC5)cc4)cc3F)C(=O)O)nc2)c(=O)c2ccncc21]

$^{1}$H NMR (400 MHz, DMSO-$d_6$): δ 11.01 (s, 1H), 9.00 (s, 1H), 8.74 (dd, J=7.9, 3.7 Hz, 1H), 8.58 (d, J=5.0 Hz, 1H), 8.46 (d, J=2.4 Hz, 1H), 8.24-8.17 (m, 2H), 8.00-7.93 (m, 2H), 7.91 (d, J=4.9 Hz, 1H), 7.73 (dd, J=8.2, 2.5 Hz, 1H), 7.46 (d, J=8.2 Hz, 1H), 7.36 (dd, J=10.3, 6.3 Hz, 1H), 7.24 (dd, J=11.2, 6.2 Hz, 1H), 4.89 (td, J=8.2, 4.9 Hz, 1H), 3.61 (s, 3H), 3.38-3.22 (m, 2H), 2.89 (ddd, J=12.3, 7.6, 4.9 Hz, 1H), 1.13-1.03 (m, 4H).; MS (ESI) m/z 705.36 (M+H)$^{+}$ (Step 2) Cyclohexyl N-[4-({[4-(Cyclopropylcarbonyl)phenyl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alaninate (B-102)

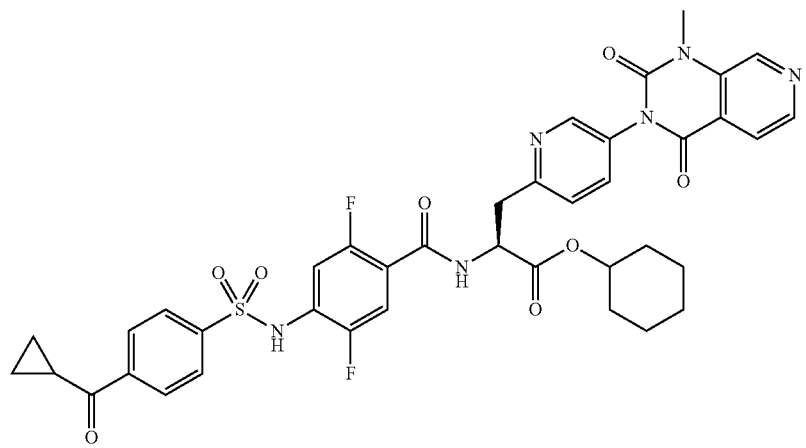 [SMILES: Cn1c(=O)n(-c2ccc(C[C@H](NC(=O)c3cc(F)c(NS(=O)(=O)c4ccc(C(=O)C5CC5)cc4)cc3F)C(=O)OC3CCCCC3)nc2)c(=O)c2ccncc21]

$^{1}$H NMR (400 MHz, DMSO-$d_6$): δ 11.02 (s, 1H), 9.00 (s, 1H), 8.86 (d, J=7.8 Hz, 1H), 8.58 (d, J=4.9 Hz, 1H), 8.45 (d, J=2.5 Hz, 1H), 8.24-8.17 (m, 2H), 8.01-7.94 (m, 2H), 7.91 (d, J=4.9 Hz, 1H), 7.73 (dd, J=8.2, 2.5 Hz, 1H), 7.46 (d, J=8.2 Hz, 1H), 7.37 (dd, J=10.2, 6.3 Hz, 1H), 7.25 (dd, J=11.1, 6.2 Hz, 1H), 4.97-4.87 (m, 1H), 4.74-4.63 (m, 1H), 3.61 (s, 3H), 2.95-2.84 (m, 1H), 1.78-1.49 (m, 4H), 1.48-1.18 (m, 6H), 1.13-1.04 (m, 4H).; MS (ESI) m/z 787.63 (M+H)$^{+}$

Example 224

Synthesis of A-103 and Synthesis of B-103

(Step 1) N-[2,5-Difluoro-4-({[4-(1H-1,2,4-triazol-1-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alanine (A-103)

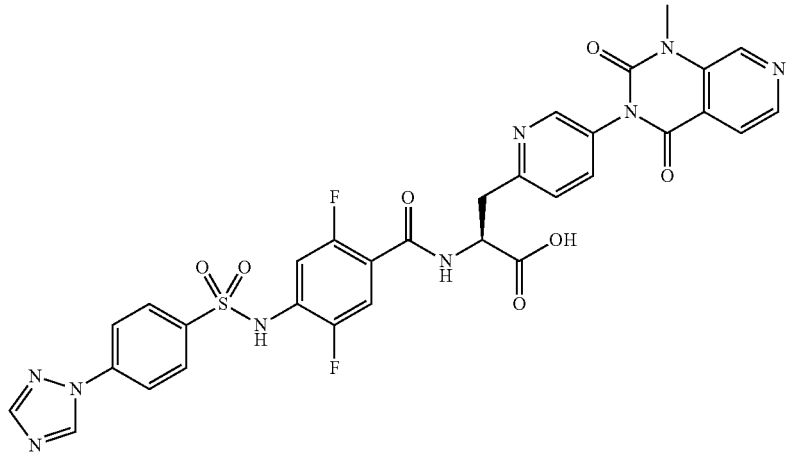 [SMILES: Cn1c(=O)n(-c2ccc(C[C@H](NC(=O)c3cc(F)c(NS(=O)(=O)c4ccc(-n5cncn5)cc4)cc3F)C(=O)O)nc2)c(=O)c2ccncc21]

$^1$H NMR (400 MHz, DMSO-d$_6$): δ 10.93 (s, 1H), 9.41 (s, 1H), 9.00 (s, 1H), 8.73 (dd, J=7.8, 3.8 Hz, 1H), 8.58 (d, J=5.0 Hz, 1H), 8.45 (d, J=2.4 Hz, 1H), 8.30 (s, 1H), 8.14-8.06 (m, 2H), 8.04-7.95 (m, 2H), 7.90 (d, J=5.0 Hz, 1H), 7.72 (dd, J=8.2, 2.5 Hz, 1H), 7.45 (d, J=8.2 Hz, 1H), 7.37 (dd, J=10.3, 6.4 Hz, 1H), 7.26 (dd, J=11.3, 6.2 Hz, 1H), 4.94-4.83 (m, 1H), 3.61 (s, 3H), 3.33-3.22 (m, 2H).; MS (ESI) m/z 704.46 (M+H)$^+$ (Step 2) Cyclohexyl N-[2,5-Difluoro-4-({[4-(1H-1,2,4-triazol-1-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alaninate (B-103)

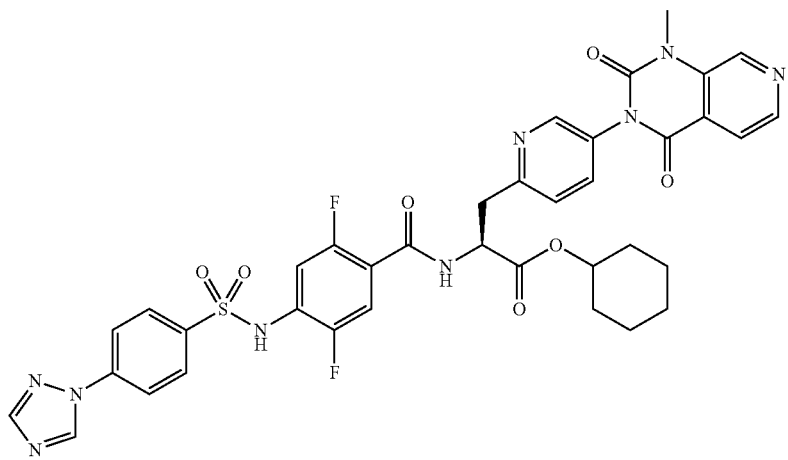 [SMILES: Cn1c(=O)n(-c2ccc(C[C@H](NC(=O)c3cc(F)c(NS(=O)(=O)c4ccc(-n5cncn5)cc4)cc3F)C(=O)OC3CCCCC3)nc2)c(=O)c2ccncc21]

$^1$H NMR (400 MHz, DMSO-d$_6$): δ 10.94 (s, 1H), 9.41 (s, 1H), 9.00 (s, 1H), 8.85 (dd, J=7.6, 3.4 Hz, 1H), 8.57 (d, J=4.9 Hz, 1H), 8.45 (d, J=2.4 Hz, 1H), 8.30 (s, 1H), 8.14-8.06 (m, 2H), 8.05-7.97 (m, 2H), 7.90 (d, J=4.9 Hz, 1H), 7.72 (dd, J=8.2, 2.5 Hz, 1H), 7.45 (d, J=8.3 Hz, 1H), 7.37 (dd, J=10.3, 6.3 Hz, 1H), 7.27 (dd, J=11.2, 6.2 Hz, 1H), 4.97-4.86 (m, 1H), 4.73-4.63 (m, 1H), 3.61 (s, 3H), 1.75-1.54 (m, 4H), 1.45-1.17 (m, 6H).; MS (ESI) m/z 786.57 (M+H)$^+$

Example 225

Synthesis of A-104 and Synthesis of B-104

(Step 1) N-[2,5-Difluoro-4-({[4-(1H-1,2,4-triazol-1-yl)phenyl]sulfonyl}amino)benzoyl]-4-(1-methyl-2,4-dioxo-1,4-dihydropyrido[3,4-d]pyrimidin-3(2H)-yl)-L-phenylalanine (A-104)

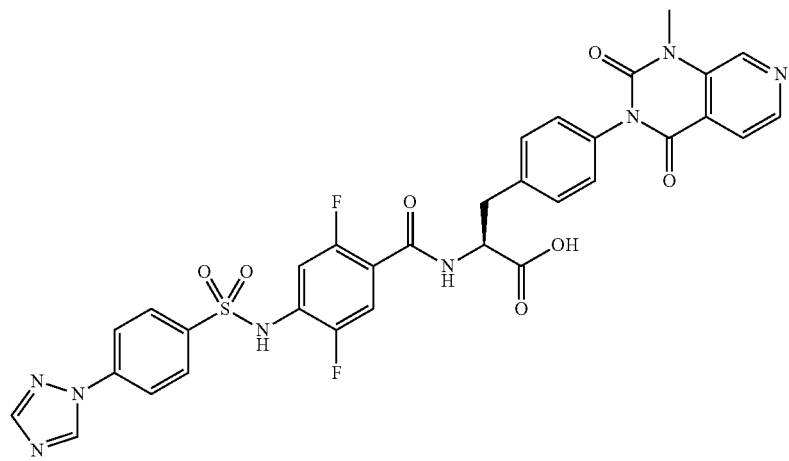 [SMILES: Cn1c(=O)n(-c2ccc(C[C@H](NC(=O)c3cc(F)c(NS(=O)(=O)c4ccc(-n5cncn5)cc4)cc3F)C(=O)O)cc2)c(=O)c2ccncc21]

$^1$H NMR (400 MHz, DMSO-$d_6$): δ 10.91 (s, 1H), 9.41 (s, 1H), 8.96 (s, 1H), 8.60 (dd, J=7.9, 2.6 Hz, 1H), 8.55 (d, J=4.9 Hz, 1H), 8.30 (s, 1H), 8.14-8.06 (m, 2H), 8.04-7.96 (m, 2H), 7.87 (d, J=4.9 Hz, 1H), 7.40-7.17 (m, 6H), 4.62 (ddd, J=9.9, 7.8, 4.6 Hz, 1H), 3.59 (s, 3H), 3.23 (dd, J=13.9, 4.4 Hz, 1H), 3.06 (dd, J=13.8, 9.9 Hz, 1H).; MS (ESI) m/z 703.48 (M+H)$^+$ (Step 2) Cyclohexyl N-[2,5-Difluoro-4-({[4-(1H-1,2,4-triazol-1-yl)phenyl]sulfonyl}amino)benzoyl]-4-(1-methyl-2,4-dioxo-1,4-dihydropyrido[3,4-d]pyrimidin-3(2H)-yl)-L-phenylalaninate (B-104)

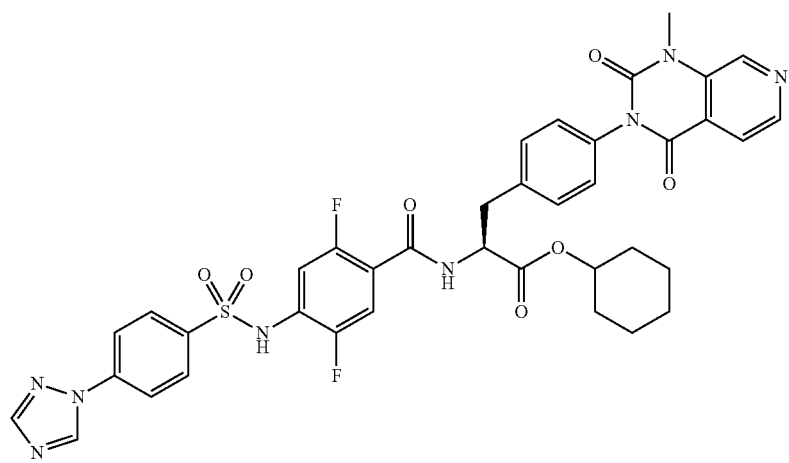 [SMILES: Cn1c(=O)n(-c2ccc(C[C@H](NC(=O)c3cc(F)c(NS(=O)(=O)c4ccc(-n5cncn5)cc4)cc3F)C(=O)OC3CCCCC3)cc2)c(=O)c2ccncc21]

$^1$H NMR (400 MHz, DMSO-$d_6$): δ 10.92 (s, 1H), 9.42 (s, 1H), 8.96 (s, 1H), 8.76 (dd, J=7.5, 2.0 Hz, 1H), 8.55 (d, J=5.0 Hz, 1H), 8.30 (s, 1H), 8.14-8.06 (m, 2H), 8.05-7.97 (m, 2H), 7.88 (d, J=5.0 Hz, 1H), 7.40-7.18 (m, 6H), 4.74-4.57 (m, 2H), 3.59 (s, 3H), 3.21-3.07 (m, 2H), 1.79-1.58 (m, 4H), 1.49-1.19 (m, 6H).; MS (ESI) m/z 785.54 (M+H)$^+$

Example 226

Synthesis of A-105 and Synthesis of B-105

(Step 1) N-[2,5-Difluoro-4-({[4-(1H-1,2,3-triazol-1-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alanine (A-105)

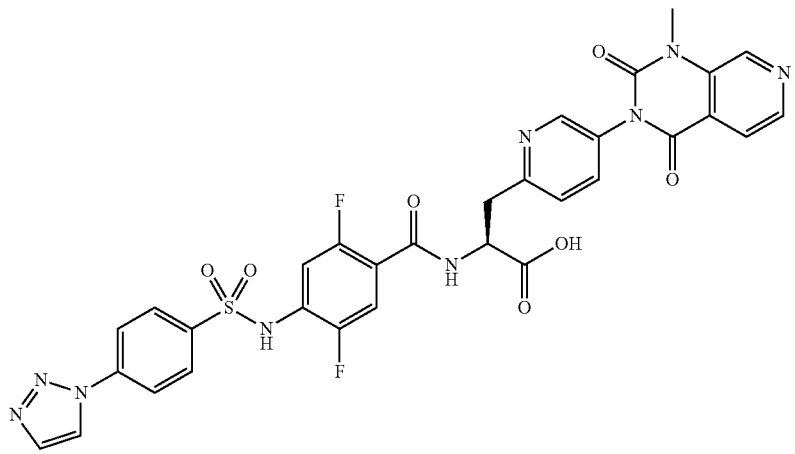 [SMILES: Cn1c(=O)n(-c2ccc(C[C@H](NC(=O)c3cc(F)c(NS(=O)(=O)c4ccc(-n5ccnn5)cc4)cc3F)C(=O)O)nc2)c(=O)c2ccncc21]

$^1$H NMR (400 MHz, DMSO-d$_6$): δ 10.97 (s, 1H), 9.00 (s, 1H), 8.94 (d, J=1.1 Hz, 1H), 8.74 (dd, J=7.9, 3.8 Hz, 1H), 8.58 (d, J=4.9 Hz, 1H), 8.46 (d, J=2.4 Hz, 1H), 8.21-8.12 (m, 2H), 8.07-7.99 (m, 3H), 7.90 (d, J=4.9 Hz, 1H), 7.73 (dd, J=8.2, 2.5 Hz, 1H), 7.46 (d, J=8.2 Hz, 1H), 7.37 (dd, J=10.3, 6.3 Hz, 1H), 7.27 (dd, J=11.2, 6.2 Hz, 1H), 4.94-4.84 (m, 1H), 3.61 (s, 3H), 3.42-3.22 (m, 2H).; MS (ESI) m/z 704.46 (M+H)$^+$ (Step 2) Cyclohexyl N-[2,5-Difluoro-4-({[4-(1H-1,2,3-triazol-1-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alaninate (B-105)

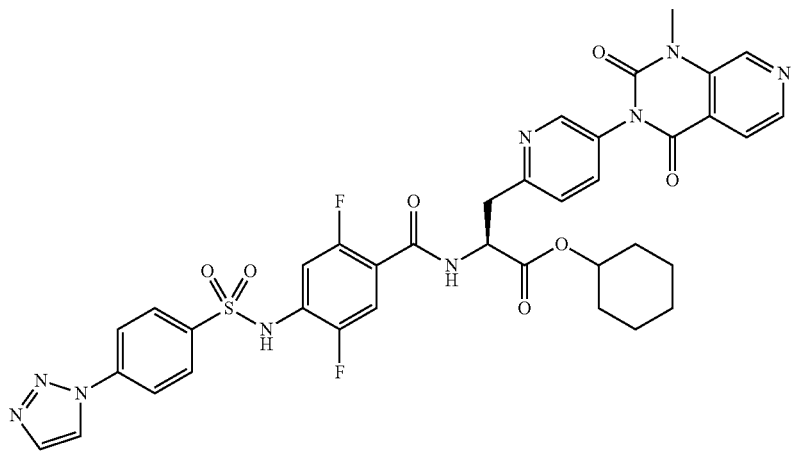 [SMILES: Cn1c(=O)n(-c2ccc(C[C@H](NC(=O)c3cc(F)c(NS(=O)(=O)c4ccc(-n5ccnn5)cc4)cc3F)C(=O)OC3CCCCC3)nc2)c(=O)c2ccncc21]

$^1$H NMR (400 MHz, DMSO-d$_6$): δ 10.98 (s, 1H), 8.99 (s, 1H), 8.94 (d, J=1.3 Hz, 1H), 8.85 (dd, J=7.7, 3.3 Hz, 1H), 8.57 (d, J=4.9 Hz, 1H), 8.45 (d, J=2.4 Hz, 1H), 8.21-8.13 (m, 2H), 8.08-7.99 (m, 3H), 7.93-7.87 (m, 1H), 7.72 (dd, J=8.2, 2.5 Hz, 1H), 7.45 (d, J=8.2 Hz, 1H), 7.38 (dd, J=10.3, 6.4 Hz, 1H), 7.28 (dd, J=11.1, 6.2 Hz, 1H), 4.97-4.87 (m, 1H), 4.72-4.63 (m, 1H), 3.61 (s, 3H), 1.76-1.51 (m, 4H), 1.45-1.17 (m, 6H).;

MS (ESI) m/z 786.57 (M+H)$^+$

Example 227

Synthesis of A-106 and Synthesis of B-106

(Step 1) N-(4-{[(2',6'-Dimethyl-3,4'-bipyridin-6-yl)sulfonyl]amino}-2,5-difluorobenzoyl)-3-[5-(1-methyl-2,4-dioxo-1,4-dihydropyrido[3,4-d]pyrimidin-3(2H)-yl)pyridin-2-yl]-L-alanine (A-106)

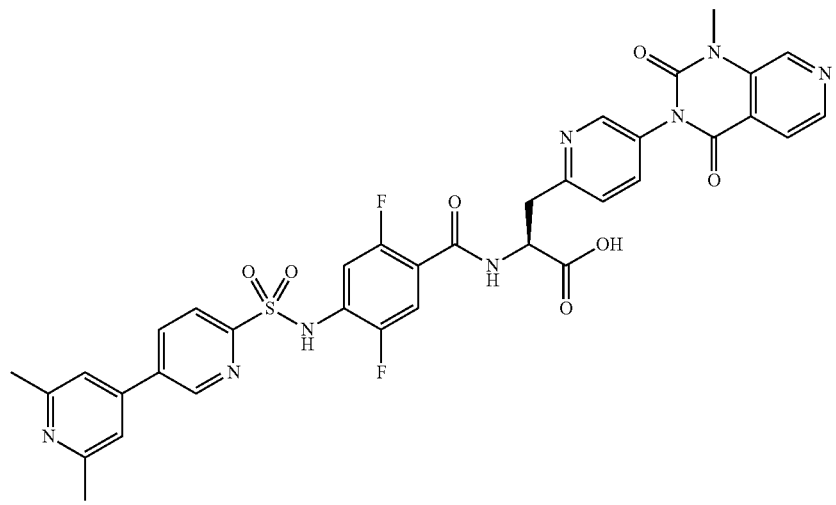 [SMILES: Cc1cc(-c2ccc(S(=O)(=O)Nc3cc(F)c(C(=O)N[C@@H](Cc4ccc(-n5c(=O)c6ccncc6n(C)c5=O)cn4)C(=O)O)cc3F)nc2)cc(C)n1]

$^1$H NMR (400 MHz, DMSO-d$_6$): δ 11.14 (s, 1H), 9.24 (d, J=2.3 Hz, 1H), 9.00 (s, 1H), 8.75 (dd, J=7.9, 3.9 Hz, 1H), 8.63-8.54 (m, 2H), 8.46 (d, J=2.3 Hz, 1H), 8.21 (d, J=8.3 Hz, 1H), 8.03 (s, 2H), 7.90 (d, J=4.9 Hz, 1H), 7.73 (dd, J=8.2, 2.5 Hz, 1H), 7.49-7.36 (m, 3H), 4.95-4.85 (m, 1H), 3.61 (s, 3H), 3.42-3.24 (m, 2H), 2.66 (s, 6H).; MS (ESI) m/z 743.28 (M+H)$^+$ (Step 2) Cyclohexyl N-(4-{[(2',6'-Dimethyl-3,4'-bipyridin-6-yl)sulfonyl]amino}-2,5-difluorobenzoyl)-3-[5-(1-methyl-2,4-dioxo-1,4-dihydropyrido[3,4-d]pyrimidin-3(2H)-yl)pyridin-2-yl]-L-alaninate (B-106)

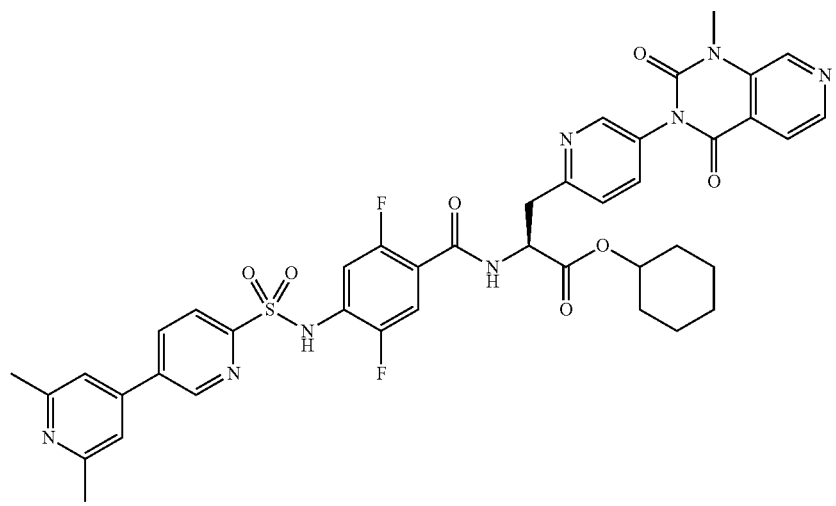 [SMILES: Cc1cc(-c2ccc(S(=O)(=O)Nc3cc(F)c(C(=O)N[C@@H](Cc4ccc(-n5c(=O)c6ccncc6n(C)c5=O)cn4)C(=O)OC4CCCCC4)cc3F)nc2)cc(C)n1]

$^1$H NMR (400 MHz, DMSO-d$_6$): δ 11.17 (s, 1H), 9.24 (d, J=2.4 Hz, 1H), 9.00 (s, 1H), 8.88 (dd, J=7.5, 3.5 Hz, 1H), 8.63-8.54 (m, 2H), 8.46 (d, J=2.4 Hz, 1H), 8.21 (d, J=8.3 Hz, 1H), 8.04 (s, 2H), 7.90 (d, J=5.0 Hz, 1H), 7.73 (dd, J=8.2, 2.5 Hz, 1H), 7.50-7.36 (m, 3H), 4.98-4.88 (m, 1H), 4.73-4.63 (m, 1H), 3.61 (s, 3H), 3.36-3.29 (m, 2H), 2.66 (s, 6H), 1.76-1.54 (m, 4H), 1.49-1.13 (m, 6H).; MS (ESI) m/z 825.36 (M+H)$^+$

Example 228

Synthesis of A-107

(Step 1) N-[2,5-Difluoro-4-({[4-(2-methoxypyrimidin-5-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alanine (A-107)

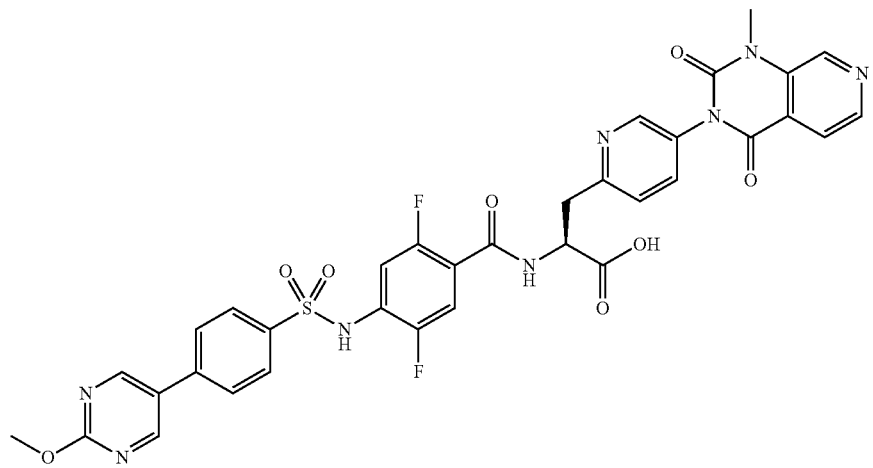 [SMILES: COc1ncc(-c2ccc(S(=O)(=O)Nc3cc(F)c(C(=O)N[C@@H](Cc4ccc(-n5c(=O)c6ccncc6n(C)c5=O)cn4)C(=O)O)cc3F)cc2)cn1]

$^1$H NMR (400 MHz, DMSO-d$_6$): δ 10.95 (s, 1H), 9.03-8.97 (m, 3H), 8.73 (dd, J=7.7, 3.9 Hz, 1H), 8.57 (d, J=4.9 Hz, 1H), 8.45 (d, J=2.4 Hz, 1H), 8.01-7.87 (m, 5H), 7.72 (dd, J=8.2, 2.5 Hz, 1H), 7.44 (d, J=8.3 Hz, 1H), 7.37 (dd, J=10.4, 6.4 Hz, 1H), 7.27 (dd, J=11.4, 6.2 Hz, 1H), 4.93-4.83 (m, 1H), 3.97 (s, 3H), 3.61 (s, 3H).; MS (ESI) m/z 745 (M+H)$^+$

Example 229

Synthesis of A-108 and Synthesis of B-108

(Step 1) N-[4-({[4-(2-Ethylpyrimidin-5-yl)phenyl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alanine (A-108)

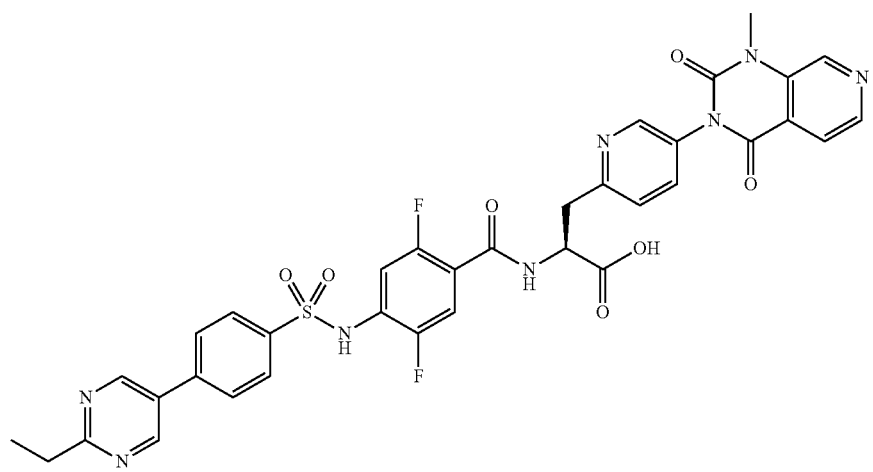 [SMILES: CCc1ncc(-c2ccc(S(=O)(=O)Nc3cc(F)c(C(=O)N[C@@H](Cc4ccc(-n5c(=O)c6ccncc6n(C)c5=O)cn4)C(=O)O)cc3F)cc2)cn1]

$^1$H NMR (400 MHz, DMSO-d$_6$): δ 11.03 (s, 1H), 9.09 (d, J=1.3 Hz, 2H), 8.97 (s, 1H), 8.75 (dd, J=7.9, 3.9 Hz, 1H), 8.57 (dd, J=4.9, 1.4 Hz, 1H), 8.46 (t, J=1.8 Hz, 1H), 8.05-7.99 (m, 2H), 7.99-7.93 (m, 2H), 7.90 (d, J=4.9 Hz, 1H), 7.77-7.69 (m, 1H), 7.46 (d, J=8.3 Hz, 1H), 7.42-7.33 (m, 1H), 7.27 (dd, J=11.3, 6.3 Hz, 1H), 4.94-4.84 (m, 1H), 3.38-3.23 (m, 2H), 2.94 (q, J=8.1 Hz, 2H), 1.30 (t, J=7.6 Hz, 3H).; MS (ESI) m/z 743.46 (M+H)$^+$ (Step 2) Cyclohexyl N-[4-({[4-(2-Ethylpyrimidin-5-yl)phenyl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alaninate (B-108)

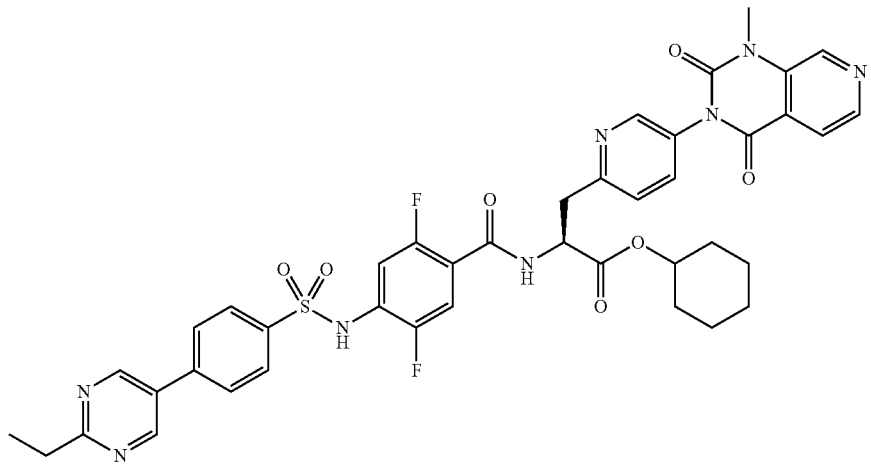 [SMILES: CCc1ncc(-c2ccc(S(=O)(=O)Nc3cc(F)c(C(=O)N[C@@H](Cc4ccc(-n5c(=O)c6ccncc6n(C)c5=O)cn4)C(=O)OC4CCCCC4)cc3F)cc2)cn1]

$^1$H NMR (400 MHz, DMSO-d$_6$): δ 10.99 (s, 1H), 9.10 (s, 2H), 8.99 (s, 1H), 8.85 (dd, J=7.6, 3.4 Hz, 1H), 8.57 (d, J=4.9 Hz, 1H), 8.45 (d, J=2.4 Hz, 1H), 8.06-7.99 (m, 2H), 7.99-7.93 (m, 2H), 7.90 (d, J=5.0 Hz, 1H), 7.73 (dd, J=8.2, 2.5 Hz, 1H), 7.46 (d, J=8.3 Hz, 1H), 7.38 (dd, J=10.3, 6.3 Hz, 1H), 7.29 (dd, J=11.3, 6.3 Hz, 1H), 4.97-4.86 (m, 1H), 4.72-4.62 (m, 1H), 3.61 (s, 3H), 3.32 (dq, J=14.5, 6.7 Hz, 2H), 2.95 (q, J=7.6 Hz, 2H), 1.75-1.52 (m, 4H), 1.45-1.22 (m, 9H).; MS (ESI) m/z 825.59 (M+H)$^+$

Example 230

Synthesis of A-109 and Synthesis of B-109

(Step 1) N-(2,5-Difluoro-4-{[(5-pyrimidin-2-ylpyridin-2-yl)sulfonyl]amino}benzoyl)-3-[5-(1-methyl-2,4-dioxo-1,4-dihydropyrido[3,2-d]pyrimidin-3(2H)-yl)pyridin-2-yl]-L-alanine (A-109)

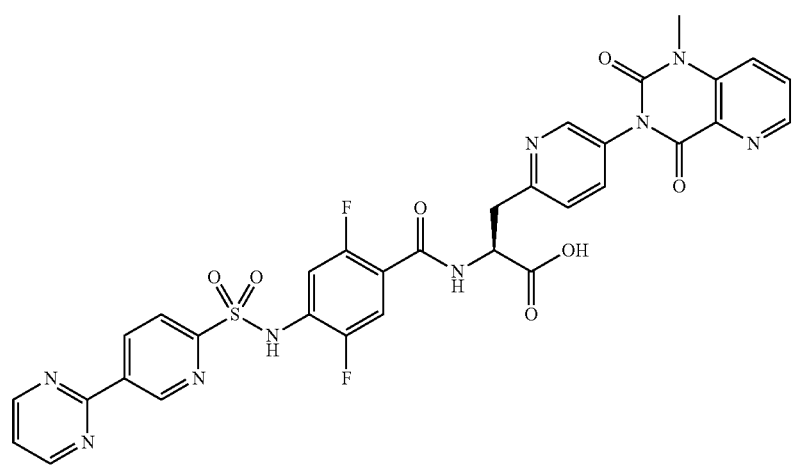 [SMILES: Cn1c(=O)n(-c2ccc(C[C@H](NC(=O)c3cc(F)c(NS(=O)(=O)c4ccc(-c5ncccn5)cn4)cc3F)C(=O)O)nc2)c(=O)c2ncccc21]

¹H NMR (400 MHz, DMSO-d₆): δ 11.10 (s, 1H), 9.58 (d, J=2.0 Hz, 1H), 9.05-8.97 (m, 2H), 8.94 (dd, J=8.2, 2.2 Hz, 1H), 8.76 (dd, J=7.8, 3.7 Hz, 1H), 8.59 (dd, J=4.4, 1.2 Hz, 1H), 8.46 (d, J=2.4 Hz, 1H), 8.17 (d, J=8.2 Hz, 1H), 8.03 (dd, J=9.0, 1.2 Hz, 1H), 7.83 (dd, J=8.6, 4.3 Hz, 1H), 7.73 (dd, J=8.2, 2.5 Hz, 1H), 7.60 (t, J=4.9 Hz, 1H), 7.46 (d, J=8.2 Hz, 1H), 7.42-7.32 (m, 2H), 4.94-4.84 (m, 1H), 3.52 (s, 3H), 3.34-3.23 (m, 2H).; MS (ESI) m/z 716.18 (M+H)⁺

(Step 2) Cyclohexyl N-(2,5-Difluoro-4-{[(5-pyrimidin-2-ylpyridin-2-yl)sulfonyl]amino}benzoyl)-3-[5-(1-methyl-2,4-dioxo-1,4-dihydropyrido[3,2-d]pyrimidin-3(2H)-yl)pyridin-2-yl]-L-alaninate (B-109)

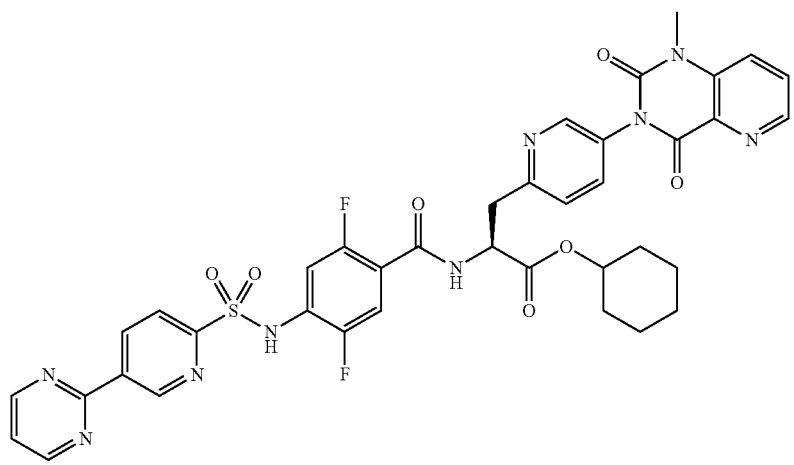 [SMILES: Cn1c(=O)n(-c2ccc(C[C@H](NC(=O)c3cc(F)c(NS(=O)(=O)c4ccc(-c5ncccn5)cn4)cc3F)C(=O)OC3CCCCC3)nc2)c(=O)c2ncccc21]

¹H NMR (400 MHz, DMSO-d₆): δ 11.11 (s, 1H), 9.58 (d, J=2.0 Hz, 1H), 9.01 (d, J=4.9 Hz, 2H), 8.94 (dd, J=8.3, 2.1 Hz, 1H), 8.89 (dd, J=7.5, 3.3 Hz, 1H), 8.59 (dd, J=4.3, 1.2 Hz, 1H), 8.46 (d, J=2.4 Hz, 1H), 8.17 (d, J=8.3 Hz, 1H), 8.03 (dd, J=8.7, 1.3 Hz, 1H), 7.83 (dd, J=8.6, 4.3 Hz, 1H), 7.73 (dd, J=8.2, 2.5 Hz, 1H), 7.60 (t, J=4.9 Hz, 1H), 7.46 (d, J=8.2 Hz, 1H), 7.42-7.33 (m, 2H), 4.97-4.87 (m, 1H), 4.73-4.63 (m, 1H), 3.52 (s, 3H), 1.77-1.52 (m, 4H), 1.48-1.19 (m, 6H).; MS (ESI) m/z 798.34 (M+H)⁺

Example 231

Synthesis of A-110 and Synthesis of B-110

(Step 1) N-(4-{[(2-Ethoxy-4-pyrimidin-2-ylphenyl)sulfonyl]amino}-2,6-difluorobenzoyl)-3-[5-(1-methyl-2,4-dioxo-1,4-dihydropyrido[3,4-d]pyrimidin-3(2H)-yl)pyridin-2-yl]-L-alanine (A-110)

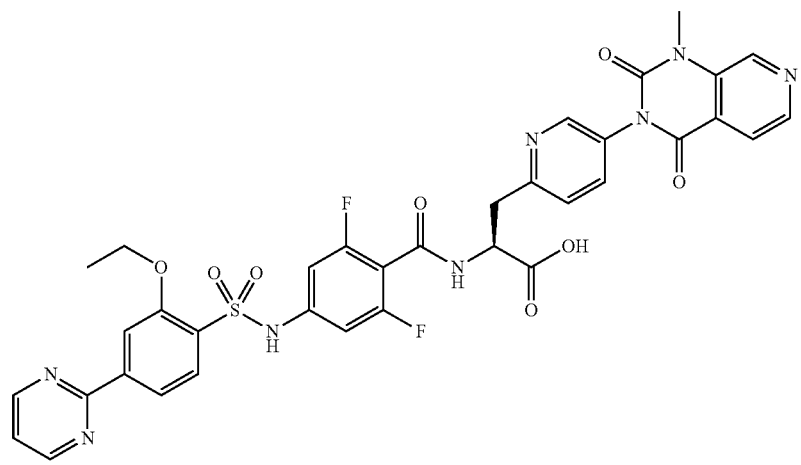 [SMILES: CCOc1cc(-c2ncccn2)ccc1S(=O)(=O)Nc1cc(F)c(C(=O)N[C@@H](Cc2ccc(-n3c(=O)c4ccncc4n(C)c3=O)cn2)C(=O)O)c(F)c1]

¹H NMR (400 MHz, DMSO-d₆): δ 10.82 (s, 1H), 9.02-8.92 (m, 4H), 8.58 (d, J=5.0 Hz, 1H), 8.46-8.41 (m, 1H), 8.14-8.04 (m, 3H), 7.90 (dd, J=5.0, 0.7 Hz, 1H), 7.71 (dd, J=8.2, 2.5 Hz, 1H), 7.54 (t, J=4.9 Hz, 1H), 7.40 (d, J=8.2 Hz, 1H), 6.75 (d, J=9.3 Hz, 2H), 4.82 (ddd, J=9.4, 7.8, 5.0 Hz, 1H), 4.33 (q, J=7.0 Hz, 2H), 3.61 (s, 3H), 3.30 (dd, J=14.5, 5.0 Hz, 1H), 3.13 (dd, J=14.5, 9.4 Hz, 1H), 1.38 (t, J=7.0 Hz, 3H).; MS (ESI) m/z 759.25 (M+H)⁺

(Step 2) Cyclohexyl N-(4-{[(2-Ethoxy-4-pyrimidin-2-yl)phenyl)sulfonyl]amino}-2,6-difluorobenzoyl)-3-[5-(1-methyl-2,4-dioxo-1,4-dihydropyrido[3,4-d]pyrimidin-3(2H)-yl)pyridin-2-yl]-L-alaninate (B-110)

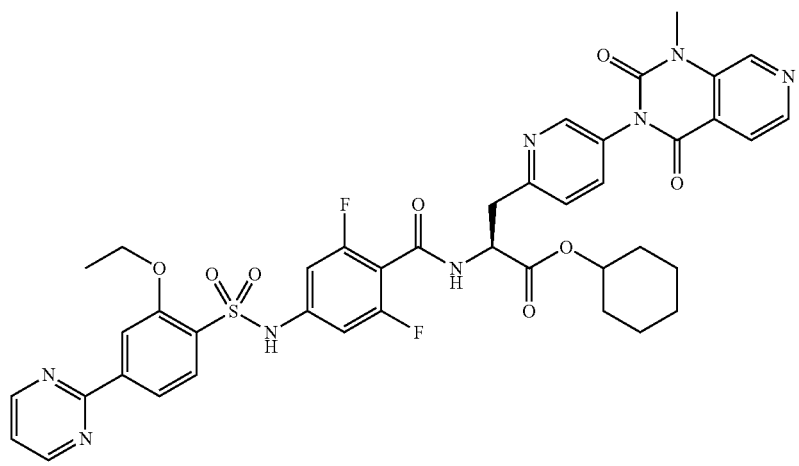 [SMILES: CCOc1cc(-c2ncccn2)ccc1S(=O)(=O)Nc1cc(F)c(C(=O)N[C@@H](Cc2ccc(-n3c(=O)c4ccncc4n(C)c3=O)cn2)C(=O)OC2CCCCC2)c(F)c1]

¹H NMR (400 MHz, DMSO-d₆): δ 10.84 (s, 1H), 9.07 (d, J=7.6 Hz, 1H), 9.02-8.94 (m, 3H), 8.58 (d, J=5.0 Hz, 1H), 8.43 (d, J=2.4 Hz, 1H), 8.10 (d, J=4.2 Hz, 3H), 7.90 (d, J=5.0 Hz, 1H), 7.70 (dd, J=8.2, 2.5 Hz, 1H), 7.55 (t, J=4.9 Hz, 1H), 7.41 (d, J=8.2 Hz, 1H), 6.77 (d, J=9.3 Hz, 2H), 4.89-4.79 (m, 1H), 4.71-4.62 (m, 1H), 4.33 (q, J=7.0 Hz, 2H), 3.61 (s, 3H), 3.32-3.22 (m, 1H), 3.22-3.11 (m, 1H), 1.77-1.58 (m, 4H), 1.48-1.15 (m, 9H).; MS (ESI) m/z 841.49 (M+H)⁺

Example 232

Synthesis of A-111 and Synthesis of B-111

(Step 1) N-[4-({[4-(2-Azetidin-1-ylpyrimidin-5-yl)phenyl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alanine (A-111)

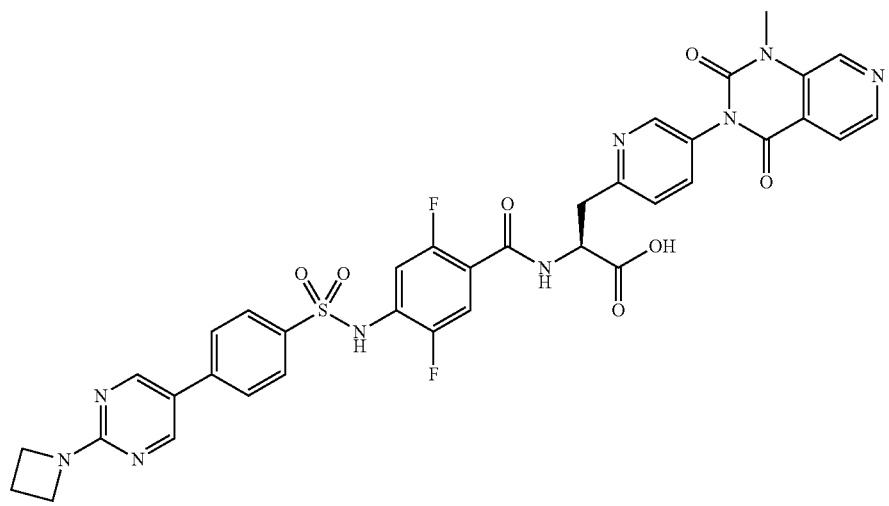 [SMILES: Cn1c(=O)n(-c2ccc(C[C@H](NC(=O)c3cc(F)c(NS(=O)(=O)c4ccc(-c5cnc(N6CCC6)nc5)cc4)cc3F)C(=O)O)nc2)c(=O)c2ccncc21]

¹H NMR (400 MHz, DMSO-d₆): δ 10.89 (s, 1H), 9.00 (s, 1H), 8.77-8.68 (m, 3H), 8.57 (d, J=5.0 Hz, 1H), 8.45 (d, J=2.4 Hz, 1H), 7.93-7.83 (m, 5H), 7.72 (dd, J=8.2, 2.5 Hz, 1H), 7.44 (d, J=8.2 Hz, 1H), 7.37 (dd, J=10.4, 6.4 Hz, 1H), 7.26 (dd, J=11.5, 6.1 Hz, 1H), 4.93-4.83 (m, 1H), 4.14-4.05 (m, 4H), 3.61 (s, 3H), 3.41-3.22 (m, 2H), 2.38-2.29 (m, 2H).; MS (ESI) m/z 770.18 (M+H)⁺

(Step 2) Cyclohexyl N-[4-({[4-(2-Azetidin-1-ylpyrimidin-5-yl)phenyl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alaninate (B-111)

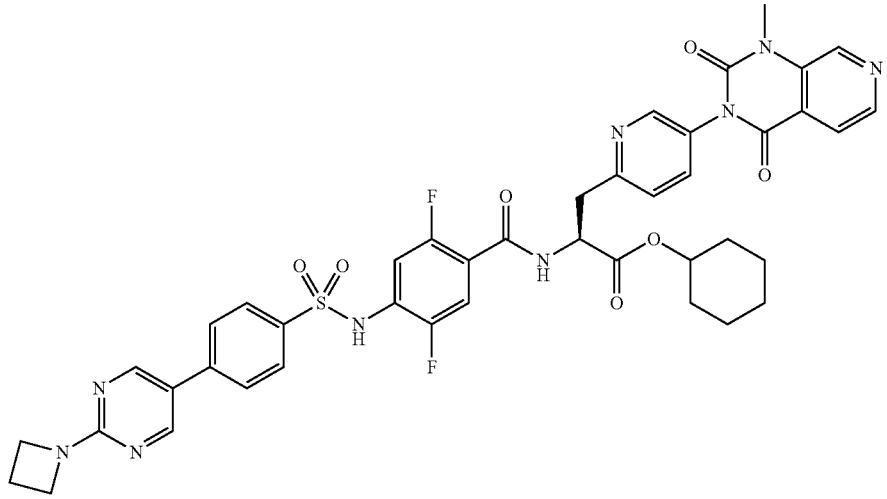 [SMILES: Cn1c(=O)n(-c2ccc(C[C@H](NC(=O)c3cc(F)c(NS(=O)(=O)c4ccc(-c5cnc(N6CCC6)nc5)cc4)cc3F)C(=O)OC3CCCCC3)nc2)c(=O)c2ccncc21]

¹H NMR (400 MHz, DMSO-d₆): δ 10.91 (s, 1H), 9.00 (s, 1H), 8.84 (dd, J=7.5, 3.4 Hz, 1H), 8.74 (s, 2H), 8.57 (d, J=4.9 Hz, 1H), 8.45 (d, J=2.4 Hz, 1H), 7.90 (d, J=5.0 Hz, 1H), 7.87 (s, 4H), 7.73 (dd, J=8.2, 2.5 Hz, 1H), 7.46 (d, J=8.2 Hz, 1H), 7.37 (dd, J=10.3, 6.3 Hz, 1H), 7.27 (dd, J=11.3, 6.2 Hz, 1H), 4.96-4.86 (m, 1H), 4.73-4.63 (m, 1H), 4.14-4.05 (m, 4H), 3.61 (s, 3H), 3.37-3.27 (m, 2H), 2.40-2.28 (m, 2H), 1.73-1.53 (m, 4H), 1.46-1.18 (m, 6H).; MS (ESI) m/z 852.34 (M+H)⁺

Example 233

Synthesis of A-112 and Synthesis of B-112

(Step 1) N-(2,5-Difluoro-4-{[(3-oxo-1,3-dihydro-2-benzofuran-5-yl)sulfonyl]amino}benzoyl)-3-[5-(1-methyl-2,4-dioxo-1,4-dihydropyrido[3,4-d]pyrimidin-3(2H)-yl)pyridin-2-yl]-L-alanine (A-112)

¹H NMR (400 MHz, DMSO-d₆): δ 11.02 (s, 1H), 9.00 (s, 1H), 8.74 (dd, J=7.9, 3.7 Hz, 1H), 8.58 (d, J=4.9 Hz, 1H), 8.46 (d, J=2.4 Hz, 1H), 8.22 (d, J=1.6 Hz, 1H), 8.17 (dd, J=8.1, 1.7 Hz, 1H), 7.94-7.86 (m, 2H), 7.73 (dd, J=8.2, 2.5 Hz, 1H), 7.45 (d, J=8.2 Hz, 1H), 7.37 (dd, J=10.3, 6.3 Hz, 1H), 7.27 (dd, J=11.2, 6.3 Hz, 1H), 5.50 (s, 2H), 4.93-4.83 (m, 1H), 3.62 (s, 3H), 3.41-3.22 (m, 2H).; MS (ESI) m/z 693.17 (M+H)⁺

(Step 2) Cyclohexyl N-(2,5-Difluoro-4-{[(3-oxo-1,3-dihydro-2-benzofuran-5-yl)sulfonyl]amino}benzoyl)-3-[5-(1-methyl-2,4-dioxo-1,4-dihydropyrido[3,4-d]pyrimidin-3(2H)-yl)pyridin-2-yl]-L-alaninate (B-112)

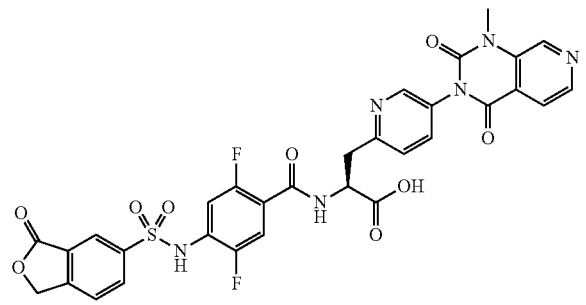 [SMILES: Cn1c(=O)n(-c2ccc(C[C@H](NC(=O)c3cc(F)c(NS(=O)(=O)c4ccc5c(c4)C(=O)OC5)cc3F)C(=O)O)nc2)c(=O)c2ccncc21]

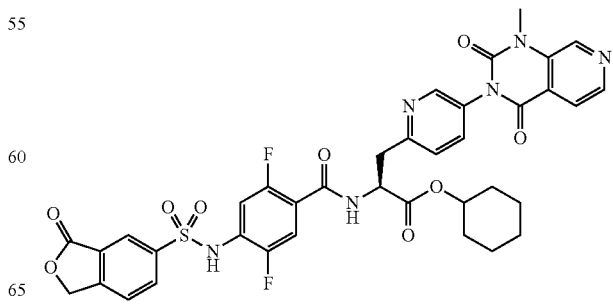

¹H NMR (400 MHz, DMSO-d₆): δ 11.03 (s, 1H), 9.00 (s, 1H), 8.86 (dd, J=7.5, 3.3 Hz, 1H), 8.58 (d, J=5.0 Hz, 1H), 8.45 (d, J=2.4 Hz, 1H), 8.25-8.15 (m, 2H), 7.94-7.87 (m, 2H), 7.73 (dd, J=8.2, 2.5 Hz, 1H), 7.46 (d, J=8.3 Hz, 1H), 7.37 (dd, J=10.3, 6.2 Hz, 1H), 7.28 (dd, J=11.1, 6.2 Hz, 1H), 5.50 (s, 2H), 4.97-4.86 (m, 1H), 4.73-4.63 (m, 1H), 3.62 (s, 3H), 3.39-3.24 (m, 2H), 1.76-1.53 (m, 4H), 1.47-1.14 (m, 6H).; MS (ESI) m/z 775.37 (M+H)⁺

Example 234

Synthesis of A-113 and Synthesis of B-113

(Step 1) N-[2,5-Difluoro-4-({[4-(4-methyl-1H-1,2,3-triazol-1-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alanine (A-113)

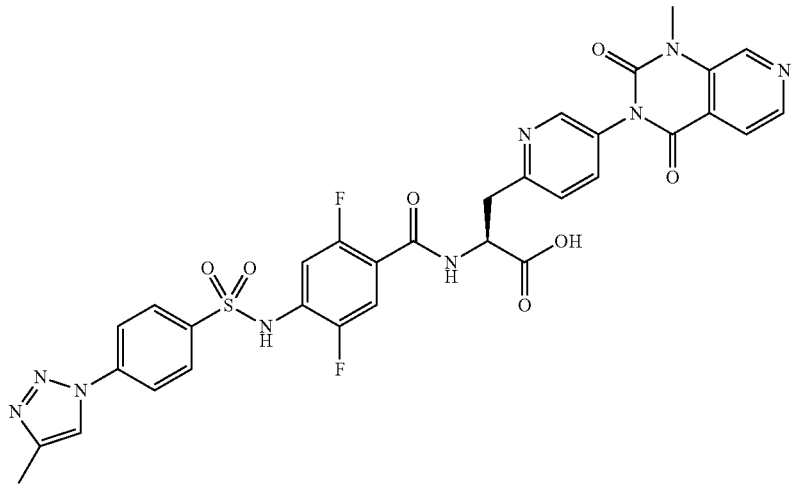 [SMILES: Cc1cn(-c2ccc(S(=O)(=O)Nc3cc(F)c(C(=O)N[C@@H](Cc4ccc(-n5c(=O)c6ccncc6n(C)c5=O)cn4)C(=O)O)cc3F)cc2)nn1]

¹H NMR (400 MHz, DMSO-d₆) δ 10.94 (s, 1H), 9.00 (s, 1H), 8.73 (dd, J=7.8, 3.7 Hz, 1H), 8.64 (d, J=1.1 Hz, 1H), 8.57 (d, J=4.9 Hz, 1H), 8.46 (d, J=2.4 Hz, 1H), 8.14-8.07 (m, 2H), 8.05-7.97 (m, 2H), 7.90 (d, J=5.0 Hz, 1H), 7.73 (dd, J=8.2, 2.5 Hz, 1H), 7.45 (d, J=8.2 Hz, 1H), 7.37 (dd, J=10.3, 6.3 Hz, 1H), 7.27 (dd, J=11.2, 6.2 Hz, 1H), 4.89 (td, J=8.2, 4.9 Hz, 1H), 3.61 (s, 3H), 3.41-3.22 (m, 2H), 2.32 (s, 3H).; MS (ESI) m/z 718.30 (M+H)⁺

(Step 2) Cyclohexyl N-[2,5-Difluoro-4-({[4-(4-methyl-1H-1,2,3-triazol-1-yl)phenyl]sulfonyl}amino)benzoyl]-3-[5-(1-methyl-2,4-dioxo-1,4-dihydropyrido[3,4-d]pyrimidin-3(2H)-yl)pyridin-2-yl]-L-alaninate (B-113)

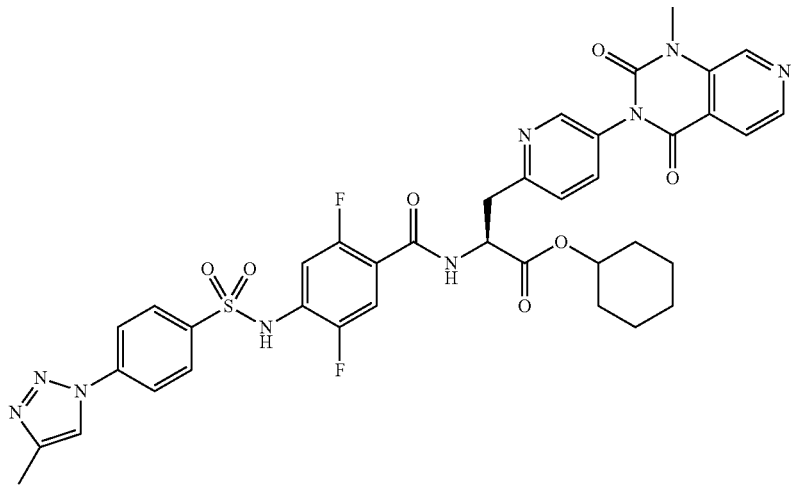 [SMILES: Cc1cn(-c2ccc(S(=O)(=O)Nc3cc(F)c(C(=O)N[C@@H](Cc4ccc(-n5c(=O)c6ccncc6n(C)c5=O)cn4)C(=O)OC4CCCCC4)cc3F)cc2)nn1]

¹H NMR (400 MHz, DMSO-d₆): δ 10.96 (s, 1H), 9.00 (s, 1H), 8.85 (dd, J=7.7, 3.3 Hz, 1H), 8.65 (d, J=1.1 Hz, 1H), 8.57 (d, J=4.9 Hz, 1H), 8.45 (d, J=2.4 Hz, 1H), 8.15-8.07 (m, 2H), 8.06-7.98 (m, 2H), 7.90 (d, J=4.9 Hz, 1H), 7.73 (dd, J=8.2, 2.5 Hz, 1H), 7.46 (d, J=8.2 Hz, 1H), 7.37 (dd, J=10.2, 6.3 Hz, 1H), 7.27 (dd, J=11.1, 6.2 Hz, 1H), 4.97-4.87 (m, 1H), 4.73-4.64 (m, 1H), 3.61 (s, 3H), 3.39-3.24 (m, 2H), 2.33 (s, 3H), 1.76-1.52 (m, 4H), 1.47-1.18 (m, 6H).; MS (ESI) m/z 800.27 (M+H)⁺

Example 235

Synthesis of A-114

(Step 1) N-(4-{[(3',5'-Difluorobiphenyl-4-yl)sulfonyl]amino}-2,5-difluorobenzoyl)-3-[5-(1-methyl-2,4-dioxo-1,4-dihydropyrido[3,4-d]pyrimidin-3(2H)-yl)pyridin-2-yl]-L-alanine (A-114)

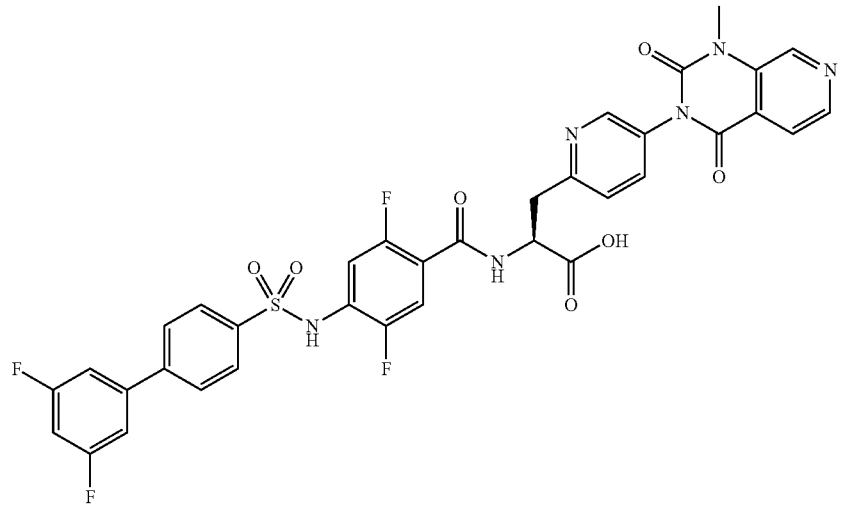 [SMILES: Cn1c(=O)n(-c2ccc(C[C@H](NC(=O)c3cc(F)c(NS(=O)(=O)c4ccc(-c5cc(F)cc(F)c5)cc4)cc3F)C(=O)O)nc2)c(=O)c2ccncc21]

¹H NMR (400 MHz, DMSO-d₆): δ 11.00 (s, 1H), 8.97 (s, 1H), 8.75 (dd, J=7.9, 3.8 Hz, 1H), 8.57 (d, J=5.0 Hz, 1H), 8.48 (d, J=2.3 Hz, 1H), 8.00-7.94 (m, 2H), 7.94-7.87 (m, 3H), 7.77 (dd, J=8.3, 2.4 Hz, 1H), 7.66-7.45 (m, 3H), 7.37 (dd, J=10.3, 6.3 Hz, 1H), 7.33-7.21 (m, 2H), 4.94-4.84 (m, 1H), 3.60 (s, 3H), 3.43-3.23 (m, 2H).; MS (ESI) m/z 749.42 (M+H)⁺

Example 236

Synthesis of A-115 and Synthesis of B-115

(Step 1) N-[4-({[5-(2-Ethylpyrimidin-5-yl)pyridin-2-yl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alanine (A-115)

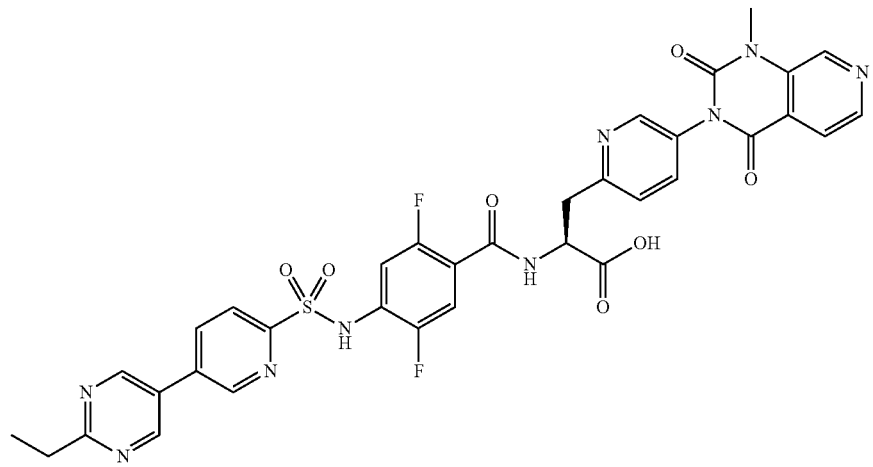

$^1$H NMR (400 MHz, DMSO-d$_6$): δ 11.12 (s, 1H), 9.22-9.14 (m, 3H), 9.00 (s, 1H), 8.74 (dd, J=7.8, 4.0 Hz, 1H), 8.57 (d, J=5.0 Hz, 1H), 8.52 (dd, J=8.3, 2.3 Hz, 1H), 8.46 (d, J=2.4 Hz, 1H), 8.15 (d, J=8.2 Hz, 1H), 7.90 (d, J=4.9 Hz, 1H), 7.73 (dd, J=8.2, 2.5 Hz, 1H), 7.49-7.35 (m, 3H), 4.95-4.84 (m, 1H), 3.61 (s, 3H), 3.41-3.23 (m, 2H), 2.96 (q, J=7.6 Hz, 2H), 1.31 (t, J=7.6 Hz, 3H).; MS (ESI) m/z 744.38 (M+H)$^+$ (Step 2) Cyclohexyl N-[4-({[5-(2-Ethylpyrimidin-5-yl)pyridin-2-yl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alaninate (B-115)

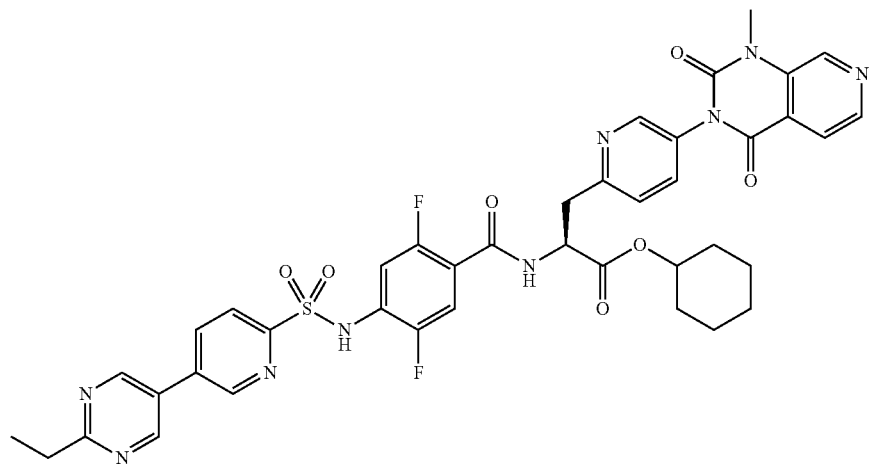

$^1$H NMR (400 MHz, DMSO-d$_6$): δ 11.12 (s, 1H), 9.22-9.14 (m, 3H), 9.00 (s, 1H), 8.74 (dd, J=7.8, 4.0 Hz, 1H), 8.57 (d, J=5.0 Hz, 1H), 8.52 (dd, J=8.3, 2.3 Hz, 1H), 8.46 (d, J=2.4 Hz, 1H), 8.15 (d, J=8.2 Hz, 1H), 7.90 (d, J=4.9 Hz, 1H), 7.73 (dd, J=8.2, 2.5 Hz, 1H), 7.49-7.35 (m, 3H), 4.95-4.84 (m, 1H), 3.61 (s, 3H), 3.41-3.23 (m, 2H), 2.96 (q, J=7.6 Hz, 2H), 1.31 (t, J=7.6 Hz, 3H).; MS (ESI) m/z 826.31 (M+H)$^+$

Example 237

Synthesis of A-116 and Synthesis of B-116

(Step 1) N-[4-({[4-(2-Ethylpyrimidin-5-yl)phenyl]sulfonyl}amino)-2,5-difluorobenzoyl]-4-(1-methyl-2,4-dioxo-1,4-dihydropyrido[3,4-d]pyrimidin-3(2H)-yl)-L-phenylalanine (A-116)

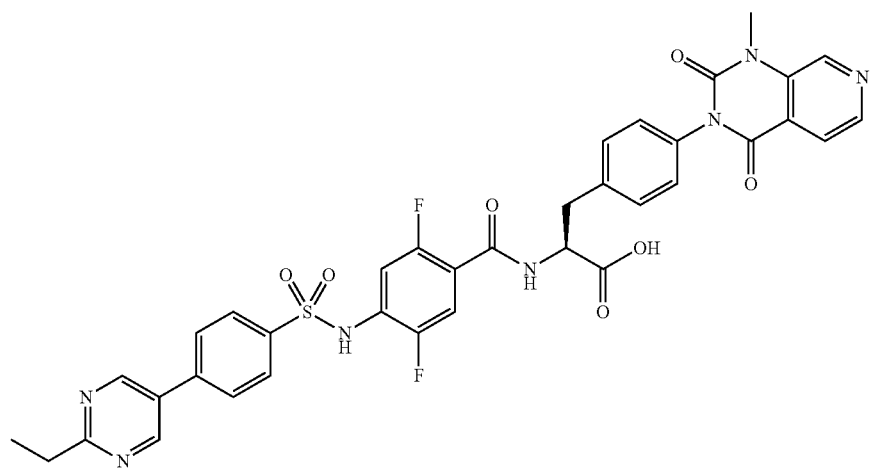

$^1$H NMR (400 MHz, DMSO-d$_6$): δ 10.95 (s, 1H), 9.10 (s, 2H), 8.96 (s, 1H), 8.60 (dd, J=7.9, 2.6 Hz, 1H), 8.54 (d, J=4.9 Hz, 1H), 8.06-7.98 (m, 2H), 7.98-7.92 (m, 2H), 7.87 (d, J=4.9 Hz, 1H), 7.40-7.17 (m, 6H), 4.62 (ddd, J=9.8, 7.8, 4.6 Hz, 1H), 3.59 (s, 3H), 3.22 (dd, J=13.9, 4.4 Hz, 1H), 3.06 (dd, J=14.0, 9.9 Hz, 1H), 2.95 (q, J=7.5 Hz, 2H), 1.30 (t, J=7.6 Hz, 3H).; MS (ESI) m/z 742.21 (M+H)$^+$ (Step 2) Cyclohexyl N-[4-({[4-(2-Ethylpyrimidin-5-yl)phenyl]sulfonyl}amino)-2,5-difluorobenzoyl]-4-(1-methyl-2,4-dioxo-1,4-dihydropyrido[3,4-d]pyrimidin-3(2H)-yl)-L-phenylalaninate (B-116)

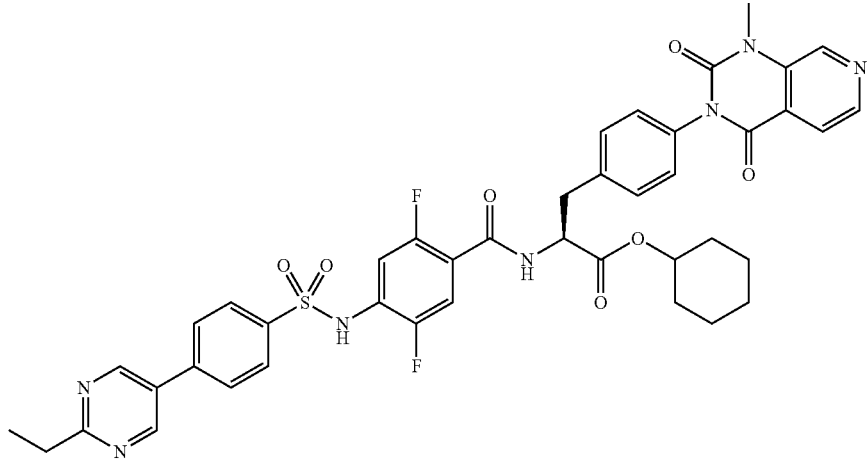

$^1$H NMR (400 MHz, DMSO-d$_6$): δ 10.97 (s, 1H), 9.10 (s, 2H), 8.96 (s, 1H), 8.76 (dd, J=7.3, 2.0 Hz, 1H), 8.54 (d, J=4.9 Hz, 1H), 8.06-7.99 (m, 2H), 7.99-7.93 (m, 2H), 7.88 (d, J=4.9 Hz, 1H), 7.40-7.34 (m, 2H), 7.34-7.24 (m, 2H), 7.24-7.18 (m, 2H), 4.74-4.57 (m, 2H), 3.59 (s, 3H), 3.22-3.04 (m, 2H), 2.95 (q, J=7.6 Hz, 2H), 1.79-1.56 (m, 4H), 1.48-1.19 (m, 9H).; MS (ESI) m/z 824.59 (M+H)$^+$

Example 238

Synthesis of A-117 and Synthesis of B-117

(Step 1) N-[4-({[4-(2-Ethylpyrimidin-5-yl)phenyl]sulfonyl}amino)-2,5-difluorobenzoyl]-3-[6-(1-methyl-2,4-dioxo-1,4-dihydropyrido[3,4-d]pyrimidin-3(2H)-yl)pyridin-3-yl]-L-alanine (A-117)

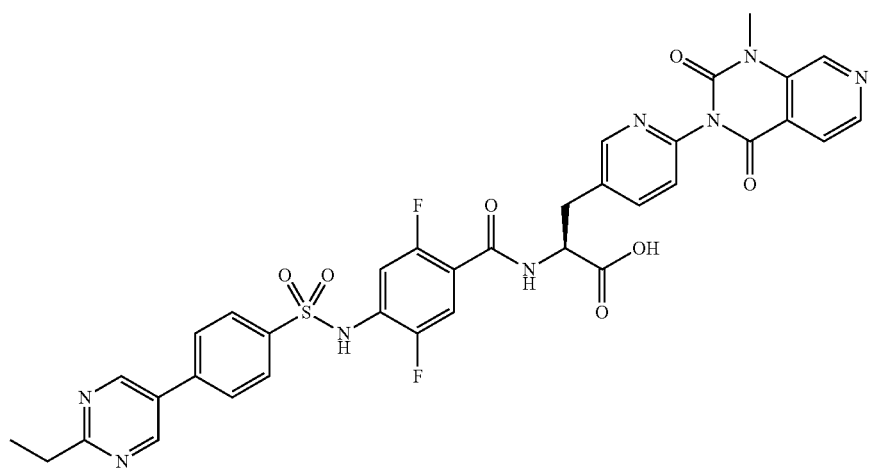

$^1$H NMR (400 MHz, DMSO-d$_6$): δ 10.95 (s, 1H), 9.10 (s, 2H), 8.99 (s, 1H), 8.69 (dd, J=8.0, 2.3 Hz, 1H), 8.56 (d, J=5.0 Hz, 1H), 8.46 (d, J=2.3 Hz, 1H), 8.05-7.99 (m, 2H), 7.99-7.92 (m, 2H), 7.92-7.85 (m, 2H), 7.40 (d, J=8.0 Hz, 1H), 7.33-7.22 (m, 2H), 4.74-4.63 (m, 1H), 3.59 (s, 3H), 3.29 (dd, J=14.2, 4.6 Hz, 1H), 3.09 (dd, J=14.1, 10.2 Hz, 1H), 2.94 (q, J=7.6 Hz, 2H), 1.30 (t, J=7.6 Hz, 3H).; MS (ESI) m/z 743.20 (M+H)$^+$ (Step 2) Cyclohexyl N-[4-({[4-(2-Ethylpyrimidin-5-yl)phenyl]sulfonyl}amino)-2,5-difluorobenzoyl]-3-[6-(1-methyl-2,4-dioxo-1,4-dihydropyrido[3,4-d]pyrimidin-3(2H)-yl)pyridin-3-yl]-L-alaninate (B-117)

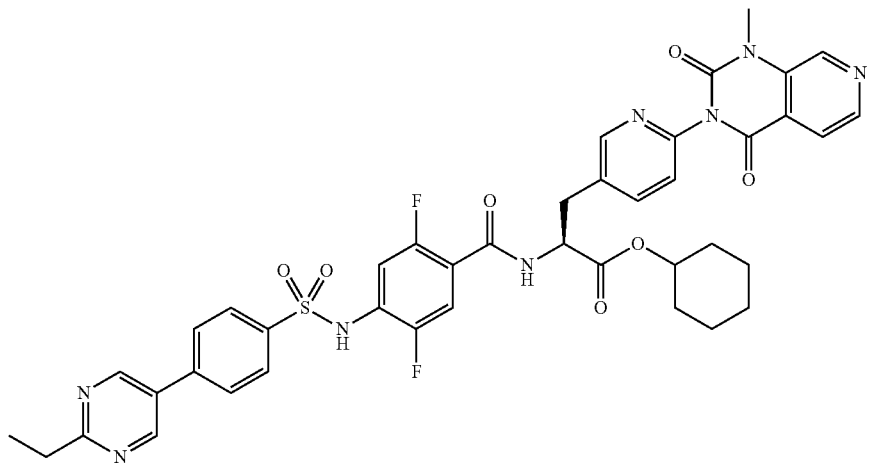

$^1$H NMR (400 MHz, DMSO-d$_6$): δ 10.97 (s, 1H), 9.10 (s, 2H), 8.99 (s, 1H), 8.84 (dd, J=7.7, 1.8 Hz, 1H), 8.56 (d, J=4.9 Hz, 1H), 8.46 (d, J=2.3 Hz, 1H), 8.06-7.99 (m, 2H), 7.99-7.94 (m, 2H), 7.92 (dd, J=8.2, 2.4 Hz, 1H), 7.89 (d, J=4.9 Hz, 1H), 7.40 (d, J=8.1 Hz, 1H), 7.32-7.23 (m, 2H), 4.75-4.66 (m, 2H), 3.59 (s, 3H), 3.29-3.19 (m, 1H), 3.18-3.07 (m, 1H), 2.94 (q, J=7.6 Hz, 2H), 1.85-1.54 (m, 4H), 1.48-1.21 (m, 9H).; MS (ESI) m/z 825.32 (M+H)$^+$

Example 239

Synthesis of A-118 and Synthesis of B-118

(Step 1) N-[4-({[4-(2-Cyclopropylpyrimidin-5-yl)phenyl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alanine (A-118)

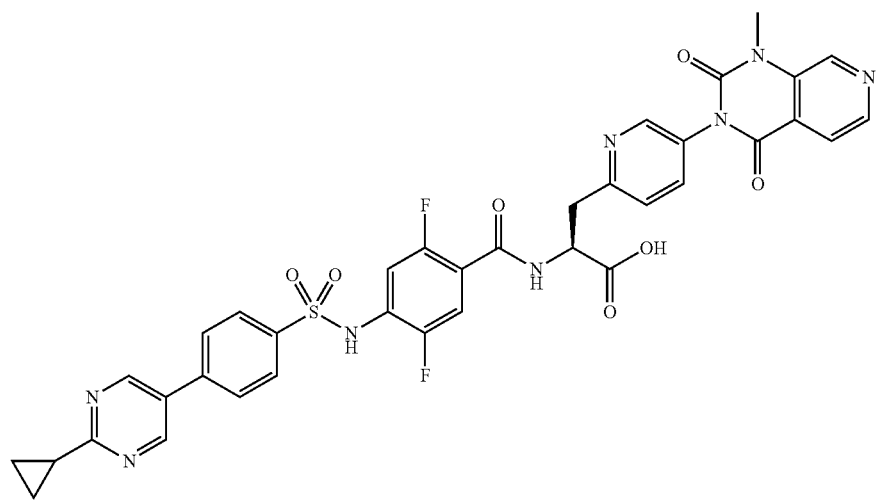 [SMILES: Cn1c(=O)n(-c2ccc(C[C@H](NC(=O)c3cc(F)c(NS(=O)(=O)c4ccc(-c5cnc(C6CC6)nc5)cc4)cc3F)C(=O)O)nc2)c(=O)c2ccncc21]

¹H NMR (400 MHz, DMSO-d₆): δ 10.96 (s, 1H), 9.03-8.97 (m, 3H), 8.73 (dd, J=7.7, 3.8 Hz, 1H), 8.57 (d, J=4.9 Hz, 1H), 8.49-8.43 (m, 1H), 8.02-7.87 (m, 5H), 7.74 (dd, J=8.2, 2.5 Hz, 1H), 7.46 (d, J=8.3 Hz, 1H), 7.37 (dd, J=10.4, 6.4 Hz, 1H), 7.27 (dd, J=11.4, 6.3 Hz, 1H), 4.94-4.83 (m, 1H), 3.61 (s, 3H), 3.41-3.22 (m, 2H), 2.31-2.20 (m, 1H), 1.15-1.00 (m, 4H).; MS (ESI) m/z 755.62 (M+H)⁺

(Step 2) Cyclohexyl N-[4-({[4-(2-Cyclopropylpyrimidin-5-yl)phenyl]sulfonyl}amino)-2,5-difluorobenzoyl]-3-[5-(1-methyl-2,4-dioxo-1,4-dihydropyrido[3,4-d]pyrimidin-3(2H)-yl)pyridin-2-yl]-L-alaninate (B-118)

stirring at room temperature for 24 hours, the liquid was made basic with 10% aqueous sodium hydroxide solution. The mixture was stirred for 15 minutes, and then filtered through Celite. The organic layer was washed with water, followed by extraction with 10% hydrochloric acid three times. The collected acidic solutions were cooled and made basic with a 20% aqueous sodium hydroxide solution, followed by extraction with dichloromethane (100 ml) three times. The organic layer was washed with saturated aqueous sodium chloride and then dried over magnesium sulfate, and the solvent was removed by distillation. Purification was conducted by silica gel column chromatography (petroleum ether:ethyl acetate=5:1 to 2:1) to obtain the title compound (1.8 g, 21%).

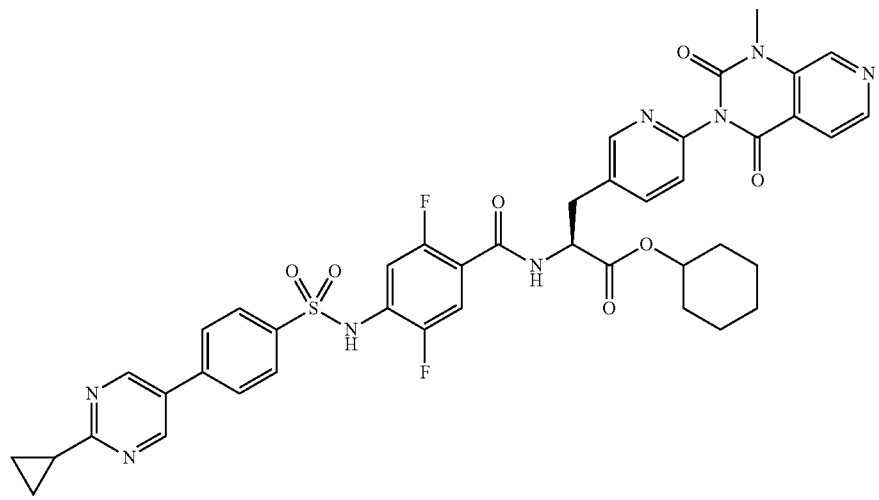 [SMILES: Cn1c(=O)n(-c2ccc(C[C@H](NC(=O)c3cc(F)c(NS(=O)(=O)c4ccc(-c5cnc(C6CC6)nc5)cc4)cc3F)C(=O)OC3CCCCC3)cn2)c(=O)c2ccncc21]

¹H NMR (400 MHz, DMSO-d₆): δ 10.97 (s, 1H), 9.03-8.97 (m, 3H), 8.85 (dd, J=7.6, 3.4 Hz, 1H), 8.57 (d, J=4.9 Hz, 1H), 8.48-8.42 (m, 1H), 8.03-7.87 (m, 5H), 7.72 (dd, J=8.2, 2.5 Hz, 1H), 7.45 (d, J=8.3 Hz, 1H), 7.38 (dd, J=10.3, 6.3 Hz, 1H), 7.28 (dd, J=11.3, 6.3 Hz, 1H), 4.96-4.86 (m, 1H), 4.73-4.62 (m, 1H), 3.61 (s, 3H), 3.38-3.23 (m, 2H), 2.30-2.20 (m, 1H), 1.75-1.51 (m, 4H), 1.47-1.18 (m, 6H), 1.15-1.00 (m, 4H).; MS (ESI) m/z 837.55 (M+H)⁺

Example 240

Synthesis of M-104

(Step 1) 4-Bromo-2-isopropylpyridine

4-Bromopyridine (8.40 g, 43.4 mmol) was dissolved in THF (200 ml), followed by cooling to −78° C. To this solution, a 3 M solution of isopropylmagnesium bromide (2.2 eq) in diethyl ether was added at once. Subsequently, phenyl chloroformate (5.61 ml, 43.4 mmol) was rapidly added dropwise. After stirring at −78° C. for 10 minutes, the mixture was stirred at room temperature, and quenched with a 20% aqueous ammonium chloride solution (120 ml). Ether (150 ml) was added, and the organic layer was washed with water (150 ml), 10% hydrochloric acid, and saturated aqueous sodium chloride. After dying over magnesium sulfate, the solvent was removed by distillation, and anhydrous toluene (200 ml) was added thereto. To this solution, a glacial acetic acid solution (120 ml) containing o-chloranil (11.8 mg, 47.9 mmol) was added at room temperature. After ¹H NMR (CDCl₃, 400 MHz): δ 8.35 (d, J=5.2 Hz, 1H), 7.35 (d, J=4.0 Hz, 1H), 7.28 (dd, J=5.2, 1.6 Hz, 1H), 3.07-3.00 (m, 1H), 1.31 (d, J=6.8 Hz, 6H).

(Step 2) Methyl 2,5-Difluoro-4-[[5-(2 isopropyl-4-pyridyl)-2-pyridyl]sulfonylamino]benzoate

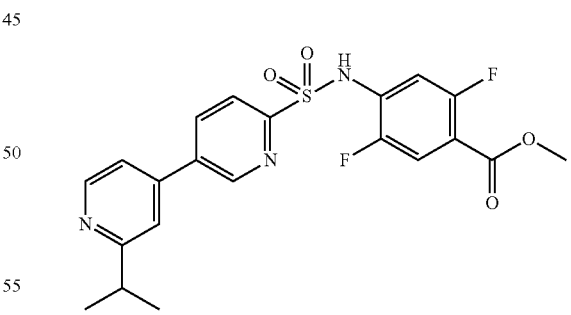

The compound obtained in (Step 1) of Example 198 (2.1 g, 5.6 mmol), the compound obtained in Step 1 above (1.34 g, 6.70 mmol), sodium carbonate (2.40 g, 22.0 mmol), and Pd(dppf)Cl₂ (170 mg, 0.230 mmol) were dissolved in DMF (50 ml) and water (5.0 ml), and the solution was degassed with nitrogen three times, followed by stirring at 90° C. overnight. The reaction liquid was diluted with water, followed by extraction with ethyl acetate several times. The organic layers were combined, washed with saturated aqueous sodium chloride, and dried over sodium sulfate. The solvent was removed by distillation, and then purification was conducted by silica gel column chromatography (petroleum ether:ethyl acetate=1:2 to 1:10) to obtain the title compound (1.74 g, 69%).

MS (ESI) m/z 448 (M+H)+

(Step 3) 2,5-Difluoro-4-[[5-(2-isopropyl-4-pyridyl)-2-pyridyl]sulfonylamino]benzoic Acid (M-104)

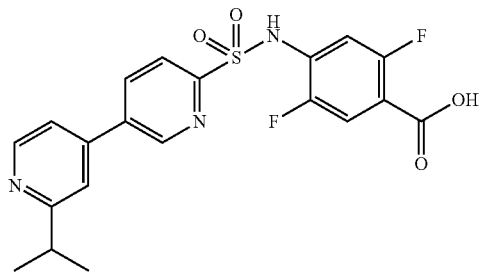 [SMILES: CC(C)c1cc(-c2ccc(S(=O)(=O)Nc3cc(F)c(C(=O)O)cc3F)nc2)ccn1]

The compound obtained in Step 2 (1.7 g, 3.8 mmol) was dissolved in methanol (10 ml), and lithium hydroxide (2 N, 10 ml) was added thereto. After stirring at room temperature for 30 minutes, the completion of the reaction was confirmed by TLC. Then, the pH was adjusted to 4 to 5 by adding 4 N hydrochloric acid. The precipitated white solid was filtered and dried to obtain the title compound (1.4 g, 85%) as a white solid.

$^1$H NMR (CD$_3$OD, 400 MHz): δ 9.02 (d, J=2.0 Hz, 1H), 8.55 (d, J=5.2 Hz, 1H), 8.40 (dd, J=8.4, 2.0 Hz, 1H), 8.18 (d, J=8.4 Hz, 1H), 7.68 (s, 1H), 7.61-7.56 (m, 3H), 3.18-3.11 (m, 1H), 1.33 (d, J=6.8 Hz, 6H).; MS (ESI) m/z 434 (M+H)+

Example 241

Synthesis of M-105

(Step 1) Methyl 4-[[4-(4-Ethyltriazol-1-yl)phenyl]sulfonylamino]-2,5-difluoro-benzoate

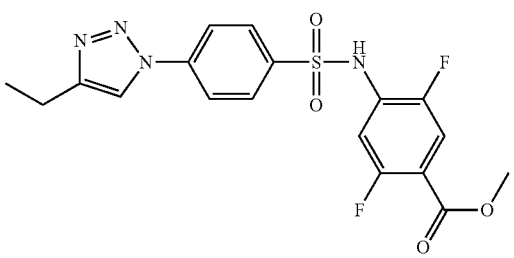 [SMILES: CCc1cn(-c2ccc(S(=O)(=O)Nc3cc(F)c(C(=O)OC)cc3F)cc2)nn1]

To a 1 L vial, L-proline (1.6 g, 20 mol %, 14 mmol), CuSO$_4$.5H$_2$O (1.7 g, 10 mol %, 6.8 mmol), sodium ascorbate (2.7 g, 20 mol %, 14 mmol), sodium azide (6.50 g, 100 mmol), potassium carbonate (11.4 g, 82.6 mmol), methyl 2-pentynoate (6.76 g, 69 mmol), the compound obtained in (Step 1) of Example 197 (31.2 g, 69 mmol), DMSO (225 ml), and water (25 ml) were sequentially added. After gently stirring at 65° C. overnight, a mixture of concentrated ammonia water (500 ml), water (1.0 L), and ethyl acetate (400 ml) was added thereto. Extraction from the water phase was conducted with ethyl acetate (600 ml×10), and the organic layer was washed with saturated aqueous sodium chloride (3.0 L), dried over sodium sulfate, and filtered. The solvent was removed by distillation under reduced pressure to obtain the title compound (14.2 g, 49%).

$^1$H NMR (CD$_3$OD, 400 MHz): δ 8.37 (s, 1H), 8.13-8.06 (m, 2H), 8.10-7.96 (m, 2H), 7.45-7.04 (m, 2H), 3.27 (s, 3H), 1.72-1.64 (m, 2H), 1.04-1.02 (m, 3H).

(Step 2) 4-[[4-(4-Ethyltriazol-1-yl)phenyl]sulfonylamino]-2,5-difluorobenzoic Acid (M-105)

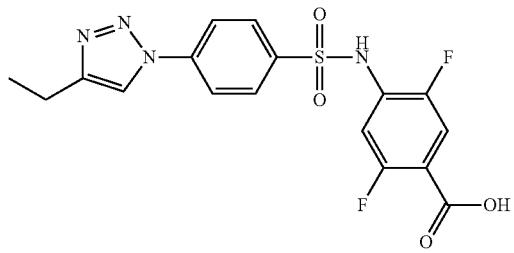 [SMILES: CCc1cn(-c2ccc(S(=O)(=O)Nc3cc(F)c(C(=O)O)cc3F)cc2)nn1]

The compound obtained in Step 1 (14.1 g, 33.4 mmol) was dissolved in methanol (60 ml), and lithium hydroxide (2 N, 30 ml) was added thereto, followed by stirring at room temperature for 30 minutes. Then, the completion of the reaction was confirmed, and then the pH was adjusted to 4 to 5 by adding 4 N hydrochloric acid. The precipitated white solid was filtered, and the obtained solid was dried to obtain the title compound as a white solid.

$^1$H NMR (DMSO-d$_6$, 400 MHz): δ 13.41 (br s, 1H), 11.10 (br s, 1H), 8.70 (s, 1H), 8.13 (d, J=8.8 Hz, 2H), 8.04 (d, J=8.8 Hz, 2H), 7.63-7.59 (m, 1H), 7.30-7.25 (m, 1H), 2.73 (q, J=7.2 Hz, 2H), 1.26 (t, J=7.2 Hz, 3H).; MS (ESI) m/z 409 (M+H)+

Example 242

Synthesis of M-106

(Step 1) Methyl 3-Cyclopropylpropynoate

A n-butyllithium hexane solution (2.5 mol/L, 30.3 ml, 75.7 mmol) was slowly added to a THF solution (50 ml) of ethynylcyclopropane (5.00 g, 75.7 mmol) at −78° C. One hour later, methyl chloroformate (17.7 g, 189 mmol) was added thereto at −78° C. The temperature of the mixture was gently raised to room temperature, and the mixture was poured into an aqueous ammonium chloride solution. After extraction with dichloromethane (50 ml×3), the extraction liquid was dried over sodium sulfate, and the residue was purified by silica gel column chromatography (petroleum ether:ethyl acetate=30:1 to 10:1) to obtain the title compound (6.1 g, 65%).

1H NMR (CDCl₃, 400 MHz): δ 3.74 (s, 3H), 1.41-1.35 (m, 1H), 0.98-0.90 (m, 4H).

(Step 2) 3-Cyclopropylpropynoic Acid

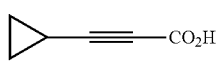

The compound obtained in Step 1 (6.10 g, 49.2 mmol) was dissolved in methanol (90 ml), and lithium hydroxide (2 N, 30 ml) was added thereto. After stirring at room temperature for 30 minutes, the completion of the reaction was confirmed by TLC. Then, the pH was adjusted to 4 to 5 by adding 4 N hydrochloric acid. The precipitated white solid was filtered and dried to obtain the title compound (4.87 g, 90%) as a white solid.

1H NMR (CDCl₃, 400 MHz): δ 1.42-1.37 (m, 1H), 0.99-0.95 (m, 4H).

(Step 3) Methyl 4-[[5-(4-Cyclopropyltriazol-1-yl)-2-pyridyl]sulfonylamino]-2,5-difluorobenzoate

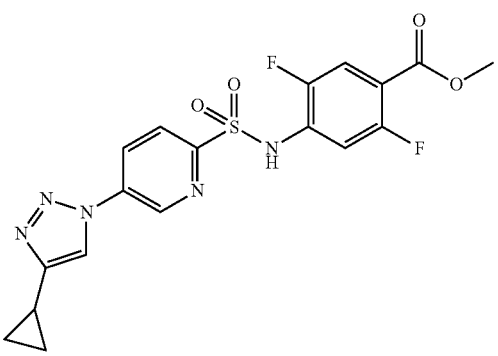 [SMILES: COC(=O)c1cc(F)c(NS(=O)(=O)c2ccc(-n3cc(C4CC4)nn3)cn2)cc1F]

L-Proline (101 mg, 20 mol %, 0.88 mmol), CuSO₄.5H₂O (110 mg, 10 mol %, 0.44 mmol), sodium ascorbate (174 mg, 20 mol %, 0.88 mmol), sodium azide (429 mg, 1.5 eq, 6.6 mmol), potassium carbonate (729 mg, 1.20 eq, 5.28 mmol), methyl 2,5-difluoro-4-[(5-iodo-2-pyridyl)sulfonylamino]benzoate (2.0 g, 4.4 mmol) obtained in (Step 1) of Example 193, 3-cyclopropylpropynoic acid (484 mg, 4.40 mmol) obtained in Step 2, DMSO (25 ml), and water (3.0 ml) were sequentially added to a 100 ml vial. The mixture was gently stirred at 65° C. overnight, and then a mixture of concentrated ammonia water (50 ml), water (100 ml), and ethyl acetate (50 ml) was added thereto. Extraction was conducted from the aqueous layer with ethyl acetate (60 ml×10), and the organic layer was washed with saturated aqueous sodium chloride (300 ml), dried over sodium sulfate, filtered, and concentrated under reduced pressure. Purification was conducted by using preparative HPLC to obtain the title compound (590 mg, 31%).

H NMR (CD₃OD, 400 MHz): δ 9.21 (d, J=2.0 Hz, 1H), 8.56-8.54 (m, 1H), 8.46 (s, 1H), 8.30 (d, J=8.8 Hz, 1H), 7.67-7.61 (m, 2H), 3.89 (s, 3H), 2.10-2.08 (m, 1H), 1.09-1.05 (m, 2H), 0.93-0.90 (m, 2H).

(Step 4) 4-[[5-(4-Cyclopropyltriazol-1-yl)-2-pyridyl]sulfonylamino-2,5-difluorobenzoic Acid (M-106)

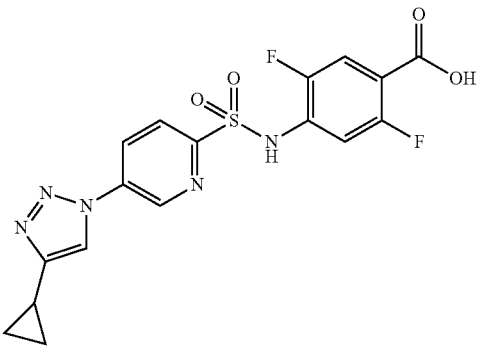 [SMILES: O=C(O)c1cc(F)c(NS(=O)(=O)c2ccc(-n3cc(C4CC4)nn3)cn2)cc1F]

The compound obtained in Step 2 (590 mg, 1.35 mmol) was dissolved in methanol (15 ml), and an aqueous sodium hydroxide solution (4 N, 3.0 ml) was added thereto. After stirring at room temperature overnight, the mixture was concentrated, and the pH was adjusted to 4 to 5 by adding 2 N hydrochloric acid. The precipitated white solid was filtered to obtain the title compound (519 mg, 91%).

H NMR (CD₃OD, 400 MHz): δ 9.21 (d, J=2.4 Hz, 1H), 8.56 (dd, J=8.8, 2.4 Hz, 1H), 8.46 (s, 1H), 8.30 (d, J=8.8 Hz, 1H), 7.66-7.59 (m, 2H), 2.11-2.06 (m, 1H), 1.09-1.05 (m, 2H), 0.92-0.90 (m, 2H).; MS (ESI) m/z 422 (M+H)⁺

Example 243

Synthesis of M-107

(Step 1) Methyl 4-[[4-(4-Cyclopropyltriazol-1-yl)phenyl]sulfonylamino]-2,5-difluorobenzoate

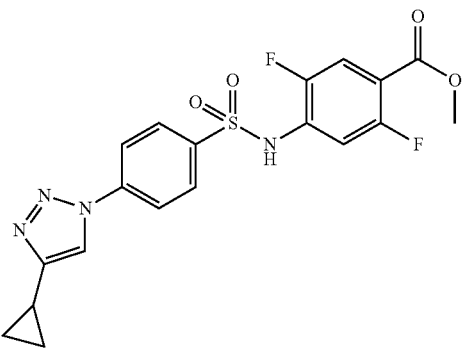 [SMILES: COC(=O)c1cc(F)c(NS(=O)(=O)c2ccc(-n3cc(C4CC4)nn3)cc2)cc1F]

L-Proline (160 mg, 20 mol %, 1.4 mmol), CuSO₄.5H₂O (170 mg, 10 mol %, 0.68 mmol), sodium ascorbate (270 mg, 20 mol %, 1.4 mmol), sodium azide (650 mg, 1.5 eq, 10 mmol), potassium carbonate (1.14 g, 1.20 eq, 8.26 mmol), 3-cyclopropylpropynoic acid (759 mg, 6.90 mmol) obtained in (Step 2) of Example 242, methyl 2,5-difluoro-4-[(4-iodophenyl)sulfonylamino]benzoate (3.12 g, 6.90 mmol), which was the compound obtained in (Step 1) of Example 197, DMSO (25 ml), and water (3.0 ml) were sequentially added to a 250 ml vial. After gentle stirring at 65° C. overnight, concentrated ammonia water (50 ml), water (100 ml), and ethyl acetate (50 ml) were added. After extraction from the aqueous layer with ethyl acetate (60 ml×10), the organic layer was washed with saturated aqueous sodium chloride (300 ml), dried over sodium sulfate, filtered, and concentrated under reduced pressure to obtain the title compound (2.12 g, 71%).

1H NMR (CD₃OD, 400 MHz): δ 8.33 (s, 1H), 8.09 (d, J=8.4 Hz, 2H), 7.96 (d, J=4.8 Hz, 2H), 7.45-7.41 (m, 1H), 7.11-7.06 (m, 1H), 3.82 (s, 3H), 2.08-2.05 (m, 1H), 1.07-1.02 (m, 2H), 0.91-0.87 (m, 2H).

(Step 2) 4-[[4-(4-Cyclopropyltriazol-1-yl)phenyl]sulfonylamino]-2,5-difluoro-benzoic Acid (M-107)

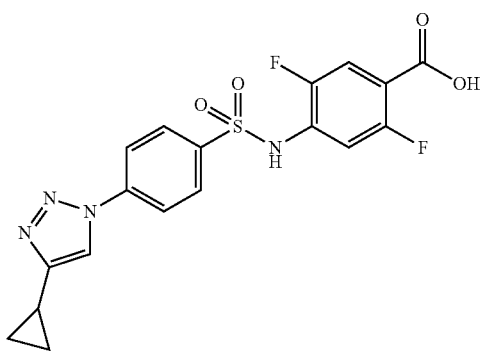 [SMILES: O=C(O)c1cc(F)c(NS(=O)(=O)c2ccc(-n3cc(C4CC4)nn3)cc2)cc1F]

The compound obtained in Step 1 (851 mg, 1.96 mmol) was dissolved in methanol (10 ml), and lithium hydroxide (2 N, 3.0 ml) was added thereto. After stirring at room temperature for 30 minutes, the completion of the reaction was confirmed by TLC. Then, the pH was adjusted to 4 to 5 by adding 4 N hydrochloric acid. The precipitated white solid was filtered and dried to obtain the title compound (750 mg, 91%) as a white solid.

1H NMR (CD₃OD, 400 MHz): δ 8.38 (s, 1H), 8.10-8.05 (m, 4H), 7.63-7.59 (m, 1H), 7.49-7.44 (m, 1H), 2.10-2.03 (m, 1H), 1.08-1.03 (m, 2H), 0.91-0.87 (m, 2H).; MS (ESI) m/z 421 (M+H)⁺

Example 244

Synthesis of M-108

(Step 1) 5-Bromo-2-(3,6-dihydro-2H-pyran-4-yl)pyrimidine

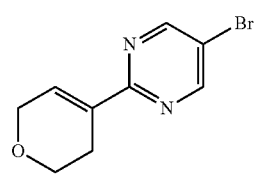 [SMILES: Brc1cnc(C2=CCOCC2)nc1]

5-Bromo-2-iodopyrimidine (5.87 g, 20.7 mmol), 2-(3,6-dihydro-2H-pyran-4-yl)-4,4,5,5-tetramethyl-1,3,2-dioxaborane (4.35 g, 20.7 mmol), potassium carbonate (5.70 g, 41.4 mmol), and Pd(dppf)Cl₂ (805 mg, 1.10 mmol) were suspended in DMF (50 ml) and water (10 ml), followed by stirring at 100° C. for 4 hours under a nitrogen atmosphere. The mixture was concentrated under reduced pressure, and the residue was purified by silica gel column chromatography (petroleum ether:ethyl acetate=5:1 to 1:1) to obtain the title compound (1.44 g, 29%).

¹H NMR (400 MHz, CDCl₃): δ 8.72 (s, 2H), 7.25 (s, 1H), 4.42-3.38 (m, 2H), 3.94-3.91 (m, 2H), 2.68-2.66 (m, 2H).

(Step 2) Methyl 4-[[4-[2-(3,6-Dihydro-2H-pyran-4-yl)pyrimidin-5-yl]phenyl]sulfonylamino]-2,5-difluorobenzoate

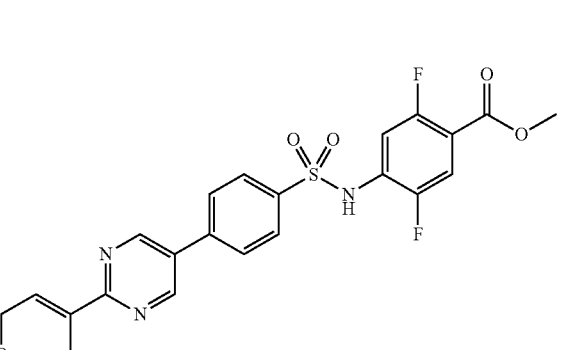

The compound obtained in Step 1 (1.44 g, 6.00 mmol), the compound obtained in (Step 1) of Example 189 (2.2 g, 6.0 mmol), sodium carbonate (1.27 g, 12.0 mmol), and Pd(dppf)Cl₂ (220 mg, 0.3 mmol) were suspended in dioxane (20 ml) and water (5.0 ml), followed by stirring at 100° C. for 8 hours. The mixture was concentrated under reduced pressure, and the residue was purified by silica gel column chromatography (petroleum ether:ethyl acetate=3:1 to 1:1) to obtain the title compound (1.2 g, 41%).

MS (ESI) m/z 488 (M+H)⁺

(Step 3) Methyl 2,5-Difluoro-4-[[4-(2-tetrahydropyran-4-ylpyrimidin-5-yl)phenyl]sulfonylamino]benzoate

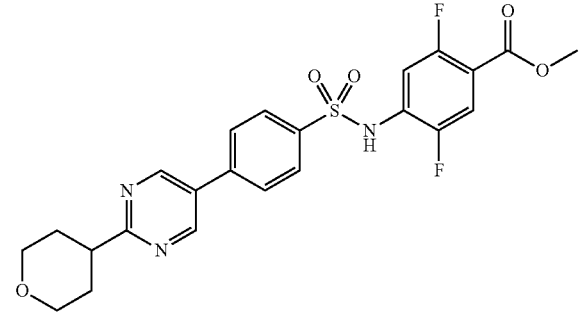 [SMILES: COC(=O)c1cc(F)c(NS(=O)(=O)c2ccc(-c3cnc(C4CCOCC4)nc3)cc2)cc1F]

The compound obtained in Step 2 (1.2 g, 2.46 mmol), Pd/C (10%, 500 mg), and methanol (10 ml) were added to a reaction vessel, followed by stirring at 50° C. for 24 hours in a hydrogen atmosphere of 50 psi. After cooling to room temperature, the mixture was filtered. The solvent was removed by distillation to obtain the title compound (843 mg, 70%).

MS (ESI) m/z 490 (M+H)⁺

(Step 4) 2,5-Difluoro-4-[[4-(2-tetrahydropyran-4-ylpyrimidin-5-yl)phenyl]sulfonylamino]benzoic Acid (M-108)

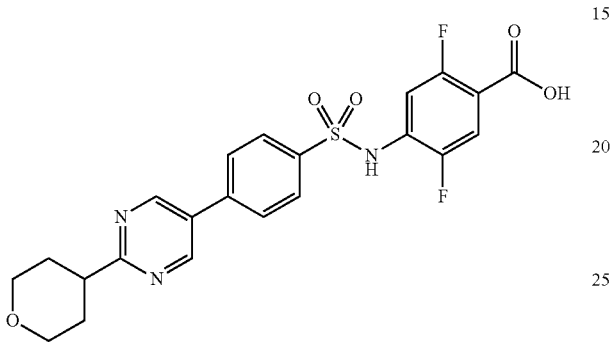

The compound obtained in Step 3 (600 mg, 1.22 mmol) was dissolved in methanol (10 ml), and aqueous lithium hydroxide solution (2 N, 3.0 ml) was added thereto. After stirring at room temperature for 2 hours, the completion of the reaction was confirmed by TLC. Then, the pH was adjusted to 4 to 5 by adding 4 N hydrochloric acid, and the precipitated white solid was filtered, dried, and washed with dichloromethane:methanol=10:1 to obtain the title compound (512 mg, 88%) as a white solid.

1H NMR (CD$_3$OD, 400 MHz): δ 9.07 (s, 2H), 8.06 (d, J=8.4 Hz, 2H), 7.93 (d, J=8.4 Hz, 2H), 7.63-7.59 (m, 1H), 7.50-7.45 (m, 1H), 4.10-4.07 (m, 2H), 3.66-3.59 (m, 2H), 3.25-3.19 (m, 1H), 2.04-1.94 (m, 4H).; MS (ESI) m/z 476 (M+H)⁺

Example 245

Synthesis of M-109

(Step 1) Chloromethyl Benzoate

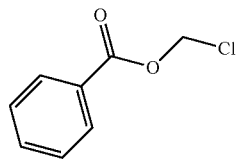 [SMILES: O=C(OCCl)c1ccccc1]

Paraformaldehyde (4.5 g) and zinc chloride (catalytic amount) were mixed with each other at 0° C. To this mixture, benzoyl chloride (20 g, 0.14 mol) was added dropwise over 1 hour. The temperature of the mixture was raised to room temperature, and then the mixture was stirred at 55° C. for 10 hours. After cooling, purification was conducted by silica gel column chromatography (petroleum ether:ethyl acetate=30:1 to 10:1) to obtain the title compound (9.7 g, 40%).

¹H NMR (CDCl$_3$, 400 MHz): δ 8.09-8.07 (m, 2H), 7.63-7.60 (m, 1H), 7.49-7.44 (m, 2H), 5.96 (s, 2H).

(Step 2) Iodomethyl Benzoate

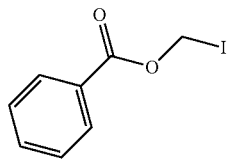 [SMILES: O=C(OCI)c1ccccc1]

Chloromethyl benzoate (10.0 g, 58.8 mmol) obtained in Step 1 and sodium iodide (17.6 g, 117 mmol) were stirred in acetonitrile (70.0 ml) at room temperature for 24 hours. The acetonitrile was removed by distillation under reduced pressure, and diethyl ether was added. The precipitated solid was filtered, thoroughly washed with diethyl ether, and dried under reduced pressure. Then, purification was conducted by silica gel column chromatography (petroleum ether:ethyl acetate=30:1 to 10:1) to obtain the title compound (14.5 g, 94%).

¹H NMR (CDCl$_3$, 400 MHz): δ 8.06-8.04 (m, 2H), 7.64-7.62 (m, 1H), 7.49-7.44 (m, 2H), 6.17 (s, 2H).

(Step 3) (5-Bromopyrimidin-2-yl)methyl Benzoate

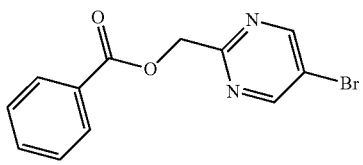 [SMILES: O=C(OCc1ncc(Br)cn1)c1ccccc1]

Zinc (21.6 g, 332 mmol) was heated at 210° C. for 10 minutes, and then cooled to 70° C. The zinc was again heated to 210° C., stirred for 10 minutes, and cooled to room temperature. DMF (100 ml) and a DMF solution (20 ml) of dibromomethane (7.72 g, 41.2 mmol) were added thereto, followed by stirring at 90° C. for 30 minutes. After cooling to room temperature, chlorotrimethylsilane (900 mg, 8.30 mmol) was added, followed by stirring at room temperature for 10 minutes. To this mixture, a DMF solution (60 ml) of the compound obtained in Step 2 (14.5 g, 55.3 mmol) was added dropwise, followed by stirring at 35° C. for 1.5 hours. 5-Bromo-2-iodopyrimidine (7.9 g, 28 mmol) and Pd(PPh₃)₂Cl₂ (3.0 g, 4.1 mmol) were suspended in DMF (80 ml), and the zinc reagent obtained above was added thereto with a syringe. The mixture was stirred under a nitrogen atmosphere at 80° C. for 2 hours, cooled to room temperature, and filtered. Water (600 ml) was added to the filtrate, followed by extraction with ethyl acetate (200 ml×3). The combined organic layer was washed with saturated aqueous sodium chloride, dried over sodium sulfate, and concentrated. After that, purification was conducted by silica gel column chromatography (petroleum ether:ethyl acetate=6:1 to 2:1) to obtain the title compound (7.38 g, 90%).

¹H NMR (CDCl₃, 400 MHz): δ 8.79 (s, 2H), 8.15-8.13 (m, 2H), 7.63-7.57 (m, 1H), 7.47-7.45 (m, 2H), 5.63 (s, 2H).

(Step 4) (5-Bromopyrimidine-2-yl)methanol

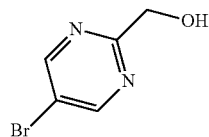

A 1 N sodium methoxide solution (50 ml, 0.50 mmol) in methanol was added to a solution (15 ml) of the compound obtained in Step 3 (7.30 g, 25.0 mmol) in methanol, followed by stirring at room temperature. After completion of the deprotection, the solvent was removed by distillation, and the residue was purified by silica gel column chromatography (dichloromethane:methanol=30:1 to 15:1) to obtain the title compound (3.58 g, 76%).

¹H NMR (CDCl₃, 400 MHz): δ 8.80 (s, 2H), 4.82 (d, J=4.0 Hz, 2H), 3.39 (s, 1H).

(Step 5) 5-Bromo-2-(methoxymethyl)pyrimidine

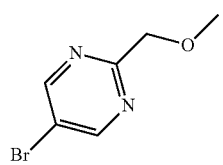

To a solution (10 ml) of the compound obtained in Step 4 (3.72 g, 19.8 mmol) in THF, sodium hydride (60%, 1.19 g, 29.7 mmol) was added at 0° C. Subsequently, methyl iodide (4.20 g, 29.7 mmol) was added thereto, followed by stirring at room temperature for 1 hour. The mixture was concentrated under reduced pressure, and the residue was purified by silica gel column chromatography to obtain the title compound (2.4 g, 60%).

(Step 6) Methyl 2,5-Difluoro-4-[[4-[2-(methoxymethyl)pyrimidin-5-yl]phenyl]sulfonylamino]benzoate

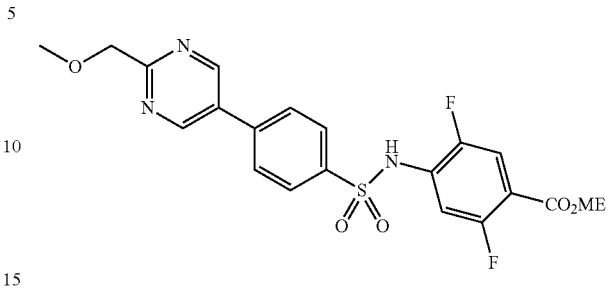

The compound obtained in Step 5 (2.30 g, 11.3 mmol), [4-[(2,5-difluoro-4-methoxycarbonyl-phenyl)sulfamoyl]phenyl]boronic acid (4.20 g, 11.3 mmol) obtained in (Step 2) of Example 189, sodium carbonate (2.40 g, 22.6 mmol), and Pd(dppf)Cl₂ (415 mg, 0.57 mmol) were suspended in dioxane (50 ml) and water (10 ml), followed by stirring at 100° C. for 8 hours. After concentration under reduced pressure, the residue was purified by silica gel column chromatography (petroleum ether:ethyl acetate=2:1 to 1:4) to obtain the title compound (2.95 g, 58%).

MS (ESI) m/z 450 (M+H)⁺

(Step 6) 2,5-Difluoro-4-[[4-[2-(methoxymethyl)pyrimidin-5-yl]phenyl]sulfonylamino]benzoic Acid

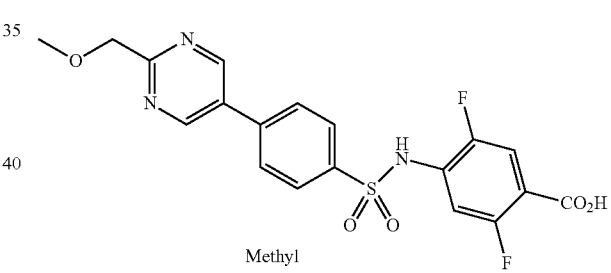

2,5-difluoro-4-[[4-[2-(methoxymethyl)pyrimidin-5-yl]phenyl]sulfonylamino]benzoate obtained in Step 5 (700 mg, 1.56 mmol) was dissolved in methanol (10 ml), and an aqueous lithium hydroxide solution (2 N, 3.0 ml) was added thereto. After stirring at room temperature for 2 hours, the completion of the reaction was confirmed by TLC. Then, the pH was adjusted to 4 to 5 by adding 4 N hydrochloric acid. The precipitated white solid was filtered, dried, and washed with dichloromethane:methanol=10:1 to obtain the title compound (617 mg, 91%) as a white solid.

¹H NMR (CD₃OD, 400 MHz): δ 9.06 (s, 2H), 8.01 (d, J=8.4 Hz, 2H), 7.90 (d, J=8.4 Hz, 2H), 7.56-7.52 (m, 1H), 7.43-7.39 (m, 1H), 4.68 (s, 2H), 3.47 (s, 3H).; MS (ESI) m/z 436 (M+H)⁺

The following group of compounds was synthesized by subjecting their corresponding intermediates among M-1 to M-109 to the same methods as in (Step 1) and (Step 2) of Example 39. Note that, in the Examples 246 to 257 below, each compound was obtained as a TFA salt, unless otherwise noted.

Example 246

Synthesis of A-119 and B-119

(Step 1) (2S)-2-[[2,5-Difluoro-4-[[5-(2-isopropyl-4-pyridyl)-2-pyridyl]sulfonylamino]benzoyl]amino]-3-[5-(1-methyl-2,4-dioxo-pyrido[3,4-d]pyrimidin-3-yl)-2-pyridyl]propanoic Acid (A-119)

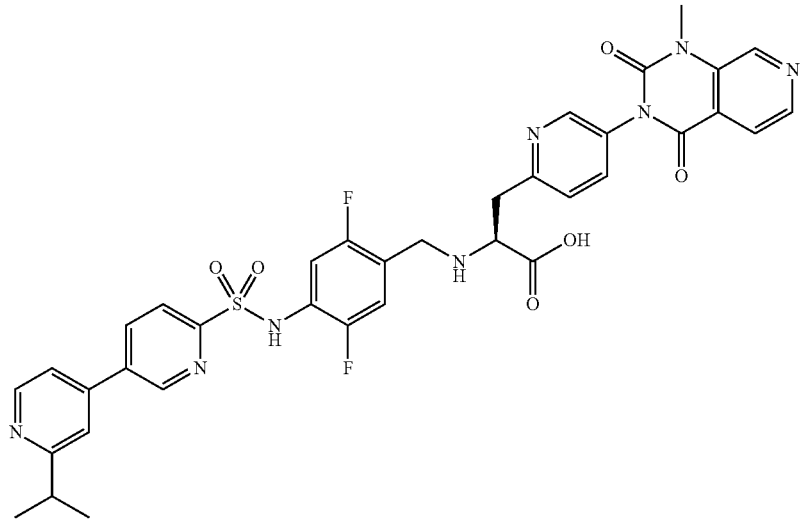 [SMILES: CC(C)c1cc(-c2ccc(S(=O)(=O)Nc3cc(F)c(CN[C@@H](Cc4ccc(-n5c(=O)c6ccncc6n(C)c5=O)cn4)C(=O)O)cc3F)nc2)ccn1]

$^1$H NMR (400 MHz, DMSO-d$_6$): δ 11.16 (s, 1H), 9.28-9.22 (m, 1H), 9.00 (s, 1H), 8.80-8.71 (m, 2H), 8.60 (dd, J=8.3, 2.3 Hz, 1H), 8.57 (d, J=4.9 Hz, 1H), 8.47 (d, J=2.4 Hz, 1H), 8.18 (d, J=8.2 Hz, 1H), 8.03 (s, 1H), 7.97-7.91 (m, 1H), 7.90 (d, J=5.0 Hz, 1H), 7.74 (dd, J=8.2, 2.5 Hz, 1H), 7.51-7.36 (m, 3H), 4.95-4.85 (m, 1H), 3.61 (s, 3H), 3.43-3.26 (m, 2H), 3.26-3.15 (m, 1H), 1.33 (d, J=6.9 Hz, 6H).; MS (ESI) m/z 757.28 (M+H)$^+$ (Step 2) Cyclohexyl (2S)-2-[[2,5-Difluoro-4-[[5-(2-isopropyl-4-pyridyl)-2-pyridyl]sulfonylamino]benzoyl]amino]-3-[5-(1-methyl-2,4-dioxo-pyrido[3,4-d]pyrimidin-3-yl)-2-pyridyl]propanoate (B-119)

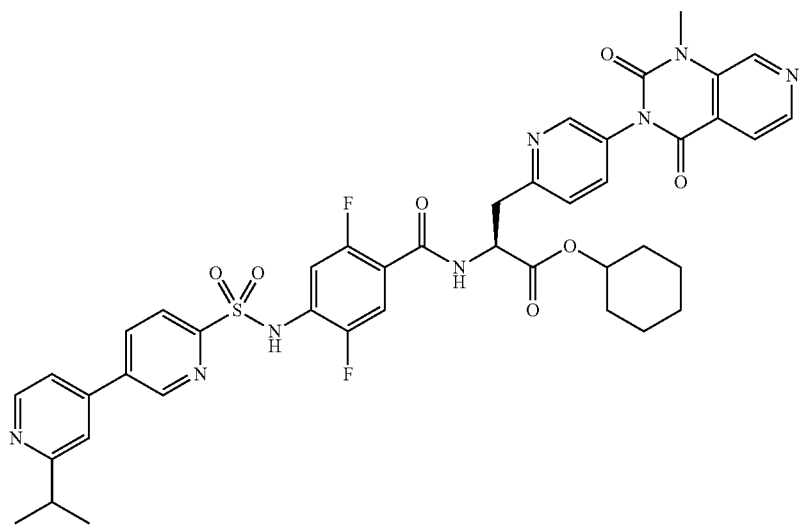 [SMILES: CC(C)c1cc(-c2ccc(S(=O)(=O)Nc3cc(F)c(C(=O)N[C@@H](Cc4ccc(-n5c(=O)c6ccncc6n(C)c5=O)cn4)C(=O)OC4CCCCC4)cc3F)nc2)ccn1]

¹H NMR (400 MHz, DMSO-d₆): δ 11.17 (s, 1H), 9.25 (d, J=2.2 Hz, 1H), 9.00 (s, 1H), 8.88 (dd, J=7.6, 3.5 Hz, 1H), 8.76 (d, J=5.6 Hz, 1H), 8.61 (dd, J=8.3, 2.3 Hz, 1H), 8.57 (d, J=5.0 Hz, 1H), 8.46 (d, J=2.4 Hz, 1H), 8.19 (d, J=8.2 Hz, 1H), 8.03 (s, 1H), 7.98-7.92 (m, 1H), 7.90 (d, J=4.9 Hz, 1H), 7.74 (dd, J=8.2, 2.5 Hz, 1H), 7.56-7.34 (m, 3H), 4.99-4.86 (m, 1H), 4.74-4.62 (m, 1H), 3.61 (s, 3H), 3.33 (dd, J=6.9, 4.4 Hz, 2H), 3.28-3.17 (m, 1H), 1.79-1.52 (m, 4H), 1.50-1.16 (m, 12H).; MS (ESI) m/z 839.59 (M+H)⁺

Example 247

Synthesis of A-120 and B-120

(Step 1) (2S)-2-[[4-[[4-[2-(Azetidin-1-yl)pyrimidin-5-yl]phenyl]sulfonylamino]-2,5-difluoro-benzoyl]amino]-3-[6-(1-methyl-2,4-dioxo-pyrido[3,4-d]pyrimidin-3-yl)-3-pyridyl]propanoic Acid (A-120)

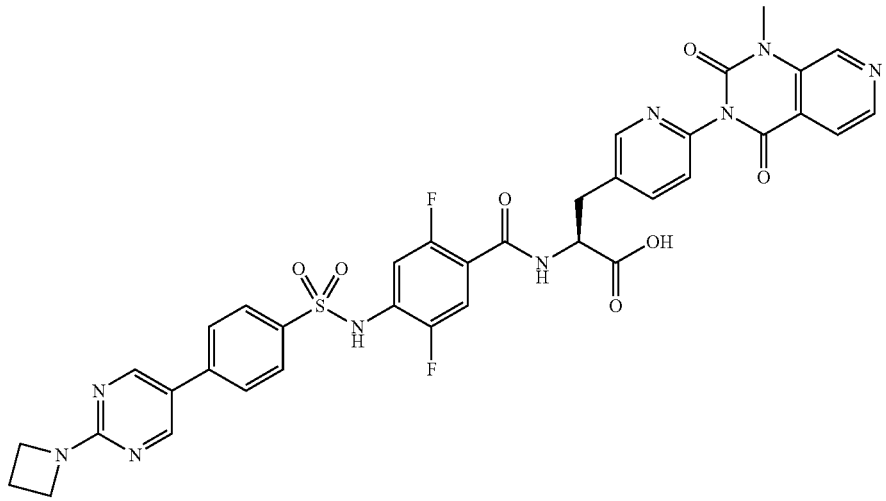 [SMILES: Cn1c(=O)n(-c2ccc(C[C@H](NC(=O)c3cc(F)c(NS(=O)(=O)c4ccc(-c5cnc(N6CCC6)nc5)cc4)cc3F)C(=O)O)cn2)c(=O)c2ccncc21]

¹H NMR (400 MHz, DMSO-d₆): δ 10.87 (s, 1H), 8.99 (s, 1H), 8.74 (s, 2H), 8.68 (dd, J=8.1, 2.2 Hz, 1H), 8.57 (d, J=4.9 Hz, 1H), 8.46 (d, J=2.3 Hz, 1H), 7.98-7.83 (m, 6H), 7.39 (d, J=8.1 Hz, 1H), 7.32-7.20 (m, 2H), 4.73-4.63 (m, 1H), 4.09 (t, J=7.5 Hz, 4H), 3.59 (s, 3H), 3.29 (dd, J=14.1, 4.6 Hz, 1H), 3.09 (dd, J=14.1, 10.2 Hz, 1H), 2.40-2.27 (m, 2H).; MS (ESI) m/z 770.42 (M+H)⁺

(Step 2) Cyclohexyl (2S)-2-[[4-[[4-[2-(Azetidin-1-yl)pyrimidin-5-yl]phenyl]sulfonylamino]-2,5-difluoro-benzoyl]amino]-3-[6-(1-methyl-2,4-dioxo-pyrido[3,4-d]pyrimidin-3-yl)-3-pyridyl]propanoate (B-120)

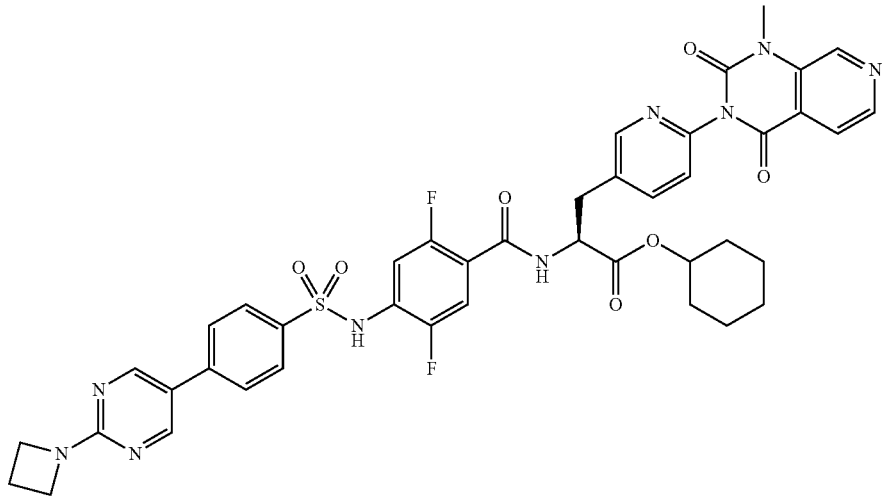 [SMILES: Cn1c(=O)n(-c2ccc(C[C@H](NC(=O)c3cc(F)c(NS(=O)(=O)c4ccc(-c5cnc(N6CCC6)nc5)cc4)cc3F)C(=O)OC3CCCCC3)cn2)c(=O)c2ccncc21]

¹H NMR (400 MHz, DMSO-d₆): δ 10.88 (s, 1H), 8.99 (s, 1H), 8.86-8.79 (m, 1H), 8.74 (s, 2H), 8.57 (d, J=5.0 Hz, 1H), 8.46 (d, J=2.3 Hz, 1H), 7.95-7.84 (m, 6H), 7.40 (d, J=8.1 Hz, 1H), 7.31-7.21 (m, 2H), 4.75-4.64 (m, 2H), 4.13-4.07 (m, 4H), 3.59 (s, 3H), 3.24 (dd, J=14.1, 5.6 Hz, 1H), 3.12 (dd, J=14.1, 9.6 Hz, 1H), 2.40-2.27 (m, 2H), 1.78-1.58 (m, 4H), 1.50-1.19 (m, 6H).; MS (ESI) m/z 852.3 (M+H)⁺

Example 248

Synthesis of A-121 and B-121

(Step 1) (2S)-2-[[4-[[4-(4-Ethyltriazol-1-yl)phenyl]sulfonylamino]-2,5-difluoro-benzoyl]amino]-3-[5-(1-methyl-2,4-dioxo-pyrido[3,4-d]pyrimidin-3-yl)-2-pyridyl]propanoic Acid (A-121)

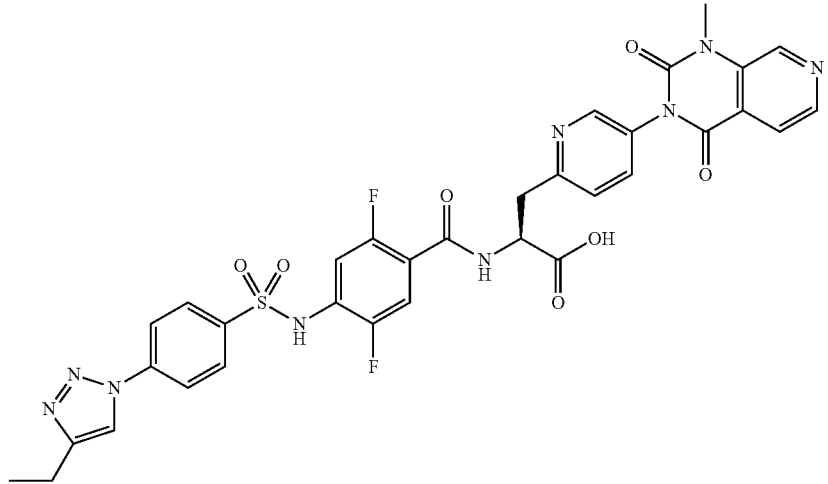 [SMILES: CCc1cn(-c2ccc(S(=O)(=O)Nc3cc(F)c(C(=O)N[C@@H](Cc4ccc(-n5c(=O)c6ccncc6n(C)c5=O)cn4)C(=O)O)cc3F)cc2)nn1]

¹H NMR (400 MHz, DMSO-d₆): δ 10.94 (s, 1H), 9.00 (s, 1H), 8.74 (dd, J=7.9, 3.7 Hz, 1H), 8.69 (s, 1H), 8.58 (d, J=4.9 Hz, 1H), 8.46 (dd, J=2.4, 0.7 Hz, 1H), 8.17-8.08 (m, 2H), 8.05-7.96 (m, 2H), 7.90 (dd, J=5.0, 0.7 Hz, 1H), 7.74 (dd, J=8.2, 2.5 Hz, 1H), 7.46 (d, J=8.3 Hz, 1H), 7.37 (dd, J=10.3, 6.4 Hz, 1H), 7.26 (dd, J=11.2, 6.2 Hz, 1H), 4.94-4.84 (m, 1H), 3.61 (s, 3H), 3.42-3.23 (m, 2H), 2.77-2.65 (m, 2H), 1.25 (t, J=7.6 Hz, 3H).; MS (ESI) m/z 732.22 (M+H)⁺

(Step 2) Cyclohexyl (2S)-2-[[4-[[4-(4-Ethyltriazol-1-yl)phenyl]sulfonylamino]-2,5-difluoro-benzoyl]amino]-3-[5-(1-methyl-2,4-dioxo-pyrido[3,4-d]pyrimidin-3-yl)-2-pyridyl]propionate (B-121)

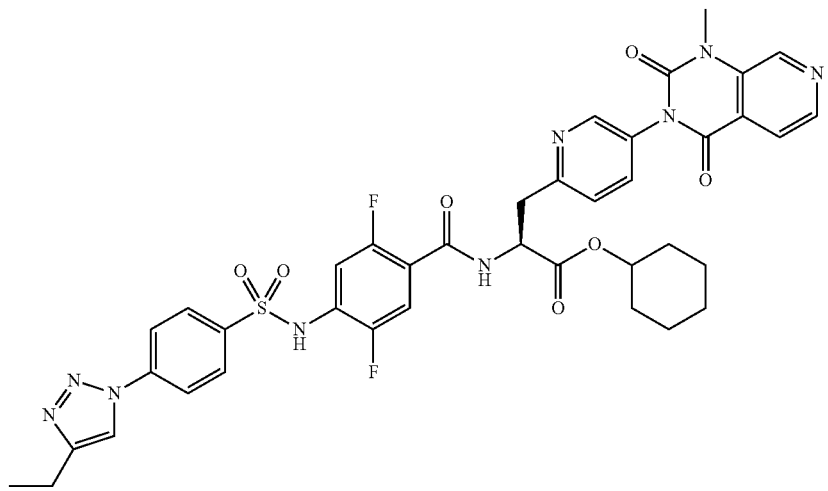 [SMILES: CCc1cn(-c2ccc(S(=O)(=O)Nc3cc(F)c(C(=O)N[C@@H](Cc4ccc(-n5c(=O)c6ccncc6n(C)c5=O)cn4)C(=O)OC4CCCCC4)cc3F)cc2)nn1]

¹H NMR (400 MHz, DMSO-d₆): δ 10.95 (s, 1H), 9.00 (s, 1H), 8.86 (dd, J=7.6, 3.3 Hz, 1H), 8.69 (d, J=0.9 Hz, 1H), 8.57 (d, J=5.0 Hz, 1H), 8.46 (d, J=2.4 Hz, 1H), 8.17-8.08 (m, 2H), 8.06-7.97 (m, 2H), 7.90 (d, J=4.9 Hz, 1H), 7.73 (dd, J=8.2, 2.5 Hz, 1H), 7.46 (d, J=8.2 Hz, 1H), 7.37 (dd, J=10.3, 6.3 Hz, 1H), 7.27 (dd, J=11.1, 6.2 Hz, 1H), 4.97-4.87 (m, 1H), 4.73-4.63 (m, 1H), 3.61 (s, 3H), 3.39-3.24 (m, 2H), 2.78-2.67 (m, 2H), 1.76-1.52 (m, 4H), 1.46-1.18 (m, 9H).; MS (ESI) m/z 814.39 (M+H)⁺

Example 249

Synthesis of A-122 and B-122

(Step 1) (2S)-2-[[4-[[4-(4-Ethyltriazol-1-yl)phenyl]sulfonylamino]-2,5-difluoro-benzoyl]amino]-3-[6-(1-methyl-2,4-dioxo-pyrido[3,4-d]pyrimidin-3-yl)-3-pyridyl]propanoic Acid (A-122)

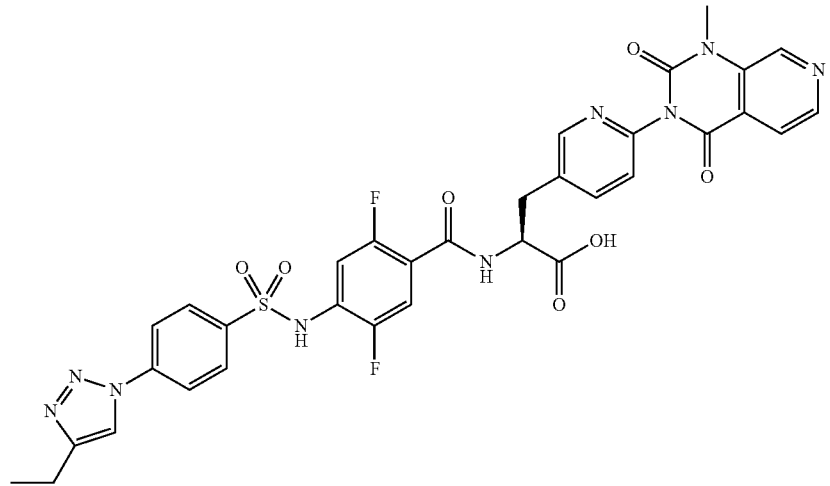 [SMILES: CCc1cn(-c2ccc(S(=O)(=O)Nc3cc(F)c(C(=O)N[C@@H](Cc4ccc(-n5c(=O)c6ccncc6n(C)c5=O)nc4)C(=O)O)cc3F)cc2)nn1]

¹H NMR (400 MHz, DMSO-d₆): δ 10.92 (s, 1H), 8.99 (s, 1H), 8.73-8.66 (m, 2H), 8.57 (d, J=4.9 Hz, 1H), 8.46 (d, J=2.3 Hz, 1H), 8.17-8.08 (m, 2H), 8.05-7.97 (m, 2H), 7.94-7.85 (m, 2H), 7.40 (d, J=8.1 Hz, 1H), 7.33-7.21 (m, 2H), 4.74-4.63 (m, 1H), 3.59 (s, 3H), 3.29 (dd, J=14.1, 4.7 Hz, 1H), 3.09 (dd, J=14.1, 10.2 Hz, 1H), 2.72 (q, J=7.6 Hz, 2H), 1.25 (t, J=7.6 Hz, 3H).; MS (ESI) m/z 732.38 (M+H)⁺

(Step 2) Cyclohexyl (2S)-2-[[4-[[4-(4-Ethyltriazol-1-yl)phenyl]sulfonylamino]-2,5-difluoro-benzoyl]amino]-3-[6-(1-methyl-2,4-dioxo-pyrido[3,4-d]pyrimidin-3-yl)-3-pyridyl]propanoate (B-122)

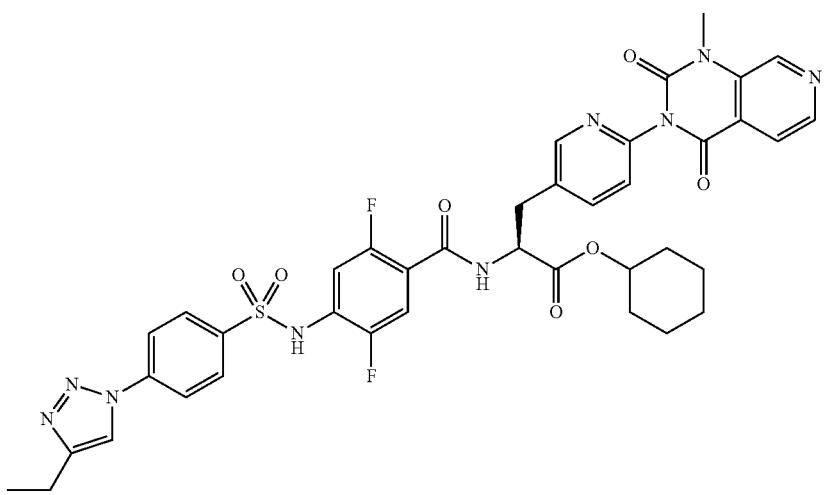 [SMILES: CCc1cn(-c2ccc(S(=O)(=O)Nc3cc(F)c(C(=O)N[C@@H](Cc4ccc(-n5c(=O)c6ccncc6n(C)c5=O)nc4)C(=O)OC4CCCCC4)cc3F)cc2)nn1]

¹H NMR (400 MHz, DMSO-d₆): δ 10.93 (s, 1H), 8.99 (s, 1H), 8.84 (dd, J=7.9, 1.7 Hz, 1H), 8.69 (s, 1H), 8.57 (d, J=5.0 Hz, 1H), 8.46 (d, J=2.3 Hz, 1H), 8.17-8.09 (m, 2H), 8.06-7.97 (m, 2H), 7.96-7.85 (m, 2H), 7.40 (d, J=8.1 Hz, 1H), 7.32-7.21 (m, 2H), 4.75-4.64 (m, 2H), 3.59 (s, 3H), 3.24 (dd, J=14.1, 5.7 Hz, 1H), 3.12 (dd, J=14.1, 9.6 Hz, 1H), 2.72 (q, J=7.6 Hz, 2H), 1.78-1.58 (m, 4H), 1.48-1.19 (m, 9H).; MS (ESI) m/z 814.39 (M+H)⁺

Example 250

Synthesis of A-123 and B-123

(Step 1) (2S)-2-[[2,5-Difluoro-4-[[4-(1,2,4-triazol-4-yl)phenyl]sulfonylamino]benzoyl]amino]-3-[6-(1-methyl-2,4-dioxo-pyrido[3,4-d]pyrimidin-3-yl)-3-pyridyl]propanoic Acid (A-123)

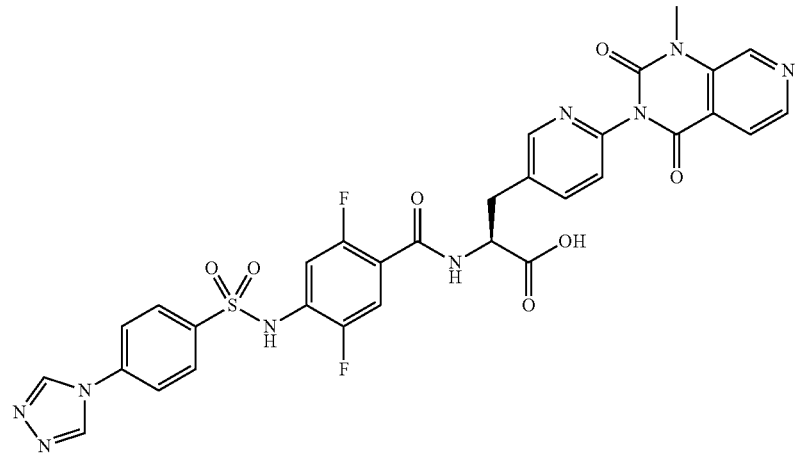 [SMILES: Cn1c(=O)n(-c2ccc(C[C@H](NC(=O)c3cc(F)c(NS(=O)(=O)c4ccc(-n5cnnc5)cc4)cc3F)C(=O)O)cn2)c(=O)c2ccncc21]

¹H NMR (400 MHz, DMSO-d₆): δ 10.95 (s, 1H), 9.22 (s, 2H), 8.99 (s, 1H), 8.69 (dd, J=8.1, 2.2 Hz, 1H), 8.57 (d, J=4.9 Hz, 1H), 8.46 (d, J=2.3 Hz, 1H), 8.06-7.98 (m, 2H), 7.98-7.93 (m, 2H), 7.93-7.85 (m, 2H), 7.40 (d, J=8.0 Hz, 1H), 7.34-7.22 (m, 2H), 4.74-4.63 (m, 1H), 3.59 (s, 3H), 3.29 (dd, J=14.1, 4.6 Hz, 1H), 3.09 (dd, J=14.1, 10.2 Hz, 1H).; MS (ESI) m/z 704.42 (M+H)⁺

(Step 2) Cyclohexyl (2S)-2-[[2,5-Difluoro-4-[[4-(1,2,4-triazol-4-yl)phenyl]sulfonylamino]benzoyl]amino]-3-[6-(1-methyl-2,4-dioxo-pyrido[3,4-d]pyrimidin-3-yl)-3-pyridyl]propanoate (B-123)

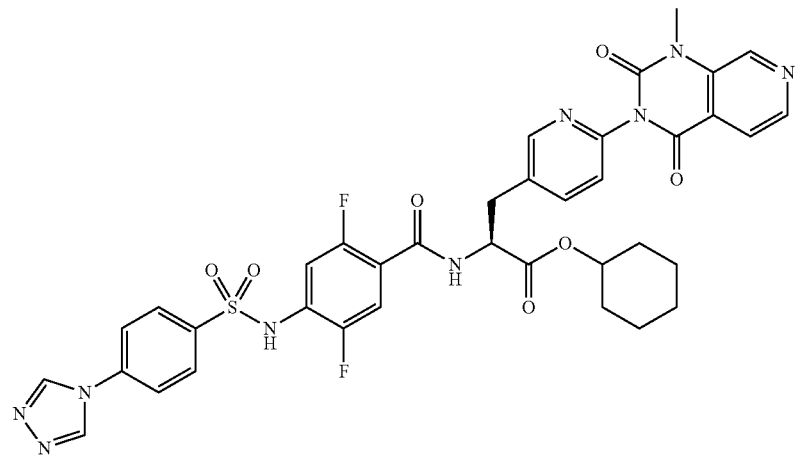 [SMILES: Cn1c(=O)n(-c2ccc(C[C@H](NC(=O)c3cc(F)c(NS(=O)(=O)c4ccc(-n5cnnc5)cc4)cc3F)C(=O)OC3CCCCC3)cn2)c(=O)c2ccncc21]

¹H NMR (400 MHz, DMSO-d₆): δ 10.97 (s, 1H), 9.23 (s, 2H), 8.99 (s, 1H), 8.84 (dd, J=7.7, 1.8 Hz, 1H), 8.57 (d, J=5.0 Hz, 1H), 8.46 (d, J=2.3 Hz, 1H), 8.06-7.99 (m, 2H), 7.99-7.94 (m, 2H), 7.92 (dd, J=8.2, 2.4 Hz, 1H), 7.88 (d, J=5.0 Hz, 1H), 7.40 (d, J=8.1 Hz, 1H), 7.33-7.23 (m, 2H), 4.76-4.65 (m, 2H), 3.60 (s, 3H), 3.24 (dd, J=14.1, 5.6 Hz, 1H), 3.13 (dd, J=14.1, 9.7 Hz, 1H), 1.79-1.57 (m, 4H), 1.51-1.19 (m, 6H).; MS (ESI) m/z 786.35 (M+H)⁺

Example 251

Synthesis of A-124 and B-124

(Step 1) (2S)-2-[[4-[[5-(4-Cyclopropyltriazol-1-yl)-2-pyridyl]sulfonylamino]-2,5-difluoro-benzoyl]amino]-3-[5-(1-methyl-2,4-dioxo-pyrido[3,4-d]pyrimidin-3-yl)-2-pyridyl]propanoic Acid (A-124)

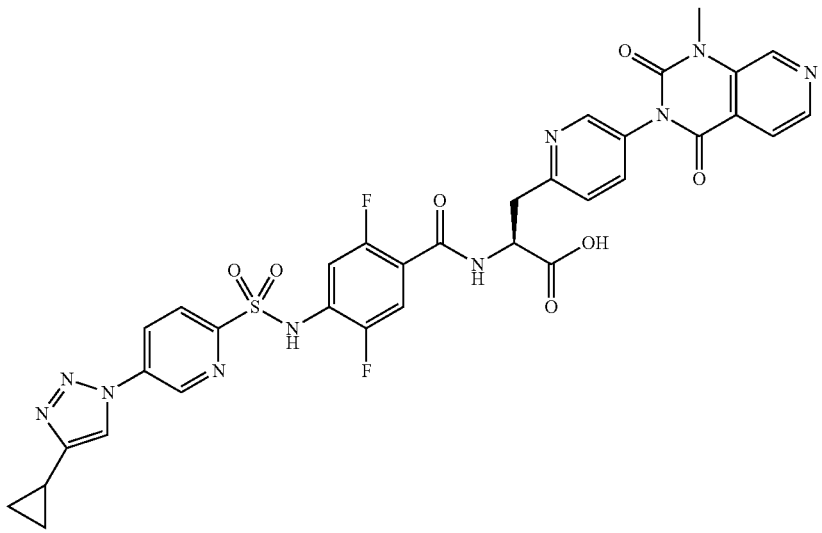 [SMILES: Cn1c(=O)n(-c2ccc(C[C@H](NC(=O)c3cc(F)c(NS(=O)(=O)c4ccc(-n5cc(C6CC6)nn5)cn4)cc3F)C(=O)O)nc2)c(=O)c2ccncc21]

¹H NMR (400 MHz, DMSO-d₆): δ 11.13 (s, 1H), 9.26 (d, J=2.5 Hz, 1H), 9.01 (s, 1H), 8.80-8.73 (m, 2H), 8.61-8.54 (m, 2H), 8.52 (d, J=2.4 Hz, 1H), 8.22 (d, J=8.6 Hz, 1H), 7.92 (d, J=5.0 Hz, 1H), 7.82 (dd, J=8.2, 2.5 Hz, 1H), 7.53 (d, J=8.3 Hz, 1H), 7.43-7.32 (m, 2H), 4.96-4.86 (m, 1H), 3.62 (s, 3H), 3.46-3.26 (m, 2H), 2.11-1.99 (m, 1H), 1.05-0.95 (m, 2H), 0.85-0.76 (m, 2H).; MS (ESI) m/z 745.46 (M+H)⁺

(Step 2) Cyclohexyl (2S)-2-[[4-[[5-(4-Cyclopropyltriazol-1-yl)-2-pyridyl]sulfonylamino]-2,5-difluoro-benzoyl]amino]-3-[5-(1-methyl-2,4-dioxo-pyrido[3,4-d]pyrimidin-3-yl)-2-pyridyl]propanoate (B-124)

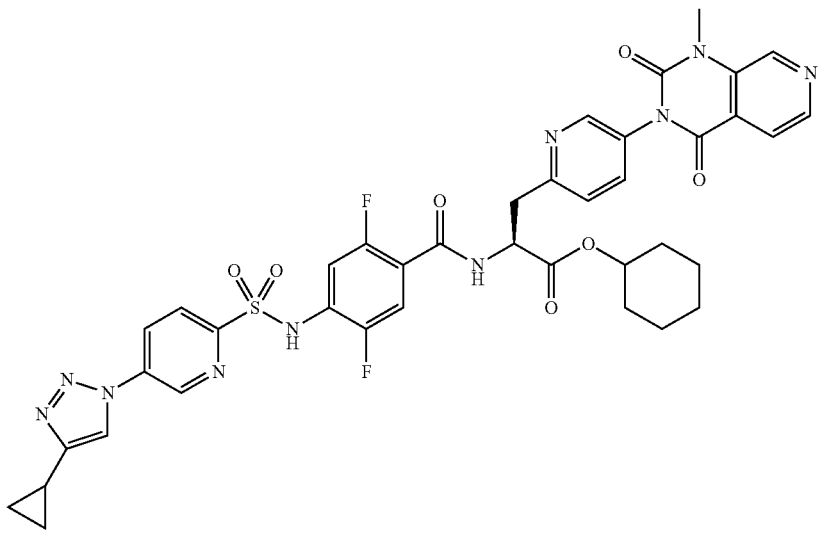 [SMILES: Cn1c(=O)n(-c2ccc(C[C@H](NC(=O)c3cc(F)c(NS(=O)(=O)c4ccc(-n5cc(C6CC6)nn5)cn4)cc3F)C(=O)OC3CCCCC3)nc2)c(=O)c2ccncc21]

¹H NMR (400 MHz, DMSO-d₆): δ 11.13 (s, 1H), 9.26 (d, J=2.5 Hz, 1H), 9.00 (s, 1H), 8.87 (dd, J=7.6, 3.4 Hz, 1H), 8.75 (s, 1H), 8.61-8.53 (m, 2H), 8.46 (d, J=2.4 Hz, 1H), 8.22 (d, J=8.6 Hz, 1H), 7.91 (d, J=5.0 Hz, 1H), 7.74 (dd, J=8.2, 2.5 Hz, 1H), 7.47 (d, J=8.2 Hz, 1H), 7.44-7.34 (m, 2H), 4.98-4.88 (m, 1H), 4.75-4.64 (m, 1H), 3.61 (s, 3H), 3.40-3.25 (m, 2H), 2.11-1.99 (m, 1H), 1.78-1.53 (m, 4H), 1.48-1.19 (m, 6H), 1.05-0.93 (m, 2H), 0.85-0.76 (m, 2H).; MS (ESI) m/z 827.55 (M+H)⁺

Example 252

Synthesis of A-125 and B-125

(Step 1) (2S)-2-[[4-[[4-(4-Cyclopropyltriazol-1-yl)phenyl]sulfonylamino]-2,5-difluoro-benzoyl]amino]-3-[4-(1-methyl-2,4-dioxo-pyrido[3,4-d]pyrimidin-3-yl)phenyl]propanoic Acid (A-125)

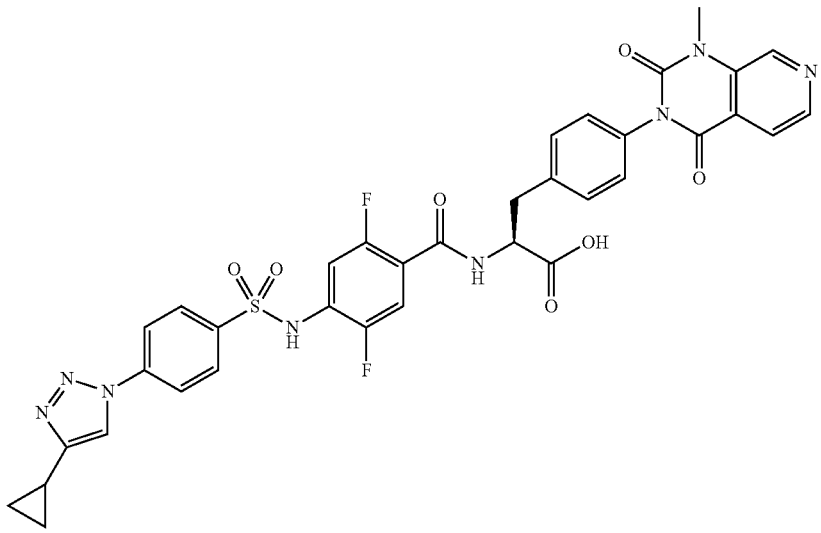 [SMILES: Cn1c(=O)n(-c2ccc(C[C@H](NC(=O)c3cc(F)c(NS(=O)(=O)c4ccc(-n5cc(C6CC6)nn5)cc4)cc3F)C(=O)O)cc2)c(=O)c2ccncc21]

¹H NMR (400 MHz, DMSO-d₆): δ 10.91 (s, 1H), 8.96 (s, 1H), 8.65 (s, 1H), 8.61 (dd, J=7.9, 2.5 Hz, 1H), 8.55 (d, J=4.9 Hz, 1H), 8.13-8.05 (m, 2H), 8.04-7.96 (m, 2H), 7.87 (d, J=5.0 Hz, 1H), 7.40-7.33 (m, 2H), 7.33-7.17 (m, 4H), 4.68-4.57 (m, 1H), 3.59 (s, 3H), 3.23 (dd, J=14.1, 4.6 Hz, 1H), 3.06 (dd, J=14.0, 9.9 Hz, 1H), 2.08-1.96 (m, 1H), 1.02-0.93 (m, 2H), 0.83-0.75 (m, 2H).; MS (ESI) m/z 743.5 (M+H)⁺

(Step 2) Cyclohexyl (2S)-2-[[4-[[4-(4-Cyclopropyl-triazol-1-yl)phenyl]sulfonylamino]-2,5-difluoro-benzoyl]amino]-3-[4-(1-methyl-2,4-dioxo-pyrido[3,4-d]pyrimidin-3-yl)phenyl]propanoate (B-125)

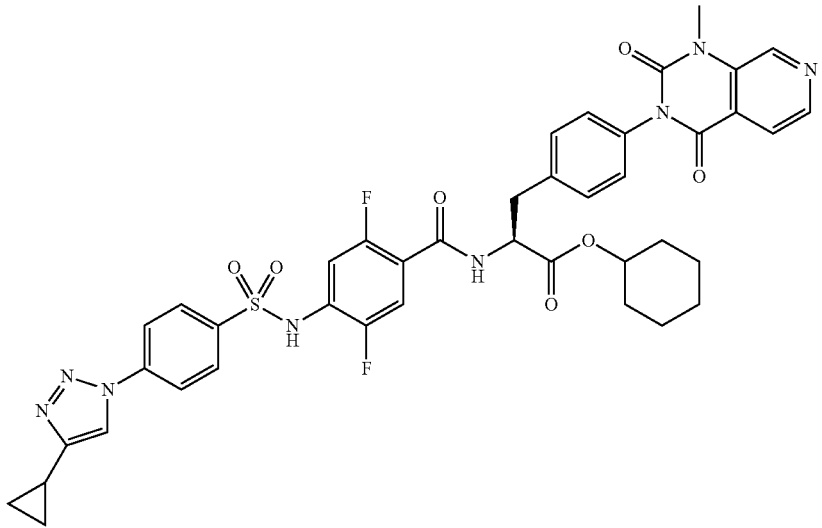

¹H NMR (400 MHz, DMSO-d₆): δ 10.93 (s, 1H), 8.96 (s, 1H), 8.76 (dd, J=7.5, 1.9 Hz, 1H), 8.65 (s, 1H), 8.55 (d, J=5.0 Hz, 1H), 8.14-8.05 (m, 2H), 8.05-7.97 (m, 2H), 7.88 (d, J=5.0 Hz, 1H), 7.41-7.33 (m, 2H), 7.33-7.17 (m, 4H), 4.75-4.58 (m, 2H), 3.59 (s, 3H), 3.22-3.04 (m, 2H), 2.10-1.96 (m, 1H), 1.80-1.56 (m, 4H), 1.50-1.17 (m, 6H), 1.02-0.93 (m, 2H), 0.84-0.75 (m, 2H).; MS (ESI) m/z 825.55 (M+H)⁺

Example 253

Synthesis of A-126 and B-126

(Step 1) (2S)-2-[[2,5-Difluoro-4-[[4-(2-tetrahydro-pyran-4-ylpyrimidin-5-yl)phenyl]sulfonylamino]benzoyl]amino]-3-[4-(1-methyl-2,4-dioxo-pyrido[3,4-d]pyrimidin-3-yl)phenyl]propanoic Acid (A-126)

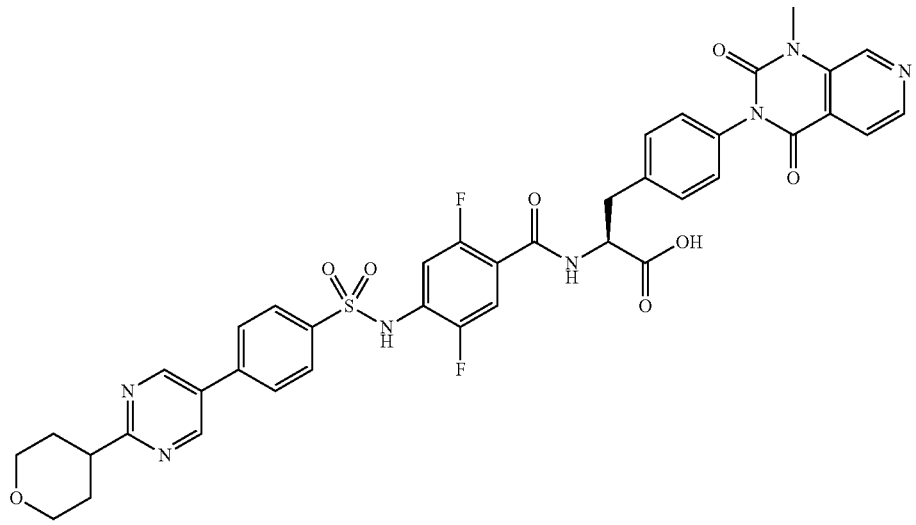 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)O)cc2)c(=O)c2ccncc21]

¹H NMR (400 MHz, DMSO-d₆): δ 10.96 (s, 1H), 9.13 (s, 2H), 8.97 (s, 1H), 8.60 (dd, J=7.9, 2.6 Hz, 1H), 8.54 (d, J=5.0 Hz, 1H), 8.07-7.99 (m, 2H), 7.99-7.92 (m, 2H), 7.88 (d, J=4.9 Hz, 1H), 7.41-7.34 (m, 2H), 7.34-7.24 (m, 2H), 7.24-7.17 (m, 2H), 4.68-4.57 (m, 1H), 4.00-3.90 (m, 2H), 3.59 (s, 3H), 3.53-3.42 (m, 2H), 3.27-3.01 (m, 3H), 1.95-1.75 (m, 4H).; MS (ESI) m/z 798.55 (M+H)⁺

(Step 2) Cyclohexyl (2S)-2-[[2,5-Difluoro-4-[[4-(2-tetrahydropyran-4-ylpyrimidin-5-yl)phenyl]sulfonylamino]benzoyl]amino]-3-[4-(1-methyl-2,4-dioxo-pyrido[3,4-d]pyrimidin-3-yl)phenyl]propionate (B-126)

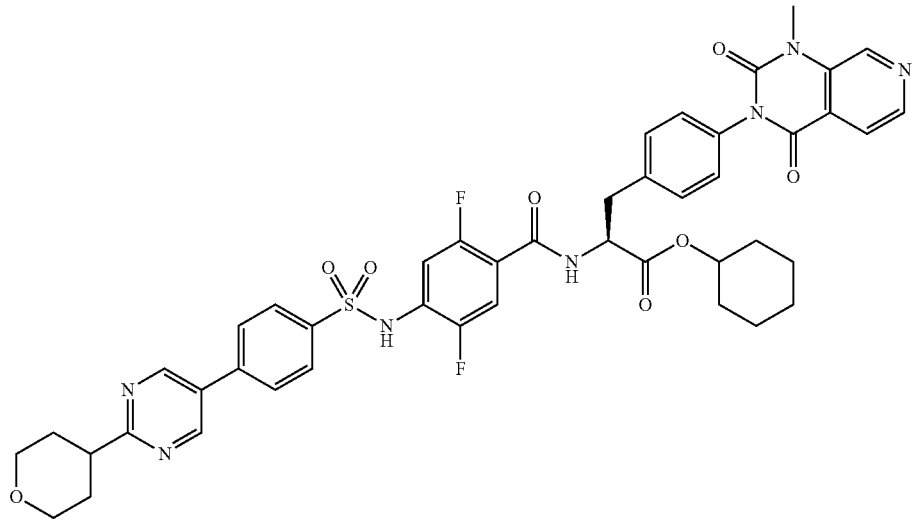 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)OC3CCCCC3)cc2)c(=O)c2ccncc21]

¹H NMR (400 MHz, DMSO-d₆): δ 10.97 (s, 1H), 9.14 (s, 2H), 8.96 (s, 1H), 8.76 (dd, J=7.5, 2.0 Hz, 1H), 8.54 (d, J=5.0 Hz, 1H), 8.07-8.00 (m, 2H), 8.00-7.93 (m, 2H), 7.88 (d, J=5.0 Hz, 1H), 7.41-7.34 (m, 2H), 7.34-7.25 (m, 2H), 7.25-7.17 (m, 2H), 4.75-4.57 (m, 2H), 4.00-3.90 (m, 2H), 3.59 (s, 3H), 3.54-3.44 (m, 2H), 3.22-3.04 (m, 3H), 1.95-1.56 (m, 8H), 1.50-1.19 (m, 6H).; MS (ESI) m/z 880.6 (M+H)⁺

Example 254

Synthesis of A-127 and B-127

(Step 1) (2S)-2-[[2,5-Difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoic Acid
(A-127)

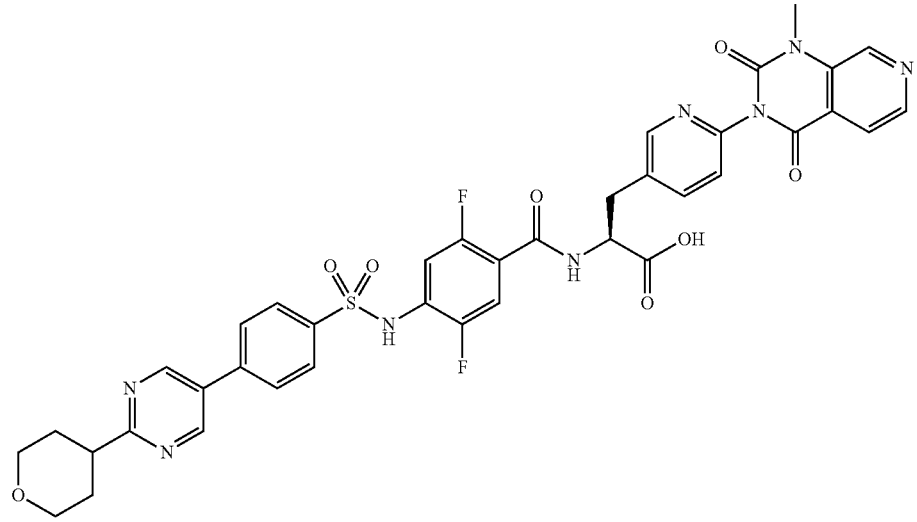 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)O)cn2)c(=O)c2ccncc21]

¹H NMR (400 MHz, DMSO-d₆): δ 10.95 (s, 1H), 9.13 (s, 2H), 8.99 (s, 1H), 8.69 (dd, J=8.2, 2.2 Hz, 1H), 8.56 (d, J=5.0 Hz, 1H), 8.46 (d, J=2.3 Hz, 1H), 8.06-7.99 (m, 2H), 7.99-7.92 (m, 2H), 7.92-7.85 (m, 2H), 7.43-7.36 (m, 1H), 7.33-7.22 (m, 2H), 4.74-4.63 (m, 1H), 4.00-3.90 (m, 2H), 3.59 (s, 3H), 3.54-3.42 (m, 2H), 3.29 (dd, J=14.1, 4.6 Hz, 1H), 3.19-3.03 (m, 2H), 1.95-1.74 (m, 4H).; MS (ESI) m/z 799.51 (M+H)⁺

(Step 2) Cyclohexyl (2S)-2-[[2,5-Difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoate
(B-127)

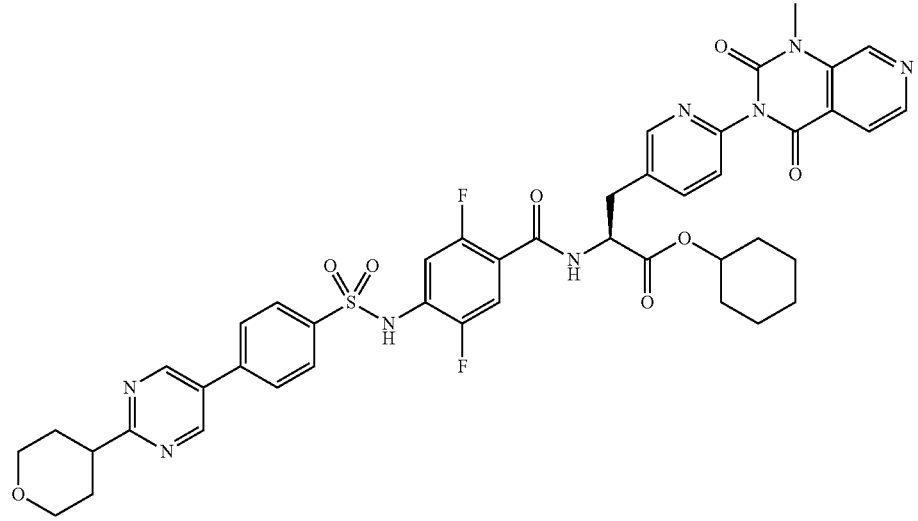 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)OC3CCCCC3)cn2)c(=O)c2ccncc21]

¹H NMR (400 MHz, DMSO-d₆): δ 10.97 (s, 1H), 9.14 (s, 2H), 8.99 (s, 1H), 8.84 (dd, J=7.9, 1.7 Hz, 1H), 8.56 (d, J=4.9 Hz, 1H), 8.46 (d, J=2.3 Hz, 1H), 8.07-7.99 (m, 2H), 8.01-7.93 (m, 2H), 7.92 (dd, J=8.1, 2.4 Hz, 1H), 7.89 (d, J=5.0 Hz, 1H), 7.40 (d, J=8.1 Hz, 1H), 7.28 (dd, J=10.6, 6.2 Hz, 2H), 4.76-4.64 (m, 2H), 4.00-3.90 (m, 2H), 3.59 (s, 3H), 3.49-3.43 (m, 2H), 3.24 (dd, J=14.1, 5.6 Hz, 1H), 3.19-3.06 (m, 2H), 1.96-1.56 (m, 8H), 1.50-1.16 (m, 6H).; MS (ESI) m/z 881.64 (M+H)⁺

Example 255

Synthesis of A-128 and B-128

(Step 1) (2S)-2-[[2,5-Difluoro-4-[[4-[2-(methoxymethyl)pyrimidin-5-yl]phenyl]sulfonylamino]benzoyl]amino]-3-[4-(1-methyl-2,4-dioxo-pyrido[3,4-d]pyrimidin-3-yl)phenyl]propanoic Acid (A-128)

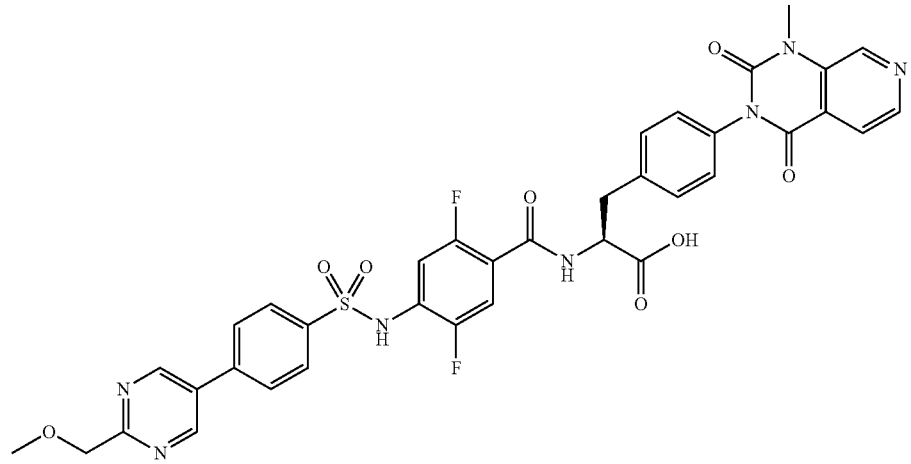 [SMILES: COCc1ncc(-c2ccc(S(=O)(=O)Nc3cc(F)c(C(=O)N[C@@H](Cc4ccc(-n5c(=O)c6ccncc6n(C)c5=O)cc4)C(=O)O)cc3F)cc2)cn1]

¹H NMR (400 MHz, DMSO-d₆): δ 10.97 (s, 1H), 9.18 (s, 2H), 8.96 (s, 1H), 8.60 (dd, J=8.0, 2.6 Hz, 1H), 8.55 (d, J=5.0 Hz, 1H), 8.10-8.02 (m, 2H), 8.02-7.94 (m, 2H), 7.88 (d, J=5.0 Hz, 1H), 7.40-7.24 (m, 4H), 7.24-7.17 (m, 2H), 4.63 (s, 3H), 3.59 (s, 3H), 3.40 (s, 3H), 3.23 (dd, J=14.0, 4.5 Hz, 1H), 3.06 (dd, J=14.0, 9.9 Hz, 1H).; MS (ESI) m/z 758.54 (M+H)⁺

(Step 2) Cyclohexyl (2S)-2-[[2,5-Difluoro-4-[[4-[2-(methoxymethyl)pyrimidin-5-yl]phenyl]sulfonylamino]benzoyl]amino]-3-[4-(1-methyl-2,4-dioxo-pyrido[3,4-d]pyrimidin-3-yl)phenyl]propanoate (B-128)

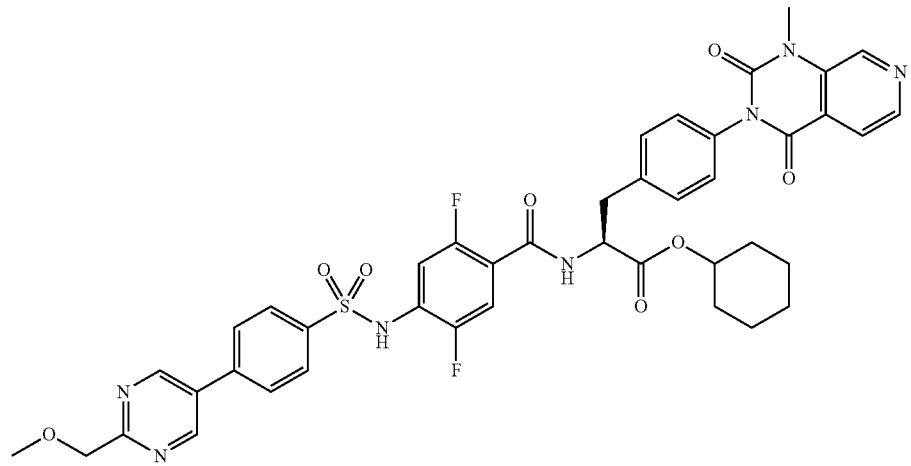 [SMILES: COCc1ncc(-c2ccc(S(=O)(=O)Nc3cc(F)c(C(=O)N[C@@H](Cc4ccc(-n5c(=O)c6ccncc6n(C)c5=O)cc4)C(=O)OC4CCCCC4)cc3F)cc2)cn1]

¹H NMR (400 MHz, DMSO-d₆): δ 10.98 (s, 1H), 9.19 (s, 2H), 8.96 (s, 1H), 8.76 (dd, J=7.6, 2.0 Hz, 1H), 8.55 (d, J=5.0 Hz, 1H), 8.10-8.02 (m, 2H), 8.02-7.94 (m, 2H), 7.88 (d, J=5.0 Hz, 1H), 7.40-7.34 (m, 2H), 7.34-7.24 (m, 2H), 7.24-7.17 (m, 2H), 4.75-4.57 (m, 4H), 3.59 (s, 3H), 3.40 (s, 3H), 3.24-3.04 (m, 2H), 1.80-1.56 (m, 4H), 1.48-1.19 (m, 6H).; MS (ESI) m/z 840.59 (M+H)⁺

Example 256

Synthesis of A-129 and B-129

(Step 1) (2S)-2-[[2,5-Difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoic Acid (A-129)

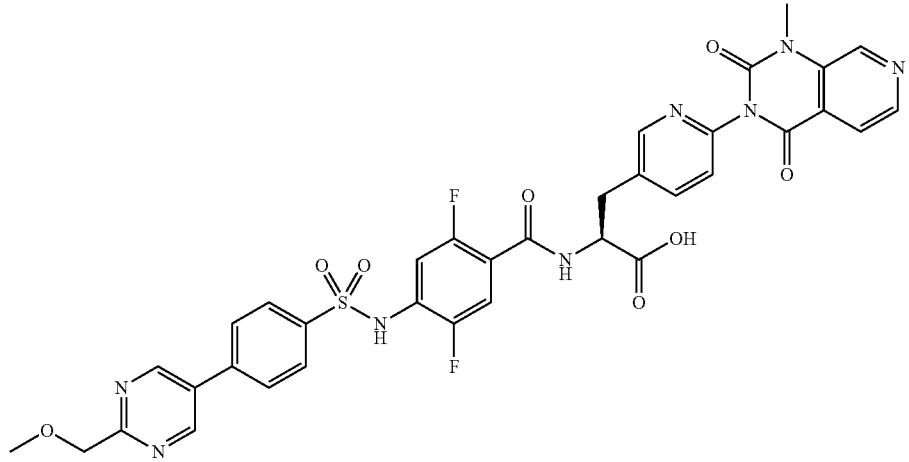

¹H NMR (400 MHz, DMSO-d₆): δ 10.96 (s, 1H), 9.18 (s, 2H), 8.99 (s, 1H), 8.69 (dd, J=8.1, 2.2 Hz, 1H), 8.56 (d, J=4.9 Hz, 1H), 8.46 (d, J=2.3 Hz, 1H), 8.09-8.01 (m, 2H), 8.01-7.93 (m, 2H), 7.93-7.85 (m, 2H), 7.40 (d, J=8.0 Hz, 1H), 7.34-7.23 (m, 2H), 4.74-4.64 (m, 1H), 4.62 (s, 2H), 3.59 (s, 3H), 3.40 (s, 3H), 3.29 (dd, J=14.0, 4.6 Hz, 1H), 3.09 (dd, J=14.1, 10.2 Hz, 1H).; MS (ESI) m/z 759.5 (M+H)⁺

(Step 2) Cyclohexyl (2S)-2-[[2,5-Difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate (B-129)

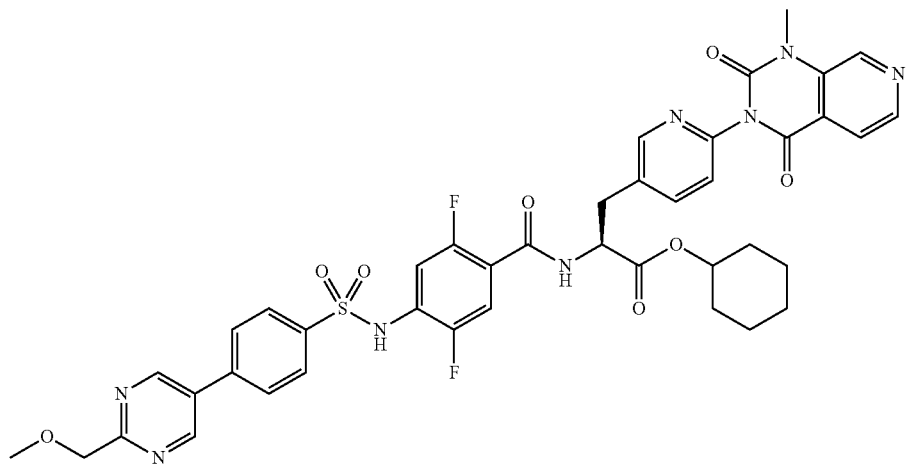 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OC4CCCCC4)cc3F)cc2)cn1]

¹H NMR (400 MHz, DMSO-d₆): δ 10.97 (s, 1H), 9.18 (s, 2H), 8.99 (s, 1H), 8.84 (dd, J=7.7, 1.7 Hz, 1H), 8.57 (d, J=5.0 Hz, 1H), 8.49-8.43 (m, 1H), 8.10-8.01 (m, 2H), 8.01-7.95 (m, 2H), 7.95-7.85 (m, 2H), 7.40 (dd, J=8.0, 0.8 Hz, 1H), 7.33-7.23 (m, 2H), 4.76-4.64 (m, 2H), 4.63 (s, 2H), 3.59 (s, 3H), 3.40 (s, 3H), 3.24 (dd, J=14.1, 5.6 Hz, 1H), 3.12 (dd, J=14.1, 9.7 Hz, 1H), 1.78-1.58 (m, 4H), 1.50-1.19 (m, 6H).; MS (ESI) m/z 841.59 (M+H)⁺

Example 257

Synthesis of A-130 and B-130

(Step 1) (2S)-2-[[4-[[4-(4-Ethyltriazol-1-yl)phenyl]sulfonylamino]-2,5-difluoro-benzoyl]amino]-3-[4-(1-methyl-2,4-dioxo-pyrido[3,4-d]pyrimidin-3-yl)phenyl]propanoic Acid (A-130)

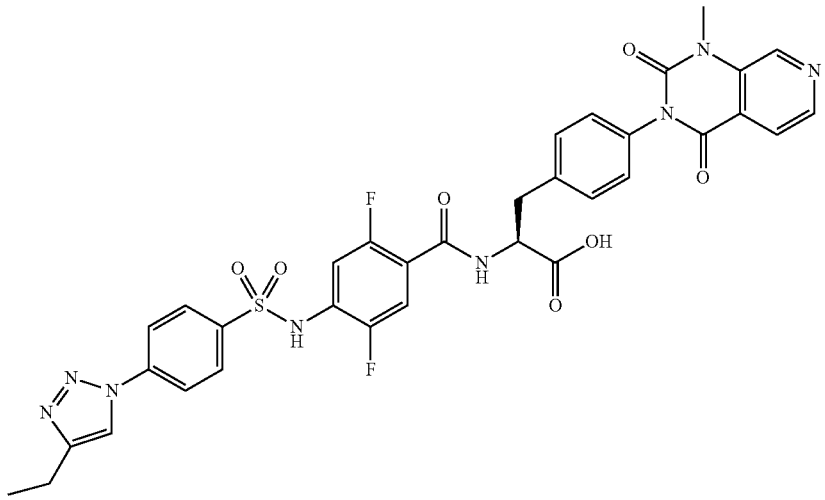 [SMILES: CCc1cn(-c2ccc(S(=O)(=O)Nc3cc(F)c(C(=O)N[C@@H](Cc4ccc(-n5c(=O)c6ccncc6n(C)c5=O)cc4)C(=O)O)cc3F)cc2)nn1]

¹H NMR (400 MHz, DMSO-d₆): δ 10.91 (s, 1H), 8.96 (s, 1H), 8.69 (s, 1H), 8.61 (dd, J=7.9, 2.5 Hz, 1H), 8.55 (d, J=5.0 Hz, 1H), 8.17-8.08 (m, 2H), 8.05-7.97 (m, 2H), 7.87 (d, J=4.9 Hz, 1H), 7.41-7.33 (m, 2H), 7.33-7.17 (m, 4H), 4.68-4.57 (m, 1H), 3.59 (s, 3H), 3.23 (dd, J=14.0, 4.6 Hz, 1H), 3.06 (dd, J=14.1, 9.9 Hz, 1H), 2.72 (q, J=7.6 Hz, 2H), 1.25 (t, J=7.6 Hz, 3H).; MS (ESI) m/z 731.5 (M+H)⁺

(Step 2) Cyclohexyl (2S)-2-[[4-[[4-(4-Ethyltriazol-1-yl)phenyl]sulfonylamino]-2,5-difluoro-benzoyl]amino]-3-[4-(1-methyl-2,4-dioxo-pyrido[3,4-d]pyrimidin-3-yl)phenyl]propanoate (B-130)

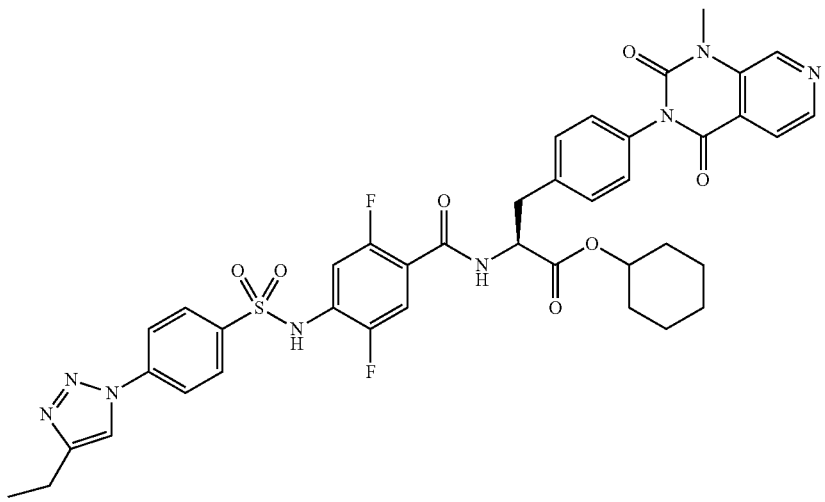 [SMILES: CCc1cn(-c2ccc(S(=O)(=O)Nc3cc(F)c(C(=O)N[C@@H](Cc4ccc(-n5c(=O)c6ccncc6n(C)c5=O)cc4)C(=O)OC4CCCCC4)cc3F)cc2)nn1]

$^1$H NMR (400 MHz, DMSO-$d_6$): δ 10.93 (s, 1H), 8.96 (s, 1H), 8.77 (dd, J=7.4, 2.0 Hz, 1H), 8.69 (s, 1H), 8.55 (d, J=5.0 Hz, 1H), 8.17-8.09 (m, 2H), 8.06-7.97 (m, 2H), 7.88 (d, J=5.0 Hz, 1H), 7.41-7.33 (m, 2H), 7.33-7.17 (m, 4H), 4.75-4.58 (m, 2H), 3.59 (s, 3H), 3.22-3.04 (m, 2H), 2.72 (q, J=7.6 Hz, 2H), 1.79-1.56 (m, 4H), 1.50-1.19 (m, 9H).; MS (ESI) m/z 813.51 (M+H)$^+$

Example 258

(1) VCAM-1/α4β1 Integrin Binding Inhibitory Activity Evaluation Test

The ability of test substances to inhibit the binding of a human T-cell line, Jurkat, which is known to express α4β1 integrin, to VCAM-1 was measured.

To 96-well microtiter plates, recombinant human VCAM-1/Fc (R&D systems) solution (1 μg/mL) diluted with buffer A (carbonate buffer, pH 9.6) was added at 50 μL/well, followed by incubation at 4° C. overnight. After washing once with PBS, Block Ace (Snow Brand Milk Products Company, Limited) was added at 150 μL/well, followed by incubation at room temperature for 2 hours. After removal, washing was conducted once with PBS.

100 μL of each test substance diluted with a binding buffer (DMEM containing 40 mM HEPES, 0.2% BSA, and 4 mM MnCl$_2$) to various concentrations and 100 μL of the Jurkat cells (2×10$^6$ cell/mL) were added to the plates coated with VCAM-1/Fc (5×10$^5$ cells/well), followed by incubation at 30° C. for 15 minutes to 60 minutes. After the cells were bound to each well, unbound cells were removed by washing with PBS. To the plates, buffer C (PBS containing 1.5% Triton X-100) was added at 50 μL/well to lyse the bound Jurkat cells. To 30 μL of the cell lysate, 30 μL of Substrate Buffer (Promega, CytoTox 96 Non-Radioactive Cytotoxicity Assay) was added, and the reaction was allowed to proceed at room temperature in a dark place for 30 minutes. To each well, 30 μL of Stop Solution (Promega, CytoTox 96 Non-Radioactive Cytotoxicity Assay) was added, and the absorbance at 490 nm was measured by using a plate reader. Here, by the obtained absorbance, the activity of the lactate dehydrogenase (LDH) dissolved into the supernatant of each well was detected. In other words, the absorbance was proportional to the number of the Jurkat cells bound to VCAM-1 and remaining on the plate. The test was duplicated. The binding ratios of the cells at various concentrations were determined, with the absorbance of a well containing no test substances taken as 100%. Then, the concentration IC$_{50}$, at which 50% binding inhibition was achieved, was calculated. Table 1 collectively shows the obtained results. Note that, among the compounds synthesized in the corresponding Examples, the compounds in the free form (Compounds A-1 to A-39) were used as the test compounds. Hereinafter, the same shall apply.

(2) MAdCAM-1/α4β7 Integrin Binding Inhibitory Activity Evaluation Test

The ability of test substances to inhibit the binding of a human B cell line, RPMI-8866, which is known to express α4β7 integrin, to MAdCAM-1 was measured.

To 96-well microtiter plates, recombinant mouse MAdCAM-1/Fc (R&D systems) solution (0.75 μg/mL) diluted with buffer A (carbonate buffer solution, pH 9.6) was added at 50 μL/well, followed by incubation at 4° C. overnight. After washing once with PBS, Block Ace (Snow Brand Milk Products Company, Limited) was added at 150 μL/well, followed by incubation at room temperature for 2 hours. After removal, washing was conducted once with PBS.

100 μL of each test substance diluted with binding buffer (DMEM containing 40 mM HEPES, 0.2% BSA, and 4 mM MnCl$_2$) to various concentrations and 100 μL of RPMI-8866 cells (2×10$^6$ cell/mL) were added to the plates coated with MAdCAM-1/Fc (5×10$^5$ cells/well), followed by incubation at 30° C. for 15 minutes to 60 minutes. After the cells were bound to each well, unbound cells were removed by washing with PBS. To the plates, buffer C (PBS containing 1.5% Triton X-100) was added at 50 μL/well to lyse the bound RPMI-8866 cells. To 30 μL of the cell lysate, 30 μL of Substrate Buffer (Promega, CytoTox 96 Non-Radioactive Cytotoxicity Assay) was added, and the reaction was allowed to proceed at room temperature in a dark place for 30 minutes. To each well, 30 μL of Stop Solution (Promega, CytoTox 96 Non-Radioactive Cytotoxicity Assay) was added, and the absorbance at 490 nm was measured by using a plate reader. Here, by the obtained absorbance, the activity of the lactate dehydrogenase (LDH) dissolved into the supernatant of each well was detected. In other words, the absorbance was proportional to the number of the RPMI-8866 cells bound to MAdCAM-1 and remaining on the plate. The test was duplicated. The binding ratios of the cells at various concentrations were determined, with the absorbance of a well containing no test substance taken as 100%. Then, the concentration IC$_{50}$, at which 50% binding inhibition was achieved, was calculated. Table 1 collectively shows the obtained results.

Note that the selectivity in the table was determined by dividing the IC$_{50}$ value in VCAM-1/α4β1 Integrin Binding Inhibitory Activity Evaluation Test by the IC$_{50}$ value in the MAdCAM-1/α4β7 integrin binding inhibitory activity evaluation test.

(3) MAdCAM-1/α4β7 Integrin Binding Inhibitory Activity Evaluation Test in the Presence of Serum (1)

The ability of test substances to inhibit the binding of a human B cell line, RPMI-8866, which is known to express α4β7 integrin, to MAdCAM-1 was measured.

To 96-well microtiter plates, recombinant mouse MAdCAM-1/Fc (R&D systems) solution (1 μg/mL) diluted with buffer A (carbonate buffer, pH 9.6) was added at 50 μL/well, followed by incubation at 4° C. overnight. After washing once with PBS, Block Ace (Snow Brand Milk Products Company, Limited) was added at 150 μL/well, followed by incubation at room temperature for 2 hours. After removal, washing was conducted once with PBS.

100 μL of each test substance diluted with a binding buffer (DMEM containing 40 mM HEPES, 0.2% BSA, and 4 mM MnCl$_2$) to various concentrations and 100 μL of RPMI-8866 cells (2×10$^6$ cell/mL) were added to plates coated with MAdCAM-1/Fc (5×10$^5$ cells/well) with human serum being contained at a final concentration of 50%, followed by incubation at 30° C. for 15 minutes to 60 minutes. After the cells were bound to each well, unbound cells were removed by washing with PBS. To the plates, buffer C (PBS containing 1.5% Triton X-100) was added at 50 μL/well to lyse the bound RPMI-8866 cells. To 30 μL of the cell lysate, 30 μL of Substrate Buffer (Promega, CytoTox 96 Non-Radioactive Cytotoxicity Assay) was added, and the reaction was allowed to proceed at room temperature in a dark place for 30 minutes. To each well, 30 μL of Stop Solution (Promega, CytoTox 96 Non-Radioactive Cytotoxicity Assay) was added, and the absorbance at 490 nm was measured by using a plate reader. Here, by the obtained absorbance, the activity of the lactate dehydrogenase (LDH) dissolved into the supernatant of each well was detected. In other words, the absorbance was proportional to the number of the RPMI-8866 cells bound to MAdCAM-1 and remaining on the plate. The test was duplicated. The binding ratios of the cells at various concentrations were determined, with the absorbance of a well containing no test substance taken as 100%. Then, the concentration $IC_{50}$, at which 50% binding inhibition was achieved, was calculated. Table 1 collectively shows the obtained results.

TABLE 1

| Compound No. | α4β7, IC50 (nM) | α4β1, IC50 (nM) | Selectivity | α4β7 with serum added, IC50 (nM) |
|---|---|---|---|---|
| Prior patent Compound WO 2002/016329 Example 50 (Comparative Example) | 6.7 | 22.5 | 3 | 2200 |
| Example 39 | 0.83 | 140 | 170 | 27 |
| Example 52 | 2.6 | 550 | 210 | 13 |
| Example 78 | 0.79 | 370 | 470 | 19 |
| Example 48 | 0.24 | 54 | 230 | 14 |
| Example 62 | 0.64 | 100 | 160 | 13 |
| Example 55 | 0.27 | 45 | 170 | 4.6 |
| Example 42 | 0.27 | 52 | 190 | 8.8 |
| Example 53 | 2.8 | 740 | 260 | 24 |
| Example 61 | 0.46 | 150 | 330 | 8.7 |
| Example 67 | 0.55 | 210 | 380 | 11 |
| Example 47 | 0.32 | 340 | 1100 | 20 |
| Example 41 | 0.26 | 130 | 500 | 6.4 |
| Example 43 | 0.90 | 220 | 240 | 12 |
| Example 51 | 6.9 | 1500 | 220 | 21 |
| Example 57 | 0.060 | 13 | 220 | 1.5 |
| Example 66 | 1.6 | 280 | 180 | 24 |
| Example 58 | 1.0 | 410 | 410 | 4.8 |
| Example 56 | 2.0 | 160 | 80 | 5.4 |
| Example 44 | 0.62 | 160 | 260 | 16 |
| Example 49 | 0.43 | 330 | 770 | 25 |
| Example 50 | 0.32 | 180 | 560 | 19 |
| Example 40 | 0.73 | 210 | 290 | 8.7 |
| Example 46 | 1.1 | 200 | 180 | 15 |
| Example 68 | 0.13 | 120 | 920 | 9.8 |
| Example 59 | 0.17 | 22 | 130 | 4.1 |
| Example 60 | 1.1 | 1200 | 1100 | 5.5 |
| Example 64 | 2.0 | 1500 | 750 | 22 |
| Example 45 | 0.97 | 500 | 520 | 21 |
| Example 73 | 0.95 | 410 | 430 | 6.5 |
| Example 72 | 1.6 | 400 | 250 | 23 |
| Example 71 | 0.098 | 22 | 220 | 0.72 |
| Example 69 | 0.21 | 31 | 150 | 1.3 |
| Example 70 | 0.41 | 270 | 660 | 21 |
| Example 65 | 0.56 | 420 | 750 | 9.7 |
| Example 63 | 0.80 | 480 | 600 | 11 |
| Example 54 | 0.077 | 18 | 230 | 1.6 |
| Example 75 | 0.38 | 310 | 820 | 4.2 |
| Example 74 | 0.39 | 520 | 1300 | 11 |
| Example 76 | 2.2 | 910 | 410 | 22 |
| Example 77 | 0.27 | 150 | 560 | 9.1 |

(4) MAdCAM-1/α4β7 Integrin Binding Inhibitory Activity Evaluation Test in the Presence of Serum (2)

The MAdCAM-1/α4β7 integrin binding inhibitory activity in the presence of serum was measured in the same manner as in Test (3) described above. Table 2 shows the results. It was found that each of the compounds listed here had preferable characteristics, with the selectivity determined by dividing the $IC_{50}$ value in the VCAM-1/α4β1 integrin binding inhibitory activity evaluation test by the $IC_{50}$ value in the MAdCAM-1/α4β7 integrin binding inhibitory activity evaluation test being 100 or higher. The VCAM-1/α4β1 integrin binding inhibitory activity evaluation test and the MAdCAM-1/α4β7 integrin binding inhibitory activity evaluation test were carried out according to the methods described in Tests (1) and (2) described above.

TABLE 2

| Example No. | α4β7 Rank of activity with serum added 10 nM or lower: A 50 nM or lower: B 200 nM or lower: C >200 nM: D (hereinafter the same) |
|---|---|
| Example 162 | B |
| Example 163 | B |
| Example 152 | A |
| Example 153 | A |
| Example 164 | B |
| Example 165 | A |
| Example 166 | B |
| Example 167 | A |
| Example 168 | A |
| Example 151 | B |
| Example 154 | B |
| Example 169 | B |
| Example 170 | A |
| Example 155 | B |
| Example 156 | B |
| Example 157 | B |
| Example 142 | B |
| Example 171 | B |

| Example No. | α4β7 Rank of activity with serum added |
|---|---|
| Example 172 | A |
| Example 173 | A |
| Example 158 | A |
| Example 174 | B |
| Example 175 | B |
| Example 139 | B |
| Example 159 | B |
| Example 176 | A |
| Example 177 | B |
| Example 178 | B |
| Example 179 | A |
| Example 180 | A |
| Example 181 | B |
| Example 143 | A |
| Example 147 | B |
| Example 144 | C |
| Example 148 | B |
| Example 182 | B |
| Example 145 | A |
| Example 183 | B |
| Example 184 | B |

| Example No. | α4β7 Rank of activity with serum added |
|---|---|
| Example 137 | C |
| Example 185 | B |
| Example 146 | B |
| Example 140 | B |
| Example 141 | B |
| Example 149 | B |
| Example 150 | B |
| Example 138 | C |
| Example 213 | B |
| Example 214 | B |
| Example 222 | C |
| Example 223 | C |
| Example 224 | B |
| Example 225 | B |
| Example 226 | B |
| Example 217 | B |

TABLE 2-continued

| Example No. | |
|---|---|
| Example 215 | B |
| Example 216 | B |
| Example 218 | B |
| Example 219 | B |
| Example 220 | B |

| Example No. | α4β7<br>Rank of activity with serum added |
|---|---|
| Example 221 | B |
| Example 227 | C |
| Example 228 | C |
| Example 229 | C |
| Example 230 | C |
| Example 231 | A |
| Example 232 | C |
| Example 233 | C |
| Example 234 | B |
| Example 235 | D |
| Example 236 | B |
| Example 237 | B |
| Example 238 | A |

As is apparent from the results in Tables 1 and 2, it can be understood that the compounds of the present invention had higher selectivity with a low effect on α4β1 and a high effect on α4β7 than the compound of Patent Literature 1. In particular, it can be understood that the compounds of the present invention had extremely high MAdCAM-1/α4β7 integrin binding inhibitory activity in the presence of serum. The high selectivity with a low effect on α4β1 and a high effect on α4β7 as described above is advantageous in that it is possible to treat more efficiently diseases to which the compounds can be applied, because the action on α4β7, which is specifically expressed in the intestinal tract, can be greatly suppressed, while the action on α4β1, which suppress the invasion of lymphocytes circulating through the entire body, can be reduced.

What is claimed is:

1. A sulfonamide compound represented by any one of the following formulae or a pharmaceutically acceptable salt thereof:

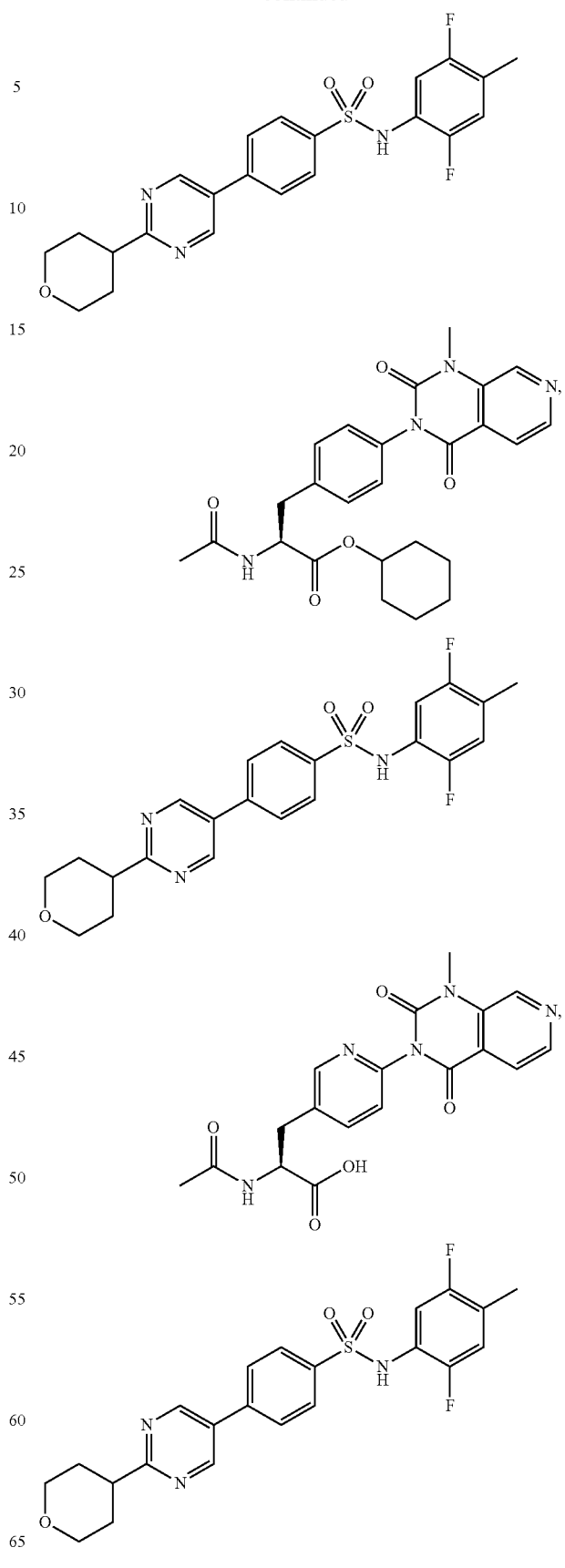

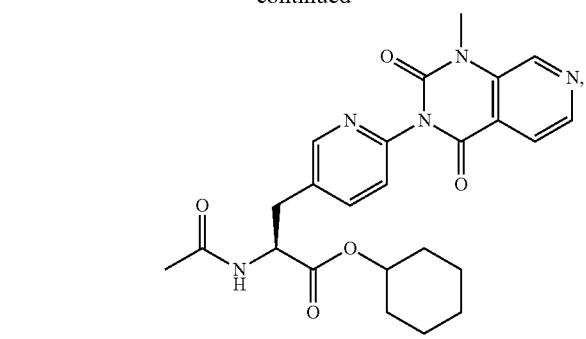
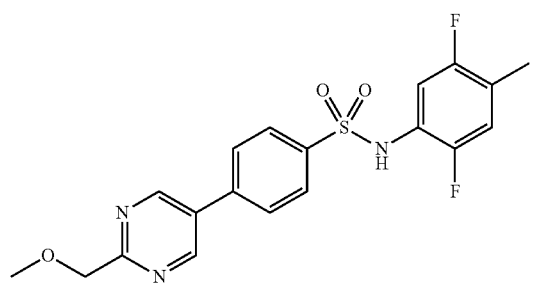
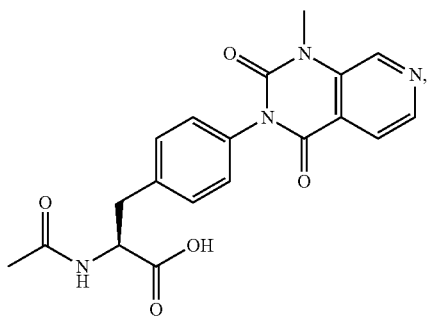
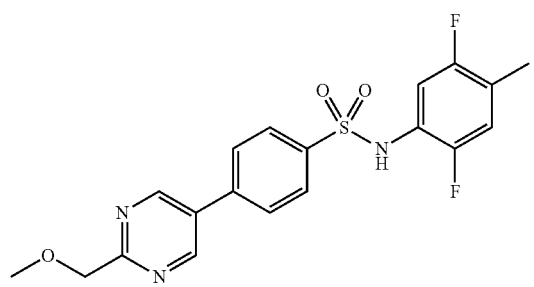
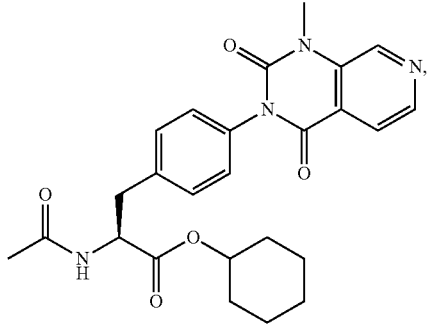
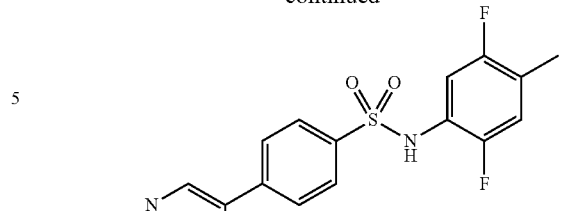
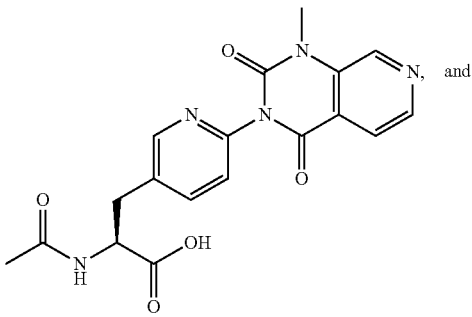
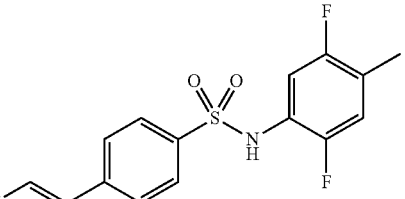
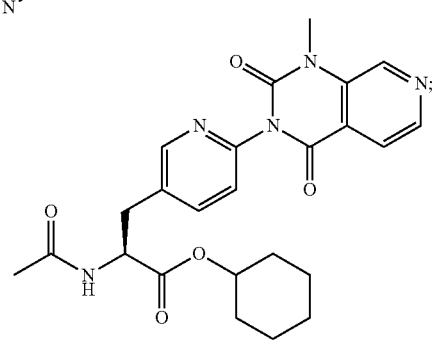
or represented by the following formula (1) or a pharmaceutically acceptable salt thereof:
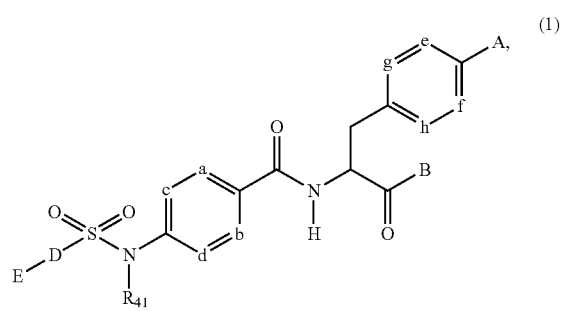
wherein
A represents a group represented by the following general formula (2-1), (2-2), or (2-3),

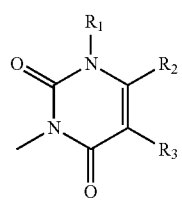

(2-1)

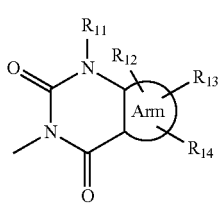

(2-2)

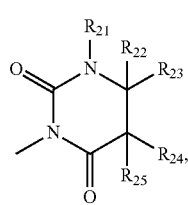

(2-3)

wherein
Arm is a cyclic alkyl group or aromatic ring containing 0, 1, 2, 3, or 4 hetero atoms selected from oxygen atoms, sulfur atoms, and nitrogen atoms, $R_1$, $R_{11}$, and $R_{21}$ each independently represent any one of a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a lower alkylamino group, a (lower alkylamino) lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, $R_{12}$, $R_{13}$, and $R_{14}$ each independently represent any one of a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a lower alkylamino group, a (lower alkylamino) lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, $R_2$, $R_3$, $R_{22}$, $R_{23}$, $R_{24}$, and $R_{25}$ each independently represent any one of a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a lower alkylamino group, a (lower alkylamino)lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, B represents any one of a lower alkoxy group optionally substituted with an aryl group(s), a hydroxyl group(s), a lower alkyl group(s), a lower alkylamino group(s), and/or a heterocyclic group(s), a hydroxyl group, and a hydroxyamino group, $R_{41}$ represents a hydrogen atom or a lower alkyl group, a, b, c, and d each independently represent C—$R_{31}$, C—$R_{32}$, C—$R_{33}$, and C—$R_{34}$, respectively, but one or two of a, b, c, and d may each represent a nitrogen atom, $R_{31}$, $R_{32}$, $R_{33}$, and $R_{34}$ each independently represent any one of a hydrogen atom, a halogen atom, a lower alkyl group, a lower alkoxy group, and a nitro group, provided that any one of $R_{31}$, $R_{32}$, $R_{33}$, and $R_{34}$ is a halogen atom or a lower alkyl group, e, f, g, and h each independently represent C—$R_{35}$, C—$R_{36}$, C—$R_{37}$, and C—$R_{38}$, respectively, but one or two of e, f, g, and h may each represent a nitrogen atom, $R_{35}$, $R_{36}$, $R_{37}$, and $R_{38}$ are each independently any one of a hydrogen atom, a halogen atom, a lower alkyl group, a lower alkoxy group, and a nitro group, D represents a phenyl group or heterocyclic group optionally having a substituent(s) selected from the group consisting of halogen atoms, hydroxyl groups, lower alkyl groups, lower alkenyl groups, lower alkynyl groups, lower alkoxy groups, lower alkylthio groups, lower hydroxyalkyl groups, lower hydroxyalkenyl groups, lower hydroxyalkoxy groups, lower halogenoalkyl groups, lower halogenoalkoxy groups, lower halogenoalkylthio groups, lower halogenoalkenyl groups, nitro groups, cyano groups, amino groups, carboxyl groups, lower alkyloxycarbonyl groups, carbamoyl groups, lower alkanoyl groups, aroyl groups, lower alkylsulfonyl groups, sulfamoyl groups, and ammonium groups, and E represents a 5- or 6-membered heterocyclic group optionally having a substituent(s) selected from the group consisting of halogen atoms, hydroxyl groups, lower alkyl groups, lower alkenyl groups, lower alkynyl groups, lower alkoxy groups, lower alkylthio groups, lower hydroxyalkyl groups, lower hydroxyalkenyl groups, lower hydroxyalkoxy groups, lower halogenoalkyl groups, lower halogenoalkoxy groups, lower halogenoalkylthio groups, lower halogenoalkenyl groups, nitro groups, cyano groups, amino groups, 4- to 6-membered cyclic amino groups, carboxyl groups, lower alkyloxycarbonyl groups, carbamoyl groups, lower alkanoyl groups, aroyl groups, lower alkylsulfonyl groups, sulfamoyl groups, and ammonium groups; an aminocarbonyl group optionally having a substituent(s) selected from the group consisting of hydroxyl groups, lower alkyl groups, lower alkenyl groups, lower alkynyl groups, lower alkoxy groups, lower hydroxyalkyl groups, lower hydroxyalkenyl groups, lower hydroxyalkoxy groups, lower halogenoalkyl groups, lower halogenoalkoxy groups, lower halogenoalkenyl groups, amino groups, lower alkylamino groups, aryl groups, heterocyclic groups, heterocycle-substituted lower alkyl groups, lower alkylsulfonyl groups, and sulfamoyl groups; a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a carboxyl group, a dihydroxyboryl group, a lower alkylcarbonyl group, a lower alkyloxycarbonyl group, a carbamoyl group, a lower alkanoyl group, an aroyl group, a lower alkylsulfonyl group, a sulfamoyl group, an ammonium group, or a lower alkylaminoalkylene group, provided that the lower alkylcarbonyl group and the lower alkyloxycarbonyl group may each be bonded to the phenyl group represented by D to form a condensed ring.

2. The sulfonamide derivative according to claim 1 or a pharmaceutically acceptable salt thereof, wherein E represents a 5- or 6-membered heterocyclic group optionally having a substituent(s) selected from the group consisting of halogen atoms, hydroxyl groups, lower alkyl groups, lower alkenyl groups, lower alkynyl groups, lower alkoxy groups, lower alkylthio groups, lower hydroxyalkyl groups, lower hydroxyalkenyl groups, lower hydroxyalkoxy groups, lower halogenoalkyl groups, lower halogenoalkoxy groups, lower halogenoalkylthio groups, lower halogenoalkenyl groups, nitro groups, cyano groups, amino groups, carboxyl groups, lower alkyloxycarbonyl groups, carbamoyl groups, lower alkanoyl groups, aroyl groups, lower alkylsulfonyl groups, sulfamoyl groups, and ammonium groups; an aminocarbonyl group optionally having a substituent(s) selected from the group consisting of hydroxyl groups, lower alkyl groups, lower alkenyl groups, lower alkynyl groups, lower alkoxy groups, lower hydroxyalkyl groups, lower hydroxyalkenyl groups, lower hydroxyalkoxy groups, lower halogenoalkyl groups, lower halogenoalkoxy groups, lower halogenoalkenyl groups, amino groups, lower alkylamino groups, aryl groups, heterocyclic groups, lower alkylsulfonyl groups, and sulfamoyl groups; a hydrogen atom, a halogen atom, a hydroxyl group, a lower alkyl group, a lower alkenyl group, a lower alkynyl group, a lower alkoxy group, a lower alkylthio group, a lower hydroxyalkyl group, a lower hydroxyalkenyl group, a lower hydroxyalkoxy group, a lower halogenoalkyl group, a lower halogenoalkoxy group, a lower halogenoalkylthio group, a lower halogenoalkenyl group, a nitro group, a cyano group, an amino group, a carboxyl group, a dihydroxyboryl group, a lower alkyloxycarbonyl group, a carbamoyl group, a lower alkanoyl group, an aroyl group, a lower alkylsulfonyl group, a sulfamoyl group, an ammonium group, or a lower alkylaminoalkylene group.

3. The sulfonamide derivative according to claim 1 or a pharmaceutically acceptable salt thereof, wherein D is a phenyl group optionally having a substituent(s) selected from the group consisting of lower alkyl groups, halogen atoms, hydroxyl groups, and lower alkoxy groups.

4. The sulfonamide derivative according to claim 1 or a pharmaceutically acceptable salt thereof, wherein D is a 6-membered aromatic heterocyclic group containing a nitrogen atom(s) as a ring-constituent atom(s) and optionally having a substituent(s) selected from the group consisting of lower alkyl groups, halogen atoms, and lower alkoxy groups.

5. The sulfonamide derivative according to claim 1 or a pharmaceutically acceptable salt thereof, wherein the heterocyclic group represented by D is a pyridyl group or pyrrole group optionally having a substituent(s) selected from the group consisting of lower alkyl groups, halogen atoms, and lower alkoxy groups.

6. The sulfonamide derivative according to claim 1 or a pharmaceutically acceptable salt thereof, wherein E is a 5- or 6-membered aromatic heterocyclic group containing 1, 2, 3, or 4 hetero atoms selected from oxygen atoms, sulfur atoms, and nitrogen atoms and optionally having a substituent(s) selected from the group consisting of lower alkyl groups, lower alkoxy groups, and halogen atoms.

7. The sulfonamide derivative according to claim 6 or a pharmaceutically acceptable salt thereof, wherein the aromatic heterocyclic group is selected from the group consisting of a pyridyl group, a pyridazyl group, a pyrimidyl group, a pyrazinyl group, a pyrrolyl group, a furanyl group, a thiophenyl group, a thiazolyl group, an oxazolyl group, a triazolyl group, and a tetrazole group.

8. The sulfonamide derivative according to claim 1 or a pharmaceutically acceptable salt thereof, wherein E is (i) an aminocarbonyl group optionally substituted with a lower alkyl group(s), a heterocyclic group(s), and/or a heterocycle-substituted lower alkyl group(s); or (ii) a lower alkylaminoalkylene group.

9. The sulfonamide derivative according to claim 1 or a pharmaceutically acceptable salt thereof, wherein $R_1$, $R_{11}$, and $R_{21}$ are lower alkyl groups.

10. The sulfonamide derivative according to claim 1 or a pharmaceutically acceptable salt thereof, wherein Arm is selected from the group consisting of a phenyl group, a pyridyl group, and an imidazolyl group.

11. The sulfonamide derivative according to claim 1 or a pharmaceutically acceptable salt thereof, wherein one of $R_{31}$, $R_{32}$, $R_{33}$, and $R_{34}$ is a halogen atom, and the rest are hydrogen atoms, or two of $R_{31}$, $R_{32}$, $R_{33}$, and $R_{34}$ are halogen atoms, and the rest are hydrogen atoms.

12. The sulfonamide derivative according to claim 1 or a pharmaceutically acceptable salt thereof, wherein A is a group represented by general formula (2-1) or (2-2), in which Arm is a pyridyl group or an imidazolyl group, and $R_1$ and $R_{11}$ are lower alkyl groups, two of $R_{31}$, $R_{32}$, $R_{33}$, and $R_{34}$ are halogen atoms, and the rest are hydrogen atoms, g is a carbon or nitrogen atom, e is a carbon or nitrogen atom, D is a phenyl group optionally having a halogen atom(s), a lower alkyl group(s), and/or a lower alkoxy group(s), a furyl group, or a pyridyl group optionally having a halogen atom(s), a lower alkyl group(s), and/or a lower alkoxy group(s), and E is a pyridyl group, pyrimidyl group, triazolyl group, or pyrrolyl group optionally having a lower alkyl group(s) and/or a 4- to 6-membered cyclic amino group(s), or an aminocarbonyl group optionally substituted with a lower alkyl or heterocycle-substituted lower alkyl group(s).

13. A pharmaceutical composition comprising the sulfonamide derivative according to claim 1 or a pharmaceutically acceptable salt thereof.

14. An agent for treating inflammatory bowel disease or multiple sclerosis, the method comprising administering an agent comprising, as an active ingredient, the sulfonamide compound according to claim 1 or a pharmaceutically acceptable salt thereof, to a patient in need thereof.

15. A compound represented by any one of the following formulae or a pharmaceutically acceptable salt thereof:

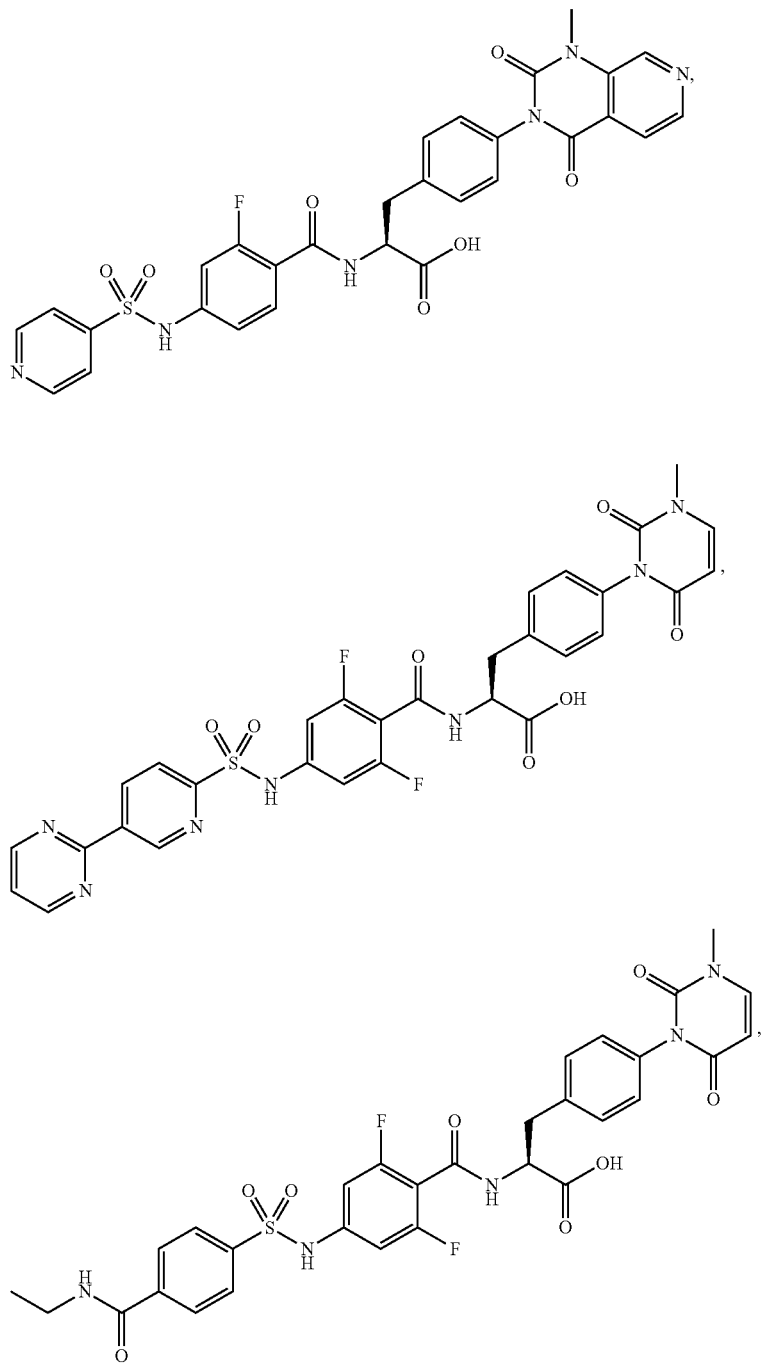

-continued
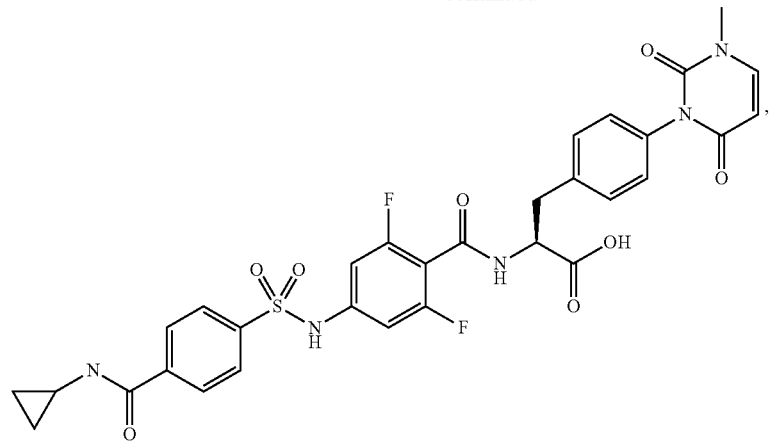
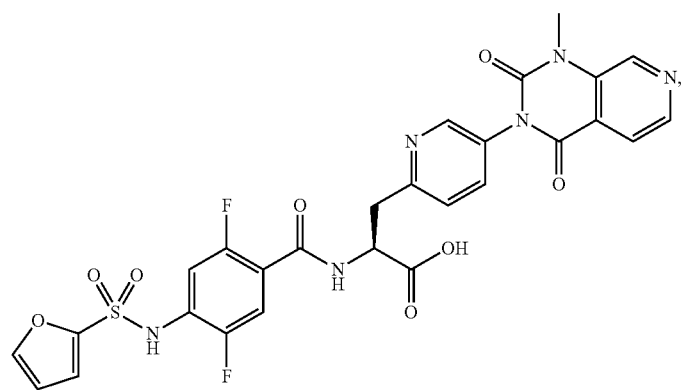
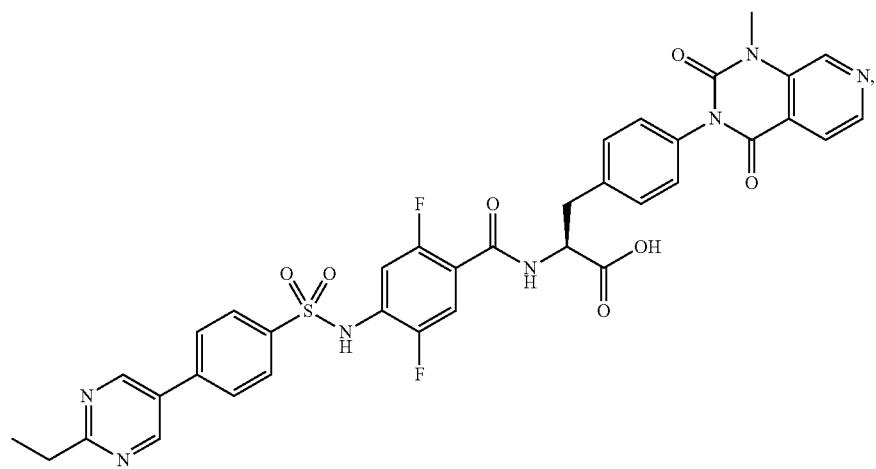

-continued
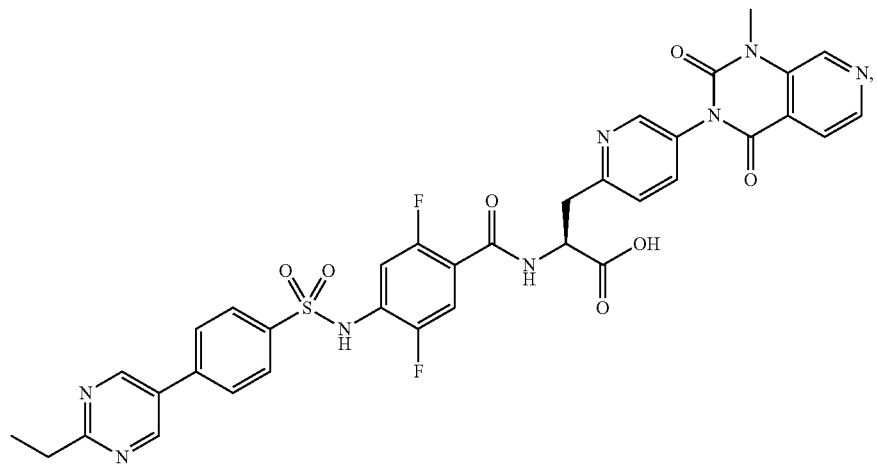
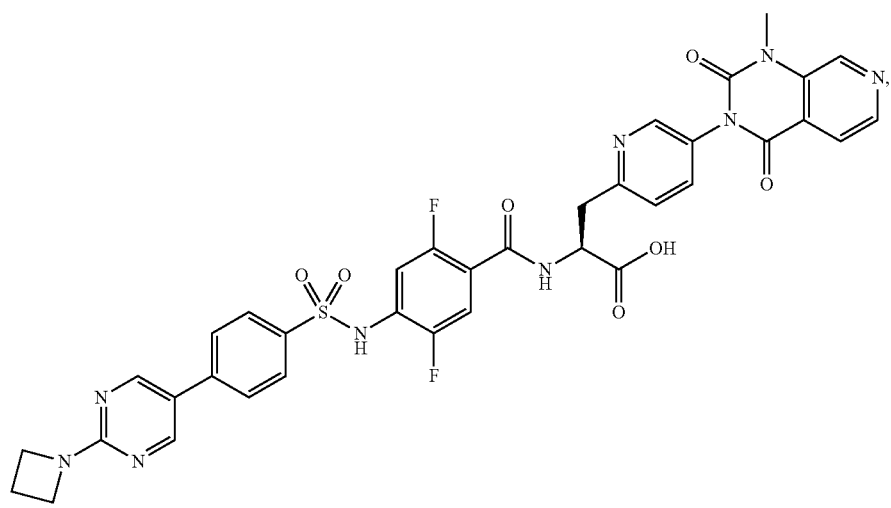
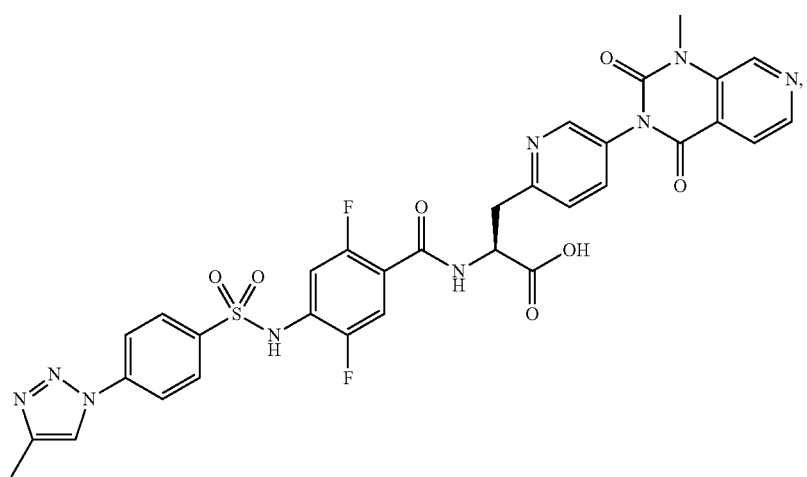

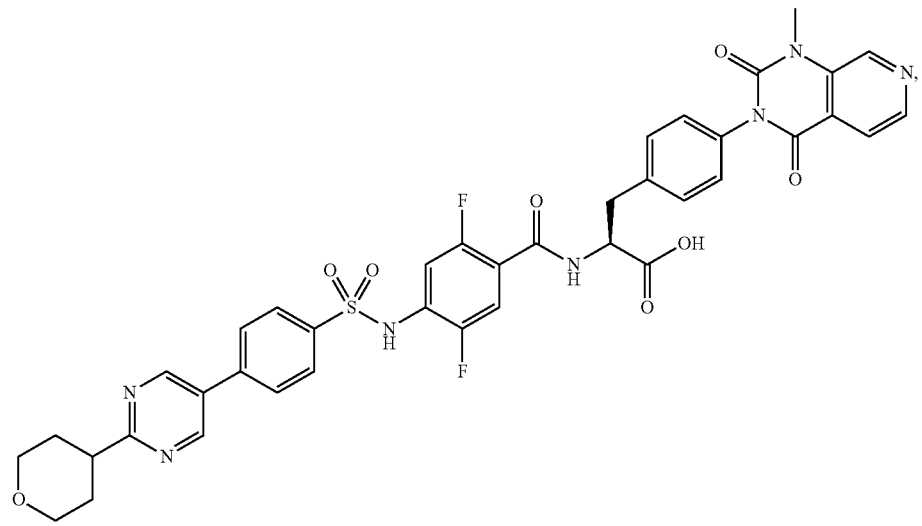
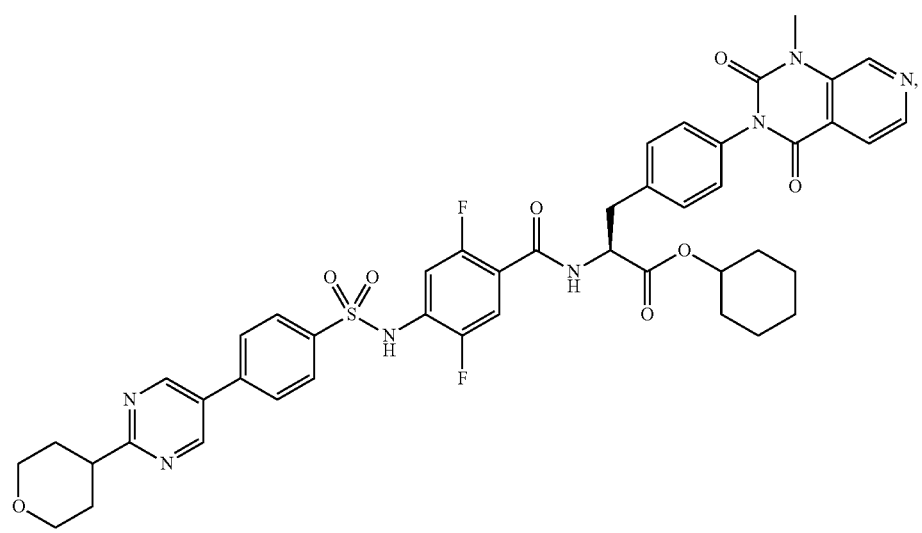
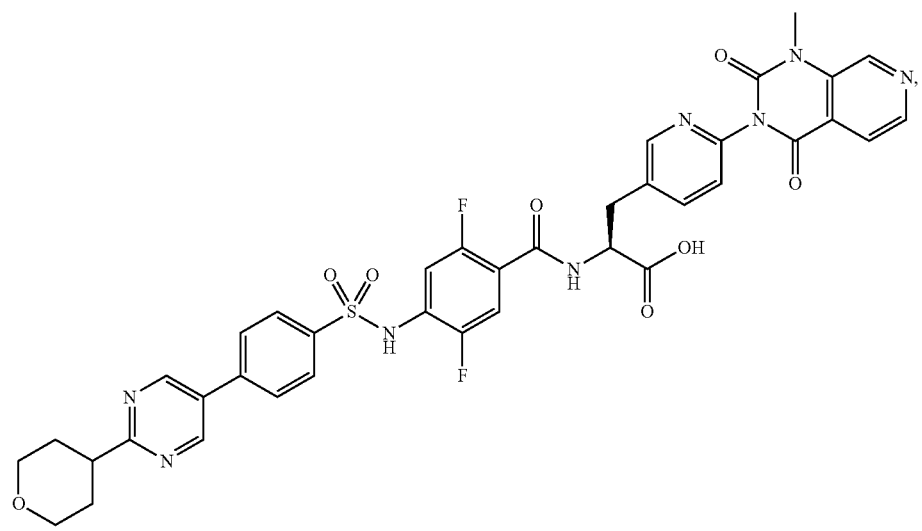

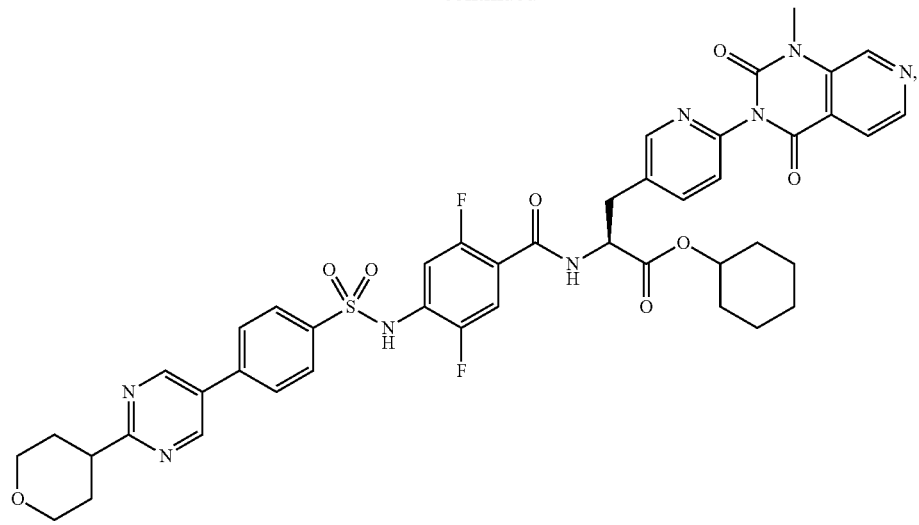
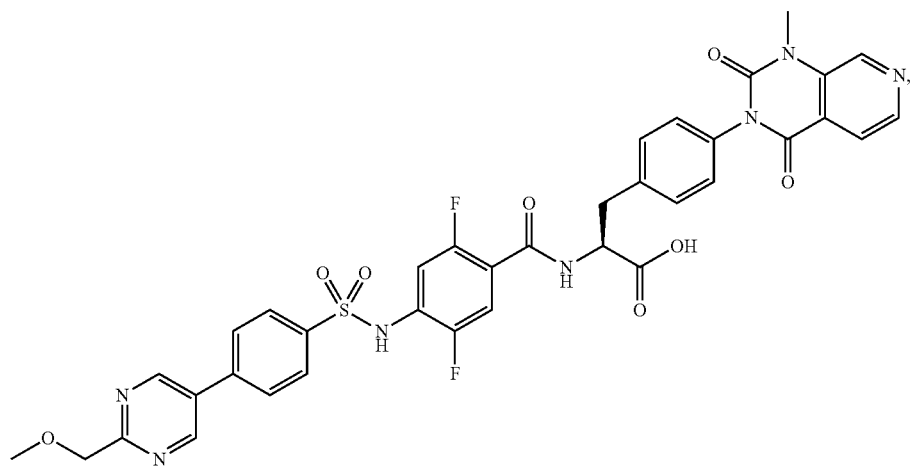
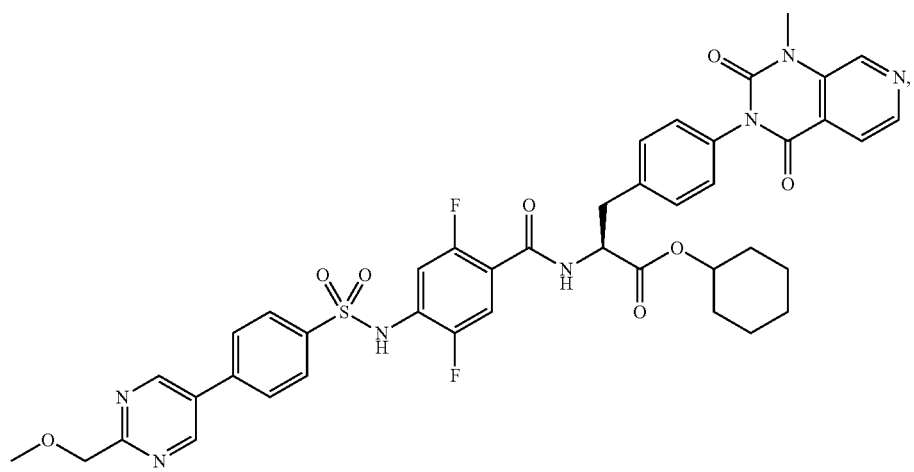 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OC4CCCCC4)cc3F)cc2)cn1]

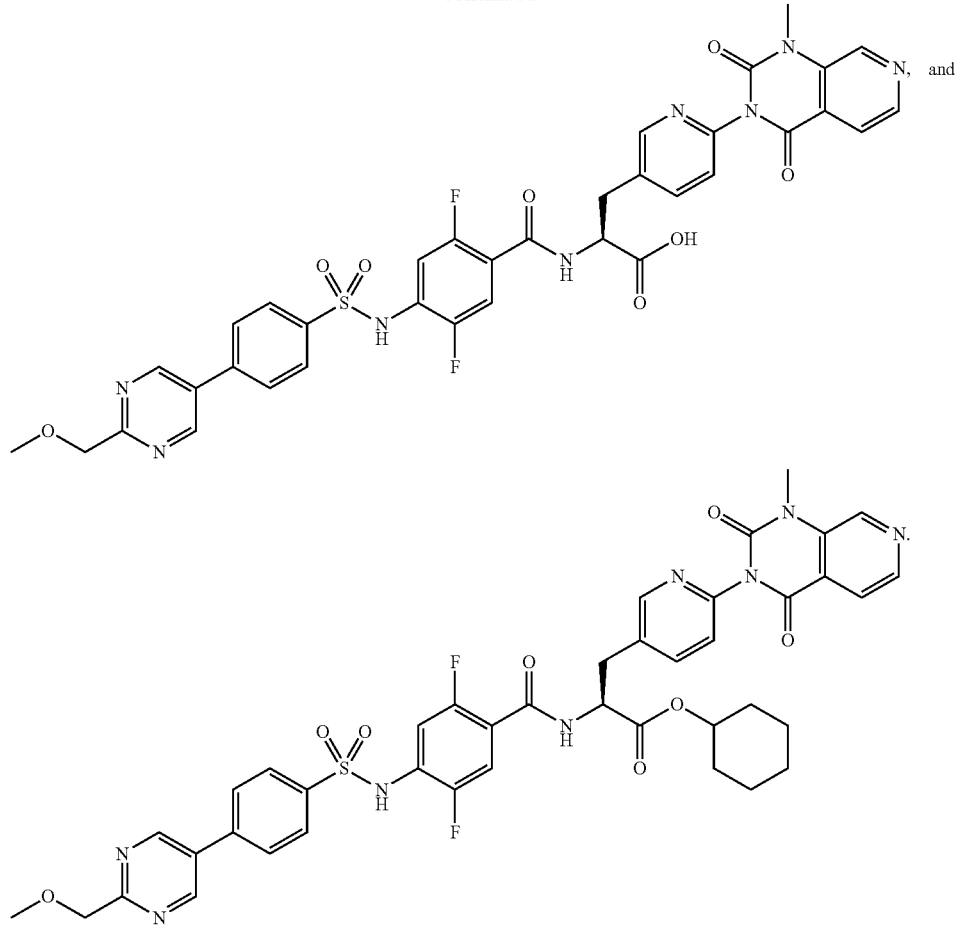
* * * * *

UNITED STATES PATENT AND TRADEMARK OFFICE
CERTIFICATE OF CORRECTION

PATENT NO. : 9,533,985 B2
APPLICATION NO. : 14/397078
DATED : January 3, 2017
INVENTOR(S) : Hirokazu Ueno et al.

It is certified that error appears in the above-identified patent and that said Letters Patent is hereby corrected as shown below:

In Claim 1, Column 417, Lines 40-65, change:

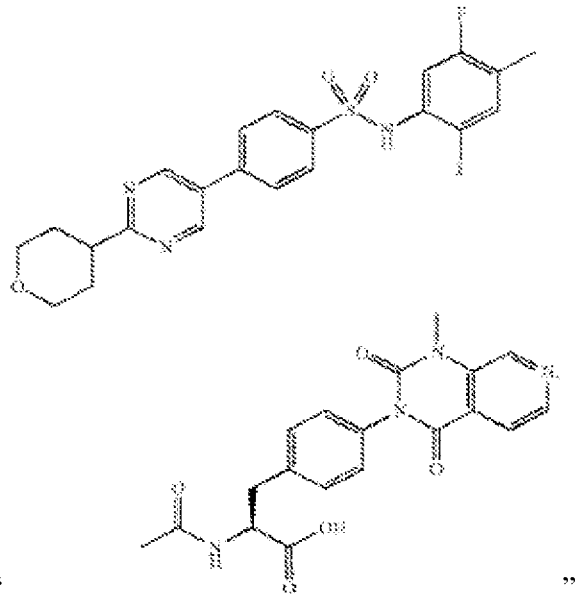

"                                                  "

To:

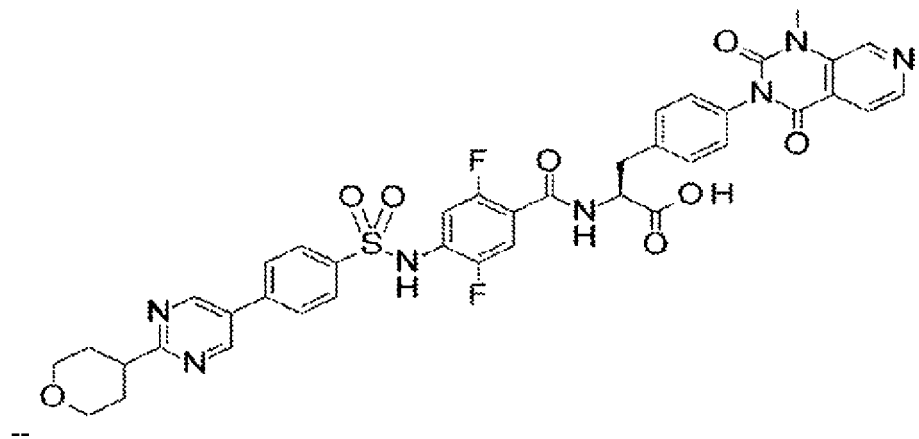

-- ,--

Signed and Sealed this
Second Day of May, 2017

Michelle K. Lee
*Director of the United States Patent and Trademark Office*

CERTIFICATE OF CORRECTION (continued)
U.S. Pat. No. 9,533,985 B2

In Claim 1, Column 418, Lines 1-25, change:

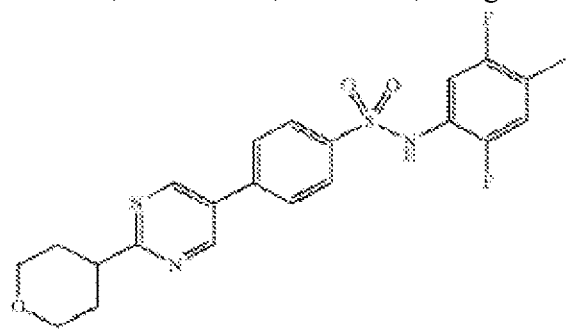

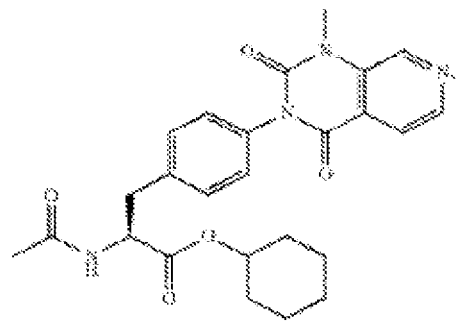

"    "

To:

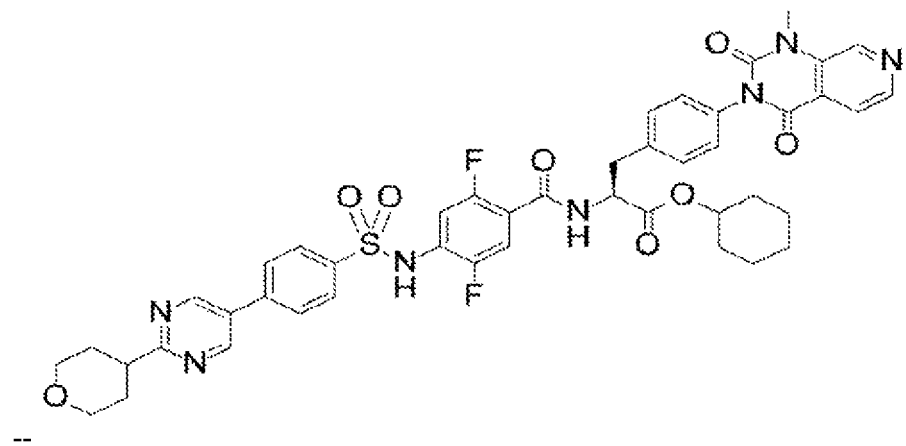

--                                                                          : --

CERTIFICATE OF CORRECTION (continued)
U.S. Pat. No. 9,533,985 B2

In Claim 1, Column 418, Lines 30-50, change:

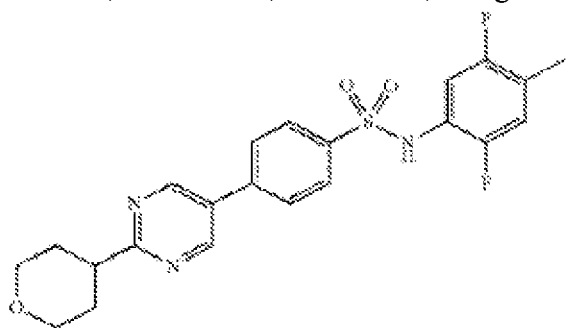

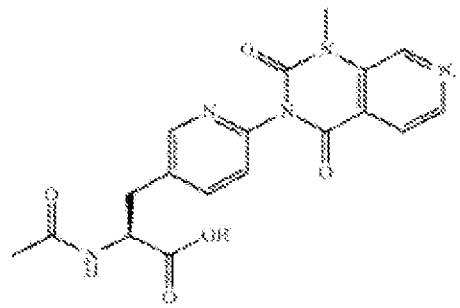

" "

To:

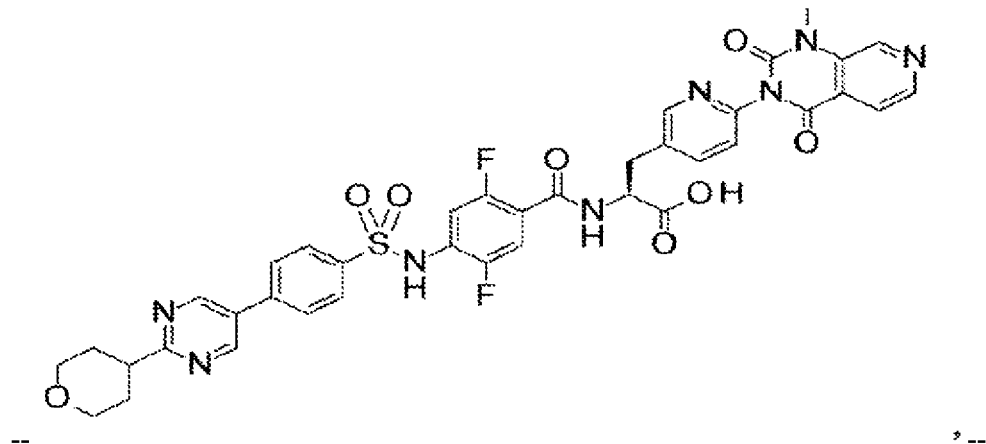

-- --

CERTIFICATE OF CORRECTION (continued)
U.S. Pat. No. 9,533,985 B2

Page 4 of 8

In Claim 1, Column 418, Line 55 to Column 419, Line 15, change:

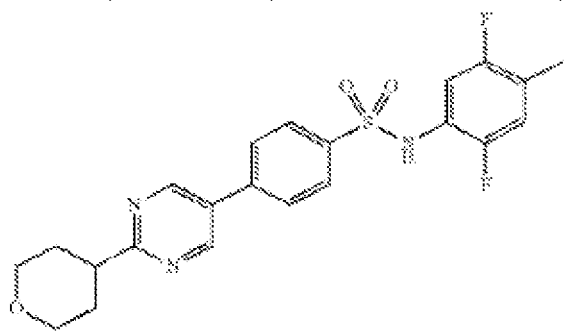

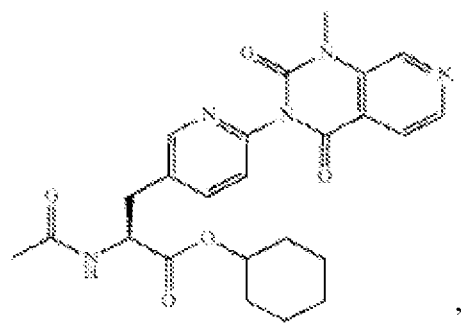

"                                                                                   "

To:

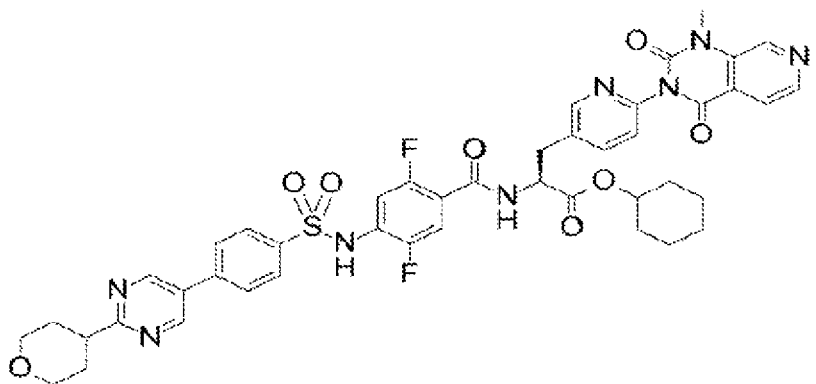

--                                                                                   , --

CERTIFICATE OF CORRECTION (continued)
U.S. Pat. No. 9,533,985 B2

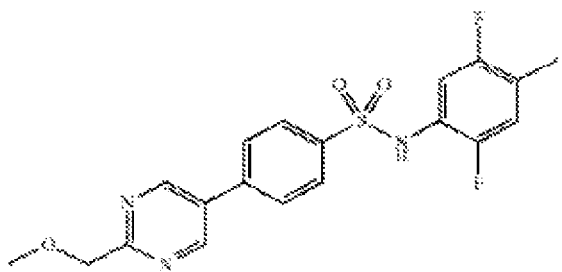

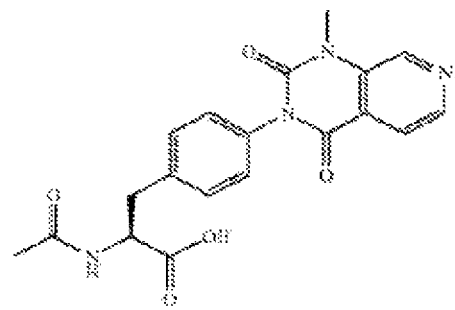

"  "

To:

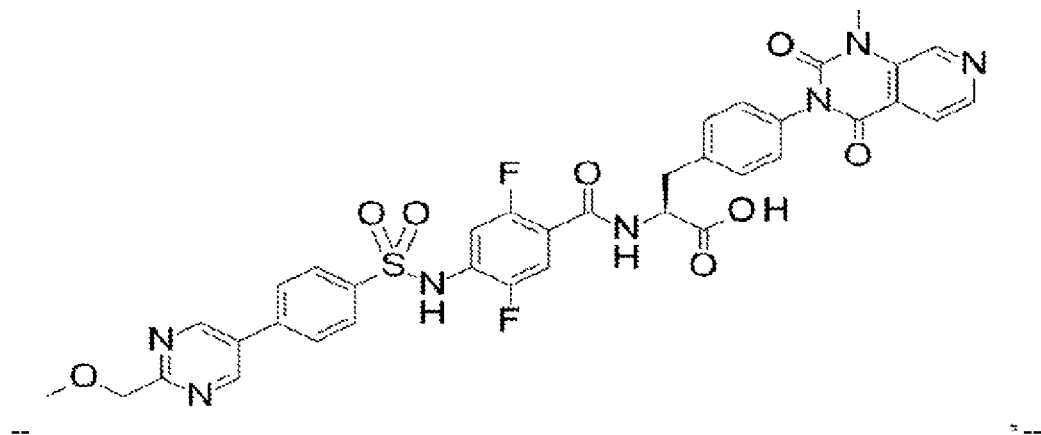

-- --

In Claim 1, Column 419, Lines 45-65, change:

"
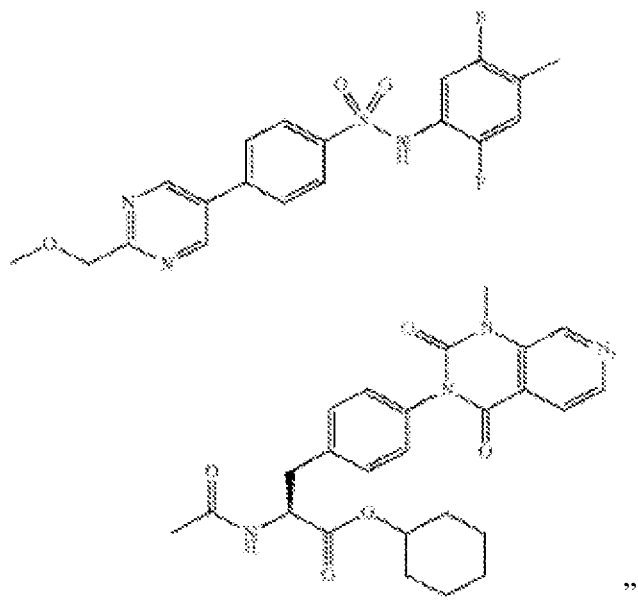
"
To:
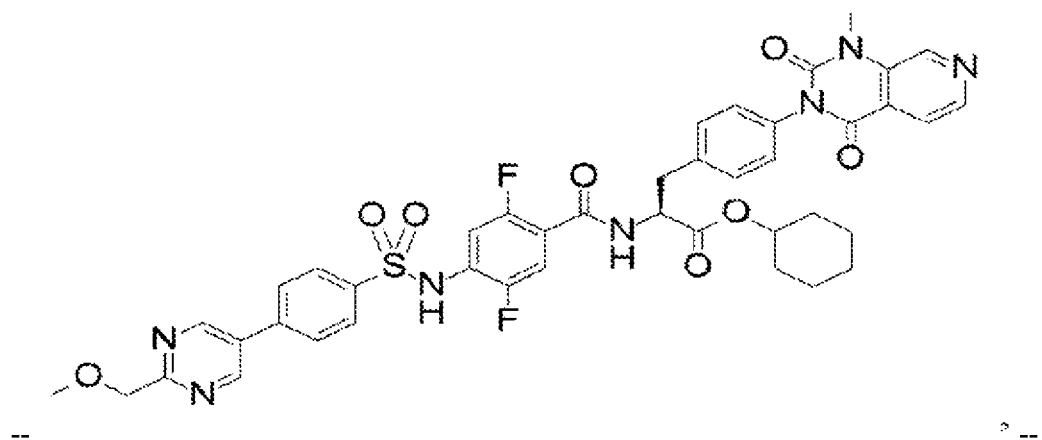
--                                                                                                                         " --
In Claim 1, Column 420, Lines 1-24, change:

CERTIFICATE OF CORRECTION (continued)  Page 7 of 8
U.S. Pat. No. 9,533,985 B2

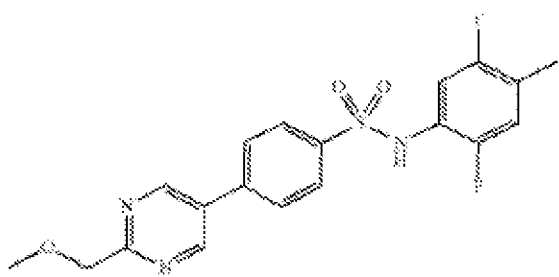

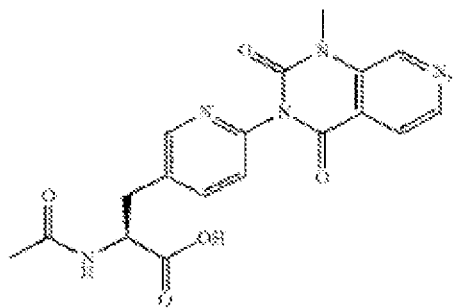

"                                                  "

To:

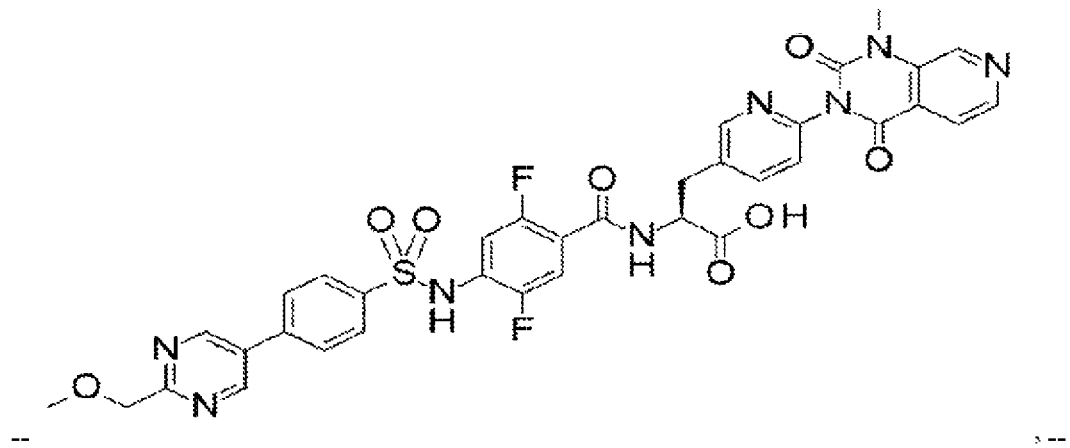

--                                                  --

In Claim 1, Column 420, Lines 25-45, change:

"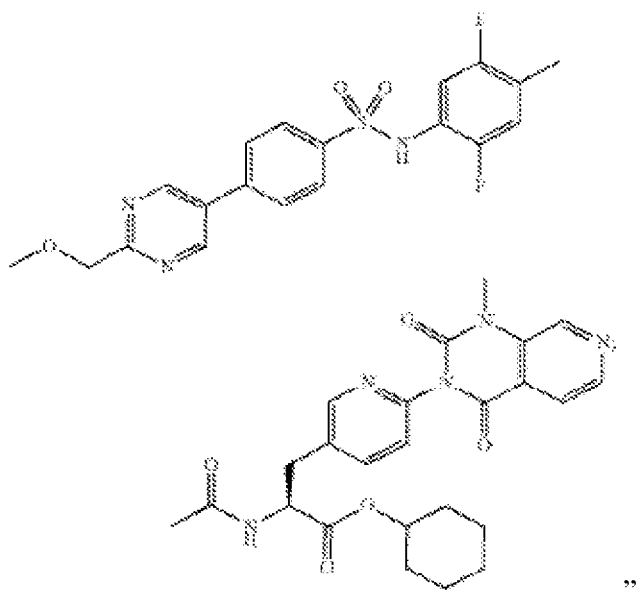"
To:
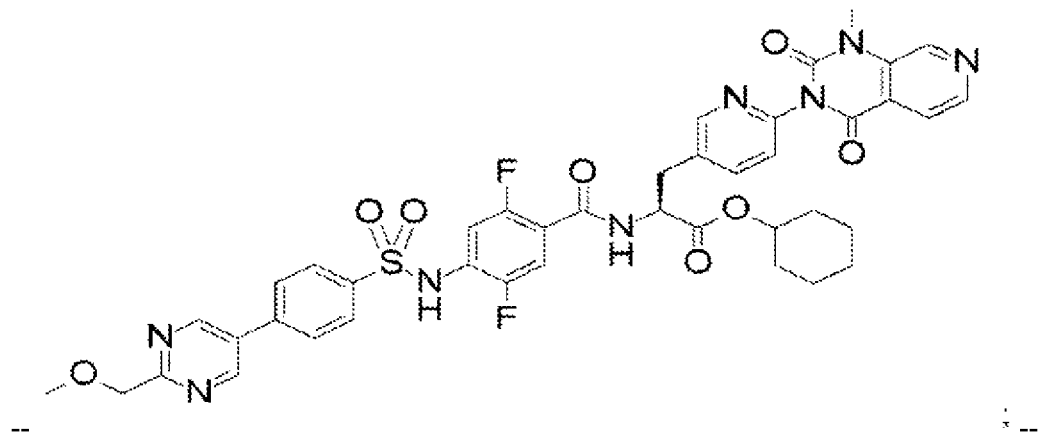
-- --